(12) United States Patent
Furmanski et al.

(10) Patent No.: US 12,071,633 B2
(45) Date of Patent: Aug. 27, 2024

(54) VIRAL VECTOR CONSTRUCTS FOR DELIVERY OF NUCLEIC ACIDS ENCODING CYTOKINES AND USES THEREOF FOR TREATING CANCER

(71) Applicant: KRIYA THERAPEUTICS, INC., Morrisville, NC (US)

(72) Inventors: Brian Furmanski, Morrisville, NC (US); Nachiketa Gupta, Morrisville, NC (US); Bruce Schnepp, Morrisville, NC (US); Michele Stone, Morrisville, NC (US)

(73) Assignee: Kriya Therapeutics, Inc., Morrisville, NC (US)

( * ) Notice: Subject to any disclaimer, the term of this patent is extended or adjusted under 35 U.S.C. 154(b) by 85 days.

(21) Appl. No.: 17/500,898

(22) Filed: Oct. 13, 2021

(65) Prior Publication Data
US 2022/0162638 A1 May 26, 2022

Related U.S. Application Data

(60) Provisional application No. 63/182,632, filed on Apr. 30, 2021, provisional application No. 63/141,921, filed on Jan. 26, 2021, provisional application No. 63/108,838, filed on Nov. 2, 2020, provisional application No. 63/091,270, filed on Oct. 13, 2020.

(51) Int. Cl.
| | |
|---|---|
| *C12N 15/86* | (2006.01) |
| *A61K 38/20* | (2006.01) |
| *A61K 39/395* | (2006.01) |
| *A61P 35/00* | (2006.01) |

(52) U.S. Cl.
CPC ............ *C12N 15/86* (2013.01); *A61K 38/208* (2013.01); *A61K 39/3955* (2013.01); *A61P 35/00* (2018.01); *C12N 2750/14132* (2013.01); *C12N 2750/14143* (2013.01); *C12N 2750/14171* (2013.01); *C12N 2830/008* (2013.01); *C12N 2840/203* (2013.01)

(58) Field of Classification Search
CPC ............ C07K 16/2803; C07K 2317/32; C07K 2317/52; A61K 47/6801; A61P 25/28
See application file for complete search history.

(56) References Cited

U.S. PATENT DOCUMENTS

| | | | |
|---|---|---|---|
| 4,861,719 A | 8/1989 | Miller | |
| 4,937,190 A | 6/1990 | Palmenberg et al. | |
| 5,139,941 A | 8/1992 | Muzyczka et al. | |
| 5,356,806 A | 10/1994 | Harris et al. | |
| 5,527,928 A | 6/1996 | Nantz et al. | |
| 5,573,764 A * | 11/1996 | Sykes | C07K 14/5434 424/85.2 |
| 5,744,625 A | 4/1998 | Nantz et al. | |
| 5,824,812 A | 10/1998 | Nantz et al. | |
| 5,869,715 A | 2/1999 | Nantz et al. | |
| 5,892,071 A | 4/1999 | Nantz et al. | |
| 5,925,623 A | 7/1999 | Nantz et al. | |
| 5,962,424 A | 10/1999 | Hallahan et al. | |
| 5,965,726 A | 10/1999 | Pavlakis et al. | |
| 5,994,104 A | 11/1999 | Anderson et al. | |
| 6,174,666 B1 | 1/2001 | Pavlakis et al. | |
| 6,204,059 B1 | 3/2001 | Samulski et al. | |
| 6,218,180 B1 | 4/2001 | Kurtzman et al. | |
| 6,291,664 B1 | 9/2001 | Pavlakis et al. | |
| 6,414,132 B1 | 7/2002 | Pavlakis et al. | |
| 6,794,498 B2 | 9/2004 | Pavlakis et al. | |
| 7,008,633 B2 | 3/2006 | Yang et al. | |
| 7,091,330 B2 * | 8/2006 | Reinherz | C07K 14/4702 435/325 |
| 7,833,754 B2 * | 11/2010 | Felber | C07K 14/5434 435/325 |
| 8,026,223 B1 | 9/2011 | Heller et al. | |
| 8,298,790 B2 | 10/2012 | Yun | |
| 8,556,882 B2 | 10/2013 | Morgan et al. | |
| 8,802,080 B2 | 8/2014 | Warrington et al. | |
| 9,163,257 B2 * | 10/2015 | Singh | C07K 14/7151 |
| 9,453,241 B2 * | 9/2016 | Pan | C12N 15/8616 |
| 9,775,918 B2 | 10/2017 | Zhong et al. | |
| 9,821,114 B2 | 11/2017 | Cabrera Aquino et al. | |

(Continued)

FOREIGN PATENT DOCUMENTS

| | | |
|---|---|---|
| EP | 3552614 A1 | 10/2019 |
| EP | 3351261 B1 | 6/2021 |

(Continued)

OTHER PUBLICATIONS

Kenkel, Viral Vectors 101: Parts of the AAV Transfer Plasmid, 2020, addgene Blog, retrieved from: https://blog.addgene.org/viral-vectors-101-parts-of-the-aav-transfer-plasmid (Year: 2020).*

(Continued)

*Primary Examiner* — Jeffrey Stucker
*Assistant Examiner* — Brittney E Donoghue
(74) *Attorney, Agent, or Firm* — Sterne, Kessler, Goldstein & Fox P.L.L.C.

(57) ABSTRACT

The present disclosure provides the gene therapy compositions comprising vectors (e.g., viral vectors) suitable for delivery of nucleic acids encoding immunomodulatory proteins or functional fragments thereof, and methods of using the same. Certain aspects of the disclosure are directed to an adeno-viral vector (AAV) delivery of nucleic acids encoding two or more immunomodulatory proteins or functional fragments thereof to a tumor.

15 Claims, 38 Drawing Sheets
Specification includes a Sequence Listing.

(56) References Cited

U.S. PATENT DOCUMENTS

| | | | |
|---|---|---|---|
| 9,840,719 B2 | 12/2017 | High et al. | |
| 10,703,797 B2* | 7/2020 | Keravala | A61P 3/00 |
| 10,787,681 B2 | 9/2020 | Wright | |
| 2003/0003583 A1 | 1/2003 | Hirsch et al. | |
| 2003/0035790 A1 | 2/2003 | Chen et al. | |
| 2003/0143212 A1 | 7/2003 | Williams et al. | |
| 2003/0147853 A1 | 8/2003 | McClelland et al. | |
| 2005/0208138 A1 | 9/2005 | Yang et al. | |
| 2006/0018880 A1 | 1/2006 | Ratliff et al. | |
| 2006/0193821 A1* | 8/2006 | Diener | A61P 29/00 424/78.37 |
| 2007/0231304 A1 | 10/2007 | Sobol et al. | |
| 2008/0038297 A1 | 2/2008 | Gupta | |
| 2009/0081131 A1 | 3/2009 | Meruelo | |
| 2009/0275107 A1 | 11/2009 | Lock et al. | |
| 2011/0002961 A1 | 1/2011 | Hermonat | |
| 2011/0212529 A1 | 9/2011 | Souza et al. | |
| 2015/0111955 A1 | 4/2015 | High et al. | |
| 2016/0089398 A1 | 3/2016 | Beech et al. | |
| 2016/0311879 A1 | 10/2016 | Sopczynski et al. | |
| 2018/0282759 A1* | 10/2018 | Hu | C12N 15/11 |
| 2019/0153469 A1 | 5/2019 | Campbell et al. | |
| 2019/0201493 A1 | 7/2019 | Becher et al. | |
| 2019/0225673 A1 | 7/2019 | Kruse et al. | |
| 2019/0365926 A1 | 12/2019 | Alexander et al. | |
| 2020/0048322 A1 | 2/2020 | Li et al. | |
| 2020/0061184 A1 | 2/2020 | Palese et al. | |
| 2020/0164008 A1 | 5/2020 | Wright et al. | |
| 2020/0239906 A1 | 7/2020 | Roeth et al. | |
| 2021/0032371 A1 | 2/2021 | Niazi et al. | |
| 2021/0032661 A1 | 2/2021 | Powell et al. | |
| 2021/0062218 A1 | 3/2021 | Campbell et al. | |
| 2021/0128710 A1 | 5/2021 | Breedlau et al. | |
| 2021/0196771 A1 | 7/2021 | Kiefer et al. | |

FOREIGN PATENT DOCUMENTS

| | | | |
|---|---|---|---|
| WO | WO-1994020517 A1 | 9/1994 | |
| WO | WO-1995031566 A1 | 11/1995 | |
| WO | WO-1996026285 A2 | 8/1996 | |
| WO | WO-1999047690 A2 | 9/1999 | |
| WO | WO-2001012234 A1 | 2/2001 | |
| WO | WO-2001091536 A2 | 12/2001 | |
| WO | WO-2001094605 A2 | 12/2001 | |
| WO | WO-2002089658 A3 | 11/2002 | |
| WO | WO-2003089011 A1 | 10/2003 | |
| WO | WO-2003089612 A3 | 10/2003 | |
| WO | WO-2004099423 A1 | 11/2004 | |
| WO | WO-2006121168 A1 | 11/2006 | |
| WO | WO-2007057368 A1 | 5/2007 | |
| WO | WO-2007126805 A2 | 11/2007 | |
| WO | WO-2008140173 A1 | 11/2008 | |
| WO | WO-2011054994 A1 | 5/2011 | |
| WO | WO-2011119773 A1 | 9/2011 | |
| WO | WO-2013053775 A1 | 4/2013 | |
| WO | WO-2013123503 A1 | 8/2013 | |
| WO | WO-2015054639 A1* | 4/2015 | A61K 39/12 |
| WO | WO-2015138616 A1* | 9/2015 | A61K 38/1787 |
| WO | WO-2015195049 A1* | 12/2015 | C12N 15/85 |
| WO | WO-2016073704 A1 | 5/2016 | |
| WO | WO-2017106795 A1 | 6/2017 | |
| WO | WO-2017201350 A1 | 11/2017 | |
| WO | WO-2018026872 A1 | 2/2018 | |
| WO | WO-2018064611 A1 | 4/2018 | |
| WO | WO-2018172961 A1* | 9/2018 | A61K 48/0058 |
| WO | WO-2018175932 A1* | 9/2018 | A61K 31/7105 |
| WO | WO-2019010219 A1 | 1/2019 | |
| WO | WO-2019123414 A1 | 6/2019 | |
| WO | WO-2020037206 A1 | 2/2020 | |
| WO | WO-2020123602 A1* | 6/2020 | A61K 41/0047 |
| WO | WO-2020160350 A1 | 8/2020 | |
| WO | WO-2021073568 A1 | 4/2021 | |
| WO | WO-2021091560 A1 | 5/2021 | |
| WO | WO-2021233849 A1 | 11/2021 | |
| WO | WO-2021239308 A1 | 12/2021 | |

OTHER PUBLICATIONS

Addgene, Adeno-associated Virus (AAV) Guide, 2019, addgene, pp. 1-4, retrieved from: https://www.addgene.org/guides/aav/#:~:text=AAV%20Serotypes,preferentially%20transducing%20specific%20cell%20types (Year: 2019).*

Shin et al., Recombinant Adeno-Associated Viral Vector Production and Purification, 2012, Methods in Molecular Biology, vol. 798, pp. 1-16 (Year: 2012).*

Hamid et al., Safety and Tumor Responses with Lambrolizumab (Anti-PD-1) in Melanoma, 2013, The New England Journal of Medicine, vol. 369, Issue 2, pp. 134-144 (Year: 2013).*

Wikipedia, CAG promoter, 2016, retrieved from: https://en.wikipedia.org/wiki/CAG_promoter (Year: 2016).*

Ahmed, S.S., et al., "Gene transfer in the liver using recombinant adeno-associated virus," *Current Protocols in Microbiology Chapter 14*:Unit14D.6, John Wiley, United States (2013), 46 pages.

Baban, C. K., et al., "Bacteria as vectors for gene therapy of cancer," *Bioengineered Bugs* 1(6):385-394, Landes Bioscience, United States (Dec. 2010).

Boshart, M., et al., "A very strong enhancer is located upstream of an immediate early gene of human cytomegalovirus," *Cell* 41(2):521-530, Cell Press, United States (Jun. 1985).

Buisseret, L., et al., "Tumor-infiltrating lymphocyte composition, organization and PD-1/ PD-L1 expression are linked in breast cancer," *Oncoimmunology* 6(1):e1257452, Taylor and Francis, United States (Dec. 2016), 13 pages.

Curiel, D. T., et al., "Gene transfer to respiratory epithelial cells via the receptor-mediated endocytosis pathway," *American Journal of Respiratory Cell and Molecular Biology* 6(3):247-252, American Thoracic Society, United States (Mar. 1992).

Di Carlo, E., et al., "The combined action of IL-15 and IL-12 gene transfer can induce tumor cell rejection without T and NK cell involvement," *Journal of Immunology* 165(6):3111-3118, American Association of Immunologists, United States (Sep. 2000).

Eisenhauer, E. A., et al., "New response evaluation criteria in solid tumours: revised RECIST guideline (version 1.1)," *European Journal of Cancer* 45(2):228-247, Elsevier, Netherlands (Jan. 2009).

Gao, G., et al., "Clades of Adeno-associated viruses are widely disseminated in human tissues," *Journal of Virology* 78(12):6381-6388, American Society For Microbiology, United States (2004).

Geisler, A., and Fechner, H., "MicroRNA-regulated viral vectors for gene therapy," *World Journal of Experimental Medicine* 6(2):37-54, Baishideng Publishing Group, United States (May 2016).

Gorman, C. M., et al., "The Rous sarcoma virus long terminal repeat is a strong promoter when introduced into a variety of eukaryotic cells by DNA-mediated transfection," *Proc Natl Acad Sci USA* 79(22):6777-6781, National Academy of Sciences, United States (Nov. 1982).

Heinzerling, L., et al., "Intratumoral injection of DNA encoding human interleukin 12 into patients with metastatic melanoma: clinical efficacy," *Human Gene Therapy* 16(1):35-48, Mary Ann Liebert Inc., United States (Jan. 2005).

Jackson, R. J., et al., "The novel mechanism of initiation of picornavirus RNA translation," *Trends in Biochemical Sciences* 15(12):477-483, Cell Press, United States (Dec. 1990).

Jackson, R. J., and Kaminski, A., "Internal initiation of translation in eukaryotes: the picornavirus paradigm and beyond," *RNA* 1(10):985-1000, Cold Spring Harbor Laboratory Press, United States (Dec. 1995).

Korman, A, J., et al., "Expression of human class II major histocompatibility complex antigens using retrovirus vectors," *Proc Natl Acad Sci USA* 84(8):2150-2154, National Academy of Sciences, United States (Apr. 1987).

Lee, S., and Margolin, K., "Cytokines in cancer immunotherapy," *Cancers* 3(4):3856-3893, MDPI, Switzerland (Oct. 2011).

(56) References Cited

OTHER PUBLICATIONS

Lee, L. R., et al., "Targeting Adeno-Associated Virus Vectors for Local Delivery to Fractures and Systemic Delivery to the Skeleton," *Mol Ther Methods Clin Dev* 15:101-111, Cell Press, United States (Sep. 2019).

Liu, Y., et al., "In situ adenoviral interleukin 12 gene transfer confers potent and long-lasting cytotoxic immunity in glioma," *Cancer Gene Therapy* 9(1): 9-15, Nature Publishing Group, United Kingdom (Jan. 2002).

Liu, Z., et al., "Systematic comparison of 2A peptides for cloning multi-genes in a polycistronic vector," *Scientific Reports* 7(1):2193, Nature Publishing Group, United Kingdom (May 2017).

Lo, C. H., et al., "Differential antitumor effect of interleukin-12 family cytokines on orthotopic hepatocellular carcinoma," *The Journal of Gene Medicine* 12(5): 423-434, John Wiley & Sons, United Kingdom (May 2010).

Lu, L., et al., "AAV2-mediated gene transfer of VEGF-Trap with potent suppression of primary breast tumor growth and spontaneous pulmonary metastases by long-term expression," *Oncology Reports* 28(4):1332-1338, Spandidos, Greece (Oct. 2012).

Maguire, C. A., et al., "Directed evolution of adeno-associated virus for glioma cell transduction," *Journal of Neurooncology* 96(3):337-347, Springer, United States (Feb. 2010).

Martinez-Campos, C., et al., "Role of TLR9 in Oncogenic Virus-Produced Cancer," *Viral Immunology* 30(2):98-105, Mary Ann Liebert Inc., United States (Mar. 2017).

Mori, S., et al., "Two novel adeno-associated viruses from cynomolgus monkey: pseudotyping characterization of capsid protein," *Virology* 330(2):375-383, Elsevier, Netherlands (Dec. 2004).

Notley, C. A., et al., "DNA methylation governs the dynamic regulation of inflammation by apoptotic cells during efferocytosis," *Scientific Reports* 7:42204, Nature Publishing Group, United Kingdom (Feb. 2017), 10 pages.

Parr, M. J., et al., "Tumor-selective transgene expression in vivo mediated by an E2F-responsive adenoviral vector," *Nature Medicine* 3(10):1145-1149, Nature Publishing Company, United Kingdom (Oct. 1997).

Pelster, M., et al., "Phase II study of ipilimumab and nivolumab (ipi/nivo) in metastatic uveal melanoma (UM)," *Journal of Clinical Oncology* 37(15_Suppl):9522, American Society of Clinical Oncology, United States (May 2019).

Putnam, D., et al., "Polymer-based gene delivery with low cytotoxicity by a unique balance of side-chain termini," *Proc Natl Acad Sci USA* 98(3):1200-1205, National Academy of Sciences, United States (Jan. 2001).

Rosenfeld, M. A., et al., "Adenovirus-mediated transfer of a recombinant alpha 1-antitrypsin gene to the lung epithelium in vivo," *Science* 252(5004):431-434, American Association for the Advancement of Science, United States (Apr. 1991).

Rosenfeld, M. A., et al., "In vivo transfer of the human cystic fibrosis transmembrane conductance regulator gene to the airway epithelium," *Cell* 68(1):143-155, Cell Press, United States (Jan. 1992).

Sato, T., et al., "Direct delivery of a cytotoxic anticancer agent into the metastatic lymph node using nano/microbubbles and ultrasound," *PLoS One* 10(4):e0123619, Public Library of Science, United States (Apr. 2015), 16 pages.

Sheppard, H. M., et al., "Recombinant adeno-associated virus serotype 6 efficiently transduces primary human melanocytes," *PLoS One* 8(4):e62753, Public Library of Science, United States (Apr. 2013), 7 pages.

Tu, S. P., et al., "Gene therapy for colon cancer by adeno-associated viral vector-mediated transfer of survivin Cys84Ala mutant," *Gastroenterology* 128(2):361-375, Elsevier, Netherlands (Feb. 2005).

Urabe, M., et al., "Scalable generation of high-titer recombinant adeno-associated virus type 5 in insect cells," *Journal of Virology* 80(4):1874-1885, American Society For Microbiology, United States (Feb. 2006).

Wasilko, D. J., et al., "The titerless infected-cells preservation and scale-up (TIPS) method for large-scale production of NO-sensitive human soluble guanylate cyclase (sGC) from insect cells infected with recombinant baculovirus," *Protein Expression and Purification* 65(2):122-132, Academic Press, United States (Jun. 2009).

Xiao, W., et al., "Route of administration determines induction of T-cell-independent humoral responses to adeno-associated virus vectors," *Molecular Therapy* 1(4):323-329, Cell Press, United States (Apr. 2000).

Xue, Z., et al., "Adeno-associated virus-mediated survivin mutant Thr34Ala cooperates with oxaliplatin to inhibit tumor growth and angiogenesis in colon cancer," *Oncology Reports* 25(4):1039-1046, Spandidos, Greece (Apr. 2011).

Yang, J., et al., "Treatment of uveal melanoma: where are we now?" *Therapeutic Advances in Medical Oncology* 10:1-17, SAGE Journals, United Kingdom (Feb. 2018).

Chiu, T., et al., "The treatment of glioblastoma multiforme through activation of microglia and TRAIL induced by rAAV2-mediated IL-12 in a syngeneic rat model," *Journal of Biomedical Science* 19:45, Biomed Central, United Kingdom (2012).

International Search Report and Written Opinion for International Application No. PCT/US2021/054871, European Patent Office, Netherlands, mailed Mar. 23, 2022, 15 pages.

Adorini, L., "Interleukin-12, a Key Cytokine in Th1-mediated Autoimmune Diseases," *Cellular and Molecular Life Sciences* 55(12):1610-1625, Springer, Switzerland (Sep. 1999).

Ahmadzadeh, M., et al., "Tumor Antigen-specific CD8 T Cells Infiltrating the Tumor Express High Levels of PD-1 and Are Functionally Impaired, " *Blood* 114(8):1537-1544, American Society of Hematology, United States (May 2009).

Algazi, A.P., et al., "Phase II Trial of IL-12 Plasmid Transfection and PD-1 Blockade in Immunologically Quiescent Melanoma," *Clinical Cancer Research* 26(12):2827-2837, The American Association for Cancer Research, United States (May 2020).

Andtbacka, R.H.I., et al., "Talimogene Laherparepvec Improves Durable Response Rate in Patients With Advanced Melanoma," Journal of Clinical Oncology 33(25):2780-2788, American Society of Clinical Oncology, United States (May 2015).

Angiolillo, A.L., et al., "Human Interferon-inducible Protein 10 is a Potent Inhibitor of Angiogenesis in Vivo," *The Journal of Experimental Medicine* 182(1):155-162, Rockefeller University Press, United States (Jul. 1995).

Aronson, S.J., et al., "A Quantitative In Vitro Potency Assay for Adeno-Associated Virus Vectors Encoding for the UGT1A1 Transgene," *Molecular Therapy Methods & Clinical Development* 18:250-258, Nature Publishing Group, United States (Jun. 2020).

Atkins, M.B., et al., "Phase I Evaluation of Intravenous Recombinant Human Interleukin 12 in Patients With Advanced Malignancies," *Clinical Cancer Research* 3(3):409-417, The American Association for Cancer Research, United States (Mar. 1997).

Atkins, M.B., et al.,"High-dose Recombinant Interleukin 2 Therapy for Patients With Metastatic Melanoma: Analysis of 270 Patients Treated Between 1985 and 1993," *Journal of Clinical Oncology* 17(7):2105-2016, American Society of Clinical Oncology, United States (Jul. 1999).

Bacon, C.M., et al.,"Interleukin 12 Induces Tyrosine Phosphorylation and Activation of STAT4 in Human Lymphocytes," *Proceedings of the National Academy of Sciences of the United States of America* 92(16):7307-7311, National Academy of Sciences, United States (Aug. 1995).

Bajetta, E., et al., "Pilot Study of Subcutaneous Recombinant Human Interleukin 12 in Metastatic Melanoma," *Clinical Cancer Research* 4(1):75-85, American Association for Cancer Research, United States (Jan. 1998).

Barrett, J.A., et al., "Regulated Intratumoral Expression of IL-12 Using a RheoSwitch Therapeutic System® (RTS®) Gene Switch as Gene Therapy for the Treatment of Glioma," *Cancer Gene Therapy* 25(5-6):106-116, Nature Publishing Group, United Kingdom (May 2018).

Bascuas, T., et al., "A Novel Non-hodgkin Lymphoma Murine Model Closer to the Standard Clinical Scenario," *Journal of Translational Medicine* 14(1):323, BioMed Central, United Kingdom (Nov. 2016).

(56) References Cited

OTHER PUBLICATIONS

Bashyam, H., "Interleukin-12: a Master Regulator," The Journal of Experimental Medicine 204(5):969, Rockefeller University Press, United States (May 2007).
Becker, C., et al., "Stepwise Regulation of TH1 Responses in Autoimmunity: IL-12-related Cytokines and Their Receptors," Inflammatory Bowel Diseases 11(8):755-764, Oxford University Press, United Kingdom (Aug. 2005).
Berraondo, P., et al., "Revisiting Interleukin-12 as a Cancer Immunotherapy Agent," Clinical Cancer Research 24(12):2716-2718 (Author Manuscript), American Association for Cancer Research, United States (May 2018).
Boehm, U., et al., "Cellular Responses to Interferon-gamma," Annual Review of Immunology 15:749-795, Annual Reviews Inc, United States (1997).
Bortolanza, S., et al., "Treatment of Pancreatic Cancer With an Oncolytic Adenovirus Expressing Interleukin-12 in Syrian Hamsters," Molecular Therapy 17(4):614-622, Cell Press, United States (Apr. 2009).
Buck, T.M and Wijnholds, J., "Recombinant Adeno-Associated Viral Vectors (rAAV)-Vector Elements in Ocular Gene Therapy Clinical Trials and Transgene Expression and Bioactivity Assays," International Journal of Molecular Sciences 21(12):4197, MDPI, Switzerland (Jun. 2020).
Burkart, C., et al., "Improving Therapeutic Efficacy of IL-12 Intratumoral Gene Electrotransfer Through Novel Plasmid Design and Modified Parameters," Gene Therapy 25(2):93-103, Nature Publishing Group, United Kingdom (Mar. 2018).
Buszello, H., et al.," Antiproliferative Effects of Four Different Cytokines on Renal Carcinoma Cell Lines," Anticancer Research, 15(3):735-738, International Institute of Anticancer Research, Greece (May-Jun. 1995).
Car, B.D., et al., "Role of Interferon-gamma in Interleukin 12-induced Pathology in Mice," The American Journal of Pathology 147(6):1693-1707, Elsevier, United States (Dec. 1995).
Car, B.D., et al., "The Toxicology of Interleukin-12: A Review," Toxicologic Pathology 27(1):58-63, Sage Publications, United States (Jan. 1999).
Chang, J., et al., "IL-12 Priming During in Vitro Antigenic Stimulation Changes Properties of CD8 T Cells and Increases Generation of Effector and Memory cell," Journal of Immunology 172(5):2818-2826, American Association of Immunologists, United States (Mar. 2004).
Chiocca, E.A., et al., "Regulatable Interleukin-12 Gene Therapy in Patients with Recurrent High-grade Glioma: Results of a Phase 1 Trial," Science Translational Medicine 11(505):eaaw5680, American Association for the Advancement of Science, United States (Aug. 2019).
Chuang, T., et al., "Electroporation-mediated IL-12 Gene Therapy in a Transplantable Canine Cancer Model," International Journal of Cancer 125(3):698-707, Wiley-Liss, United States (Mar. 2009).
Conry, R.M., et al.,"Talimogene Laherparepvec: First in Class Oncolytic Virotherapy," Human vaccines & Immunotherapeutics 14(4):839-846 (Accepted Manuscript), Taylor & Francis, United States (Feb. 2018).
Craig, D.J., et al.,"Resident Memory T Cells and Their Effect on Cancer," Vaccines 8(4):562, MDPI AG, Switzerland (Oct. 2020).
Cress, D.E., et al., "The Rheoswitch System for Inducible Up-and Down-regulation of Gene Expression," Cancer Research 66(8 Supplement):27, American Association Cancer Research, United States (Apr. 2006).
De Felipe, P., et al., "Use of the 2A Sequence From Foot-and-mouth Disease Virus in the Generation of Retroviral Vectors for Gene Therapy," Gene Therapy 6(2):198-208, Nature Publishing Group, England (Feb. 1999).
Diaz-Montero, C.M., et al., "Synergy of Brief Activation of CD8 T-cells in the Presence of IL-12 and Adoptive Transfer into Lymphopenic Hosts Promotes Tumor Clearance and Anti-tumor Memory," American Journal of Cancer Research 1(7):882-896, e-Century Pub. Corp, United States (Aug. 2011).

Dobrzanski, M.J., et al.,"Type 1 and Type 2 CD8+ Effector T cell Subpopulations Promote Long-term Tumor Immunity and Protection to Progressively Growing Tumor," Journal of Immunology 164(2):916-925, American Association of Immunologists, United States (Jan. 2000).
Dua, P., et al.,"A Tutorial on Target-Mediated Drug Disposition (TMDD) Models," CPT: Pharmacometrics & Systems Pharmacology 4(6):324-337, Wiley, United States (Jun. 2015).
Essner, R., et al.,"Contemporary Surgical Treatment of Advanced-stage Melanoma," Archives of Surgery 139(9):961-966, American Medical Association, United States (Sep. 2004).
Flotte, T.R., et al., "Phase 2 Clinical Trial of a Recombinant Adeno-associated Viral Vector Expressing A1-antitrypsin: Interim Results," Human Gene Therapy 22(10):1239-1247, Liebert, United States (Oct. 2011).
Francois, A., et al., "Accurate Titration of Infectious AAV Particles Requires Measurement of Biologically Active Vector Genomes and Suitable Controls," Molecular Therapy Methods & Clinical Development 10:223-236, Cell Press, United States (Jul. 2018).
Fuchs, S, P., et al.,"Recombinant AAV Vectors for Enhanced Expression of Authentic IgG," PloS one 11(6):e0158009, Public Library of Science, United States (Jun. 2016).
Fyfe, G., et al., "Results of Treatment of 255 Patients With Metastatic Renal Cell Carcinoma Who Received High-dose Recombinant Interleukin-2 Therapy," Journal of Clinical Oncology 13(3):688-696, American Society of Clinical Oncology, United States (Mar. 1995).
George, L.A., et al., "Hemophilia B Gene Therapy with a High-Specific-Activity Factor IX Variant," The New England Journal of Medicine 377(23):2215-2227, Massachusetts Medical Society, United States (Dec. 2017).
George, L.A., et al., "Long-Term Follow-Up of the First in Human Intravascular Delivery of AAV for Gene Transfer: AAV2-hFIX16 for Severe Hemophilia B," Molecular Therapy 28(9):2073-2082, Cell Press, United States (Sep. 2020).
Gorbatyuk, O.S., et al., "Biodistribution of Adeno-associated Virus Type 2 With Mutations in the Capsid That Contribute to Heparan Sulfate Proteoglycan Binding," Virus Research 274:197771, Elsevier Science, Netherlands (Sep. 2019).
Grishanin, R., et al., "Preclinical Evaluation of ADVM-022, a Novel Gene Therapy Approach to Treating Wet Age-Related Macular Degeneration," Molecular Therapy 27(1):118-129, Cell Press, United States (Jan. 2019).
Haines, B.B., et al.,"ONCR-177, an Oncolytic HSV-1 Designed to Potently Activate Systemic Antitumor Immunity," Cancer Immunology Research 9(3):291-308, American Association for Cancer Research, United States (Mar. 2021).
Hamid, O., et al., "Five-year Survival Outcomes for Patients With Advanced Melanoma Treated With Pembrolizumab in KEYNOTE-001," Annals of Oncology 30(4):582-588, Elsevier, United kingdom (Jan. 2019).
Han, Y., et al., "PD-1/PD-L1 pathway: Current Researches in Cancer," American Journal of Cancer Research 10(3):727-742, e-Century Pub. Corp, United States (Mar. 2020).
Hellman, H.O., et al., "ESMO TAT Virtual Congress: Preliminary Safety, Antitumour Activity and Pharmacodynamic Results of the Human Intratumoral Immunotherapy (HIT-IT) Trial of MEDI1191 (mRNA IL-12) in Patients with Advanced Solid Tumours and Superficial Lesions.," [Conference presentation] European Society for Medical Oncology (EMSO) Congress 2021, Virtual Event (Sep. 2021).
Hewitt, S.L., et al., "Intratumoral IL12 mRNA Therapy Promotes TH1 Transformation of the Tumor Microenvironment," Clinical Cancer Research 26(23):6284-6298, American Association for Cancer Research, United States (Dec. 2020).
Jacobs, L., et al., "Intratumoral DNA-based Delivery of Checkpoint-inhibiting Antibodies and Interleukin 12 Triggers T Cell Infiltration and Anti-tumor Response," Cancer Gene Therapy 29(7):984-992 (Author Manuscript), Nature Publishing Group, United Kingdom (Jul. 2022).
Jax Notes (The Jackson Laboratory). Alopecia in C57BL 6 and related mouse strains.https://www.jax.org/news-and-insights/1987/

(56) References Cited

OTHER PUBLICATIONS october/alopecia-in-c57bl-6-and-related-mousestrains#. Published Oct. 16, 1987. Accessed Nov. 13, 2023.

Kobayashi, M., et al., "Identification and Purification of Natural Killer Cell Stimulatory Factor (NKSF), a Cytokine With Multiple Biologic Effects on Human Lymphocytes," The Journal of Experimental Medicine 170(3):827-845, Rockefeller University Press, United States (Sep. 1989).

Lasek W., et al., "Interleukin 12: Still a Promising Candidate for Tumor Immunotherapy?," Cancer Immunology and Immunotherapy, 63(5):419-435, Springer Verlag, Berlin. (2014).

Lee, D. W., et al., "ASTCT Consensus Grading for Cytokine Release Syndrome and Neurologic Toxicity Associated with Immune Effector Cells," Biology of Blood and Marrow Transplantation 25(4):625-638, Carden Jennings Publishing, United States (Dec. 2018).

Leonard, J.P, et al., "Effects of Single-dose Interleukin-12 Exposure on Interleukin-12-associated Toxicity and Interferon-gamma Production," Blood 90(7):2541-2548, Elsevier, United States (Oct. 1997).

Lin, L., "Ex vivo Conditioning with IL-12 Protects Tumor-infiltrating CD8+ T Cells from Negative Regulation by Local IFN-γ," Cancer Immunology, Immunotherapy 68(3):395-405, Springer Verlag, Germany (Dec. 2018).

Little, R., et al., "Activity of Subcutaneous Interleukin-12 in AIDS-related Kaposi Sarcoma," Blood 107(12):4650-7457, Elsevier, United States (Feb. 2006).

Lo, C., et al., "Differential Antitumor Effect of Interleukin-12 Family Cytokines on Orthotopic Hepatocellular Carcinoma," The Journal of Gene Medicine 12(5):423-434, John Wiley & Sons, United Kingdom (Mar. 2010).

Loo, K., et al., "Partially Exhausted Tumor-infiltrating Lymphocytes Predict Response to Combination Immunotherapy," JCI Insight 2(14):e93433, American Society for Clinical Investigation, United States (Jul. 2017).

Lyakh, L., et al., "Regulation of interleukin-12/interleukin-23 Production and the T-helper 17 Response in Humans," Immunological Reviews 226:112-31, Wiley-Blackwell, United Kingdom (Dec. 2008).

Malo, M.E., et al., "Mechanistic Insights into Synergy between Melanin-Targeting Radioimmunotherapy and Immunotherapy in Experimental Melanoma," International Journal of Molecular Sciences 21(22):8721, MDPI, Switzerland (Nov. 2020).

Mami-Chouaib, F., et al., "Resident Memory T Cells, Critical Components in Tumor Immunology," Journal for Immunotherapy of Cancer 6(1):87, BMJ Publishing Group Ltd, United Kingdom (Sep. 2018).

Mcnab, F., et al., "Type I Interferons in Infectious Disease," Nature Reviews. Immunology 15(2):87-103, Nature Publishing Group, United Kingdom (Feb. 2015).

Mehrotra, P.T., et al., "Effects of IL-12 on the Generation of Cytotoxic Activity in Human CD8+ T Lymphocytes," Journal of Immunology 151(5):2444-5242, American Association of Immunologists, United States (Sep. 1993).

Mendell, J.R., et al., "Single-Dose Gene-Replacement Therapy for Spinal Muscular Atrophy," The New England Journal of Medicine 377(18):1713-1722, Massachusetts Medical Society, United States (Nov. 2017).

Migden, M.R., et al., "PD-1 Blockade with Cemiplimab in Advanced Cutaneous Squamous-Cell Carcinoma," The New England Journal of Medicine 379(4):341-351, Massachusetts Medical Society, United States (Jun. 2018).

Mirlekar, B and Pylayeva-Gupta, Y., "IL-12 Family Cytokines in Cancer and Immunotherapy," Cancers 13(2):167, MDPI, Switzerland (Jan. 2021).

Miyazaki, J., et al., "Expression Vector System Based on the Chicken Beta-actin Promoter Directs Efficient Production of Interleukin-5," Gene 79(2):269-77, Elsevier, Netherlands (Jul. 1989).

Motzer, R.J., et al., "Phase I Trial of Subcutaneous Recombinant Human Interleukin-12 in Patients With Advanced Renal Cell Carcinoma," Clinical Cancer Research 4(5):1183-1191, The Association, United States (May 1998).

Mukhopadhyay, A., et al., "Characterization of Abscopal Effects of Intratumoral Electroporation-mediated IL-12 Gene Therapy," Gene Therapy 26(1-2):1-15, Nature Publishing Group, United Kingdom (Oct. 2018).

Munoz, N.M., et al., "Influence of Injection Technique, Drug Formulation and Tumor Microenvironment on Intratumoral Immunotherapy Delivery and Efficacy," Journal for Immunotherapy of Cancer 9(2):e001800, BMJ Publishing Group Ltd, United Kingdom (Feb. 2021).

Naso, M.F., et al., "Adeno-Associated Virus (AAV) as a Vector for Gene Therapy," BioDrugs 31(4):317-334, Springer International, New Zealand (Jul. 2017).

Nguyen, K.G., et al., "Localized Interleukin-12 for Cancer Immunotherapy," Frontiers in Immunology 11:575597, Frontiers Research Foundation, Switzerland (Oct. 2020).

Ohaegbulam, K.C., et al., "Human Cancer Immunotherapy with Antibodies to the PD-1 and PD-L1 Pathway," Trends in Molecular Medicine 21(1):24-33, Elsevier Science Ltd, United Kingdom (Jan. 2015).

Ohs, I., et al., "Restoration of Natural Killer Cell Anti-metastatic Activity by IL-12 and Checkpoint Blockade," Cancer Research 77(24):7059-7071 (Author Manuscript), American Association for Cancer Research, United States (Oct. 2017).

Oncorus, Inc. SEC Filing, Form S-1. https://www.sec.gov/Archives/edgar/data/1671818/000119312520244199/d818914ds1.htm. Filed Sep. 11, 2020. Accessed Jan. 27, 2022.

Orange, J.S., et al., "Mechanism of Interleukin 12-mediated Toxicities During Experimental Viral Infections: Role of Tumor Necrosis Factor and Glucocorticoids," The Journal of Experimental Medicine 181(3):901-914, Rockefeller University Press, United States (Mar. 1995).

Parra-Guillen, Z.P., et al., "Target-mediated Disposition Model Describing the Dynamics of IL 12 and IFNγ After Administration of a Mifepristone-inducible Adenoviral Vector for IL-12 Expression in Mice," The AAPS Journal 15(1):183-194, American Association of Pharmaceutical Scientists, United States (Nov. 2012).

Pasi, K.J., et al., "Multiyear Follow-up of AAV5-hFVIII-SQ Gene Therapy for Hemophilia A," The New England Journal of Medicine 382(1):29-40, Massachusetts Medical Society, United States (Jan. 2020).

Pasquet, L., et al., "Pre-clinical Investigation of the Synergy Effect of Interleukin-12 Gene-electro-transfer During Partially Irreversible Electropermeabilization Against Melanoma," BMJ Publishing Group Ltd, United Kingdom (Jun. 2019).

Patel, D.M., et al., "Design of a Phase I Clinical Trial to Evaluate M032, a Genetically Engineered HSV-1 Expressing IL-12, in Patients With Recurrent/progressive Glioblastoma Multiforme, Anaplastic Astrocytoma, or Gliosarcoma," Human Gene Therapy Clinical Development 27(2):69-78, Mary Ann Liebert Inc., United States (May 2016).

Pavlin, D., et al., "Local and Systemic Antitumor Effect of Intratumoral and Peritumoral IL-12 Electrogene Therapy on Murine Sarcoma," Cancer Biology & Therapy 8(22):2114-2122, Taylor & Francis, United States (Nov. 2009).

Portielje, J.E.A., et al., "Repeated Administrations of Interleukin (IL)-12 are Associated with Persistently Elevated Plasma Levels of IL-10 and Declining IFN-gamma, Tumor Necrosis Factor-alpha, IL-6, and IL-8 Responses," Clinical Cancer Research 9(1):76-83, The Association, United States (Jan. 2003).

Puca, E., et al., "The Antibody-based Delivery of Interleukin-12 to Solid Tumors Boosts NK and CD8+ T Cell Activity and Synergizes With Immune Checkpoint Inhibitors," International Journal of Cancer 146(9):2518-2530, Wiley-Liss, United States (Aug. 2019).

Rabinowitz, J.E., et al., "Cross-packaging of a Single Adeno-associated Virus (AAV) Type 2 Vector Genome into Multiple AAV Serotypes Enables Transduction with Broad Specificity," Journal of Virology 76(2):791-801, American Society For Microbiology, United States (Jan. 2002).

(56) References Cited

OTHER PUBLICATIONS

Rangarajan, S., et al., "AAV5-Factor VIII Gene Transfer in Severe Hemophilia A," The New England Journal of Medicine 377(26):2519-2530, Massachusetts Medical Society, United States (Dec. 2017).

Rosmalen, M.V., et al., "Tuning the Flexibility of Glycine-serine Linkers to Allow Rational Design of Multidomain Proteins," Biochemistry 56(50):6565-6574, American Chemical Society, United States (Nov. 2017).

Roth, J.C., et al., "Evaluation of the Safety and Biodistribution of M032, an Attenuated Herpes Simplex Virus Type 1 Expressing hIL-12, after Intracerebral Administration to Aotus Nonhuman Primates," Human Gene Therapy Clinical Development 25(1):16-27, Mary Ann Liebert Inc, United States (Feb. 2014).

Rubinstein, M.P., et al., "Ex Vivo Interleukin-12-priming During CD8(+) T Cell Activation Dramatically Improves Adoptive T Cell Transfer Antitumor Efficacy in a Lymphodepleted Host," Journal of the American College of Surgeons 214(4):700-707, Lippincott Williams & Wilkins, Inc, United States (Apr. 2012).

Rubinstein, M.P., et al., "Interleukin-12 Enhances the Function and Anti-tumor Activity in Murine and Human CD8(+) T cells," Cancer Immunology Immunotherapy 64(5):539-549, Springer Verlag, Germany (Feb. 2015).

Rudman, S.M., et al., "A Phase 1 Study of AS1409, a Novel Antibody-cytokine Fusion Protein, in Patients With Malignant Melanoma or Renal Cell Carcinoma," Clinical Cancer Research 17(7):1998-2005, The Association, United States (Mar. 2011).

Russell, S., et al., "Efficacy and Safety of Voretigene Neparvovec (AA V2-hRPE65v2) in Patients with RPE65-mediated Inherited Retinal Dystrophy: a Randomised, Controlled, Open-label, Phase 3 Trial," Lancet 390(10097):849-860, Elsevier, United Kingdom (Aug. 2017).

Sad, S., et al., "Cytokine-induced Differentiation of Precursor Mouse CD8+ T Cells into Cytotoxic CD8+ T Cells Secreting Th1 or Th2 Cytokines," Immunity 2(3):271-279, Cell Press, United States (Mar. 1995).

Sangro, B., et al., "Phase I Trial of Intratumoral Injection of an Adenovirus Encoding Interleukin-12 for Advanced Digestive Tumors," Journal of Clinical Oncology 22(8):1389-1397, American Society of Clinical Oncology, United States (Apr. 2004).

Santomasso, B.D., et al., "Management of Immune-Related Adverse Events in Patients Treated With Chimeric Antigen Receptor T-Cell Therapy: ASCO Guideline," Journal of Clinical Oncology 39(35):3978-3992, American Society of Clinical Oncology, United States (Nov. 2021).

Schoenhaut, D.S., et al., "Cloning and expression of murine IL-12," Journal of Immunology 148(11):3433-3440, American Association of Immunologists, United States (Jun. 1992).

Sgadari, C., et al., "Inhibition of Angiogenesis by Interleukin-12 is Mediated by the Interferon-inducible Protein 10," Blood 87(9):3877-3882, Elsevier, United States (May 1996).

Sharpe, A.H., et al., "The Function of Programmed Cell Death 1 and Its Ligands in Regulating Autoimmunity and Infection," Nature Immunology 8(3):239-245, Nature America Inc., United States (Mar. 2007).

Sheth, R.A., et al., "Assessment of Image-Guided Intratumoral Delivery of Immunotherapeutics in Patients With Cancer," JAMA Network Open 3(7):e207911, American Medical Association, United States (Jul. 2020).

Smith, S.G., et al., "Intravesical Chitosan/interleukin-12 Immunotherapy Induces Tumor-specific Systemic Immunity Against Murine Bladder Cancer," Cancer Immunology Immunotherapy 64(6):689-696, Springer Verlag, Germany (Mar. 2015).

Srivastava, A., "In Vivo Tissue-tropism of Adeno-associated Viral Vectors," Current Opinion in Virology 21:75-80, Elsevier, Netherlands (Sep. 2016).

Starbeck-Miller, G.R., et al., "IL-12 and type I Interferon Prolong the Division of Activated CD8 T Cells by Maintaining High-affinity IL-2 Signaling in Vivo," The Journal of Experimental Medicine 211(1):105-120, Rockefeller University Press, United States (Dec. 2013).

Steding, C.E., et al., "The Role of Interleukin-12 on Modulating Myeloid-derived Suppressor Cells, Increasing Overall Survival and Reducing Metastasis," Immunology 133(2):221-238, Blackwell Scientific Publications, United Kingdom (Jun. 2011).

Stern, A.S., et al., "Purification to Homogeneity and Partial Characterization of Cytotoxic Lymphocyte Maturation Factor From Human B-lymphoblastoid Cells," Proceedings of the National Academy of Sciences of the United States of America 87(17):6808-6812, National Academy of Sciences, United States (Sep. 1990).

Sypek, J.P., et al., "Resolution of Cutaneous Leishmaniasis: Interleukin 12 Initiates a Protective T Helper Type 1 Immune Response," The Journal of Experimental Medicine 177(6):1797-1802, Rockefeller University Press, United States (Jun. 1993).

Telli, M.L., et al., "Intratumoral Plasmid IL 12 Expands CD8+ T Cells and Induces a CXCR3 Gene Signature in Triple-negative Breast Tumors That Sensitizes Patients to Anti-PD-1 Therapy," Clinical Cancer Research 27(9):2481-2493 (Author Manuscript), AmericanAssociation for Cancer Research, United States (May 2021).

Tian, S., et al., "FurinDB: a Database of 20-residue Furin Cleavage Site Motifs, Substrates and Their Associated Drugs," International Journal of Molecular Sciences 12(2):1060-1065, MDPI, Switzerland (Feb. 2011).

Tsokas, K., et al., "Reducing Risks and Delays in the Translation of Cell and Gene Therapy Innovations Into Regulated Products," NAM perspectives, National Academy of Medicine, United States (Sep. 2019).

Ullrich, K.A., et al., "Immunology of IL-12: an Update on Functional Activities and Implications for Disease," EXCLI Journal 19:1563-1589, University of Mainz, Germany (Dec. 2020).

Veinalde, R., et al., "Oncolytic Measles Virus Encoding Interleukin-12 Mediates Potent Antitumor Effects Through T Cell Activation," Oncoimmunology 6(4):e1285992, Taylor & Francis, United States (Jan. 2017).

Vo, J.L., et al., "Neoadjuvant Immunotherapy With Chitosan and Interleukin-12 to Control Breast Cancer Metastasis," Oncoimmunology 3(12):e968001, Taylor & Francis, United States (Dec. 2014).

Voest, E.E., et al., "Inhibition of Angiogenesis in Vivo by Interleukin 12," Journal of the National Cancer Institute 87(8):581-586, Oxford University Press, United States (Apr. 1995).

Wall, L., et al., "IFN-gamma Induces Apoptosis in Ovarian Cancer Cells in Vivo and in Vitro," Clinical Cancer Research 9(7):2487-2496, The Association, United States (Jul. 2003).

Wang, P., et al., "Re-designing Interleukin-12 to Enhance Its Safety and Potential as an Anti-tumor Immunotherapeutic Agent," Nature Communications 8(1):1395, Nature Publishing Group, United Kingdom (Nov. 2017).

Watkins, S.K., et al., "IL-12 Rapidly Alters the Functional Profile of Tumor-associated and Tumor-infiltrating Macrophages in Vitro and in Vivo," Journal of Immunology 178(3):1357-1362, American Association of Immunologists, United States (Feb. 2007).

Weiss, G.R., et al., "Phase 1 Study of the Intravesical Administration of Recombinant Human Interleukin-12 in Patients With Recurrent Superficial Transitional Cell Carcinoma of the Bladder," Journal of Immunotherapy 26(4):343-348, Lippincott Williams & Wilkins, United States (2003).

Winkler, M., et al., "Viral Clearance in a Downstream AAV Process: Case Study Using a Model Virus Panel and a Noninfectious Surrogate," BioProcess International 19(4):38-45, PJB Publications Ltd., United States (Apr. 2021).

Wu, C., et al., "Combination of Radiation and Interleukin 12 Eradicates Large Orthotopic Hepatocellular Carcinoma Through Immunomodulation of Tumor Microenvironment," Oncoimmunology 7(9):e1477459, Taylor & Francis, United States (Jul. 2018).

Yamashita, Y.I., et al., "Electroporation-mediated Interleukin-12 Gene Therapy for Hepatocellular Carcinoma in the Mice Model," Cancer Research 61(3):1005-1012, American Association for Cancer Research, United States (Feb. 2001).

Younes, A., et al., "Phase II Clinical Trial of Interleukin-12 in Patients With Relapsed and Refractory non-Hodgkin's Lymphoma and Hodgkin's Disease," Clinical Cancer Research 10(16):5432-5438, American Association for Cancer Research, United States (Aug. 2004).

(56) References Cited

OTHER PUBLICATIONS

Yu, J.X., et al., "Trends in Clinical Development for PD-1/PD-L1 Inhibitors," Nature reviews. Drug discovery 19(3):163-164, Nature Publishing Group, United Kingdom (Mar. 2020).

Yu, Y., et al., "Adoptive Transfer of Tc1 or Tc17 Cells Elicits Antitumor Immunity Against Established Melanoma Through Distinct Mechanisms," Journal of Immunology 190(4):1873-1881, American Association of Immunologists, United States (Jan. 2013).

Zen, Z., "Infectious Titer Assay for Adeno-associated Virus Vectors With Sensitivity Sufficient to Detect Single Infectious Events," Human Gene Therapy 15(7):709-715, M.A. Liebert, United States (Jul. 2004).

Zhao, J., et al., "Differential Effects of IL-12 on Tregs and non-Treg T Cells: Roles of IFN-γ, IL-2 and IL-2R," PloS one 7(9):e46241, Public Library of Science, United States (Sep. 2012).

Zou, J., et al., "Differential Associations Between the Cytoplasmic Regions of the Interleukin-12 Receptor Subunits Beta1 and Beta2 and JAK Kinases," The Journal of Biological Chemistry 272(9):6073-6077, Elsevier Inc. on behalf of American Society for Biochemistry and Molecular Biology, United States (Feb. 1997).

Zou, J.J., et al., "Structure-function Analysis of the P35 Subunit of Mouse Interleukin 12," The Journal of Biological Chemistry 270(11):5864-5871, Elsevier Inc. on behalf of American Society for Biochemistry and Molecular Biology, United States (Mar. 1995).

Schultz, J., et al., "Induction of long-lasting cytokine effect by injection of IL-12 encoding plasmid DNA," Cancer Gene Ther 7(12):1557-1565, Nature Publishing Group, United Kingdom (Dec. 2000).

* cited by examiner

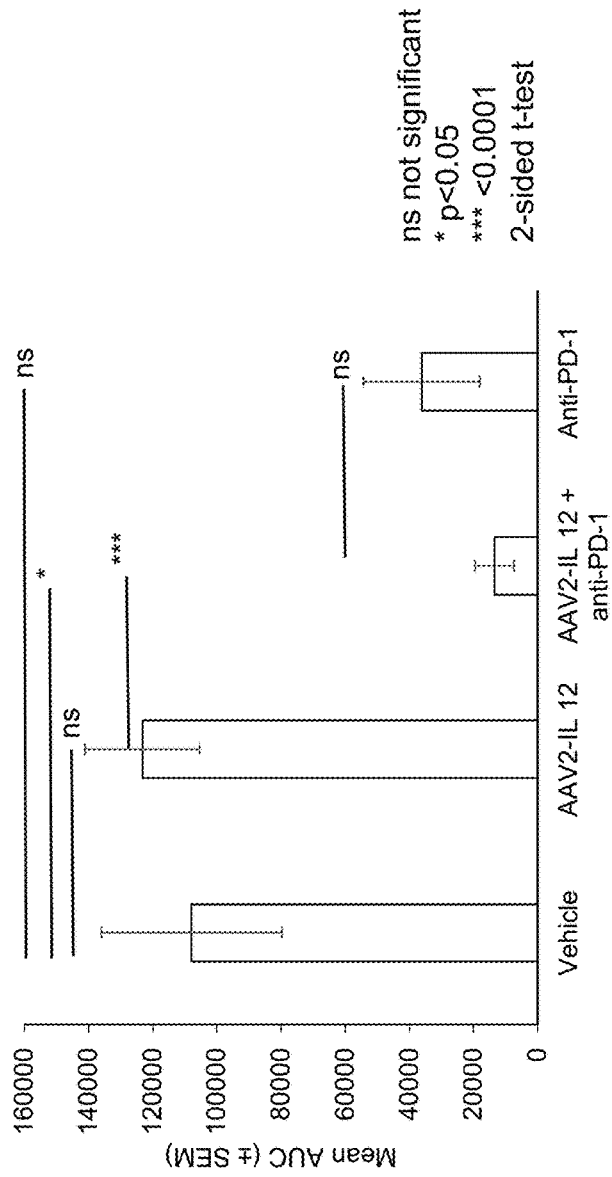
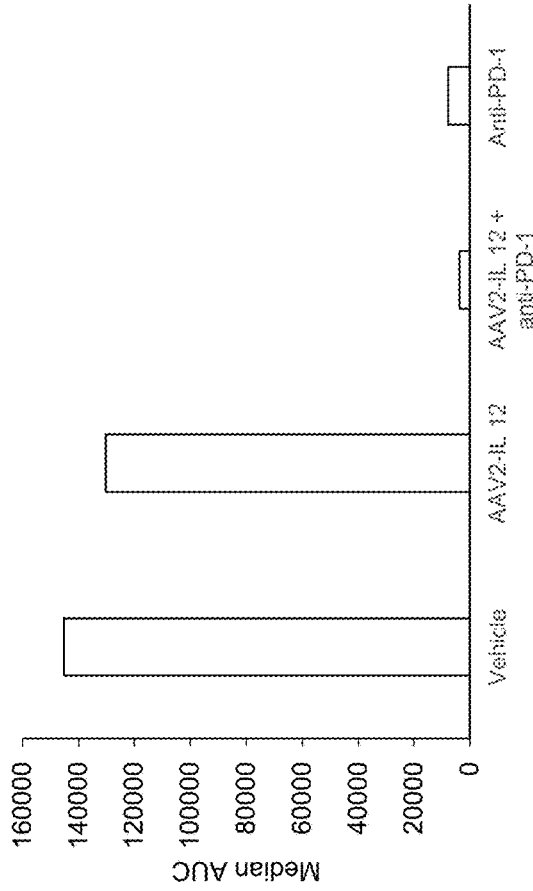
FIG. 8A
FIG. 8B

VIRAL VECTOR CONSTRUCTS FOR DELIVERY OF NUCLEIC ACIDS ENCODING CYTOKINES AND USES THEREOF FOR TREATING CANCER

CROSS REFERENCE TO RELATED APPLICATIONS

The present application claims the priority benefit of U.S. Provisional Application No. 63/182,632, filed Apr. 30, 2021; U.S. Provisional Application No. 63/141,921, filed Jan. 26, 2021; U.S. Provisional Application No. 63/108,838, filed Nov. 2, 2020; and U.S. Provisional Application No. 63/091,270, filed Oct. 13, 2020, each of which is hereby incorporated by reference in its entirety.

REFERENCE TO SEQUENCE LISTING SUBMITTED ELECTRONICALLY VIA EFS-WEB

The content of the electronically submitted sequence listing in ASCII text file (Name: 4525_0320005_Seqlisting_ST25.txt; Size: 254,500 bytes; and Date of Creation: Oct. 9, 2023), filed with the application, is incorporated herein by reference in its entirety.

FIELD OF DISCLOSURE

The present disclosure pertains to the medical field including oncology and gene therapy. Certain aspects of the disclosure relate to compositions and methods for expressing immunomodulatory proteins (e.g., cytokines) or functional fragments thereof and uses thereof.

BACKGROUND

Cytokines participate in regulation of the immune system. When used in cancer therapy, cytokines can act as immunomodulatory agents that have anti-tumor effects and can increase the immune response towards different types of tumors. However, rapid blood clearance and lack of tumor specificity require systemic administration of high doses of a cytokine in order to achieve a concentration of the cytokine at the tumor site and/or other relevant tissues (e.g., lymph nodes and spleen) sufficient to activate an immune response or have an antitumor effect. However, high levels of systemic cytokine can lead to severe toxicity and adverse reactions clinically.

BRIEF SUMMARY

In some aspects, provided herein are compositions (e.g., gene therapy compositions) and methods comprising a combination of (a) a viral vector (e.g., AAV capsid) comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 or PDL-1 inhibitor). In some aspects, the viral vector (e.g., AAV capsid comprising a polynucleotide, also referred to herein as an AAV particle) and the checkpoint inhibitor are delivered in combination (e.g., simultaneously or sequentially). In some aspects, the viral vector (e.g., AAV particle) described herein can be administered prior to, at the same time, or after the administration of a checkpoint inhibitor. In some aspects, the polynucleotide comprises: (i) a first nucleic acid encoding a first cytokine subunit or functional fragment thereof; and (ii) a second nucleic acid encoding a second cytokine subunit or functional fragment thereof. In some aspects, the first nucleic acid comprises a nucleic acid encoding an IL-12 p35 subunit and/or a nucleic acid encoding an IL-12 p40 subunit. In some aspects, the second nucleic acid comprises a nucleic acid encoding an IL-12 p35 subunit and/or a nucleic acid encoding an IL-12 p40 subunit.

In some aspects, the first nucleic acid encodes a polypeptide having at least 85%, 90%, 95%, 96%, 97%, 98%, 99%, or 100% identity to the amino acid sequence of any of SEQ ID NO: 80 or 81, or any amino acid sequence in Table 3. In some aspects, the nucleic acid encoding the first nucleic acid (e.g., a nucleic acid encoding an IL-12 p35 subunit and/or a nucleic acid encoding an IL-12 p40 subunit) does not include an in-frame stop codon (e.g., TGA, TAG, and TAA). In some aspects, the first nucleic acid and/or the second nucleic acid comprises a nucleic acid sequence having at least 85%, 90%, 95%, 96%, 97%, 98%, 99%, or 100% identity to any of SEQ ID NO: 5-10, 77, 92, or any nucleic acid sequence in Table 2. In some aspects, the first nucleic acid and/or the second nucleic acid comprises a nucleic acid sequence having at least 85%, 90%, 95%, 96%, 97%, 98%, 99%, or 100% identity to a reverse complement of any of SEQ ID NO: 5-10, 77, 92, or any nucleic acid sequence in Table 2. In some aspects, the first nucleic acid comprises a nucleic acid sequence having at least 95%, 96%, 97%, 98%, 99%, or 100% identity to SEQ ID NO: 77, and the second nucleic acid comprises a nucleic acid sequence having at least 95%, 96%, 97%, 98%, 99%, or 100% identity to SEQ ID NO: 8.

In some aspects, provided herein are compositions and methods comprising one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof. In some aspects, each delivery vector (e.g., viral vector) comprises a polynucleotide comprising the first nucleic acid and the second nucleic acid. In some aspects, each delivery vector (e.g., viral vector) comprises either the first nucleic acid or the second nucleic acid, wherein two or more delivery vectors are delivered in combination (e.g., simultaneously or sequentially). In some aspects, the delivery vector comprises constructs comprising nucleic acids encoding a first immunomodulatory protein and the subunits of a second immunomodulatory protein.

In some aspects, a delivery vector (e.g., viral vector) for delivery of (i) a first nucleic acid encoding a first immunomodulatory protein, one or more subunits thereof, or functional fragment thereof and/or (ii) a second nucleic acid encoding a second immunomodulatory protein, one or more subunits thereof, or functional fragment thereof is administered in combination with a checkpoint inhibitor. In some aspects, the delivery vector described herein can be administered prior to, at the same time, or after the administration of a checkpoint inhibitor. In some aspects, the viral vector comprises constructs comprising nucleic acids encoding a first immunomodulatory protein and the subunits of a second immunomodulatory protein.

In some aspects, two or more delivery vectors (e.g., viral vectors) described herein are delivered in combination (e.g., simultaneously or sequentially) and further in combination with a checkpoint inhibitor. In some aspects, the two or more delivery vectors described herein can be administered prior to, at the same time, or after the administration of a checkpoint inhibitor.

In some aspects, provided herein is a composition comprising: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector).

In some aspects, provided herein is a polynucleotide comprising: (a) a first nucleic acid encoding a first cytokine, one or more subunits thereof, or functional fragment thereof; and (b) a second nucleic acid encoding a second cytokine, one or more subunits thereof, or functional fragment thereof.

In some aspects, the first immunomodulatory protein or functional fragment thereof and/or the second immunomodulatory protein or functional fragment thereof is a cytokine or functional fragment thereof.

In some aspects, the cytokine (e.g., the first cytokine and/or the second cytokine) is selected from the group consisting of tumor necrosis factor alpha (TNF-α), a type I interferon (INF), a type II IFN, interleukin (IL)-2, IL-12, IL-15, IL-21, IL-23, IL-27, IL-18, IL-1, IL-3, IL-4, IL-5, IL-6, IL-7, IL-8, IL-9, IL-10, IL17, IL33, TL1A, CD40L, granulocyte-macrophage colony-stimulating factor (GM-CSF), any functional fragment thereof, and any combination thereof.

In some aspects, the first immunomodulatory and the second immunomodulatory proteins are cytokines.

In some aspects, the first immunomodulatory protein (e.g., the cytokine) is IL-12 or a functional fragment thereof. In some aspects, the first nucleic acid comprises an IL-12 p35 gene and/or an IL-12 p40 gene. In some aspects, the first immunomodulatory protein (e.g., the cytokine) is IL-12 or a functional fragment thereof. In some aspects, the first nucleic acid comprises a nucleic acid encoding an IL-12 p35 subunit and/or a nucleic acid encoding an IL-12 p40 subunit. In some aspects, the first nucleic acid encodes a polypeptide having at least 85%, 90%, 95%, 96%, 97%, 98%, 99%, or 100% identity to the amino acid sequence of any of SEQ ID NO: 80 or 81, or any amino acid sequence in Table 3. In some aspects, the nucleic acid encoding the first nucleic acid (e.g., a nucleic acid encoding an IL-12 p35 subunit and/or a nucleic acid encoding an IL-12 p40 subunit) does not include an in-frame stop codon (e.g., TGA, TAG, and TAA). In some aspects, the first nucleic acid comprises a nucleic acid sequence having at least 85%, 90%, 95%, 96%, 97%, 98%, 99%, or 100% identity to any of SEQ ID NO: 5-10, 77, or any nucleic acid sequence in Table 2. In some aspects, the first nucleic acid comprises a nucleic acid sequence having at least 85%, 90%, 95%, 96%, 97%, 98%, 99%, or 100% identity to a reverse complement of any of SEQ ID NO: 5-10, 77, 92, or any nucleic acid sequence in Table 2.

In some aspects, the second immunomodulatory protein (e.g., the cytokine) comprises IL-15 or a functional fragment thereof. In some aspects, the second nucleic acid comprises an IL-15 gene. In some aspects, the second nucleic acid comprises a nucleic acid sequence having at least 85%, 90%, 95%, 96%, 97%, 98%, 99%, or 100% identity to any of SEQ ID NO: 11-13, 58, or any nucleic acid sequence in Table 4. In some aspects, the second nucleic acid comprises a nucleic acid sequence having at least 85%, 90%, 95%, 96%, 97%, 98%, 99%, or 100% identity to a reverse complement of any of SEQ ID NO: 11-13, 58, or any nucleic acid sequence in Table 4.

In some aspects, provided herein are compositions and methods comprising one or more delivery vectors (e.g., viral vectors) for delivery of one or more polynucleotides encoding the combination of IL-12, one or more subunits thereof, or a functional fragment thereof and IL-15 or a functional fragment thereof. In some aspects, a delivery vector (e.g., a viral vector, a non-viral vectors, a plasmid, a lipid, protein particle, a bacterial vector, a lysosome, a virus-like particle, a polymeric particle, an exosome, or a vault particle). In some aspects, each delivery vector is an AAV capsid (e.g., an AAV2 capsid) which comprises a polynucleotide encoding IL-12, one or more subunits thereof, or a functional fragment thereof and a polynucleotide encoding IL-15 or a functional fragment thereof.

In some aspects, each delivery vector is an AAV capsid (e.g., an AAV2 capsid) comprising either a polynucleotide encoding IL-12, one or more subunits thereof, or a functional fragment thereof or a polynucleotide encoding IL-15 or a functional fragment thereof, wherein two or more of the AAV capsids are delivered in combination (e.g., simultaneously or sequentially), e.g., intratumorally, intravenously, intrasplenically, intrathecally, intrahepatically, via intraosseous infusion, intradermal, intraparenchymal, via delivery to salivary gland, or via delivery into a lymph node. In some aspects, the AAV capsid (e.g., an AAV2 capsid) comprising a polynucleotide encoding IL-12, one or more subunits thereof, or a functional fragment thereof is administered intratumorally.

In some aspects, provided herein are compositions and methods comprising one or more delivery vectors (e.g., viral vectors) for delivery of one or more polynucleotides encoding the combination of IL-18 or a functional fragment thereof and IL-15 or a functional fragment thereof. In some aspects, each delivery vector is an AAV capsid (e.g., an AAV2 capsid) which comprises a polynucleotide encoding IL-18 or a functional fragment thereof and a polynucleotide encoding IL-15 or a functional fragment thereof. In some aspects, each delivery vector is an AAV capsid (e.g., an AAV2 capsid) comprising either a polynucleotide encoding IL-18 or a functional fragment thereof or a polynucleotide encoding IL-15 or a functional fragment thereof, wherein two or more of the AAV capsids are delivered in combination (e.g., simultaneously or sequentially), e.g., intratumorally, intrasplenically, intrathecally, intrahepatically, via intraosseous infusion, intradermal, intraparenchymal, via delivery to salivary gland, or via delivery into a lymph node. In some aspects, the AAV capsid (e.g., an AAV2 capsid) comprising a polynucleotide encoding IL-18 or a functional fragment thereof or a polynucleotide encoding IL-15 or a functional fragment thereof is administered intratumorally.

In some aspects, provided herein are compositions and methods comprising one or more delivery vectors (e.g., viral vectors) for delivery of one or more polynucleotides encoding the combination of IL-12, one or more subunits thereof, or a functional fragment thereof and IL-2 or a functional fragment thereof. In some aspects, each delivery vector is an AAV capsid (e.g., an AAV2 capsid) which comprises a polynucleotide encoding IL-12, one or more subunits thereof, or a functional fragment thereof and a polynucleotide encoding IL-2 or a functional fragment thereof. In some aspects, each delivery vector is an AAV capsid (e.g., an AAV2 capsid) comprising either a polynucleotide encoding IL-12, one or more subunits thereof, or a functional fragment thereof or a polynucleotide encoding IL-2 or a functional fragment thereof, wherein two or more of the AAV capsids are delivered in combination (e.g., simultaneously or sequentially), e.g., intratumorally, intravenously, intrasplenically, intrathecally, intrahepatically, via intraosseous infusion, intradermal, intraparenchymal, via delivery to salivary gland, or via delivery into a lymph node. In some aspects, the AAV capsid (e.g., an AAV2 capsid) comprising a polynucleotide encoding IL-12 or a functional fragment thereof or a polynucleotide encoding IL-2 or a functional fragment thereof is administered intratumorally.

In some aspects, provided herein are compositions and methods comprising one or more delivery vectors (e.g., viral vectors) for delivery of one or more polynucleotides encoding the combination of IL-18 or a functional fragment thereof and IL-2 or a functional fragment thereof. In some aspects, each delivery vector is an AAV capsid (e.g., an AAV2 capsid) which comprises a polynucleotide encoding IL-18 or a functional fragment thereof and a polynucleotide encoding IL-2 or a functional fragment thereof. In some aspects, each delivery vector is an AAV capsid (e.g., an AAV2 capsid) comprising either a polynucleotide encoding IL-18 or a functional fragment thereof or a polynucleotide encoding IL-2 or a functional fragment thereof, wherein two or more of the AAV capsids are delivered in combination (e.g., simultaneously or sequentially), e.g., intratumorally, intravenously, intrasplenically, intrathecally, intrahepatically, via intraosseous infusion, intradermal, intraparenchymal, via delivery to salivary gland, or via delivery into a lymph node. In some aspects, the AAV capsid (e.g., an AAV2 capsid) comprising a polynucleotide encoding IL-18 or a functional fragment thereof or a polynucleotide encoding IL-2 or a functional fragment thereof is administered intratumorally.

In some aspects, provided herein are compositions and methods comprising one or more delivery vectors (e.g., viral vectors) for delivery of one or more polynucleotides encoding the combination of IL-21 or a functional fragment thereof and IL-15 or a functional fragment thereof. In some aspects, each delivery vector is an AAV capsid (e.g., an AAV2 capsid) which comprises a polynucleotide encoding IL-21 or a functional fragment thereof and a polynucleotide encoding IL-15 or a functional fragment thereof. In some aspects, each delivery vector is an AAV capsid (e.g., an AAV2 capsid) comprising either a polynucleotide encoding IL-21 or a functional fragment thereof or a polynucleotide encoding IL-15 or a functional fragment thereof, wherein two or more of the AAV capsids are delivered in combination (e.g., simultaneously or sequentially), e.g., intratumorally, intravenously, intrasplenically, intrathecally, intrahepatically, via intraosseous infusion, intradermal, intraparenchymal, via delivery to salivary gland, or via delivery into a lymph node. In some aspects, the AAV capsid (e.g., an AAV2 capsid) comprising a polynucleotide encoding IL-21 or a functional fragment thereof or a polynucleotide encoding IL-15 or a functional fragment thereof is administered intratumorally.

In some aspects, the first immunomodulatory protein or functional fragment thereof or the second immunomodulatory protein or functional fragment thereof is a soluble natural killer (NK), B-cell, T-cell, neutrophil and/or macrophage ligand.

In some aspects, the first immunomodulatory protein or functional fragment thereof or the second immunomodulatory protein or functional fragment thereof is selected from the group consisting of soluble CD40 ligand (CD40L), CD19 ligand (CD19L), CD48 ligand (CD48L), CD20 ligand (CD20L), any functional fragment thereof, and any combination thereof.

In some aspects, the polynucleotides disclosed herein further comprise a promoter.

In some aspects, the promoter comprises a first promoter which is operably linked to the first nucleic acid.

In some aspects, the promoter comprises a second promoter which is operably linked to the second nucleic acid.

In some aspects, the promoter is a constitutively active promoter, a cell-type specific promoter, or an inducible promoter.

In some aspects, the promoter comprises a CBA promoter, a CMV promoter, an EF-1a (Elongation Factor 1a) promoter, aRSV (Rous Sarcoma Virus) promoter, an Ubiquitin (UbC) promoter, or any combination thereof.

In some aspects, the polynucleotides disclosed herein further comprise an internal ribosomal entry site (IRES) sequence, a furin cleavage sequence, a 2A self-processing peptide sequence (including an F2A, E2A, P2A or T2A self-processing peptide), or a combination thereof. In some aspects, the polynucleotide comprises a furin cleavage sequence and a 2A self-processing peptide sequence (e.g., F2A).

In some aspects, the polynucleotides disclosed herein further comprise an enhancer sequence, an intron sequence, or a combination thereof.

In some aspects, the polynucleotides disclosed herein further comprises a poly(A) (pA) sequence (e.g., a growth hormome pA).

In some aspects, the polynucleotide of the disclosure comprises a promoter operably linked to an IL-12 p35 gene or functional fragment thereof (e.g., corresponding to SEQ ID NO: 77), a furin cleavage sequence and/or a 2A self-processing peptide sequence (including an F2A, E2A, P2A or T2A self-processing peptide), and an IL-12 p40 gene or a functional fragment thereof (e.g., corresponding to SEQ ID NO: 8); and a pA sequence (e.g., a growth hormone pA).

In some aspects, the first nucleic acid comprises a promoter operably linked to an IL-12 p35 gene or functional fragment thereof, an IRES sequence, and an IL-15 gene or a functional fragment thereof; and the second nucleic acid comprises a promoter operably linked to an IL-12 p40 gene or functional fragment thereof. In some aspects, the first nucleic acid comprises a promoter operably linked to a nucleic acid encoding an IL-12 p35 subunit or functional fragment thereof, an IRES sequence, and an IL-15 gene or a functional fragment thereof; and the second nucleic acid comprises a promoter operably linked to a nucleic acid encoding an IL-12 p40 subunit or functional fragment thereof.

In some aspects, the first nucleic acid comprises a promoter operably linked to an IL-12 p35 gene or functional fragment thereof, a furin cleavage sequence and/or a 2A self-processing peptide sequence (including an F2A, E2A, P2A or T2A self-processing peptide), and an IL-12 p40 gene or a functional fragment thereof; and the second nucleic acid comprises a promoter operably linked to an IL-15 gene or functional fragment thereof. In some aspects, the first nucleic acid comprises a promoter operably linked to a nucleic acid encoding an IL-12 p35 subunit or functional fragment thereof, a furin cleavage sequence and/or a 2A self-processing peptide sequence (including an F2A, E2A, P2A or T2A self-processing peptide), and a nucleic acid encoding an IL-12 p40 subunit or a functional fragment thereof; and the second nucleic acid comprises a promoter operably linked to an IL-15 gene or functional fragment thereof.

In some aspects, the first nucleic acid further comprises an intron sequence, a pA sequence, an enhancer sequence, or any combination thereof.

In some aspects, the first nucleic acid further comprises a human growth hormone (hGH) pA sequence.

In some aspects, the first nucleic acid further comprises an intron sequence and a bovine growth hormone (BGH) pA sequence.

In some aspects, the second nucleic acid further comprises an intron sequence, a pA sequence, an enhancer sequence, or any combination thereof.

In some aspects, the second nucleic acid further comprises an SV40 intron sequence and a synthetic (SYN) pA sequence.

In some aspects, the promoter of the first nucleic acid comprises a CMV promoter, a CBA promoter, an EF-1a (Elongation Factor 1a) promoter, aRSV (Rous Sarcoma Virus) promoter, or an Ubiquitin (UbC) promoter.

In some aspects, the promoter of the second nucleic acid comprises a CMV promoter, a CBA promoter, an EF-1a (Elongation Factor 1a) promoter, aRSV (Rous Sarcoma Virus) promoter, or an Ubiquitin (UbC) promoter.

Certain aspects of the disclosure are directed to an expression construct comprising a formula selected from:

(a) X-I1-P1-E-P2-I2-X'-T-Y;

(b) Y-I1-P1-E-P2-I2-X-T-X';

(c) pA-X-I1-L-P1-E-P2-I2-X-T-Y-pA;

(d) pA-Y-I1-L-P1-E-P2-I2-X-T-X'-pA;

(e) P1-X-T-X'-pA; or (f) E-P1-I1-X-T-X'-pA;

wherein X and X' encode subunits of a first immunomodulatory molecule; I1 and I2 each is an intron; P and P2 each is a promoter; E is an enhancer; T is a translation modification sequence; Y encodes a second immunomodulatory molecule; L is a long-terminal repeat; and pA is a polyA sequence.

In some aspects, X is a nucleic acid encoding an IL-12 p35 subunit or a functional fragment thereof or a nucleic acid encoding an IL-12 p40 subunit or a functional fragment thereof. In some aspects, X' is a nucleic acid encoding an IL-12 p35 subunit or a functional fragment thereof or a nucleic acid encoding an IL-12 p40 subunit or a functional fragment thereof. In some aspects, X (e.g., the nucleic acid encoding an IL-12 p35 subunit and/or an IL-12 p40 subunit) does not include an in-frame stop codon (e.g., TGA, TAG, and TAA).

In some aspects, P1 or P2 comprises a CBA promoter, a CMV promoter, an EF-1a (Elongation Factor 1a) promoter, aRSV (Rous Sarcoma Virus) promoter, an Ubiquitin (UbC) promoter, or any combination thereof. In some aspects, P1 or P2 comprises a CBA promoter or fragment thereof.

In some aspects, E comprises a CMV enhancer sequence.

In some aspects, I1 or I2 comprises a SV40 intron sequence or a CAG intron sequence.

In some aspects, T is an internal ribosomal entry site (IRES) sequence, a furin cleavage sequence, a 2A self-processing peptide sequence (including an F2A, E2A, P2A or T2A self-processing peptide), or any combination thereof. In some aspects, T is a furin cleavage sequence followed by a 2A self-processing peptide sequence (F2A).

In some aspects, the expression construct further comprises a Kozak sequence.

In some aspects, the expression construct further comprising a microRNA binding site.

In some aspects, X comprises a gene encoding an IL-12 subunit (e.g., IL-12 p35 or IL-12 p40) or a functional fragment thereof and X' comprises a gene encoding an IL-12 subunit (e.g., IL-12 p40 or IL-12 p35) or functional fragment thereof. In some aspects, the gene encoding an IL-12 subunit is an IL-12 p35 gene or an IL-12 p40 gene. In some aspects, X comprises a nucleic acid encoding an IL-12 p35 subunit or a functional fragment thereof and X' comprises a nucleic acid encoding an IL-12 p40 subunit or functional fragment thereof; P1 comprises a CBA promoter or fragment thereof; T comprises a furin cleavage sequence followed by a 2A self-processing peptide (F2A); pA comprises a human growth hormone (hGH) pA sequence; and optionally, E comprises a CMV enhancer sequence and I1 comprises a CAG intron.

In some aspects, X is a gene encoding an IL-12 subunit or a functional fragment thereof; X' a gene encoding an IL-12 subunit or functional fragment thereof, and Y is IL-15 gene or a functional fragment thereof. In some aspects, the gene encoding an IL-12 subunit is an IL-12 p35 gene or an IL-12 p40 gene. In some aspects, X is a nucleic acid encoding an IL-12 subunit or a functional fragment thereof; X' a nucleic acid encoding an IL-12 subunit or functional fragment thereof, and Y is IL-15 gene or a functional fragment thereof. In some aspects, the nucleic acid encoding an IL-12 subunit is a nucleic acic encoding an IL-12 p35 subunit or a nucleic acic encoding an IL-12 p40 subunit.

In some aspects, X is a nucleic acid encoding an IL-12 subunit or a functional fragment thereof and X' is a nucleic acid encoding an IL-12 subunit or functional fragment thereof.

In some aspects, one or more of the pA comprises a human growth hormone (hGH) pA sequence, a bovine growth hormone (BGH) pA sequence, or a synthetic (SYN) pA sequence.

In some aspects, I1, I2, or both comprises a SV40 intron sequence. In some aspects, I1, I2, or both comprises a CAG intron sequence.

In some aspects, E comprises a CMV enhancer sequence.

In some aspects, the polynucleotides disclosed herein further comprise two inverted terminal repeats (ITRs). In some aspects, the polynucleotide comprises an expression cassette comprising the first nucleic acid and/or the second nucleic acid flanked by ITR sequences.

In some aspects, the disclosure is directed to a polynucleotide comprising a nucleic acid sequence having at least 80%, 85%, 90%, 95% 96%, 97%, 98%, 99%, or 100% identity to any of SEQ ID NOs: 5-37, 48-57, 77, 82, 83, 92, any nucleic acid shown in Table 2, Table 4, or Table 5, or any combinations thereof.

In some aspects, a polynucleotide of the disclosure comprises a nucleic acid sequence having at least 80%, 85%, 90%, 95% 96%, 97%, 98%, 99%, or 100% identity to any of SEQ ID NOs: 5-37, 48-57, 60, 61, 68, 71, 77, 82, 83, 85, 86, 88, 92, any nucleic acid sequence shown in Table 2, Table 4, Table 5, Table 6, or any combinations thereof.

In some aspects, provided herein is a composition comprising a polynucleotide disclosed herein and a delivery vector. In some aspects, the composition is suitable for an intratumoral delivery. In some aspects, the composition is suitable for an intravenous delivery. In some aspects, the composition is suitable for an intrathecal delivery. In some aspects, the composition is suitable for an intrahepatic delivery. In some aspects, the composition is suitable for a delivery to a lymphoid organ (e.g., a spleen, a lymph node, or a bone marrow).

In some aspects, the delivery vector is selected from the group consisting of a viral vector, a plasmid, a lipid, a protein particle, a bacterial vector, a lysosome, a virus-like particle, a polymeric particle, an exosome, and a vault particle.

In some aspects, the delivery vector is selected from the group consisting of an adeno-associated viral (AAV) vector, an adenoviral vector, a lentiviral vector, or a retroviral vector.

In some aspects, wherein the delivery vector is a recombinant AAV (rAAV) vector comprising an AAV serotype selected from the group consisting of AAV1, AAV2, AAV3, AAV4, AAV5, AAV6, AAV7, AAV8, AAVrh8, AAV9, AAV10, AAVrh10, AAV11, and AAV12.

In some aspects, the rAAV vector is an AAV2 serotype. In some aspects, the rAAV is modified relative to the wild-type serotype.

In some aspect, provided herein is an adeno-associated virus (AAV) capsid comprising a polynucleotide disclosed herein (e.g., a polynucleotide comprising an expression cassette comprising the first nucleic acid and/or the second nucleic acid flanked by ITR sequences), wherein the AAV capsid is suitable for an intratumoral delivery of the nucleic acids disclosed herein.

In some aspect, provided herein is an adeno-associated virus (AAV) capsid comprising a polynucleotide disclosed herein (e.g., a polynucleotide comprising an expression cassette comprising the first nucleic acid and/or the second nucleic acid flanked by ITR sequences), wherein the AAV capsid is suitable for an intravenous delivery of the nucleic acids disclosed herein.

In some aspect, provided herein is an adeno-associated virus (AAV) capsid comprising a polynucleotide disclosed herein (e.g., a polynucleotide comprising an expression cassette comprising the first nucleic acid and/or the second nucleic acid flanked by ITR sequences), wherein the AAV capsid is suitable for a delivery of the nucleic acids disclosed herein to a lymphoid organ (e.g., a spleen, a lymph node, or a bone marrow).

In some aspects, the AAV capsid comprises an AAV serotype selected from the group consisting of AAV1, AAV2, AAV3, AAV4, AAV5, AAV6, AAV7, AAV8, AAVrh8, AAV9, AAV10, AAVrh10, AAV11, and AAV12.

In some aspects, the AAV serotype is AAV2. In some aspects, the AAV is modified relative to the wild-type serotype.

In some aspects, the immunomodulatory proteins or functional fragments thereof are immunostimulatory proteins or functional fragments thereof.

In some aspects, provided herein is a method of expressing two or more immunomodulatory proteins or functional fragments thereof in a subject in need thereof comprising administering an effective amount of a combination of the first nucleic acid and the second nucleic acid disclosed herein using one or more delivery vectors disclosed herein, the polynucleotides disclosed herein, the compositions, or the AAV capsids (e.g., AAV particle) disclosed herein to the subject. In some aspects, the administration is intratumoral. In some aspects, the administration is intravenous. In some aspects, the administration is intrasplenic. In some aspects, the administration is intrathecal. In some aspects, the administration is intrahepatic. In some aspects, the administration is intraosseous. In some aspects, the administration is into a lymph node. In some aspects, the administration is intradermal. In some aspects, the administration is intraparenchymal. In some aspects, the administration is via delivery to salivary gland. In some aspects, the AAV capsid (e.g., AAV particle) has an AAV2 serotype.

In some aspects, provided herein is a method of delivering two or more immunomodulatory proteins functional fragments thereof to a tumor comprising administering a combination of the first nucleic acid and the second nucleic acid disclosed herein using one or more delivery vectors disclosed herein, the polynucleotides disclosed herein, the polynucleotides, the compositions, or the AAV capsids (e.g., AAV2 particles) disclosed herein to the tumor by direct injection.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., AAV2 particles) disclosed herein to the subject, wherein the administration is intratumoral.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., rAAV2) disclosed herein to the subject, wherein the administration is intravenous.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., AAV2 particles) disclosed herein to the subject, wherein the administration is intrasplenic.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., AAV2 particles) disclosed herein to the subject, wherein the administration is intrathecal.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., AAV2 particles) disclosed herein to the subject, wherein the administration is intrahepatic.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., AAV2 particles) disclosed herein to the subject, wherein the administration is intraosseous.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., AAV2 particles) disclosed herein to the subject, wherein the administration is into a lymph node.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., AAV2 particles) disclosed herein to the subject, wherein the administration is intradermal.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., AAV2 particles) disclosed herein to the subject, wherein the administration is intraparenchymal.

In some aspects, provided herein is a method of treating or reducing symptoms in a subject suffering from a tumor comprising administering a combination of the first nucleic acid and the second nucleic acid disclosed herein using one or more delivery vectors disclosed herein, the polynucleotides disclosed herein, the compositions, or the AAV capsids (e.g., AAV2 particles) disclosed herein to the subject, wherein the administration is via delivery to salivary gland.

In some aspects, the subject suffers from a solid tumor cancer. In some aspects, the solid tumor is a sarcoma, a carcinoma, or a lymphoma. In some aspects, the solid tumor is a surface lesion. In some aspects, the solid tumor is a visceral tumor.

In some aspects, the subject suffers from a cancer selected from the group consisting of skin cancer, gastrointestinal cancer, breast cancer, brain cancer, bone cancer, thoracic cancer, head and neck cancer, gynecologic cancer, urologic cancer, ocular cancer, and any combination thereof.

In some aspects, cancer is selected from a group consisting of:
  skin cancer (e.g., metastatic melanoma, cutaneous malignant melanoma, cutaneous squamous cell carcinoma, basal cell carcinoma);
  breast cancer (e.g., invasive breast cancer, triple-negative breast cancer, inflammatory breast cancer);
  brain cancer (e.g., glioblastoma multiforme, medulloblastoma, pituitary carcinoma, brain stem gliomas, astrocytomas, oligodendrogliomas, hemangiopericytomas, germ cell tumors, pineal tumors);
  bone cancer (e.g., chordomas, chondrosarcomas, osteosarcomas, Ewing sarcomas, fibrosarcomas, adamantiomas, giant cell tumors);
  head and neck cancer (e.g., head and neck squamous cell carcinoma (HNSCC); salivary gland cancer, oropharyngeal cancer, hypopharyngeal cancer, laryngeal cancer, lip and oral cavity cancer, nasopharyngeal cancer, thyroid cancer, cancer of the parathyroid gland, paranasal sinus and nasal cavity cancer);
  gynecologic cancer (e.g., ovarian cancer, uterine cancer, fallopian tube cancer, endometrial cancer, cervical cancer, vaginal cancer, vulvar cancer);
  urologic cancer (e.g., renal cancer, urethral cancer, urothelial cancer, bladder cancer, cancer of the kidney or ureter, cancer of the renal pelvis, testicular cancer, penile cancer, cancer of the adrenal gland);
  gastrointestinal cancer (e.g., cancer of the anal region, bile duct cancer, colon cancer, cancer of the small intestine, esophageal cancer, gallbladder cancer, gastrointestinal stromal tumors, liver cancer, pancreatic cancer,
  ocular cancer (e.g. uveal melanoma, retinoblastoma, Merkel cell carcinoma, intraocular malignant melanoma, mucosa-associated lymphoid tissue lymphoma, orbital lymphoma, orbital sarcoma, lacrimal gland tumors);
  thoracic cancer (e.g., non-small cell lung cancer, small cell lung cancer, mesothelioma, thymic malignancies, tracheal tumors, some esophageal cancer),
  leukemia (e.g., chronic or acute leukemia, acute myeloid leukemia (AML), chronic myeloid leukemia (CML), acute lymphoblastic leukemia (ALL) (including non-T cell ALL), chronic lymphocytic leukemia (CLL)),
  lymphoma (e.g., Hodgkin's lymphoma, non-Hodgkin's lymphoma (NHL), Waldenström macroglobulinaemia, primary mediastinal large B cell lymphoma (PMBC), diffuse large B cell lymphoma (DLBCL), follicular lymphoma (FL), transformed follicular lymphoma, splenic marginal zone lymphoma (SMZL), cutaneous T-cell lymphoma (CTCL), lymphocytic lymphoma, primary CNS lymphoma),
  other blood cancer (e.g., multiple myeloma)
  cancer of the endocrine system, sarcoma of soft tissue, neoplasm of the central nervous system (e.g., CNS; atypical teratoid/rhabdoid tumor, spinal axis tumor), tumor angiogenesis, Kaposi's sarcoma, epidermoid cancer, environmentally induced cancers including those induced by asbestos, other B cell malignancies, neuroblastoma (including olfactory neuroblastoma), rhabdomyosarcoma, and any combination thereof.

In some aspects, the solid tumor is a surface lesion. In some aspects, the solid tumor is a visceral tumor.

In some aspects, the method of treating or reducing symptoms in a subject in need thereof comprises administering the composition, the gene therapy, the polynucleotide, the expression cassette, or the AAV capsid of the present disclosure to the subject in combination with a checkpoint inhibitor.

In some aspects, the checkpoint inhibitor comprises an inhibitor for programmed cell death protein 1 (PD-1), programmed death-ligand 1 (PD-L1), cytotoxic T-lymphocyte-associated protein 4 (CTLA-4), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, inducible T-cell costimulatory (ICOS), B7-H3, or any combination thereof.

In some aspects, the checkpoint inhibitor is a PD-1 inhibitor. In some aspects, the checkpoint inhibitor is a PD-L1 inhibitor. In some aspects, the checkpoint inhibitor is a CTLA-4 inhibitor. In some aspects, the checkpoint inhibitor is a combination of checkpoint inhibitors, including a combination of PD-1 inhibitors, a combination of PD-L1 inhibitors, a combination of CTLA-4 inhibitors, a combination of LAG-3 inhibitors, a combination of TIGIT inhibitors, a combination of TIM-3 inhibitors, a combination of VISTA inhibitors, a combination of BTLA inhibitors, a combination of ICOS inhibitors, a combination of B7-H3 inhibitors, or a combination of any combination thereof.

In some aspects, the checkpoint inhibitor comprises pembrolizumab, nivolumab, cemiplimab, toripalimab, spartalizumab, dostarlimab-gxly, tislelizumab, balstilimab, BI-754091, zimberelimab, INCMGA00012, camrelizumab, or any combination thereof. In some aspects, the checkpoint inhibitor comprises pembrolizumab or nivolumab.

In some aspects, the checkpoint inhibitor comprises durvalumab, atezolizumab, avelumabor, or any combination thereof.

In some aspects, the checkpoint inhibitor comprises ipilimumab, tremelimumab (formerly ticilimumab), zalifrelimab, quavonlimab, BA3071, YH001, or any combination thereof.

In some aspects, the checkpoint inhibitor comprises relatlimab, BI-754111, favezelimab, eftilagimod alpha, LAG525, fianlimab, TSR-033, Sym022, FS118, MGD013, mavezelimab, INCAGN02385 or any combination thereof.

In some aspects, the checkpoint inhibitor comprises BMS-986207, domvanalimab, AB308, tiragolumab, AGEN1327, vibostolimab (MK-7864), etigalimab, or any combination thereof.

In some aspects, the checkpoint inhibitor comprises cobolimab, BMS-986258, TSR-022, MBG453, Sym023, INCAGN2390, LY3321367, SHR-1702, INCAGN02390, sabotolimab, R07121661, or any combination thereof.

In some aspects, the checkpoint inhibitor comprises JNJ-61610588 (CI-8993), CA-170, or any combination thereof.

In some aspects, the checkpoint inhibitor comprises INBRX-106, PF-04518600, cudarolimab (IBI101), TAB004 (JS004), or any combination thereof.

In some aspects, the checkpoint inhibitor comprises GSK3359609, vopratelimab (JTX-2011), MEDI-570, alomfilimab (KY1044), or any combination thereof.

In some aspects, the checkpoint inhibitor comprises enoblituzumab, DS-7300a, orlotamab, or any combination thereof.

In some aspects, the gene therapy, the composition, the polynucleotide, the expression cassette, or the AAV capsid of the present disclosure can be administered prior to, at the same time, or after the administration of a checkpoint inhibitor.

In some aspects, provided herein is a composition comprising: (a) a polynucleotide comprising a nucleic acid encoding a cytokine, one or more subunits thereof, or functional fragment thereof; and (b) a viral vector (e.g., AAV capsid, e.g., AAV2 serotype). In some aspects, the polynucleotide comprises: (i) a first nucleic acid encoding a first cytokine subunit or functional fragment thereof; and (ii) a second nucleic acid encoding a second cytokine subunit or functional fragment thereof.

In some aspects, the cytokine is selected from the group consisting of IL-12, tumor necrosis factor alpha (TNF-α), a type I interferon (INF), a type II IFN, IL-2, IL-15, IL-21, IL-23, IL-27, IL-18, IL-1, IL-3, IL-4, IL-5, IL-6, IL-7, IL-8, IL-9, IL-10, IL17, IL33, TL1A, CD40L, granulocyte-macrophage colony-stimulating factor (GM-CSF), and any combination thereof. In some aspects, the cytokine is IL-12.

In some aspects, the polynucleotide comprises a nucleic acid encoding an IL-12 p35 subunit and/or a nucleic acid encoding an IL-12 p40 subunit. In some aspects, the nucleic acid (e.g., the first nucleic acid) encoding an IL-12 p35 subunit and/or the nucleic acid encoding encoding an IL-12 p40 subunit does not include an in-frame stop codon (e.g., TGA, TAG, and TAA).

In some aspects, the polynucleotide further comprises one or more promoters. In some aspects, the construct can comprise a promoter for the nucleic acid encoding a first cytokine subunit (e.g., an IL-12 p35 subunit) and a promoter for the nucleic acid sequence encoding a second cytokine subunit (e.g., an IL-12 p40 subunit). In some aspects, the two or more promoters are the same. In some aspects, the two or more promoters are different. In some aspects, one promoter can drive the expression of both the first cytokine subunit (e.g., an IL-12 p35 subunit) and the second cytokine subunit (e.g., an IL-12 p40 subunit). In some aspects, the nucleic acid encoding an IL-12 p35 subunit and/or the nucleic acid encoding encoding an IL-12 p40 subunit does not include an in-frame stop codon (e.g., TGA, TAG, and TAA).

In some aspects, the promoter is a constitutively active promoter, a cell-type specific promoter, or an inducible promoter. In some aspects, the promoter comprises a CBA promoter, a CMV promoter, an EF-1a (Elongation Factor 1a) promoter, a RSV (Rous Sarcoma Virus) promoter, an Ubiquitin (UbC) promoter, or any combination thereof. In some aspects, the promoter comprises a CBA promoter. In some aspects, the promoter comprises a CMV enhancer, a CBA promoter, and a CAG intron sequence (e.g., SEQ ID NO: 71).

In some aspects, the polynucleotide further comprises translation modification sequence, e.g., a furin cleavage sequence, a 2A self-processing peptide sequence (including an F2A, E2A, P2A or T2A self-processing peptide), an internal ribosomal entry site (IRES) sequence or any combination thereof. In some aspects, the nucleic acid comprises the combination of a furin cleavage sequence followed by a nucleic acid encoding a 2A self-processing peptide sequence (F2A). In some aspects, the furin cleavage sequence followed by the 2A self-processing peptide sequence (F2A) is located between the first nucleic acid encoding an IL-12 p35 subunit or a functional fragment thereof or an IL-12 p40 subunit or a functional fragment thereof and the second nucleic acid encoding an IL-12 p35 subunit or a functional fragment thereof or an IL-12 p40 subunit or a functional fragment thereof. In some aspects, the first nucleic acid (e.g., nucleic acid encoding an IL-12 p35 subunit and/or the nucleic acid encoding encoding an IL-12 p40 subunit) does not include an in-frame stop codon (e.g., TGA, TAG, and TAA).

In some aspects, the polynucleotide further comprises a poly(A) (pA) sequence. In some aspects, the pA sequence is a human growth hormone (HGH) pA sequence. In some aspects, the pA sequence is a bovine growth hormone (BGH) pA sequence.

In some aspects, provided herein is a composition comprising (a) a polynucleotide comprising a CMV enhancer, a CBA promoter or fragment thereof operably linked to a first nucleic acid encoding an IL-12 p35 subunit or a functional fragment thereof, a furin cleavage sequence followed by a 2A self-processing peptide sequence (F2A), a second nucleic acid encoding an IL-12 p40 subunit or a functional fragment thereof, and a human growth hormone (HGH) pA sequence; and (b) a viral vector (e.g., an AAV capsid). In some aspects, the polynucleotide further comprise an intron sequence (e.g., a CAG intron).

In some aspects, provided herein is a composition comprising (a) a polynucleotide comprising a CMV enhancer, a CBA promoter or fragment thereof operably linked to a first nucleic acid encoding an IL-12 p35 subunit or a functional fragment thereof, a furin cleavage sequence followed by a 2A self-processing peptide (F2A), a second nucleic acid encoding an IL-12 p40 subunit or a functional fragment thereof, and a bovine growth hormone (BGH) pA sequence; and (b) a viral vector (e.g., an AAV capsid).

In some aspects, the nucleic acid encoding the IL-12 p35 subunit comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77. In some aspects, the nucleic acid encoding the IL-12 p40 subunit comprises a sequence at least 85%, at least 90%, at least 96%, at least 97%, at least 98%, at least 99%, or 100% identical to SEQ ID NO: 8, SEQ ID NO: 9, SEQ ID NO: 10, or SEQ ID NO: 92. In some aspects, the nucleic acid encoding an IL-12 p35 subunit does not include an in-frame stop codon (e.g., TGA, TAG, and TAA). In some aspects, the nucleic acid encoding the IL-12 p35 subunit comprises a sequence at least 85%, at least 90%, at least 96%, at least 97%, at least 98%, at least 99%, or 100% identical to SEQ ID NO: 77. In some aspects, the nucleic acid encoding an IL-12 p40 subunit does not include an in-frame stop codon (e.g., TGA, TAG, and TAA). In some aspects, the nucleic acid encoding the IL-12 p40 subunit comprises a sequence at least 85%, at least 90%, at least 96%, at least 97%, at least 98%, at least 99%, or 100% identical to SEQ ID NO: 92.

In some aspects, provided herein is a method of treating or reducing symptoms in a subject suffering from a tumor, comprising administering to the subject a composition comprising (a) a polynucleotide comprising (i) a first nucleic acid encoding an IL-12 p35 subunit or functional fragment thereof and (ii) a second nucleic acid encoding an IL-12 p40 subunit or functional fragment thereof, and (b) an AAV vector (e.g., AAV2 serotype).

In some aspects, provided herein is a method of reducing the size of a tumor in a subject in need thereof comprising administering to the subject a composition comprising (a) a polynucleotide comprising (i) a first nucleic acid encoding an IL-12 p35 subunit or functional fragment thereof and (ii) a second nucleic acid encoding an IL-12 p40 subunit or functional fragment thereof, and (b) an AAV vector (e.g., AAV2 serotype).

In some aspects, the nucleic acid encoding an IL-12 p35 subunit and/or IL-12 p40 subunit does not include an in-frame stop codon (e.g., TGA, TAG, and TAA).

In some aspects, the administration is intratumoral, intravenous, intraperitoneal, intrasplenic, intrathecal, intrahepatic, intraosseous, intradermal, intraparenchymal, via delivery to salivary gland, or into a lymph node.

In some aspects, the tumor is derived from a cancer selected from the group consisting of hepatocellular carcinoma, colon carcinoma, melanoma, and any combination thereof. In some aspects, the subject suffers from a cancer selected from the group consisting of hepatocellular carcinoma, colon carcinoma, melanoma, and any combination thereof.

In some aspects, the tumor is derived from a cancer selected from the group consisting of skin cancer (e.g., metastatic melanoma, cutaneous malignant melanoma, cutaneous squamous cell carcinoma, basal cell carcinoma); breast cancer (e.g., invasive breast cancer, triple-negative breast cancer, inflammatory breast cancer); brain cancer (e.g., glioblastoma multiforme, medulloblastoma, pituitary carcinoma, brain stem gliomas, astrocytomas, oligodendrogliomas, hemangiopericytomas, germ cell tumors, pineal tumors); bone cancer (e.g., chordomas, chondrosarcomas, osteosarcomas, Ewing sarcomas, fibrosarcomas, adamantiomas, giant cell tumors); head and neck cancer (e.g., head and neck squamous cell carcinoma [HNSCC]; salivary gland cancer, oropharyngeal cancer, hypopharyngeal cancer, laryngeal cancer, lip and oral cavity cancer, nasopharyngeal cancer, thyroid cancer, cancer of the parathyroid gland, paranasal sinus and nasal cavity cancer); gynecologic cancer (e.g., ovarian cancer, uterine cancer, fallopian tube cancer, endometrial cancer, cervical cancer, vaginal cancer, vulvar cancer); urologic cancer (e.g., renal cancer, urethral cancer, urothelial cancer, bladder cancer, cancer of the kidney or ureter, cancer of the renal pelvis, testicular cancer, penile cancer, cancer of the adrenal gland); gastrointestinal cancer (e.g., cancer of the anal region, bile duct cancer, colon cancer, cancer of the small intestine, esophageal cancer, gallbladder cancer, gastrointestinal stromal tumors, liver cancer, pancreatic cancer, rectal cancer, stomach/gastric cancer); ocular cancer (e.g. uveal melanoma, retinoblastoma, Merkel cell carcinoma, intraocular malignant melanoma, mucosa-associated lymphoid tissue lymphoma, orbital lymphoma, orbital sarcoma, lacrimal gland tumors); thoracic cancer (e.g., non-small cell lung cancer, small cell lung cancer, mesothelioma, thymic malignancies, tracheal tumors, some esophageal cancer), leukemia (e.g., chronic or acute leukemia, acute myeloid leukemia (AML), chronic myeloid leukemia (CML), acute lymphoblastic leukemia (ALL) (including non-T cell ALL), chronic lymphocytic leukemia (CLL)), lymphoma (e.g., Hodgkin's lymphoma, non-Hodgkin's lymphoma (NHL), Waldenström macroglobulinaemia, primary mediastinal large B cell lymphoma (PMBC), diffuse large B cell lymphoma (DLBCL), follicular lymphoma (FL), transformed follicular lymphoma, splenic marginal zone lymphoma (SMZL), cutaneous T-cell lymphoma (CTCL), lymphocytic lymphoma, primary CNS lymphoma), other blood cancer (e.g., multiple myeloma), cancer of the endocrine system, sarcoma of soft tissue, neoplasm of the central nervous system (e.g., CNS; atypical teratoid/rhabdoid tumor, spinal axis tumor), tumor angiogenesis, Kaposi's sarcoma, epidermoid cancer, environmentally induced cancers including those induced by asbestos, other B cell malignancies, neuroblastoma (including olfactory neuroblastoma), rhabdomyosarcoma, and any combination thereof.

In some aspects, the composition further comprises a checkpoint inhibitor.

In some aspects, the checkpoint inhibitor comprises an inhibitor for programmed cell death protein 1 (PD-1), programmed death-ligand 1 (PD-L1), cytotoxic T-lymphocyte-associated protein 4 (CTLA-4), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, inducible T-cell costimulatory (ICOS), B7-H3, or any combination thereof.

In some aspects, the checkpoint inhibitor is a combination of checkpoint inhibitors, including a combination of PD-1 inhibitors, a combination of PD-L1 inhibitors, a combination of CTLA-4 inhibitors, a combination of LAG-3 inhibitors, a combination of TIGIT inhibitors, a combination of TIM-3 inhibitors, a combination of VISTA inhibitors, a combination of BTLA inhibitors, a combination of ICOS inhibitors, a combination of B7-H3 inhibitors, or a combination of any combination thereof.

In some aspects, the checkpoint inhibitor is a PD-1 inhibitor. In some aspects, the PD-1 inhibitor is an anti-PD-1 antibody. In some aspects, the checkpoint inhibitor comprises pembrolizumab, nivolumab, cemiplimab, toripalimab, spartalizumab, dostarlimab-gxly, tislelizumab, balstilimab, BI-754091, zimberelimab, INCMGA00012, camrelizumab, or any combination thereof. In some aspects, the checkpoint inhibitor comprises pembrolizumab or nivolumab.

In some aspects, the checkpoint inhibitor is a PD-L1 inhibitor. In some aspects, the checkpoint inhibitor comprises durvalumab, atezolizumab, avelumabor, or any combination thereof.

In some aspects, the checkpoint inhibitor is a CTLA-4 inhibitor. In some aspects, the checkpoint inhibitor comprises ipilimumab, tremelimumab (formerly ticilimumab), zalifrelimab, quavonlimab, BA3071, YH001, or any combination thereof.

In some aspects, the composition disclosed herein, the polynucleotide disclosed herein, or the AAV capsid disclosed herein is administered prior to, at the same time, or after the administration of the checkpoint inhibitor.

BRIEF DESCRIPTION OF DRAWINGS

FIG. 8A and FIG. 8B show tumor regression as measured by mean area under the curve (AUC) (FIG. 8A) or by median area under the curve (AUC) (FIG. 8B) of tumor growth in a syngeneic H22 hepatocellular cancer mouse model after treatment with vehicle, AAV2-IL12, AAV2-IL12 and an anti-PD-1 antibody, or an anti-PD-1 antibody. In FIG. 8A, data are expressed as the mean values±standard error of the mean (SEM). (ns=not significant; *p<0.05; **<0.0001; 2-sided t-test).

In FIG. 10A, data are expressed as the mean values #standard error of the mean (SEM). (ns=not significant; *p<0.05; ***<0.0001; 2-sided t-test).

In FIG. 12A, data are expressed as the mean values±standard error of the mean (SEM). (ns=not significant; *p<0.05; ***<0.0001; 2-sided t-test).

Each line represents an individual mouse. Horizontal dashed line (-----) represents a maximum tumor volume (animals are euthanized once this volume is exceeded). The x-axis represents the number of days after treatment (0, 5, 10, 15, 20, 25, and 30 days).

Figure 13A:
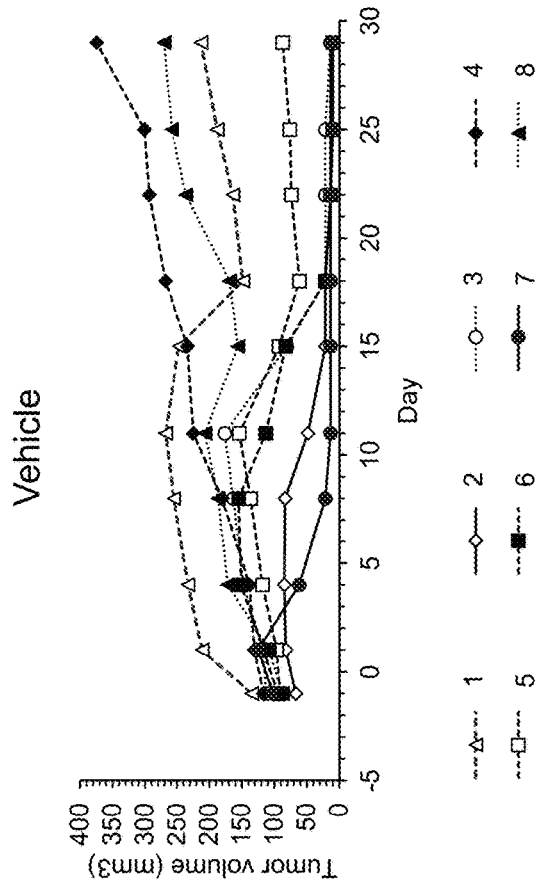
FIG. 13A-13D show tumor regression as measured by tumor volume ($mm^3$) in a syngeneic Hepa1-6 hepatocellular cancer mouse model after treatment with vehicle (FIG. 13A), AAV2-IL12 (FIG. 13B), an anti-PD-1 antibody (FIG. 13C), or AAV2-IL12 and an anti-PD-1 antibody (FIG. 13D).
Figure 13B:
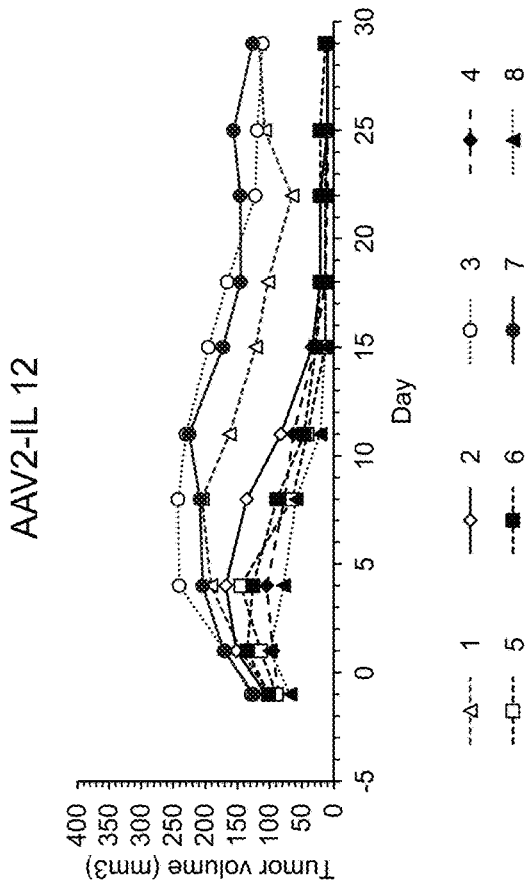
Figure 13C:
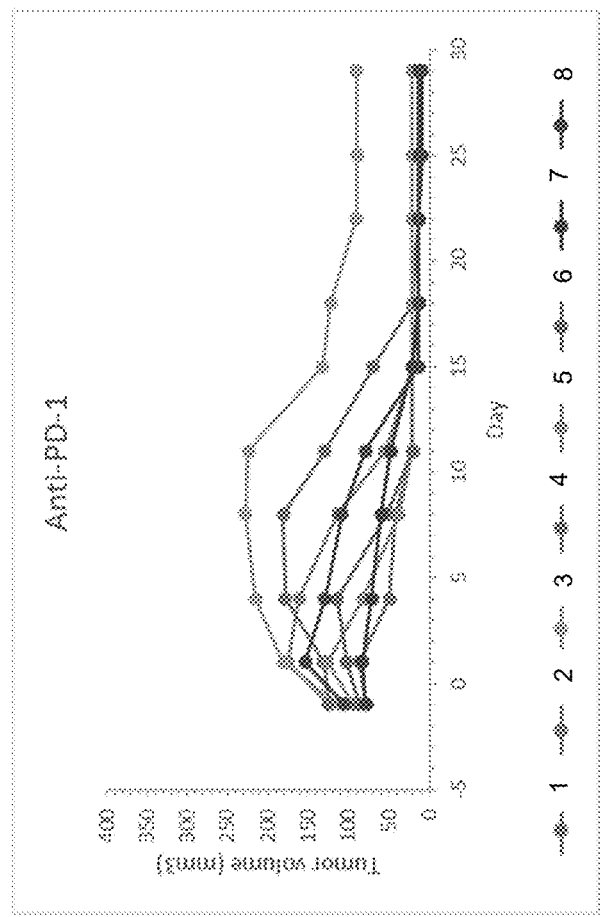
Figure 13D:
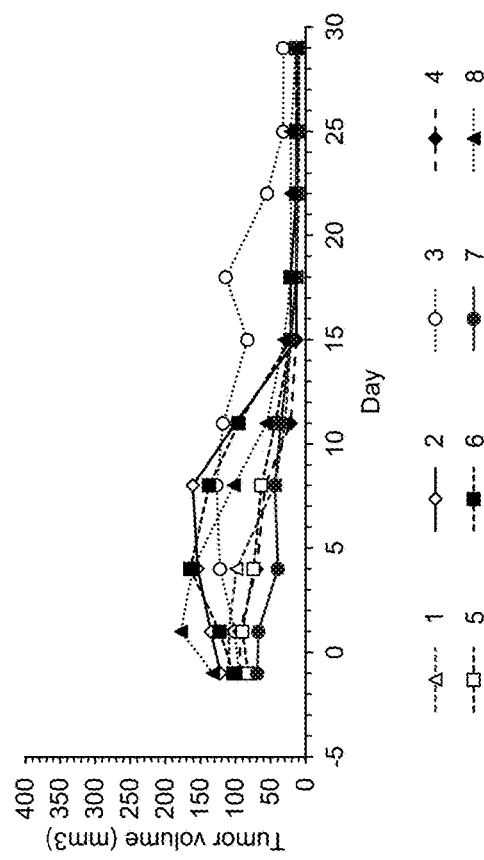
Figure 13E:
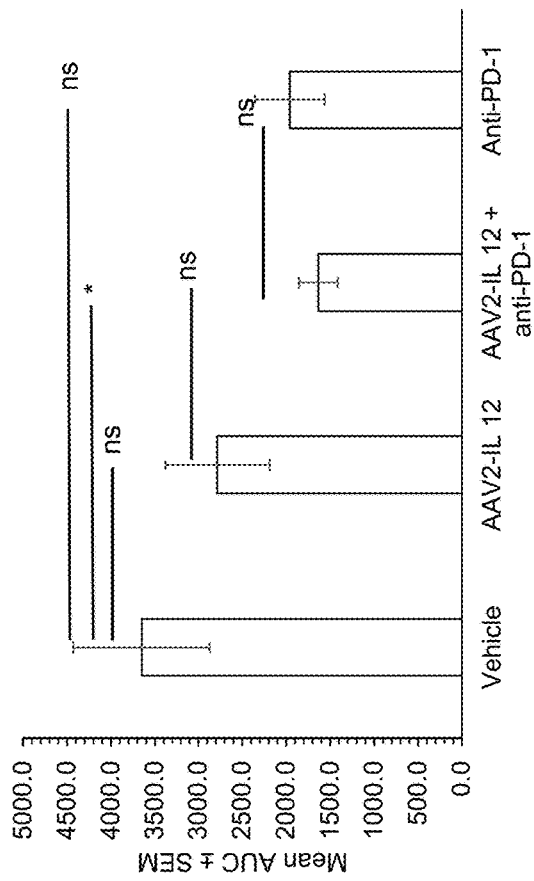
Figure 13F:
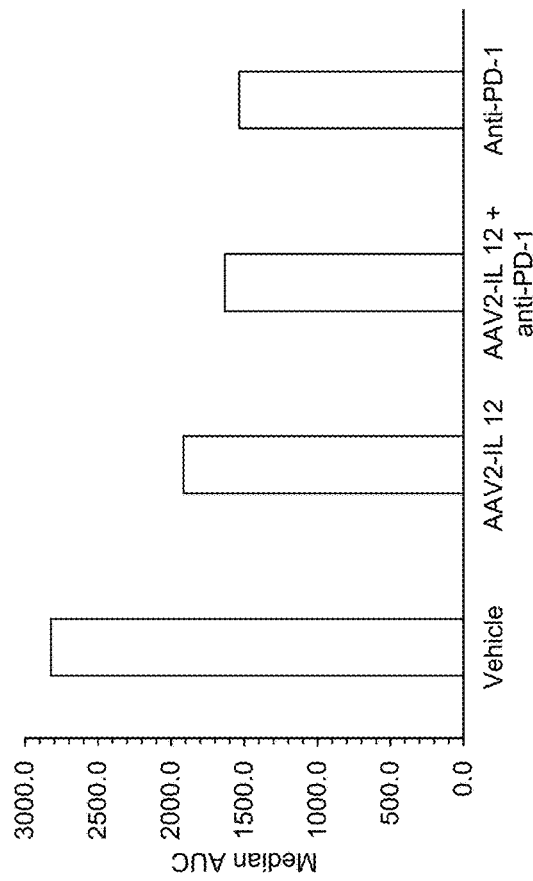

FIG. 13E-13F show tumor regression as measured by mean area under the curve (AUC) (FIG. 13E) or by median area under the curve (AUC) (FIG. 13F) of tumor growth in a syngeneic Hepa1-6 hepatocellular cancer mouse model after treatment with control (vehicle), AAV2-IL12, AAV2-IL12 and an anti-PD-1 antibody, or an anti-PD-1 antibody. In FIG. 13E, data are expressed as the mean values±standard error of the mean (SEM). (ns=not significant).

Figure 14A:
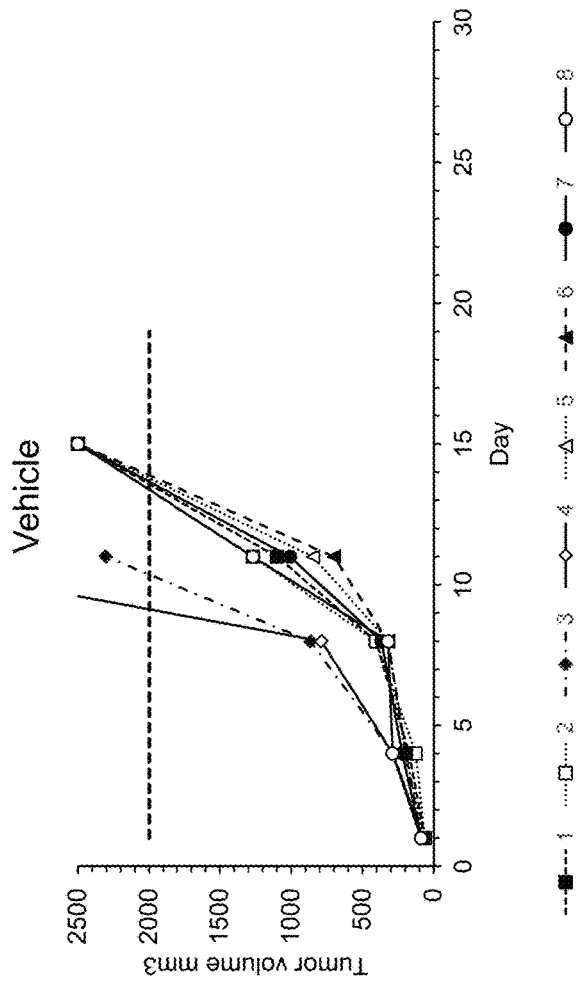
Figure 14B:
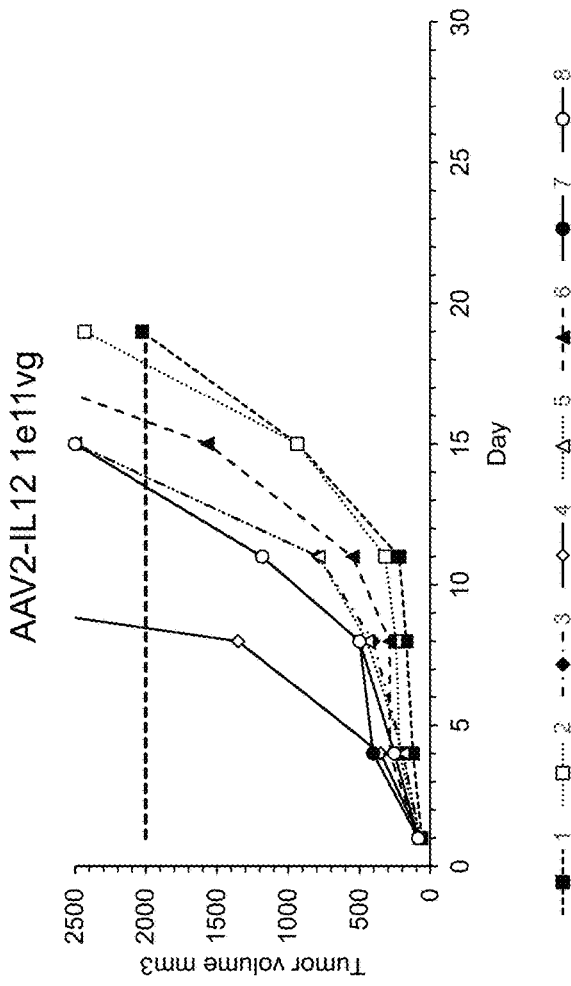
Figure 14C:
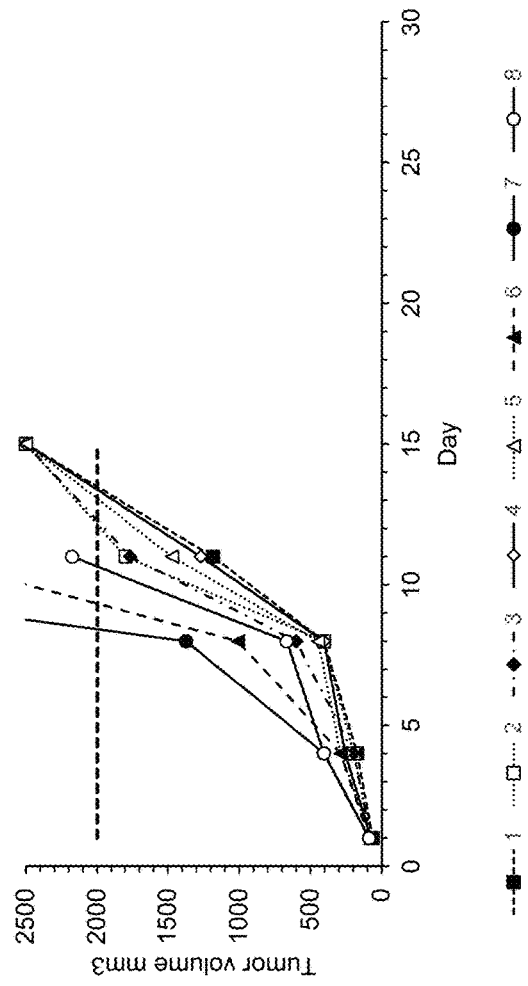
Figure 14D:
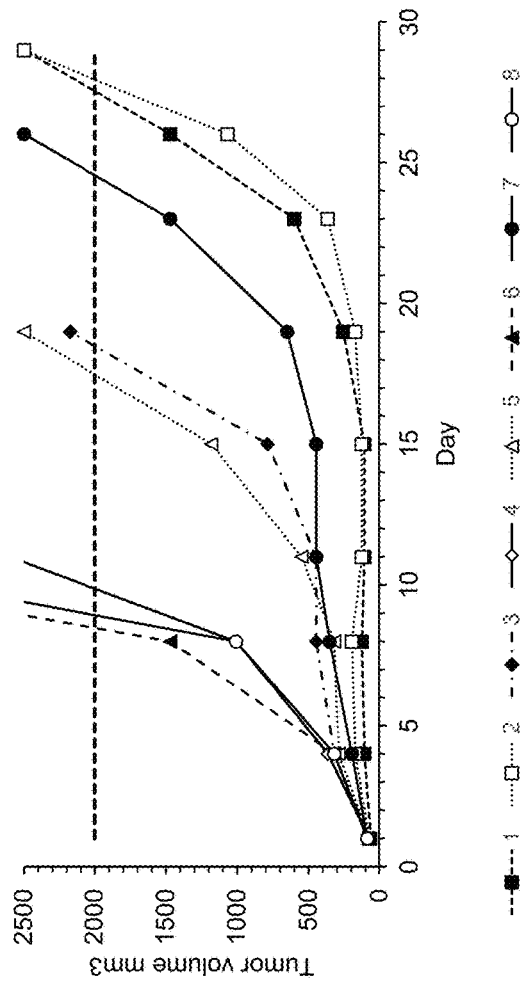

FIG. 14A-14D show tumor regression as measured by tumor volume ($mm^3$) in a syngeneic B16F10 melanoma cancer mouse model after treatment with vehicle (FIG. 14A), AAV2-IL12 (FIG. 14B), an anti-PD-1 antibody (FIG. 14C), or AAV2-IL12 and an anti-PD-1 antibody (FIG. 14D). Each line represents an individual mouse. Horizontal dashed line (-----) represents a maximum tumor volume (animals are euthanized once this volume is exceeded). The x-axis represents the number of days after treatment (0, 5, 10, 15, 20, 25, and 30 days).

Figure 15A:
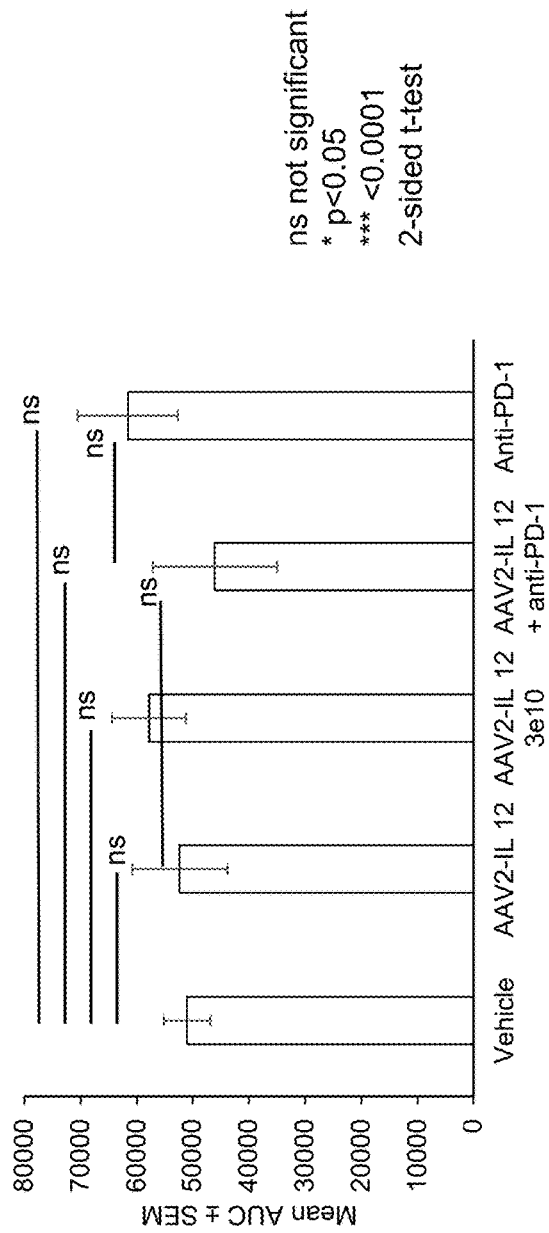
Figure 15B:
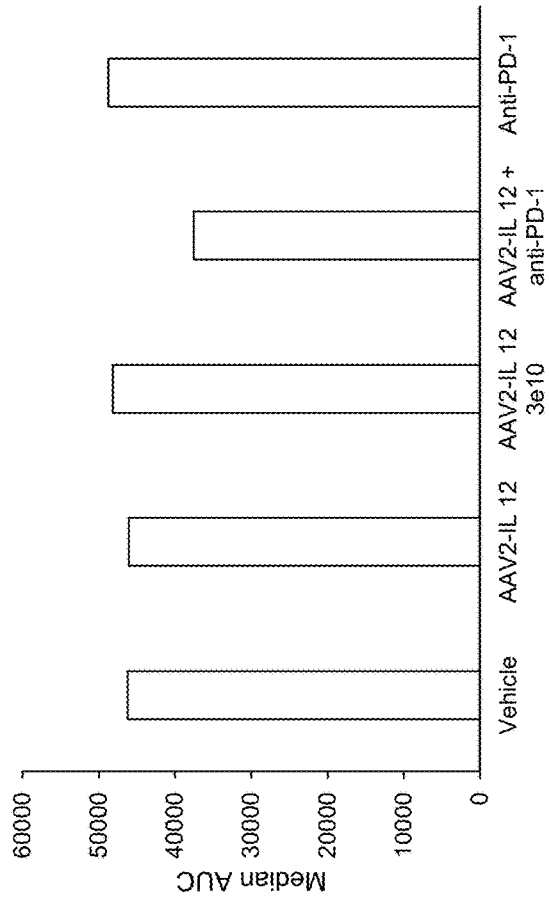

FIG. 15A and FIG. 15B show tumor regression as measured by mean area under the curve (AUC) (FIG. 15A) or by median area under the curve (AUC) (FIG. 15B) of tumor growth in a syngeneic B16F10 melanoma cancer mouse model after treatment with vehicle, AAV2-IL12, AAV2-IL12 and an anti-PD-1 antibody, or an anti-PD-1 antibody. In FIG. 15A, data are expressed as the mean values±standard error of the mean (SEM). (ns=not significant; *$p<0.05$; ***<0.0001; 2-sided t-test).

Figure 16:
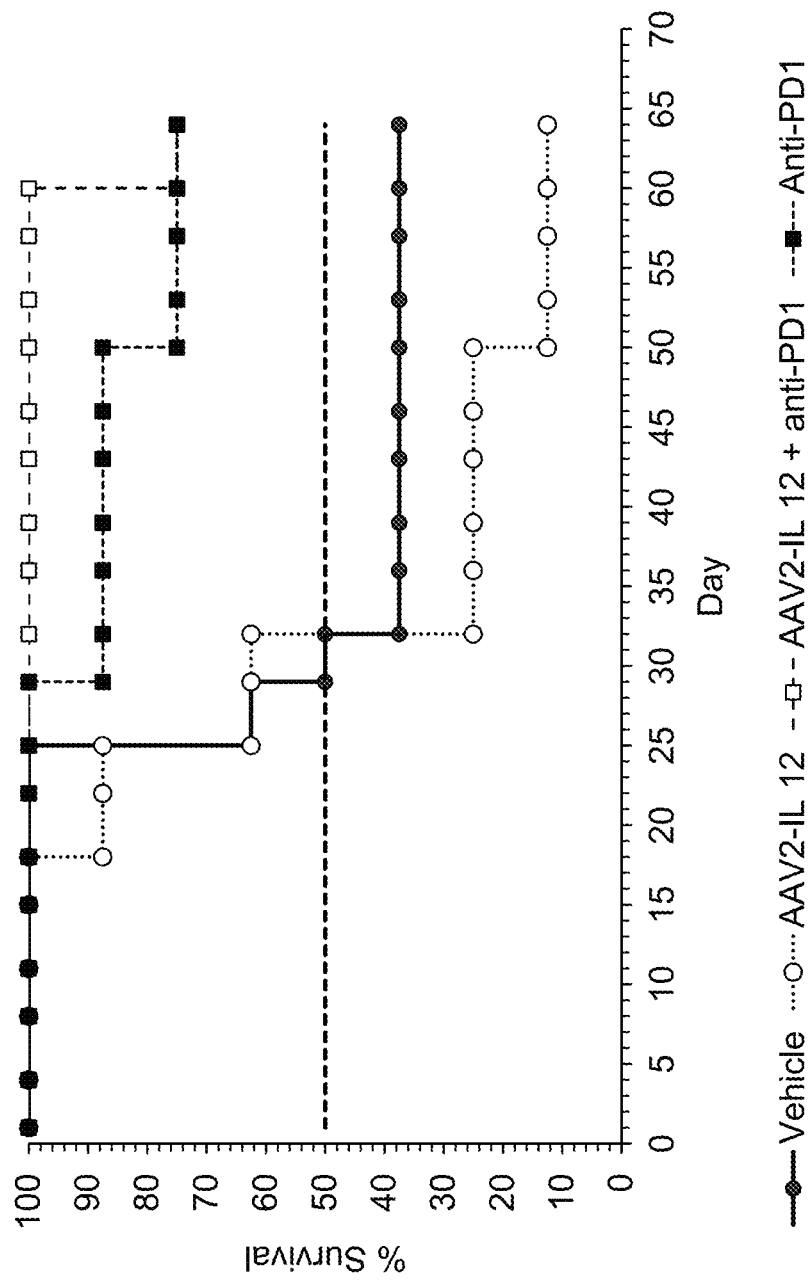

FIG. 16 shows overall survival (% survival) of a syngeneic H22 hepatocellular cancer mouse model after treatment with vehicle, AAV2-IL12, AAV2-IL12 and an anti-PD-1 antibody, or an anti-PD-1 antibody. The x-axis represents the number of days after treatment (0, 5, 10, 15, 20, 25, 30, 35, 50, 45, and 50 days). Horizontal dashed line (-----) indicates 50% survival.

Figure 17:
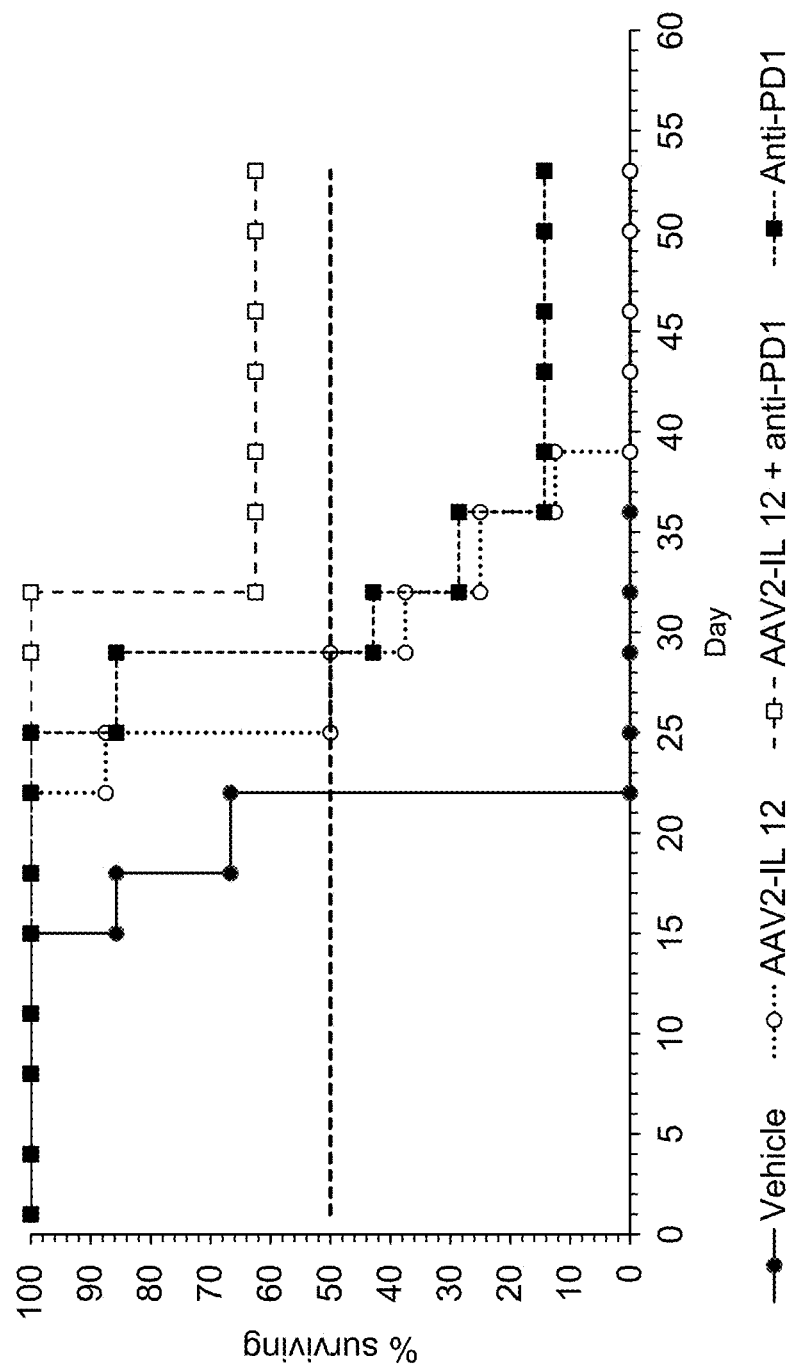

FIG. 17 shows overall survival (% survival) of a syngeneic MC38 colorectal cancer mouse model after treatment with vehicle, AAV-IL12, AAV-IL12 and an anti-PD-1 antibody, or an anti-PD-1 antibody. The x-axis represents the number of days after treatment (0, 5, 10, 15, 20, 25, 30, 35, 50, 45, and 50 days). Horizontal dashed line (-----) indicates 50% survival.

Figure 18:
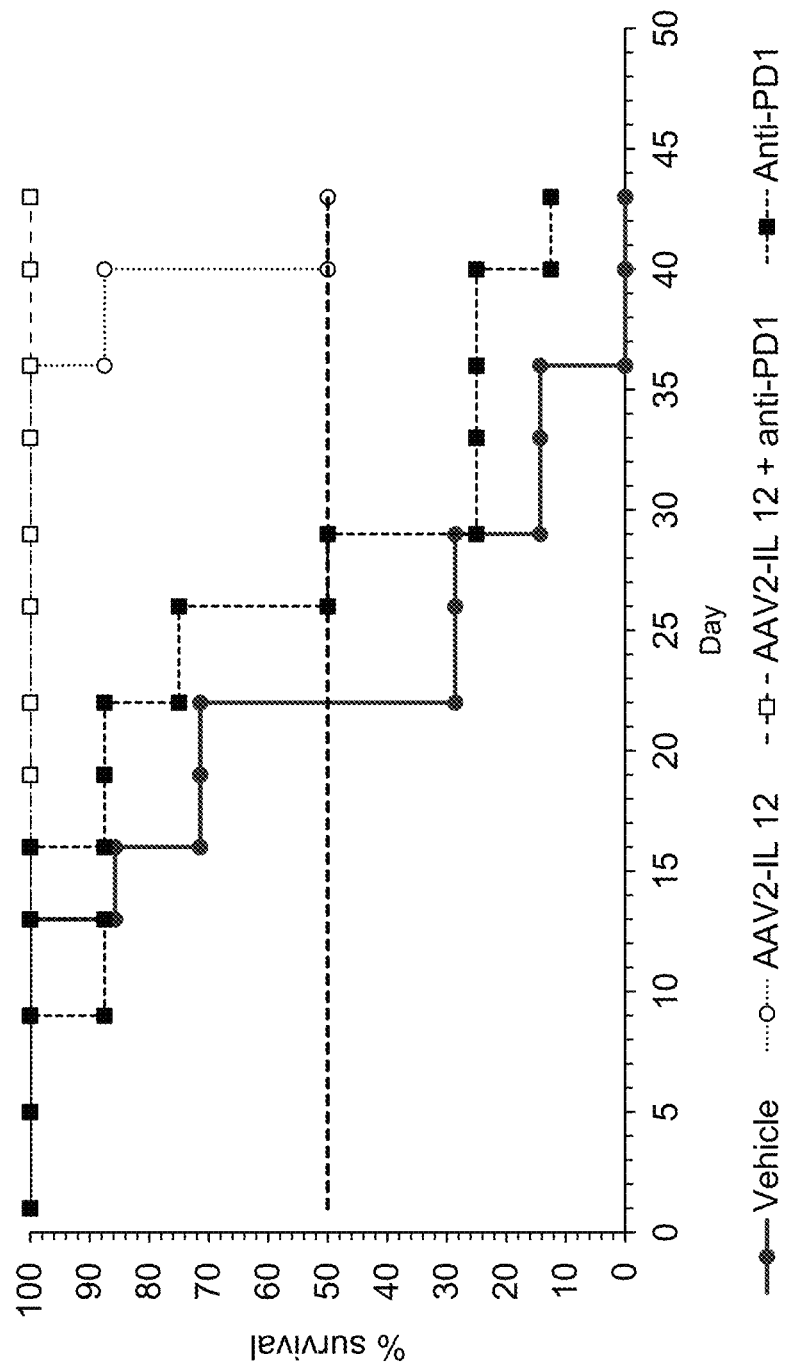

FIG. 18 shows overall survival (% survival) of a syngeneic Cloudman S91 melanoma cancer mouse model after treatment with vehicle, AAV2-IL12, AAV2-IL12 and an anti-PD-1 antibody, or an anti-PD-1 antibody. The x-axis represents the number of days after treatment (0, 5, 10, 15, 20, 25, 30, 35, 50, 45, and 50 days). Horizontal dashed line (-----) indicates 50% survival.

Figure 19:
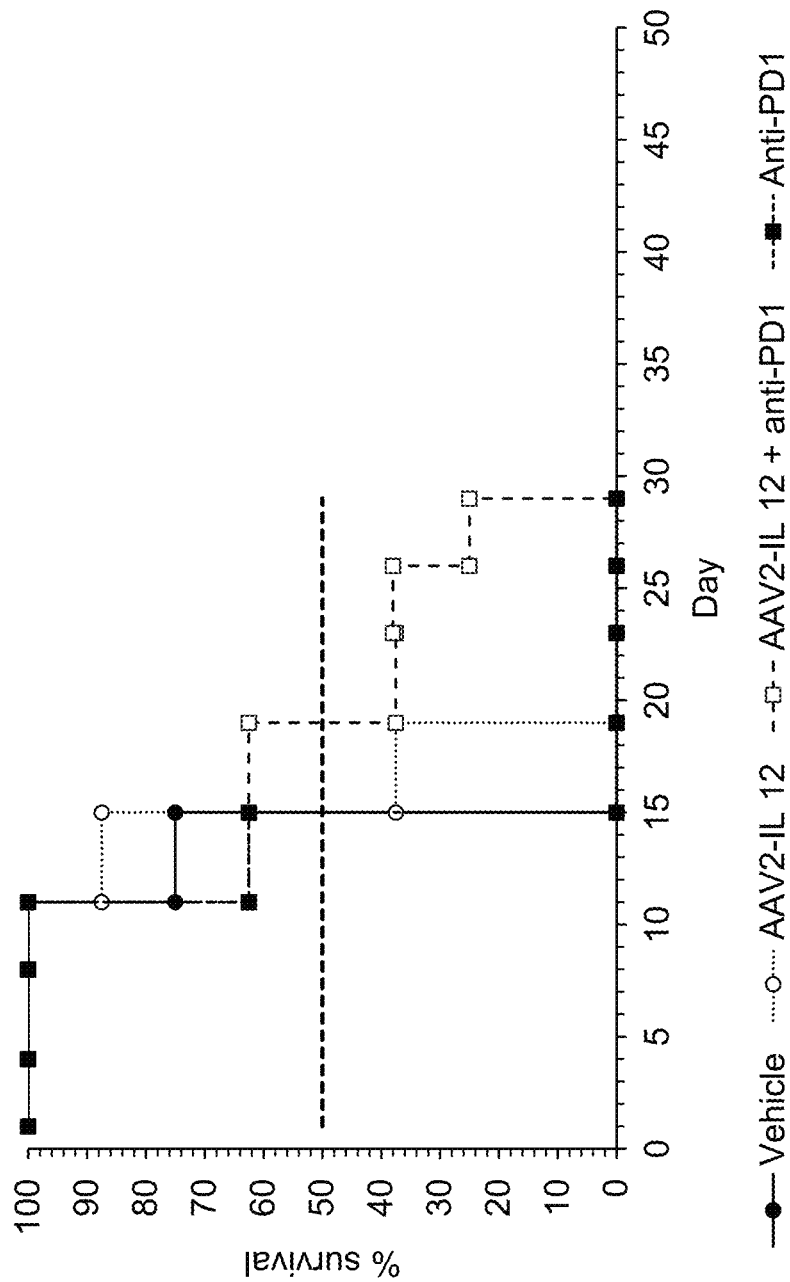

FIG. 19 shows overall survival (% survival) of a syngeneic B16F10 melanoma cancer mouse model after treatment with vehicle, AAV2-IL12, AAV2-IL12 and an anti-PD-1 antibody, or an anti-PD-1 antibody. The x-axis represents the number of days after treatment (0, 5, 10, 15, 20, 25, 30, 35, 50, 45, and 50 days).

FIG. 20A-FIG. 20E show mean body weight change relative to day 1 (%) of syngeneic H22 hepatocellular (FIG. 20A), B16F10 melanoma (FIG. 20B), Cloudman S91 melanoma (FIG. 20C) MC38 colorectal (FIG. 20D), and Hepa1-6 hepatocellular cancer mouse models (FIG. 20E) after treatment with vehicle, AAV2-IL2 ($1\times10^{11}$ viral genomes or $3\times10^{10}$ viral genomes), AAV2-IL12 ($1\times10^{11}$ viral genomes) and an anti-PD-1 antibody, or an anti-PD-1 antibody.

Figure 21:
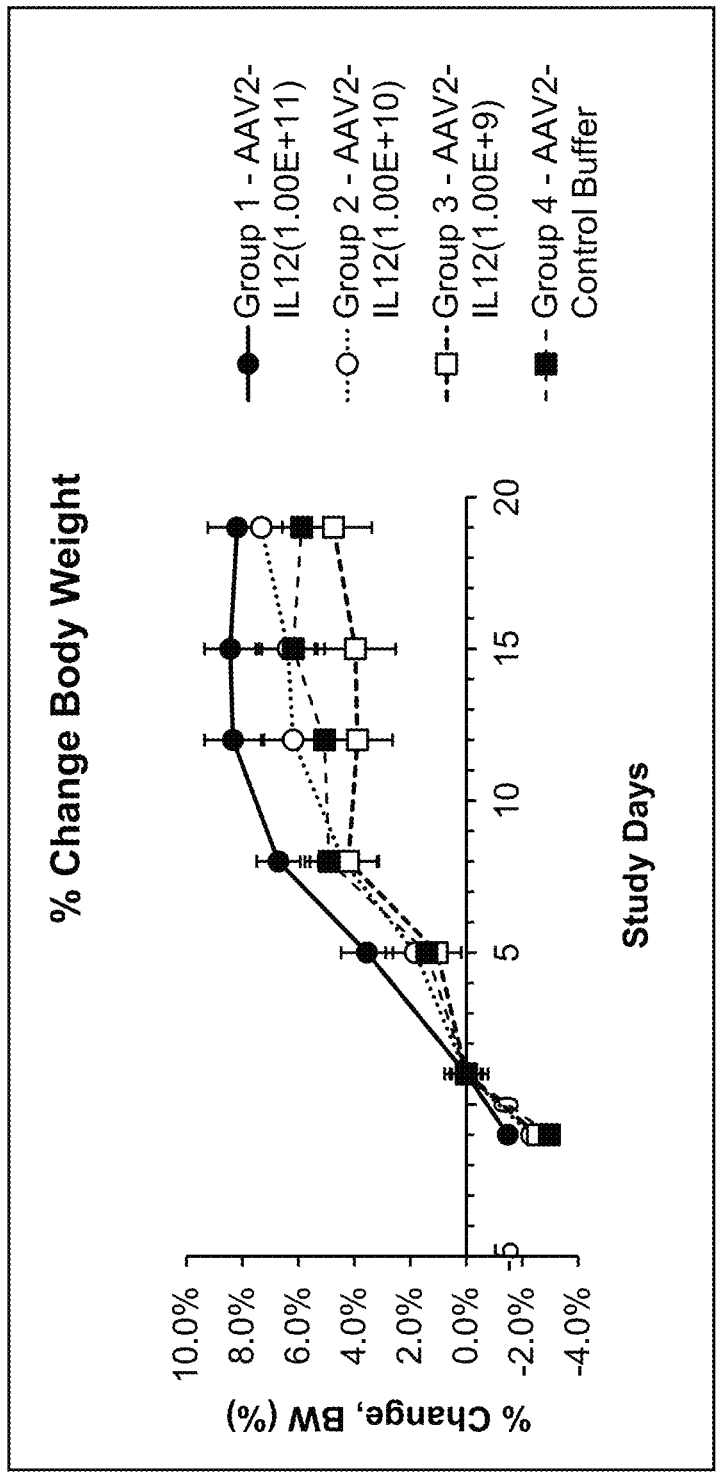

FIG. 21 shows body weight (grams) of normal mice that were intravenously administered AAV2-IL12 in escalated doses in escalated doses ($1\times10^9$ viral genomes, $1\times10^{10}$ viral genomes, or $1\times10^{11}$ viral genomes) or control buffer.

Figure 22:
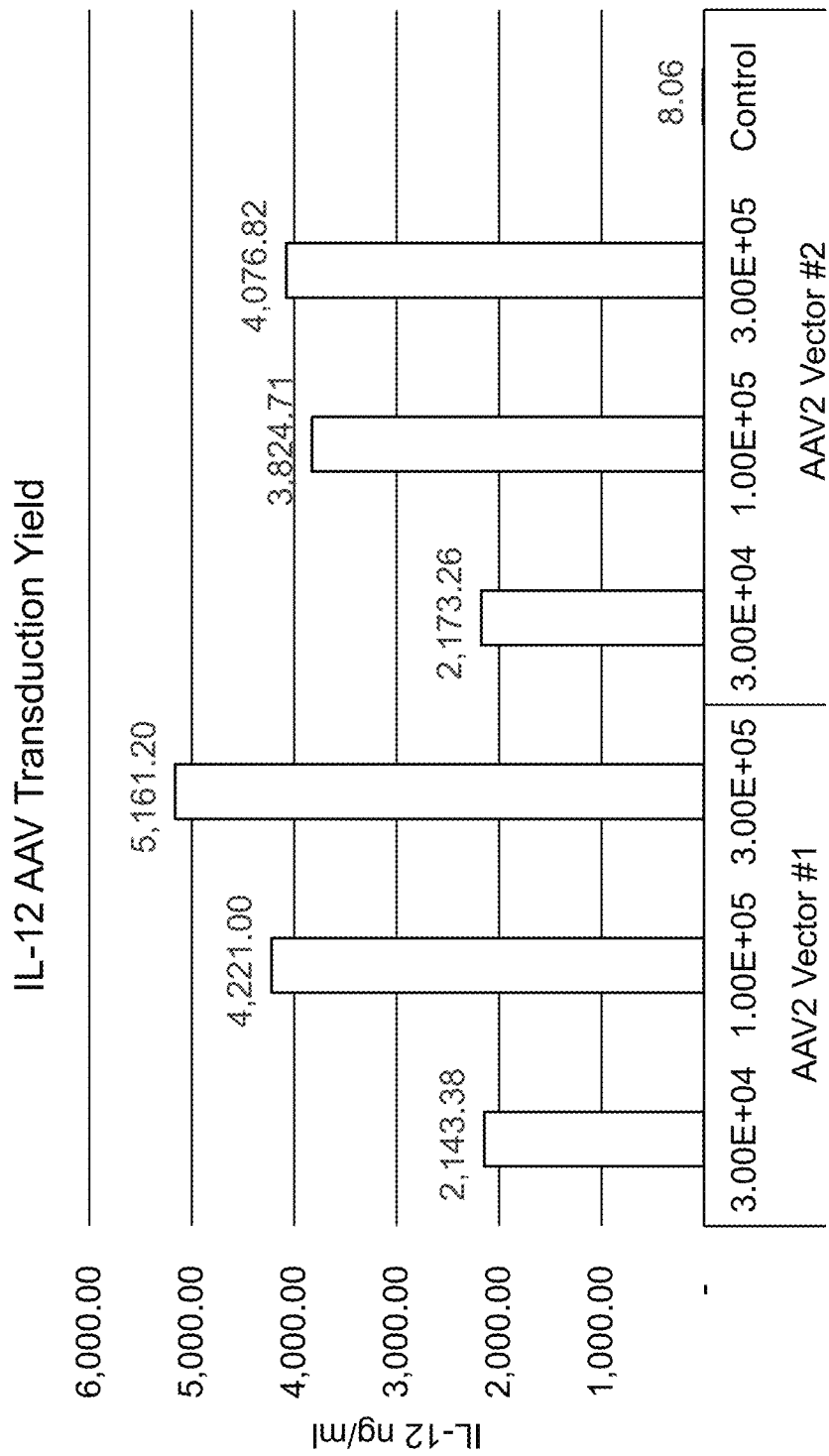

FIG. 22 shows IL12 expression (ng/mL) in vitro after administration of an AAV2-IL12 construct (either AAV2 vector #1 (AAV2-CAG-mIL12a-IRES-mIL12b-bgh PA) or AAV2 vector #2 (AAV2-CAG-mIL12a-F2A-mIL12b-hgh PA).

Figure 23A:
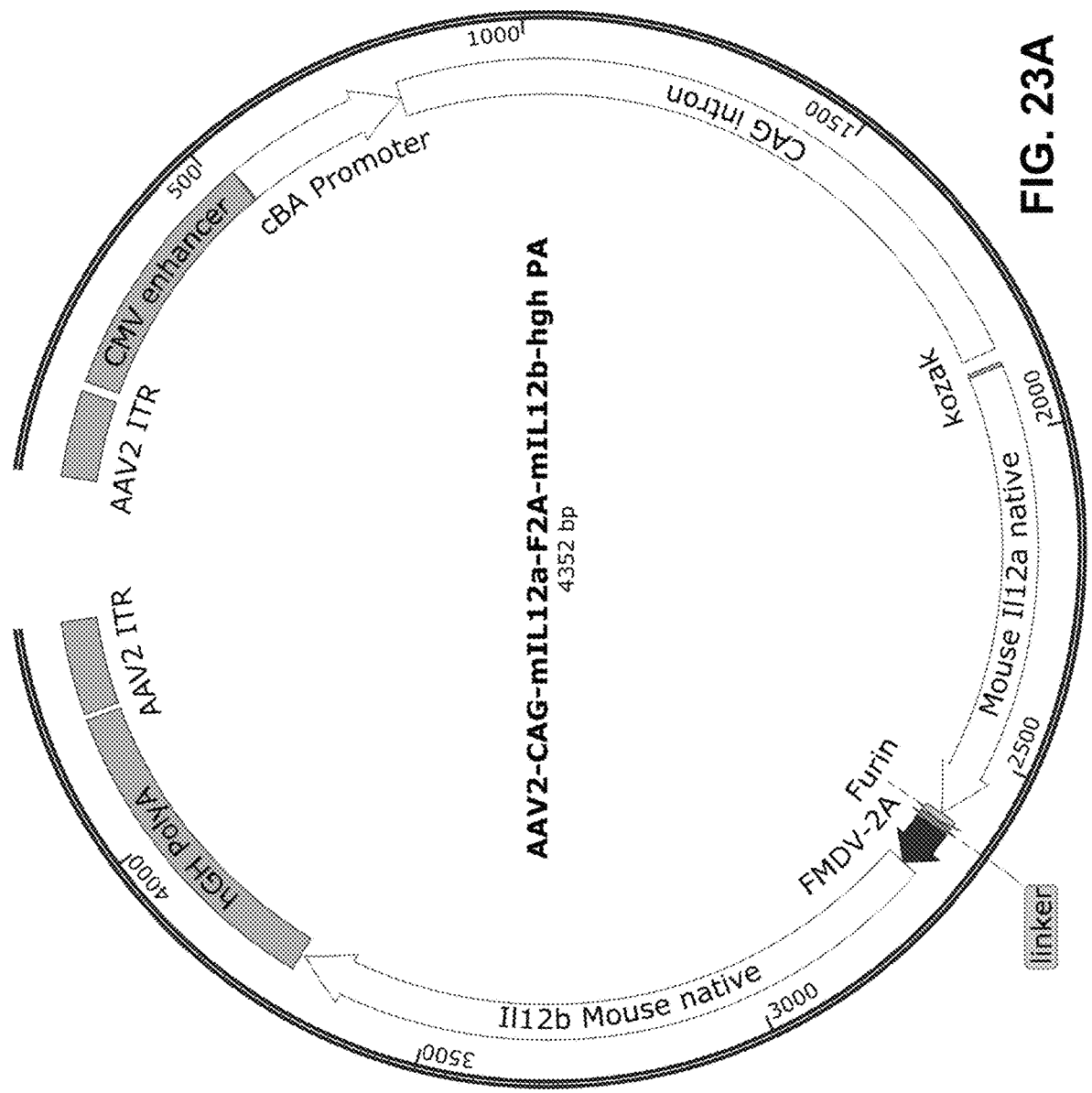

FIG. 23A shows an AAV2 construct designed with an expression cassette comprising a CMV enhancer, a CBA promoter, a CAG intron, a Kozak sequence, a first nucleic acid encoding a mouse native IL-12 p35 subunit, a furin cleavage sequence followed by a 2A self-processing peptide (F2A), a second nucleic acid encoding a mouse native IL-12 p40 subunit, and a human growth hormone (hGH) polyA signal sequence, which is flanked by ITR sequences ("AAV2-CAG-mIL12a-F2A-mIL12b-hgh PA").

Figure 23B:
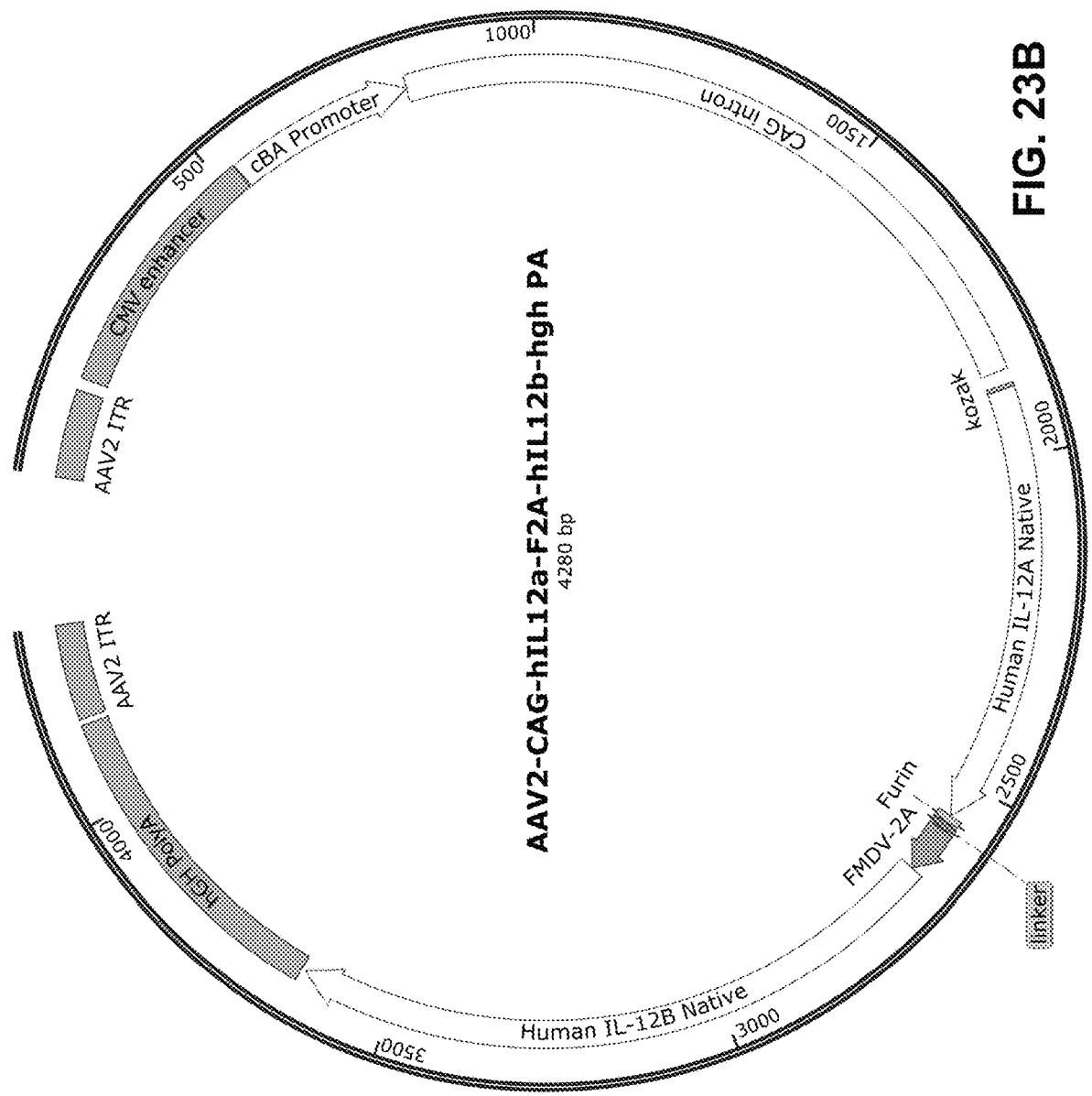

FIG. 23B shows an AAV2 construct designed with an expression cassette comprising a CMV enhancer, a CBA promoter, a CAG intron, a Kozak sequence, a first nucleic acid encoding a human native IL-12 p35 subunit, a furin cleavage sequence followed by a 2A self-processing peptide (F2A), a second nucleic acid encoding a human native IL-12 p40 subunit, and a human growth hormone (hGH) polyA signal sequence, which is flanked by ITR sequences ("AAV2-CAG-hIL12a-F2A-hIL12b-hgh PA").

DETAILED DESCRIPTION OF THE DISCLOSURE

Some aspects of the present disclosure are directed to compositions (e.g., gene therapy compositions) and/or combinations and methods comprising one or more viral vectors (e.g., an AAV vector) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof. In some aspects, each viral vector (e.g., AAV vector) comprises a polynucleotide (e.g., an expression cassette) comprising the first nucleic acid and the second nucleic acid. In some aspects, each delivery vector (e.g., viral vector) comprises either the first nucleic acid or the second nucleic acid, wherein two or more viral vectors (e.g., AAV vector) are delivered in combination (e.g., simultaneously or sequentially). In some aspects, the delivery vector comprises constructs comprising nucleic acids encoding a first immunomodulatory protein and the subunits of a second immunomodulatory protein.

In some aspects, the disclosure is directed to a composition comprising: (a) a polynucleotide (e.g., an expression cassette) comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector). In some aspects, the expression cassette comprises nucleic acids encoding a first immunomodulatory protein and the subunits of a second immunomodulatory protein.

In some aspects, the disclosure is directed to a polynucleotide (e.g., an expression cassette) comprising: (a) a first nucleic acid encoding a first cytokine, one or more subunits thereof, or functional fragment thereof; and (b) a second nucleic acid encoding a second cytokine, one or more subunits thereof, or functional fragment thereof.

In some aspects, the disclosure is directed to a composition comprising: (a) a polynucleotide comprising a first nucleic acid encoding a first immunomodulatory protein (e.g., a cytokine), one or more subunits thereof, or functional fragment thereof and a second nucleic acid encoding a second immunomodulatory protein (e.g., a cytokine), one or more subunits thereof, or functional fragment thereof; and (b) a delivery vector (e.g., a viral vector). Some aspects of the present disclosure are directed to a polynucleotide comprising: (a) a first nucleic acid encoding a first cytokine, one or more subunits thereof, or functional fragment thereof; and (b) a second nucleic acid encoding a second cytokine, one or more subunits thereof, or functional fragment thereof.

In some aspects, the disclosure is directed to an adeno-associated virus (AAV) capsid comprising one or more of the polynucleotides disclosed herein, wherein the AAV capsid is suitable for an intratumoral delivery of the nucleic acid(s) encoding immunomodulatory proteins (e.g., cytokines) disclosed herein.

In some aspects, the disclosure is directed to an adeno-associated virus (AAV) capsid comprising one or more of the polynucleotides disclosed herein, wherein the AAV capsid is suitable for an intravenous delivery of the nucleic acid(s) encoding immunomodulatory proteins (e.g., cytokines) disclosed herein.

In some aspects, the disclosure is directed to an adeno-associated virus (AAV) capsid comprising one or more of the polynucleotides disclosed herein, wherein the AAV capsid is suitable for a delivery of the nucleic acid(s) encoding immunomodulatory proteins (e.g., cytokines) disclosed herein to a lymphoid organ (e.g., a spleen, a lymph node, or a bone marrow).

In some aspects, the AAV capsid comprises an AAV serotype, wherein the AAV serotype is AAV2. In some aspects, the AAV is modified relative to the wild-type serotype.

Some aspects of the disclosure are directed to a method of expressing two or more immunomodulatory proteins, the subunits thereof, or functional fragments thereof in a subject in need thereof comprising administering an effective amount of the compositions (e.g., gene therapy compositions) or the AAV capsids disclosed herein to the subject. In some aspects, the administration is intratumoral. In some aspects, the administration is intravenous. In some aspects, the administration is intrasplenic. In some aspects, the administration is intrathecal. In some aspects, the administration is intrahepatic. In some aspects, the administration is intraosseous. In some aspects, the administration is into a lymph node. In some aspects, the administration is intradermal. In some aspects, the administration is intraparenchymalv. In some aspects, the administration is a delivery to salivary gland.

In some aspects, the expression is intratumoral. In some aspects, the composition is administered intratumorally by direct injection. In some aspects, the direct injection comprises multiple injections of the composition to the tumor. In some aspects, the administration is a single dose comprising one or more injections.

Some aspects of the disclosure are directed to a method of delivering nucleic acids encoding two or more immunomodulatory proteins, the subunits thereof, or functional fragments thereof to a tumor comprising administering the compositions (e.g., gene therapy compositions), the polynucleotides, or the AAV capsids disclosed herein, wherein the administration is to the tumor by direct injection.

Some aspects of the disclosure are directed to a method of treating or reducing symptoms in a subject suffering from a tumor comprising administering a composition (e.g., gene therapy composition), a polynucleotide, an expression cassette, or an AAV capsid (e.g., AAV2 particles) disclosed herein to the subject, wherein the administration is intratumoral, intravenous, intrasplenic, intrathecal, intrahepatic, intraosseous, intradermal, intraparenchymal, via delivery to salivary gland, or into a lymph node.

In some aspects, the subject suffers from a cancer selected from the group consisting of a skin cancer, a gastrointestinal cancer, breast cancer, brain cancer, or any combination thereof. In some aspects, cancer is selected from a group consisting of melanoma, colorectal cancer, breast cancer, glioblastoma multiforme, and any combination thereof.

In some aspects, the subject suffers from a cancer selected from the group consisting of skin cancer (e.g., metastatic melanoma, cutaneous malignant melanoma, cutaneous squamous cell carcinoma, basal cell carcinoma); breast cancer (e.g., invasive breast cancer, triple-negative breast cancer, inflammatory breast cancer); brain cancer (e.g., glioblastoma multiforme, medulloblastoma, pituitary carcinoma, brain stem gliomas, astrocytomas, oligodendrogliomas, hemangiopericytomas, germ cell tumors, pineal tumors); bone cancer (e.g., chordomas, chondrosarcomas, osteosarcomas, Ewing sarcomas, fibrosarcomas, adamantiomas, giant cell tumors); head and neck cancer (e.g., head and neck squamous cell carcinoma [HNSCC]; salivary gland cancer, oropharyngeal cancer, hypopharyngeal cancer, laryngeal cancer, lip and oral cavity cancer, nasopharyngeal cancer, thyroid cancer, cancer of the parathyroid gland, paranasal sinus and nasal cavity cancer); gynecologic cancer (e.g., ovarian cancer, uterine cancer, fallopian tube cancer, endometrial cancer, cervical cancer, vaginal cancer, vulvar cancer); urologic cancer (e.g., renal cancer, urethral cancer, urothelial cancer, bladder cancer, cancer of the kidney or ureter, cancer of the renal pelvis, testicular cancer, penile cancer, cancer of the adrenal gland); gastrointestinal cancer (e.g., cancer of the anal region, bile duct cancer, colon cancer, cancer of the small intestine, esophageal cancer, gallbladder cancer, gastrointestinal stromal tumors, liver cancer, pancreatic cancer, rectal cancer, stomach/gastric cancer); ocular cancer (e.g. uveal melanoma, retinoblastoma, Merkel cell carcinoma, intraocular malignant melanoma, mucosa-associated lymphoid tissue lymphoma, orbital lymphoma, orbital sarcoma, lacrimal gland tumors); thoracic cancer (e.g., non-small cell lung cancer, small cell lung cancer, mesothelioma, thymic malignancies, tracheal tumors, some esophageal cancer), leukemia (e.g., chronic or acute leukemia, acute myeloid leukemia (AML), chronic myeloid leukemia (CML), acute lymphoblastic leukemia (ALL) (including non-T cell ALL), chronic lymphocytic leukemia (CLL)), lymphoma (e.g., Hodgkin's lymphoma, non-Hodgkin's lymphoma (NHL), Waldenström macroglobulinaemia, primary mediastinal large B cell lymphoma (PMBC), diffuse large B cell lymphoma (DLBCL), follicular lymphoma (FL), transformed follicular lymphoma, splenic marginal zone lymphoma (SMZL), cutaneous T-cell lymphoma (CTCL), lymphocytic lymphoma, primary CNS lymphoma), other blood cancer (e.g., multiple myeloma), cancer of the endocrine system, sarcoma of soft tissue, neoplasm of the central nervous system (e.g., CNS; atypical teratoid/rhabdoid tumor, spinal axis tumor), tumor angiogenesis, Kaposi's sarcoma, epidermoid cancer, environmentally induced cancers including those induced by asbestos, other B cell malignancies, neuroblastoma (including olfactory neuroblastoma), rhabdomyosarcoma, and any combination thereof.

In some aspects, the constructs, polynucleotides, expression cassettes, delivery vectors, and compositions disclosed herein are designed to (a) introduce, eliminate, or reduce immunostimulatory motifs, (b) utilize optimal genome length, (c) reduce reverse packaging, (d) enhance expression in target tissues and/or cells, (e) reduce or increase CpG motifs, or (f) any combination thereof.

Non-limiting examples of the various aspects are shown in the present disclosure.

I. Definitions

In order that the present disclosure can be more readily understood, certain terms are first defined. Additional definitions are set forth throughout the detailed disclosure.

It is to be noted that the term "a" or "an" entity refers to one or more of that entity; for example, "a nucleic acid sequence," is understood to represent one or more nucleic acid sequences, unless stated otherwise. As such, the terms "a" (or "an"), "one or more," and "at least one" can be used interchangeably herein.

Furthermore, "and/or", where used herein, is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "at least" prior to a number or series of numbers is understood to include the number adjacent to the term "at least," and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range. "At least" is also not limited to integers (e.g., "at least 5%" includes 5.0%, 5.1%, 5.18% without consideration of the number of significant figures).

As used herein, "no more than" or "less than" is understood as the value adjacent to the phrase and logical lower values or integers, as logical from context, to zero. When "no more than" is present before a series of numbers or a range, it is understood that "no more than" can modify each of the numbers in the series or range.

As used herein, the term "immune response" refers to a biological response within an organism against a foreign agent or abnormal cell (e.g., a tumor cell), wherein the response protects the organism against such agents/cells and diseases caused by them. An immune response is mediated by the action of a cell of the immune system (e.g., a T lymphocyte (T cell), B lymphocyte (B cell), natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the organism's body of invading pathogens, cells or tissues infected with pathogens, cancerous or other abnormal cells, or, in cases of autoimmunity or pathological inflammation, normal human cells or tissues. In some aspects, an immune reaction includes, e.g., activation or inhibition of a T cell, e.g., an effector T cell or a Th cell, such as a $CD4^+$ or $CD8^+$ T cell, or the inhibition of a regulatory T cell (Treg cell).

As used herein, the term an "immunomodulatory protein," "immune modulator," "immunoregulatory protein," or "immunoregulator" refers to an agent, e.g., a component of a signaling pathway, that can be involved in stimulating, modulating, regulating, or modifying an immune response. "Modulating," "regulating," or "modifying" an immune response refers to any alteration in a cell of the immune system or in the activity of such cell (e.g., an effector T cell). Such modulation includes stimulation or suppression of the immune system which can be manifested by an increase or decrease in the number of various cell types, an increase or decrease in the activity of these cells, or any other changes which can occur within the immune system. Both inhibitory and stimulatory immunomodulators have been identified, some of which can have enhanced function in a tumor microenvironment. In some aspects, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets can include, for example, receptors on the surface of a cell ("immunomodulatory receptors") and receptor ligands ("immunomodulatory ligands"). In some aspects, the immunomodulatory protein is a cytokine. In some aspects, the immunomodulatory protein is a soluble natural killer (NK) cell, B lymphocyte cell, T lymphocyte cell, neutrophil, or macrophage ligand.

As used herein, the term "functional fragment thereof" refers to a fragment or portion of a protein, e.g., an immunomodulatory protein, that is still capable of one or functions associated with the full protein (e.g., stimulating, modulating, regulating, or modifying an immune response).

As used herein, the term "checkpoint inhibitor" refers to an inhibitor for a negative checkpoint regulator or an inhibitor for a binding partner of a negative checkpoint regulator. In some aspects, In certain aspects, the negative checkpoint regulator comprises programmed cell death protein 1 (PD-1), programmed death ligand 1 (PD-L1), cytotoxic T-lymphocyte-associated protein 4 (CTLA-4), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, inducible T-cell costimulatory (ICOS), B7-H3, or any combination thereof.

As used herein, the term "cytokine" refers to one or more factors that exert effects on cells, for example, influencing growth or proliferation. In some aspects, cytokines can possess one or more of the following properties: ability to mediate and/or regulate immune defense functions by acting as messengers between the various immune cells; functioning over short distances with a brief half-life; produced by a variety of cells types; ability to act on diverse cell targets within the immune system and/or on organs; ability to stimulate and/or inhibit growth; and/or directly or indirectly causing a cytokine cascade. In some aspects, cytokines can include interleukins, interferons, colony stimulating factors and tumour necrosis factor. Non-limiting examples of cytokines which can be used alone or in combination in the practice of the present disclosure include, tumor necrosis factor-α (TNFα), a type I interferon (IFN), a type II IFN, interleukin-2 (IL-2), interleukin-12 (IL-12), interleukin-15 (IL-15), interleukin-21 (IL-21), interleukin-23 (IL-23), interleukin-27 (IL-27), interleukin-18 (IL-18), IL-1, IL-3, IL-4, IL-5, IL-6, IL-7, IL-8, IL-9, IL-10, IL17, IL33, TL1A, CD40L, stem cell factor (SCF), interleukin-3 (IL-3), interleukin-4 (IL-4), interleukin-6 (IL-6), interleukin-11 (IL-11), interleukin-13 (IL-13), granulocyte-colony stimulating factor (G-CSF), granulocyte macrophage-colony stimulating factor (GM-CSF), interleukin-1 beta (IL-1B), prostaglandin E2 (PGE2), MIP-11, leukemia inhibitory factor (LIF), c-kit ligand, thrombopoietin (TPO) and flt3 ligand. It is intended, although not always explicitly stated, that molecules having similar biological activity as wild-type or purified cytokines (e.g., recombinantly produced cytokines, functional fragments, or muteins thereof) are intended to be used within the scope of the disclosure.

The term "subunit" refers to a polypeptide that can assemble with another polypeptide to form a complex (e.g., a heterodimer). In some aspects, the cytokine can comprise a single encoded polypeptide or multiple encoded polypeptide subunits (e.g., p35 and p40 subunits). For example, p35 subunit can be subunit alpha of interleukin 12 (also known as IL-12A, cytotoxic lymphocyte maturation factor p35, or interleukin-12 subunit p35). For example, p40 subunit can be subunit beta of interleukin 12 (also known as IL-12B, natural killer cell stimulatory factor 2, cytotoxic lymphocyte maturation factor p40, or interleukin-12 subunit p40).

A "heterodimer" refers to a polypeptide composed of two polypeptide chains differing in composition. For example, interleukin 12 is a heterodimer consisting of one p35 subunit and one p40 subunit.

The term "immunotherapy" refers to the treatment of a disease by inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease (e.g., cancer).

As used herein, the term "toll-like receptor 9 (TLR9)" a protein that in humans is encoded by the TLR9 gene. TLR9 has also been designated as CD289 (cluster of differentiation 289). It is a member of the toll-like receptor (TLR) family. TLR9 is a receptor expressed in immune system cells including dendritic cells, macrophages, natural killer cells, and other antigen presenting cells. TLR9 recognizes unmethylated bacterial CpG DNA and initiates a signaling cascade leading to the production of proinflammatory cytokines. See e.g., Martínez-Campos C, et al., *Viral Immunology*. 30(2):98-105 (2017); Notley C A et al., *Scientific Reports*. 7: 42204 (2017). The stimulatory effect of CpG DNA is conferred by unmethylated CpG dinucleotides in particular base contexts (CpG motifs) that also determine the species-specific activity of CpG DNA. CpG motifs containing the core sequence GACGTT highly stimulate mouse TLR9, whereas CpG motifs containing more than one CpG and the core sequence GTCGTT are optimal inducers of human TLR9. Cancer, infection, and tissue damage can all modulate TLR9 expression and activation. In some aspects, the nucleic acids, the constructs, polynucleotides, and/or expression cassettes disclosed herein comprise sequences with reduced or eliminated toll-like receptor 9 (TLR9) stimulatory motifs.

"Immunostimulating therapy" or "immunomodulatory therapy" refers to a therapy that results in increasing (inducing or enhancing) an immune response in a subject, e.g., for treating cancer.

As used herein, the term "delivery vector" or "vector" refers to any vehicle for the cloning of and/or transfer of a nucleic acid into a host cell, such as a plasmid, phage, transposon, cosmid, chromosome, artificial chromosome, virus, virion, etc. A vector can be a replicon to which another nucleic acid segment can be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "delivery vector" or "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini. Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), β-galactosidase (LacZ), ß-glucuronidase (Gus), and the like. Selectable markers can also be considered to be reporters. In some aspects, the delivery vector is selected from the group consisting of a viral vector (e.g., an AAV vector), a plasmid, a lipid, a protein particle, a bacterial vector, a lysosome, a virus-like particle, a polymeric particle, an exosome, or a vault particle.

Some aspects of the disclosure are directed to biological vectors, which can include viruses, particularly attenuated and/or replication-deficient viruses.

As used herein, the term "promoter" refers to a DNA sequence recognized by the machinery of the cell, or introduced synthetic machinery, required to initiate the transcription of a gene. The term "promoter" is also meant to encompass those nucleic acid elements sufficient for promoter-dependent gene expression controllable for cell-type specific, tissue-specific or inducible by external signals or agents; such elements can be located in the 5' or 3' regions of the native gene. In some aspects, the promoter is a constitutively active promoter, a cell-type specific promoter, or an inducible promoter.

In some aspects, microRNA targeting sequences are included to increase specificity of vector-mediated transgene expression. See e.g., Anja Geisler and Henry Fechner, World J Exp Med., 20; 6(2):37-54 (2016).

As used herein, the term "enhancer" is a cis-acting element that stimulates or inhibits transcription of adjacent genes. An enhancer that inhibits transcription is also referred to as a "silencer." Enhancers can function (e.g., can be associated with a coding sequence) in either orientation, over distances of up to several kilobase pairs (kb) from the coding sequence and from a position downstream of a transcribed region.

As used herein, the term "regulatable promoter" is any promoter whose activity is affected by a cis or trans acting factor (e.g., an inducible promoter, such as an external signal or agent).

As used herein, the term "constitutive promoter" is any promoter that directs RNA production in many or all tissue/cell types at most times, e.g., the human CMV immediate early enhancer/promoter region that promotes constitutive expression of cloned DNA inserts in mammalian cells.

The terms "transcriptional regulatory protein," "transcriptional regulatory factor," and "transcription factor" are used interchangeably herein, and refer to a nuclear protein that binds a DNA response element and thereby transcriptionally regulates the expression of an associated gene or genes. Transcriptional regulatory proteins generally bind directly to a DNA response element, however in some cases binding to DNA can be indirect by way of binding to another protein that in turn binds to, or is bound to a DNA response element.

As used herein, the term "termination signal sequence" can be any genetic element that causes RNA polymerase to terminate transcription, such as for example a polyadenylation (polyA or pA) signal sequence. A polyadenylation signal sequence is a recognition region necessary for endonuclease cleavage of an RNA transcript that is followed by the polyadenylation consensus sequence AATAAA. A polyadenylation signal sequence provides a "polyA site," i.e., a site on a RNA transcript to which adenine residues will be added by post-transcriptional polyadenylation.

As used herein, the term "multicistronic" or "multicistronic vector" refers to a nucleic acid sequence having two or more open reading frames (e.g., genes). An open reading frame in this context is a sequence of codons that is translatable into a polypeptide or protein (e.g. protein subunits, e.g., cytokine subunits). "Bicistronic" or "bicistronic vector" refers to a nucleic acid sequence having two open reading frames (e.g., genes). An open reading frame in this context is a sequence of codons that is translatable into a polypeptide or protein (e.g. protein subunits, e.g., cytokine subunits). In some aspects, the construct of the disclosure is a multicistronic (e.g., bicistronic) construct (e.g., comprising cytokine (e.g., IL-12) subunits).

As used herein, the term "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson R J et al., Trends Biochem Sci 15(12):477-83 (199); Jackson R J and Kaminski, A. RNA 1(10):985-1000 (1995). "Under translational control of an IRES" as used herein means that translation is associated with the IRES and proceeds in a cap-independent manner.

The term "self-processing cleavage site" or "self-processing cleavage sequence," as used herein refers to a post-translational or co-translational processing cleavage site or sequence. Such a "self-processing cleavage" site or sequence refers to a DNA or amino acid sequence, exemplified herein by a 2A site, sequence or domain or a 2A-like site, sequence or domain. Suitable 2A sites include the F2A, E2A, P2A or T2A self-processing sites. The term "self-processing peptide" is defined herein as the peptide expression product of the DNA sequence that encodes a self-processing cleavage site or sequence, which upon translation, mediates rapid intramolecular (cis) cleavage of a protein or polypeptide comprising the self-processing cleavage site to yield discrete mature protein or polypeptide products.

As used herein, the term "additional proteolytic cleavage site," refers to a sequence that is incorporated into an expression construct of the disclosure adjacent a self-processing cleavage site, such as a 2A or 2A like sequence, and provides a means to remove additional amino acids that remain following cleavage by the self-processing cleavage sequence. Exemplary "additional proteolytic cleavage sites" are described herein and include, but are not limited to, furin cleavage sites with the consensus sequence RXK(R)R (SEQ ID NO: 1).

Such furin cleavage sites can be cleaved by endogenous subtilisin-like proteases, such as furin and other serine proteases within the protein secretion pathway. In some aspects, other exemplary "additional proteolytic cleavage sites" can be used, as described in e.g., Lie et al., Sci Rep 7, 2193 (2017).

The terms "operatively linked," "operatively inserted," "operatively positioned," "under control" or "under transcriptional control" means that the promoter is in the correct location and orientation in relation to the nucleic acid to control RNA polymerase initiation and expression of the gene. In some aspects, the term "operably linked" means that a DNA sequence and a regulatory sequence(s) are connected in such a way as to permit gene expression when the appropriate molecules (e.g., transcriptional activator proteins) are bound to the regulatory sequence(s). In some aspects, the term "operably inserted" means that the DNA of interest introduced into the cell is positioned adjacent a DNA sequence which directs transcription and translation of the introduced DNA (i.e., facilitates the production of, e.g., a polypeptide encoded by a DNA of interest).

The term "expression vector", "expression construct" or "expression cassette" means any type of genetic construct containing a nucleic acid in which part or all of the nucleic acid encoding sequence is capable of being transcribed.

A "viral vector" refers to a sequence that comprises one or more polynucleotide regions encoding or comprising a molecule of interest, e.g., a protein, a peptide, and an oligonucleotide or a plurality thereof. Viral vectors can be used to deliver genetic materials into cells. Viral vectors can be modified for specific applications. In some aspects, the delivery vector of the disclosure is a viral vector selected from the group consisting of an adeno-associated viral (AAV) vector, an adenoviral vector, a lentiviral vector, or a retroviral vector.

The term "adeno-associated virus vector" or "AAV vector" as used herein refers to any vector that comprises or derives from components of an adeno-associated vector and is suitable to infect mammalian cells, preferably human cells. The term AAV vector typically designates an AAV-type viral particle or virion comprising a payload. The AAV vector can be derived from various serotypes, including combinations of serotypes (i.e., "pseudotyped" AAV) or from various genomes (e.g., single stranded or self-complementary). In addition, the AAV vector can be replication defective and/or targeted. As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAVrh8, AAVrh10, AAVrh.74, snake AAV, avian AAV, bovine AAV, canine AAV, equine AAV, ovine AAV, goat AAV, shrimp AAV, those AAV serotypes and clades disclosed by Gao et al. (J. Virol. 78:6381 (2004)) and Moris et al. (Virol. 33:375 (2004)), and any other AAV now known or later discovered. See, e.g., FIELDS et al. VIROLOGY, volume 2, chapter 69 (4th ed., Lippincott-Raven Publishers). In some aspects, an "AAV vector" includes a derivative of a known AAV vector. In some aspects, an "AAV vector" includes a modified or an artificial AAV vector. The terms "AAV genome", "AAV capsid", and "AAV vector" can be used interchangeably. In some aspects, the AAV vector is modified or mutated relative to the wild-type AAV serotype sequence.

As used herein, an "AAV particle" is an AAV virus that comprises an AAV vector having at least one payload region (e.g., a polynucleotide encoding a cytokine) and at least one inverted terminal repeat (ITR) region. In some aspects, the terms "AAV vectors of the present disclosure" or "AAV vectors" refer to AAV vectors comprising a polynucleotide encoding a cytokine, e.g., encapsulated in an AAV particle.

A "coding sequence" or a sequence "encoding" a particular molecule (e.g., a therapeutic molecule) is a nucleic acid that is transcribed (in the case of DNA) or translated (in the case of mRNA) into polypeptide, in vitro or in vivo, when operably linked to an appropriate regulatory sequence, such as a promoter. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the coding sequence.

The term "derived from," as used herein, refers to a component that is isolated from or made using a specified molecule or organism, or information (e.g., amino acid or nucleic acid sequence) from the specified molecule or organism. For example, a nucleic acid sequence (e.g., an AAV vector) that is derived from a second nucleic acid sequence (e.g., another AAV vector) can include a nucleotide sequence that is identical or substantially similar to the nucleotide sequence of the second nucleic acid sequence.

In the case of a polynucleotide disclosed herein, the derived species can be obtained by, for example, naturally occurring mutagenesis, artificial directed mutagenesis or artificial random mutagenesis. The mutagenesis used to derive polynucleotides can be intentionally directed or intentionally random, or a mixture of each. The mutagenesis of a polynucleotide to create a different polynucleotide derived from the first can be a random event (e.g., caused by polymerase infidelity) and the identification of the derived polynucleotide can be made by appropriate screening methods.

As used herein, the term "mutation" refers to any changing of the structure of a gene, resulting in a variant (also called "mutant") form that can be transmitted to subsequent generations. Mutations in a gene can be caused by the alternation of single base in DNA, or the deletion, insertion, or rearrangement of larger sections of genes or chromosomes.

As used herein, the term "administration" refers to the administration of a composition of the present disclosure (e.g., an AAV vector or a composition (e.g., gene therapy composition) disclosed herein) to a subject or system. Administration to an animal subject (e.g., to a human) can be by any appropriate route, such as direct injection into a tumor.

As used herein, the terms "re-administration," "repeat administration," and "redosing" refer to an administration of one or more additional dose(s) of a therapeutic agent, e.g., a gene therapy, a delivery construct, an AAV capsid, or a composition of the disclosure, following a first administration.

As used herein, the term "modified" refers to a changed state or structure of a molecule of the disclosure. Molecules can be modified in many ways including chemically, structurally, and functionally.

As used herein, the term "synthetic" means produced, prepared, and/or manufactured by the hand of man. Synthesis of polynucleotides or polypeptides or other molecules of the present disclosure can be chemical or enzymatic.

"Nucleic acid," "polynucleotide," and "oligonucleotide," are used interchangeably in the present application. These terms refer only to the primary structure of the molecule. Thus, these terms include double- and single-stranded DNA, as well as double- and single-stranded RNA. The terms "nucleic acid," "polynucleotide," and "oligonucleotide," as used herein, are defined as it is generally understood by the skilled person as a molecule comprising two or more covalently linked nucleosides. Such covalently bound nucleosides can also be referred to as nucleic acid molecules or oligomers. Polynucleotides can be made recombinantly, enzymatically, or synthetically, e.g., by solid-phase chemical synthesis followed by purification. When referring to a sequence of the polynucleotide or nucleic acid, reference is made to the sequence or order of nucleobase moieties, or modifications thereof, of the covalently linked nucleotides or nucleosides.

The term "mRNA," as used herein, refers to a single stranded RNA that encodes the amino acid sequence of one or more polypeptide chains.

The term "antisense," as used herein, refers to a nucleic acid that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides can hybridize to each other even if they are not completely complementary to each other, provided that each has at least one region that is substantially complementary to the other.

The terms "antisense strand" and "guide strand" refer to the strand of a dsRNA, e.g., an shRNA, that includes a region that is substantially complementary to a target sequence, e.g., mRNA. The antisense strand has sequence sufficiently complementary to the desired target mRNA sequence to direct target-specific silencing, e.g., complementarity sufficient to trigger the destruction of the desired target mRNA by the RNAi machinery or process.

The terms "sense strand" and "passenger strand," as used herein, refer to the strand of a dsRNA, e.g., an shRNA, that includes a region that is substantially complementary to a region of the antisense strand as that term is defined herein. The antisense and sense strands of a dsRNA, e.g., an shRNA, are hybridized to form a duplex structure.

As used herein, the term "polypeptide" is intended to encompass a singular "polypeptide" as well as plural "polypeptides," and comprises any chain or chains of two or more amino acids. Thus, as used herein, a "peptide," a "peptide subunit," a "protein," an "amino acid chain," an "amino acid sequence," or any other term used to refer to a chain or chains of two or more amino acids, are included in the definition of a "polypeptide," even though each of these terms can have a more specific meaning. The term "polypeptide" can be used instead of, or interchangeably with any of these terms. The term further includes polypeptides which have undergone post-translational or post-synthesis modifications, for example, conjugation of a palmitoyl group, glycosylation, acetylation, phosphorylation, amidation, derivatization by known protecting/blocking groups, proteolytic cleavage, or modification by non-naturally occurring amino acids. The term "peptide," as used herein encompasses full length peptides and fragments, variants or derivatives thereof. A "peptide" as disclosed herein, can be part of a fusion polypeptide comprising additional components such as, e.g., an Fc domain or an albumin domain, to increase half-life. A peptide as described herein can also be derivatized in a number of different ways. A peptide described herein can comprise modifications including e.g., conjugation of a palmitoyl group.

The term a "therapeutic agent" or "therapeutic molecule" includes a compound or molecule that, when present in an effective amount, produces a desired therapeutic effect, pharmacologic and/or physiologic effect on a subject in need thereof. It includes any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition. In some aspects, the therapeutic molecule is a immunomodulatory protein (e.g., a cytokine) or functional fragment thereof.

As used herein, the term "inhibitor" refers to any agent that reduces the level and/or activity of a protein. Non-limiting examples of inhibitors include dsRNA, e.g., siRNA or shRNA, and vectors, e.g., AAV, comprising polynucleotides encoding dsRNA, e.g., siRNA or shRNA. The term "reducing," as used herein, is used interchangeably with "silencing," "downregulating," "suppressing," and other similar terms, and includes any level of reduction.

The phrase "contacting a cell" (e.g., contacting a cell with an AAV vector, an AAV capsid, or the composition (e.g., gene therapy composition) of the disclosure) as used herein, includes contacting a cell directly or indirectly. In some aspects, contacting a cell with an AAV vector, an AAV capsid, or the composition (e.g., gene therapy composition) includes contacting a cell in vitro with the composition (e.g., gene therapy composition), the AAV vector, or the AAV capsid or contacting a cell in vivo with the AAV vector, the AAV capsid, or the composition (e.g., gene therapy composition). Thus, for example, the AAV vector, the AAV capsid, or the composition (e.g., gene therapy composition) can be put into physical contact with the cell by the individual performing the method, or alternatively, the AAV vector, the AAV capsid, or the composition (e.g., gene therapy composition) can be put into a situation that will permit or cause it to subsequently come into contact with the cell.

In some aspects, contacting a cell in vitro can be done, for example, by incubating the cell with the AAV vector. In some aspects, contacting a cell in vivo can be done, for example, by injecting the AAV vector, the AAV capsid, or the composition (e.g., gene therapy composition) of the disclosure into or near the tissue where the cell is located (e.g., a tumor), or by injecting the AAV vector, the AAV capsid, or the composition (e.g., gene therapy composition) into another area, e.g., the bloodstream or the subcutaneous space, such that the agent will subsequently reach the tissue where the cell to be contacted is located. For example, the AAV vector can be encapsulated and/or coupled to a ligand that directs the AAV vector to a site of interest. Combinations of in vitro and in vivo methods of contacting are also possible. For example, a cell can be contacted in vitro with an AAV vector, an AAV capsid, or the composition (e.g., gene therapy composition) and subsequently transplanted into a subject.

In some aspects, contacting a cell with an AAV vector, an AAV capsid, or the composition (e.g., gene therapy composition) of the present disclosure includes "introducing" or "delivering" (directly or indirectly) the AAV vector, the AAV capsid, or the composition (e.g., gene therapy composition) into the cell by facilitating or effecting uptake or absorption into the cell. Introducing an AAV vector, an AAV capsid, or the composition (e.g., gene therapy composition) into a cell can be in vitro and/or in vivo. For example, for in vivo introduction, an AAV vector, an AAV capsid, the composition (e.g., gene therapy composition) can be injected into a specific tissue site (e.g., the locus where a therapeutic effect is desired) or administered systemically (e.g., administering a AAV vector targeted to a locus where a therapeutic effect is desired). In vitro introduction into a cell includes methods known in the art such as electroporation and lipofection.

As used herein, the terms "effective amount," "therapeutically effective amount," and a "sufficient amount" of, e.g., an AAV vector, an AAV capsid, or the composition (e.g., gene therapy composition) disclosed herein refer to a quantity sufficient to, when administered to the subject, including a human, effect beneficial or desired results, including clinical results, and, as such, an "effective amount" or synonym thereto depends on the context in which it is being applied. In some aspects, a therapeutically effective amount of an agent (e.g., an AAV vector, an AAV capsid, the composition (e.g., gene therapy composition) disclosed herein) is an amount that results in a beneficial or desired result in a subject as compared to a control.

The amount of a given agent (e.g., an AAV vector, an AAV capsid, or the composition (e.g., gene therapy composition) disclosed herein) will correspond to such an amount will vary depending upon various factors, such as the given agent, the pharmaceutical formulation, the route of administration, the type of disease or disorder, the identity of the subject (e.g., age, sex, and/or weight) or host being treated, and the like.

As used herein, the term "gene therapy" is the insertion of nucleic acid sequences (e.g., a polynucleotide comprising a promoter operably linked to a nucleic acid encoding an immunomodulatory protein (e.g., a cytokine or subunit thereof) or functional fragment thereof as disclosed herein) into an individual's cells and/or tissues to treat, reduce the symptoms of, or reduce the likelihood of a disease. Gene therapy also includes insertion of transgene that are inhibitory in nature, i.e., that inhibit, decrease or reduce expression, activity or function of an endogenous gene or protein, such as an undesirable or aberrant (e.g., pathogenic) gene or protein. Such transgenes can be exogenous. An exogenous molecule or sequence is understood to be molecule or sequence not normally occurring in the cell, tissue and/or individual to be treated. Both acquired and congenital diseases are amenable to gene therapy.

The term "prophylactically effective amount," as used herein, includes the amount of an agent, (e.g., an AAV vector, an AAV capsid, or the composition (e.g., gene therapy composition) disclosed (herein) that, when administered to a subject having or predisposed to have a disease or disorder (e.g., a cancer), is sufficient to prevent, reduce the symptoms of, or ameliorate the disease or disorder or one or more symptoms of the disease or disorder. Ameliorating the disease or disorder includes slowing the course of the disease or disorder or reducing the severity of later-developing disease or disorder. The "prophylactically effective amount" can vary depending on the characteristics of the agent, e.g., an AAV vector, an AAV capsid, or the composition (e.g., gene therapy composition), how the agent is administered, the degree of risk of disease, and the history, age, weight, family history, genetic makeup, the types of preceding or concomitant treatments, if any, and other individual characteristics of the patient to be treated.

As used herein, "off target" refers to any unintended effect on any one or more target, gene, or cellular transcript.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "transfection" refers to methods to introduce exogenous nucleic acids into a cell. Methods of transfection include, but are not limited to, chemical methods, physical treatments and cationic lipids or mixtures. The list of agents that can be transfected into a cell is large and includes, e.g., siRNA, shRNA, sense and/or anti-sense sequences, DNA encoding one or more genes and organized into an expression plasmid, e.g., a vector.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values can be generated using the sequence comparison computer program BLAST.

By "level" is meant a level or activity of a protein, or mRNA encoding the protein, optionally as compared to a reference. The reference can be any useful reference, as defined herein. By a "decreased level" or an "increased level" of a protein is meant a decrease or increase in protein level, as compared to a reference.

A level of a protein can be expressed in mass/vol (e.g., g/dL, mg/mL, μg/mL, ng/mL) or percentage relative to total protein or mRNA in a sample.

The term "pharmaceutical composition," as used herein, represents a composition comprising a compound or molecule described herein, e.g., an AAV vector disclosed herein, formulated with a pharmaceutically acceptable excipient, and can be manufactured or sold with the approval of a governmental regulatory agency as part of a therapeutic regimen for the treatment of disease in a mammal.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient.

By a "reference" is meant any useful reference used to compare protein or mRNA levels or activity. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration.

As used herein, the term "subject" refers to any organism to which a composition disclosed herein, e.g., an AAV vector or composition (e.g., gene therapy composition) of the present disclosure, can be administered, e.g., for experimental, diagnostic, prophylactic, and/or therapeutic purposes. Typical subjects include any animal (e.g., mammals such as mice, rats, rabbits, non-human primates, and humans). A subject can seek or be in need of treatment, require treatment, be receiving treatment, be receiving treatment in the future, or be a human or animal who is under care by a trained professional for a particular disease or condition.

In some aspects, the human can be immunocompromised or immunodeficient. In some aspects, the human can be elderly. In some aspects, the human can be immunocompromised or imminodeficient and elderly.

A "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. In some aspects, the methods of the present disclosure can be used to reduce the tumor size of a tumor derived from, for example, skin cancer (e.g., metastatic melanoma, cutaneous malignant melanoma, cutaneous squamous cell carcinoma, basal cell carcinoma); breast cancer (e.g., invasive breast cancer, triple-negative breast cancer, inflammatory breast cancer); brain cancer (e.g., glioblastoma multiforme, medulloblastoma, pituitary carcinoma, brain stem gliomas, astrocytomas, oligodendrogliomas, hemangiopericytomas, germ cell tumors, pineal tumors); bone cancer (e.g., chordomas, chondrosarcomas, osteosarcomas, Ewing sarcomas, fibrosarcomas, adamantiomas, giant cell tumors); head and neck cancer (e.g., head and neck squamous cell carcinoma [HN-SCC]; salivary gland cancer, oropharyngeal cancer, hypopharyngeal cancer, laryngeal cancer, lip and oral cavity cancer, nasopharyngeal cancer, thyroid cancer, cancer of the parathyroid gland, paranasal sinus and nasal cavity cancer); gynecologic cancer (e.g., ovarian cancer, uterine cancer, fallopian tube cancer, endometrial cancer, cervical cancer, vaginal cancer, vulvar cancer); urologic cancer (e.g., renal cancer, urethral cancer, urothelial cancer, bladder cancer, cancer of the kidney or ureter, cancer of the renal pelvis, testicular cancer, penile cancer, cancer of the adrenal gland); gastrointestinal cancer (e.g., cancer of the anal region, bile duct cancer, colon cancer, cancer of the small intestine, esophageal cancer, gallbladder cancer, gastrointestinal stromal tumors, liver cancer, pancreatic cancer, rectal cancer, stomach/gastric cancer); ocular cancer (e.g. uveal melanoma, retinoblastoma, Merkel cell carcinoma, intraocular malignant melanoma, mucosa-associated lymphoid tissue lymphoma, orbital lymphoma, orbital sarcoma, lacrimal gland tumors); thoracic cancer (e.g., non-small cell lung cancer, small cell lung cancer, mesothelioma, thymic malignancies, tracheal tumors, some esophageal cancer), leukemia (e.g., chronic or acute leukemia, acute myeloid leukemia (AML), chronic myeloid leukemia (CML), acute lymphoblastic leukemia (ALL) (including non-T cell ALL), chronic lymphocytic leukemia (CLL)), lymphoma (e.g., Hodgkin's lymphoma, non-Hodgkin's lymphoma (NHL), Waldenström macroglobulinaemia, primary mediastinal large B cell lymphoma (PMBC), diffuse large B cell lymphoma (DLBCL), follicular lymphoma (FL), transformed follicular lymphoma, splenic marginal zone lymphoma (SMZL), cutaneous T-cell lymphoma (CTCL), lymphocytic lymphoma, primary CNS lymphoma), other blood cancer (e.g., multiple myeloma), cancer of the endocrine system, sarcoma of soft tissue, neoplasm of the central nervous system (e.g., CNS; atypical teratoid/rhabdoid tumor, spinal axis tumor), tumor angiogenesis, Kaposi's sarcoma, epidermoid cancer, environmentally induced cancers including those induced by asbestos, other B cell malignancies, neuroblastoma (including olfactory neuroblastoma), rhabdomyosarcoma, and any combination of said cancers.

The term "tumor" as used herein refers to any mass of tissue that results from excessive cell growth or proliferation, either benign (non-cancerous) or malignant (cancerous), including pre-cancerous lesions.

The term a "lymphoid organ" as used herein refers to primary lymphoid organs, which include the bone marrow and the thymus and secondary lymphoid organs, which include the lymph nodes, the spleen, the tonsils and certain tissue in various mucous membrane layers in the body (for instance in the bowel).

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. In some aspects, treating reduces or lessens the symptoms associated with a disease or disorder. In some aspects, the treating results in a beneficial or desired clinical result.

Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. In some aspects, treatment includes eliciting a clinically significant response without excessive levels of side effects. In some aspects, treatment includes prolonging survival as compared to expected survival if not receiving treatment. As used herein, the term "amelioration" or "ameliorating" refers to a lessening of severity of at least one indicator of a condition or disease. As used herein, the term "preventing" or "prevention" refers to delaying or forestalling the onset, development or progression of a condition or disease for a period of time, including weeks, months, or years.

II. Immunomodulatory Proteins and Polynucleotides of Interest

The present disclosure provides compositions, e.g., gene therapy compositions, comprising a polynucleotide comprising a nucleic acid encoding an immunomodulatory protein, one or more subunits thereof, or functional fragment thereof. In some aspects, the immunomodulatory protein is a cytokine, or a soluble natural killer (NK) cell, B cell, T cell, neutrophil, or macrophage ligand, or any combination thereof. In some aspects, the immunomodulatory protein is a cytokine. In some aspects, the immunomodulatory protein is a soluble natural killer (NK) cell, B cell, T cell neutrophil, or macrophage ligand.

Cytokines

Cytokines are proteinaceous signaling compounds that are mediators of the immune response. They control many different cellular functions including proliferation, differentiation and cell survival/apoptosis. Cytokines are also involved in several pathophysiological processes including viral infections and autoimmune diseases. Cytokines are synthesized under various stimuli by a variety of cells, including those of both the innate (monocytes, macrophages, dendritic cells) and adaptive (T and B cells) immune systems.

Table 1 shows a classification of cytokine receptor families.

TABLE 1

| Classification of Cytokine Receptor Families | | |
|---|---|---|
| Receptor Family | Ligands | Structure/Function |
| Type I Cytokine Receptors | IL-2 | Composed of multimeric chains. Signals through JAK-STAT pathway using common signaling chain. Contains cytokine binding chains. |
| | IL-3 | |
| | IL-4 | |
| | IL-5 | |
| | IL-6 | |
| | IL-7 | |
| | IL-9 | |

TABLE 1-continued

Classification of Cytokine Receptor Families

| Receptor Family | Ligands | Structure/Function |
|---|---|---|
| | IL-11 | |
| | IL-12 | |
| | IL-13 | |
| | IL-15 | |
| | IL-21 | |
| | IL-23 | |
| | IL-27 | |
| | IL-33 | |
| Type I Cytokine Receptors | Erythropoietin GM-CSF G-CSF Growth hormone Prolactin Oncostatin M Leukemia inhibitory factor | Composed of multimeric chains. Signals through JAK-STAT pathway using common signaling chain. Contains cytokine binding chains. |
| Type II Cytokine Receptors | IFN-α/β IFN-ψ IL-10 IL-20 IL-22 IL-28 | Immunoglobulin-like domains. Uses heterodimer and multimeric chains. Signals through JAK-STAT. |
| Immunoglobulin Superfamily Receptors | IL-1 CSF1 c-kit IL-18 | Shares homology with immunoglobulin structures. |
| IL-17 Receptor | IL-17 IL-17B IL-17C IL-17D IL-17E IL-17F | |
| G Protein-Coupled Receptors (GPCR) | IL-8 CC chemokines CXC chemokine | Functions to mediate cell activation and migration. |
| TGF-β receptors ½ | TGF-β | |
| Tumor Necrosis Factor Receptors (TNFR) | CD27 CD30 CD40 CD120 Lymphotoxin-β | Functions as co-stimulatory and co-inhibitory receptors. |

CD - cluster of differentiation;
c-kit - mast/stem cell growth factor receptor;
CSF - colony-stimulating factor;
G-CSF - granulocyte-colony stimulating factor;
GM-CSF - granulocyte-macrophage colony stimulating factor;
IL - interleukin;
JAK - janus kinase;
STAT - signal transducer and activator of transcription;
TGF - transforming growth factor. See e.g., Lee S. et al., Cancers, 3:3856-3893 (2011).

In some aspects, the present disclosure is directed to a nucleic acid encoding a cytokine selected from any of the cytokines show in Table 1 or a nucleic acid encoding one or more subunits of a cytokine selected from any of the multi-subunit (e.g., heterodimeric) cytokines show in Table 1.

The present disclosure provides compositions (e.g., gene therapy compositions) and AAV vectors comprising a polynucleotide comprising a first nucleic acid encoding a first cytokine, one or more subunits thereof, or functional fragment thereof and/or a second nucleic acid encoding a second cytokine, one or more subunits thereof, or functional fragment thereof. In some aspects, the composition (e.g., gene therapy composition) comprises a multicistronic (e.g., bicistronic) construct (e.g., comprising cytokine (e.g., IL-12) subunits).

In some aspects, provided herein is a composition (e.g., a gene therapy composition) comprising: (a) a polynucleotide comprising a nucleic acid encoding an immunomodulatory protein, one or more subunits thereof, or functional fragment thereof (e.g., a cytokine or one or more subunits thereof); and (b) a delivery vector (e.g., an AAV capsid).

In some aspects, the cytokine is full-length, a functional fragment of a cytokine, or a functional variant of a cytokine, e.g., a cytokine comprising one or more mutations. In some aspects, the cytokine is a heterodimeric cytokine composed of more than one subunit. In some aspects, the cytokine molecule can be a monomer or a dimer. In some aspects, the cytokine molecule further comprises a receptor domain, e.g., a cytokine receptor domain.

In some aspects, the cytokine is selected from the group consisting of tumor necrosis factor alpha (TNF-α), a type I interferon (INF), a type II IFN, interleukin (IL)-2, IL-12, IL-15, IL-21, IL-23, IL-27, IL-18, IL-1, IL-3, IL-4, IL-5, IL-6, IL-7, IL-8, IL-9, IL-10, IL17, IL33, TL1A, CD40L, granulocyte-macrophage colony-stimulating factor (GM-CSF), any functional fragment thereof, and any combination thereof.

IFN-γ can promote Treg fragility, and can reduce suppression in the tumor microenvironment. IL-21 and IL-23 can induce Tregs to produce pro-inflammatory IL-17 and/or convert Tregs to T helper 17 cells (Th17) T cell subset. IL-12 promotes IFN-γ production in Tregs, leading Treg fragility and a general pro-immunogenic environment. TNF-α both impairs Treg development and reduces the function of existing Tregs. Thus, these cytokines can impair Treg development, reduce Treg function, or induce Treg trans-differentiation into the immune activating cells. In the context of cancer, it is desired to reduce Treg activity. See e.g., Int'l Publ. No. WO2019/010219.

The present disclosure also provides a polynucleotide comprising: (a) a first nucleic acid encoding a first cytokine subunit or functional fragment thereof; and (b) a second nucleic acid encoding a second cytokine subunit or functional fragment thereof.

The present disclosure also provides a polynucleotide comprising: (a) a first nucleic acid encoding a first cytokine, one or more subunits thereof, or functional fragment thereof; and (b) a second nucleic acid encoding a second cytokine, one or more subunits thereof, or functional fragment thereof.

In some aspects, the first cytokine is IL-12, IL-18, IL-21, or a functional fragment thereof. In some aspects, the first nucleic acid comprises an IL-12 p35 gene and/or an IL-12 p40 gene. In some aspects, the first cytokine is IL-12 or a functional fragment thereof. In some aspects, the first nucleic acid comprises a nucleic acid encoding an IL-12 p35 subunit and/or a nucleic acid encoding an IL-12 p40 subunit.

In some aspects, the first nucleic acid (e.g., nucleic acid encoding an IL-12 p35 subunit and/or the nucleic acid encoding an IL-12 p40 subunit) does not include an in-frame stop codon (e.g., TGA, TAG, and TAA).

In some aspects, the first nucleic acid comprises a nucleic acid sequence having at least 85%, 90%, 95%, 96%, 97%, 98%, 99%, or 100% identity to SEQ ID NOs: 5-10, 77, 92, or any nucleic acid sequence shown in Table 2, or any combination thereof. In some aspects, the first nucleic acid comprises a nucleic acid sequence having at least 85%, 90%, 95%, 96%, 97%, 98%, 99%, or 100% identity to a reverse complement of SEQ ID NOs: 5-10, 77, 92, or any nucleic acid sequence shown in Table 2, or any combination thereof.

In some aspects, the polynucleotide of the disclosure comprises one or more nucleic acids comprising a nucleic acid sequence having at least 85%, 90%, 95% 96%, 97%, 98%, 99%, or 100% identity to SEQ ID NOs: 5-10, 77, 92, or any nucleic acid sequence shown in Table 2, or any combination thereof. In some aspects, the polynucleotide of the disclosure comprises one or more nucleic acids comprising a nucleic acid sequence having at least 85%, 90%, 95% 96%, 97%, 98%, 99%, or 100% identity to a reverse complement of SEQ ID NOs: 5-10, 77, 92, or any nucleic acid sequence shown in Table 2, or any combination thereof.

TABLE 2

IL-12 Nucleic Acid Sequences

| IL-12 | IL-12 Nucleic Acid Sequence (SEQ ID NO) |
|---|---|
| Human IL-12A (p35) ("wild-type" no CpG modification) | ATGTGTCCAGCGCGC AGCCTCCTCCTTGTG GCTACCCTGGTCCTC CTGGACCACCTCAGT TTGGCCAGAAACCTC CCCGTGGCCACTCCA GACCCAGGAATGTTC CCATGCCTTCACCAC TCCCAAAACCTGCTG AGGGCCGTCAGCAAC ATGCTCCAGAAGGCC AGACAAACTCTAGAA TTTTACCCTTGCACT TCTGAAGAGATTGAT CATGAAGATATCACA AAAGATAAAACCAGC ACAGTGGAGGCCTGT TTACCATTGGAATTA ACCAAGAATGAGAGT TGCCTAAATTCCAGA GAGACCTCTTTCATA ACTAATGGGAGTTGC CTGGCCTCCAGAAAG ACCTCTTTTATGATG GCCCTGTGCCTTAGT AGTATTTATGAAGAC TTGAAGATGTACCAG GTGGAGTTCAAGACC ATGAATGCAAAGCTT CTGATGGATCCTAAG AGGCAGATCTTTCTA GATCAAAACATGCTG GCAGTTATTGATGAG CTGATGCAGGCCCTG AATTTCAACAGTGAG ACTGTGCCACAAAAA TCCTCCCTTGAAGAA CCGGATTTTTATAAA ACTAAAATCAAGCTC TGCATACTTCTTCAT GCTTTCcggATTCGG GCAGTGACTATTGAT AGAGTGATGAGCTAT CTGAATGCTTCCTGA (SEQ ID NO: 5) |
| Human IL-12A (p35) ("wild-type" no CpG modification and no in-frame stop codon) | ATGTGTCCAGCGCGC AGCCTCCTCCTTGTG GCTACCCTGGTCCTC CTGGACCACCTCAGT TTGGCCAGAAACCTC CCCGTGGCCACTCCA GACCCAGGAATGTTC CCATGCCTTCACCAC TCCCAAAACCTGCTG AGGGCCGTCAGCAAC ATGCTCCAGAAGGCC AGACAAACTCTAGAA TTTTACCCTTGCACT TCTGAAGAGATTGAT CATGAAGATATCACA AAAGATAAAACCAGC ACAGTGGAGGCCTGT TTACCATTGGAATTA ACCAAGAATGAGAGT TGCCTAAATTCCAGA GAGACCTCTTTCATA ACTAATGGGAGTTGC CTGGCCTCCAGAAAG |

TABLE 2-continued

IL-12 Nucleic Acid Sequences

| IL-12 | IL-12 Nucleic Acid Sequence (SEQ ID NO) |
|---|---|
| | ACCTCTTTTATGATG GCCCTGTGCCTTAGT AGTATTTATGAAGAC TTGAAGATGTACCAG GTGGAGTTCAAGACC ATGAATGCAAAGCTT CTGATGGATCCTAAG AGGCAGATCTTTCTA GATCAAAACATGCTG GCAGTTATTGATGAG CTGATGCAGGCCCTG AATTTCAACAGTGAG ACTGTGCCACAAAAA TCCTCCCTTGAAGAA CCGGATTTTTATAAA ACTAAAATCAAGCTC TGCATACTTCTTCAT GCTTTCcggATTCGG GCAGTGACTATTGAT AGAGTGATGAGCTAT CTGAATGCTTCC (SEQ ID NO: 77) |
| Human IL-12A (p35) (with CpG modification) | ATGTGTCCAGCGCGC AGCCTCCTCCTTGTG GCTACCCTGGTCCTC CTGGACCACCTCAGT TTGGCCAGAAACCTC CCTGTGGCCACTCCA GACCCAGGAATGTTC CCATGCCTTCACCAC TCCCAAAACCTGCTG AGGGCTGTCAGCAAC ATGCTCCAGAAGGCC AGACAAACTCTAGAA TTTTACCCTTGCACT TCTGAAGAGATTGAT CATGAAGATATCACA AAAGATAAAACCAGC ACAGTGGAGGCCTGT TTACCATTGGAATTA ACCAAGAATGAGAGT TGCCTAAATTCCAGA GAGACCTCTTTCATA ACTAATGGGAGTTGC CTGGCCTCCAGAAAG ACCTCTTTTATGATG GCCCTGTGCCTTAGT AGTATTTATGAAGAC TTGAAGATGTACCAG GTGGAGTTCAAGACC ATGAATGCAAAGCTT CTGATGGATCCTAAG AGGCAGATCTTTCTA GATCAAAACATGCTG GCAGTTATTGATGAG CTGATGCAGGCCCTG AATTTCAACAGTGAG ACTGTGCCACAAAAA TCCTCCCTTGAAGAA CCTGATTTTTATAAA ACTAAAATCAAGCTC TGCATACTTCTTCAT GCTTTCcggATTCGC GCAGTGACTATTGAT AGAGTGATGAGCTAT CTGAATGCTTCCTGA (SEQ ID NO: 6) |
| Human IL-12A (p35) (with CpG modification) | ATGTGTCCAGCTAGG AGCCTCCTCCTTGTG GCTACCCTGGTCCTC CTGGACCACCTCAGT TTGGCCAGAAACCTC CCTGTGGCCACTCCA |

TABLE 2-continued

IL-12 Nucleic Acid Sequences

| IL-12 | IL-12 Nucleic Acid Sequence (SEQ ID NO) |
|---|---|
| | GACCCAGGAATGTTC |
| | CCATGCCTTCACCAC |
| | TCCCAAAACCTGCTG |
| | AGGGCAGTCAGCAAC |
| | ATGCTCCAGAAGGCC |
| | AGACAAACTCTAGAA |
| | TTTTACCCTTGCACT |
| | TCTGAAGAGATTGAT |
| | CATGAAGATATCACA |
| | AAAGATAAAACCAGC |
| | ACAGTGGAGGCCTGT |
| | TTACCATTGGAATTA |
| | ACCAAGAATGAGAGT |
| | TGCCTAAATTCCAGA |
| | GAGACCTCTTTCATA |
| | ACTAATGGGAGTTGC |
| | CTGGCCTCCAGAAAG |
| | ACCTCTTTTATGATG |
| | GCCCTGTGCCTTAGT |
| | AGTATTTATGAAGAC |
| | TTGAAGATGTACCAG |
| | GTGGAGTTCAAGACC |
| | ATGAATGCAAAGCTT |
| | CTGATGGATCCTAAG |
| | AGGCAGATCTTTCTA |
| | GATCAAAACATGCTG |
| | GCAGTTATTGATGAG |
| | CTGATGCAGGCCCTG |
| | AATTTCAACAGTGAG |
| | ACTGTGCCACAAAAA |
| | TCCTCCCTTGAAGAA |
| | CCTGATTTTTATAAA |
| | ACTAAAATCAAGCTC |
| | TGCATACTTCTTCAT |
| | GCTTTCcggATTAGG |
| | GCAGTGACTATTGAT |
| | AGAGTGATGAGCTAT |
| | CTGAATGCTTCCTGA |
| | (SEQ ID NO: 7) |
| Human IL-12B (p40) ("wild-type" no CpG modification and with stop codon) | ATGTGTCACCAGCAG |
| | TTGGTCATCTCTTGG |
| | TTTTCCCTGGTTTTT |
| | CTGGCATCTCCCCTC |
| | GTGGCCATATGGGAA |
| | CTGAAGAAAGATGTT |
| | TATGTCGTAGAATTG |
| | GATTGGTATCCGGAT |
| | GCCCCTGGAGAAATG |
| | GTGGTCCTCACCTGT |
| | GACACCCCTGAAGAA |
| | GATGGTATCACCTGG |
| | ACCTTGGACCAGAGC |
| | AGTGAGGTCTTAGGC |
| | TCTGGCAAACCCTG |
| | ACCATCCAAGTCAAA |
| | GAGTTTGGAGATGCT |
| | GGCCAGTACACCTGT |
| | CACAAAGGAGGCGAG |
| | GTTCTAAGCCATTCG |
| | CTCCTGCTGCTTCAC |
| | AAAAGGAAGATGGA |
| | ATTTGGTCCACTGAT |
| | ATTTTAAAGGACCAG |
| | AAAGAACCCAAAAAT |
| | AAGACCTTTCTAAGA |
| | TGCGAGGCCAAGAAT |
| | TATTCTGGACGTTTC |
| | ACCTGCTGGTGGCTG |
| | ACGACAATCAGTACT |
| | GATTTGACATTCAGT |
| | GTCAAAAGCAGCAGA |
| | GGCTCTTCTGACCCC |
| | CAAGGGGTGACGTGC |
| | GGAGCTGCTACACTC |

| IL-12 | IL-12 Nucleic Acid Sequence (SEQ ID NO) |
|---|---|
| | TCTGCAGAGAGAGTC |
| | AGAGGGGACAACAAG |
| | GAGTATGAGTACTCA |
| | GTGGAGTGCCAGGAG |
| | GACAGTGCCTGCCCA |
| | GCTGCTGAGGAGAGT |
| | CTGCCCATTGAGGTg |
| | ATGGTGGATGCCGTT |
| | CACAAGCTCAAGTAT |
| | GAAAACTACACCAGC |
| | AGCTTCTTCATCAGG |
| | GACATCATCAAACCT |
| | GACCCACCCAAGAAC |
| | TTGCAGCTGAAGCCA |
| | TTAAAGAATTCTCGG |
| | CAGGTGGAGGTCAGC |
| | TGGGAGTACCCTGAC |
| | ACCTGGAGTACTCCA |
| | CATTCCTACTTCTCC |
| | CTGACATTCTGCGTT |
| | CAaGTCAGGGCAAG |
| | AGCAAGAGAGAAAAG |
| | AAAGATAGAGTCTTC |
| | ACGGACAAGACCTCA |
| | GCCACGGTCATCTGC |
| | CGCAAAAATGCCAGC |
| | ATTAGCGTGCGGGCC |
| | CAGGACCGCTACTAT |
| | AGCTCATCTTGGAGC |
| | GAATGGGCATCTGTG |
| | CCCTGCAGTTGA |
| | (SEQ ID NO: 8) |
| Human IL-12B (p40) (with CpG modification) | TGTGTCACCAGCAGT |
| | TGGTCATCTCTTGGT |
| | TTTCCCTGGTTTTTC |
| | TGGCATCTCCCCTTG |
| | TGGCCATATGGGAAC |
| | TGAAGAAAGATGTTT |
| | ATGTGGTAGAATTGG |
| | ATTGGTATCCTGATG |
| | CCCCTGGAGAAATGG |
| | TGGTCCTCACCTGTG |
| | ACACCCCTGAAGAAG |
| | ATGGTATCACCTGGA |
| | CCTTGGACCAGAGCA |
| | GTGAGGTCTTAGGCT |
| | CTGGCAAACCCTGA |
| | CCATCCAAGTCAAAG |
| | AGTTTGGAGATGCTG |
| | GCCAGTACACCTGTC |
| | ACAAAGGAGGGGAGG |
| | TTCTAAGCCATTCCC |
| | TCCTGCTGCTTCACA |
| | AAAAGGAAGATGGAA |
| | TTTGGTCCACTGATA |
| | TTTTAAAGGACCAGA |
| | AAGAACCCAAAAATA |
| | AGACCTTTCTAAGAT |
| | GTGAGGCCAAGAATT |
| | ATTCTGGAAGGTTCA |
| | CCTGCTGGTGGCTGA |
| | CTACAATCAGTACTG |
| | ATTTGACATTCAGTG |
| | TCAAAAGCAGCAGAG |
| | GCTCTTCTGACCCCC |
| | AAGGGGTGACATGCG |
| | GAGCTGCTACACTCT |
| | CTGCAGAGAGAGTCA |
| | GAGGGGACAACAAGG |
| | AGTATGAGTACTCAG |
| | TGGAGTGCCAGGAGG |
| | ACAGTGCCTGCCCAG |
| | CTGCTGAGGAGAGTC |
| | TGCCCATTGAGGTgA |

TABLE 2-continued

IL-12 Nucleic Acid Sequences

| IL-12 | IL-12 Nucleic Acid Sequence (SEQ ID NO) |
|---|---|
| | TGGTGGATGCGGTTC<br>ACAAGCTCAAGTATG<br>AAAACTACACCAGCA<br>GCTTCTTCATCAGGG<br>ACATCATCAAACCTG<br>ACCCACCCAAGAACT<br>TGCAGCTGAAGCCAT<br>TAAAGAATTCTAGGC<br>AGGTGGAGGTCAGCT<br>GGGAGTACCCTGACA<br>CCTGGAGTACTCCAC<br>ATTCCTACTTCTCCC<br>TGACATTCTGTGTTC<br>AaGTCCAGGGCAAGA<br>GCAAGAGAGAAAAGA<br>AAGATAGAGTCTTCA<br>CTGACAAGACCTCAG<br>CCACAGTCATCTGCC<br>GCAAAAATGCCAGCA<br>TTTCAGTGCGGGCCC<br>AGGACCGCTACTATA<br>GCTCATCTTGGTCAG<br>AATGGGCATCTGTGC<br>CCTGCAGTTGA<br>(SEQ ID NO: 9) |
| Human IL-12B (p40) (with CpG modification) | ATGTGTCACCAGCAG<br>TTGGTCATCTCTTGG<br>TTTTCCCTGGTTTTT<br>CTGGCATCTCCCCTT<br>GTGGCCATATGGGAA<br>CTGAAGAAAGATGTT<br>TATGTGGTAGAATTG<br>GATTGGTATCCTGAT<br>GCCCCTGGAGAAATG<br>GTGGTCCTCACCTGT<br>GACACCCCTGAAGAA<br>GATGGTATCACCTGG<br>ACCTTGGACCAGAGC<br>AGTGAGGTCTTAGGC<br>TCTGGCAAAACCCTG<br>ACCATCCAAGTCAAA<br>GAGTTTGGAGATGCT<br>GGCCAGTACACCTGT<br>CACAAAGGAGGGGAG<br>GTTCTAAGCCATTCC<br>CTCCTGCTGCTTCAC<br>AAAAAGGAAGATGGA<br>ATTTGGTCCACTGAT<br>ATTTTAAAGGACCAG<br>AAAGAACCCAAAAAT<br>AAGACCTTTCTAAGA<br>TGTGAGGCCAAGAAT<br>TATTCTGGAAGGTTC<br>ACCTGCTGGTGGCTG<br>ACTACAATCAGTACT<br>GATTTGACATTCAGT<br>GTCAAAAGCAGCAGA<br>GGCTCTTCTGACCCC<br>CAAGGGGTGACATGT<br>GGAGCTGCTACACTC<br>TCTGCAGAGAGTC<br>AGAGGGGACAACAAG<br>GAGTATGAGTACTCA<br>GTGGAGTGCCAGGAG<br>GACAGTGCCTGCCCA<br>GCTGCTGAGGAGAGT<br>CTGCCCATTGAGGTg<br>ATGGTGGATGCAGTT<br>CACAAGCTCAAGTAT<br>GAAAACTACACCAGC<br>AGCTTCTTCATCAGG<br>GACATCATCAAACCT<br>GACCCACCCAAGAAC<br>TTGCAGCTGAAGCCA |

| IL-12 | IL-12 Nucleic Acid Sequence (SEQ ID NO) |
|---|---|
| | TTAAAGAATTCTAGG<br>CAGGTGGAGGTCAGC<br>TGGGAGTACCCTGAC<br>ACCTGGAGTACTCCA<br>CATTCCTACTTCTCC<br>CTGACATTCTGTGTT<br>CAaGTCCAGGGCAAG<br>AGCAAGAGAGAAAAG<br>AAAGATAGAGTCTTC<br>ACTGACAAGACCTCA<br>GCCACAGTCATCTGC<br>AGGAAAAATGCCAGC<br>ATTTCAGTGAGGGCC<br>CAGGACAGaTACTAT<br>AGCTCATCTTGGTCA<br>GAATGGGCATCTGTG<br>CCCTGCAGTTGA<br>(SEQ ID NO: 10) |
| WT mouse IL-12A (p35) (no in-frame stop codon) | atggtcagcgttcca<br>acagcctcaccctcg<br>gcatccagcagctcc<br>tctcagtgccggtcc<br>agcatgtgtcaatca<br>cgctacctcctctttt<br>cgctacctcctctttt<br>ttggccaccettgcc<br>ctcctaaaccacctc<br>agtttggccagggtc<br>attccagtctctgga<br>cctgccaggtgtctt<br>agccagtcccgaaac<br>ctgctgaagaccaca<br>gatgacatggtgaag<br>acggccagagaaaaa<br>ctgaaacattattcc<br>tgcactgctgaagac<br>atcgatcatgaagac<br>atcacacgggaccaa<br>accagcacattgaag<br>acctgtttaccactg<br>gaactacacaagaac<br>gagagttgcctggct<br>actagagagacttct<br>tccacaacaagaggg<br>agctgcctgccccca<br>cagaagacgtctttg<br>atgatgaccctgtgc<br>cttggtagcatctat<br>gaggacttgaagatg<br>taccagacagagttc<br>caggccatcaacgca<br>gcacttcagaatcac<br>aaccatcagcagatc<br>attctagacaagggc<br>atgctggtggccatc<br>gatgagctgatgcag<br>tctctgaatcataat<br>ggcgagactctgcgc<br>cagaaacctcctgtg<br>ggagaagcagaccct<br>tacagagtgaaaatg<br>aagtctctgcatcctg<br>cttcacgcctttcagc<br>acccgcgtcgtgacc<br>atcaacagggtgatg<br>ggctatctgagctcc<br>gcc<br>(SEQ ID NO: 90) |
| WT mouse IL-12B (p40) | atgtgtcctcagaag<br>ctaaccatctcctgg<br>tttgccatcgttttg<br>ctggtgtctccactc<br>atggccatgtgggag<br>ctggagaaagacgtt |

TABLE 2-continued

IL-12 Nucleic Acid Sequences

| IL-12 | IL-12 Nucleic Acid Sequence (SEQ ID NO) |
|---|---|
| | tatgttgtagaggtg gactggactcccgat gcccctggagaaaca gtgaacctcacctgt gacacgcctgaagaa gatgacatcacctgg acctcagaccagaga catggagtcataggc tctggaaagaccctg accatcactgtcaaa gagtttctagatgct ggccagtacacctgc cacaaaggaggcgag actctgagccactca catctgctgctccac aagaaggaaaatgga atttggtccactgaa attttaaaaaatttc aaaaacaagactttt ctgaagtgtgaagca ccaaattactccgga cggttcacgtgctca tggctggtgcaaaga aacatggacttgaag ttcaacatcaagagc agtagcagttcccct gactctcgggcagtg acatgtggaatggcg tctctgtctgcagag aaggtcacactggac caaagggactatgag aagtattcagtgtcc tgccaggaggatgtc acctgcccaactgcc gaggagaccctgccc attgaactggcgttg gaagcacggcagcag aataaatatgagaac tacagcaccagcttc ttcatcagggacatc atcaaaccagacccg cccaagaacttgcag atgaagcctttgaag aactcacaggtggag gtcagctgggagtac cctgactcctggagc actccccattcctac ttctccctcaagttc tttgttcgaatccag cgcaagaaagaaaag atgaaggagacagag gaggggtgtaaccag aaaggagcgttcctc gtagagaagacatct accgaagtccaatgc aaaggcgggaatgtc tgcgtgcaagctcag gatgctattacaat tcctcatgcagcaag tgggcatgtgttccc tgcagggtccgatcc tga (SEQ ID NO: 91) |
| Human IL-12B (p40) ("wild-type" no CpG modification and no in-frame stop codon) | ATGTGTCACCAGCAG TTGGTCATCTCTTGG TTTTCCCTGGTTTTT CTGGCATCTCCCCTC GTGGCCATATGGGAA CTGAAGAAAGATGTT TATGTCGTAGAATTG GATTGGTATCCGGAT GCCCCTGGAGAAATG GTGGTCCTCACCTGT GACACCCCTGAAGAA GATGGTATCACCTGG ACCTTGGACCAGAGC AGTGAGGTCTTAGGC TCTGGCAAAACCCTG ACCATCCAAGTCAAA GAGTTTGGAGATGCT GGCCAGTACACCTGT CACAAAGGAGGCGAG GTTCTAAGCCATTCG CTCCTGCTGCTTCAC AAAAAGGAAGATGGA ATTTGGTCCACTGAT ATTTTAAAGGACCAG AAAGAACCCAAAAAT AAGACCTTTCTAAGA TGCGAGGCCAAGAAT TATTCTGGACGTTTC ACCTGCTGGTGGCTG ACGACAATCAGTACT GATTTGACATTCAGT GTCAAAAGCAGCAGA GGCTCTTCTGACCCC CAAGGGGTGACGTGC GGAGCTGCTACACTC TCTGCAGAGAGAGTC AGAGGGGACAACAAG GAGTATGAGTACTCA GTGGAGTGCCAGGAG GACAGTGCCTGCCCA GCTGCTGAGGAGAGT CTGCCCATTGAGGTg ATGGTGGATGCCGTT CACAAGCTCAAGTAT GAAAACTACACCAGC AGCTTCTTCATCAGG GACATCATCAAACCT GACCCACCCAAGAAC TTGCAGCTGAAGCCA TTAAAGAATTCTCGG CAGGTGGAGGTCAGC TGGGAGTACCCTGAC ACCTGGAGTACTCCA CATTCCTACTTCTCC CTGACATTCTGCGTT CAaGTCCAGGGCAAG AGCAAGAGAGAAAAG AAAGATAGAGTCTTC ACGGACAAGACCTCA GCCACGGTCATCTGC CGCAAAAATGCCAGC ATTAGCGTGCGGGCC CAGGACCGCTACTAT AGCTCATCTTGGAGC GAATGGGCATCTGTG CCCTGCAGT (SEQ ID NO: 92) |

TABLE 3

IL-12 Amino Acid Sequences

| IL-12 | IL-12 Amino Acid Sequences (SEQ ID NO) |
|---|---|
| Mouse IL-12A (p35) NP_001152896 | MVSVPTASPSASSSSSQCRS SMCQSRYLLFLATLALLNHL SLARVIPVSGPARCLSQSRN LLKTTDDMVKTAREKLKHYS CTAEDIDHEDITRDQTSTLK TCLPLELHKNESCLATRETS STTRGSCLPPQKTSLMMTLC LGSTYEDLKMYQTEFQAINA |

TABLE 3-continued

IL-12 Amino Acid Sequences

| IL-12 | IL-12 Amino Acid Sequences (SEQ ID NO) |
|---|---|
| | ALQNHNHQQIILDKGMLVAI<br>DELMQSLNHNGETLRQKPPV<br>GEADPYRVKMKLCILLHAFS<br>TRVVTINRVMGYLSSA<br>(SEQ ID NO: 78) |
| Mouse IL-12B (p40) NP_001290173 | MCPQKLTISWFAIVLLVSPL<br>MAMWELEKDVYVVEVDWTPD<br>APGETVNLTCDTPEEDDITW<br>TSDQRHGVIGSGKTLTITVK<br>EFLDAGQYTCHKGGETLSHS<br>HLLLHKKENGIWSTEILKNE<br>KNKTFLKCEAPNYSGRFTCS<br>WLVQRNMDLKENIKSSSSP<br>DSRAVTCGMASLSAEKVTLD<br>QRDYEKYSVSCQEDVTCPTA<br>EETLPIELALEARQQNKYEN<br>YSTSFFIRDIIKPDPPKNLQ<br>MKPLKNSQVEVSWEYPDSWS<br>TPHSYFSLKFFVRIQRKKEK<br>MKETEEGCNQKGAFLVEKTS<br>TEVQCKGGNVCVQAQDRYYN<br>SSCSKWACVPCRVRS<br>(SEQ ID NO: 79) |
| Human IL-12A (p35) NP_000873 | MWPPGSASQPPPSPAAATGL<br>HPAARPVSLQCRLSMCPARS<br>LLLVATLVLLDHLSLARNLP<br>VATPDPGMFPCLHHSQNLLR<br>AVSNMLQKARQTLEFYPCTS<br>EEIDHEDITKDKTSTVEACL<br>PLELTKNESCLNSRETSFIT<br>NGSCLASRKTSFMMALCLSS<br>IYEDLKMYQVEEKTMNAKLL<br>MDPKRINFLDQNMLAVIDEL<br>MQALNENSETVPQKSSLEEP<br>DFYKTKIKLCILLHAFRIRA<br>VTIDRVMSYLNAS<br>(SEQ ID NO: 80) |
| Human IL-12B (p40) NP_002178 | MCHQQLVISWFSLVFLASPL<br>VAIWELKKDVYVVELDWYPD<br>APGEMVVLTCDTPEEDGITW<br>TLDQSSEVLGSGKTLTDQVK<br>EFGDAGQYTCHKGGEVLSHS<br>LLLLHKKEDGIWSTDILKDQ<br>KEPKNKTFLRCEAKNYSGRF<br>TCWWLTTISTDLTFSVKSSR<br>GSSDPQGVTCGAATLSAERV<br>RGDNKEYEYSVECQEDSACP<br>AAEESLPIEVMVDAVHKLKY<br>ENYTSSFFIRDIIKPDPPKN<br>LQLKPLKNSRQVEVSWEYPD<br>TWSTPHSYFSLTFCVQVQGK<br>SKREKKDRVFTDKTSATVIC<br>RKNASISVRAQDRYYSSSWS<br>EWASVPCS<br>(SEQ ID NO: 81) |

IL-12

In some aspects, the cytokine is an IL-12 molecule, e.g., a full length, a functional fragment of IL-12, or a variant of IL-12, e.g., human IL-12. In some aspects, the IL-12 molecule is a wild-type, human IL12. In other embodiments, the IL-12 molecule is a variant of human IL-12, e.g., having one or more amino acid modifications. In some aspects, the composition (e.g., gene therapy composition) comprises a construct of the disclosure, which is a multicistronic (e.g., bicistronic) construct (e.g., comprising IL-12A and IL-12B subunits).

Interleukin-12 (IL-12) is a heterodimeric cytokine composed of p35 and p40 subunits which are encoded by 2 separate genes, IL-12A and IL-12B, respectively. IL-12 is involved in the differentiation of naive T cells into Th1 cells. It is known as a T cell-stimulating factor, which can stimulate the growth and function of T cells. It stimulates the production of IFN-γ and TNF-α from T cells and natural killer (NK) cells, and reduces IL-4 mediated suppression of IFN-γ. T cells that produce IL-12 have a coreceptor, CD30, which is associated with IL-12 activity.

IL-12 plays an important role in the activities of NK cells and T lymphocytes. IL-12 mediates enhancement of the cytotoxic activity of NK cells and CD8$^+$ cytotoxic T lymphocytes. There also seems to be a link between IL-2 and the signal transduction of IL-12 in NK cells. IL-2 stimulates the expression of two IL-12 receptors, IL-12R-pi and IL-12R-P2, maintaining the expression of a critical protein involved in IL-12 signaling in NK cells. Enhanced functional response is demonstrated by IFN-γ production and killing of target cells.

IL-12 also has anti-angiogenic activity, which means it can block the formation of new blood vessels. It does this by increasing production of IFN-γ, which in turn increases the production of a chemokine called inducible protein-10 (IP-10 or CXCL10). IP-10 then mediates this anti-angiogenic effect. Because of its ability to induce immune responses and its anti-angiogenic activity, there has been an interest in testing IL-12 as a possible anti-cancer drug.

IL-12 binds to the IL-12 receptor, which is a heterodimeric receptor formed by IL-12R-βî and IL-12R-P2. IL-12R-P2 is considered to play a key role in IL-12 function, since it is found on activated T cells and is stimulated by cytokines that promote Th1 cells development and inhibited by those that promote Th2 cells development. Upon binding, IL-12R-P2 becomes tyrosine phosphorylated and provides binding sites for kinases, Tyk2 and Jak2. These are important in activating critical transcription factor proteins such as STAT4 that are implicated in IL-12 signaling in T cells and NK cells. IL-12 is a potent cytokine with the potential to reshape the anti-inflammatory environment in solid tumors. However, its clinical utility has been limited by severe toxicities both from soluble administration or from adoptively transferred T cells engineered to secrete IL-12. See e.g., U.S. Pat. No. 8,026,223B1; Int'l Publ. No. WO2019/010219; Liu, Y., et al., *Cancer Gene Ther.*, 9:9-15 (2002); Heinzerling L, et al., *Hum Gene Ther.*, 16(1):35-48 (2005).

In some aspects, provided herein is are polynucleotides, compositions, and viral vectors comprising an enhancer (e.g., a CMV enhancer), a promoter, for example, a constitutive promoter (e.g., a CBA promoter or fragment thereof) operably linked to a first nucleic acid encoding a first IL-12 subunit or a functional fragment thereof (e.g., an IL-12 p35 subunit or an IL-12 p40 subunit), a translation modification sequence (e.g., a furin cleavage sequence followed by a 2A self-processing peptide (F2A)), a second nucleic acid encoding an IL-12 subunit or a functional fragment thereof (e.g., an IL-12 p35 subunit or an IL-12 p40 subunit), and a pA sequence (e.g., a human growth hormone (HGH) or a bovine growth hormone (BGH) pA sequence). In some aspects, the polynucleotides, compositions, and viral vectors further comprise an intron (e.g., a CAG intron). In some aspects, the polynucleotides, compositions, and viral vectors further comprise a Kozak sequence.

In some aspects, the first nucleic acid encodes a polypeptide having at least 85%, 90%, 95%, 96%, 97%, 98%, 99%, or 100% identity to the amino acid sequence of any of SEQ ID NO: 80 or 81, or any amino acid sequence in Table 3. In some aspects, the second nucleic acid encodes a polypeptide having at least 85%, 90%, 95%, 96%, 97%, 98%, 99%, or 100% identity to the amino acid sequence of any of SEQ ID NO: 80 or 81, or any amino acid sequence in Table 3. In some aspects, the first nucleic acid (e.g., a nucleic acid encoding an IL-12 p35 subunit) does not include an in-frame stop codon (e.g., TGA, TAG, and TAA).

In some aspects, the nucleic acid encoding the IL-12 p35 subunit comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77. In some aspects, the nucleic acid encoding the IL-12 p40 subunit comprises a sequence at least 85%, at least 90%, at least 96%, at least 97%, at least 98%, at least 99%, or 100% identical to SEQ ID NO: 8, SEQ ID NO: 9, SEQ ID NO: 10, or SEQ ID NO: 92.

In some aspects, the polynucleotide of the disclosure comprises a promoter operably linked to an IL-12 p35 gene or functional fragment thereof (e.g., corresponding to SEQ ID NO: 77), a furin cleavage sequence and/or a 2A self-processing peptide sequence (including an F2A, E2A, P2A or T2A self-processing peptide), and an IL-12 p40 gene or a functional fragment thereof (e.g., corresponding to SEQ ID NO: 8); and a pA sequence (e.g., a growth hormome pA). In some aspects, the promoter comprises a CBA promoter or a fragment thereof; and, optionally, a CMV enhancer is included. In some aspects, the promoter is a CBA promoter or fragment thereof. In some aspects, the polynucleotide further comprise an intron (e.g., a CAG intron). In some aspects, the polynucleotide further comprise a Kozak sequence In some aspects, the second cytokine is IL-15, IL-2, or a functional fragment thereof. In some aspects, the second nucleic acid comprises an IL-15 gene. In some aspects, the second nucleic acid comprises a nucleic acid sequence having at least 85%, 90%, 95% 96%, 97%, 98%, 99%, or 100% identity to SEQ ID NOs: 11-13, 58, or any nucleic acid shown in Table 4, or any combination thereof. In some aspects, the second nucleic acid comprises a nucleic acid sequence having at least 85%, 90%, 95% 96%, 97%, 98%, 99%, or 100% identity to a reverse complement of SEQ ID NOs: 11-13, 58, or any nucleic acid shown in Table 4, or any combination thereof. In some aspects, the polynucleotide of the disclosure comprises one or more nucleic acids comprising a nucleic acid sequence having at least 85%, 90%, 95% 96%, 97%, 98%, 99%, or 100% identity to SEQ ID NOs: 11-13, 58, or any nucleic acid sequence shown in Table 4, or any combination thereof. In some aspects, the polynucleotide of the disclosure comprises one or more nucleic acids comprising a nucleic acid sequence having at least 85%, 90%, 95% 96%, 97%, 98%, 99%, or 100% identity to a reverse complement of SEQ ID NOs: 11-13, 58, or any nucleic acid sequence shown in Table 4, or any combination thereof.

TABLE 4

IL-15 Nucleic Acid Sequences

| IL-15 | IL-15 Nucleic Acid Sequence (SEQ ID NO) |
|---|---|
| IL-15 ("wild-type" no CpG modification) | ATGAGAATTTCGAAACCACA TTTGAGAAGTATTTCCATCC AGTGCTACTTGTGTTTACTT CTAAACAGTCATTTTCTAAC TGAAGCTGGCATTCATGTCT TCATTTTGGGCTGTTTCtct GCAGGGCTTCCTAAAACAGA AGCCAACTGGGTGAATGTAA TAAGTGATTTGAAAAAAATT GAAGATCTTATTCAATCTAT GCATATTGATGCTACTTTAT ATACGGAAAGTGATGTTCAC CCCAGTTGCAAAGTAACAGC AATGAAGTGCTTTCTCTTGG AGTTACAAGTTATTTCACTT GAGTCCGGAGATGCAAGTAT TCATGATACAGTAGAAAATC TGATCATCCTAGCAAACAAC AGTTTGTCTTCTAATGGGAA TGTAACAGAATCTGGATGCA AAGAATGTGAGGAACTGGAG GAAAAAAATATTAAAGAATT TTTGCAGAGTTTTGTACATA TTGTCCAAATGTTCATCAAC ACTTCTTGA (SEQ ID NO: 11) |
| IL-15 (with CpG modification) | ATGAGAATTAGCAAACCACA TTTGAGAAGTATTTCCATCC AGTGCTACTTGTGTTTACTT CTAAACAGTCATTTTCTAAC TGAAGCTGGCATTCATGTCT TCATTTTGGGCTGTTTCtct GCAGGGCTTCCTAAAACAGA AGCCAACTGGGTGAATGTAA TAAGTGATTTGAAAAAAATT GAAGATCTTATTCAATCTAT GCATATTGATGCTACTTTAT ATACTGAAAGTGATGTTCAC CCCAGTTGCAAAGTAACAGC AATGAAGTGCTTTCTCTTGG AGTTACAAGTTATTTCACTT GAGAGCGGAGATGCAAGTAT TCATGATACAGTAGAAAATC TGATCATCCTAGCAAACAAC AGTTTGTCTTCTAATGGGAA TGTAACAGAATCTGGATGCA AAGAATGTGAGGAACTGGAG GAAAAAAATATTAAAGAATT TTTGCAGAGTTTTGTACATA TTGTCCAAATGTTCATCAAC ACTTCTTGA (SEQ ID NO: 12) |
| IL-15 (with CpG modification) | ATGAGAATTAGCAAACCACA TTTGAGAAGTATTTCCATCC AGTGCTACTTGTGTTTACTT CTAAACAGTCATTTTCTAAC TGAAGCTGGCATTCATGTCT TCATTTTGGGCTGTTTCtct GCAGGGCTTCCTAAAACAGA AGCCAACTGGGTGAATGTAA TAAGTGATTTGAAAAAAATT GAAGATCTTATTCAATCTAT GCATATTGATGCTACTTTAT ATACTGAAAGTGATGTTCAC CCCAGTTGCAAAGTAACAGC AATGAAGTGCTTTCTCTTGG AGTTACAAGTTATTTCACTT GAGTCAGGAGATGCAAGTAT TCATGATACAGTAGAAAATC TGATCATCCTAGCAAACAAC AGTTTGTCTTCTAATGGGAA TGTAACAGAATCTGGATGCA AAGAATGTGAGGAACTGGAG |

TABLE 4-continued

IL-15 Nucleic Acid Sequences

| IL-15 | IL-15 Nucleic Acid Sequence (SEQ ID NO) |
|---|---|
| | GAAAAAAATATTAAAGAATT<br>TTTGCAGAGTTTTGTACATA<br>TTGTCCAAATGTTCATCAAC<br>ACTTCTTGA<br>(SEQ ID NO: 13) |
| IL-15 (splice variant modification) | ATGAGAATTTCGAAACCACA<br>TTTGAGAAGTATTTCCATCC<br>AGTGCTACTTGTGTTTACTT<br>CTAAACAGTCATTTTCTAAC<br>TGAAGCTGGCATTCATGTCT<br>TCATTTTGGGCTGTTTCTCT<br>GCTGGGCTTCCTAAAACAGA<br>AGCCAACTGGGTGAATGTAA<br>TAAGTGATTTGAAAAAAATT<br>GAAGATCTTATTCAATCTAT<br>GCATATTGATGCTACTTTAT<br>ATACGGAAAGTGATGTTCAC<br>CCCAGTTGCAAAGTAACAGC<br>AATGAAGTGCTTTCTCTTGG<br>AGTTACAAGTTATTTCACTT<br>GAGTCCGGAGATGCAAGTAT<br>TCATGATACAGTAGAAAATC<br>TGATCATCCTAGCAAACAAC<br>AGTTTGTCTTCTAATGGGAA<br>TGTAACAGAATCTGGATGCA<br>AAGAATGTGAGGAACTGGAG<br>GAAAAAAATATTAAAGAATT<br>TTTGCAGAGTTTTGTACATA<br>TTGTCCAAATGTTCATCAAC<br>ACTTCTTGA<br>(SEQ ID NO: 58) |

IL-15

In some aspects, the cytokine is an IL-15 molecule, e.g., a full length, a functional fragment of IL-15, or a variant of IL-15, e.g., human IL-15. In some aspects, the IL-15 molecule is a wild-type, human IL-15. In other embodiments, the IL-15 molecule is a variant of human IL-15, e.g., having one or more amino acid modifications.

IL-15 is a four α-helix bundle cytokine displaying IL-2-like immunomodulatory functions, supporting the proliferation and differentiation of T cells, B cells, and NK cells. In addition, IL-15 has been reported to control differentiation of NK cells from bone marrow precursors, to stimulate NK antitumor cytolytic functions, and to act as a chemotactic stimulus for NK cells. The critical role of IL-15 in NK cell development and function was also evidenced in IFN-regulatory factor 1 (IRF-1) knockout mice, which lack IL-15 expression and display an NK-deficient phenotype. Thus, IL-15 has been regarded as a suitable candidate for cancer immunotherapy or gene therapy strategies. See e.g., Di Carlo et al., *J Immunol*, 165(6):3111-3118 (2000).

Figure 1B:
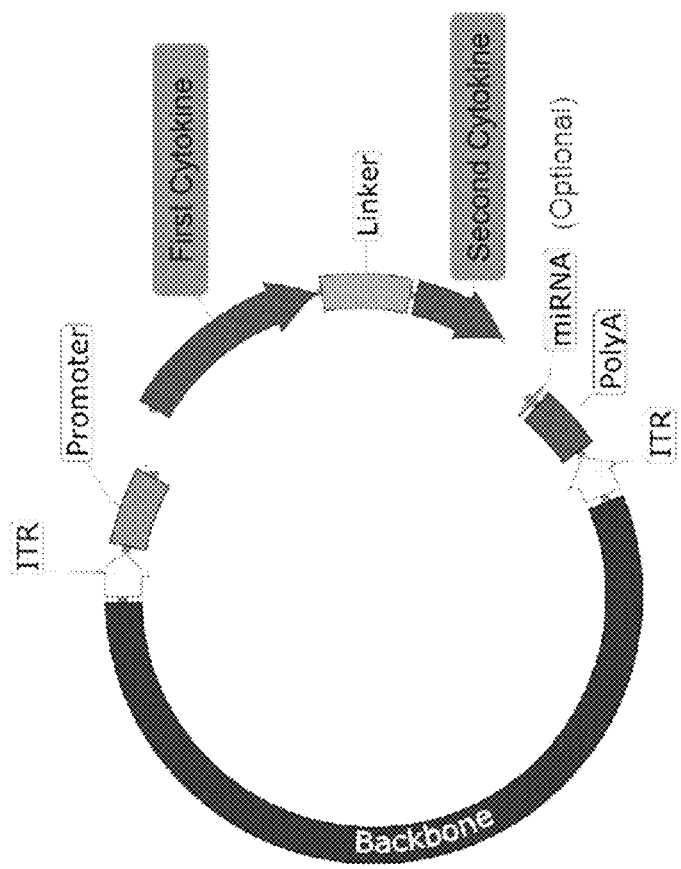
FIG. 1B shows an exemplary AAV construct designed with an expression cassette comprising a promoter, an open reading frame (ORF) (comprising a sequence encoding a first cytokine, a linker, and a sequence encoding a second cytokine), an optional miRNA, and a poly(A) signal sequence, which is flanked by ITR sequences. The construct further comprises a backbone.
Figure 1A:
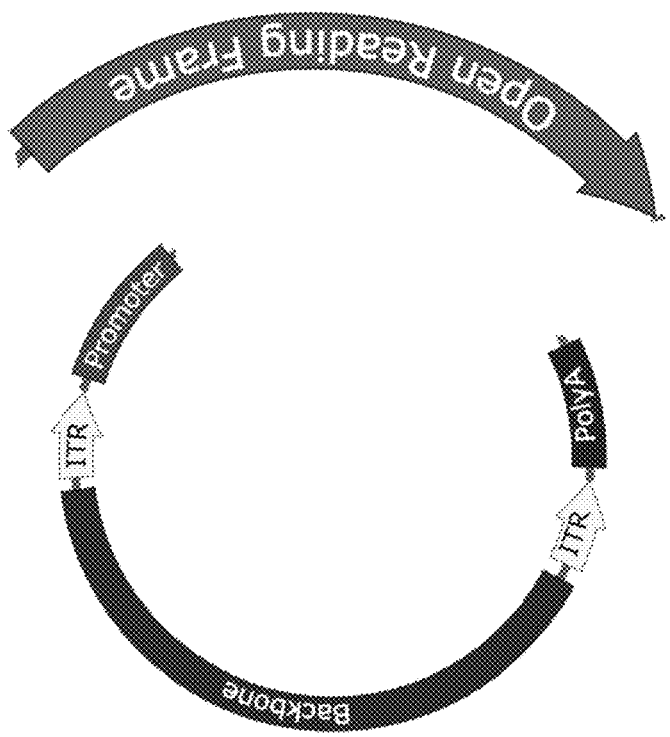
FIG. 1A shows an exemplary AAV construct designed to include a backbone, flanking ITRs, a promoter, polyA, and open reading frame (ORF).
Figure 2A:
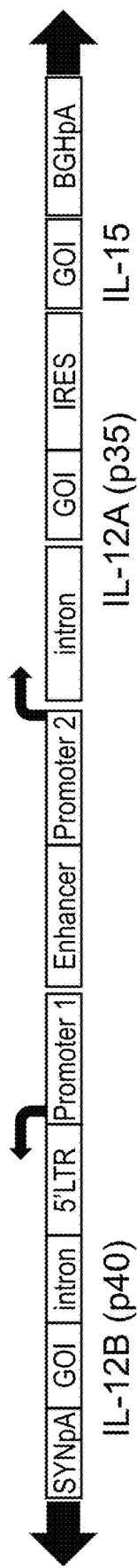
FIG. 2A shows an exemplary expression cassette comprising: a synthetic (SYN) poly(A) (pA) (SYNpA) sequence; gene of interest (GOI) (e.g., an IL-12 p40 gene); an intron sequence; 5' long terminal repeat (LTR), a promoter (Promoter 1); an enhancer sequence; a second promoter (Promoter 2); intron; gene of interest (GOI) (e.g., an IL-12 p35 gene); an internal ribosomal entry site (IRES) sequence; gene of interest (GOI) (e.g., an IL-15 gene); and a polyA (e.g., a bovine growth hormone (BGH) pA (BGHpA)) sequence.

In some aspects, the first nucleic acid comprises a promoter operably linked to an IL-12 p35 gene or functional fragment thereof, an IRES sequence, and an IL-15 gene or a functional fragment thereof; and the second nucleic acid comprises a promoter operably linked to an IL-12 p40 gene or functional fragment thereof. (see FIG. 2A). In some aspects, the first nucleic acid comprises a promoter operably linked to a nucleic acid encoding an IL-12 p35 subunit or functional fragment thereof, an IRES sequence, and, optionally, an IL-15 gene or a functional fragment thereof; and the second nucleic acid comprises a promoter operably linked to a nucleic acid encoding an IL-12 p40 subunit or functional fragment thereof. In some aspects, the first nucleic acid comprises a promoter operably linked to a nucleic acid encoding an IL-12 p40 subunit or functional fragment thereof, an IRES sequence, and, optionally, an IL-15 gene or a functional fragment thereof; and the second nucleic acid comprises a promoter operably linked to a nucleic acid encoding an IL-12 p35 subunit or functional fragment thereof.

Figure 2B:
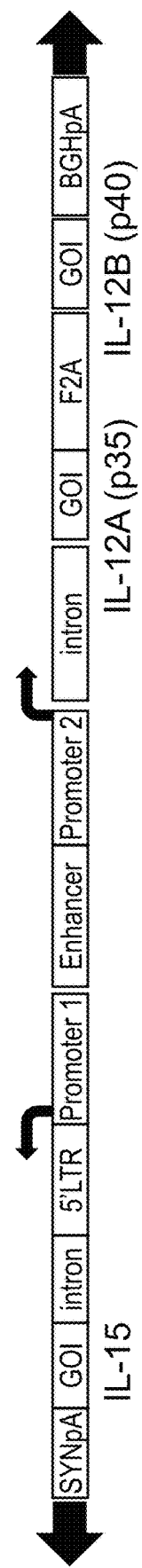
FIG. 2B shows an exemplary expression cassette comprising: a synthetic (SYN) poly(A) (pA) (SYNpA) sequence; gene of interest (GOI) (an IL-15 gene); an intron sequence; 5' long terminal repeat (LTR), a promoter (Promoter 1); an enhancer sequence; a second promoter (Promoter 2); an intron; gene of interest (GOI) (an IL-12 p35 gene); a furin cleavage sequence followed by the 2A self-processing peptide (F2A); gene of interest (GOI) (an IL-12 p40 gene); and a polyA (e.g., a bovine growth hormone (BGH) pA (BGHpA)) sequence.
Figure 2C:
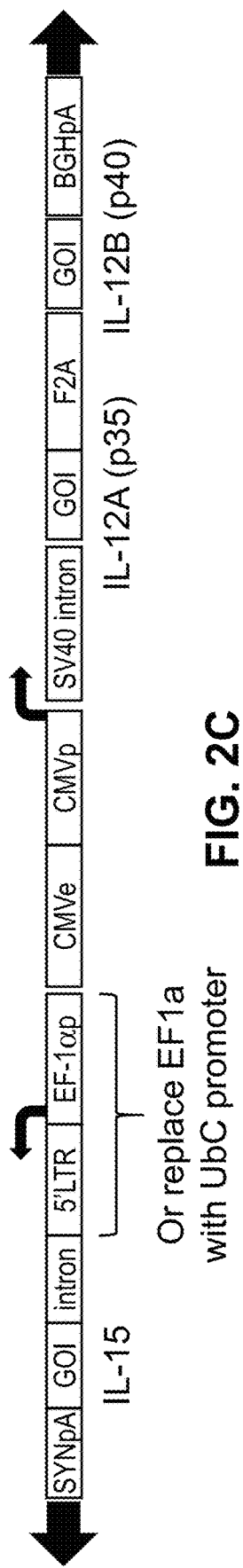
FIG. 2C and FIG. 2D show an exemplary multicistronic expression cassettes including two promoters and three genes of interest (e.g., IL-15, IL-12A, or IL-12B).
Figure 2D:
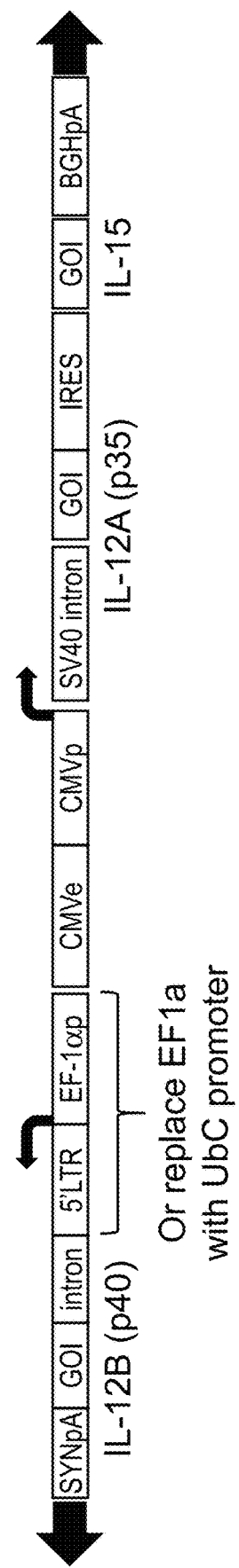

In some aspects, the first nucleic acid comprises a promoter operably linked to an IL-12 p35 gene or functional fragment thereof, a furin cleavage sequence and/or a 2A self-processing peptide (including an F2A, E2A, P2A or T2A self-processing peptide), and an IL-12 p40 gene or a functional fragment thereof; and the second nucleic acid comprises a promoter operably linked to an IL-15 gene or functional fragment thereof. (see FIG. 2B). In some aspects, the first nucleic acid comprises a promoter operably linked to a nucleic acid encoding an IL-12 p35 subunit or functional fragment thereof, a furin cleavage sequence and/or a 2A self-processing peptide (including an F2A, E2A, P2A or T2A self-processing peptide), and a nucleic acid encoding an IL-12 p40 subunit or a functional fragment thereof; and, optionally, a second nucleic acid comprises a promoter operably linked to an IL-15 gene or functional fragment thereof. In some aspects, the first nucleic acid comprises a promoter operably linked to a nucleic acid encoding an IL-12 p40 subunit or functional fragment thereof, a furin cleavage sequence and/or a 2A self-processing peptide (including an F2A, E2A, P2A or T2A self-processing peptide), and a nucleic acid encoding an IL-12 p35 subunit or a functional fragment thereof; and, optionally, a second nucleic acid comprises a promoter operably linked to an IL-15 gene or functional fragment thereof.

In some aspects, the first nucleic acid comprises a promoter operably linked to an IL-12 p35 gene or functional fragment thereof, an IRES sequence, and an IL-15 gene or a functional fragment thereof; and the second nucleic acid comprises a promoter operably linked to an IL-12 p40 gene or functional fragment thereof, wherein the construct comprises a nucleic acid sequence having at least 80%, 85%, 90%, 95% 96%, 97%, 98%, 99%, or 100% identity to any of SEQ ID NOs: 14-37 and 48-57 or any nucleic acid shown in Table 5.

In some aspects, the first nucleic acid comprises a promoter operably linked to an IL-12 p35 gene or functional fragment thereof, a furin cleavage sequence and/or a 2A self-processing peptide (including an F2A, E2A, P2A or T2A self-processing peptide), and an IL-12 p40 gene or a functional fragment thereof; and the second nucleic acid comprises a promoter operably linked to an IL-15 gene or functional fragment thereof, wherein the construct comprises a nucleic acid sequence having at least 80%, 85%, 90%, 95% 96%, 97%, 98%, 99%, or 100% identity to any of SEQ ID NOs: 14-37 and 48-57 or any nucleic acid shown in Table 5.

TABLE 5

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
| | Human EF-1a-wild-type IL-12A/IL-12B/IL-15-IRES (no CpG modification) | (SEQ ID NO: 14) |
| 2 | Human EF-1a-wild-type IL-12A/IL-12B/IL-15-F2A(no CpG modification) | (SEQ ID NO: 15) |
| 3 | Human EF-1a-modified IL-12A/IL-12B/IL-15-IRES(with CpG modification) | (SEQ ID NO: 16) |
| 4 | Human EF1a-modified IL-12A/IL-12B/IL-15-F2A(with CpG modification) | (SEQ ID NO: 17) |
| 5 | Human EF1a-modified IL-12A/IL-12B/IL-15-IRES (with CpG modification) | (SEQ ID NO: 18) |
| 6 | Human EF-1a-modified IL-12A/IL-12B/IL-15-F2A(with CpG modification) | (SEQ ID NO: 19) |
| 7 | Human EF-1a-wild-type IL-12A/IL-12B/IL-15-ODN-IRES (no CpG modification) | (SEQ ID NO: 20) |
| 8 | Human EF-1a-wild-type IL-12A/IL-12B/IL-15-ODN-F2A (no CpG modification) | (SEQ ID NO: 21) |
| 9 | Human UbC-wild-type IL-12A/IL-12B/IL-15-IRES (no CpG modification) | (SEQ ID NO: 22) |
| 10 | Human UbC-wild-type IL-12A/IL-12B/IL-15-F2A(no CpG modification) | (SEQ ID NO: 23) |
| 11 | Human UbC-modified IL-12A/IL-12B/IL-15-IRES(with CpG modification) | (SEQ ID NO: 24) |
| 12 | Human UbC-modified IL-12A/IL-12B/IL-15-F2A(with CpG modification) | (SEQ ID NO: 25) |
| 13 | Human UbC-modified IL-12A/IL-12B/IL-15-IRES (with CpG modification) | (SEQ ID NO: 26) |
| 14 | Human UbC-modified IL-12A/IL-12B/IL-15-F2A-(with CpG modification) | (SEQ ID NO: 27) |
| 15 | Human UbC-wild-type IL-12A/IL-12B/IL-15-ODN-IRES (no CpG modification) | (SEQ ID NO: 28) |
| 16 | Human UbC-wild-type IL-12A/IL-12B/IL-15-ODN-F2A (no CpG modifiation) | (SEQ ID NO: 29) |
| 17 | Human CMV-wild-type IL-12A/IL-12B--F2A(no CpG modification) | (SEQ ID NO: 30) |
| 18 | Human CMV-wild-type IL-15 (no CpG modification) | (SEQ ID NO: 31) |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
| 19 | Human CAG-wild-type IL-12A/IL-12B-IRES (no CpG modification) construct | CTGCGCGCTCGCTCGCTCACTGAGGCCGCCCGGGCAAAGCCCG GGCGTCGGGCGACCTTTGGTCGCCCGGCCTCAGTGAGCGAGCG AGCGCGCAGAGAGGGAGTGGCCAACTCCATCACTAGGGGTTCC TTAGTATTAAACGCGTGTCGACATTGATTATTGACTAGTTATT AATAGTAATCAATTACGGGGTCATTAGTTCATAGCCCATATAT GGAGTTCCGCGTTACATAACTTACGGTAAATGGCCCGCCTGGC TGACCGCCCAACGACCCCCGCCCATTGACGTCAATAATGACGT ATGTTCCCATAGTAACGCCAATAGGGACTTTCCATTGACGTCA ATGGGTGGACTATTTACGGTAAACTGCCCACTTGGCAGTACAT CAAGTGTATCATATGCCAAGTACGCCCCCTATTGACGTCAATG ACGGTAAATGGCCCGCCTGGCATTATGCCCAGTACATGACCTT ATGGGACTTTCCTACTTGGCAGTACATCTACGTATTAGTCATC GCTATTACCATGGGTCGAGGTGAGCCCCACGTTCTGCTTCACT CTCCCCATCTCCCCCCCCTCCCCACCCCCAATTTTGTATTTAT TTATTTTTTAATTATTTTGTGCAGCGATGGGGGCGGGGGGGGG GGGGGCGCGCGCCAGGCGGGGCGGGGCGGGGCGAGGGGCGGGG CGGGGCGAGGCGGAGAGGTGCGGCGGCAGCCAATCAGAGCGGC GCGCTCCGAAAGTTTCCTTTTATGGCGAGGCGGCGGCGGCGGC GGCCCTATAAAAAGCGAAGCGCGCGGCGGGCGGGAGTCGCTGC GCGCTGCCTTCGCCCCGTGCCCGCTCCGCCGCCGCCTCGCGC CGCCCGCCCCGGCTCTGACTGACCGCGTTACTCCCACAGGTGA GCGGGCGGGACGGCCCTTCTCCTCCGGGCTGTAATTAGCGCTT GGTTTAATGACGGCTCGTTTCTTTTCTGTGGCTGCGTGAAAGC CTTGAGGGGCTCCGGGAGGGCCCTTTGTGCGGGGGGAGCGGCT CGGGGGGTGCGTGCGTGTGTGTGTGCGTGGGGAGCGCCGCGTG CGGCTCCGCGCTGCCCGGCGGCTGTGAGCGCTGCGGGCGCGGC GCGGGGCTTTGTGCGCTCCGCAGTGTGCGCGAGAGGAGCGCGG CCGGGGGCGGTGCCACGCGGTGCGGGGGGGGCTGCGAGGGGAA CAAAGGCTGCGTGCGGGGTGTGTGCGTGGGGGGGGTGAGCAGG GGGTGTGGGCGCGGCGGTCGGGCTGTAACCCCCCCCTGCACCC CCCTCCCCGAGTTGCTGAGCACGGCCCGGCTTCGGGTGCGGGG CTCCGTGCGGGGCGTGGCGCGGGGCTCGCCGTGCCGGGCGGGG GGTGGCGGCGGGTGGGGGTGCCGGGCGGGGCGGGGCCGCCTCG GGCCGGGAGGGCTCGGGGAGGGGCGCGGCGGCCCCCGGAGC GCCGGCGGCTGTCGAGGCGCGGCGAGCCGCAGCCATTGCCTTT TATGGTAATCGTGCGAGAGGGCGCAGGGACTTCCTTTGTCCCA AATCTGTGCGGAGCCGAAATCTGGGAGGCGCCGCCGCACCCCC TCTAGCGGGCGCGGGGCGAAGCGGTGCGGCGCCGGCAGGAAGG AAATGGGCGGGAGGGCCTTCGTGCGTCGCCGCGCCGCCGTCC CCTTCTCCCTCTCCAGCCTCGGGGCTGTCCGCGGGGGGACGGC TGCCTTCGGGGGGGACGGGGCAGGGCGGGGTTCGGCTTCTGGC GTGTGACCGGCGGTCTAGACTCTGCTAACCTTGTTCATGCCTT CTTCTCTTTCCTACAGCTCCTGGGCAACGTGCTGGTTGTTGTG CTGTCTCATCATTTTGGCAAAGAATTCAAGCTTCCAGCTAGCG CCACCATGTGTCCAGCGCGCAGCCTCCTCCTTGTGGCTACCCT GGTCCTCCTGGACCACCTCAGTTTGGCCAGAAACCTCCCCGTG GCCACTCCAGACCCAGGAATGTTCCCATGCCTTCACCACTCCC AAAACCTGCTGAGGGCCGTCAGCAACATGCTCCAGAAGGCCAG ACAAACTCTAGAATTTTACCCTTGCACTTCTGAAGAGATTGAT CATGAAGATATCACAAAAGATAAAACCAGCACAGTGGAGGCCT GTTTACCATTGGAATTAACCAAGAATGAGAGTTGCCTAAATTC CAGAGAGACCTCTTTCATAACTAATGGGAGTTGCCTGGCCTCC AGAAAGACCTCTTTTATGATGGCCCTGTGCCTTAGTAGTATTT ATGAAGACTTGAAGATGTACCAGGTGGAGTTCAAGACCATGAA TGCAAAGCTTCTGATGGATCCTAAGAGGCAGATCTTTCTAGAT CAAAACATGCTGGCAGTTATTGATGAGCTGATGCAGGCCCTGA ATTTCAACAGTGAGACTGTGCCACAAAAATCCTCCCTTGAAGA ACCGGATTTTTATAAAACTAAAATCAAGCTCTGCATACTTCTT CATGCTTTCCGGATTCGGGCAGTGACTATTGATAGAGTGATGA GCTATCTGAATGCTTCCTGAGCCCCTCTCCCTCCCCCCCCCT AACGTTACTGGCCGAAGCCGCTTGGAATAAGGCCGGTGTGCGT TTGTCTATATGTTATTTTCCACCATATTGCCGTCTTTTGGCAA TGTGAGGGCCCGGAAACCTGGCCCTGTCTTCTTGACGAGCATT CCTAGGGGTCTTTCCCCTCTCGCCAAAGGAATGCAAGGTCTGT TGAATGTCGTGAAGGAAGCAGTTCCTCTGGAAGCTTCTTGAAG ACAAACAACGTCTGTAGCGACCCTTTGCAGGCAGCGGAACCCC CCACCTGGCGACAGGTGCCTCTGCGGCCAAAAGCCACGTGTAT AAGATACACCTGCAAAGGCGGCACAACCCCAGTGCCACGTTGT GAGTTGGATAGTTGTGGAAAGAGTCAAATGGCTCTCCTCAAGC GTATTCAACAAGGGGCTGAAGGATGCCCAGAAGGTACCCCATT GTATGGGATCTGATCTGGGGCCTCGGTACACATGCTTTACATG TGTTTAGTCGAGGTTAAAAAAACGTCTAGGCCCCCCGAACCAC |

TABLE 5-continued

IL-12 and/or IL-15 Exemplary Expression Cassette or Construct Nucleic Acid Sequence

| 1 | Expression Cassette | IL-12 and/or IL-15 Expression Cassette or Construct Nucleic Acid Sequence (SEQ ID NO) |
|---|---|---|
| | | GGGGACGTGGTTTTCCTTTGAAAAACACGATGATAATATGCC<br>ACAATGTGTCACCAGCAGTTGGTCATCTCTTGGTTTTCCCTGG<br>TTTTTCTGGCATCTCCCCTCGTGGCCATATGGGAACTGAAGAA<br>AGATGTTTATGTCGTAGAATTGGATTGGTATCCGGATGCCCCT<br>GGAGAAATGGTGGTCCTCACCTGTGACACCCCTGAAGAAGATG<br>GTATCACCTGGACCTTGGACCAGAGCAGTGAGGTCTTAGGCTC<br>TGGCAAAACCCTGACCATCCAAGTCAAAGAGTTTGGAGATGCT<br>GGCCAGTACACCTGTCACAAAGGAGGCGAGGTTCTAAGCCATT<br>CGCTCCTGCTGCTTCACAAAAAGGAAGATGGAATTTGGTCCAC<br>TGATATTTTAAAGGACCAGAAAGAACCCAAAAATAAGACCTTT<br>CTAAGATGCGAGGCCAAGAATTATTCTGGACGTTTCACCTGCT<br>GGTGGCTGACGACAATCAGTACTGATTTGACATTCAGTGTCAA<br>AAGCAGCAGAGGCTCTTCTGACCCCCAAGGGGTGACGTGCGGA<br>GCTGCTACACTCTCTGCAGAGAGAGTCAGAGGGGACAACAAGG<br>AGTATGAGTACTCAGTGGAGTGCCAGGAGGACAGTGCCTGCCC<br>AGCTGCTGAGGAGAGTCTGCCCATTGAGGTGATGGTGGATGCC<br>GTTCACAAGCTCAAGTATGAAAACTACACCAGCAGCTTCTTCA<br>TCAGGGACATCATCAAACCTGACCCACCCAAGAACTTGCAGCT<br>GAAGCCATTAAAGAATTCTCGGCAGGTGGAGGTCAGCTGGGAG<br>TACCCTGACACCTGGAGTACTCCACATTCCTACTTCTCCCTGA<br>CATTCTGCGTTCAAGTCCAGGGCAAGAGCAAGAGAGAAAAGAA<br>AGATAGAGTCTTCACGGACAAGACCTCAGCCACGGTCATCTGC<br>CGCAAAAATGCCAGCATTAGCGTGCGGGCCCAGGACCGCTACT<br>ATAGCTCATCTTGGAGCGAATGGGCATCTGTGCCCTGCAGTTG<br>ACAATTGCTGTGCCTTCTAGTTGCCAGCCATCTGTTGTTTGCC<br>CCTCCCCCGTGCCTTCCTTGACCCTGGAAGGTGCCACTCCCAC<br>TGTCCTTTCCTAATAAAATGAGGAAATTGCATCGCATTGTCTG<br>AGTAGGTGTCATTCTATTCTGGGGGGTGGGGTGGGGCAGGACA<br>GCAAGGGGGAGGATTGGGAAGACAATAGCAGGCATGCTGGGGA<br>TGCGGTGGGCTCTATGGAGCTCGAGAGGGAACCCCTAGTGATGG<br>AGTTGGCCACTCCCTCTCTGCGCGCTCGCTCGCTCACTGAGGC<br>CGGGCGACCAAAGGTCGCCCGACGCCCGGGCTTTGCCCGGGCG<br>GCCTCAGTGAGCGAGCGAGCGCGCAGCTGCAGATCTG (SEQ<br>ID NO: 34) |
| 19 | Human CAG-wild-type IL-12A/IL-12B-IRES (no CpG modification) expression sequence | GCTAGCGCCACCATGTGTCCAGCGCGCAGCCTCCTCCTTGTGG<br>CTACCCTGGTCCTCCTGGACCACCTCAGTTTGGCCAGAAACCT<br>CCCCGTGGCCACTCCAGACCCAGGAATGTTCCCATGCCTTCAC<br>CACTCCCAAAACCTGCTGAGGGCCGTCAGCAACATGCTCCAGA<br>AGGCCAGACAAACTCTAGAATTTTACCCTTGCACTTCTGAAGA<br>GATTGATCATGAAGATATCACAAAAGATAAAACCAGCACAGTG<br>GAGGCCTGTTTACCATTGGAATTAACCAAGAATGAGAGTTGCC<br>TAAATTCCAGAGAGACCTCTTTCATAACTAATGGGAGTTGCCT<br>GGCCTCCAGAAAGACCTCTTTTATGATGGCCCTGTGCCTTAGT<br>AGTATTTATGAAGACTTGAAGATGTACCAGGTGGAGTTCAAGA<br>CCATGAATGCAAAGCTTCTGATGGATCCTAAGAGGCAGATCTT<br>TCTAGATCAAAACATGCTGGCAGTTATTGATGAGCTGATGCAG<br>GCCCTGAATTTCAACAGTGAGACTGTGCCACAAAAATCCTCCC<br>TTGAAGAACCGGATTTTTATAAAACTAAAATCAAGCTCTGCAT<br>ACTTCTTCATGCTTTCCGGATTCGGGCAGTGACTATTGATAGA<br>GTGATGAGCTATCTGAATGCTTCCTGAGCCCCTCTCCCTCCCC<br>CCCCCCTAACGTTACTGGCCGAAGCCGCTTGGAATAAGGCCGG<br>TGTGCGTTTGTCTATATGTTATTTTCCACCATATTGCCGTCTT<br>TTGGCAATGTGAGGGCCCGGAAACCTGGCCCTGTCTTCTTGAC<br>GAGCATTCCTAGGGGTCTTTCCCCTCTCGCCAAAGGAATGCAA<br>GGTCTGTTGAATGTCGTGAAGGAAGCAGTTCCTCTGGAAGCTT<br>CTTGAAGACAAACAACGTCTGTAGCGACCCTTTGCAGGCAGCG<br>GAACCCCCCACCTGGCGACAGGTGCCTCTGCGGCAAAAGCCA<br>CGTGTATAAGATACACCTGCAAAGGCGGCACAACCCCAGTGCC<br>ACGTTGTGAGTTGGATAGTTGTGGAAAGAGTCAAATGGCTCTC<br>CTCAAGCGTATTCAACAAGGGGCTGAAGGATGCCCAGAAGGTA<br>CCCCATTGTATGGGATCTGATCTGGGGCCTCGGTACACATGCT<br>TTACATGTGTTTAGTCGAGGTTAAAAAAACGTCTAGGCCCCCC<br>GAACCACGGGGACGTGGTTTTCCTTTGAAAAACACGATGATAA<br>TATGGCCACAATGTGTCACCAGCAGTTGGTCATCTCTTGGTTT<br>TCCCTGGTTTTTCTGGCATCTCCCCTCGTGGCCATATGGGAAC<br>TGAAGAAAGATGTTTATGTCGTAGAATTGGATTGGTATCCGGA<br>TGCCCCTGGAGAAATGGTGGTCCTCACCTGTGACACCCCTGAA<br>GAAGATGGTATCACCTGGACCTTGGACCAGAGCAGTGAGGTCT<br>TAGGCTCTGGCAAAACCCTGACCATCCAAGTCAAAGAGTTTGG<br>AGATGCTGGCCAGTACACCTGTCACAAAGGAGGCGAGGTTCTA<br>AGCCATTCGCTCCTGCTGCTTCACAAAAAGGAAGATGGAATTT<br>GGTCCACTGATATTTTAAAGGACCAGAAAGAACCCAAAAATAA |

TABLE 5-continued

IL-12 and/or IL-15 Exemplary Expression Cassette or Construct Nucleic Acid Sequence

| 1 | Expression Cassette | IL-12 and/or IL-15 Expression Cassette or Construct Nucleic Acid Sequence (SEQ ID NO) |
|---|---|---|
|   |   | GACCTTTCTAAGATGCGAGGCCAAGAATTATTCTGGACGTTTC<br>ACCTGCTGGTGGCTGACGACAATCAGTACTGATTTGACATTCA<br>GTGTCAAAAGCAGCAGAGGCTCTTCTGACCCCCAAGGGGTGAC<br>GTGCGGAGCTGCTACACTCTCTGCAGAGAGAGTCAGAGGGGAC<br>AACAAGGAGTATGAGTACTCAGTGGAGTGCCAGGAGGACAGTG<br>CCTGCCCAGCTGCTGAGGAGAGTCTGCCCATTGAGGTGATGGT<br>GGATGCCGTTCACAAGCTCAAGTATGAAAACTACACCAGCAGC<br>TTCTTCATCAGGGACATCATCAAACCTGACCCACCCAAGAACT<br>TGCAGCTGAAGCCATTAAAGAATTCTCGGCAGGTGGAGGTCAG<br>CTGGGAGTACCCTGACACCTGGAGTACTCCACATTCCTACTTC<br>TCCCTGACATTCTGCGTTCAAGTCCAGGGCAAGAGCAAGAGAG<br>AAAAGAAAGATAGAGTCTTCACGGACAAGACCTCAGCCACGGT<br>CATCTGCCGCAAAAATGCCAGCATTAGCGTGCGGGCCCAGGAC<br>CGCTACTATAGCTCATCTTGGAGCGAATGGGCATCTGTGCCCT<br>GCAGTTGACAATTG (SEQ ID NO: 35) |
| 20 | Human CAG-wild-type IL-15 (no CpG modification) construct | (SEQ ID NO: 36) |
| 20 | Human CAG-wild-type IL-15 (no CpG modification) expression sequence | (SEQ ID NO: 37) |
| 21 | Mouse EF1a-wild-type IL-15 (no CpG modification) and modified IL-12B (with CpG modification) full construct and expression sequences | SEQ ID NOs: 38 and 39, respectively |
| 22 | Mouse EF1a-modified IL-12B/IL-15 (CpG modified) full construct and expression sequences | SEQ ID NOs: 40 and 41, respectively |
| 23 | Mouse CAG-wild-type IL-12B-IRES (not CpG modified) full construct and expression sequences | SEQ ID NOs: 42 and 43, respectively |
| 24 | Mouse CAG-wild-type IL-15 (not CpG modified) full construct and expression sequences | SEQ ID NOs: 44 and 45, respectively |
| 25 | Mouse CAG-wild-type IL-12B-F2A (not CpG modified) expression sequence | SEQ ID NOs: 46 and 47, respectively |
| 26 | Human CAG-modified IL-12A/IL-12B-F2A (CpG modified) construct | CTGCGCGCTCGCTCGCTCACTGAGGCCGCCCGGGCAAAGCCCG<br>GGCGTCGGGCGACCTTTGGTCGCCCGGCCTCAGTGAGCGAGCG<br>AGCGCGCAGAGAGGGAGTGGCCAACTCCATCACTAGGGGTTCC<br>TTAGTATTAAACGCGTGTCGACATTGATTATTGACTAGTTATT<br>AATAGTAATCAATTACGGGGTCATTAGTTCATAGCCCATATAT<br>GGAGTTCCGCGTTACATAACTTACGGTAAATGGCCCGCCTGGC<br>TGACCGCCCAACGACCCCCGCCCATTGACGTCAATAATGACGT<br>ATGTTCCCATAGTAACGCCAATAGGGACTTTCCATTGACGTCA<br>ATGGGTGGACTATTTACGGTAAACTGCCCACTTGGCAGTACAT<br>CAAGTGTATCATATGCCAAGTACGCCCCCTATTGACGTCAATG<br>ACGGTAAATGGCCCGCCTGGCATTATGCCCAGTACATGACCTT<br>ATGGGACTTTCCTACTTGGCAGTACATCTACGTATTAGTCATC<br>GCTATTACCATGGGTCGAGGTGAGCCCCACGTTCTGCTTCACT<br>CTCCCCATCTCCCCCCCCTCCCCACCCCCAATTTTGTATTTAT<br>TTATTTTTTAATTATTTTGTGCAGCGATGGGGGCGGGGGGGG<br>GGGGGCGCGCGCCAGGCGGGGCGGGGCGGGGCGAGGGGCGGGG<br>CGGGGCGAGGCGGAGAGGTGCGGCGGCAGCCAATCAGAGCGGC<br>GCGCTCCGAAAGTTTCCTTTTATGGCGAGGCGGCGGCGGCGGC<br>GGCCCTATAAAAAGCGAAGCGCGCGGCGGGCGGGAGTCGCTGC<br>GCGCTGCCTTCGCCCCGTGCCCCGCTCCGCCGCCGCCTCGCGC<br>CGCCCGCCCCGGCTCTGACTGACCGCGTTACTCCCACAGGTGA<br>GCGGGCGGGACGGCCCTTCTCCTCCGGGCTGTAATTAGCGCTT<br>GGTTTAATGACGGCTCGTTTCTTTTCTGTGGCTGCGTGAAAGC<br>CTTGAGGGGCTCCGGGAGGGCCCTTTGTGCGGGGGGAGCGGCT<br>CGGGGGGTGCGTGCGTGTGTGTGCGTGGGGAGCGCCGCGTG<br>CGGCTCCGCGCTGCCCGGCGGCTGTGAGCGCTGCGGGCGCGGC<br>GCGGGGCTTTGTGCGCTCCGCAGTGTGCGCGAGAGGAGCGCGG |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
| | | CCGGGGGCGGTGCCACGCGGTGCGGGGGGGGCTGCGAGGGGAA
CAAAGGCTGCGTGCGGGGTGTGTGCGTGGGGGGGGTGAGCAGG
GGGTGTGGGCGCGGCGGTCGGGCTGTAACCCCCCCCTGCACCC
CCCTCCCCGAGTTGCTGAGCACGGCCCGGCTTCGGGTGCGGGG
CTCCGTGCGGGGCGTGGCGCGGGGCTCGCCGTGCCGGGCGGGG
GGTGGCGGCGGGTGGGGGTGCCGGGCGGGGCGGGGCCGCCTCG
GGCCGGGGAGGGCTCGGGGGAGGGGCGCGGCGGCCCCCGGAGC
GCCGGCGGCTGTCGAGGCGCGGCGAGCCGCAGCCATTGCCTTT
TATGGTAATCGTGCGAGAGGGCGCAGGGACTTCCTTTGTCCCA
AATCTGTGCGGAGCCGAAATCTGGGAGGCGCCGCCGCACCCCC
TCTAGCGGGCGCGGGGCGAAGCGGTGCGGCGCCGGCAGGAAGG
AAATGGGCGGGGAGGGCCTTCGTGCGTCGCCGCGCCGCCGTCC
CCTTCTCCCTCTCCAGCCTCGGGGCTGTCCGCGGGGGGACGGC
TGCCTTCGGGGGGGACGGGGCAGGGCGGGGTTCGGCTTCTGGC
GTGTGACCGGCGGTCTAGACTCTGCTAACCATGTTCATGCCTT
CTTCTCTTTCCTACAGCTCCTGGGCAACGTGCTGGTTGTTGTG
CTGTCTCATCATTTTGGCAAAGAATTCAAGCTTCCAGCTAGCG
CCACCATGTGTCCAGCTAGGAGCCTCCTCCTTGTGGCTACCCT
GGTCCTCCTGGACCACCTCAGTTTGGCCAGAAACCTCCCTGTG
GCCACTCCAGACCCAGGAATGTTCCCATGCCTTCACCACTCCC
AAAACCTGCTGAGGGCAGTCAGCAACATGCTCCAGAAGGCCAG
ACAAACTCTAGAATTTTACCCTTGCACTTCTGAAGAGATTGAT
CATGAAGATATCACAAAAGATAAAACCAGCACAGTGGAGGCCT
GTTTACCATTGGAATTAACCAAGAATGAGAGTTGCCTAAATTC
CAGAGAGACCTCTTTCATAACTAATGGGAGTTGCCTGGCCTCC
AGAAAGACCTCTTTTATGATGGCCCTGTGCCTTAGTAGTATTT
ATGAAGACTTGAAGATGTACCAGGTGGAGTTCAAGACCATGAA
TGCAAAGCTTCTGATGGATCCTAAGAGGCAGATCTTTCTAGAT
CAAAACATGCTGGCAGTTATTGATGAGCTGATGCAGGCCCTGA
ATTTCAACAGTGAGACTGTGCCACAAAAATCCTCCCTTGAAGA
ACCTGATTTTTATAAAACTAAAATCAAGCTCTGCATACTTCTT
CATGCTTTCCGGATTAGGGCAGTGACTATTGATAGAGTGATGA
GCTATCTGAATGCTTCCAGAAAGAGAAGGAGTGGCTCAGGAGC
CCCTGTGAAACAGACCCTGAACTTTGACCTCTTGAAGCTTGCT
GGGGATGTGGAGTCTAATCCTGGTCCAATGTGTCACCAGCAGT
TGGTCATCTCTTGGTTTTCCCTGGTTTTTCTGGCATCTCCCCT
TGTGGCCATATGGGAACTGAAGAAAGATGTTTATGTGGTAGAA
TTGGATTGGTATCCTGATGCCCCTGGAGAAATGGTGGTCCTCA
CCTGTGACACCCCTGAAGAAGATGGTATCACCTGGACCTTGGA
CCAGAGCAGTGAGGTCTTAGGCTCTGGCAAAACCCTGACCATC
CAAGTCAAAGAGTTTGGAGATGCTGGCCAGTACACCTGTCACA
AAGGAGGGGAGGTTCTAAGCCATTCCCTCCTGCTGCTTCACAA
AAAGGAAGATGGAATTTGGTCCACTGATATTTTAAAGGACCAG
AAAGAACCCAAAAATAAGACCTTTCTAAGATGTGAGGCCAAGA
ATTATTCTGGAAGGTTCACCTGCTGGTGGCTGACTACAATCAG
TACTGATTTGACATTCAGTGTCAAAAGCAGCAGAGGCTCTTCT
GACCCCCAAGGGGTGACATGTGGAGCTGCTACACTCTCTGCAG
AGAGAGTCAGAGGGGACAACAAGGAGTATGAGTACTCAGTGGA
GTGCCAGGAGGACAGTGCCTGCCCAGCTGCTGAGGAGAGTCTG
CCCATTGAGGTGATGGTGGATGCAGTTCACAAGCTCAAGTATG
AAAACTACACCAGCAGCTTCTTCATCAGGGACATCATCAAACC
TGACCCACCCAAGAACTTGCAGCTGAAGCCATTAAAGAATTCT
AGGCAGGTGGAGGTCAGCTGGGAGTACCCTGACACCTGGAGTA
CTCCACATTCCTACTTCTCCCTGACATTCTGTGTTCAAGTCCA
GGGCAAGAGCAAGAGAGAAAAGAAAGATAGAGTCTTCACTGAC
AAGACCTCAGCCACAGTCATCTGCAGGAAAAATGCCAGCATTT
CAGTGAGGGCCCAGGACAGATACTATAGCTCATCTTGGTCAGA
ATGGGCATCTGTGCCCTGCAGTTGACAATTGCTGTGCCTTCTA
GTTGCCAGCCATCTGTTGTTTGCCCCTCCCCCGTGCCTTCCTT
GACCCTGGAAGGTGCCACTCCCACTGTCCTTTCCTAATAAAAT
GAGGAAATTGCATCGCATTGTCTGAGTAGGTGTCATTCTATTC
TGGGGGGTGGGGTGGGCAGGACAGCAAGGGGGAGGATTGGGA
AGACAATAGCAGGCATGCTGGGGATGCGGTGGGCTCTATGGAG
CTCGAGAGGAACCCCTAGTGATGGAGTTGGCCACTCCCTCTCT
GCGCGCTCGCTCGCTCACTGAGGCCGGGCGACCAAAGGTCGCC
CGACGCCCGGGCTTTGCCCGGGCGGCCTCAGTGAGCGAGCGAG
CGCGCAGCTGCAGATCTG (SEQ ID NO: 48) |
| 26 | Human CAG-modified IL-12A/IL-12B-F2A (CpG modified) expression sequence | GCTAGCGCCACCATGTGTCCAGCTAGGAGCCTCCTCCTTGTGG
CTACCCTGGTCCTCCTGGACCACCTCAGTTTGGCCAGAAACCT
CCCTGTGGCCACTCCAGACCCAGGAATGTTCCCATGCCTTCAC
CACTCCCAAAACCTGCTGAGGGCAGTCAGCAACATGCTCCAGA
AGGCCAGACAAACTCTAGAATTTTACCCTTGCACTTCTGAAGA |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
| | | GATTGATCATGAAGATATCACAAAAGATAAAACCAGCACAGTG GAGGCCTGTTTACCATTGGAATTAACCAAGAATGAGAGTTGCC TAAATTCCAGAGAGACCTCTTTCATAACTAATGGGAGTTGCCT GGCCTCCAGAAGACCTCTTTTATGATGGCCCTGTGCCTTAGT AGTATTTATGAAGACTTGAAGATGTACCAGGTGGAGTTCAAGA CCATGAATGCAAAGCTTCTGATGGATCCTAAGAGGCAGATCTT TCTAGATCAAAACATGCTGGCAGTTATTGATGAGCTGATGCAG GCCCTGAATTTCAACAGTGAGACTGTGCCACAAAAATCCTCCC TTGAAGAACCTGATTTTTATAAAACTAAAATCAAGCTCTGCAT ACTTCTTCATGCTTTCCGGATTAGGGCAGTGACTATTGATAGA GTGATGAGCTATCTGAATGCTTCCAGAAAGAGAAGGAGTGGCT CAGGAGCCCCTGTGAAACAGACCCTGAACTTTGACCTCTTGAA GCTTGCTGGGGATGTGGAGTCTAATCCTGGTCCAATGTGTCAC CAGCAGTTGGTCATCTCTTGGTTTTCCCTGGTTTTTCTGGCAT CTCCCCTTGTGGCCATATGGGAACTGAAGAAAGATGTTTATGT GGTAGAATTGGATTGGTATCCTGATGCCCCTGGAGAAATGGTG GTCCTCACCTGTGACACCCCTGAAGAAGATGGTATCACCTGGA CCTTGGACCAGAGCAGTGAGGTCTTAGGCTCTGGCAAAACCCT GACCATCCAAGTCAAAGAGTTTGGAGATGCTGGCCAGTACACC TGTCACAAAGGAGGGAGGTTCTAAGCCATTCCCTCCTGCTGC TTCACAAAAAGGAAGATGGAATTTGGTCCACTGATATTTTAAA GGACCAGAAAGAACCCAAAAATAAGACCTTTCTAAGATGTGAG GCCAAGAATTATTCTGGAAGGTTCACCTGCTGGTGGCTGACTA CAATCAGTACTGATTTGACATTCAGTGTCAAAAGCAGCAGAGG CTCTTCTGACCCCCAAGGGGTGACATGTGGAGCTGCTACACTC TCTGCAGAGAGAGTCAGAGGGGACAACAAGGAGTATGAGTACT CAGTGGAGTGCCAGGAGGACAGTGCCTGCCCAGCTGCTGAGGA GAGTCTGCCCATTGAGGTGATGGTGGATCAGTTCACAAGCTC AAGTATGAAAACTACACCAGCAGCTTCTTCATCAGGGACATCA TCAAACCTGACCCACCCAAGAACTTGCAGCTGAAGCCATTAAA GAATTCTAGGCAGGTGGAGGTCAGCTGGGAGTACCCTGACACC TGGAGTACTCCACATTCCTACTTCTCCCTGACATTCTGTGTTC AAGTCCAGGGCAAGAGCAAGAGAGAAAAGAAAGATAGAGTCTT CACTGACAAGACCTCAGCCACAGTCATCTGCAGGAAAAATGCC AGCATTTCAGTGAGGGCCCAGGACAGATACTATAGCTCATCTT GGTCAGAATGGGCATCTGTGCCCTGCAGTTGACAATTG (SEQ ID NO: 49) |
| 27 | Human CAG-modified IL-12A/IL-12B-F2A (CpG modified) construct | CTGCGCGCTCGCTCGCTCACTGAGGCCGCCCGGGCAAAGCCCG GGCGTCGGGCGACCTTTGGTCGCCCGGCCTCAGTGAGCGAGCG AGCGCGCAGAGAGGGAGTGGCCAACTCCATCACTAGGGGTTCC TTAGTATTAAACGCGTGTCGACATTGATTATTGACTAGTTATT AATAGTAATCAATTACGGGGTCATTAGTTCATAGCCCATATAT GGAGTTCCGCGTTACATAACTTACGGTAAATGGCCCGCCTGGC TGACCGCCCAACGACCCCCGCCCATTGACGTCAATAATGACGT ATGTTCCCATAGTAACGCCAATAGGGACTTTCCATTGACGTCA ATGGGTGGACTATTTACGGTAAACTGCCCACTTGGCAGTACAT CAAGTGTATCATATGCCAAGTACGCCCCCTATTGACGTCAATG ACGGTAAATGGCCCGCCTGGCATTATGCCCAGTACATGACCTT ATGGGACTTTCCTACTTGGCAGTACATCTACGTATTAGTCATC GCTATTACCATGGGTCGAGGTGAGCCCCACGTTCTGCTTCACT CTCCCCATCTCCCCCCCTCCCCACCCCCAATTTTGTATTTAT TTATTTTTTAATTATTTTGTGCAGCGATGGGGGCGGGGGGGG GGGGGCGCGCGCCAGGCGGGGCGGGGCGGGCGAGGGCGGGG CGGGGCGAGGCGGAGAGGTGCGGCGGCAGCCAATCAGAGCGGC GCGCTCCGAAAGTTTCCTTTTATGGCGAGGCGGCGGCGGCGGC GGCCCTATAAAAAGCGAAGCGCGCGGCGGGCGGGAGTCGCTGC GCGCTGCCTTCGCCCCGTGCCCCGCTCCGCCGCCGCCTCGCGC CGCCCGCCCCGGCTCTGACTGACCGCGTTACTCCCACAGGTGA GCGGGCGGGACGGCCCTTCTCCTCCGGGCTGTAATTAGCGCTT GGTTTAATGACGGCTCGTTTCTTTTCTGTGGCTGCGTGAAAGC CTTGAGGGGCTCCGGGAGGGCCCTTTGTGCGGGGGGAGCGGCT CGGGGGGTGCGTGCGTGTGTGTGCGTGGGGAGCGCCGCGTG CGGCTCCGCGCTGCCCGGCGGCTGTGAGCGCTGCGGGCGCGGC GCGGGGCTTTGTGCGCTCCGCAGTGTGCGCGAGAGGAGCGCGG CCGGGGGCGGTGCCACGCGGTGCGGGGGGGCTGCGAGGGGAA CAAAGGCTGCGTGCGGGGTGTGTGCGTGGGGGGGGTGAGCAGG GGGTGTGGGCGGCGGTCGGGCTGTAACCCCCCCCTGCACCC CCCTCCCCGAGTTGCTGAGCACGGCCCGGCTTCGGGTGCGGGG CTCCGTGCGGGGCGTGGCGCGGGGCTCGCCGTGCCGGCCGGGG GGTGGCGGCGGGTGGGGGTGCCGGGCGGGGCGGGGCCGCCTCG GGCCGGGGAGGGCTCGGGGGAGGGGCGCGGCGGCCCCGGAGC GCCGGCGGCTGTCGAGGCGCGGCGAGCCGCAGCCATTGCCTTT |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
| | | TATGGTAATCGTGCGAGAGGGCGCAGGGACTTCCTTTGTCCCA<br>AATCTGTGCGGAGCCGAAATCTGGGAGGCGCCGCCGCACCCCC<br>TCTAGCGGGCGCGGGGCGAAGCGGTGCGGCGCCGGCAGGAAGG<br>AAATGGGCGGGGAGGGCCTTCGTGCGTCGCCGCGCCGCCGTCC<br>CCTTCTCCCTCTCCAGCCTCGGGGCTGTCCGCGGGGGGACGGC<br>TGCCTTCGGGGGGGACGGGGCAGGGCGGGGTTCGGCTTCTGGC<br>GTGTGACCGGCGGTCTAGACTCTGCTAACCATGTTCATGCCTT<br>CTTCTCTTTCCTACAGCTCCTGGGCAACGTGCTGGTTGTTGTG<br>CTGTCTCATCATTTTGGCAAAGAATTCAAGCTTCCAGCTAGCG<br>CCACCATGTGTCCAGCGCGCAGCCTCCTCCTTGTGGCTACCCT<br>GGTCCTCCTGGACCACCTCAGTTTGGCCAGAAACCTCCCTGTG<br>GCCACTCCAGACCCAGGAATGTTCCCATGCCTTCACCACTCCC<br>AAAACCTGCTGAGGGCTGTCAGCAACATGCTCCAGAAGGCCAG<br>ACAAACTCTAGAATTTTACCCTTGCACTTCTGAAGAGATTGAT<br>CATGAAGATATCACAAAAGATAAAACCAGCACAGTGGAGGCCT<br>GTTTACCATTGGAATTAACCAAGAATGAGAGTTGCCTAAATTC<br>CAGAGAGACCTCTTTCATAACTAATGGGAGTTGCCTGGCCTCC<br>AGAAAGACCTCTTTTATGATGGCCCTGTGCCTTAGTAGTATTT<br>ATGAAGACTTGAAGATGTACCAGGTGGAGTTCAAGACCATGAA<br>TGCAAAGCTTCTGATGGATCCTAAGAGGCAGATCTTTCTAGAT<br>CAAAACATGCTGGCAGTTATTGATGAGCTGATGCAGGCCCTGA<br>ATTTCAACAGTGAGACTGTGCCACAAAAATCCTCCCTTGAAGA<br>ACCTGATTTTTATAAAACTAAAATCAAGCTCTGCATACTTCTT<br>CATGCTTTCCGGATTCGCGCAGTGACTATTGATAGAGTGATGA<br>GCTATCTGAATGCTTCCAGAAAGAGAAGGAGTGGCTCAGGAGC<br>CCCTGTGAAACAGACCCTGAACTTTGACCTCTTGAAGCTTGCT<br>GGGGATGTGGAGTCTAATCCTGGTCCAATGTGTCACCAGCAGT<br>TGGTCATCTCTTGGTTTTCCCTGGTTTTTCTGGCATCTCCCCT<br>TGTGGCCATATGGGAACTGAAGAAAGATGTTTATGTGGTAGAA<br>TTGGATTGGTATCCTGATGCCCCTGGAGAAATGGTGGTCCTCA<br>CCTGTGACACCCCTGAAGAAGATGGTATCACCTGGACCTTGGA<br>CCAGAGCAGTGAGGTCTTAGGCTCTGGCAAAACCCTGACCATC<br>CAAGTCAAAGAGTTTGGAGATGCTGGCCAGTACACCTGTCACA<br>AAGGAGGGGAGGTTCTAAGCCATTCCCTCCTGCTGCTTCACAA<br>AAAGGAAGATGGAATTTGGTCCACTGATATTTTAAAGGACCAG<br>AAAGAACCCAAAAATAAGACCTTTCTAAGATGTGAGGCCAAGA<br>ATTATTCTGGAAGGTTCACCTGCTGGTGGCTGACTACAATCAG<br>TACTGATTTGACATTCAGTGTCAAAAGCAGCAGAGGCTCTTCT<br>GACCCCCAAGGGGTGACATGCGGAGCTGCTACACTCTCTGCAG<br>AGAGAGTCAGAGGGGACAACAAGGAGTATGAGTACTCAGTGGA<br>GTGCCAGGAGGACAGTGCCTGCCCAGCTGCTGAGGAGAGTCTG<br>CCCATTGAGGTGATGGTGGATGCGGTTCACAAGCTCAAGTATG<br>AAAACTACACCAGCAGCTTCTTCATCAGGGACATCATCAAACC<br>TGACCCACCCAAGAACTTGCAGCTGAAGCCATTAAAGAATTCT<br>AGGCAGGTGGAGGTCAGCTGGGAGTACCCTGACACCTGGAGTA<br>CTCCACATTCCTACTTCTCCCTGACATTCTGTGTTCAAGTCCA<br>GGGCAAGAGCAAGAGAGAAAAGAAAGATAGAGTCTTCACTGAC<br>AAGACCTCAGCCACAGTCATCTGCCGCAAAAATGCCAGCATTT<br>CAGTGCGGGCCCAGGACCGCTACTATAGCTCATCTTGGTCAGA<br>ATGGGCATCTGTGCCCTGCAGTTGACAATTGCTGTGCCTTCTA<br>GTTGCCAGCCATCTGTTGTTTGCCCCTCCCCCGTGCCTTCCTT<br>GACCCTGGAAGGTGCCACTCCCACTGTCCTTTCCTAATAAAAT<br>GAGGGAAATTGCATCGCATTGTCTGAGTAGGTGTCATTCTATTC<br>TGGGGGGTGGGGTGGGGCAGGACAGCAAGGGGGAGGATTGGGA<br>AGACAATAGCAGGCATGCTGGGGATGCGGTGGGCTCTATGGAG<br>CTCGAGAGGAACCCCTAGTGATGGAGTTGGCCACTCCCTCTCT<br>GCGCGCTCGCTCGCTCACTGAGGCCGGGCGACCAAAGGTCGCC<br>CGACGCCCGGGCTTTGCCCGGGCGGCCTCAGTGAGCGAGCGAG<br>CGCGCAGCTGCAGATCTG (SEQ ID NO:50) |
| 27 | Human CAG-modified IL-12A/IL-12B-F2A (CpG modified) expression sequence | GCTAGCGCCACCATGTGTCCAGCGCGCAGCCTCCTCCTTGTGG<br>CTACCCTGGTCCTCCTGGACCACCTCAGTTTGGCCAGAAACCT<br>CCCTGTGGCCACTCCAGACCCAGGAATGTTCCCATGCCTTCAC<br>CACTCCCAAAACCTGCTGAGGGCTGTCAGCAACATGCTCCAGA<br>AGGCCAGACAAACTCTAGAATTTTACCCTTGCACTTCTGAAGA<br>GATTGATCATGAAGATATCACAAAAGATAAAACCAGCACAGTG<br>GAGGCCTGTTTACCATTGGAATTAACCAAGAATGAGAGTTGCC<br>TAAATTCCAGAGAGACCTCTTTCATAACTAATGGGAGTTGCCT<br>GGCCTCCAGAAAGACCTCTTTTATGATGGCCCTGTGCCTTAGT<br>AGTATTTATGAAGACTTGAAGATGTACCAGGTGGAGTTCAAGA<br>CCATGAATGCAAAGCTTCTGATGGATCCTAAGAGGCAGATCTT<br>TCTAGATCAAAACATGCTGGCAGTTATTGATGAGCTGATGCAG<br>GCCCTGAATTTCAACAGTGAGACTGTGCCACAAAAATCCTCCC |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
| | | TTGAAGAACCTGATTTTTATAAAACTAAAATCAAGCTCTGCAT<br>ACTTCTTCATGCTTTCCGGATTCGCGCAGTGACTATTGATAGA<br>GTGATGAGCTATCTGAATGCTTCCAGAAAGAGAAGGAGTGGCT<br>CAGGAGCCCCTGTGAAACAGACCCTGAACTTTGACCTCTTGAA<br>GCTTGCTGGGGATGTGGAGTCTAATCCTGGTCCAATGTGTCAC<br>CAGCAGTTGGTCATCTCTTGGTTTTCCCTGGTTTTTCTGGCAT<br>CTCCCCTTGTGGCCATATGGGAACTGAAGAAAGATGTTTATGT<br>GGTAGAATTGGATTGGTATCCTGATGCCCCTGGAGAAATGGTG<br>GTCCTCACCTGTGACACCCCTGAAGAAGATGGTATCACCTGGA<br>CCTTGGACCAGAGCAGTGAGGTCTTAGGCTCTGGCAAAACCCT<br>GACCATCCAAGTCAAAGAGTTTGGAGATGCTGGCCAGTACACC<br>TGTCACAAAGGAGGGAGGTTCTAAGCCATTCCCTCCTGCTGC<br>TTCACAAAAGGAAGATGGAATTTGGTCCACTGATATTTTAAA<br>GGACCAGAAAGAACCCAAAAATAAGACCTTTCTAAGATGTGAG<br>GCCAAGAATTATTCTGGAAGGTTCACCTGCTGGTGGCTGACTA<br>CAATCAGTACTGATTTGACATTCAGTGTCAAAAGCAGCAGAGG<br>CTCTTCTGACCCCCAAGGGGTGACATGCGGAGCTGCTACACTC<br>TCTGCAGAGAGAGTCAGAGGGGACAACAAGGAGTATGAGTACT<br>CAGTGGAGTGCCAGGAGGACAGTGCCTGCCCAGCTGCTGAGGA<br>GAGTCTGCCCATTGAGGTGATGGTGGATGCGGTTCACAAGCTC<br>AAGTATGAAAACTACACCAGCAGCTTCTTCATCAGGGACATCA<br>TCAAACCTGACCCACCCAAGAACTTGCAGCTGAAGCCATTAAA<br>GAATTCTAGGCAGGTGGAGGTCAGCTGGGAGTACCCTGACACC<br>TGGAGTACTCCACATTCCTACTTCTCCCTGACATTCTGTGTTC<br>AAGTCCAGGGCAAGAGCAAGAGAGAAAAGAAAGATAGAGTCTT<br>CACTGACAAGACCTCAGCCACAGTCATCTGCCGCAAAAATGCC<br>AGCATTTCAGTGCGGGCCCAGGACCGCTACTATAGCTCATCTT<br>GGTCAGAATGGGCATCTGTGCCCTGCAGTTGACAATTG (SEQ ID NO: 51) |
| 28 | Human CAG-modified IL-12A/IL-12B-IRES (CpG modified) construct | CTGCGCGCTCGCTCGCTCACTGAGGCCGCCCGGGCAAAGCCCG<br>GGCGTCGGGCGACCTTTGGTCGCCCGGCCTCAGTGAGCGAGCG<br>AGCGCGCAGAGAGGGAGTGGCCAACTCCATCACTAGGGGTTCC<br>TTAGTATTAAACGCGTGTCGACATTGATTATTGACTAGTTATT<br>AATAGTAATCAATTACGGGGTCATTAGTTCATAGCCCATATAT<br>GGAGTTCCGCGTTACATAACTTACGGTAAATGGCCCGCCTGGC<br>TGACCGCCCAACGACCCCCGCCCATTGACGTCAATAATGACGT<br>ATGTTCCCATAGTAACGCCAATAGGGACTTTCCATTGACGTCA<br>ATGGGTGGACTATTTACGGTAAACTGCCCACTTGGCAGTACAT<br>CAAGTGTATCATATGCCAAGTACGCCCCCTATTGACGTCAATG<br>ACGGTAAATGGCCCGCCTGGCATTATGCCCAGTACATGACCTT<br>ATGGGACTTTCCTACTTGGCAGTACATCTACGTATTAGTCATC<br>GCTATTACCATGGGTCGAGGTGAGCCCCACGTTCTGCTTCACT<br>CTCCCCATCTCCCCCCCCTCCCCACCCCCAATTTTGTATTTAT<br>TTATTTTTTAATTATTTTGTGCAGCGATGGGGCGGGGGGGG<br>GGGGGCGCGCGCCAGGCGGGGCGGGGCGGGGCGAGGGGCGGGG<br>CGGGGCGAGGCGGAGAGGTGCGGCGGCAGCCAATCAGAGCGGC<br>GCGCTCCGAAAGTTTCCTTTTATGGCGAGGCGGCGGCGGCGGC<br>GGCCCTATAAAAAGCGAAGCGCGCGGCGGGCGGGAGTCGCTGC<br>GCGCTGCCTTCGCCCCGTGCCCGCTCCGCCGCCGCCTCGCGC<br>CGCCCGCCCCGGCTCTGACTGACCGCGTTACTCCCACAGGTGA<br>GCGGGCGGGACGGCCCTTCTCCTCCGGGCTGTAATTAGCGCTT<br>GGTTTAATGACGGCTCGTTTCTTTTCTGTGGCTGCGTGAAAGC<br>CTTGAGGGGCTCCGGGAGGGCCCTTTGTGCGGGGGGAGCGGCT<br>CGGGGGGTGCGTGCGTGTGTGTGTGCGTGGGGAGCGCCGCGTG<br>CGGCTCCGCGCTGCCCGGCGGCTGTGAGCGCTGCGGGCGCGGC<br>GCGGGGCTTTGTGCGCTCCGCAGTGTGCGCGAGAGGAGCGCGG<br>CCGGGGGCGGTGCCACGCGGTGCGGGGGGGCTGCGAGGGGAA<br>CAAAGGCTGCGTGCGGGGTGTGTGCGTGGGGGGGTGAGCAGG<br>GGGTGTGGGCGCGGCGGTCGGGCTGTAACCCCCCCCCTGCACCC<br>CCCTCCCCGAGTTGCTGAGCACGGCCCGGCTTCGGGTGCGGGG<br>CTCCGTGCGGGGCGTGGCGCGGGGCTCGCCGTGCCGGCGGGG<br>GGTGGCGGCGGGTGGGGGTGCCGGGCGGGGCGGGGCCGCCTCG<br>GGCCGGGGAGGGCTCGGGGGAGGGGCGCGGCGGCCCCCGGAGC<br>GCCGGCGGCTGTCGAGGCGCGGCGAGCCGCAGCCATTGCCTTT<br>TATGGTAATCGTGCGAGAGGGCGCAGGGACTTCCTTTGTCCCA<br>AATCTGTGCGGAGCCGAAATCTGGGAGGCGCCGCCGCACCCCC<br>TCTAGCGGGCGCGGGGCGAAGCGGTGCGGCGCCGGCAGGAAGG<br>AAATGGGCGGGAGGGCCTTCGTGCGTCGCCGCGCCGCCGTCC<br>CCTTCTCCCTCTCCAGCCTCGGGGCTGTCCGCGGGGGACGGC<br>TGCCTTCGGGGGGACGGGGCAGGGCGGGGTTCGGCTTCTGGC<br>GTGTGACCGGCGGTCTAGACTCTGCTAACCATGTTCATGCCTT<br>CTTCTCTTTCCTACAGCTCCTGGGCAACGTGCTGGTTGTTGTG |

TABLE 5-continued

IL-12 and/or IL-15 Exemplary Expression Cassette or Construct Nucleic Acid Sequence

| 1 | Expression Cassette | IL-12 and/or IL-15 Expression Cassette or Construct Nucleic Acid Sequence (SEQ ID NO) |
|---|---|---|
| | | CTGTCTCATCATTTTGGCAAAGAATTCAAGCTTCCAGCTAGCG<br>CCACCATGTGTCCAGCTAGGAGCCTCCTCCTTGTGGCTACCCT<br>GGTCCTCCTGGACCACCTCAGTTTGGCCAGAAACCTCCCTGTG<br>GCCACTCCAGACCCAGGAATGTTCCCATGCCTTCACCACTCCC<br>AAAACCTGCTGAGGGCAGTCAGCAACATGCTCCAGAAGGCCAG<br>ACAAACTCTAGAATTTTACCCTTGCACTTCTGAAGAGATTGAT<br>CATGAAGATATCACAAAAGATAAAACCAGCACAGTGGAGGCCT<br>GTTTACCATTGGAATTAACCAAGAATGAGAGTTGCCTAAATTC<br>CAGAGAGACCTCTTTCATAACTAATGGGAGTTGCCTGGCCTCC<br>AGAAAGACCTCTTTTATGATGGCCCTGTGCCTTAGTAGTATTT<br>ATGAAGACTTGAAGATGTACCAGGTGGAGTTCAAGACCATGAA<br>TGCAAAGCTTCTGATGGATCCTAAGAGGCAGATCTTTCTAGAT<br>CAAAACATGCTGGCAGTTATTGATGAGCTGATGCAGGCCCTGA<br>ATTTCAACAGTGAGACTGTGCCACAAAAATCCTCCCTTGAAGA<br>ACCTGATTTTTATAAAACTAAAATCAAGCTCTGCATACTTCTT<br>CATGCTTTCCGGATTAGGGCAGTGACTATTGATAGAGTGATGA<br>GCTATCTGAATGCTTCCTGAGCCCCTCTCCCTCCCCCCCCCCT<br>AACGTTACTGGCCGAAGCCGCTTGGAATAAGGCCGGTGTGCGT<br>TTGTCTATATGTTATTTTCCACCATATTGCCGTCTTTTGGCAA<br>TGTGAGGGCCCGGAAACCTGGCCCTGTCTTCTTGACGAGCATT<br>CCTAGGGGTCTTTCCCCTCTCGCCAAAGGAATGCAAGGTCTGT<br>TGAATGTCGTGAAGGAAGCAGTTCCTCTGGAAGCTTCTTGAAG<br>ACAAACAACGTCTGTAGCGACCCTTTGCAGGCAGCGGAACCCC<br>CCACCTGGCGACAGGTGCCTCTGCGGCCAAAAGCCACGTGTAT<br>AAGATACACCTGCAAAGGCGGCACAACCCCAGTGCCACGTTGT<br>GAGTTGGATAGTTGTGGAAAGAGTCAAATGGCTCTCCTCAAGC<br>GTATTCAACAAGGGGCTGAAGGATGCCCAGAAGGTACCCCATT<br>GTATGGGATCTGATCTGGGGCCTCGGTACACATGCTTTACATG<br>TGTTTAGTCGAGGTTAAAAAAACGTCTAGGCCCCCCGAACCAC<br>GGGGACGTGGTTTTCCTTTGAAAAACACGATGATAATATGGCC<br>ACAATGTGTCACCAGCAGTTGGTCATCTCTTGGTTTTCCCTGG<br>TTTTTCTGGCATCTCCCCTTGTGGCCATATGGGAACTGAAGAA<br>AGATGTTTATGTGGTAGAATTGGATTGGTATCCTGATGCCCCT<br>GGAGAAATGGTGGTCCTCACCTGTGACACCCCTGAAGAAGATG<br>GTATCACCTGGACCTTGGACCAGAGCAGTGAGGTCTTAGGCTC<br>TGGCAAAACCCTGACCATCCAAGTCAAAGAGTTTGGAGATGCT<br>GGCCAGTACACCTGTCACAAAGGAGGGGAGGTTCTAAGCCATT<br>CCCTCCTGCTGCTTCACAAAAAGGAAGATGGAATTTGGTCCAC<br>TGATATTTTAAAGGACCAGAAAGAACCCAAAAATAAGACCTTT<br>CTAAGATGTGAGGCCAAGAATTATTCTGGAAGGTTCACCTGCT<br>GGTGGCTGACTACAATCAGTACTGATTTGACATTCAGTGTCAA<br>AAGCAGCAGAGGCTCTTCTGACCCCCAAGGGGTGACATGTGGA<br>GCTGCTACACTCTCTGCAGAGAGAGTCAGAGGGGACAACAAGG<br>AGTATGAGTACTCAGTGGAGTGCCAGGAGGACAGTGCCTGCCC<br>AGCTGCTGAGGAGAGTCTGCCCATTGAGGTGATGGTGGATGCA<br>GTTCACAAGCTCAAGTATGAAAACTACACCAGCAGCTTCTTCA<br>TCAGGGACATCATCAAACCTGACCCACCCAAGAACTTGCAGCT<br>GAAGCCATTAAAGAATTCTAGGCAGGTGGAGGTCAGCTGGGAG<br>TACCCTGACACCTGGAGTACTCCACATTCCTACTTCTCCCTGA<br>CATTCTGTGTTCAAGTCCAGGGCAAGAGCAAGAGAGAAAAGAA<br>AGATAGAGTCTTCACTGACAAGACCTCAGCCACAGTCATCTGC<br>AGGAAAAATGCCAGCATTTCAGTGAGGGCCCAGGACAGATACT<br>ATAGCTCATCTTGGTCAGAATGGGCATCTGTGCCCTGCAGTTG<br>ACAATTGCTGTGCCTTCTAGTTGCCAGCCATCTGTTGTTTGCC<br>CCTCCCCCGTGCCTTCCTTGACCCTGGAAGGTGCCACTCCCAC<br>TGTCCTTTCCTAATAAAATGAGGAAATTGCATCGCATTGTCTG<br>AGTAGGTGTCATTCTATTCTGGGGGGTGGGGTGGGGCAGGACA<br>GCAAGGGGGAGGATTGGGAAGACAATAGCAGGCATGCTGGGGA<br>TGCGGTGGGCTCTATGGAGCTCGAGAGGAACCCCTAGTGATGG<br>AGTTGGCCACTCCCTCTCTGCGCGCTCGCTCGCTCACTGAGGC<br>CGGGCGACCAAAGGTCGCCCGACGCCCGGGCTTTGCCCGGGCG<br>GCCTCAGTGAGCGAGCGAGCGCGCAGCTGCAGATCTG (SEQ ID NO: 52) |
| 28 | Human CAG-modified IL-12A/IL-12B-IRES (CpG modified) expression sequence | GCTAGCGCCACCATGTGTCCAGCTAGGAGCCTCCTCCTTGTGG<br>CTACCCTGGTCCTCCTGGACCACCTCAGTTTGGCCAGAAACCT<br>CCCTGTGGCCACTCCAGACCCAGGAATGTTCCCATGCCTTCAC<br>CACTCCCAAAACCTGCTGAGGGCAGTCAGCAACATGCTCCAGA<br>AGGCCAGACAAACTCTAGAATTTTACCCTTGCACTTCTGAAGA<br>GATTGATCATGAAGATATCACAAAAGATAAAACCAGCACAGTG<br>GAGGCCTGTTTACCATTGGAATTAACCAAGAATGAGAGTTGCC<br>TAAATTCCAGAGAGACCTCTTTCATAACTAATGGGAGTTGCCT<br>GGCCTCCAGAAAGACCTCTTTTATGATGGCCCTGTGCCTTAGT |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
|   |   | AGTATTTATGAAGACTTGAAGATGTACCAGGTGGAGTTCAAGA CCATGAATGCAAAGCTTCTGATGGATCCTAAGAGGCAGATCTT TCTAGATCAAAACATGCTGGCAGTTATTGATGAGCTGATGCAG GCCCTGAATTTCAACAGTGAGACTGTGCCACAAAAATCCTCCC TTGAAGAACCTGATTTTTATAAAACTAAAATCAAGCTCTGCAT ACTTCTTCATGCTTTCCGGATTAGGGCAGTGACTATTGATAGA GTGATGAGCTATCTGAATGCTTCCTGAGCCCCTCTCCCTCCCC CCCCCCTAACGTTACTGGCCGAAGCCGCTTGGAATAAGGCCGG TGTGCGTTTGTCTATATGTTATTTTCCACCATATTGCCGTCTT TTGGCAATGTGAGGGCCCGGAAACCTGGCCCTGTCTTCTTGAC GAGCATTCCTAGGGGTCTTTCCCCTCTCGCCAAAGGAATGCAA GGTCTGTTGAATGTCGTGAAGGAAGCAGTTCCTCTGGAAGCTT CTTGAAGACAAACAACGTCTGTAGCGACCCTTTGCAGGCAGCG GAACCCCCCACCTGGCGACAGGTGCCTCTGCGGCCAAAAGCCA CGTGTATAAGATACACCTGCAAAGGCGGCACAACCCCAGTGCC ACGTTGTGAGTTGGATAGTTGTGGAAAGAGTCAAATGGCTCTC CTCAAGCGTATTCAACAAGGGGCTGAAGGATGCCCAGAAGGTA CCCCATTGTATGGGATCTGATCTGGGGCCTCGGTACACATGCT TTACATGTGTTTAGTCGAGGTTAAAAAAACGTCTAGGCCCCCC GAACCACGGGGACGTGGTTTTCCTTTGAAAAACACGATGATAA TATGGCCACAATGTGTCACCAGCAGTTGGTCATCTCTTGGTTT TCCCTGGTTTTTCTGGCATCTCCCCTTGTGGCCATATGGGAAC TGAAGAAAGATGTTTATGTGGTAGAATTGGATTGGTATCCTGA TGCCCCTGGAGAAATGGTGGTCCTCACCTGTGACACCCCTGAA GAAGATGGTATCACCTGGACCTTGGACCAGAGCAGTGAGGTCT TAGGCTCTGGCAAAACCCTGACCATCCAAGTCAAAGAGTTTGG AGATGCTGGCCAGTACACCTGTCACAAAGGAGGGGAGGTTCTA AGCCATTCCCTCCTGCTGCTTCACAAAAAGGAAGATGGAATTT GGTCCACTGATATTTTAAAGGACCAGAAAGAACCCAAAAATAA GACCTTTCTAAGATGTGAGGCCAAGAATTATTCTGGAAGGTTC ACCTGCTGGTGGCTGACTACAATCAGTACTGATTTGACATTCA GTGTCAAAAGCAGCAGAGGCTCTTCTGACCCCCAAGGGGTGAC ATGTGGAGCTGCTACACTCTCTGCAGAGAGAGTCAGAGGGGAC AACAAGGAGTATGAGTACTCAGTGGAGTGCCAGGAGGACAGTG CCTGCCCAGCTGCTGAGGAGAGTCTGCCCATTGAGGTGATGGT GGATGCAGTTCACAAGCTCAAGTATGAAAACTACACCAGCAGC TTCTTCATCAGGGACATCATCAAACCTGACCCACCCAAGAACT TGCAGCTGAAGCCATTAAAGAATTCTAGGCAGGTGGAGGTCAG CTGGGAGTACCCTGACACCTGGAGTACTCCACATTCCTACTTC TCCCTGACATTCTGTGTTCAAGTCCAGGGCAAGAGCAAGAGAG AAAAGAAAGATAGAGTCTTCACTGACAAGACCTCAGCCACAGT CATCTGCAGGAAAAATGCCAGCATTTCAGTGAGGGCCCAGGAC AGATACTATAGCTCATCTTGGTCAGAATGGGCATCTGTGCCCT GCAGTTGACAATTG (SEQ ID NO: 53) |
| 29 | Human CAG-modified IL-12A/IL-12B-IRES (CpG modified) construct | CTGCGCGCTCGCTCGCTCACTGAGGCCGCCCGGGCAAAGCCCG GGCGTCGGGCGACCTTTGGTCGCCCGGCCTCAGTGAGCGAGCG AGCGCGCAGAGAGGGAGTGGCCAACTCCATCACTAGGGGTTCC TTAGTATTAAACGCGTGTCGACATTGATTATTGACTAGTTATT AATAGTAATCAATTACGGGGTCATTAGTTCATAGCCCATATAT GGAGTTCCGCGTTACATAACTTACGGTAAATGGCCCGCCTGGC TGACCGCCCAACGACCCCCGCCCATTGACGTCAATAATGACGT ATGTTCCCATAGTAACGCCAATAGGGACTTTCCATTGACGTCA ATGGGTGGACTATTTACGGTAAACTGCCCACTTGGCAGTACAT CAAGTGTATCATATGCCAAGTACGCCCCCTATTGACGTCAATG ACGGTAAATGGCCCGCCTGGCATTATGCCCAGTACATGACCTT ATGGGACTTTCCTACTTGGCAGTACATCTACGTATTAGTCATC GCTATTACCATGGTCGAGGTGAGCCCCACGTTCTGCTTCACT CTCCCCATCTCCCCCCCCTCCCCACCCCCAATTTTGTATTTAT TTATTTTTTAATTATTTTGTGCAGCGATGGGGGCGGGGGGGG GGGGGCGCGCGCCAGGCGGGGCGGGGCGGGGCGAGGGGCGGGG CGGGGCGAGGCGGAGAGGTGCGGCGGCAGCCAATCAGAGCGGC GCGCTCCGAAAGTTTCCTTTTATGGCGAGGCGGCGGCGGCGGC GGCCCTATAAAAAGCGAAGCGCGCGGCGGGCGGGAGTCGCTGC GCGCTGCCTTCGCCCCGTGCCCGCTCCGCCGCCGCCTCGCGC CGCCCGCCCCGGCTCTGACTGACCGCGTTACTCCCACAGGTGA GCGGGCGGGACGGCCCTTCCTCCTCGGGCTGTAATTAGCGCTT GGTTTAATGACGGCTCGTTTCTTTTCTGTGGCTGCGTGAAAGC CTTGAGGGGCTCCGGGAGGGCCCTTTGTGCGGGGGGAGCGGCT CGGGGGGTGCGTGCGTGTGTGTGTGCGTGGGGAGCGCCGCGTG CGGCTCCGCGCTGCCCGGCGGCTGTGAGCGCTGCGGGCGCGGC GCGGGGCTTTGTGCGCTCCGCAGTGTGCGCGAGAGGGAGCGCGG CCGGGGGCGGTGCCACGCGGTGCGGGGGGGGCTGCGAGGGGAA |

TABLE 5-continued

IL-12 and/or IL-15 Exemplary Expression Cassette or Construct Nucleic Acid Sequence

| 1 | Expression Cassette | IL-12 and/or IL-15 Expression Cassette or Construct Nucleic Acid Sequence (SEQ ID NO) |
|---|---|---|
| | | CAAAGGCTGCGTGCGGGGTGTGTGCGTGGGGGGGGTGAGCAGG<br>GGGTGTGGGCGCGGCGGTCGGGCTGTAACCCCCCCCTGCACCC<br>CCCTCCCCGAGTTGCTGAGCACGGCCCGGCTTCGGGTGCGGGG<br>CTCCGTGCGGGCGTGGCGCGGGGCTCGCCGTGCCGGGCGGGG<br>GGTGGCGGCGGGTGGGGGTGCCGGGCGGGGCGGGGCCGCCTCG<br>GGCCGGGAGGGCTCGGGGGAGGGGCGCGGCGGCCCCCGGAGC<br>GCCGGCGGCTGTCGAGGCGCGGCGAGCCGCAGCCATTGCCTTT<br>TATGGTAATCGTGCGAGAGGGCGCAGGGACTTCCTTTGTCCCA<br>AATCTGTGCGGAGCCGAAATCTGGGAGGCGCCGCCGCACCCCC<br>TCTAGCGGGCGCGGGGCGAAGCGGTGCGGCGCCGGCAGGAAGG<br>AAATGGGCGGGGAGGGCCTTCGTGCGTCGCCGCGCCGCCGTCC<br>CCTTCTCCCTCTCCAGCCTCGGGGCTGTCCGCGGGGGGACGGC<br>TGCCTTCGGGGGGGACGGGGCAGGGCGGGGTTCGGCTTCTGGC<br>GTGTGACCGGCGGTCTAGACTCTGCTAACCATGTTCATGCCTT<br>CTTCTCTTTCCTACAGCTCCTGGGCAACGTGCTGGTTGTTGTG<br>CTGTCTCATCATTTTGGCAAAGAATTCAAGCTTCCAGCTAGCG<br>CCACCATGTGTCCAGCGCGCAGCCTCCTCCTTGTGGCTACCCT<br>GGTCCTCCTGGACCACCTCAGTTTGGCCAGAAACCTCCCTGTG<br>GCCACTCCAGACCCAGGAATGTTCCCATGCCTTCACCACTCCC<br>AAAACCTGCTGAGGGCTGTCAGCAACATGCTCCAGAAGGCCAG<br>ACAAACTCTAGAATTTTACCCTTGCACTTCTGAAGAGATTGAT<br>CATGAAGATATCACAAAAGATAAAACCAGCACAGTGGAGGCCT<br>GTTTACCATTGGAATTAACCAAGAATGAGAGTTGCCTAAATTC<br>CAGAGAGACCTCTTTCATAACTAATGGGAGTTGCCTGGCCTCC<br>AGAAAGACCTCTTTTATGATGGCCCTGTGCCTTAGTAGTATTT<br>ATGAAGACTTGAAGATGTACCAGGTGGAGTTCAAGACCATGAA<br>TGCAAAGCTTCTGATGGATCCTAAGAGGCAGATCTTTCTAGAT<br>CAAAACATGCTGGCAGTTATTGATGAGCTGATGCAGGCCCTGA<br>ATTTCAACAGTGAGACTGTGCCACAAAAATCCTCCCTTGAAGA<br>ACCTGATTTTTATAAAACTAAAATCAAGCTCTGCATACTTCTT<br>CATGCTTTCCGGATTCGCGCAGTGACTATTGATAGAGTGATGA<br>GCTATCTGAATGCTTCCTGAGCCCCTCTCCCTCCCCCCCCCCT<br>AACGTTACTGGCCGAAGCCGCTTGGAATAAGGCCGGTGTGCGT<br>TTGTCTATATGTTATTTTCCACCATATTGCCGTCTTTTGGCAA<br>TGTGAGGGCCCGGAAACCTGGCCCTGTCTTCTTGACGAGCATT<br>CCTAGGGGTCTTTCCCCTCTCGCCAAAGGAATGCAAGGTCTGT<br>TGAATGTCGTGAAGGAAGCAGTTCCTCTGGAAGCTTCTTGAAG<br>ACAAACAACGTCTGTAGCGACCCTTTGCAGGCAGCGGAACCCC<br>CCACCTGGCGACAGGTGCCTCTGCGGCCAAAAGCCACGTGTAT<br>AAGATACACCTGCAAAGGCGGCACAACCCCAGTGCCACGTTGT<br>GAGTTGGATAGTTGTGGAAAGAGTCAAATGGCTCTCCTCAAGC<br>GTATTCAACAAGGGGCTGAAGGATGCCCAGAAGGTACCCCATT<br>GTATGGGATCTGATCTGGGGCCTCGGTACACATGCTTTACATG<br>TGTTTAGTCGAGGTTAAAAAAACGTCTAGGCCCCCCGAACCAC<br>GGGGACGTGGTTTTCCTTTGAAAAACACGATGATAATATGGCC<br>ACAATGTGTCACCAGCAGTTGGTCATCTCTTGGTTTTCCCTGG<br>TTTTTCTGGCATCTCCCCTTGTGGCCATATGGGAACTGAAGAA<br>AGATGTTTATGTGGTAGAATTGGATTGGTATCCTGATGCCCCT<br>GGGAGAAATGGTGGTCCTCACCTGTGACACCCCTGAAGAAGATG<br>GTATCACCTGGACCTTGGACCAGAGCAGTGAGGTCTTAGGCTC<br>TGGCAAAACCCTGACCATCCAAGTCAAAGAGTTTGGAGATGCT<br>GGCCAGTACACCTGTCACAAAGGAGGGGAGGTTCTAAGCCATT<br>CCCTCCTGCTGCTTCACAAAAAGGAAGATGGAATTTGGTCCAC<br>TGATATTTTAAAGGACCAGAAAGAACCCAAAAATAAGACCTTT<br>CTAAGATGTGAGGCCAAGAATTATTCTGGAAGGTTCACCTGCT<br>GGTGGCTGACTACAATCAGTACTGATTTGACATTCAGTGTCAA<br>AAGCAGCAGAGGCTCTTCTGACCCCCAAGGGGTGACATGCGGA<br>GCTGCTACACTCTCTGCAGAGAGTCAGAGGGGACAACAAGG<br>AGTATGAGTACTCAGTGGAGTGCCAGGAGGACAGTGCCTGCCC<br>AGCTGCTGAGGAGAGTCTGCCCATTGAGGTGATGGTGGATGCG<br>GTTCACAAGCTCAAGTATGAAAACTACACCAGCAGCTTCTTCA<br>TCAGGGACATCATCAAACCTGACCCACCCAAGAACTTGCAGCT<br>GAAGCCATTAAAGAATTCTAGGCAGGTGGAGGTCAGCTGGGAG<br>TACCCTGACACCTGGAGTACTCCACATTCCTACTTCTCCCTGA<br>CATTCTGTGTTCAAGTCCAGGGCAAGAGCAAGAGAGAAAAGAA<br>AGATAGAGTCTTCACTGACAAGACCTCAGCCACAGTCATCTGC<br>CGCAAAAATGCCAGCATTTCAGTGCGGGCCCAGGACCGCTACT<br>ATAGCTCATCTTGGTCAGAATGGGCATCTGTGCCCTGCAGTTG<br>ACAATTGCTGTGCCTTCTAGTTGCCAGCCATCTGTTGTTTGCC<br>CCTCCCCGTGCCTTCCTTGACCCTGGAAGGTGCCACTCCCAC<br>TGTCCTTTCCTAATAAAATGAGGAAATTGCATCGCATTGTCTG<br>AGTAGGTGTCATTCTATTCTGGGGGGTGGGTGGGGCAGGACA<br>GCAAGGGGGAGGATTGGGAAGACAATAGCAGGCATGCTGGGGA |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
|  |  | TGCGGTGGGCTCTATGGAGCTCGAGAGGAACCCCTAGTGATGG AGTTGGCCACTCCCTCTCTGCGCGCTCGCTCGCTCACTGAGGC CGGGCGACCAAAGGTCGCCCGACGCCCGGGCTTTGCCCGGGCG GCCTCAGTGAGCGAGCGAGCGCGCAGCTGCAGATCTG (SEQ ID NO: 54) |
| 29 | Human CAG-modified IL-12A/IL-12B-IRES (CpG modified) expression sequence | GCTAGCGCCACCATGTGTCCAGCGCGCAGCCTCCTCCTTGTGG CTACCCTGGTCCTCCTGGACCACCTCAGTTTGGCCAGAAACCT CCCTGTGGCCACTCCAGACCCAGGAATGTTCCCATGCCTTCAC CACTCCCAAAACCTGCTGAGGGCTGTCAGCAACATGCTCCAGA AGGCCAGACAAACTCTAGAATTTTACCCTTGCACTTCTGAAGA GATTGATCATGAAGATATCACAAAAGATAAAACCAGCACAGTG GAGGCCTGTTTACCATTGGAATTAACCAAGAATGAGAGTTGCC TAAATTCCAGAGAGACCTCTTTCATAACTAATGGGAGTTGCCT GGCCTCCAGAAAGACCTCTTTTATGATGGCCCTGTGCCTTAGT AGTATTTATGAAGACTTGAAGATGTACCAGGTGGAGTTCAAGA CCATGAATGCAAAGCTTCTGATGGATCCTAAGAGGCAGATCTT TCTAGATCAAAACATGCTGGCAGTTATTGATGAGCTGATGCAG GCCCTGAATTTCAACAGTGAGACTGTGCCACAAAAATCCTCCC TTGAAGAACCTGATTTTTATAAAACTAAAATCAAGCTCTGCAT ACTTCTTCATGCTTTCCGGATTCGCGCAGTGACTATTGATAGA GTGATGAGCTATCTGAATGCTTCCTGAGCCCCTCTCCCTCCCC CCCCCCTAACGTTACTGGCCGAAGCCGCTTGGAATAAGGCCGG TGTGCGTTTGTCTATATGTTATTTTCCACCATATTGCCGTCTT TTGGCAATGTGAGGGCCCGGAAACCTGGCCCTGTCTTCTTGAC GAGCATTCCTAGGGGTCTTTCCCCTCTCGCCAAAGGAATGCAA GGTCTGTTGAATGTCGTGAAGGAAGCAGTTCCTCTGGAAGCTT CTTGAAGACAAACAACGTCTGTAGCGACCCTTTGCAGGCAGCG GAACCCCCCACCTGGCGACAGGTGCCTCTGCGGCCAAAAGCCA CGTGTATAAGATACACCTGCAAAGGCGGCACAACCCCAGTGCC ACGTTGTGAGTTGGATAGTTGTGGAAAGAGTCAAATGGCTCTC CTCAAGCGTATTCAACAAGGGGCTGAAGGATGCCCAGAAGGTA CCCCATTGTATGGGATCTGATCTGGGGCCTCGGTACACATGCT TTACATGTGTTTAGTCGAGGTTAAAAAAACGTCTAGGCCCCCC GAACCACGGGGACGTGGTTTTCCTTTGAAAAACACGATGATAA TATGGCCACAATGTGTCACCAGCAGTTGGTCATCTCTTGGTTT TCCCTGGTTTTTCTGGCATCTCCCCTTGTGGCCATATGGGAAC TGAAGAAAGATGTTTATGTGGTAGAATTGGATTGGTATCCTGA TGCCCCTGGAGAAATGGTGGTCCTCACCTGTGACACCCCTGAA GAAGATGGTATCACCTGGACCTTGGACCAGAGCAGTGAGGTCT TAGGCTCTGGCAAAACCCTGACCATCCAAGTCAAAGAGTTTGG AGATGCTGGCCAGTACACCTGTCACAAAGGAGGGGAGGTTCTA AGCCATTCCCTCCTGCTGCTTCACAAAAAGGAAGATGGAATTT GGTCCACTGATATTTTAAAGGACCAGAAAGAACCCAAAAATAA GACCTTTCTAAGATGTGAGGCCAAGAATTATTCTGGAAGGTTC ACCTGCTGGTGGCTGACTACAATCAGTACTGATTTGACATTCA GTGTCAAAAGCAGCAGAGGCTCTTCTGACCCCCAAGGGGTGAC ATGCGGAGCTGCTACACTCTCTGCAGAGAGAGTCAGAGGGGAC AACAAGGAGTATGAGTACTCAGTGGAGTGCCAGGAGGACAGTG CCTGCCCAGCTGCTGAGGAGAGTCTGCCCATTGAGGTGATGGT GGATGCGGTTCACAAGCTCAAGTATGAAAACTACACCAGCAGC TTCTTCATCAGGGACATCATCAAACCTGACCCACCCAAGAACT TGCAGCTGAAGCCATTAAAGAATTCTAGGCAGGTGGAGGTCAG CTGGGAGTACCCTGACACCTGGAGTACTCCACATTCCTACTTC TCCCTGACATTCTGTGTTCAAGTCCAGGGCAAGAGCAAGAGAG AAAAGAAAGATAGAGTCTTCACTGACAAGACCTCAGCCACAGT CATCTGCCGCAAAAATGCCAGCATTTCAGTGCGGGCCCAGGAC CGCTACTATAGCTCATCTTGGTCAGAATGGGCATCTGTGCCCT GCAGTTGACAATTG (SEQ ID NO: 55) |
| 30 | Human CAG-wild-type IL-12A/IL-12B-F2A (CpG modified) construct | CTGCGCGCTCGCTCGCTCACTGAGGCCGCCCGGGCAAAGCCCG GGCGTCGGGCGACCTTTGGTCGCCCGGCCTCAGTGAGCGAGCG AGCGCGCAGAGAGGGAGTGGCCAACTCCATCACTAGGGGTTCC TTAGTATTTAAACGCGTGTCGACATTGATTATTGACTAGTTATT AATAGTAATCAATTACGGGGTCATTAGTTCATAGCCCATATAT GGAGTTCCGCGTTACATAACTTACGGTAAATGGCCCGCCTGGC TGACCGCCCAACGACCCCCGCCCATTGACGTCAATAATGACGT ATGTTCCCATAGTAACGCCAATAGGGACTTTCCATTGACGTCA ATGGGTGGACTATTTACGGTAAACTGCCCACTTGGCAGTACAT CAAGTGTATCATATGCCAAGTACGCCCCCTATTGACGTCAATG ACGGTAAATGGCCCGCCTGGCATTATGCCCAGTACATGACCTT ATGGGACTTTCCTACTTGGCAGTACATCTACGTATTAGTCATC GCTATTACCATGGGTCGAGGTGAGCCCCACGTTCTGCTTCACT |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
| | | CTCCCCATCTCCCCCCCCTCCCCACCCCCAATTTTGTATTTAT<br>TTATTTTTAATTATTTTGTGCAGCGATGGGGCGGGGGGGG<br>GGGGGCGCGCGCCAGGCGGGGCGGGGCGGGGCGAGGGGCGGGG<br>CGGGGCGAGGCGGAGAGGTGCGGCGGCAGCCAATCAGAGCGGC<br>GCGCTCCGAAAGTTTCCTTTTATGGCGAGGCGGCGGCGGCGGC<br>GGCCCTATAAAAAGCGAAGCGCGCGGCGGGCGGGAGTCGCTGC<br>GCGCTGCCTTCGCCCCGTGCCCCGCTCCGCCGCCGCCTCGCGC<br>CGCCCGCCCCGGCTCTGACTGACCGCGTTACTCCCACAGGTGA<br>GCGGGCGGGACGGCCCTTCTCCTCCGGGCTGTAATTAGCGCTT<br>GGTTTAATGACGGCTCGTTTCTTTTCTGTGGCTGCGTGAAAGC<br>CTTGAGGGGCTCCGGGAGGGCCCTTTGTGCGGGGGGAGCGGCT<br>CGGGGGGTGCGTGCGTGTGTGTGCGTGGGGAGCGCCGCGTG<br>CGGCTCCGCGCTGCCCGGCGGCTGTGAGCGCTGCGGGCGCGGC<br>GCGGGGCTTTGTGCGCTCCGCAGTGTGCGCGAGAGGAGCGCGG<br>CCGGGGGCGGTGCCACGCGGTGCGGGGGGGGCTGCGAGGGGAA<br>CAAAGGCTGCGTGCGGGGTGTGTGCGTGGGGGGGGTGAGCAGG<br>GGGTGTGGGCGCGGCGGTCGGGCTGTAACCCCCCCTGCACCC<br>CCCTCCCCGAGTTGCTGAGCACGGCCCGGCTTCGGGTGCGGGG<br>CTCCGTGCGGGGCGTGGCGCGGGGCTCGCCGTGCCGGGCGGGG<br>GGTGGCGGCGGGTGGGGGTGCCGGGCGGGGCGGGGCCGCCTCG<br>GGCCGGGGAGGGCTCGGGGGAGGGGCGCGGCGGCCCCCGGAGC<br>GCCGGCGGCTGTCGAGGCGCGGCGAGCCGCAGCCATTGCCTTT<br>TATGGTAATCGTGCGAGAGGGCGCAGGGACTTCCTTTGTCCCA<br>AATCTGTGCGGAGCCGAAATCTGGGAGGCGCCGCCGCACCCCC<br>TCTAGCGGGCGCGGGGCGAAGCGGTGCGGCGCCGGCAGGAAGG<br>AAATGGGCGGGGAGGGCCTTCGTGCGTCGCCGCGCCGCCGTCC<br>CCTTCTCCCTCTCCAGCCTCGGGGCTGTCCGCGGGGGGACGGC<br>TGCCTTCGGGGGGGACGGGGCAGGGCGGGGTTCGGCTTCTGGC<br>GTGTGACCGGCGGTCTAGACTCTGCTAACCATGTTCATGCCTT<br>CTTCTCTTTCCTACAGCTCCTGGGCAACGTGCTGGTTGTTGTG<br>CTGTCTCATCATTTTGGCAAAGAATTCAAGCTTCCAGCTAGCG<br>CCACCATGTGTCCAGCGCGCAGCCTCCTCCTTGTGGCTACCCT<br>GGTCCTCCTGGACCACCTCAGTTTGGCCAGAAACCTCCCCGTG<br>GCCACTCCAGACCCAGGAATGTTCCCATGCCTTCACCACTCCC<br>AAAACCTGCTGAGGGCCGTCAGCAACATGCTCCAGAAGGCCAG<br>ACAAACTCTAGAATTTTACCCTTGCACTTCTGAAGAGATTGAT<br>CATGAAGATATCACAAAAGATAAAACCAGCACAGTGGAGGCCT<br>GTTTACCATTGGAATTAACCAAGAATGAGAGTTGCCTAAATTC<br>CAGAGAGACCTCTTTCATAACTAATGGGAGTTGCCTGGCCTCC<br>AGAAAGACCTCTTTTATGATGGCCCTGTGCCTTAGTAGTATTT<br>ATGAAGACTTGAAGATGTACCAGGTGGAGTTCAAGACCATGAA<br>TGCAAAGCTTCTGATGGATCCTAAGAGGCAGATCTTTCTAGAT<br>CAAAACATGCTGGCAGTTATTGATGAGCTGATGCAGGCCCTGA<br>ATTTCAACAGTGAGACTGTGCCACAAAAATCCTCCCTTGAAGA<br>ACCGGATTTTTATAAAACTAAAATCAAGCTCTGCATACTTCTT<br>CATGCTTTCCGGATTCGGGCAGTGACTATTGATAGAGTGATGA<br>GCTATCTGAATGCTTCCAGAAAGAGAAGGAGTGGCTCAGGAGC<br>CCCTGTGAAACAGACCCTGAACTTTGACCTCTTGAAGCTTGCT<br>GGGGATGTGGAGTCTAATCCTGGTCCAATGTGTCACCAGCAGT<br>TGGTCATCTCTTGGTTTTCCCTGGTTTTTCTGGCATCTCCCCT<br>CGTGGCCATATGGGAACTGAAGAAAGATGTTTATGTCGTAGAA<br>TTGGATTGGTATCCGGATGCCCCTGGAGAAATGGTGGTCCTCA<br>CCTGTGACACCCCTGAAGAAGATGGTATCACCTGGACCTTGGA<br>CCAGAGCAGTGAGGTCTTAGGCTCTGGCAAAACCCTGACCATC<br>CAAGTCAAAGAGTTTGGAGATGCTGGCCAGTACACCTGTCACA<br>AAGGAGGCGAGGTTCTAAGCCATTCGCTCCTGCTGCTTCACAA<br>AAAGGAAGATGGAATTTGGTCCACTGATATTTTAAAGGACCAG<br>AAAGAACCCAAAAATAAGACCTTTCTAAGATGCGAGGCCAAGA<br>ATTATTCTGGACGTTTCACCTGCTGGTGGCTGACGACAATCAG<br>TACTGATTTGACATTCAGTGTCAAAAGCAGCAGAGGCTCTTCT<br>GACCCCCAAGGGGTGACGTGCGGAGCTGCTACACTCTCTGCAG<br>AGAGAGTCAGAGGGGACAACAAGGAGTATGAGTACTCAGTGGA<br>GTGCCAGGAGGACAGTGCCTGCCCAGCTGCTGAGGAGAGTCTG<br>CCCATTGAGGTGATGGTGGATGCCGTTCACAAGCTCAAGTATG<br>AAAACTACACCAGCAGCTTCTTCATCAGGGACATCATCAAACC<br>TGACCCACCCAAGAACTTGCAGCTGAAGCCATTAAAGAATTCT<br>CGGCAGGTGGAGGTCAGCTGGGAGTACCCTGACACCTGGAGTA<br>CTCCACATTCCTACTTCTCCCTGACATTCTGCGTTCAAGTCCA<br>GGGCAAGAGCAAGAGAGAAAAGAAAGATAGAGTCTTCACGGAC<br>AAGACCTCAGCCACGGTCATCTGCCGCAAAAATGCCAGCATTA<br>GCGTGCGGGCCCAGGACCGCTACTATAGCTCATCTTGGAGCGA<br>ATGGGCATCTGTGCCCTGCAGTTGACAATTGCTGTGCCTTCTA<br>GTTGCCAGCCATCTGTTGTTTGCCCCTCCCCCGTGCCTTCCTT |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
| | | GACCCTGGAAGGTGCCACTCCCACTGTCCTTTCCTAATAAAT GAGGAAATTGCATCGCATTGTCTGAGTAGGTGTCATTCTATTC TGGGGGGTGGGGTGGGGCAGGACAGCAAGGGGGAGGATTGGGA AGACAATAGCAGGCATGCTGGGGATGCGGTGGGCTCTATGGAG CTCGAGAGGAACCCCTAGTGATGGAGTTGGCCACTCCCTCTCT GCGCGCTCGCTCGCTCACTGAGGCCGGGCGACCAAAGGTCGCC CGACGCCCGGGCTTTGCCCGGGCGGCCTCAGTGAGCGAGCGAG CGCGCAGCTGCAGATCTG (SEQ ID NO: 56) |
| 31 | Human CAG-wild-type IL-12A/IL-12B-F2A (CpG modified) expression sequence | GCTAGCGCCACCATGTGTCCAGCGCGCAGCCTCCTCCTTGTGG CTACCCTGGTCCTCCTGGACCACCTCAGTTTGGCCAGAAACCT CCCCGTGGCCACTCCAGACCCAGGAATGTTCCCATGCCTTCAC CACTCCCAAAACCTGCTGAGGGCCGTCAGCAACATGCTCCAGA AGGCCAGACAAACTCTAGAATTTTACCCTTGCACTTCTGAAGA GATTGATCATGAAGATATCACAAAAGATAAAACCAGCACAGTG GAGGCCTGTTTACCATTGGAATTAACCAAGAATGAGAGTTGCC TAAATTCCAGAGAGACCTCTTTCATAACTAATGGGAGTTGCCT GGCCTCCAGAAAGACCTCTTTTATGATGGCCCTGTGCCTTAGT AGTATTTATGAAGACTTGAAGATGTACCAGGTGGAGTTCAAGA CCATGAATGCAAAGCTTCTGATGGATCCTAAGAGGCAGATCTT TCTAGATCAAAACATGCTGGCAGTTATTGATGAGCTGATGCAG GCCCTGAATTTCAACAGTGAGACTGTGCCACAAAAATCCTCCC TTGAAGAACCGGATTTTTATAAAACTAAAATCAAGCTCTGCAT ACTTCTTCATGCTTTCCGGATTCGGGCAGTGACTATTGATAGA GTGATGAGCTATCTGAATGCTTCCAGAAAGAGAAGGAGTGGCT CAGGAGCCCCTGTGAAACAGACCCTGAACTTTGACCTCTTGAA GCTTGCTGGGGATGTGGAGTCTAATCCTGGTCCAATGTGTCAC CAGCAGTTGGTCATCTCTTGGTTTTCCCTGGTTTTTCTGGCAT CTCCCCTCGTGGCCATATGGGAACTGAAGAAAGATGTTTATGT CGTAGAATTGGATTGGTATCCGGATGCCCCTGGAGAAATGGTG GTCCTCACCTGTGACACCCCTGAAGAAGATGGTATCACCTGGA CCTTGGACCAGAGCAGTGAGGTCTTAGGCTCTGGCAAAACCCT GACCATCCAAGTCAAAGAGTTTGGAGATGCTGGCCAGTACACC TGTCACAAAGGAGGCGAGGTTCTAAGCCATTCGCTCCTGCTGC TTCACAAAAAGGAAGATGGAATTTGGTCCACTGATATTTTAAA GGACCAGAAAGAACCCAAAAATAAGACCTTTCTAAGATGCGAG GCCAAGAATTATTCTGGACGTTTCACCTGCTGGTGGCTGACGA CAATCAGTACTGATTTGACATTCAGTGTCAAAAGCAGCAGAGG CTCTTCTGACCCCCAAGGGGTGACGTGCGGAGCTGCTACACTC TCTGCAGAGAGAGTCAGAGGGGACAACAAGGAGTATGAGTACT CAGTGGAGTGCCAGGAGGACAGTGCCTGCCCAGCTGCTGAGGA GAGTCTGCCCATTGAGGTGATGGTGGATGCCGTTCACAAGCTC AAGTATGAAAACTACACCAGCAGCTTCTTCATCAGGGACATCA TCAAACCTGACCCACCCAAGAACTTGCAGCTGAAGCCATTAAA GAATTCTCGGCAGGTGGAGGTCAGCTGGGAGTACCCTGACACC TGGAGTACTCCACATTCCTACTTCTCCCTGACATTCTGCGTTC AAGTCCAGGGCAAGAGCAAGAGAGAAAAGAAAGATAGAGTCTT CACGGACAAGACCTCAGCCACGGTCATCTGCCGCAAAAATGCC AGCATTAGCGTGCGGGCCCAGGACCGCTACTATAGCTCATCTT GGAGCGAATGGGCATCTGTGCCCTGCAGTTGACAATTG (SEQ ID NO: 57) |
| 32 | CMV enhancer-CBA promoter-WT human IL-12A (no in-frame stop codon)-F2A-WT human IL-12B (with stop codon)-HGH polyA | ctgcgcgctcgctcgctcactgaggccgcccgggcaaagcccg ggcgtcgggcgacctttggtcgcccggcctcagtgagcgagcg agcgcgcagagagggagtggccaactccatcactaggggttcc ttagtattaaacgcgtgtcgacattgattattgactagttatt aatagtaatcaattacggggtcattagttcatagcccatatat ggagttccgcgttacataacttacggtaaatggcccgcctggc tgaccgcccaacgacccccgcccattgacgtcaataatgacgt atgttcccatagtaacgccaatagggactttccattgacgtca atggtgactatttacggtaaactgcccacttggcagtacat caagtgtatcatatgccaagtacgccccctattgacgtcaatg acggtaaatggcccgcctggcattatgcccagtacatgacctt atgggactttcctacttggcagtacatctacgtattagtcatc gctattaccatggtcgaggtgagccccacgttctgcttcact ctccccatctccccccctccccaccccaattttgtatttat ttattttttaattattttgtgcagcgatggggcggggggggg ggggcgcgcgccaggcggggcggggcgggcgaggggcgggg cggggcgaggcggagaggtgcggcggcagccaatcagagcggc gcgctccgaaagtttccttttatggcgaggcggcggcggcggc ggccctataaaaagcgaagcgcgcggcgggcgggagtcgctgc gcgctgccttcgccccgtgccccgctccgccgccgcctcgcgc cgcccgcccggctctgactgaccgcgttactcccacaggtga |

TABLE 5-continued

IL-12 and/or IL-15 Exemplary Expression Cassette or
Construct Nucleic Acid Sequence

| 1 | Expression Cassette | IL-12 and/or IL-15 Expression Cassette or Construct Nucleic Acid Sequence (SEQ ID NO) |
|---|---|---|
| | | gcgggcgggacggcccttctcctccgggctgtaattagcgctt ggtttaatgacggctcgtttcttttctgtggctgcgtgaaagc cttgaggggctccgggagggccctttgtgcgggggggagcggct cggggggtgcgtgcgtgtgtgtgtgcgtggggagcgccgcgtg cggctccgcgctgcccggcggctgtgagcgctgcgggcgcggc gcggggctttgtgcgctccgcagtgtgcgcgagaggagcgcgg ccggggcggtgccacgcggtgcggggggggctgcgaggggaa caaaggctgcgtgcggggtgtgtgcgtggggggggtgagcagg gggtgtgggcgcggcggtcgggctgtaaccccccctgcaccc ccctccccgagttgctgagcacggcccggcttcgggtgcgggg ctccgtgcggggcgtggcgcggggctcgccgtgccgggcgggg ggtggcggcgggtggggtgccggcggggcggggccgcctcg ggccgggagggctcggggagggcgcggcggccccccggagc gccggcggctgtcgaggcgcggcggcgagccgcagccattgcctt tatggtaatcgtgcgagagggcgcagggacttcctttgtccca aatctgtgcggagccgaaatctgggaggcgccgccgcacccc tctagcgggcgcggggcgaagcggtgcggcgccggcaggaagg aaatgggcggggagggccttcgtgcgtcgccgcgccgccgtcc ccttctccctctccagcctcggggctgtccgcggggggacggc tgccttcggggggggacgggcagggcggggttcggcttctggc gtgtgaccggcggtctagactctgctaaccatgttcatgcctt cttctctttcctacagctcctgggcaacgtgctggttgttgtg ctgtctcatcattttggcaaagaattcaagcttccagctagcg ccaccatgtgtccagcgcgcagcctcctccttgtggctaccct ggtcctcctggaccacctcagtttggccagaaacctccccgtg gccactccagacccaggaatgttcccatgccttcaccactccc aaaacctgctgagggccgtcagcaacatgctccagaaggccag acaaactctagaattttaccccttgcacttctgaagagattgat catgaagatatcacaaaagataaaaccagcacagtggaggcct gtttaccattggaattaaccaagaatgagagttgcctaaattc cagagagacctctttcataactaatgggagttgcctggcctcc agaaagacctcttttatgatggccctgtgccttagtagtattt atgaagacttgaagatgtaccaggtggagttcaagaccatgaa tgcaaagcttctgatggatcctaagaggcagatctttctagat caaaacatgctggcagttattgatgagctgatgcaggccctga atttcaacagtgagactgtgccacaaaaatcctcccttgaaga accggattttttataaaactaaaatcaagctctgcatacttctt catgctttccggattcgggcagtgactattgatagagtgatga gctatctgaatgcttccagaaagagaaggagtggctcaggagc ccctgtgaaacagaccctgaactttgacctcttgaagcttgct ggggatgtggagtctaatcctggtccaatgtgtcaccagcagt tggtcatctcttggttttccctggttttttctggcatctcccct cgtggccatatgggaactgaagaaagatgtttatgtcgtagaa ttggattggtatccggatgcccctggagaaatggtggtcctca cctgtgacacccctgaagaagatggtatcacctggaccttgga ccagagcagtgaggtcttaggctctggcaaaaccctgaccatc caagtcaaagagtttggagatgctggccagtacacctgtcaca aaggaggcgaggttctaagccattcgctcctgctgcttcacaa aaaggaagatggaatttggtccactgatattttaaaggaccag aaagaacccaaaaataagacctttctaagatgcgaggccaaga attattctggacgtttcacctgctggtggctgacgacaatcag tactgatttgacattcagtgtcaaaagcagcagaggctcttct gaccccaaggggtgacgtgcggagctgctacactctctgcag agagagtcagaggggacaacaaggagtatgagtactcagtgga gtgccaggaggacagtgcctgcccagctgctgaggagagtctg cccattgaggtgatggtggatgccgttcacaagctcaagtatg aaaactacaccagcagcttcttcatcagggacatcatcaaacc tgacccacccaagaacttgcagctgaagccattaaagaattct cggcaggtggaggtcagctgggagtaccctgacacctggagta ctccacattcctactttctccctgacattctgcgttcaagtcca gggcaagagcaagagagaaaagaaagatagagtcttcacggac aagacctcagccacggtcatctgccgcaaaaatgccagcatta gcgtgcgggcccaggaccgctactatagctcatcttggagcga atgggcatctgtgcctgcagttgacaattggatctacgggtg gcatccctgtgaccctccccagtgcctctcctggccctggaa gttgccactccagtgcccaccagccttgtcctaataaaattaa gttgcatcattttgtctgactaggtgtccttctataatattat gggtggaggggggtggtatggagcaaggggcaagttgggaag acaacctgtagggcctgcggggtctattgggaaccaagctgga gtgcagtggcacaatcttggctcactgcaatctccgcctcctg ggttcaagcgattctcctgcctcagcctcccgagttgttggga ttccaggcatgcatgaccaggctcagctaattttgtttttt ggtagagacggggtttcaccatattggccaggctggtctccaa |

TABLE 5-continued

IL-12 and/or IL-15 Exemplary Expression Cassette or Construct Nucleic Acid Sequence

| 1 | Expression Cassette | IL-12 and/or IL-15 Expression Cassette or Construct Nucleic Acid Sequence (SEQ ID NO) |
|---|---|---|
| | | ctcctaatctcaggtgatctacccaccttggcctcccaaattg<br>ctgggattacaggcgtgaaccactgctcccttccctgtccttc<br>tggagctcgagaggaaccccctagtgatggagttggccactccc<br>tctctgcgcgctcgctcgctcactgaggccgggcgaccaaagg<br>tcgcccgacgcccgggctttgcccgggcggcctcagtgagcga<br>gcgagcgcgcagctgcagatctg<br>(SEQ ID NO: 82) |
| 33 | CMV enhancer-CBA promoter-WT mouse IL-12A (no in-frame stop codon)-F2A-WT mouse IL-12B (with stop codon)-HGH polyA | ctgcgcgctcgctcgctcactgaggccgcccgggcaaagcccg<br>ggcgtcgggcgacctttggtcgcccggcctcagtgagcgagcg<br>agcgcgcagagagggagtggccaactccatcactaggggttcc<br>ttagtattaaacgcgtgtcgacattgattattgactagttatt<br>aatagtaatcaattacggggtcattagttcatagcccatatat<br>ggagttccgcgttacataacttacggtaaatggcccgcctggc<br>tgaccgcccaacgaccccgcccattgacgtcaataatgacgt<br>atgttcccatagtaacgccaatagggactttccattgacgtca<br>atgggtggactatttacggtaaactgcccacttggcagtacat<br>caagtgtatcatatgccaagtacgccccctattgacgtcaatg<br>acggtaaatggcccgcctggcattatgcccagtacatgacctt<br>atgggactttcctacttggcagtacatctacgtattagtcatc<br>gctattaccatgggtcgaggtgagccccacgttctgcttcact<br>ctccccatctccccccctccccaccccaattttgtatttat<br>ttattttttaattattttgtgcagcgatggggggggggggggg<br>ggggcgcgcgccaggcggggcggggcggggcgaggggcgggg<br>cggggcgaggcggagaggtgcggcggcagccaatcagagcggc<br>gcgctccgaaagtttccttttatggcgaggcggcggcggcggc<br>ggccctataaaaagcgaagcgcgcggcgggcgggagtcgctgc<br>gcgctgccttcgccccgtgccccgctccgccgccgcctcgcgc<br>cgcccgcccggctctgactgaccgcgttactcccacaggtga<br>gcgggcgggacggcccttctcctccgggctgtaattagcgctt<br>ggtttaatgacggctcgtttcttttctgtggctgcgtgaaagc<br>cttgaggggctccgggagggcccttttgtgcggggggagcggct<br>cggggggtgcgtgcgtgtgtgtgtgcgtggggagcgccgcgtg<br>cggctccgcgctgcccggcggctgtgagcgctgcgggcgcggc<br>gcggggctttgtgcgctccgcagtgtgcgcgagaggagcgcgg<br>ccggggcggtgccacgcggtgcggggggggctgcgaggggaa<br>caaaggctgcgtgcggggtgtgtgcgtggggggggtgagcagg<br>gggtgtgggcgcggcggtcgggctgtaaccccccctgcaccc<br>ccctccccgagttgctgagcacggcccggcttcgggtgcgggg<br>ctccgtgcggggcgtggcgcggggctcgccgtgccgggcgggg<br>ggtggcggcgggtgggggtgccgggcggggcggggccgcctcg<br>ggccggggagggctcggggggagggcgcggcggccccgagc<br>gccggcggctgtcgaggcgcggcgagccgcagccattgccttt<br>tatggtaatcgtgcgagagggcgcagggacttcctttgtccca<br>aatctgtgcggagccgaaatctgggaggcgccgccgcaccccc<br>tctagcgggcgcggggcgaagcggtgcggcgccggcaggaagg<br>aaatgggcggggagggccttcgtgcgtcgccgcgccgccgtcc<br>ccttctccctctccagcctcggggctgtccgcgggggggacggc<br>tgccttcgggggggacggggcagggcggggttcggcttctggc<br>gtgtgaccggcggtctagactctgctaaccatgttcatgcctt<br>cttctctttcctacagctcctgggcaacgtgctggttgttgtg<br>ctgtctcatcattttggcaaagaattcaagcttccagctagcg<br>ccaccatggtcagcgttccaacagcctcaccctcggcatccag<br>cagctcctctcagtgccggtccagcatgtgtcaatcacgctac<br>ctcctcttttggccacccttgccctcctaaaccacctcagtt<br>tggccagggtcattccagtctctggacctgccaggtgtcttag<br>ccagtcccgaaacctgctgaagaccacagatgacatggtgaag<br>acggccagagaaaaactgaaacattattcctgcactgctgaag<br>acatcgatcatgaagacatcacacgggaccaaaccagcacatt<br>gaagacctgtttaccactggaactacacaagaacgagagttgc<br>ctggctactagagagacttcttccacaacaagagggagctgcc<br>tgccccccacagaagacgtctttgatgatgaccctgtgccttgg<br>tagcatctatgaggacttgaagatgtaccagacagagttccag<br>gccatcaacgcagcacttcagaatcacaaccatcagcagatca<br>ttctagacaagggcatgctggtggccatcgatgagctgatgca<br>gtctctgaatcataatggcgagactctgcgccagaaacctcct<br>gtgggagaagcagacccttacagagtgaaaatgaagctctgca<br>tcctgcttcacgccttcagcacccgcgtcgtgaccatcaacag<br>ggtgatgggctatctgagctccgccagaaagagaaggagtggc<br>tcaggagcccctgtgaaacagaccctgaactttgacctcttga<br>agcttgctggggatgtggagtctaatcctggtccaatgtgtcc<br>tcagaagctaaccatctcctggtttgccatcgttttgctggtg<br>tctccactcatggccatgtgggagctggagaaagacgtttatg |

TABLE 5-continued

IL-12 and/or IL-15 Exemplary Expression Cassette or
Construct Nucleic Acid Sequence

| 1 Expression Cassette | IL-12 and/or IL-15 Expression Cassette or Construct Nucleic Acid Sequence (SEQ ID NO) |
|---|---|
| | ttgtagaggtggactggactcccgatgccctggagaaacagt gaacctcacctgtgacacgcctgaagaagatgacatcacctgg acctcagaccagagacatggagtcataggctctggaaagaccc tgaccatcactgtcaaagagtttctagatgctggccagtacac ctgccacaaaggaggcgagactctgagccactcacatctgctg ctccacaagaaggaaaatgaatttggtccactgaaattttaa aaaatttcaaaaacaagactttcctgaagtgtgaagcaccaaa ttactccggacggttcacgtgctcatggctggtgcaaagaaac atggacttgaagttcaacatcaagagcagtagcagttccctg actctcgggcagtgacatgtggaatggctctctgtctgcaga gaaggtcacactggaccaaagggactatgagaagtattcagtg tcctgccaggaggatgtcacctgcccaactgccaggagaccc tgcccattgaactggcgttggaagcacggcagcagaataaata tgagaactacagcaccagcttcttcatcagggacatcatcaaa ccagacccgcccaagaacttgcagatgaagcctttgaagaact cacaggtggaggtcagctgggagtaccctgactcctggagcac tccccattcctacttctccctcaagttctttgttcgaatccag cgcaagaaagaaaagatgaaggagacagaggaggggtgtaacc agaaaggagcgttcctcgtagagaagacatctaccgaagtcca atgcaaaggcgggaatgtctgcgtgcaagctcaggatcgctat tacaattcctcatgcagcaagtgggcatgtgttccctgcaggg tccgatcctgacaattggatctacgggtggcatccctgtgacc cctcccagtgcctctcctggccctggaagttgccactccagt gccaccagccttgtcctaataaaattaagttgcatcattttg tctgactaggtgtccttctataatattatggggtggaggggg tggtatggagcaagggcaagttgggaagacaacctgtagggc ctgcggggtctattgggaaccaagctggagtgcagtggcacaa tcttggctcactgcaatctccgcctcctgggttcaagcgattc tcctgcctcagcctcccgagttgttgggattccaggcatgcat gaccaggctcagctaatttttgttttttggtagagacggggt ttcaccatattggccaggctggtctccaactcctaatctcagg tgatctacccaccttggcctcccaaattgctgggattacaggc gtgaaccactgctcccttccctgtccttctggagctcgagagg aaccccctagtgatggagttggccactccctctctgcgcgctcg ctcgctcactgaggccgggcgaccaaaggtcgcccgacgcccg ggctttgcccggcggcctcagtgagcgagcgagcgcgcagct gcagatctg (SEQ ID NO: 83) |

TABLE 6

Human IL-12A (p35) and IL-12B (p40) Exemplary Construct
Nucleic Acid Sequences

| SEQ ID NOs | Name | Nucleic Acid Sequence |
|---|---|---|
| SEQ ID NO: 84 | AAV2 5' ITR | ctgcgcgctcgctcgctcactgaggccgcccgggcaaagcccgggcgtcgg gcgacctttggtcgcccggcctcagtgagcgagcgagcgcgcagagagga gtggccaactccatcactaggggttcct |
| SEQ ID NO: 68 | CMV Enhancer | gacattgattattgactagttattaatagtaatcaattacggggtcattagttcatag cccatatatggagttccgcgttacataacttacggtaaatggcccgcctggctga ccgcccaacgaccccgcccattgacgtcaataatgacgtatgttcccatagta acgccaatagggactttccattgacgtcaatgggtggactatttacggtaaactg cccacttggcagtacatcaagtgtatcatatgccaagtacgccccctattgacgt caatgacggtaaatggcccgcctggcattatgcccagtacatgaccttatggga ctttcctacttggcagtacatctacgtattagtcatcgctattaccatg |
| SEQ ID NO: 85 | Chicken Beta Actin (CBA) Promoter | tcgaggtgagccccacgttctgatcactctccccatctcccccccctcccacc cccaattttgtatttatttattttttaattattttgtgcagcgatggggggcgggggg gggggcgcgcgccaggcggggcggggcgggcgaggggcggggcg gggcgaggcggagaggtgcggcggcagccaatcagagcggcgcgctccg aaagtttccttttatggcgaggcggcggcggcggcggccctataaaaagcgaa gcgcgcggcgggcg |
| SEQ ID NO: 86 | CAG Intron | ggagtcgctgcgcgctgccttcgccccgtgccccgctccgccgccgcctcgc gccgcccgccccggctctgactgaccgcgttactcccacaggtgagcgggcg ggacggcccttctcctccgggctgtaattagcgcttggtttaatgacggctcgttt cttttctgtggctgcgtgaaagccttgaggggctccggggaggccctttgtgcg gggggagcggctcggggggtgcgtgcgtgtgtgtgtgcgtggggagcgccg cgtgcggctccgcgctgcccggcggctgtgagcgctgcgggcgcggcgcg |

TABLE 6-continued

Human IL-12A (p35) and IL-12B (p40) Exemplary Construct
Nucleic Acid Sequences

| SEQ ID NOs | Name | Nucleic Acid Sequence |
|---|---|---|
| | | gggctttgtgcgctccgcagtgtgcgcgagaggagcgcggccggggcggt<br>gccacgcggtgcgggggggctgcgaggggaacaaaggctgcgtgcggg<br>gtgtgtgcgtgggggggtgagcaggggtgtgggcgcggcggtcgggctg<br>taaccccccctgcaccccctccccgagttgctgagcacggcccggcttcgg<br>gtgcgggctccgtgcggggcgtggcgcggggctcgccgtgccggcggg<br>gggtggcggcgggtgggggtgccggcggggcggggccgcctcgggccg<br>gggagggctcgggggaggggcgcggcggcccccggagcgccggcggct<br>gtcgaggcgcggcgagccgcagccgcattgccttttatggtaatcgtgcgagagg<br>gcgcagggacttcctttgtcccaaatctgtgcggagccgaaatctgggaggcg<br>ccgccgcaccccctctagcgggcgcggggcgaagcggtgcggcgccggca<br>ggaaggaaatgggcggggagggccttcgtgcgtcgccgcgccgccgtcccc<br>ttctccctctccagcctcggggctgtccgcggggggacggctgcctcggggg<br>gacggggcagggcggggttcggcttctggcgtgtgaccggcggtctagact<br>ctgctaaccatgttcatgccttatctattctacagctcctgggcaacgtgctggt<br>tgttgtgctgtctcatcattttggcaaa |
| SEQ ID NO: 87 | Kozak | gccac |
| SEQ ID NO: 77 | IL-12A (p35)<br>("wild-type" no<br>CpG<br>modification<br>and no in-frame<br>stop codon) | ATGTGTCCAGCGCGCAGCCTCCTCCTTGTGGCTACCCTGGTCCTCC<br>TGGACCACCTCAGTTTGGCCAGAAACCTCCCCGTGGCCACTCCAGA<br>CCCAGGAATGTTCCCATGCCTTCACCACTCCCAAAACCTGCTGAGG<br>GCCGTCAGCAACATGCTCCAGAAGGCCAGACAAACTCTAGAATTTT<br>ACCCTTGCACTTCTGAAGAGATTGATCATGAAGATATCACAAAAGA<br>TAAAACCAGCACAGTGGAGGCCTGTTTACCATTGGAATTAACCAAG<br>AATGAGAGTTGCCTAAATTCCAGAGAGACCTCTTTCATAACTAATG<br>GGAGTTGCCTGGCCTCCAGAAAGACCTCTTTTATGATGGCCCTGTG<br>CCTTAGTAGTATTTATGAAGACTTGAAGATGTACCAGGTGGAGTTC<br>AAGACCATGAATGCAAAGCTTCTGATGGATCCTAAGAGGCAGATCT<br>TTCTAGATCAAAACATGCTGGCAGTTATTGATGAGCTGATGCAGGC<br>CCTGAATTTCAACAGTGAGACTGTGCCACAAAAATCCTCCCTTGAA<br>GAACCGGATTTTTATAAAACTAAATCAAGCTCTGCATACTTCTTC<br>ATGCTTTCcggATTCGGGCAGTGACTATTGATAGAGTGATGAGCTA<br>TCTGAATGCTTCC |
| SEQ ID NO: 60 | Combined<br>Furin Cleavage<br>Site and Linker | agaaagagaaggagtggctcagga |
| SEQ ID NO: 61 | 2A site | gcccctgtgaaacagaccctgaactttgacctcttgaagatgctggggatgtgg<br>agtctaatcctggtcca |
| SEQ ID NO: 8 | IL-12B (p40)<br>("wild-type" no<br>CpG<br>modification<br>and with stop<br>codon) | ATGTGTCACCAGCAGTTGGTCATCTCTTGGTTTTCCCTGGTTTTTC<br>TGGCATCTCCCCTCGTGGCCATATGGGAACTGAAGAAAGATGTTTA<br>TGTCGTAGAATTGGATTGGTATCCGGATGCCCCCTGGAGAAATGGTG<br>GTCCTCACCTGTGACACCCCTGAAGAAGATGGTATCACCTGGACCT<br>TGGACCAGAGCAGTGAGGTCTTAGGCTCTGGCAAAACCCTGACCAT<br>CCAAGTCAAAGAGTTTGGAGATGCTGGCCAGTACACCTGTCACAAA<br>GGAGGCGAGGTTCTAAGCCATTCGCTCCTGCTGCTTCACAAAAAGG<br>AAGATGGAATTTGGTCCACTGATATTTTAAAGGACCAGAAAGAACC<br>CAAAAATAAGACCTTTCTAAGATGCGAGGCCAAGAATTATTCTGGA<br>CGTTTCACCTGCTGGTGGCTGACGACAATCAGTACTGATTTGACAT<br>TCAGTGTCAAAAGCAGCAGAGGCTCTTCTGACCCCCAAGGGGTGAC<br>GTGCGGAGCTGCTACACTCTCTGCAGAGAGAGTCAGAGGGGACAAC<br>AAGGAGTATGAGTACTCAGTGGAGTGCCAGGAGGACAGTGCCTGCC<br>CAGCTGCTGAGGAGAGTCTGCCCATTGAGGTgATGGTGGATGCCGT<br>TCACAAGCTCAAGTATGAAAACTACACCAGCAGCTTCTTCATCAGG<br>GACATCATCAAACCTGACCCACCCAAGAACTTGCAGCTGAAGCCAT<br>TAAAGAATTCTCGGCAGGTGGAGGTCAGCTGGGAGTACCCTGACAC<br>CTGGAGTACTCCACATTCCTACTTCTCCCTGACATTCTGCGTTCAa<br>GTCCAGGGCAAGAGCAAGAGAGAAAAGAAAGATAGAGTCTTCACGG<br>ACAAGACCTCAGCCACGGTCATCTGCCGCAAAAATGCCAGCATTAG<br>CGTGCGGGCCCAGGACCGCTACTATAGCTCATCTTGGAGCGAATGG<br>GCATCTGTGCCCTGCAGTTGA |
| SEQ ID NO: 88 | Human growth<br>hormone<br>(HGH) poly(A) | gatctacgggtggcatccctgtgacccctccccagtgcctctcctggccctgga<br>agttgccactccagtgcccaccagccttgtcctaataaaattaagttgcatcattt<br>gtctgactaggtgtcttctataatattatgggtggaggggggtggtatggagc<br>aaggggcaagttgggaagacaacctgtaggggcctgcggggtctattgggaac<br>caagctggagtgcagtggcacaatcttggctcactgcaatctccgcctcctggg<br>ttcaagcgattctcctgcctcagcctcccgagttgttgggattccaggcatgcatg<br>accaggctcagctaatttttgtttttttggtagagacggggtttcaccatattggcc<br>aggctggtctccaactcctaatctcaggtgatctacccaccttggcctcccaaatt<br>gctgggattacaggcgtgaaccactgctcccttccctgtccttctg |

TABLE 6-continued

Human IL-12A (p35) and IL-12B (p40) Exemplary Construct
Nucleic Acid Sequences

| SEQ ID NOs | Name | Nucleic Acid Sequence |
|---|---|---|
| SEQ ID NO: 89 | AAV2 3' ITR | aggaacccctagtgatggagttggccactccctctctgcgcgctcgctcgctca ctgaggccgggcgaccaaaggtcgcccgacgcccgggctttgcccgggcgg cctcagtgagcgagcgagcgcgcagctgcagatctg |

In some aspects of the disclosure are directed to a polynucleotide comprising a nucleic acid sequence having at least 80%, 85%, 90%, 95% 96%, 97%, 98%, 99%, or 100% identity to any of SEQ ID NOs: 5-37 and 48-57, any nucleic acid shown in Table 2, Table 4, or Table 5, or any combinations thereof.

In some aspects of the disclosure are directed to a polynucleotide comprising a nucleic acid sequence having at least 80%, 85%, 90%, 95% 96%, 97%, 98%, 99%, or 100% identity to any of SEQ ID NOs: 8, 60, 61, 68, 71, 77, 82, and 84-89, any nucleic acid shown in Table 6, or any combinations thereof. In some aspects of the disclosure are directed to a polynucleotide comprising a nucleic acid sequence having at least 80%, 85%, 90%, 95% 96%, 97%, 98%, 99%, or 100% identity to SEQ ID NOs: 82.

In some aspects of the disclosure are directed to a polynucleotide encoding an amino acid sequence having at least 80%, 85%, 90%, 95% 96%, 97%, 98%, 99%, or 100% identity to SEQ ID NOs: 78, 79, or a combinations thereof.

In some aspects of the disclosure are directed to a polynucleotide encoding an amino acid sequence having at least 80%, 85%, 90%, 95% 96%, 97%, 98%, 99%, or 100% identity to SEQ ID NOs: 80, 81, or a combinations thereof.

In some aspects, the polynucleotide comprises: (i) a first nucleic acid encoding a first cytokine subunit or functional fragment thereof; and (ii) a second nucleic acid encoding a second cytokine subunit or functional fragment thereof. In some aspects, the polynucleotide comprises a nucleic acid encoding an IL-12 p35 subunit, wherein the nucleic acid comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77. In some aspects, the polynucleotide comprises a nucleic acid encoding the IL-12 p40 subunit, wherein the nucleic acid comprises a sequence at least 85%, at least 90%, at least 96%, at least 97%, at least 98%, at least 99%, or 100% identical to SEQ ID NO: 8, SEQ ID NO: 9, SEQ ID NO: 10, or SEQ ID NO: 92. In some aspects, the polynucleotide comprises (i) a nucleic acid encoding an IL-12 p35 subunit, wherein the nucleic acid comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77; and (ii) a nucleic acid encoding the IL-12 p40 subunit, wherein the nucleic acid comprises a sequence at least 85%, at least 90%, at least 96%, at least 97%, at least 98%, at least 99%, or 100% identical to SEQ ID NO: 8, SEQ ID NO: 9, SEQ ID NO: 10, SEQ ID NO: 92.

In some aspects, the immunomodulatory protein is a soluble natural killer (NK) cell, B cell, T cell, neutrophil, or macrophage ligand. In some aspects, the first immunomodulatory protein or functional fragment thereof or the second immunomodulatory protein or functional fragment thereof is selected from the group consisting of soluble CD40 ligand (CD40L), CD19 ligand (CD19L), CD48 ligand (CD48L), CD20 ligand (CD20L), any functional fragment thereof, and any combination thereof.

Also provided herein are polynucleotides encoding the immunomodulatory proteins or functional fragments thereof described herein that are modified, e.g., by codon/RNA modification, replacement with heterologous signal sequences, and elimination of mRNA instability elements. Methods to generate modified nucleic acids encoding an immunomodulatory protein or functional fragment thereof described herein for recombinant expression by introducing codon changes (e.g., a codon change that encodes the same amino acid due to the degeneracy of the genetic code) and/or eliminating inhibitory regions in the mRNA can be carried out by adapting the methods described in, e.g., U.S. Pat. Nos. 5,965,726; 6,174,666; 6,291,664; 6,414,132; and 6,794,498, accordingly, each of which is incorporated herein by reference in its entirety.

A polynucleotide encoding an immunomodulatory protein or functional fragment thereof can be generated from nucleic acid from a suitable source using methods well known in the art (e.g., PCR and other molecular cloning methods).

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In some aspects, the polynucleotide is a cDNA or a DNA lacking one more endogenous introns. In some aspects, a polynucleotide is a non-naturally occurring polynucleotide. In some aspects, a polynucleotide is recombinantly produced. In some aspects, the polynucleotides are isolated. In some aspects, the polynucleotides are substantially pure. In some aspects, a polynucleotide is purified from natural components. In some aspects, the construct of the disclosure is a multicistronic (e.g., bicistronic) construct (e.g., comprising nucleic acids encoding cytokine (e.g., IL-12) subunits). In some aspects, the multicistronic (e.g., bicistronic) construct further comprises an F2A or IRES element. In some aspects, the multicistronic construct comprises an F2A, E2A, P2A or T2A element. In some aspects, the multicistronic construct comprises an F2A element.

In some aspects, the viral vector comprises a polynucleotide comprising coding regions for two or more immunomodulatory proteins of interest or functional fragments thereof. The two or more immunomodulatory proteins of interest or functional fragments thereof can be the same or different from each other. When it is desired to include coding regions for two or more immunomodulatory proteins of interest or functional fragments thereof, two or more individual polypeptide chains, or two or more subunits of a immunomodulatory protein of interest or functional fragment thereof in one viral vector, each additional coding region beyond the first is preferably linked to an element that facilitates co-expression of the proteins in host cells, such as an internal ribosomal entry sequence (IRES) element (See e.g., U.S. Pat. No. 4,937,190), or a 2A element. In some aspects, IRES or 2A elements (e.g., F2A, E2A, P2A or T2A) can be used when a single vector comprises sequences encoding each subunit of a multi-subunit protein.

The viral vector can include coding regions for two or more immunomodulatory proteins of interest or functional fragments thereof. For example, the viral vector can include the coding region for a first immunomodulatory protein of interest or functional fragment thereof and the coding region for a second immunomodulatory protein of interest or functional fragments thereof. The first immunomodulatory protein of interest or functional fragment thereof and the second immunomodulatory protein of interest or functional fragment thereof can be the same or different. In some aspects, the viral vector can include the coding region(s) for a third or a fourth immunomodulatory protein of interest or functional fragments thereof. The third and the fourth immunomodulatory protein of interest or functional fragments thereof can be the same or different. The total length of the two or more immunomodulatory proteins of interest or functional fragments thereof encoded by one viral vector can vary. For example, the total length of the two or more proteins can be at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

In some aspects, provided herein is a polynucleotide comprising a nucleic acid encoding a cytokine or functional fragment thereof, wherein the cytokine is selected from the group consisting of interleukin (IL)-12, tumor necrosis factor alpha (TNF-α), a type I interferon (INF), a type II IFN, IL-2, IL-15, IL-21, IL-23, IL-27, IL-18, IL-1, IL-3, IL-4, IL-5, IL-6, IL-7, IL-8, IL-9, IL-10, IL17, IL33, TL1A, CD40L, granulocyte-macrophage colony-stimulating factor (GM-CSF), any functional fragment thereof, and any combination thereof.

In some aspects, the cytokine is IL-12, IL-18, IL-21, or a functional fragment thereof. In some aspects, the polynucleotide comprises: (i) a first nucleic acid encoding a first IL-12 subunit or functional fragment thereof; and (ii) a second nucleic acid encoding a second IL-12 subunit or functional fragment thereof. In some aspects, the nucleic acid comprises a nucleic acid encoding an IL-12 p35 subunit and/or a nucleic acid encoding an IL-12 p40 subunit. In some aspects, the nucleic acid comprises a nucleic acid sequence having at least 85%, 90%, 95% 96%, 97%, 98%, 99%, or 100% identity any of SEQ ID NO: 5-10 or any nucleic acid sequence in Table 2, or any combination thereof. In some aspects, the polynucleotide comprises (i) a nucleic acid encoding an IL-12 p35 subunit, wherein the nucleic acid comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77; and/or (ii) a nucleic acid encoding the IL-12 p40 subunit, wherein the nucleic acid comprises a sequence at least 85%, at least 90%, at least 96%, at least 97%, at least 98%, at least 99%, or 100% identical to SEQ ID NO: 8, SEQ ID NO: 9, SEQ ID NO: 10, SEQ ID NO: 92.

The Kozak consensus sequence, Kozak consensus or Kozak sequence, is known as a sequence which occurs on eukaryotic mRNA and has the consensus (gcc)gccRccAUGG, where R is a purine (adenine or guanine) three bases upstream of the start codon (AUG), which is followed by another "G." In some aspects, the vector comprises a nucleotide sequence having at least about 85%, at least about 90%, at least about 95% sequence identity, or more to the Kozak consensus sequence. In some aspects, the vector comprises a Kozak consensus sequence. In some aspects, the vector includes a Kozak consensus sequence after the polynucleotide encoding one or more immunomodulatory proteins of interest of functional fragments thereof is inserted into the vector, e.g., at the restrict site downstream of the promoter. For example, the vector can include a nucleotide sequence of GCCGCCATG (SEQ ID NO: 2), where the ATG is the start codon of the protein of interest. In some aspects, the vector comprises a nucleotide sequence of GCGGCCGCCATG (SEQ ID NO: 3), where the ATG is the start codon of the protein of interest.

The immunomodulatory protein of interest can be isolated and purified, if desired, in accordance with conventional methods known to those skilled in the art. For example, a lysate can be prepared of the expression host cells and the lysate can be purified using HPLC, hydrophobic interaction chromatography (HIC), anion exchange chromatography, cation exchange chromatography, size exclusion chromatography, ultrafiltration, gel electrophoresis, affinity chromatography, and/or other purification techniques.

III. Constructs

Some aspects of the disclosure are directed to a nucleic acid construct or an expression construct (e.g., comprising an expression cassette) having a eukaryotic promoter operably linked to a DNA of interest that encodes an immunomodulatory protein, one or more subunits thereof, or functional fragment thereof. In some aspects, the constructs containing the DNA sequence (or the corresponding RNA sequence) which can be used in accordance with the disclosure can be any eukaryotic expression construct containing the DNA or the RNA sequence of interest. For example, a plasmid or viral construct (e.g. an AAV vector) can be cleaved to provide linear DNA having ligatable termini. These termini are bound to exogenous DNA having complementary, like ligatable termini to provide a biologically functional recombinant DNA molecule having an intact replicon and a desired phenotypic property. In some aspects, the construct is capable of replication in both eukaryotic and prokaryotic hosts, which constructs can comprise backbones known in the art and are commercially available.

In some aspects, the exogenous (i.e., donor) DNA used in the disclosure is obtained from suitable cells, and the constructs can be prepared using techniques well known in the art. Likewise, techniques for obtaining expression of exogenous DNA or RNA sequences in a genetically altered host cell are known in the art (see e.g., Kormal et al., Proc. Natl. Acad. Sci. USA, 84:2150-2154 (1987); Sambrook et al. Molecular Cloning: a Laboratory Manual, 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

In some aspects, the expression construct of the disclosure is a multicistronic (e.g., bicistronic) construct (e.g., comprising nucleic acids encoding cytokine (e.g., IL-12) subunits). In some aspects, the multicistronic (e.g., bicistronic) construct further comprises an F2A or IRES element. In some aspects, the multicistronic construct comprises an F2A element.

In some aspects, the disclosure is directed to an expression construct (e.g., comprising an expression cassette) comprising or defined by a formula selected from:

(a) X-I1-P1-E-P2-I2-X'-T-Y;

(b) Y-I1-P1-E-P2-I2-X-T-X';

(c) pA-X-I1-L-P1-E-P2-I2-X-T-Y-pA;

(d) pA-Y-I1-L-P1-E-P2-I2-X-T-X'-pA;

(e) E-P1-I1-X-T-X'-pA; or (f) P1-X-T-X'-pA.

wherein X and X' encode subunits of a first immunomodulatory molecule; I1 and I2 is an intron; P1 and P2 is a promoter; E is an enhancer; T is a translation modification sequence; Y encodes a second immunomodulatory molecule; L is a long-terminal repeat; and pA is a polyA sequence. In some aspects, X can be a nucleic acid encoding an IL-12 p35 subunit or a functional fragment thereof or a nucleic acid encoding an IL-12 p40 subunit or a functional fragment thereof. In some aspects, X' can be a nucleic acid encoding an IL-12 p35 subunit or a functional fragment thereof or a nucleic acid encoding an IL-12 p40 subunit or a functional fragment thereof.

In some aspects, E is a CMV enhancer, P1 is CBA promoter, I1 or I2 is a CAG intron, X is a nucleic acid encoding an IL-12 p35 subunit or a functional fragment thereof, T is a furin cleavage sequence followed by the 2A self-processing peptide sequence (F2A), X' is a nucleic acid encoding an IL-12 p40 subunit or a functional fragment thereof, and pA is a a human growth hormone (HGH) pA.

In some aspects, provided herein is construct comprising a polynucleotide comprising a CMV enhancer, a CBA promoter operably linked to a first nucleic acid encoding a human IL-12 p35 subunit or a functional fragment thereof, a furin cleavage sequence followed by a 2A self-processing peptide (F2A), a second nucleic acid encoding a human IL-12 p40 subunit or a functional fragment thereof, and a human growth hormone (HGH) pA sequence. In some aspects, the construct further comprises an intron sequence (e.g., a CAG intron) and a Kozak sequence.

In some aspects, the nucleic acid encoding an IL-12 p35 subunit does not include an in-frame stop codon (e.g., TGA, TAG, and TAA).

In some aspects, the construct contains a promoter to facilitate expression of the DNA of interest (e.g., a first or second immunomodulatory molecule, one or more subunits thereof, or a functional fragment thereof) within a tumor. In some aspects, the promoter is a strong, eukaryotic promoter such as a promoter from cytomegalovirus (CMV), mouse mammary tumor virus (MMTV), Rous sarcoma virus (RSV), or adenovirus. Exemplary promoters include, but are not limited to the promoter from the immediate early gene of human CMV (Boshart et al., Cell 41:521-530 (1985) and the promoter from the long terminal repeat (LTR) of RSV (Gorman et al., Proc. Natl. Acad. Sci. USA 79:6777-6781 (1982)). In some aspects, the promoter is a CBA promoter, a CMV promoter, an EF-1a (Elongation Factor 1a) promoter, aRSV (Rous Sarcoma Virus) promoter, an Ubiquitin (UbC) promoter, or any combination thereof.

Alternatively, the promoter used can be a tissue-specific promoter. In some aspects, the promoter can target expression to a tumor or limit expression to the tumor (e.g., to the tumor being treated by a method of the disclosure).

In some aspects, the construct (e.g., expression construct) can comprise two or more promoters, e.g., a first promoter for the first nucleic acid encoding a first immunomodulatory protein, subunit thereof, or functional fragment thereof and a second promoter for the second nucleic acid sequence encoding a second immunomodulatory protein, subunit thereof, or functional fragment thereof. In some aspects, the two or more promoters are the same. In some aspects the two or more promoters are different. In some aspects, the promoter comprises a CBA promoter, a CMV promoter, an EF-1a (Elongation Factor 1a) promoter, aRSV (Rous Sarcoma Virus) promoter, an Ubiquitin (UbC) promoter, or any combination thereof.

In some aspects, the nucleic acid sequence encoding the first promoter and the nucleic acid sequence encoding the second promoter are operably linked. In some aspects, the nucleic acid sequence encoding the first promoter and the nucleic acid sequence encoding the second promoter are operably linked by a pause element. In some aspects, the pause element comprises a nucleotide sequence at least 85%, 86%, 87%, 88%, 89%, 90%, 91%, 92%, 93%, 94%, 95%, 96%, 97%, 98%, 99%, or 100% identical to SEQ ID NO: 74.

In some aspects, the construct (e.g., expression construct) can comprise a translation modification sequence. In some aspects, the translation modification sequence is selected from an internal ribosomal entry site (IRES) sequence, a 2A self-processing peptide (e.g., a F2A peptide, a P2A peptide, an E2A peptide, or a T2A peptide), a furin cleavage sequence, or any combination thereof. In some aspects, the constructs of the disclosure can include an internal ribosomal entry site (IRES) sequence, a F2A peptide, a P2A peptide, an E2A peptide, a T2A peptide, a furin cleavage sequence, or a combination thereof. In some aspects, the IRES comprises a nucleotide sequence with at least 85%, 86%, 87%, 88%, 89%, 90%, 91%, 92%, 93%, 94%, 95%, 96%, 97%, 98%, 99%, or 100% identical to SEQ ID NO: 59. In some aspects, the furin cleavage site comprises a nucleotide sequence with at least 85%, 86%, 87%, 88%, 89%, 90%, 91%, 92%, 93%, 94%, 95%, 96%, 97%, 98%, 99%, or 100% identical to SEQ ID NO: 60. In some aspects, the 2a site comprises a nucleotide sequence with at least 85%, 86%, 87%, 88%, 89%, 90%, 91%, 92%, 93%, 94%, 95%, 96%, 97%, 98%, 99%, or 100% identical to SEQ ID NO: 61.

In some aspects, the constructs of the disclosure (e.g., expression constructs) can further comprise an enhancer sequence, an intron sequence, a long terminal repeat (LTR) sequence, or any combination thereof. In some aspects, the enhancer sequence is a CMV enhancer sequence. In some aspects, the CMV enhancer comprises a nucleotide sequence with at least 85%, 86%, 87%, 88%, 89%, 90%, 91%, 92%, 93%, 94%, 95%, 96%, 97%, 98%, 99%, or 100% identical to SEQ ID NO: 68. In some aspects, the intron is an SV40 intron. In some aspects, the intron is a chimera of the human beta globin intron and the immunoglobulin heavy chain intron. In some aspects, the intron is a CAG intron. In some aspects, the intron has a nucleotide sequence with at least 85%, 86%, 87%, 88%, 89%, 90%, 91%, 92%, 93%, 94%, 95%, 96%, 97%, 98%, 99%, or 100% identical to any of SEQ ID NOs: 66, 71, 76, and 86.

In some aspects, the constructs of the disclosure (e.g., expression constructs) can further comprise a poly(A) (pA) sequence. In some aspects, the pA sequence is a synthetic pA (SYNpA) sequence, a BGHpA sequence, a HGHpA, or a combination thereof. In some aspects, the SYNpA comprises a nucleotide sequence with at least 85%, 86%, 87%, 88%, 89%, 90%, 91%, 92%, 93%, 94%, 95%, 96%, 97%, 98%, 99%, or 100% identical to SEQ ID NO: 72. In some aspects, the BGHpA comprises a nucleotide sequence with at least 85%, 86%, 87%, 88%, 89%, 90%, 91%, 92%, 93%, 94%, 95%, 96%, 97%, 98%, 99%, or 100% identical to SEQ ID NO: 73. In some aspects, the HGHpA comprises a nucleotide sequence with at least 85%, 86%, 87%, 88%, 89%, 90%, 91%, 92%, 93%, 94%, 95%, 96%, 97%, 98%, 99%, or 100% identical to SEQ ID NO: 88.

In some aspects, the constructs of the disclosure (e.g., expression constructs) can include the first nucleic acid comprising a promoter operably linked to an IL-12 p35 gene or functional fragment thereof, an IRES sequence, and an IL-15 gene or a functional fragment thereof; and the second nucleic acid comprising a promoter operably linked to an IL-12 p40 gene or functional fragment thereof. In some aspects, the constructs of the disclosure can include the first nucleic acid comprising a promoter operably linked to an IL-12 p35 gene or functional fragment thereof, a furin cleavage sequence and/or a 2A self-processing peptide (e.g., an F2A, E2A, P2A or T2A self-processing peptide), and an IL-12 p40 gene or a functional fragment thereof; and the second nucleic acid comprising a promoter operably linked to an IL-15 gene or functional fragment thereof.

In some aspects, the constructs of the disclosure (e.g., expression constructs) can include the first nucleic acid comprising a promoter operably linked to a nucleic acid encoding an IL-12 p35 subunit or functional fragment thereof, an IRES sequence; and the second nucleic acid comprising a promoter operably linked to a nucleic acid encoding an IL-12 p40 subunit or functional fragment thereof. In some aspects, the constructs of the disclosure (e.g., expression constructs) can include the first nucleic acid comprising a promoter operably linked to a nucleic acid encoding an IL-12 p40 subunit or functional fragment thereof, an IRES sequence; and the second nucleic acid comprising a promoter operably linked to a nucleic acid encoding an IL-12 p35 subunit or functional fragment thereof. In some aspects, the constructs of the disclosure can include the first nucleic acid comprising a promoter operably linked to a nucleic acid encoding an IL-12 p35 subunit or functional fragment thereof, a furin cleavage sequence and/or a 2A self-processing peptide (e.g., an F2A, E2A, P2A or T2A self-processing peptide), and a second nucleic acid encoding an IL-12 p40 subunit or a functional fragment thereof. In some aspects, the constructs of the disclosure can include the first nucleic acid comprising a promoter operably linked to a nucleic acid encoding an IL-12 p40 subunit or functional fragment thereof, a furin cleavage sequence and/or a 2A self-processing peptide, and a second nucleic acid encoding an IL-12 p35 subunit or a functional fragment thereof.

In some aspects, first nucleic acid (e.g., the nucleic acid encoding an IL-12 p35 subunit) does not include an in-frame stop codon (e.g., TGA, TAG, and TAA).

In some aspects, the first nucleic acid further comprises an intron sequence, a pA sequence, an enhancer sequence, or any combination thereof. In some aspects, the first nucleic acid further comprises an intron sequence and a human growth hormone (HGH) pA sequence. In some aspects, the first nucleic acid further comprises an intron sequence and a bovine growth hormone (BGH) pA sequence.

In some aspects, the first nucleic acid further comprises an intron sequence (e.g, a CAG intron). In some aspects, the second nucleic acid further comprises an intron sequence, a pA sequence, an enhancer sequence, or any combination thereof. In some aspects, the second nucleic acid further comprises an SV40 intron sequence and a synthetic (SYN) pA sequence.

In some aspects, the promoter of the first nucleic acid comprises a CBA promoter, a CMV promoter, a EF-1a (Elongation Factor 1a) promoter, aRSV (Rous Sarcoma Virus) promoter, an Ubiquitin (UbC) promoter, or any combination thereof. In some aspects, the promoter of the second nucleic acid comprises a CBA promoter, a CMV promoter, a EF-1a (Elongation Factor 1a) promoter, aRSV (Rous Sarcoma Virus) promoter, an Ubiquitin (UbC) promoter, a CMV enhancer fused to a EF1α promoter, CMV promoter fused to an SV40 intron, a CMV promoter fused to a CMV enhancer, or any combination thereof. In some aspects, the one or more promoters has a nucleic acid sequence comprising at least 85%, 86%, 87%, 88%, 89%, 90%, 91%, 92%, 93%, 94%, 95%, 96%, 97%, 98%, 99%, or 100% identical to any one of SEQ ID NOs: 67-71 or 85.

In some aspects, the constructs of the disclosure (e.g., expression constructs) can also comprise a microRNA (miR) binding site. In some aspects, the microRNA binding site is included to improve safety and allow tumor-specific expression. In some aspects, the microRNA binding site can act as conditional switches to control expression based on the expression of its complementary microRNA that is selected because it is absent or expressed at low level in tumors compared to expression in normal healthy tissues. In some aspects, inclusion of a microRNA binding site can restrict expression of immunomodulatory proteins disclosed herein to tumor cells while sparing normal tissues. In some aspects, the microRNA target binding sites are selected from a binding site for miR-1-3p, miR-122-5p, miR-124-3p, miR-126-3p, miR-128-3p, miR-137, miR-143-3p, miR-204-5p, miR-217, miR-219a-5p, or any combination thereof. In some aspects, the miRNA binding site is a miR-142 binding site. In some aspects, In some aspects, the miRNA binding site comprises four miR-142 binding sites separated by spacers. In some aspects, the miR-142 binding site has a nucleic acid sequence at least 85%, 86%, 87%, 88%, 89%, 90%, 91%, 92%, 93%, 94%, 95%, 96%, 97%, 98%, 99%, or 100% identical to SEQ ID NO: 64. In some aspects, the 4×miR-142 binding site has a nucleic acid sequence at least 85%, 86%, 87%, 88%, 89%, 90%, 91%, 92%, 93%, 94%, 95%, 96%, 97%, 98%, 99%, or 100% identical to SEQ ID NO: 65.

In some aspects, provided herein is a construct comprising a polynucleotide comprising a CMV enhancer (e.g., SEQ ID NO: 68), a CBA promoter (e.g., SEQ ID NO: 85) operably linked to a first nucleic acid encoding a human IL-12 p35 subunit or a functional fragment thereof (e.g., SEQ ID NO: 77), a furin cleavage sequence followed by a 2A self-processing peptide (F2A), a second nucleic acid encoding a human IL-12 p40 subunit or a functional fragment thereof (e.g., SEQ ID NO: 8), and a human growth hormone (HGH) pA sequence (e.g., SEQ ID NO: 88). In some aspects, the construct further comprises an intron sequence (e.g., a CAG intron, e.g., SEQ ID NO: 86) and a Kozak sequence. In some aspects, the construct comprises a CMV enhancer, a CBA promoter, and a CAG intron (e.g., SEQ ID NO: 71).

In some aspects, the constructs of the disclosure (e.g., expression constructs) can also include other components such as a marker (e.g., an antibiotic resistance gene (such as an ampicillin resistance gene) or β-galactosidase) to aid in selection of cells containing and/or expressing the construct, an origin of replication for stable replication of the construct in a bacterial cell (preferably, a high copy number origin of replication), a nuclear localization signal, or other elements which facilitate production of the DNA construct, the protein encoded thereby, or both.

For eukaryotic expression, the construct (e.g., expression construct) can comprise at a minimum a eukaryotic promoter operably linked to a DNA of interest, which is in turn operably linked to a polyadenylation sequence. The polyadenylation signal sequence can be selected from any of a variety of polyadenylation signal sequences known in the art. In some aspects, the polyadenylation signal sequence is the SV40 early polyadenylation signal sequence. The construct can also include one or more introns, which can increase levels of expression of the DNA of interest, particularly where the DNA of interest is a cDNA (e.g., contains no introns of the naturally-occurring sequence). Any of a variety of introns known in the art can be used (e.g., the human β-globin intron, which is inserted in the construct at a position 5' to the DNA of interest).

The DNA of interest can be inserted into a construct so that the immunomodulatory protein, one or more subunits thereof, or functional fragment thereof is expressed as a fusion protein (e.g., a fusion protein having β-galactosidase or a portion thereof at the N-terminus and the therapeutic protein at the C-terminal portion). Production of a fusion protein can facilitate identification of transformed cells expressing the protein (e.g., by enzyme-linked immunosorbent assay (ELISA) using an antibody which binds to the fusion protein).

In some aspects, the nucleic acids, the constructs, polynucleotides, and/or expression cassettes disclosed herein comprise sequences with modified CpG content; and/or reduced or eliminated toll-like receptor 9 (TLR9) stimulatory motifs.

The vectors for delivery of the DNA of interest can be either viral or non-viral, or can be composed of naked DNA admixed with an adjuvant such as viral particles (e.g., AAV particle) or cationic lipids or liposomes. An "adjuvant" is a substance that does not by itself produce the desired effect, but acts to enhance or otherwise improve the action of the active compound. The precise vector and vector formulation used will depend upon several factors such as the tumor targeted for gene transfer.

In certain aspects, a composition comprising a delivery vector, e.g., a viral vector, comprising a nucleic acid construct or an expression construct comprising a first nucleic acid encoding a first immunomodulatory protein, subunit thereof, or functional fragment thereof and/or a second nucleic acid encoding a second immunomodulatory protein, subunit thereof, or functional fragment thereof is suitable for intratumoral delivery.

In certain aspects, a composition comprising a delivery vector, e.g., a viral vector, comprising a nucleic acid construct or an expression construct comprising a first nucleic acid encoding a first immunomodulatory protein, subunit thereof, or functional fragment thereof and/or a second nucleic acid encoding a second immunomodulatory protein, subunit thereof, or functional fragment thereof is suitable for intravenous delivery.

In certain aspects, a composition comprising a delivery vector, e.g., a viral vector, comprising a nucleic acid construct or an expression construct comprising a first nucleic acid encoding a first immunomodulatory protein, subunit thereof, or functional fragment thereof and/or a second nucleic acid encoding a second immunomodulatory protein, subunit thereof or functional fragment thereof is suitable for a delivery to a lymphoid organ (e.g., a spleen, a lymph node, or a bone marrow).

In some aspects, the constructs disclosed herein comprise one or more of the elements listed in Table 7.

TABLE 7

Nucleic Acid Sequences of Elements in Constructs to Generate a Cytokine

| SEQ ID NOs | Name | Nucleic Acid Sequence |
|---|---|---|
| SEQ ID NO: 59 | IRES | GCCCCTCTCCCTCCCCCCCC CCTAACGTTACTGGCCGAAG CCGCTTGGAATAAGGCCGGT GTGCGTTTGTCTATATGTTA TTTTCCACCATATTGCCGTC TTTTGGCAATGTGAGGGCCC GGAAACCTGGCCCTGTCTTC TTGACGAGCATTCCTAGGGG TCTTTCCCCTCTCGCCAAAG GAATGCAAGGTCTGTTGAAT GTCGTGAAGGAAGCAGTTCC TCTGGAAGCTTCTTGAAGAC AAACAACGTCTGTAGCGACC CTTTGCAGGCAGCGGAACCC CCCACCTGGCGACAGGTGCC TCTGCGGCCAAAAGCCACGT GTATAAGATACACCTGCAAA GGCGGCACAACCCCAGTGCC ACGTTGTGAGTTGGATAGTT GTGGAAAGAGTCAAATGGCT CTCCTCAAGCGTATTCAACA AGGGGCTGAAGGATGCCCAG AAGGTACCCCATTGTATGGG ATCTGATCTGGGGCCTCGGT ACACATGCTTTACATGTGTT TAGTCGAGGTTAAAAAAACG TCTAGGCCCCCCGAACCACG GGGACGTGGTTTTCCTTTGA AAAACACGATGATAATATGG CCACA |
| SEQ ID NO: 60 | Furin cleaveage site | AGAAAGAGAAGGAGTGGCTC AGGA |
| SEQ ID NO: 61 | 2A site | GCCCCTGTGAAACAGACCCT GAACTTTGACCTCTTGAAGC TTGCTGGGGATGTGGAGTCT AATCCTGGTCCA |
| SEQ ID NO: 62 | IL-2 leader | ATGTACAGGATGCAACTCCT GTCTTGCATTGCACTAAGTC TTGCACTTGTCACAAACTCG |
| SEQ ID NO: 63 | IL-10 leader | ATGCACAGCTCAGCACTGCT CTGTTGCCTGGTCCTCCTGA CTGGGGTGAGGGCC |
| SEQ ID NO: 64 | miR-142 binding site | TCCATAAAGTAGGAAACACT ACA |
| SEQ ID NO: 65 | 4x miR-142 binding site | TCCATAAAGTAGGAAACACT ACActatTCCATAAAGTAGG AAACACTACAtcacTCCATA AAGTAGGAAACACTACAagt cTCCATAAAGTAGGAAACAC TACA |
| SEQ ID NO: 66 | SV40 intron | GTAAGTTTAGTCTTTTTGTC TTTTATTTCAGGTCCCGGAT CCGGTGGTGGTGCAAATCAA AGAACTGCTCCTCAGTGGAT GTTGCCTTTACTTCTAG |
| SEQ ID NO: 67 | EF-1α | GCTCCGGTGCCCGTCAGTGG GCAGAGCGCACATCGCCCAC AGTCCCCGAGAAGTTGGGGG GAGGGGTCGGCAATTGAACC GGTGCCTAGAGAAGGTGGCG CGGGGTAAACTGGGAAAGTG |

TABLE 7-continued

Nucleic Acid Sequences of Elements in
Constructs to Generate a Cytokine

| SEQ ID NOs | Name | Nucleic Acid Sequence |
|---|---|---|
| | | ATGTCGTGTACTGGCTCCGC<br>CTTTTTCCCGAGGGTGGGGG<br>AGAACCGTATATAAGTGCAG<br>TAGTCGCCGTGAACGTTCTT<br>TTTCGCAACGGGTTTGCCGC<br>CAGAACACAG |
| SEQ ID NO: 68 | CMV enhancer | GACATTGATTATTGACTAGT<br>TATTAATAGTAATCAATTAC<br>GGGGTCATTAGTTCATAGCC<br>CATATATGGAGTTCCGCGTT<br>ACATAACTTACGGTAAATGG<br>CCCGCCTGGCTGACCGCCCA<br>ACGACCCCGCCCATTGACG<br>TCAATAATGACGTATGTTCC<br>CATAGTAACGCCAATAGGGA<br>CTTTCCATTGACGTCAATGG<br>GTGGACTATTTACGGTAAAC<br>TGCCCACTTGGCAGTACATC<br>AAGTGTATCATATGCCAAGT<br>ACGCCCCCTATTGACGTCAA<br>TGACGGTAAATGGCCCGCCT<br>GGCATTATGCCCAGTACATG<br>ACCTTATGGGACTTTCCTAC<br>TTGGCAGTACATCTACGTAT<br>TAGTCATCGCTATTACCATG |
| SEQ ID NO: 69 | CMVp | GTGATGCGGTTTTGGCAGTA<br>CATCAATGGGCGTGGATAGC<br>GGTTTGACTCACGGGGATTT<br>CCAAGTCTCCACCCCATTGA<br>CGTCAATGGGAGTTTGTTTT<br>GGCACCAAAATCAACGGGAC<br>TTTCCAAAATGTCGTAACAA<br>CTCCGCCCCATTGACGCAAA<br>TGGGCGGTAGGCGTGTACGG<br>TGGGAGGTCTATATAAGCAG<br>AGCTCGTTTAGTGAACCG |
| SEQ ID NO: 70 | CMV ehancer and promoter (CMVe/p) | GACATTGATTATTGACTAGT<br>TATTAATAGTAATCAATTAC<br>GGGGTCATTAGTTCATAGCC<br>CATATATGGAGTTCCGCGTT<br>ACATAACTTACGGTAAATGG<br>CCCGCCTGGCTGACCGCCCA<br>ACGACCCCGCCCATTGACG<br>TCAATAATGACGTATGTTCC<br>CATAGTAACGCCAATAGGGA<br>CTTTCCATTGACGTCAATGG<br>GTGGACTATTTACGGTAAAC<br>TGCCCACTTGGCAGTACATC<br>AAGTGTATCATATGCCAAGT<br>ACGCCCCCTATTGACGTCAA<br>TGACGGTAAATGGCCCGCCT<br>GGCATTATGCCCAGTACATG<br>ACCTTATGGGACTTTCCTAC<br>TTGGCAGTACATCTACGTAT<br>TAGTCATCGCTATTACCATG<br>GTGATGCGGTTTTGGCAGTA<br>CATCAATGGGCGTGGATAGC<br>GGTTTGACTCACGGGGATTT<br>CCAAGTCTCCACCCCATTGA<br>CGTCAATGGGAGTTTGTTTT<br>GGCACCAAAATCAACGGGAC<br>TTTCCAAAATGTCGTAACAA<br>CTCCGCCCCATTGACGCAAA<br>TGGGCGGTAGGCGTGTACGG<br>TGGGAGGTCTATATAAGCAG<br>AGCTCGTTTAGTGAACCG |
| SEQ ID NO: 71 | CAG Promoter | GTCGACATTGATTATTGACT<br>AGTTATTAATAGTAATCAAT<br>TACGGGGTCATTAGTTCATA<br>GCCCATATATGGAGTTCCGC |

TABLE 7-continued

Nucleic Acid Sequences of Elements in
Constructs to Generate a Cytokine

| SEQ ID NOs | Name | Nucleic Acid Sequence |
|---|---|---|
| | | GTTACATAACTTACGGTAAA<br>TGGCCCGCCTGGCTGACCGC<br>CCAACGACCCCCGCCCATTG<br>ACGTCAATAATGACGTATGT<br>TCCCATAGTAACGCCAATAG<br>GGACTTTCCATTGACGTCAA<br>TGGGTGGACTATTTACGGTA<br>AACTGCCCACTTGGCAGTAC<br>ATCAAGTGTATCATATGCCA<br>AGTACGCCCCCTATTGACGT<br>CAATGACGGTAAATGGCCCG<br>CCTGGCATTATGCCCAGTAC<br>ATGACCTTATGGGACTTTCC<br>TACTTGGCAGTACATCTACG<br>TATTAGTCATCGCTATTACC<br>ATGGGTCGAGGTGAGCCCCA<br>CGTTCTGCTTCACTCTCCCC<br>ATCTCCCCCCCCTCCCCACC<br>CCCAATTTTGTATTTATTTA<br>TTTTTTAATTATTTTGTGCA<br>GCGATGGGGGCGGGGGGGG<br>GGGGGCGCGCGCCAGGCGGG<br>GCGGGGCGGGGCGAGGGGCG<br>GGGCGGGGCGAGGCGGAGAG<br>GTGCGGCGGCAGCCAATCAG<br>AGCGGCGCGCTCCGAAAGTT<br>TCCTTTTATGGCGAGGCGGC<br>GGCGGCGGCGGCCCTATAAA<br>AAGCGAAGCGCGCGGCGGGC<br>GGGAGTCGCTGCGCGCTGCC<br>TTCGCCCCGTGCCCCGCTCC<br>GCCGCCGCCTCGCGCCGCCC<br>GCCCCGGCTCTGACTGACCG<br>CGTTACTCCCACAGGTGAGC<br>GGGCGGGACGGCCCTTCTCC<br>TCCGGGCTGTAATTAGCGCT<br>TGGTTTAATGACGGCTCGTT<br>TCTTTTCTGTGGCTGCGTGA<br>AAGCCTTGAGGGGCTCCGGG<br>AGGGCCCTTTGTGCGGGGGG<br>AGCGGCTCGGGGGGTGCGTG<br>CGTGTGTGTGCGTGGGGA<br>GCGCCGCGTGCGGCTCCGCG<br>CTGCCCGGCGGCTGTGAGCG<br>CTGCGGGCGCGGCGCGGGGC<br>TTTGTGCGCTCCGCAGTGTG<br>CGCGAGAGGAGCGCGGCCGG<br>GGGCGGTGCCACGCGGTGCG<br>GGGGGGGCTGCGAGGGGAAC<br>AAAGGCTGCGTGCGGGGTGT<br>GTGCGTGGGGGGGTGAGCA<br>GGGGGTGTGGGCGCGGCGGT<br>CGGGCTGTAACCCCCCCCTG<br>CACCCCCCTCCCCGAGTTGC<br>TGAGCACGGCCCGGCTTCGG<br>GTGCGGGGCTCCGTGCGGGG<br>CGTGGCGCGGGGCTCGCCGT<br>GCCGGGCGGGGGGTGGCGGC<br>GGGTGGGGGTGCCGGGCGGG<br>GCGGGGCCGCCTCGGCCGG<br>GGAGGGCTCGGGGAGGGGC<br>GCGGCGGCCCCCGGAGCGCC<br>GGCGGCTGTCGAGGCGCGGC<br>GAGCCGCAGCCATTGCCTTT<br>TATGGTAATCGTGCGAGAGG<br>GCGCAGGGACTTCCTTTGTC<br>CCAAATCTGTGCGGAGCCGA<br>AATCTGGGAGGCGCCGCCGC<br>ACCCCCTCTAGCGGGCGCGG<br>GGCGAAGCGGTGCGGCGCCG<br>GCAGGAAGGAAATGGGCGGG<br>GAGGGCCTTCGTGCGTCGCC<br>GCGCCGCCGTCCCCTTCTCC<br>CTCTCCAGCCTCGGGGCTGT |

TABLE 7-continued

Nucleic Acid Sequences of Elements in
Constructs to Generate a Cytokine

| SEQ ID NOs | Name | Nucleic Acid Sequence |
|---|---|---|
|  |  | CCGCGGGGGACGGCTGCCT TCGGGGGGACGGGGCAGGG CGGGGTTCGGCTTCTGGCGT GTGACCGGCGGTCTAGACTC TGCTAACCATGTTCATGCCT TCTTCTCTTTCCTACAGCTC CTGGGCAACGTGCTGGTTGT TGTGCTGTCTCATCATTTTG GCAAA |
| SEQ ID NO: 72 | Synthetic poly(A) | AATAAAGATCTTTATTTTC ATTAGATCTGTGTGTTGGTT TTTTGTGTG |
| SEQ ID NO: 73 | BGH poly(A) | CTGTGCCTTCTAGTTGCCAG CCATCTGTTGTTTGCCCCTC CCCCGTGCCTTCCTTGACCC TGGAAGGTGCCACTCCCACT GTCCTTTCCTAATAAAATGA GGAAATTGCATCGCATTGTC TGAGTAGGTGTCATTCTATT CTGGGGGTGGGGTGGGGCA GGACAGCAAGGGGGAGGATT GGGAAGACAATAGCAGGCAT GCTGGGGATGCGGTGGGCTC TATG |
| SEQ ID NO: 74 | Pause element | AACATACGCTCTCCATCAAA ACAAAACGAAACAAAACAAA CTAGCAAAATAGGCTGTCCC CAGTGCAAGTGCAGGTGCCA GAACATTTCTCT |
| SEQ ID NO: 75 | 5' LTR | GGGGCTCGCATCTCTCCTTC ACGCGCCCGCCGCCCTACCT GAGGCCGCCATCCACGCCGG TTGAGTCGCGTTCTGCCGCC TCCCGCCTGTGGTGCCTCCT GAACTGCGTCCGCCGTCTAG GTAAGTTTAAAGCTCAGGTC GAGACCGGGCCTTTGTCCGG CGCTCCCTTGGAGCCTACCT AGACTCAGCCGGCTCTCCAC GCTTTGCCTGACCCTGCTTG CTCAACTCTACGTCTTTGTT TCGTTTTCTGTTCTGCGCCG TTACAGATC |
| SEQ ID NO: 76 | Intron (chimera of Human betaglobin intron and immunoglobulin heavy chain intron) | GTAAGTATCAAGGTTACAAG ACAGGTTTAAGGAGACCAAT AGAAACTGGGCTTGTCGAGA CAGAGAAGACTCTTGCGTTT CTGATAGGCACCTATTGGTC TTACTGACATCCACTTTGCC TTTCTCTCCACAG |

III.A. Delivery Vectors

In some aspects, the delivery vector is a viral vector, a non-viral vectors, a plasmid, a lipid, a protein particle, a bacterial vector, a lysosome, a virus-like particle, a polymeric particle, an exosome, or a vault particle.

In certain aspects, a composition comprising a delivery vector (e.g., a viral vector, a non-viral vectors, a plasmid, a lipid, a protein particle, a bacterial vector, a lysosome, a virus-like particle, a polymeric particle, an exosome, or a vault particle) comprising a first nucleic acid encoding or comprising a first immunomodulatory protein, one or or more subunits thereof, or a functional fragment thereof and/or a second nucleic acid encoding or comprising a second immunomodulatory protein, one or more subunits thereof, or a functional fragment thereof is suitable for delivery to a tumor.

III.A.1. Non-Viral Vectors

In some aspects, the DNA of interest can be administered using a non-viral vector. "Non-viral vector," as used herein is meant to include naked DNA, chemical formulations containing naked DNA (e.g., a formulation of DNA and cationic compounds (e.g., dextran sulfate)), and naked DNA mixed with an adjuvant such as a viral particle (i.e., the DNA of interest is not contained within the viral particle, but the transforming formulation is composed of both naked DNA and viral particles (e.g., AAV particles) (see e.g., Curiel et al., Am. J. Respir. Cell Mol. Biol. 6:247-52 (1992)). Thus the "non-viral vector" can include vectors composed of DNA plus viral particles where the viral particles do not contain the DNA of interest within the viral genome.

In some aspects, the non-viral vector is a bacterial vector. See e.g., Baban et al., Bioeng Bugs., 1(6):385-394 (2010).

In some aspects, the DNA of interest can be complexed with polycationic substances such as poly-L-lysine or DEAC-dextran, targeting ligands, and/or DNA binding proteins (e.g., histones). DNA- or RNA-liposome complex formulations comprise a mixture of lipids which bind to genetic material (DNA or RNA) and facilitate delivery of the nucleic acid into the cell. Liposomes which can be used in accordance with the disclosure include DOPE (dioleyl phosphatidyl ethanol amine), CUDMEDA (N-(5-cholestrum-3-β-ol 3-urethanyl)-N',N'-dimethylethylene diamine).

Lipids which can be used in accordance with the disclosure include, but are not limited to, DOPE (Dioleoyl phosphatidylethanolamine), cholesterol, and CUDMEDA (N-(5-cholestrum-3-ol 3 urethanyl)-N',N'-dimethylethylenediamine). As an example, DNA can be administered in a solution containing one of the following cationic liposome formulations: Lipofectin™ (LTI/BRL), Transfast™ (Promega Corp), Tfx50™ (Promega Corp), Tfx10™ (Promega Corp), or Tfx20™ (Promega Corp). The concentration of the liposome solutions range from about 2.5% to 15% volume:volume, preferably about 6% to 12% volume:volume. Further exemplary methods and compositions for formulation of nucleic acid (e.g., DNA, including DNA or RNA not contained within a viral particle) for delivery according to the method of the disclosure are described in U.S. Pat. Nos. 5,892,071; 5,744,625; 5,925, 623; 5,527,928; 5,824,812; 5,869,715.

In some aspects, protein particles can be used in accordance with the disclosure for polymer-based gene delivery. See e.g., Putnam et al., PNAS 98 (3): 1200-1205 (2001).

In some aspects, the DNA of interest can be administered as a chemical formulation of DNA or RNA coupled to a carrier molecule (e.g., an antibody or a receptor ligand) which facilitates delivery to host cells for the purpose of altering the biological properties of the host cells. The term "chemical formulations" refers to modifications of nucleic acids to allow coupling of the nucleic acid compounds to a carrier molecule such as a protein or lipid, or derivative thereof.

In certain aspects, a composition comprising a non-viral delivery vector comprising a first nucleic acid encoding or comprising a first immunomodulatory protein or functional fragment thereof and/or a second nucleic acid encoding or comprising a second immunomodulatory protein or functional fragment thereof disclosed herein is suitable for intratumoral delivery.

In certain aspects, a composition comprising a non-viral delivery vector comprising a first nucleic acid encoding or comprising a first immunomodulatory protein or functional fragment thereof and/or a second nucleic acid encoding or comprising a second immunomodulatory protein or functional fragment thereof disclosed herein is suitable for intravenous delivery.

In certain aspects, a composition comprising a non-viral delivery vector comprising a first nucleic acid encoding or comprising a first immunomodulatory protein or functional fragment thereof and/or a second nucleic acid encoding or comprising a second immunomodulatory protein or functional fragment thereof disclosed herein is suitable for a delivery to a lymphoid organ (e.g., a spleen, a lymph node, or a bone marrow).

III.A.2. Viral Vectors

In general, viral vectors used in accordance with the disclosure are composed of a viral particle derived from a naturally-occurring virus which has been genetically altered to render the virus replication-defective and to express a recombinant gene of interest in accordance with the disclosure. Once the virus delivers its genetic material to a cell, it does not generate additional infectious virus but does introduce exogenous recombinant genes into the cell, preferably into the genome of the cell.

In some aspects, the viral vector is a retrovirus, an adenovirus, an adeno-associated virus (AAV), a herpes simplex virus (HSV), a cytomegalovirus (CMV), a vaccinia or a poliovirus vectors. In some aspects, retroviral vectors are less preferred since retroviruses require replicating cells and secretory glands are composed of mostly slowly replicating and/or terminally differentiated cells. In some aspects, adenovirus and AAV are preferred viral vectors since this virus efficiently infects slowly replicating and/or terminally differentiated cells. In some aspects, the delivery vector (e.g., viral vector) is selected from the group consisting of an adeno-associated viral (AAV) vector, an adenoviral vector, a lentiviral vector, or a retroviral vector.

Where a replication-deficient virus is used as the viral vector, the production of infective virus particles containing either DNA or RNA corresponding to the DNA of interest can be produced by introducing the viral construct into a recombinant cell line which provides the missing components essential for viral replication. In some aspects, transformation of the recombinant cell line with the recombinant viral vector will not result in production of replication-competent viruses, e.g., by homologous recombination of the viral sequences of the recombinant cell line into the introduced viral vector. Methods for production of replication-deficient viral particles containing a nucleic acid of interest are well known in the art and are described in, e.g., Rosenfeld et al., Science 252:431-434 (1991) and Rosenfeld et al., Cell 68:143-155 (1992) (adenovirus); U.S. Pat. No. 5,139,941 (adeno-associated virus); U.S. Pat. No. 4,861,719 (retrovirus); and U.S. Pat. No. 5,356,806 (vaccinia virus).

Certain aspects of the disclosure are directed to a viral delivery vector comprising a polynucleotide comprising a first nucleic acid encoding an IL-12 subunit (e.g., IL-12 p35) or a functional fragment thereof and/or a second nucleic acid encoding an IL-12 subunit (e.g., IL-12 p40) or functional fragment thereof disclosed herein.

Certain aspects of the disclosure are directed to a viral delivery vector comprising a polynucleotide comprising a CMV enhancer (e.g., SEQ ID NO: 68), a CBA promoter (e.g., SEQ ID NO: 71) operably linked to a first nucleic acid encoding a human IL-12 p35 subunit or a functional fragment thereof (e.g., SEQ ID NO: 77), a furin cleavage sequence followed by a 2A self-processing peptide (F2A), a second nucleic acid encoding a human IL-12 p40 subunit or a functional fragment thereof (e.g., SEQ ID NO: 8), and a human growth hormone (HGH) pA sequence (e.g., SEQ ID NO: 88). In some aspects, the construct further comprises an intron sequence (e.g., a CAG intron, e.g., SEQ ID NO: 86) and a Kozak sequence. In some aspects, the construct comprises a CMV enhancer, a CBA promoter, and a CAG intron (e.g., SEQ ID NO: 71).

In certain aspects, a composition comprising a viral delivery vector comprising a first nucleic acid encoding or comprising a first immunomodulatory protein or functional fragment thereof and/or a second nucleic acid encoding or comprising a second immunomodulatory protein or functional fragment thereof disclosed herein is suitable for intratumoral delivery.

In certain aspects, a composition comprising a viral delivery vector comprising a first nucleic acid encoding or comprising a first immunomodulatory protein or functional fragment thereof and/or a second nucleic acid encoding or comprising a second immunomodulatory protein or functional fragment thereof disclosed herein is suitable for intravenous delivery.

In certain aspects, a composition comprising a viral delivery vector comprising a first nucleic acid encoding or comprising a first immunomodulatory protein or functional fragment thereof and/or a second nucleic acid encoding or comprising a second immunomodulatory protein or functional fragment thereof disclosed herein is suitable for a delivery to a lymphoid organ (e.g., a spleen, a lymph node, or a bone marrow).

In some aspects, the viral vector is suitable for delivery to a solid tumor (e.g., a sarcoma, a carcinomas, or a lymphoma) by direct injection. In some aspects, the solid tumor is a surface lesion. In some aspects, the solid tumor is a visceral tumor.

In some aspects of the disclosure, the viral vector disclosed herein can be administered in combination with a checkpoint inhibitor.

IV. Adeno-Associated Virus (AAV)-Mediated Gene Therapy

AAV, a parvovirus belonging to the genus Dependovirus, has several attractive features not found in other viruses. For example, AAV can infect a wide range of host cells, including non-dividing cells. Furthermore, AAV can infect cells from different species. Importantly, AAV has not been associated with any human or animal disease, and does not appear to alter the physiological properties of the host cell upon integration. Finally, AAV is stable at a wide range of physical and chemical conditions, which lends itself to production, storage, and transportation requirements.

The AAV genome, a linear, single-stranded DNA molecule containing approximately 4700 nucleotides (the AAV-2 genome consists of 4681 nucleotides), generally comprises an internal non-repeating segment flanked on each end by inverted terminal repeats (ITRs). The ITRs are approximately 145 nucleotides in length (AAV-1 has ITRs of 143 nucleotides) and have multiple functions, including serving as origins of replication, and as packaging signals for the viral genome.

The internal non-repeated portion of the genome includes two large open reading frames (ORFs), known as the AAV replication (rep) and capsid (cap) regions. These ORFs encode replication and capsid gene products, respectively: replication and capsid gene products (i.e., proteins) allow for the replication, assembly, and packaging of a complete AAV virion. More specifically, a family of at least four viral proteins are expressed from the AAV rep region: Rep 78, Rep 68, Rep 52, and Rep 40, all of which are named for their apparent molecular weights. The AAV cap region encodes at least three proteins: VP1, VP2, and VP3.

AAV is a helper-dependent virus, requiring co-infection with a helper virus (e.g., adenovirus, herpesvirus, or vaccinia virus) in order to form functionally complete AAV virions. In the absence of co-infection with a helper virus, AAV establishes a latent state in which the viral genome inserts into a host cell chromosome or exists in an episomal form, but infectious virions are not produced. Subsequent infection by a helper virus "rescues" the integrated genome, allowing it to be replicated and packaged into viral capsids, thereby reconstituting the infectious virion. While AAV can infect cells from different species, the helper virus must be of the same species as the host cell. Thus, for example, human AAV will replicate in canine cells that have been co-infected with a canine adenovirus.

To produce recombinant AAV (rAAV) virions containing the HNA, a suitable host cell line is transfected with an AAV vector containing the HNA, but lacking rep and cap. The host cell is then infected with wild-type (wt) AAV and a suitable helper virus to form rAAV virions. Alternatively, wt AAV genes (known as helper function genes, comprising rep and cap) and helper virus function genes (known as accessory function genes) can be provided in one or more plasmids, thereby eliminating the need for wt AAV and helper virus in the production of rAAV virions. The helper and accessory function gene products are expressed in the host cell where they act in trans on the rAAV vector containing the heterologous gene. The heterologous gene is then replicated and packaged as though it were a wt AAV genome, forming a recombinant AAV virion. When a patient's cells are transduced with the resulting rAAV virion, the HNA enters and is expressed in the patient's cells. Because the patient's cells lack the rep and cap genes, as well as the accessory function genes, the rAAV virion cannot further replicate and package its genomes. Moreover, without a source of rep and cap genes, wt AAV virions cannot be formed in the patient's cells. See e.g., U.S. Appl. Publ. No. 2003/0147853.

In some aspects, AAV vectors of the present disclosure can comprise or be derived from any natural or recombinant AAV serotype. According to the present disclosure, the AAV serotype can be, but is not limited to, AAV1, AAV2, AAV3, AAV4, AAV5, AAV6, AAV7, AAV8, AAVrh8, AAV9, AAV10, AAVrh10, AAV11, and AAV12. In some aspects, the AAV serotype is AAV2.

Certain aspects of the disclosure are directed to a composition comprising an AAV delivery vector comprising a polynucleotide comprising a first nucleic acid encoding an IL-12 subunit (e.g., IL-12 p35) or a functional fragment thereof and/or a second nucleic acid encoding an IL-12 subunit (e.g., IL-12 p40) or functional fragment thereof disclosed herein.

Certain aspects of the disclosure are directed to a composition comprising an AAV delivery vector comprising a polynucleotide comprising a CMV enhancer (e.g., SEQ ID NO: 68), a CBA promoter (e.g., SEQ ID NO: 85) operably linked to a first nucleic acid encoding a human IL-12 p35 subunit or a functional fragment thereof (e.g., SEQ ID NO: 77), a furin cleavage sequence followed by a 2A self-processing peptide (F2A), a second nucleic acid encoding a human IL-12 p40 subunit or a functional fragment thereof (e.g., SEQ ID NO: 8), and a human growth hormone (HGH) pA sequence (e.g., SEQ ID NO: 88). In some aspects, the polynucleotide further comprises an intron sequence (e.g., a CAG intron, e.g., SEQ ID NO: 86) and a Kozak sequence. In some aspects, the polynucleotide comprises a CMV enhancer, a CBA promoter, and a CAG intron (e.g., SEQ ID NO: 71).

In certain aspects, a composition comprising an AAV delivery vector comprising a first nucleic acid encoding or comprising a first immunomodulatory protein or functional fragment thereof and/or a second nucleic acid encoding or comprising a second immunomodulatory protein or functional fragment thereof disclosed herein is suitable for intratumoral delivery.

In certain aspects, a composition comprising an AAV delivery vector comprising a first nucleic acid encoding or comprising a first immunomodulatory protein or functional fragment thereof and/or a second nucleic acid encoding or comprising a second immunomodulatory protein or functional fragment thereof disclosed herein is suitable for intravenous delivery.

In certain aspects, a composition comprising an AAV delivery vector comprising a first nucleic acid encoding or comprising a first immunomodulatory protein or functional fragment thereof and/or a second nucleic acid encoding or comprising a second immunomodulatory protein or functional fragment thereof disclosed herein is suitable for a delivery to a lymphoid organ (e.g., a spleen, a lymph node, or a bone marrow).

In some aspects, a composition comprising an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for intratumoral delivery.

In some aspects, a composition comprising an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for intravenous delivery.

In some aspects, a composition comprising an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for a delivery to a lymphoid organ (e.g., a spleen, a lymph node, or a bone marrow).

In some aspects, the viral vector and the checkpoint inhibitor are delivered in combination (e.g., simultaneously or sequentially). In some aspects, the viral vector described herein can be administered prior to, at the same time, or after the administration of a checkpoint inhibitor. In some aspects, the polynucleotide comprises: (i) a first nucleic acid encoding a first cytokine subunit (e.g., an IL-12 p35 subunit or an IL-12 p40 subunit) or functional fragment thereof; and (ii) a second nucleic acid encoding a second cytokine subunit (e.g., an IL-12 p35 subunit or an IL-12 p40 subunit) or functional fragment thereof. In some aspects, the nucleic acid encoding an IL-12 p35 subunit does not include an in-frame stop codon (e.g., TGA, TAG, and TAA).

In some aspects, the AAV delivery vector is suitable for delivery to a solid tumor (e.g., a sarcoma, a carcinoma, or a lymphoma) by direct injection. In some aspects, the solid tumor is a surface lesion. In some aspects, the solid tumor is a visceral tumor.

IV.A. AAV Vector Components

IV.A.1. Inverted Terminal Repeats (ITRs)

The AAV vectors of the present disclosure comprise a viral genome with at least one ITR region and a payload region, e.g., a polynucleotide encoding one or more immunomodulatory protein (e.g., IL-12 or one or more subunits thereof) or functional fragment thereof. In some aspects the AAV vector comprises two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into AAV vectors of the disclosure can be comprised of naturally occurring polynucleotide sequences or recombinantly derived polynucleotide sequences.

The ITRs can be derived from the same serotype as the capsid, selected from any of the serotypes listed herein, or a derivative thereof. The ITR can be of a different serotype from the capsid. In some aspects, the AAV vector has more than one ITR. In a non-limiting example, the AAV vector has a viral genome comprising two ITRs. In some aspects, the ITRs are of the same serotype as one another. In some aspects, the ITRs are of different serotypes. Non-limiting examples include zero, one or both of the ITRs having the same serotype as the capsid. In some aspects both ITRs of the AAV vector are AAV2 ITRs.

Independently, each ITR can be about 75 to about 175 nucleotides in length. An ITR can be about 100-105 nucleotides in length, about 106-110 nucleotides in length, about 111-115 nucleotides in length, about 116-120 nucleotides in length, about 121-125 nucleotides in length, about 126-130 nucleotides in length, about 131-135 nucleotides in length, about 136-140 nucleotides in length, about 141-145 nucleotides in length or about 146-150 nucleotides in length. In some aspects, the ITRs are about 140-142 nucleotides in length. Non-limiting examples of ITR length are about 102, about 140, about 141, about 142, about 145 nucleotides in length, and those having at least 95% identity thereto.

In some aspects, the AAV vector comprises at least one inverted terminal repeat having a length such as, but not limited to, about 75-80, about 75-85, about 75-100, about 80-85, about 80-90, about 80-105, about 85-90, about 85-95, about 85-110, about 90-95, about 90-100, about 90-115, about 95-100, about 95-105, about 95-120, about 100-105, about 100-110, about 100-125, about 105-110, about 105-115, about 105-130, about 110-115, about 110-120, about 110-135, about 115-120, about 115-125, about 115-140, about 120-125, about 120-130, about 120-145, about 125-130, about 125-135, about 125-150, about 130-135, about 130-140, about 130-155, about 135-140, about 135-145, about 135-160, about 140-145, about 140-150, about 140-165, about 145-150, about 145-155, about 145-170, about 150-155, about 150-160, about 150-175, about 155-160, about 155-165, about 160-165, about 160-170, about 165-170, about 165-175, or about 170-175 nucleotides.

In some aspects, the length of a first and/or a second ITR regions for the AAV vector can be about 75-80, about 75-85, about 75-100, about 80-85, about 80-90, about 80-105, about 85-90, about 85-95, about 85-110, about 90-95, about 90-100, about 90-115, about 95-100, about 95-105, about 95-120, about 100-105, about 100-110, about 100-125, about 105-110, about 105-115, about 105-130, about 110-115, about 110-120, about 110-135, about 115-120, about 115-125, about 115-140, about 120-125, about 120-130, about 120-145, about 125-130, about 125-135, about 125-150, about 130-135, about 130-140, about 130-155, about 135-140, about 135-145, about 135-160, about 140-145, about 140-150, about 140-165, about 145-150, about 145-155, about 145-170, about 150-155, about 150-160, about 150-175, about 155-160, about 155-165, about 160-165, about 160-170, about 165-170, about 165-175, and about 170-175 nucleotides.

In some aspects, the AAV vector comprises a nucleic acid encoding an immunomodulatory protein (e.g., IL-12 or one or more subunits thereof) or functional fragment thereof which can be located near the 5' end of the flip ITR in the vector. In some aspects, the AAV vector comprises a nucleic acid encoding an immunomodulatory protein (e.g., IL-12 or one or more subunits thereof) or functional fragment thereof disclosed herein which can be located near the 3' end of the flip ITR in the vector. In some aspects, the AAV vector comprises a nucleic acid sequence encoding an immunomodulatory protein (e.g., IL-12 or one or more subunits thereof) or functional fragment thereof disclosed herein which can be located near the 5' end of the flop ITR in the vector. In some aspects, the AAV vector comprises a nucleic acid sequence encoding an immunomodulatory protein (e.g., IL-12 or one or more subunits thereof) or functional fragment thereof disclosed herein which can be located near the 3' end of the flop ITR in the vector. In some aspects, the AAV vector comprises a nucleic acid sequence encoding an immunomodulatory protein (e.g., IL-12 or one or more subunits thereof) or functional fragment thereof disclosed herein which can be located between the 5' end of the flip ITR and the 3' end of the flop ITR in the vector. In some aspects, the AAV vector comprises a nucleic acid sequence encoding an immunomodulatory protein (e.g., IL-12 or one or more subunits thereof) or functional fragment thereof disclosed herein which can be located between (e.g., halfway between the 5' end of the flip ITR and 3' end of the flop ITR or the 3' end of the flop ITR and the 5' end of the flip ITR), the 3' end of the flip ITR and the 5' end of the flip ITR in the vector.

In some aspects, the AAV vector comprises a nucleic acid sequence encoding an immunomodulatory protein (e.g., IL-12 or one or more subunits thereof) or functional fragment thereof disclosed herein which can be located within about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or more than about 30 nucleotides downstream or upstream from the 5' or 3' end of an ITR (e.g., Flip or Flop ITR) in the vector.

As another non-limiting example, the AAV vector comprises a nucleic acid sequence encoding an immunomodulatory protein (e.g., IL-12 or one or more subunits thereof) or functional fragment thereof disclosed herein which can be located within about 1-5, about 1-10, about 1-15, about 1-20, about 1-25, about 1-30, about 5-10, about 5-15, about 5-20, about 5-25, about 5-30, about 10-15, about 10-20, about 10-25, about 10-30, about 15-20, about 15-25, about 15-30, about 20-25, about 20-30 or about 25-30 nucleotides downstream or upstream from the 5' or 3' end of an ITR (e.g., Flip or Flop ITR) in the vector.

In some aspects, the AAV vector comprises a nucleic acid sequence encoding an immunomodulatory protein (e.g., IL-12 or one or more subunits thereof) or functional fragment thereof disclosed herein which can be located within the first about 1%, about 2%, about 3%, about 4%, about 5%, about 6%, about 7%, about 8%, about 9%, about 10%, about 15%, about 20%, about 25% or more than about 25% of the nucleotides upstream from the 5' or 3' end of an ITR (e.g., Flip or Flop ITR) in the vector.

As another non-limiting example, the AAV vector comprises a nucleic acid sequence encoding an immunomodulatory protein (e.g., IL-12 or one or more subunits thereof) or functional fragment thereof disclosed herein which can be located with the first about 1-5%, about 1-10%, about 1-15%, about 1-20%, about 1-25%, about 5-10%, about 5-15%, about 5-20%, about 5-25%, about 10-15%, about 10-20%, about 10-25%, about 15-20%, about 15-25%, or about 20-25% downstream from the 5' or 3' end of an ITR (e.g., Flip or Flop ITR) in the vector.

Certain aspects of the disclosure are directed to an AAV vector comprising a polynucleotide comprising polynucleotide comprising a first nucleic acid encoding an IL-12 subunit (e.g., IL-12 p35) or a functional fragment thereof and/or a second nucleic acid encoding an IL-12 subunit (e.g., IL-12 p40) or functional fragment thereof disclosed herein, wherein the polynucleotide further comprises ITR sequences (e.g., AAV2 ITRs).

Certain aspects of the disclosure are directed to a viral delivery vector comprising a polynucleotide comprising a CMV enhancer (e.g., SEQ ID NO: 68), a CBA promoter (e.g., SEQ ID NO: 85) operably linked to a first nucleic acid encoding a human IL-12 p35 subunit or a functional fragment thereof (e.g., SEQ ID NO: 77), a furin cleavage sequence followed by a 2A self-processing peptide (F2A), a second nucleic acid encoding a human IL-12 p40 subunit or a functional fragment thereof (e.g., SEQ ID NO: 8), and a human growth hormone (HGH) pA sequence (e.g., SEQ ID NO: 88). In some aspects, the polynucleotide further comprises an intron sequence (e.g., a CAG intron, e.g., SEQ ID NO: 86), a Kozak sequence, and ITR sequences (e.g., AAV2 ITRs). In some aspects, the polynucleotide comprises a CMV enhancer, a CBA promoter, and a CAG intron (e.g., SEQ ID NO: 71).

IV.A.2. Promoters

In some aspects, the payload region of the AAV vector comprises at least one element to enhance the nucleic acid specificity and/or expression. Non-limiting examples of elements to enhance the nucleic acid specificity and expression include, e.g., promoters, endogenous miRNAs, post-transcriptional regulatory elements (PREs), polyadenylation (Poly A) signal sequences and upstream enhancers (USEs), CMV enhancers, and introns.

Expression of nucleic acid of the present disclosure after delivery to or integration in the genomic DNA of a target cell can require a specific promoter, including but not limited to, a promoter that is species specific, inducible, tissue-specific, or cell cycle-specific (Parr et al., Nat. Med. 3: 1145-9 (1997); the contents of which are herein incorporated by reference in their entirety).

In some aspects, the promoter is deemed to be efficient when it drives expression of the immunomodulatory protein (e.g., IL-12 or one or more subunits thereof) or functional fragment thereof disclosed herein carried in the payload region of the AAV vector. In some aspects, the promoter is a promoter deemed to be efficient when it drives expression of the immunomodulatory protein (e.g., IL-12 or one or more subunits thereof) or functional fragment thereof of the present disclosure in the cell being targeted (e.g., a tumor cell).

Promoters can be naturally occurring or non-naturally occurring. Non-limiting examples of promoters include viral promoters and mammalian promoters. In some aspects, the promoters can be human promoters. In some aspects, the promoter can be truncated. Promoters which drive or promote expression in most tissues include, but are not limited to, human elongation factor 1a-subunit (EF 1a), cytomegalovirus (CMV) immediate-early enhancer and/or promoter, chicken β-actin (CBA) and its derivative CAG, B glucuronidase (GUSB), or ubiquitin C (UBC). In some aspects, the promoter is a CBA promoter, a CMV promoter, a EF-1a (Elongation Factor 1a) promoter, aRSV (Rous Sarcoma Virus) promoter, an Ubiquitin (UbC) promoter, or any combination thereof. In some aspects, tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons, astrocytes, or oligodendrocytes.

Non-limiting examples of muscle-specific promoters include mammalian muscle creatine kinase (MCK) promoter, mammalian desmin (DES) promoter, mammalian troponin I (TNNI2) promoter, and mammalian skeletal alpha-actin (ASKA) promoter (see, e.g. U.S. Patent Publication US 20110212529, the contents of which are herein incorporated by reference in their entirety). Non-limiting examples of tissue-specific expression elements for neurons include neuron-specific enolase (NSE), platelet-derived growth factor (PDGF), platelet-derived growth factor B-chain (PDGF-B), synapsin (Syn), methyl-CpG binding protein 2 (MeCP2), Ca2+/calmodulin-dependent protein kinase II (CaMKII), metabotropic glutamate receptor 2 (mGluR2), neurofilament light (NFL) or heavy (NFH), ß-globin minigene ηβ2, preproenkephalin (PPE), enkephalin (Enk) and excitatory amino acid transporter 2 (EAAT2) promoters. Non-limiting examples of tissue-specific expression elements for astrocytes include glial fibrillary acidic protein (GFAP) and EAAT2 promoters. A non-limiting example of a tissue-specific expression element for oligodendrocytes includes the myelin basic protein (MBP) promoter. In some aspects, the promoter is a CAG promoter.

In some aspects, the promoter can be less than 1 kb. In some aspects, the promoter can have a length between about 15-20, about 10-50, about 20-30, about 30-40, about 40-50, about 50-60, about 50-100, about 60-70, about 70-80, about 80-90, about 90-100, about 100-110, about 100-150, about 110-120, about 120-130, about 130-140, about 140-150, about 150-160, about 150-200, about 160-170, about 170-180, about 180-190, about 190-200, about 200-210, about 200-250, about 210-220, about 220-230, about 230-240, about 240-250, about 250-260, about 250-300, about 260-270, about 270-280, about 280-290, about 290-300, about 200-300, about 200-400, about 200-500, about 200-600, about 200-700, about 200-800, about 300-400, about 300-500, about 300-600, about 300-700, about 300-800, about 400-500, about 400-600, about 400-700, about 400-800, about 500-600, about 500-700, about 500-800, about 600-700, about 600-800 or about 700-800 nucleotides.

In some aspects, the promoter can be a combination of two or more components of the same or different starting or parental promoters such as, but not limited to, CMV and CBA. In some aspects, the promoter comprises a CBA promoter, a CMV promoter, a EF-1a (Elongation Factor 1a) promoter, aRSV (Rous Sarcoma Virus) promoter, an Ubiquitin (UbC) promoter, or any combination thereof. In some aspects, one of the two or more promoters is a CMV enhancer fused to a EF1α promoter. In some aspects, one of the two or more promoters is a CMV promoter fused to an SV40 intron. In some aspects, one of the two or more promoters is a CMV enhancer fused to a CMV promoter. In some aspects, one of the two or more promoters has a nucleic acid sequence comprising at least 85%, 86%, 87%, 88%, 89%, 90%, 91%, 92%, 93%, 94%, 95%, 96%, 97%, 98%, 99%, or 100% identical to any one of SEQ ID NOs: 67-71 or 85.

In some aspects, each component in the promoter can have a length between about 200-300, about 200-400, about 200-500, about 200-600, about 200-700, about 200-800, about 300-400, about 300-500, about 300-600, about 300-700, about 300-800, about 400-500, about 400-600, about 400-700, about 400-800, about 500-600, about 500-700, about 500-800, about 600-700, about 600-800 or about 700-800 nucleotides. In some aspects, the promoter is a combination of a 382 nucleotide CMV-enhancer sequence and a 260 nucleotide CBA-promoter sequence.

In some aspects, the promoter combination comprises a CMV enhancer, a CBA promoter, and a CAG intron (e.g., SEQ ID NO: 71).

In some aspects, the AAV vector comprises a ubiquitous promoter. Non-limiting examples of ubiquitous promoters include, e.g., CMV, CBA (including derivatives CAG, CBh, etc.), EF-1a, PGK, UBC, GUSB (hGBp), and UCOE (promoter of HNRPA2B1-CBX3).

In some aspects, the promoter is not cell specific. In some aspects, the promoter is a ubiquitin c (UBC) promoter. The UBC promoter can have a size of 300-350 nucleotides. In some aspects, the UBC promoter is 332 nucleotides. In some aspects, the promoter is a β-glucuronidase (GUSB) promoter. The GUSB promoter can have a size of 350-400 nucleotides. In some aspects, the GUSB promoter is 378 nucleotides. In some aspects, the promoter is a neurofilament light (NFL) promoter. The NFL promoter can have a size of 600-700 nucleotides. In some aspects, the NFL promoter is 650 nucleotides. In some aspects, the construct can be AAV-promoter-CMV/globin intron-modulatory polynucleotide-RBG, where the AAV can be self-complementary and the AAV can be the DJ serotype.

In some aspects, the AAV vector comprises a Pol III promoter. In some aspects, the AAV vector comprises a PI promoter. In some aspects, the AAV vector comprises a FXN promoter. In some aspects, the promoter is a phosphoglycerate kinase 1 (PGK) promoter. In some aspects, the promoter is a chicken β-actin (CBA) promoter. In some aspects, the promoter is a CAG promoter which is a construct comprising the cytomegalovirus (CMV) enhancer fused to the chicken beta-actin (CBA) promoter with a chimeric intron. In some aspects, the promoter is a cytomegalovirus (CMV) promoter. In some aspects, the AAV vector comprises a H1 promoter. In some aspects, the AAV vector comprises a U6 promoter. In some aspects, the AAV vector comprises a SP6 promoter.

In some aspects, the promoter is a liver or a skeletal muscle promoter. Non-limiting examples of liver promoters include human a-1-antitrypsin (hAAT) and thyroxine binding globulin (TBG). Non-limiting examples of skeletal muscle promoters include Desmin, MCK or synthetic C5-12. In some aspects, the promoter is an RNA pol III promoter. In some aspects, the RNA pol III promoter is U6. In some aspects, the RNA pol III promoter is H1. In some aspects, the AAV vector comprises two promoters. In some aspects, the promoters are an EF1a promoter and a CMV promoter.

In some aspects, the AAV vector comprises an enhancer element, a promoter and/or a 5'UTR intron. The enhancer element, also referred to herein as an "enhancer," can be, but is not limited to, a CMV enhancer, the promoter can be, but is not limited to, a CMV, CBA, UBC, GUSB, NSE, Synapsin, MeCP2, EF1α, and GFAP promoter and the 5'UTR/intron can be, but is not limited to, SV40, a chimera of a betaglobin intron and a immunoglobulin heavy chain intron, and CBA-MVM (Minute virus of mice). In some aspects, the enhancer, promoter and/or intron used in combination can be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter, (9) GFAP promoter, (10) H1 promoter; (11) U6 promoter; (12) 12) CMV enhancer, EF1α promoter; (13) CMV promoter, SV40 intron; (14) CMV enhancer, CMV promoter; or (15) chimera of human betaglobin intron and immunoglobulin heavy chain intron, CMV enhancer, EF1α promoter, CMV promoter, SV40 intron. In some aspects, the AAV vector comprises a CMV early enhancer/chicken β actin (CAG) promoter. In some aspects, the AAV vector comprises an engineered promoter. In some aspects the AAV vector comprises a promoter from a naturally expressed protein.

In some aspects, the construct can comprise two or more promoters, e.g., a promoter for the nucleic acid encoding a heavy chain and a promoter for the nucleic acid sequence encoding a light chain. In some aspects, the two or more promoters are the same. In some aspects, the construct can comprise a promoter for the nucleic acid encoding a first cytokine subunit (e.g., an IL-12 p35 subunit or an IL-12 p40 subunit) and a promoter for the nucleic acid sequence encoding a second cytokine subunit (e.g., an IL-12 p40 subunit or IL-12 p35 subunit). In some aspects, the two or more promoters are the same. In some aspects, the two or more promoters are different.

IV.A.3. Untranslated Regions (UTRs)

By definition, wild-type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs can be engineered into UTRs to enhance transcribed product stability and production. In some aspects, a 5' UTR from mRNA normally expressed in the liver (e.g., albumin, serum amyloid A, Apolipoprotein A/B/E, transferrin, alpha fetoprotein, erythropoietin, or Factor VIII) can be used in AAV vector of the disclosure to enhance expression, e.g., in brain tissue, and specifically in neuronal cells.

Wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG (SEQ ID NO: 4), where R is a purine (adenine or guanine) three bases upstream of the start codon (ATG), which is followed by another 'G. In some aspects, the 5'UTR in a AAV vector of the present disclosure includes a Kozak sequence. In some aspects, the 5'UTR in a AAV vector of the present disclosure does not include a Kozak sequence.

Wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in its entirety). Class I AREs, such as, but not limited to, c-Myc and MyoD, contain several dispersed copies of an AUUUA (SEQ ID NO: 32) motif within U-rich regions. Class II AREs, such as, but not limited to, GM-CSF and TNF-α, possess two or more overlapping UUAUUUA(U/A)(U/A) (SEQ ID NO: 33) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In some aspects, the 3' UTR of an AAV vector of the present disclosure can include an oligo(dT) sequence for addition of a poly-A tail. In some aspects, an AAV vector of the present disclosure can include at least one miRNA seed, binding site or full sequence. microRNAs (or miRNA or miR) are 19-25 nucleotide noncoding RNAs that bind to the sites of nucleic acid targets and down-regulate gene expression either by reducing nucleic acid molecule stability or by inhibiting translation. A microRNA sequence comprises a "seed" region, i.e., a sequence in the region of positions 2-8 of the mature microRNA, which sequence has perfect Watson-Crick complementarity to the miRNA target sequence of the nucleic acid.

In some aspects, an AAV vector of the present disclosure can be engineered to include, alter or remove at least one miRNA binding site, sequence or seed region.

Any UTR from any gene known in the art can be incorporated into an AAV vector of the present disclosure. These UTRs, or portions thereof, can be placed in the same orientation as in the gene from which they were selected or they can be altered in orientation or location. In some aspects, the UTR used in an AAV vector of the present disclosure can be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR can be altered relative to a wild-type or native UTR by the change in orientation or location as taught above or can be altered by the inclusion of additional nucleotides, deletion of nucleotides, swapping or transposition of nucleotides. In some aspects, an AAV vector of the present disclosure comprises at least one artificial UTRs which is not a variant of a wild-type UTR. In some aspects, an AAV vector of the present disclosure comprises UTRs which have been selected from a family of transcripts whose proteins share a common function, structure, feature or property.

IV.A.4. Polyadenylation Sequence

In some aspects, the AAV vectors of the present disclosure comprise at least one polyadenylation sequence. The AAV vectors of the present disclosure can comprise a polyadenylation sequence between the 3' end of the payload coding sequence and the 5' end of the 3'ITR.

In some aspects, the polyadenylation sequence or "poly A sequence" can range from absent to about 500 nucleotides in length.

In some aspects, the polyadenylation sequence is about 50-100, about 50-150, about 50-160, about 50-200, about 60-100, about 60-150, about 60-160, about 60-200, about 70-100, about 70-150, about 70-160, about 70-200, about 80-100, about 80-150, about 80-160, about 80-200, about 90-100, about 90-150, about 90-160, or about 90-200 nucleotides in length.

In some aspects, the AAV vector comprises a nucleic acid sequence encoding an immunomodulatory protein (e.g., IL-12 or one or more subunits thereof) or functional fragment thereof disclosed herein which can be located upstream of the polyadenylation sequence in the vector. In some aspects, the AAV vector comprises a nucleic acid sequence encoding an immunomodulatory protein or functional fragment thereof disclosed herein which can be located downstream of a promoter such as, but not limited to, CMV, U6, CAG, CBA or a CBA promoter with a SV40 intron, MVM intron, or a human betaglobin intron in the vector.

In some aspects, the AAV vector of the present disclosure comprises a nucleic acid sequence encoding an immunomodulatory protein (e.g., IL-12 or one or more subunits thereof) or functional fragment thereof disclosed herein which can be located within about 1-5, about 1-10, about 1-15, about 1-20, about 1-25, about 1-30, about 5-10, about 5-15, about 5-20, about 5-25, about 5-30, about 10-15, about 10-20, about 10-25, about 10-30, about 15-20, about 15-25, about 15-30, about 20-25, about 20-30 or about 25-30 nucleotides downstream from the promoter and/or upstream of the polyadenylation sequence in the vector.

In some aspects, the AAV vector comprises a rabbit globin polyadenylation (poly A) signal sequence. In some aspects, the AAV vector comprises a human growth hormone polyadenylation (poly A) signal sequence. In some aspects, the AAV vector comprises a human growth hormone polyadenylation (poly A) (HGHpA) signal sequence. In some aspects, HGHpA has a nucleic acid sequence at least 85%, 86%, 87%, 88%, 89%, 90%, 91%, 92%, 93%, 94%, 95%, 96%, 97%, 98%, 99%, or 100% identical to SEQ ID NO: 88. In some aspects, the AAV vector comprises a bovine growth hormone polyadenylation (poly A) (BGHpA) signal sequence. In some aspects, BGHpA has a nucleic acid sequence at least 85%, 86%, 87%, 88%, 89%, 90%, 91%, 92%, 93%, 94%, 95%, 96%, 97%, 98%, 99%, or 100% identical to SEQ ID NO: 73. In some aspects, the AAV vector comprises a synthetic (SYN) polyadenylation (poly A) (SYNpA) signal sequence. In some aspects, SYNpA has a nucleic acid sequence at least 85%, 86%, 87%, 88%, 89%, 90%, 91%, 92%, 93%, 94%, 95%, 96%, 97%, 98%, 99%, or 100% identical to SEQ ID NO: 72.

IV.A.5. Introns

In some aspects, the payload region of an AAV vector of the present disclosure comprises at least one element to enhance the expression such as one or more introns or portions thereof. Non-limiting examples of introns include, MVM (67-97 bps), FIX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps). In some aspects, the chimeric intron can be a chimera of a human betaglobin intron and a human immunoglobin heavy chain intron. In some aspects, the intron can have a nucleotide sequence with at least 85%, 86%, 87%, 88%, 89%, 90%, 91%, 92%, 93%, 94%, 95%, 96%, 97%, 98%, 99%, or 100% identical to any of SEQ ID NOs: 66 and 76.

In some aspects, the intron or intron portion can be between about 100 and about 500 nucleotides in length. In some aspects, the intron can have a length between about 80-100, about 80-120, about 80-140, about 80-160, about 80-180, about 80-200, about 80-250, about 80-300, about 80-350, about 80-400, about 80-450, about 80-500, about 200-300, about 200-400, about 200-500, about 300-400, about 300-500, or about 400-500 nucleotides.

In some aspects, the AAV vector can comprise a promoter such as, but not limited to, CMV, CBA, or U6. In some aspects, the promoter for an AAV vector of the present disclosure is a CMV promoter. In some aspects, the promoter for an AAV vector of the present disclosure is a CBA promoter. In some aspects, the AAV vector can comprise a CBA promoter, a CMV promoter, a EF-1a (Elongation Factor 1a) promoter, aRSV (Rous Sarcoma Virus) promoter, an Ubiquitin (UbC) promoter, or any combination thereof. As another non-limiting example, the promoter for an AAV vector of the present disclosure is a U6 promoter. In some aspects, the AAV vector can comprise a CMV and a U6 promoter. In some aspects, the AAV vector can comprise a H1 promoter. In some aspects, the AAV vector can comprise a CBA promoter. In some aspects, the AAV vector can comprise a chimeric intron. In some aspects, the AAV vector of the present disclosure is a CBA promoter, a CMV promoter, a EF-1a (Elongation Factor 1a) promoter, aRSV (Rous Sarcoma Virus) promoter, an Ubiquitin (UbC) promoter, a CMV enhancer fused to a EF1α promoter, a CMV promoter fused to an SV40 intron, a CMV enhancer fused to a CMV promoter, or any combination thereof. In some aspects, the promoter comprises a nucleotide sequence with at least 85%, 86%, 87%, 88%, 89%, 90%, 91%, 92%, 93%, 94%, 95%, 96%, 97%, 98%, 99%, or 100% identical to any one of SEQ ID NOs: 67-71 or 85.

In some aspects, the encoded immunomodulatory protein (e.g., IL-12 or one or more subunits thereof) or functional fragment thereof disclosed herein can be located downstream of a promoter in an expression vector such as, but not limited to, CMV, U6, HI, CBA, CAG, or a CBA promoter with an intron such as SV40 or others known in the art. Further, the encoded immunomodulatory protein or functional fragment thereof disclosed herein can also be located upstream of the polyadenylation sequence in an expression vector. In some aspects, the encoded immunomodulatory protein (e.g., IL-12 or one or more subunits thereof) or functional fragment thereof disclosed herein can be located within about 1-5, about 1-10, about 1-15, about 1-20, about 1-25, about 1-30, about 5-10, about 5-15, about 5-20, about 5-25, about 5-30, about 10-15, about 10-20, about 10-25, about 10-30, about 15-20, about 15-25, about 15-30, about 20-25, about 20-30 or about 25-30 nucleotides downstream from the promoter and/or upstream of the polyadenylation sequence in the vector.

IV.A.6. Filler Sequences

In some aspects, the AAV vector comprises one or more filler sequences (also referred to as "stuffer sequences"). In some aspects, the AAV vector comprises one or more filler sequences in order to have the length of the AAV vector be the optimal size for packaging. In some aspects, the AAV vector comprises at least one filler sequence in order to have the length of the AAV vector be about 2.0-2.5 kb, e.g., about 2.3 kb. In some aspects, the AAV vector comprises at least one filler sequence in order to have the length of the AAV vector be about 4.6 kb. In some aspects, the vector backbone comprises a filler sequence.

In some aspects, the AAV vector comprises one or more filler sequences in order to reduce the likelihood that a hairpin structure of the vector genome (e.g., a modulatory polynucleotide described herein, e.g., IL-12 or one or more subunits thereof) can be read as an inverted terminal repeat (ITR) during expression and/or packaging. In some aspects, the AAV vector comprises at least one filler sequence in order to have the length of the AAV vector be about 2.0-2.5 kb, e.g., about 2.3 kb. In some aspects, the AAV vector comprises at least one filler sequence in order to have the length of the AAV vector be about 4.6 kb.

In some aspects, the AAV vector is a single stranded (ss) AAV vector and comprises one or more filler sequences which have a length about between 0.1 kb and about 3.8 kb, such as, but not limited to, about 0.1 kb, about 0.2 kb, about 0.3 kb, about 0.4 kb, about 0.5 kb, about 0.6 kb, about 0.7 kb, about 0.8 kb, about 0.9 kb, about 1 kb, about 1.1 kb, about 1.2 kb, about 1.3 kb, about 1.4 kb, about 1.5 kb, about 1.6 kb, about 1.7 kb, about 1.8 kb, about 1.9 kb, about 2 kb, about 2.1 kb, about 2.2 kb, about 2.3 kb, about 2.4 kb, about 2.5 kb, about 2.6 kb, about 2.7 kb, about 2.8 kb, about 2.9 kb, about 3 kb, about 3.1 kb, about 3.2 kb, about 3.3 kb, about 3.4 kb, about 3.5 kb, about 3.6 kb, about 3.7 kb, or about 3.8 kb.

In some aspects, the AAV vector is a self-complementary (sc) AAV vector and comprises one or more filler sequences which have a length about between 0.1 kb and about 1.5 kb, such as, but not limited to, about 0.1 kb, about 0.2 kb, about 0.3 kb, about 0.4 kb, about 0.5 kb, about 0.6 kb, about 0.7 kb, about 0.8 kb, about 0.9 kb, about 1 kb, about 1.1 kb, about 1.2 kb, about 1.3 kb, about 1.4 kb, or about 1.5 kb.

In some aspects, the AAV vector comprises any portion of a filler sequence. The vector can comprise, e.g., about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99% of a filler sequence.

In some aspects, the AAV vector is a single stranded (ss) AAV vector and comprises one or more filler sequences in order to have the length of the AAV vector be about 4.6 kb. In some aspects, the AAV vector comprises at least one filler sequence and the filler sequence is located 3' to the 5' ITR sequence. In some aspects, the AAV vector comprises at least one filler sequence and the filler sequence is located 5' to a promoter sequence. In some aspects, the AAV vector comprises at least one filler sequence and the filler sequence is located 3' to the polyadenylation signal sequence. In some aspects, the AAV vector comprises at least one filler sequence and the filler sequence is located 5' to the 3' ITR sequence. In some aspects, the AAV vector comprises at least one filler sequence, and the filler sequence is located between two intron sequences. In some aspects, the AAV vector comprises at least one filler sequence, and the filler sequence is located within an intron sequence. In some aspects, the AAV vector comprises two filler sequences, and the first filler sequence is located 3' to the 5' ITR sequence and the second filler sequence is located 3' to the polyadenylation signal sequence. In some aspects, the AAV vector comprises two filler sequences, and the first filler sequence is located 5' to a promoter sequence and the second filler sequence is located 3' to the polyadenylation signal sequence. In some aspects, the AAV vector comprises two filler sequences, and the first filler sequence is located 3' to the 5' ITR sequence and the second filler sequence is located 5' to the 5' ITR sequence.

In some aspects, the AAV vector is a self-complementary (sc) AAV vector and comprises one or more filler sequences in order to have the length of the AAV vector be about 2.3 kb. In some aspects, the AAV vector comprises at least one filler sequence and the filler sequence is located 3' to the 5' ITR sequence. In some aspects, the AAV vector comprises at least one filler sequence and the filler sequence is located 5' to a promoter sequence. In some aspects, the AAV vector comprises at least one filler sequence and the filler sequence is located 3' to the polyadenylation signal sequence. In some aspects, the AAV vector comprises at least one filler sequence and the filler sequence is located 5' to the 3' ITR sequence.

In some aspects, the AAV vector comprises at least one filler sequence, and the filler sequence is located between two intron sequences. In some aspects, the AAV vector comprises at least one filler sequence, and the filler sequence is located within an intron sequence. In some aspects, the AAV vector comprises two filler sequences, and the first filler sequence is located 3' to the 5' ITR sequence and the second filler sequence is located 3' to the polyadenylation signal sequence. In some aspects, the AAV vector comprises two filler sequences, and the first filler sequence is located 5' to a promoter sequence and the second filler sequence is located 3' to the polyadenylation signal sequence. In some aspects, the AAV vector comprises two filler sequences, and the first filler sequence is located 3' to the 5' ITR sequence and the second filler sequence is located 5' to the 5' ITR sequence.

In some aspects, the AAV vector can comprise one or more filler sequences between one of more regions of the AAV vector. In some aspects, the filler region can be located before a region such as, but not limited to, a payload region, an ITR, a promoter region, an intron region, an enhancer region, and/or a polyadenylation signal sequence region. In some aspects, the filler region can be located after a region such as, but not limited to, a payload region, an ITR, a promoter region, an intron region, an enhancer region, and/or a polyadenylation signal sequence region. In some aspects, the filler region can be located before and after a region such as, but not limited to, a payload region, an ITR, a promoter region, an intron region, an enhancer region, and/or a polyadenylation signal sequence region.

In some aspects, the AAV vector can comprise one or more filler sequences which bifurcates at least one region of the AAV vector. The bifurcated region of the AAV vector can comprise about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99% of the of the region to the 5' of the filler sequence region.

In some aspects, the filler sequence can bifurcate at least one region so that about 10% of the region is located 5' to the filler sequence and about 90% of the region is located 3' to the filler sequence. In some aspects, the filler sequence can bifurcate at least one region so that about 20% of the region is located 5' to the filler sequence and about 80% of the region is located 3' to the filler sequence. In some aspects, the filler sequence can bifurcate at least one region so that about 30% of the region is located 5' to the filler sequence and about 70% of the region is located 3' to the filler sequence. In some aspects, the filler sequence can bifurcate at least one region so that about 40% of the region is located 5' to the filler sequence and about 60% of the region is located 3' to the filler sequence. In some aspects, the filler sequence can bifurcate at least one region so that about 50% of the region is located 5' to the filler sequence and about 50% of the region is located 3' to the filler sequence. In some aspects, the filler sequence can bifurcate at least one region so that about 60% of the region is located 5' to the filler sequence and about 40% of the region is located 3' to the filler sequence. In some aspects, the filler sequence can bifurcate at least one region so that about 70% of the region is located 5' to the filler sequence and about 30% of the region is located 3' to the filler sequence. In some aspects, the filler sequence can bifurcate at least one region so that about 80% of the region is located 5' to the filler sequence and about 20% of the region is located 3' to the filler sequence. In some aspects, the filler sequence can bifurcate at least one region so that about 90% of the region is located 5' to the filler sequence and about 10% of the region is located 3' to the filler sequence.

In some aspects, the AAV vector comprises a filler sequence after the 5' ITR. In some aspects, the AAV vector comprises a filler sequence after the promoter region. In some aspects, the AAV vector comprises a filler sequence after the payload region. In some aspects, the AAV vector comprises a filler sequence after the intron region. In some aspects, the AAV vector comprises a filler sequence after the enhancer region. In some aspects, the AAV vector comprises a filler sequence after the polyadenylation signal sequence region. In some aspects, the AAV vector comprises a filler sequence before the promoter region. In some aspects, the AAV vector comprises a filler sequence before the payload region. In some aspects, the AAV vector comprises a filler sequence before the intron region.

In some aspects, the AAV vector comprises a filler sequence before the enhancer region. In some aspects, the AAV vector comprises a filler sequence before the polyadenylation signal sequence region. In some aspects, the AAV vector comprises a filler sequence before the 3' ITR. In some aspects, a filler sequence can be located between two regions, such as, but not limited to, the 5' ITR and the promoter region. In some aspects, a filler sequence can be located between two regions, such as, but not limited to, the 5' ITR and the payload region.

In some aspects, a filler sequence can be located between two regions, such as, but not limited to, the 5' ITR and the intron region. In some aspects, a filler sequence can be located between two regions, such as, but not limited to, the 5' ITR and the enhancer region. In some aspects, a filler sequence can be located between two regions, such as, but not limited to, the 5' ITR and the polyadenylation signal sequence region. In some aspects, a filler sequence can be located between two regions, such as, but not limited to, the promoter region and the payload region.

In some aspects, a filler sequence can be located between two regions, such as, but not limited to, the promoter region and the intron region. In some aspects, a filler sequence can be located between two regions, such as, but not limited to, the promoter region and the enhancer region. In some aspects, a filler sequence can be located between two regions, such as, but not limited to, the promoter region and the polyadenylation signal sequence region. In some aspects, a filler sequence can be located between two regions, such as, but not limited to, the promoter region and the 3' ITR.

In some aspects, a filler sequence can be located between two regions, such as, but not limited to, the payload region and the intron region. In some aspects, a filler sequence can be located between two regions, such as, but not limited to, the payload region and the enhancer region. In some aspects, a filler sequence can be located between two regions, such as, but not limited to, the payload region and the polyadenylation signal sequence region. In some aspects, a filler sequence can be located between two regions, such as, but not limited to, the payload region and the 3' ITR.

In some aspects, a filler sequence can be located between two regions, such as, but not limited to, the intron region and the enhancer region. In some aspects, a filler sequence can be located between two regions, such as, but not limited to, the intron region and the polyadenylation signal sequence region. In some aspects, a filler sequence can be located between two regions, such as, but not limited to, the intron region and the 3' ITR. In some aspects, a filler sequence can be located between two regions, such as, but not limited to, the enhancer region and the polyadenylation signal sequence region. In some aspects, a filler sequence can be located between two regions, such as, but not limited to, the enhancer region and the 3' ITR. In some aspects, a filler sequence can be located between two regions, such as, but not limited to, the polyadenylation signal sequence region and the 3' ITR.

In some aspects, an AAV vector can comprise two filler sequences. The two filler sequences can be located between two regions as described herein.

IV.A.7. Method for Producing Recombinant AAVs

The present disclosure provides also methods for the generation of AAV particles, by viral genome replication in a viral replication cell comprising contacting the viral replication cell with an AAV polynucleotide or AAV genome (e.g., an AAV vector of the present disclosure). In the context of the present disclosure, the AAV vectors disclosed herein, e.g., AAV vectors comprising at least one polynucleotide encoding an immunomodulatory protein (e.g., IL-12 or one or more subunits thereof) or functional fragment thereof disclosed herein, are considered AAV payload construct vectors.

In some aspects, an AAV particle is produced by a method comprising the steps of:
(1) co-transfecting competent bacterial cells with a bacmid vector and either a viral construct vector and/or AAV payload construct vector,
(2) isolating the resultant viral construct expression vector and AAV payload construct expression vector and separately transfecting viral replication cells,
(3) isolating and purifying resultant payload and viral construct particles comprising viral construct expression vector or AAV payload construct expression vector,
(4) co-infecting a viral replication cell with both the AAV payload and viral construct particles comprising viral construct expression vector or AAV payload construct expression vector, and
(5) harvesting and purifying the viral particle comprising a parvoviral genome.

In one aspect, the present disclosure provides a method for producing an AAV particle comprising the steps of (1) simultaneously co-transfecting mammalian cells, such as, but not limited to HEK293 cells, with a payload region (e.g., polynucleotide encoding an immunomodulatory protein or functional fragment thereof of the present disclosure), a construct expressing rep and cap genes and a helper construct, and (2) harvesting and purifying the AAV particle comprising a viral genome.

In some aspects, the AAV particles can be produced in a viral replication cell that comprises an insect cell. Growing conditions for insect cells in culture, and production of heterologous products in insect cells in culture are well-known in the art, see, e.g., U.S. Pat. No. 6,204,059.

The viral replication cell can be selected from any biological organism, including prokaryotic (e.g., bacterial) cells, and eukaryotic cells, including, insect cells, yeast cells and mammalian cells. Viral replication cells can comprise mammalian cells such as A549, WEH1, 3T3, 10T1/2, BHK, MDCK, COS 1, COS 7, BSC 1, BSC 40, BMT 10, VERO. W138, HeLa, HEK293, Saos, C2C12, L cells, HT1080, HepG2 and primary fibroblast, hepatocyte and myoblast cells derived from mammals. Viral replication cells comprise cells derived from mammalian species including, but not limited to, human, monkey, mouse, rat, rabbit, and hamster or cell type, including but not limited to fibroblast, hepatocyte, tumor cell, cell line transformed cell, etc.

Viral production disclosed herein describes processes and methods for producing AAV particles that contact a target cell to deliver a payload, e.g. a recombinant viral construct, which comprises a polynucleotide sequence encoding a payload such as an immunomodulatory protein or functional fragment thereof disclosed herein.

In some aspects, the AAV particles can be produced in a viral replication cell that comprises a mammalian cell. Viral replication cells commonly used for production of recombinant AAV particles include, but are not limited to 293 cells, COS cells, HeLa cells, and KB cells.

In some aspects, AAV particles are produced in mammalian cells wherein all three VP proteins are expressed at a stoichiometry approaching 1:1:10 (VP1:VP2:VP3). The regulatory mechanisms that allow this controlled level of expression include the production of two mRNAs, one for VP1, and the other for VP2 and VP3, produced by differential splicing.

In some aspects, AAV particles are produced in mammalian cells using a triple transfection method wherein a payload construct, parvoviral Rep and parvoviral Cap and a helper construct are comprised within three different constructs. The triple transfection method of the three components of AAV particle production can be utilized to produce small lots of virus for assays including transduction efficiency, target tissue (tropism) evaluation, and stability.

In some aspects, the viral construct vector and the AAV payload construct vector can be each incorporated by a transposon donor/acceptor system into a bacmid, also known as a baculovirus plasmid, by standard molecular biology techniques known and performed by a person skilled in the art. Transfection of separate viral replication cell populations produces two baculoviruses, one that comprises the viral construct expression vector, and another that comprises the AAV payload construct expression vector. The two baculoviruses can be used to infect a single viral replication cell population for production of AAV particles.

Baculovirus expression vectors for producing viral particles in insect cells, including but not limited to Spodoptera frugiperda (Sf9) cells, provide high titers of viral particle product. Recombinant baculovirus encoding the viral construct expression vector and AAV payload construct expression vector initiates a productive infection of viral replicating cells. Infectious baculovirus particles released from the primary infection secondarily infect additional cells in the culture, exponentially infecting the entire cell culture population in a number of infection cycles that is a function of the initial multiplicity of infection (MOI), see, e.g., Urabe, M. et al., J Virol. 2006 February; 80 (4): 1874-85, the contents of which are herein incorporated by reference in their entirety.

Production of AAV particles with baculovirus in an insect cell system can address known baculovirus genetic and physical instability. Baculovirus-infected viral producing cells are harvested into aliquots that can be cryopreserved in liquid nitrogen; the aliquots retain viability and infectivity for infection of large-scale viral producing cell culture (Wasilko D J et al., Protein Expr Purif. 2009 June; 65(2): 122-32).

In some aspects, stable viral replication cells permissive for baculovirus infection are engineered with at least one stable integrated copy of any of the elements necessary for AAV replication and viral particle production including, but not limited to, the entire AAV genome, Rep and Cap genes, Rep genes, Cap genes, each Rep protein as a separate transcription cassette, each VP protein as a separate transcription cassette, the AAP (assembly activation protein), or at least one of the baculovirus helper genes with native or non-native promoters.

In some aspects, AAV particle production can be modified to increase the scale of production. Transfection of replication cells in large-scale culture formats can be carried out according to any methods known in the art.

In some aspects, cell culture bioreactors can be used for large scale viral production. In some cases, bioreactors comprise stirred tank reactors.

IV.A.8. Cell Lysis

Cells of the disclosure, including, but not limited to viral production cells, can be subjected to cell lysis according to any methods known in the art. Cell lysis can be carried out to obtain one or more agents (e.g. viral particles) present within any cells of the disclosure.

Cell lysis methods can be chemical or mechanical. Chemical cell lysis typically comprises contacting one or more cells with one or more lysis agent. Mechanical lysis typically comprises subjecting one or more cells to one or more lysis condition and/or one or more lysis force. In some aspects, chemical lysis can be used to lyse cells. As used herein, the term "lysis agent" refers to any agent that can aid in the disruption of a cell. In some cases, lysis agents are introduced in solutions, termed lysis solutions or lysis buffers. As used herein, the term "lysis solution" refers to a solution (typically aqueous) comprising one or more lysis agent. In addition to lysis agents, lysis solutions can include one or more buffering agents, solubilizing agents, surfactants, preservatives, cryoprotectants, enzymes, enzyme inhibitors and/or chelators.

Concentrations of salts can be increased or decreased to obtain an effective concentration for rupture of cell membranes. Lysis agents comprising detergents can include ionic detergents or non-ionic detergents. Detergents can function to break apart or dissolve cell structures including, but not limited to cell membranes, cell walls, lipids, carbohydrates, lipoproteins and glycoproteins.

In some aspects, mechanical cell lysis is carried out. Mechanical cell lysis methods can include the use of one or more lysis condition and/or one or more lysis force. As used herein, the term "lysis condition" refers to a state or circumstance that promotes cellular disruption. Lysis conditions can comprise certain temperatures, pressures, osmotic purity, salinity and the like. In some aspects, lysis conditions comprise increased or decreased temperatures. In some aspects, lysis conditions comprise changes in temperature to promote cellular disruption. Cell lysis carried out according to such aspects can include freeze-thaw lysis.

As used herein, the term "lysis force" refers to a physical activity used to disrupt a cell. Lysis forces can include, but are not limited to mechanical forces, sonic forces, gravitational forces, optical forces, electrical forces and the like. Cell lysis carried out by mechanical force is referred to herein as "mechanical lysis." Mechanical forces that can be used according to mechanical lysis can include high shear fluid forces.

In some aspects, a method for harvesting AAV particles without lysis can be used for efficient and scalable AAV particle production. In a non-limiting example, AAV particles can be produced by culturing an AAV particle lacking a heparin binding site, thereby allowing the AAV particle to pass into the supernatant, in a cell culture, collecting supernatant from the culture; and isolating the AAV particle from the supernatant, as described in U.S. Patent Application 20090275107.

IV.A.9. AAV Purification

Cell lysates comprising viral particles can be subjected to clarification. Clarification refers to initial steps taken in purification of viral particles from cell lysates. Clarification serves to prepare lysates for further purification by removing larger, insoluble debris. Clarification steps can include, but are not limited to centrifugation and filtration.

In some aspects, AAV particles can be purified from clarified cell lysates by one or more methods of chromatography. Chromatography refers to any number of methods known in the art for separating out one or more elements from a mixture. Such methods can include, but are not limited to ion exchange chromatography (e.g. cation exchange chromatography and anion exchange chromatography), immunoaffinity chromatography and size-exclusion chromatography.

V. Methods of Treatment and Use

Some aspects of the present disclosure are directed to a method of delivering an immunomodulatory protein (e.g., two or more immunomodulatory proteins (e.g., cytokines), one or more subunits thereof, or functional fragments thereof) to a tumor, comprising administering a polynucleotide, an AAV capsid (e.g., AAV particle), or a composition (e.g., gene therapy composition) of the present disclosure to a subject in need thereof. In some aspects, the methods of the disclosure comprise delivery of a multicistronic (e.g., bicistronic) construct (e.g., comprising nucleic acids encoding cytokine (e.g., IL-12) subunits). In some aspects, the methods of the disclosure further comprise administering a checkpoint inhibitor (e.g., a PD-1 inhibitor).

In some aspects, the method of delivering two or more immunomodulatory proteins (e.g., cytokines), one or more subunits thereof, or functional fragments thereof comprises administering to a tumor by direct injection of a composition comprising one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof.

In some aspects, the method of delivering an immunomodulatory protein (e.g., a cytokine or one or more subunits thereof, or functional fragments thereof) comprises administering to a tumor by direct injection of a composition comprising a delivery vector (e.g., a viral vector) for delivery of a (i) a first nucleic acid encoding a first cytokine subunit (e.g., an IL-12 p35 subunit or an IL-12 p40 subunit), or functional fragment thereof and (ii) a second nucleic acid encoding a second cytokine subunit (e.g., an IL-12 p40 subunit or an IL-12 p35 subunit), or functional fragment thereof. In some aspects, the first nucleic acid (e.g., nucleic acid encoding an IL-12 p35 subunit) does not include an in-frame stop codon (e.g., TGA, TAG, and TAA).

In some aspects, the nucleic acid encoding an IL-12 p35 subunit comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77. In some aspects, the nucleic acid encoding the IL-12 p40 subunit comprises a sequence at least 85%, at least 90%, at least 96%, at least 97%, at least 98%, at least 99%, or 100% identical to SEQ ID NO: 8, SEQ ID NO: 9, SEQ ID NO: 10, or SEQ ID NO: 92. In some aspects, the delivery vector (e.g., AAV vector) comprises a polynucleotide comprising (i) a nucleic acid encoding an IL-12 p35 subunit, wherein the nucleic acid comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77; and (ii) a nucleic acid encoding the IL-12 p40 subunit, wherein the nucleic acid comprises a sequence at least 85%, at least 90%, at least 96%, at least 97%, at least 98%, at least 99%, or 100% identical to SEQ ID NO: 8, SEQ ID NO: 9, SEQ ID NO: 10, or SEQ ID NO: 92.

Certain aspects of the disclosure are directed to a combination therapy comprising: (a) a first composition comprising an adeno-associated virus (AAV) vector comprising a polynucleotide comprising (i) a promoter, (ii) a first nucleic acid encoding a first Interleukin-12 (IL-12) subunit or functional fragment thereof, (iii) a translation modification sequence, and (iv) a second nucleic acid encoding a second IL-12 subunit or functional fragment thereof; and (b) a second composition comprising a checkpoint inhibitor.

In some aspects, the AAV vector is an AAV serotype 2 (AAV2) vector.

In some aspects, the translation modification sequence comprises a furin cleavage sequence, a 2A self-processing peptide sequence, an internal ribosomal entry site (IRES) sequence, or any combination thereof. In some aspects, the translation modification sequence comprises a furin cleavage sequence and a 2A self-processing peptide sequence (F2A).

In some aspects, the promoter comprises a CAG promoter, a CBA promoter, a CMV promoter, an EF-1a (Elongation Factor 1a) promoter, a RSV (Rous Sarcoma Virus) promoter, an Ubiquitin (UbC) promoter, or any combination thereof.

In some aspects, the polynucleotide further comprises a poly(A) (pA) sequence.

In some aspects, the polynucleotide further comprises two inverted terminal repeat (ITR) sequences.

In some aspects, the checkpoint inhibitor comprises an inhibitor for programmed cell death protein 1 (PD-1), programmed death-ligand 1 (PD-L1), cytotoxic T-lymphocyte-associated protein 4 (CTLA-4), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, inducible T-cell costimulatory (ICOS), B7-H3, or any combination thereof.

In some aspects, the checkpoint inhibitor comprises a programmed cell death protein 1 (PD-1) inhibitor (e.g., an anti-PD-1 antibody). In some aspects, the anti-PD-1 antibody is pembrolizumab or nivolumab.

In some aspects, the first Interleukin-12 (IL-12) subunit comprises an amino acid sequence having at least 85%, 90%, 95%, 96%, 97%, 98%, 99%, or 100% identity to SEQ ID NO: 80 and the second IL-12 subunit comprises an amino acid sequence having at least 85%, 90%, 95%, 96%, 97%, 98%, 99%, or 100% identity to SEQ ID NO: 81.

In some aspects, the first nucleic acid comprises a nucleic acid sequence having at least 85%, 90%, 95%, 96%, 97%, 98%, 99%, or 100% identity to SEQ ID NO: 5, SEQ ID NO: 6, SEQ ID NO: 7, or SEQ ID NO: 77, and the second nucleic acid comprises a nucleic acid sequence having at least 85%, 90%, 95%, 96%, 97%, 98%, 99%, or 100% identity to SEQ ID NO: 8, SEQ ID NO: 9, SEQ ID NO: 10, or SEQ ID NO: 92.

In some aspects, the polynucleotide comprises a nucleic acid sequence having at least 85%, 90%, 95%, 96%, 97%, 98%, 99%, or 100% identity to SEQ ID NO: 82.

In some aspects, the first composition is suitable for an intratumoral delivery and the second composition is suitable for an intravenous delivery.

Certain aspects of the disclosure are directed to methods of treating a subject suffering from a tumor comprising administering a combination therapy disclosed herein to the subject. In some aspects, the first composition is administered intratumorally. In some aspects, the first composition is administered to multiple sites of the tumor. In some aspects, the first composition is administered prior to, at the same time, or after the administration of the second composition.

In some aspects, the tumor is derived from a cancer selected from the group consisting of a skin cancer; a breast cancer; a brain cancer; a bone cancer; a head and neck cancer; a salivary gland cancer; a gynecologic cancer; a urologic cancer; a gastrointestinal cancer; an ocular cancer; a thoracic cancer; a blood cancer; a cancer of the endocrine system; a sarcoma of soft tissue; a neoplasm of the central nervous system; and any combination thereof.

In some aspects, the tumor is derived from a cancer selected from the group consisting of hepatocellular carcinoma, colon carcinoma, and melanoma.

Certain aspects of the disclosure are directed to a method of use comprising administering a composition comprising a delivery vector (e.g., a viral vector) for delivery of a (i) a first nucleic acid encoding a first cytokine subunit (e.g., an IL-12 p35 subunit or an IL-12 p40 subunit), or functional fragment thereof and (ii) a second nucleic acid encoding a second cytokine subunit (e.g., an IL-12 p40 subunit or an IL-12 p35 subunit), or functional fragment thereof. In some aspects, the nucleic acid encoding an IL-12 p35 subunit comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77. In some aspects, the nucleic acid encoding the IL-12 p40 subunit comprises a sequence at least 85%, at least 90%, at least 96%, at least 97%, at least 98%, at least 99%, or 100% identical to SEQ ID NO: 8, SEQ ID NO: 9, SEQ ID NO: 10, or SEQ ID NO: 92.

Certain aspects of the disclosure are directed to a method of use comprising administering a polynucleotide comprising a polynucleotide comprising (i) a nucleic acid encoding an IL-12 p35 subunit, wherein the nucleic acid comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77; and/or (ii) a nucleic acid encoding the IL-12 p40 subunit, wherein the nucleic acid comprises a sequence at least 85%, at least 90%, at least 96%, at least 97%, at least 98%, at least 99%, or 100% identical to SEQ ID NO: 8, SEQ ID NO: 9, SEQ ID NO: 10, or SEQ ID NO: 92.

Certain aspects of the disclosure are directed to a method of use comprising administering a composition comprising (a) a polynucleotide comprising a CMV enhancer, a CBA promoter or fragment thereof operably linked to a first nucleic acid encoding an IL-12 p35 subunit or a functional fragment thereof, a furin cleavage sequence followed by a 2A self-processing peptide (F2A), a second nucleic acid encoding an IL-12 p40 subunit or a functional fragment thereof, and a human growth hormone (HGH) pA sequence; and (b) a viral vector (e.g., an AAV capsid). In some aspects, the polynucleotide further comprises an intron (e.g., a CAG intron), a Kozak sequence and/or ITR sequences.

Certain aspects of the disclosure are directed to a composition, a polynucleotide, AAV capsid, or the expression construct of the disclosure for use in therapy or prophylaxis.

Certain aspects of the disclosure are directed to the composition, the polynucleotide, AAV capsid or the expression construct for use in gene therapy.

Certain aspects of the disclosure are directed to the composition, the polynucleotide, AAV capsid or the expression construct for use in cancer therapy.

Certain aspects of the disclosure are directed to the composition, the polynucleotide, AAV capsid or the expression construct for use in a method as defined in the present disclosure.

Use of the composition, the polynucleotide, AAV capsid, or the expression construct of the present disclosure, for the manufacture of a medicament for use in therapy or prophylaxis. In certain aspects, the therapy or prophylaxis comprises a method as defined in the disclosure.

Certain aspects of the disclosure are directed to a plurality of compostions for for use in therapy or prophylaxis.

Certain aspects of the disclosure are directed to a plurality of compostions for for use in gene therapy.

Certain aspects of the disclosure are directed to a plurality of compostions for for use in cancer therapy.

In some aspects, the plurality of compostions comprise a composition comprising an AAV delivery vector comprising a polynucleotide comprising a nucleic acid encoding a cytokine, one or more subunits thereof, or functional fragment thereof (e.g., IL-12, or one or more subunits thereof); and (b) a checkpoint inhibitor (e.g., a PD-1 inhibitor).

The compositions, the polynucleotides, AAV capsids, and the expression constructs of the present disclosure can be tested in proven animal models and the resulting data will provide the human version of the compositions, the polynucleotides, AAV capsids, and the expression constructs for use in human subjects.

In some aspects, each delivery vector (e.g., viral vector) comprises a polynucleotide comprising the first nucleic acid (e.g., encoding a first cytokine subunit) and the second nucleic acid (e.g., encoding a second cytokine subunit). In some aspects, each delivery vector (e.g., viral vector) comprises either the first nucleic acid or the second nucleic acid, wherein two or more delivery vectors are delivered in combination (e.g., simultaneously or sequentially).

In some aspects, the method of delivering two or more immunomodulatory proteins (e.g., cytokines) or functional fragments thereof comprises administering to a tumor by direct injection of a composition comprising: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector).

In some aspects, the method of delivering two or more immunomodulatory proteins (e.g., cytokines) or functional fragments thereof comprises administering to a tumor by direct injection of a composition comprising a polynucleotide comprising: (a) a first nucleic acid encoding a first cytokine, one or more subunits thereof, or functional fragment thereof; and (b) a second nucleic acid encoding a second cytokine, one or more subunits thereof, or functional fragment thereof.

In some aspects, the method of delivering an immunomodulatory protein (e.g., cytokine) or functional fragments thereof comprises administering to a tumor by direct injection of a composition comprising a polynucleotide comprising: (a) a first nucleic acid encoding a first cytokine subunit, or functional fragment thereof; and (b) a second nucleic acid encoding a second cytokine subunit, or functional fragment thereof.

In some aspects, the method of delivering two or more immunomodulatory proteins (e.g., cytokines) or functional fragments thereof comprises administering to a tumor by direct injection of a delivery vector (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof.

In some aspects, the method of delivering a cytokine or functional fragment thereof comprises administering to a tumor by direct injection of a delivery vector (e.g., a viral vector, a non-viral vectors, a plasmid, a lipid, protein particle, a bacterial vector, a lysosome, a virus-like particle, a polymeric particle, an exosome, or a vault particle) comprising an expression construct comprising a promoter which is operably linked to a first nucleic acid encoding a first cytokine subunit (e.g., an IL-12 subunit), or functional fragment thereof and a translation modification sequence (e.g., an F2A) linked to a second nucleic acid encoding a second cytokine subunit (e.g., an IL-12 subunit), or functional fragment thereof. In some aspects, the translation modification sequence is selected from a 2A self-processing peptide (e.g., a F2A peptide, a P2A peptide, an E2A peptide, or a T2A peptide), a furin cleavage sequence, an internal ribosomal entry site (IRES) sequence, or any combination thereof. In some aspects, the expressing construct can further comprise a polyA.

Some aspects of the present disclosure are directed to a method of expressing one or more immunomodulatory proteins (e.g., cytokines), one or more subunits thereof, or functional fragments thereof in a subject in need thereof, comprising administering a polynucleotide, an AAV capsid, or a composition (e.g., gene therapy composition) of the present disclosure to a subject in need thereof.

In some aspects, the method of expressing two or more immunomodulatory proteins (e.g., cytokines) or functional fragments thereof in a subject in need thereof comprises administering to a tumor by direct injection of a composition comprising one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof. In some aspects, each delivery vector (e.g., viral vector) comprises a polynucleotide comprising the first nucleic acid and the second nucleic acid. In some aspects, each delivery vector (e.g., viral vector) comprises either the first nucleic acid or the second nucleic acid, wherein two or more delivery vectors are delivered in combination (e.g., simultaneously or sequentially).

In some aspects, the method of expressing one or more immunomodulatory proteins (e.g., cytokines) or functional fragments thereof in a subject in need thereof comprises administering to a tumor by direct injection of a composition comprising comprising one or more delivery vectors (e.g., viral vectors) comprising a promoter which is operably linked to a first nucleic acid encoding a first cytokine subunit (e.g., an IL-12 subunit), or functional fragment thereof and a translation modification sequence (e.g., an F2A) linked to a second nucleic acid encoding a second cytokine subunit (e.g., an IL-12 subunit), or functional fragment thereof.

In some aspects, the method of expressing two or more immunomodulatory proteins (e.g., cytokines) or functional fragments thereof in a subject in need thereof comprises administering to a tumor by direct injection of a composition comprising: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector).

In some aspects, the method of expressing one or more immunomodulatory proteins (e.g., cytokines) or functional fragments thereof in a subject in need thereof comprises administering to a tumor by direct injection of a composition comprising an expression construct comprising: a promoter which is operably linked to a first nucleic acid encoding a first cytokine subunit (e.g., an IL-12 subunit), or functional fragment thereof and a translation modification sequence (e.g., an F2A) linked to a second nucleic acid encoding a second cytokine subunit (e.g., an IL-12 subunit), or functional fragment thereof.

In some aspects, the method of expressing two or more immunomodulatory proteins (e.g., cytokines) or functional fragments thereof in a subject in need thereof comprises administering an effective amount of the composition (e.g., gene therapy composition), the polynucleotide, or the AAV capsid of the present disclosure to the subject. In some aspects, the method of expressing two or more immunomodulatory proteins (e.g., cytokines) or functional fragments thereof comprises intratumorally administering a delivery vector (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof.

In some aspects, the method of expressing one or more immunomodulatory proteins (e.g., cytokines) or functional fragments thereof in a subject in need thereof comprises administering an effective amount of the composition (e.g., gene therapy composition), the polynucleotide, or the AAV capsid of the present disclosure to the subject. In some aspects, the method of expressing one or more immunomodulatory proteins (e.g., cytokines) or functional fragments thereof comprises intratumorally administering a delivery vector (e.g., a viral vector) comprising: a promoter which is operably linked to a first nucleic acid encoding a first cytokine subunit (e.g., an IL-12 subunit), or functional fragment thereof and a translation modification sequence (e.g., an F2A) linked to a second nucleic acid encoding a second cytokine subunit (e.g., an IL-12 subunit), or functional fragment thereof.

In some aspects, the method of expressing two or more immunomodulatory proteins (e.g., cytokines) or functional fragments thereof comprises intravenously administering a delivery vector (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof.

Some aspects of the present disclosure are directed to a method of treating or reducing symptoms in a subject in need thereof, comprising administering a polynucleotide, an AAV capsid, or a composition (e.g., gene therapy composition) of the present disclosure to a subject suffering from a tumor.

In some aspects, the method of treating or reducing symptoms in a subject suffering from a tumor comprises administering to a tumor by direct injection of a composition comprising one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof. In some aspects, each delivery vector (e.g., viral vector) comprises a polynucleotide comprising the first nucleic acid and the second nucleic acid. In some aspects, each delivery vector (e.g., viral vector) comprises either the first nucleic acid or the second nucleic acid, wherein two or more delivery vectors are delivered in combination (e.g., simultaneously or sequentially). In some aspects, a delivery vector (e.g., viral vector) for delivery of (i) a first nucleic acid encoding a first immunomodulatory protein, one or more subunits thereof, or functional fragment thereof and/or (ii) a second nucleic acid encoding a second immunomodulatory protein, one or more subunits thereof, or functional fragment thereof is administered in combination (e.g., simultaneously or sequentially) with a checkpoint inhibitor.

In some aspects, the method of treating or reducing symptoms in a subject suffering from a tumor comprises administering to a tumor by direct injection of a composition comprising one or more delivery vectors (e.g., viral vectors) comprising: a promoter which is operably linked to a first nucleic acid encoding a first cytokine subunit (e.g., an IL-12 subunit), or functional fragment thereof and a translation modification sequence (e.g., an F2A) linked to a second nucleic acid encoding a second cytokine subunit (e.g., an IL-12 subunit), or functional fragment thereof. In some aspects, the delivery vector (e.g., viral vector) is delivered in combination (e.g., simultaneously or sequentially) with a checkpoint inhibitor (e.g., a PD-1 inhibitor).

In some aspects, two or more delivery vectors described herein are delivered in combination (e.g., simultaneously or sequentially) and further in combination with a checkpoint inhibitor.

In some aspects, the method of treating or reducing symptoms in a subject suffering from a tumor comprises administering to a tumor by direct injection of a composition comprising: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector).

In some aspects, the method of treating or reducing symptoms in a subject suffering from a tumor comprises administering to a tumor by direct injection of a composition comprising: (a) a polynucleotide comprising (i) a first nucleic acid encoding an IL-12 p35 subunit or functional fragment thereof and (ii) a second nucleic acid encoding an IL-12 p40 subunit or functional fragment thereof, and (b) a delivery vector (e.g., an AAV vector). In some aspects, the delivery vector (e.g., viral vector) is delivered in combination (e.g., simultaneously or sequentially) with a checkpoint inhibitor (e.g., a PD-1 inhibitor).

In some aspects, provided herein is a method of reducing the size of a tumor in a subject in need thereof comprising administering to the subject a composition comprising (a) a polynucleotide comprising (i) a first nucleic acid encoding an IL-12 p35 subunit or functional fragment thereof and (ii) a second nucleic acid encoding an IL-12 p40 subunit or functional fragment thereof, and (b) (b) a delivery vector (e.g., an AAV vector). In some aspects, the delivery vector (e.g., viral vector) is delivered in combination (e.g., simultaneously or sequentially) with a checkpoint inhibitor (e.g., a PD-1 inhibitor).

In some aspects, the method of treating or reducing symptoms in a subject in need thereof comprises administering the gene therapy, the polynucleotide, or the AAV capsid of the present disclosure to the subject.

In some aspects, the methods disclosed herein comprise re-administering a gene therapy, a polynucleotide, a AAV capsid, or a composition of the present disclosure to the subject.

In some aspects, the subject suffers from a tumor. In some aspects, the tumor is derived from a cancer selected from the group consisting of skin cancer (e.g., metastatic melanoma, cutaneous malignant melanoma, cutaneous squamous cell carcinoma, basal cell carcinoma); breast cancer (e.g., invasive breast cancer, triple-negative breast cancer, inflammatory breast cancer); brain cancer (e.g., glioblastoma multiforme, medulloblastoma, pituitary carcinoma, brain stem gliomas, astrocytomas, oligodendrogliomas, hemangiopericytomas, germ cell tumors, pineal tumors); bone cancer (e.g., chordomas, chondrosarcomas, osteosarcomas, Ewing sarcomas, fibrosarcomas, adamantiomas, giant cell tumors); head and neck cancer (e.g., head and neck squamous cell carcinoma [HNSCC]; salivary gland cancer, oropharyngeal cancer, hypopharyngeal cancer, laryngeal cancer, lip and oral cavity cancer, nasopharyngeal cancer, thyroid cancer, cancer of the parathyroid gland, paranasal sinus and nasal cavity cancer); gynecologic cancer (e.g., ovarian cancer, uterine cancer, fallopian tube cancer, endometrial cancer, cervical cancer, vaginal cancer, vulvar cancer); urologic cancer (e.g., renal cancer, urethral cancer, urothelial cancer, bladder cancer, cancer of the kidney or ureter, cancer of the renal pelvis, testicular cancer, penile cancer, cancer of the adrenal gland); gastrointestinal cancer (e.g., cancer of the anal region, bile duct cancer, colon cancer, cancer of the small intestine, esophageal cancer, gallbladder cancer, gastrointestinal stromal tumors, liver cancer, pancreatic cancer, rectal cancer, stomach/gastric cancer); ocular cancer (e.g. uveal melanoma, retinoblastoma, Merkel cell carcinoma, intraocular malignant melanoma, mucosa-associated lymphoid tissue lymphoma, orbital lymphoma, orbital sarcoma, lacrimal gland tumors); thoracic cancer (e.g., non-small cell lung cancer, small cell lung cancer, mesothelioma, thymic malignancies, tracheal tumors, some esophageal cancer), leukemia (e.g., chronic or acute leukemia, acute myeloid leukemia (AML), chronic myeloid leukemia (CML), acute lymphoblastic leukemia (ALL) (including non-T cell ALL), chronic lymphocytic leukemia (CLL)), lymphoma (e.g., Hodgkin's lymphoma, non-Hodgkin's lymphoma (NHL), Waldenström macroglobulinaemia, primary mediastinal large B cell lymphoma (PMBC), diffuse large B cell lymphoma (DLBCL), follicular lymphoma (FL), transformed follicular lymphoma, splenic marginal zone lymphoma (SMZL), cutaneous T-cell lymphoma (CTCL), lymphocytic lymphoma, primary CNS lymphoma), other blood cancer (e.g., multiple myeloma), cancer of the endocrine system, sarcoma of soft tissue, neoplasm of the central nervous system (e.g., CNS; atypical teratoid/rhabdoid tumor, spinal axis tumor), tumor angiogenesis, Kaposi's sarcoma, epidermoid cancer, environmentally induced cancers including those induced by asbestos, other B cell malignancies, neuroblastoma (including olfactory neuroblastoma), rhabdomyosarcoma, and any combination of said cancers. In some aspects, the tumor is derived from a cancer selected from the group consisting of hepatocellular carcinoma, colon carcinoma, melanoma, and any combination thereof.

In some aspects, the subject suffers from a cancer. In some aspects, the subject suffers from a cancer selected from the group consisting of skin cancer (e.g., metastatic melanoma, cutaneous malignant melanoma, cutaneous squamous cell carcinoma, basal cell carcinoma); breast cancer (e.g., invasive breast cancer, triple-negative breast cancer, inflammatory breast cancer); brain cancer (e.g., glioblastoma multiforme, medulloblastoma, pituitary carcinoma, brain stem gliomas, astrocytomas, oligodendrogliomas, hemangiopericytomas, germ cell tumors, pineal tumors); bone cancer (e.g., chordomas, chondrosarcomas, osteosarcomas, Ewing sarcomas, fibrosarcomas, adamantiomas, giant cell tumors); head and neck cancer (e.g., head and neck squamous cell carcinoma [HNSCC]; salivary gland cancer, oropharyngeal cancer, hypopharyngeal cancer, laryngeal cancer, lip and oral cavity cancer, nasopharyngeal cancer, thyroid cancer, cancer of the parathyroid gland, paranasal sinus and nasal cavity cancer); gynecologic cancer (e.g., ovarian cancer, uterine cancer, fallopian tube cancer, endometrial cancer, cervical cancer, vaginal cancer, vulvar cancer); urologic cancer (e.g., renal cancer, urethral cancer, urothelial cancer, bladder cancer, cancer of the kidney or ureter, cancer of the renal pelvis, testicular cancer, penile cancer, cancer of the adrenal gland); gastrointestinal cancer (e.g., cancer of the anal region, bile duct cancer, colon cancer, cancer of the small intestine, esophageal cancer, gallbladder cancer, gastrointestinal stromal tumors, liver cancer, pancreatic cancer, rectal cancer, stomach/gastric cancer); ocular cancer (e.g. uveal melanoma, retinoblastoma, Merkel cell carcinoma, intraocular malignant melanoma, mucosa-associated lymphoid tissue lymphoma, orbital lymphoma, orbital sarcoma, lacrimal gland tumors); thoracic cancer (e.g., non-small cell lung cancer, small cell lung cancer, mesothelioma, thymic malignancies, tracheal tumors, some esophageal cancer), leukemia (e.g., chronic or acute leukemia, acute myeloid leukemia (AML), chronic myeloid leukemia (CML), acute lymphoblastic leukemia (ALL) (including non-T cell ALL), chronic lymphocytic leukemia (CLL)), lymphoma (e.g., Hodgkin's lymphoma, non-Hodgkin's lymphoma (NHL), Waldenström macroglobulinaemia, primary mediastinal large B cell lymphoma (PMBC), diffuse large B cell lymphoma (DLBCL), follicular lymphoma (FL), transformed follicular lymphoma, splenic marginal zone lymphoma (SMZL), cutaneous T-cell lymphoma (CTCL), lymphocytic lymphoma, primary CNS lymphoma), other blood cancer (e.g., multiple myeloma), cancer of the endocrine system, sarcoma of soft tissue, neoplasm of the central nervous system (e.g., CNS; atypical teratoid/rhabdoid tumor, spinal axis tumor), tumor angiogenesis, Kaposi's sarcoma, epidermoid cancer, environmentally induced cancers including those induced by asbestos, other B cell malignancies, neuroblastoma (including olfactory neuroblastoma), rhabdomyosarcoma, and any combination of said cancers. In some aspects, the subject suffers from a cancer selected from the group consisting of a skin cancer, a gastrointestinal cancer, breast cancer, brain cancer, or any combination thereof.

In some aspects, cancer is selected from a group consisting of melanoma, colorectal cancer, breast cancer, glioblastoma multiforme, and any combination thereof.

In some aspects, the subject suffers from melanoma (e.g., uveal melanoma). See e.g., Sheppard et al., PLOS 8(4): e62753 (2013); Yang J. et al., Ther Adv Med Oncol. 2018; 10, published 2018 Feb. 21, 2018; Pelster et al., *Journal of Clinical Oncology* 37(15):9522-9522 (2019). In some aspects, the subject suffers from metastatic melanoma.

In some aspects, the subject suffers from colorectal cancer. See e.g., Tu S P et al., Gastroenterology, 128:361-375 (2005); Xue Z. et al., Oncology Reports., 25:1039-1046 (2011).

In some aspects, the subject suffers from breast cancer. See e.g., Lu L. et al., Oncol Rep., 28(4): 1332-1338 (2012).

In some aspects, the subject suffers from glioblastoma multiforme (GMB). See e.g., Maguire C A, et al., *J Neurooncol.* 96(3): 337-347 (2010).

In some aspects, the methods of the present disclosure can be used to reduce the tumor size of a tumor derived from, for example, skin cancer (e.g., metastatic melanoma, cutaneous malignant melanoma, cutaneous squamous cell carcinoma, basal cell carcinoma); breast cancer (e.g., invasive breast cancer, triple-negative breast cancer, inflammatory breast cancer); brain cancer (e.g., glioblastoma multiforme, medulloblastoma, pituitary carcinoma, brain stem gliomas, astrocytomas, oligodendrogliomas, hemangiopericytomas, germ cell tumors, pineal tumors); bone cancer (e.g., chordomas, chondrosarcomas, osteosarcomas, Ewing sarcomas, fibrosarcomas, adamantiomas, giant cell tumors); head and neck cancer (e.g., head and neck squamous cell carcinoma [HNSCC]; salivary gland cancer, oropharyngeal cancer, hypopharyngeal cancer, laryngeal cancer, lip and oral cavity cancer, nasopharyngeal cancer, thyroid cancer, cancer of the parathyroid gland, paranasal sinus and nasal cavity cancer); gynecologic cancer (e.g., ovarian cancer, uterine cancer, fallopian tube cancer, endometrial cancer, cervical cancer, vaginal cancer, vulvar cancer); urologic cancer (e.g., renal cancer, urethral cancer, urothelial cancer, bladder cancer, cancer of the kidney or ureter, cancer of the renal pelvis, testicular cancer, penile cancer, cancer of the adrenal gland); gastrointestinal cancer (e.g., cancer of the anal region, bile duct cancer, colon cancer, cancer of the small intestine, esophageal cancer, gallbladder cancer, gastrointestinal stromal tumors, liver cancer, pancreatic cancer, rectal cancer, stomach/gastric cancer); ocular cancer (e.g. uveal melanoma, retinoblastoma, Merkel cell carcinoma, intraocular malignant melanoma, mucosa-associated lymphoid tissue lymphoma, orbital lymphoma, orbital sarcoma, lacrimal gland tumors); thoracic cancer (e.g., non-small cell lung cancer, small cell lung cancer, mesothelioma, thymic malignancies, tracheal tumors, some esophageal cancer), leukemia (e.g., chronic or acute leukemia, acute myeloid leukemia (AML), chronic myeloid leukemia (CML), acute lymphoblastic leukemia (ALL) (including non-T cell ALL), chronic lymphocytic leukemia (CLL)), lymphoma (e.g., Hodgkin's lymphoma, non-Hodgkin's lymphoma (NHL), Waldenström macroglobulinaemia, primary mediastinal large B cell lymphoma (PMBC), diffuse large B cell lymphoma (DLBCL), follicular lymphoma (FL), transformed follicular lymphoma, splenic marginal zone lymphoma (SMZL), cutaneous T-cell lymphoma (CTCL), lymphocytic lymphoma, primary CNS lymphoma), other blood cancer (e.g., multiple myeloma), cancer of the endocrine system, sarcoma of soft tissue, neoplasm of the central nervous system (e.g., CNS; atypical teratoid/rhabdoid tumor, spinal axis tumor), tumor angiogenesis, Kaposi's sarcoma, epidermoid cancer, environmentally induced cancers including those induced by asbestos, other B cell malignancies, neuroblastoma (including olfactory neuroblastoma), rhabdomyosarcoma, and combinations of said cancers. In some aspects, the solid tumor is a surface lesion. In some aspects, the solid tumor is a visceral tumor.

In some aspects, the subject suffers from metastatic cancer. In some aspects, the subject suffers from advance or metastatic melanoma, cutaneous squamous cell carcinoma, colorectal cancer, prostate cancer, breast cancer or esophageal cancer.

In some aspects, the method of treating or reducing symptoms in a subject in need thereof comprises administering a gene therapy, a polynucleotide, an AAV capsid, or a composition of the present disclosure to the subject in combination with a checkpoint inhibitor.

In some aspects, the checkpoint inhibitor comprises an inhibitor for programmed cell death protein 1 (PD-1), programmed death-ligand 1 (PD-L1), cytotoxic T-lymphocyte-associated protein 4 (CTLA-4), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, inducible T-cell costimulatory (ICOS), B7-H3, or any combination thereof.

In some aspects, the checkpoint inhibitor is a PD-1 inhibitor. In some aspects, the checkpoint inhibitor is a PD-L1 inhibitor. In some aspects, the PD-1 inhibitor is an anti-PD-1 antibody. In some aspects, the checkpoint inhibitor comprises pembrolizumab, nivolumab, cemiplimab, toripalimab, spartalizumab, dostarlimab-gxly, tislelizumab, balstilimab, BI-754091, zimberelimab, INCMGA00012, camrelizumab, or any combination thereof.

In some aspects, the checkpoint inhibitor is a PD-L1 inhibitor. In some aspects, the PD-L1 inhibitor is an anti-PD-L1 antibody. In some aspects, the checkpoint inhibitor comprises durvalumab, atezolizumab, avelumabor, or any combination thereof.

In some aspects, the checkpoint inhibitor is a CTLA-4 inhibitor. In some aspects, the checkpoint inhibitor comprises ipilimumab, tremelimumab (formerly ticilimumab), zalifrelimab, quavonlimab, BA3071, YH001, or any combination thereof.

In some aspects, the gene therapy, the polynucleotide, or the AAV capsid of the present disclosure can be administered prior to, at the same time, or after the administration of a checkpoint inhibitor.

In some aspects, the methods disclosed herein can be practiced through the administration of the composition (e.g., gene therapy composition) comprising the AAV vector, the AAV vector, the AAV capsid, a cell comprising an AAV vector of the present disclosure, a cell comprising the AAV capsid of the present disclosure, a cell comprising a polynucleotide encoding an immunomodulatory protein (e.g., a second cytokine) or functional fragment thereof of the present disclosure integrated into its genomic DNA, or a pharmaceutical compositions comprising any of the above. Thus, methods disclosed herein reciting the administration of an AAV vector of the present disclosure can be also practiced by administering any of these compositions.

Based on the methods disclosed herein, the composition (e.g., gene therapy composition) comprising an AAV vector, an AAV vector, or an AAV capsid of the present disclosure for use in therapy, or for use as a medicament, or for use in treating a disease or disorder (e.g., a tumor or a cancer) in a subject in need thereof is contemplated. In some aspects, the gene therapy constructs comprising the coding sequences for the immunomodulatory proteins (e.g., cytokines), one or more subunits thereof, or functional fragments thereof, as disclosed herein, can provide durable passive protection.

In some aspects, the composition (e.g., gene therapy composition), the polynucleotide, or AAV capsid disclosed herein is administered intratumorally, e.g., by direct injection to the tumor.

In some aspects, the composition (e.g., gene therapy composition), the polynucleotide, or AAV capsid disclosed herein is administered intravenously.

In some aspects, the composition (e.g., gene therapy composition), the polynucleotide, or AAV capsid disclosed herein is administered intrathecally.

In some aspects, the composition (e.g., gene therapy composition), the polynucleotide, or AAV capsid disclosed herein is administered intrahepatically.

When administered to a subject with a cancer, in certain aspects, the composition (e.g., gene therapy composition), the polynucleotide, or AAV capsid of the present disclosure can up-regulate an immune response and enhance the tumor targeting of the subject's immune system. In some aspects, the cancer being treated is characterized by infiltration of leukocytes (T-cells, B-cells, macrophages, dendritic cells, monocytes) into the tumor microenvironment, or so-called "hot tumors" or "inflammatory tumors." In some aspects, the cancer being treated is characterized by low levels or undetectable levels of leukocyte infiltration into the tumor microenvironment, or so-called "cold tumors" or "non-inflammatory tumors." In some aspects, the composition (e.g., gene therapy composition), the polynucleotide, or AAV capsid of the present disclosure is administered in an amount and for a time sufficient to convert a "cold tumor" into a "hot tumor", i.e., said administering results in the infiltration of leukocytes (such as T-cells) into the tumor microenvironment. The term, "distal tumor" or "distant tumor" as used herein refers to a tumor that has spread from the original (or primary) tumor to distant organs or distant tissues, e.g., lymph nodes. In some aspects, the composition (e.g., gene therapy composition), the polynucleotide, or AAV capsid of the present disclosure treats a tumor after the metastatic spread. In some aspects, the composition (e.g., gene therapy composition), the polynucleotide, or AAV capsid disclosed herein is administered intrasplenically. In some aspects, the composition (e.g., gene therapy composition), the polynucleotide, or AAV capsid disclosed herein is administered intrathecally. In some aspects, the composition (e.g., gene therapy composition), the polynucleotide, or AAV capsid disclosed herein is administered intrahepatically. In some aspects, the composition (e.g., gene therapy composition), the polynucleotide, or AAV capsid disclosed herein is administered via intraosseous infusion. In some aspects, the composition (e.g., gene therapy composition), the polynucleotide, or AAV capsid disclosed herein is administered intradermally. In some aspects, the composition (e.g., gene therapy composition), the polynucleotide, or AAV capsid disclosed herein is administered via intraparenchymal route. In some aspects, the composition (e.g., gene therapy composition), the polynucleotide, or AAV capsid disclosed herein is administered to salivary gland. In some aspects, the composition (e.g., gene therapy composition), the polynucleotide, or AAV capsid disclosed herein is administered into a lymph node (e.g., via direct injection). In some aspects, the lymph node is a metastatic lymph node.

In some aspects, anti-tumor efficacy in a subject can be assessed for overall response rate (using RECIST v1.1 (or similar) (see e.g., Eisenhauer et al., Eur J Cancer, 45:228-247 (2009))) for a gene therapy, a polynucleotide, an AAV capsid, or a composition disclosed herein, which can be administered either as a monotherapy or a combination therapy with a checkpoint inhibitor in a subject in need thereof. In some aspects, the subject has progressed on an anti-PD-1 antibody therapy.

In some aspects, the best overall objective response rate (ORR) is improved against the known rates for checkpoint inhibition as a monotherapy in a similar subject population. The ORR is equal to the sum of the complete response (CR) plus the partial response (PR).

In some aspects, useful biomarkers can include the PD-L1 expression levels (e.g., as assessed by immunohistochemistry (IHC)), and tumor-infiltrating lymphocytes (TIL) profile (e.g., as assessed by CD8+ T cell density in tumor tissue), as described in e.g., Buisseret L., et al., Oncoimmunology. 6(1): e1257452 (2017). In some aspects, changes in PD-L1 expression can be assessed pre- and post-treatment.

VI. Pharmaceutical Compositions

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a promoter operably linked to a nucleic acid sequence that encodes an immunomodulatory protein (e.g., a cytokine), one or more subunits thereof, or functional fragment thereof as disclosed herein and a pharmaceutically-acceptable excipient or carrier in a form suitable for intratumoral administration.

In some aspects, a pharmaceutical composition disclosed herein comprises an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for intratumoral administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a promoter operably linked to a nucleic acid sequence that encodes an immunomodulatory protein (e.g., a cytokine), one or more subunits thereof, or functional fragment thereof as disclosed herein and a pharmaceutically-acceptable excipient or carrier in a form suitable for intravenous administration.

In some aspects, a pharmaceutical composition disclosed herein comprises an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for intravenous administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a promoter operably linked to a nucleic acid sequence that encodes an immunomodulatory protein (e.g., a cytokine), one or more subunits thereof, or functional fragment thereof as disclosed herein and a pharmaceutically-acceptable excipient or carrier in a form suitable for intrasplenic administration.

In some aspects, a pharmaceutical composition disclosed herein comprises an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for intrasplenic administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a promoter operably linked to a nucleic acid sequence that encodes an immunomodulatory protein (e.g., a cytokine), one or more subunits thereof, or functional fragment thereof as disclosed herein and a pharmaceutically-acceptable excipient or carrier in a form suitable for intrathecal administration.

In some aspects, a pharmaceutical composition disclosed herein comprises an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for intrathecal administration.

In some aspects, a pharmaceutical composition disclosed herein comprises a delivery vector of the present disclosure (e.g., a viral vector, a non-viral vectors, a plasmid, a lipid, protein particle, a bacterial vector, or a lysosome) comprising a promoter operably linked to a nucleic acid sequence that encodes an immunomodulatory protein (e.g., a cytokine), one or more subunits thereof, or functional fragment thereof as disclosed herein and a pharmaceutically-acceptable excipient or carrier in a form suitable for intrahepatic administration.

In some aspects, a pharmaceutical composition disclosed herein comprises an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for intrahepatic administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a promoter operably linked to a nucleic acid sequence that encodes an immunomodulatory protein (e.g., a cytokine), one or more subunits thereof, or functional fragment thereof as disclosed herein and a pharmaceutically-acceptable excipient or carrier in a form suitable for intraosseous administration.

In some aspects, a pharmaceutical composition disclosed herein comprises an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for intraosseous administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a promoter operably linked to a nucleic acid sequence that encodes an immunomodulatory protein (e.g., a cytokine), one or more subunits thereof, or functional fragment thereof as disclosed herein and a pharmaceutically-acceptable excipient or carrier in a form suitable for administration into a lymph node.

In some aspects, a pharmaceutical composition disclosed herein comprises an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for administration into a lymph node.

In some aspects, a pharmaceutical composition disclosed herein comprises an AAV delivery vector comprising a polynucleotide comprising a nucleic acid encoding a cytokine, one or more subunits thereof, or functional fragment thereof (e.g., IL-12, or one or more subunits thereof); and, optionally, (b) a checkpoint inhibitor (e.g., a PD-1 inhibitor) is suitable for intraperitoneal administration.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for intratumoral administration. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for intratumoral administration. In some aspects, each delivery vector (e.g., viral vector) comprises a polynucleotide comprising the first nucleic acid and the second nucleic acid.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for intravenous administration. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for intravenous administration.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for intrasplenic administration. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for intrasplenic administration.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for intrathecal administration. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for intrathecal administration.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for intrahepatic administration. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for intrahepatic administration.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for intraosseous administration. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for intraosseous administration.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for intradermal administration. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for intradermal administration.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for intraparenchymal administration. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for intraparenchymal administration.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for administration via delivery to salivary gland. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for administration via delivery to salivary gland.

In some aspects, the pharmaceutical composition comprises one or more delivery vectors (e.g., viral vectors) for delivery of a combination of (i) a first nucleic acid encoding a first immunomodulatory protein, one or more subunits thereof, or functional fragment thereof and (ii) a second nucleic acid encoding a second immunomodulatory protein, one or more subunits thereof, or functional fragment thereof, and a pharmaceutically-acceptable excipient or carrier in a form suitable for administration into a lymph node. In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for administration into a lymph node.

In some aspects, the pharmaceutical composition comprises one or more delivery vectors (e.g., viral vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof, and a pharmaceutically-acceptable excipient or carrier in a form suitable for intraperitoneal administration.

In some aspects, each delivery vector (e.g., viral vector) comprises either the first nucleic acid or the second nucleic acid, wherein two or more delivery vectors are delivered in combination (e.g., simultaneously or sequentially).

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for intratumoral administration. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for intratumoral administration.

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for intravenous administration. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for intravenous administration.

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for intrasplenic administration. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for intrasplenic administration.

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for intrathecal administration. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for intrathecal administration.

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for intrahepatic administration. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for intrahepatic administration.

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for intraosseous administration. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for intraosseous administration.

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for intradermal administration. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for intradermal administration.

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for intraparenchymal administration. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for intraparenchymal administration.

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for administration via delivery to salivary gland. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for administration via delivery to salivary gland.

In some aspects, the pharmaceutical composition comprises: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector), and a pharmaceutically-acceptable excipient or carrier in a form suitable for administration into a lymph node. In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for administration into a lymph node.

In some aspects, the pharmaceutical composition comprises: (a) a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; and (b) a delivery vector (e.g., viral vector), and a pharmaceutically-acceptable excipient or carrier in a form suitable for intraperitoneal administration.

In some aspects, the pharmaceutical composition comprises a polynucleotide comprising: (a) a first nucleic acid encoding a first cytokine, one or more subunits thereof, or functional fragment thereof; and (b) a second nucleic acid encoding a second cytokine, one or more subunits thereof, or functional fragment thereof, and a pharmaceutically-acceptable excipient or carrier in a form suitable for intratumoral administration.

In some aspects, the pharmaceutical composition comprises a polynucleotide comprising: (a) a first nucleic acid encoding a first cytokine, one or more subunits thereof, or functional fragment thereof; and (b) a second nucleic acid encoding a second cytokine, one or more subunits thereof, or functional fragment thereof, and a pharmaceutically-acceptable excipient or carrier in a form suitable for intravenous administration. In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for intratumoral administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for intravenous administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for intrasplenic administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for intrathecal administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for intrahepatic administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for intraosseous administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for intradermal administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for intraparenchymal administration.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for administration via delivery to salivary gland.

In some aspects, a pharmaceutical composition disclosed herein comprises a delivery vector of the present disclosure (e.g., a viral vector, a non-viral vectors, a plasmid, a lipid, protein particle, a bacterial vector, a lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof and a pharmaceutically-acceptable excipient or carrier in a form suitable for administration into a lymph node.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for intratumoral administration.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for intravenous administration.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for intrasplenic administration.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for intrathecal administration.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for intrahepatic administration.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for intraosseous administration.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for intradermal administration.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for intraparenchymal administration.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for administration via delivery to salivary gland.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for administration into a lymph node.

In some aspects, the pharmaceutical composition comprises a polynucleotide comprising: (i) a promoter, (ii) a first nucleic acid encoding a first cytokine subunit or functional fragment thereof, (iii) a translation modification sequence, and (iv) a second nucleic acid encoding a second cytokine subunit or functional fragment thereof, and a pharmaceutically-acceptable excipient or carrier in a form suitable for intraperitoneal administration.

In some aspects, the first cytokine subunit and the second cytokine subunit are IL-12 subunits. In some aspects, the first nucleic acid or the second nucleic acid comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77. In some aspects, the first nucleic acid or the second nucleic acid comprises a sequence at least 85%, at least 90%, at least 96%, at least 97%, at least 98%, at least 99%, or 100% identical to SEQ ID NO: 8, SEQ ID NO: 9, or SEQ ID NO: 10.

Pharmaceutically acceptable excipients or carriers are determined in part by the particular composition being administered, as well as by the particular method used to administer the composition.

Accordingly, there is a wide variety of suitable formulations of pharmaceutical compositions comprising a delivery vector of the present disclosure (e.g., an AAV vector) or a plurality thereof (see, e.g., Remington's Pharmaceutical Sciences, Mack Publishing Co., Easton, Pa. 18th ed. (1990)) and/or one or more shRNA disclosed herein. The pharmaceutical compositions are generally formulated sterile and in full compliance with all Good Manufacturing Practice (GMP) regulations of the U.S. Food and Drug Administration. In some aspects, the pharmaceutical composition comprises more than one AAV vector of the present disclosure, wherein each vector comprises at least one polynucleotide encoding at least one disclosed herein.

In some aspects, a pharmaceutical composition comprises (i) one or more delivery vectors disclosed herein (e.g., AAV vectors or AAV capsids), and (ii) one or more therapeutic agents for the treatment of a disorder. In some aspects, the one or more delivery vectors disclosed herein (e.g., AAV vectors or AAV capsids) and the one or more therapeutic agents for a disease or disorder (e.g., a cancer, a tumor) are co-administered as separate pharmaceutical compositions.

In some aspects, a pharmaceutical composition comprising one or more delivery vectors disclosed herein (e.g., AAV vectors or AAV capsids) is administered prior to the administration of a pharmaceutical composition comprising one or more therapeutic agents for the treatment of a disease or disorder (e.g., a cancer, a tumor). In some aspects, a pharmaceutical composition comprising one or more delivery vectors disclosed herein (e.g., AAV vectors or AAV capsids) is administered after the administration of a pharmaceutical composition comprising one or more therapeutic agents for the treatment of a disease or disorder (e.g., a cancer, a tumor). In some aspects, a pharmaceutical composition comprising one or more delivery vectors disclosed herein (e.g., AAV vectors or AAV capsids) is administered concurrently with a pharmaceutical composition comprising one or more therapeutic agents for the treatment of a disease or disorder (e.g., a cancer, a tumor).

Also provided herein are pharmaceutical compositions comprising delivery vectors disclosed herein (e.g., AAV vectors or AAV capsids) having the desired degree of purity, and a pharmaceutically acceptable carrier or excipient, in a form suitable for administration to a subject. Pharmaceutically acceptable excipients or carriers can be determined in part by the particular composition being administered, as well as by the particular method used to administer the composition. Accordingly, there is a wide variety of suitable formulations of pharmaceutical compositions comprising a plurality of vectors, e.g., AAV vectors described herein. (See, e.g., Remington's Pharmaceutical Sciences, Mack Publishing Co., Easton, Pa. 21st ed. (2005)). The pharmaceutical compositions are generally formulated sterile and in full compliance with all Good Manufacturing Practice (GMP) regulations of the U.S. Food and Drug Administration.

Acceptable carriers, excipients, or stabilizers are nontoxic to recipients (e.g., animals or humans) at the dosages and concentrations employed.

Examples of carriers or diluents include, but are not limited to, water, saline, Ringer's solutions, dextrose solution, and 5% human serum albumin. Except insofar as any conventional media or compound is incompatible with the delivery vectors disclosed herein (e.g., AAV vectors or AAV capsids), use thereof in the compositions is contemplated. In some aspects, a pharmaceutical composition is formulated to be compatible with its intended route of administration. The delivery vectors disclosed herein (e.g., AAV vectors or AAV capsids) can be administered by intravenous, parenteral, topical, intravenous, oral, subcutaneous, intra-arterial, intradermal, transdermal, rectal, intracranial, intraperitoneal, intranasal, intratumoral, intramuscular route or as inhalants. In some aspects, the pharmaceutical composition comprising the delivery vectors disclosed herein (e.g., AAV vectors or AAV capsids) is administered intratumorally, e.g. by direct injection. In some aspects, the pharmaceutical composition comprising the delivery vectors disclosed herein (e.g., AAV vectors or AAV capsids) is administered intravenously. In some aspects, the pharmaceutical composition comprising the delivery vectors disclosed herein (e.g., AAV vectors or AAV capsids) is administered intrasplenically. In some aspects, the pharmaceutical composition comprising the delivery vectors disclosed herein (e.g., AAV vectors or AAV capsids) is administered intrathecally. In some aspects, the pharmaceutical composition comprising the delivery vectors disclosed herein (e.g., AAV vectors or AAV capsids) is administered intrahepatically. In some aspects, the pharmaceutical composition comprising the delivery vectors disclosed herein (e.g., AAV vectors or AAV capsids) is administered via intraosseous infusion. In some aspects, the pharmaceutical composition comprising the delivery vectors disclosed herein (e.g., AAV vectors or AAV capsids) is administered intradermally. In some aspects, the pharmaceutical composition comprising the delivery vectors disclosed herein (e.g., AAV vectors or AAV capsids) is administered via intraparenchymal route.

In some aspects, the pharmaceutical composition comprising the delivery vectors disclosed herein (e.g., AAV vectors or AAV capsids) is administered via delivery to salivary gland. In some aspects, the pharmaceutical composition comprising the delivery vectors disclosed herein (e.g., AAV vectors or AAV capsids) is administered via direct injection into a lymph node. In some aspects, the lymph node is a metastatic lymph node.

The delivery vectors disclosed herein (e.g., AAV vectors or AAV capsids) can optionally be administered in combination with other therapeutic agents that are at least partly effective in treating the disease, disorder or condition for which the delivery vectors disclosed herein (e.g., AAV vectors or AAV capsids) are intended. In some aspects, the vectors disclosed herein are administered in combination with a PD-1 inhibitor (e.g., an anti-PD-1 antibody).

The delivery vectors disclosed herein (e.g., AAV vectors or AAV capsids) can be formulated using one or more excipients to (1) increase stability; (2) increase cell transfection or transduction; (3) permit the sustained or delayed release; or (4) alter the biodistribution (e.g., target the AAV vector to specific tissues or cell types).

VII. Administration

The compositions (e.g., gene therapy compositions) and delivery vectors disclosed herein (e.g., AAV vectors or AAV capsids) can be administered by any route which results in a therapeutically effective outcome. In some aspects, the methods disclosed herein can comprise re-administering a gene therapy, a polynucleotide, a AAV capsid, or a composition of the present disclosure to the subject.

In some aspects, the administration (or delivery) is intratumorally, intravenously, intrasplenically, intrathecally, intrahepatically, via intraosseous infusion, intradermal, intraparenchymal, via delivery to salivary gland, or via delivery into a lymph node.

In some aspects, the delivery can be intratumoral, e.g., by direct injection to the tumor. In some aspects, the compositions (e.g., gene therapy compositions) and delivery vectors disclosed herein (e.g., AAV vectors or AAV capsids) is administered as a single dose. In some aspects, the single dose can comprise one or more injections. In some aspects, the single dose includes multiple injections into different regions of the tumor.

In some aspects, the delivery can be intravenous.

In some aspects, the delivery can be intrasplenic. See e.g., Xiao et al., *Molecular Therapy: Methods & Clinical Development*, 1(4):323-329 (2000); Ahmed et al., "Gene transfer in the liver using recombinant adeno-associated virus." *Current Protocols in Microbiology* vol. Chapter 14 (2013).

In some aspects, the delivery can be intrathecal delivery.

In some aspects, the delivery can be intrahepatic delivery.

In some aspects, the delivery can be intraosseous. See e.g., Lee et al., *Molecular Therapy: Methods & Clinical Development*, 15:101-111 (2019).

In some aspects, the delivery can be intradermal.

In some aspects, the delivery can be intraparenchymal.

In some aspects, the delivery can be to salivary gland.

In some aspects, the delivery can be directly into a lymph node. In some aspects, the lymph node is a metastatic lymph node. See e.g., Sato et al., *PLOS One.*, 2015; 10(4): e0123619; published online Apr. 21, 2015.

In some aspects, a vector (e.g., either a viral vector (e.g., an AAV vector) or non-viral vector (including naked DNA)) comprising a nucleic acid is administered to a tumor. Because the vector is presented to the cells from "outside" the body, the immunological and inflammatory reactions that are commonly observed as a result of the administration of transforming formulations and their adjuvants into blood and interstitial fluid may be avoided.

The amount of nucleic acid to transform a sufficient number of tumor cells and provide for expression of therapeutic levels of the protein can be assessed, e.g., using an animal model (e.g., a rodent (mouse or rat) or other mammalian animal model) to assess factors such as the efficiency of transformation, the levels of protein expression achieved, the susceptibility of the targeted secretory gland cells to transformation, and the amounts of vector and/or nucleic acid required to transform tumor cells.

The precise amount of vector and/or nucleic acid administered will vary greatly according to a number of factors including the susceptibility of the target cells to transformation, the size and weight of the subject, the levels of protein expression desired, and the condition to be treated.

The methods of the disclosure can be used to accomplish delivery of the immunomodulatory proteins or functional fragments thereof to the bloodstream on either a long-term basis (e.g., by repeated administration of the construct) or on a short-term basis (e.g., for several hours or a few days). In this regard, the disclosure takes advantage of the normal turnover of the cells that are transformed by the introduced construct in order to provide a means for controlling dosage of the polypeptide to the bloodstream.

In some aspects, a delivery vector of the present disclosure (e.g., a viral vector, a non-viral vectors, a plasmid, a lipid, protein particle, a bacterial vector, protein particle, a bacterial vector, a lysosome, a virus-like particle, a polymeric particle, an exosome, or a vault particle) comprising a promoter operably linked to a nucleic acid sequence that encodes an immunomodulatory protein or functional fragment thereof is administered by direct injection to a tumor.

In some aspects, a delivery vector of the present disclosure (e.g., a viral vector, a non-viral vectors, a plasmid, a lipid, protein particle, a bacterial vector, protein particle, a bacterial vector, or lysosome, a virus-like particle, a polymeric particle, an exosome, or a vault particle) comprising a first promoter which is operably linked to a first nucleic acid encoding a first immunomodulatory protein (e.g., a first cytokine), one or more subunits thereof, or functional fragment thereof and a second promoter which is operably linked to a second nucleic acid encoding a second immunomodulatory protein (e.g., a second cytokine), one or more subunits thereof, or functional fragment thereof is administered by direct injection to a tumor.

In some aspects, a delivery vector of the present disclosure (e.g., a viral vector) comprises (i) a promoter, (ii) a first nucleic acid encoding a first cytokine subunit (e.g., an IL-12 p35 subunit) or functional fragment thereof, (iii) a translation modification sequence, and (iv) a second nucleic acid encoding a second cytokine subunit (e.g., an IL-12 p40 subunit) or functional fragment thereof is administered by direct injection to a tumor.

The compositions (e.g., gene therapy compositions) and delivery vectors disclosed herein (e.g., AAV vectors or AAV capsids) can be administered in any suitable form, either as a liquid solution or suspension, as a solid form suitable for liquid solution or suspension in a liquid solution.

In some aspects, the composition (e.g., gene therapy composition) or AAV capsid disclosed herein is administered to a human. In further aspects, the composition (e.g., gene therapy composition) or AAV capsid disclosed herein is administered to an elderly human (i.e., human ≥65 years of age). In other aspects, the composition (e.g., gene therapy composition) or AAV capsid disclosed herein is administered to a human who is immunocompromised or immunodeficient. In some aspects, the human who is immunocompromised or immunodeficient has been diagnosed, is undergoing treatment, or has recovered from a B-cell immunodeficiencies, T-cell immunodeficiencies, phagocyte disorders, complement defects, chronic and/or serious disease, immunomodulatory medications, and other. B-cell immunodeficiencies include, for example, Brutons' agammaglobulinemia, common variable immunodeficiency, hyper-IgM syndrome and selective IgA deficiency. In some aspects, the T-cell immunodeficiencies include, for example, DiGeorge syndrome, Bare lymphocyte syndrome, and Omenn's syndrome. Phagocyte disorders include, for example, chronic granulomatous disease, Leukocyte adhesion deficiency, Chediak-Higashi syndrome, and Cyclic neutropenia Kostman diseases. Complement defects include C1, C2, or C4 deficiency—defects in clearing immunocomplexes, C3 or C5 deficiency—block in alternative and classical pathways, and C6, C7, C8, or C9 deficiency—defect in MAC assembly and function. Chronic and/or serious disease include, for example, HIV/AIDS, Cancer (e.g., leukemia, lymphoma), Chronic inflammatory diseases treated w/high-level immunosuppressive meds, and Metabolic diseases (e.g., diabetes, obesity, uremia). Immunomodulatory medications include, for example, Cytotoxic agents/chemotherapy, High-dose corticosteroids, and Disease-modifying anti-rheumatic drugs (DMARDs). Additional immunodeficiencies include, for example, malnutrition, ageing, surgery (e.g., splenectomy), and Inherited defects other than PIDs (e.g. Down Syndrome; Cystic Fibrosis, Sickle Cell Disease).

In some aspects, provided herein is a combination therapy comprising a) the composition (e.g., gene therapy composition) disclosed herein, the polynucleotide disclosed herein, or the AAV capsid disclosed herein, and b) a checkpoint inhibitor.

In some aspects, the checkpoint inhibitor comprises an inhibitor for programmed cell death protein 1 (PD-1), programmed death-ligand 1 (PD-L1), cytotoxic T-lymphocyte-associated protein 4 (CTLA-4), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, inducible T-cell costimulatory (ICOS), B7-H3, or any combination thereof.

In some aspects, the checkpoint inhibitor is a PD-1 inhibitor. In some aspects, the checkpoint inhibitor is a PD-L1 inhibitor. In some aspects, the PD-1 inhibitor is an anti-PD-1 antibody. In some aspects, the checkpoint inhibitor comprises pembrolizumab, nivolumab, cemiplimab, toripalimab, spartalizumab, dostarlimab-gxly, tislelizumab, balstilimab, BI-754091, zimberelimab, INCMGA00012, camrelizumab, or any combination thereof.

In some aspects, the checkpoint inhibitor is a PD-L1 inhibitor. In some aspects, the checkpoint inhibitor comprises durvalumab, atezolizumab, avelumabor, or any combination thereof.

In some aspects, the checkpoint inhibitor is a CTLA-4 inhibitor. In some aspects, the checkpoint inhibitor comprises ipilimumab, tremelimumab (formerly ticilimumab), zalifrelimab, quavonlimab, BA3071, YH001, or any combination thereof.

In some aspects, the composition (e.g., gene therapy composition) disclosed herein, the polynucleotide disclosed herein, or the AAV capsid disclosed herein is administered prior to, at the same time, or after the administration of the checkpoint inhibitor.

In some aspects, the composition (e.g., gene therapy composition) disclosed herein is administered prior to, at the same time, or after the administration of the checkpoint inhibitor.

In some aspects, the polynucleotide disclosed herein is administered prior to, at the same time, or after the administration of the checkpoint inhibitor.

In some aspects, the AAV capsid disclosed herein is administered prior to, at the same time, or after the administration of the checkpoint inhibitor.

In some aspects, the composition (e.g., gene therapy composition) disclosed herein is administered in the same composition as the checkpoint inhibitor.

In some aspects, the polynucleotide disclosed herein is administered in the same composition as of the checkpoint inhibitor.

In some aspects, the AAV capsid disclosed herein is administered in the same composition as the checkpoint inhibitor.

In some aspects, the composition (e.g., gene therapy composition) disclosed herein is administered in a different composition than the checkpoint inhibitor.

In some aspects, the polynucleotide disclosed herein is administered in a different composition than the checkpoint inhibitor.

In some aspects, the AAV capsid disclosed herein is administered in a different composition than the checkpoint inhibitor.

In some aspects, the checkpoint inhibitor is administered intravenously (e.g., intravenous infusion). In some aspects, the checkpoint inhibitor is administered as a single dose. In some aspects, the checkpoint inhibitor is administered in multiple doses.

In some aspects, the checkpoint inhibitor (e.g., nivolumab) is administered intravenously at a dose of about 240 mg every 2 weeks or about 480 mg every 4 weeks.

In some aspects, the checkpoint inhibitor (e.g., pembrolizumab) is administered intravenously at a dose of 200 mg every 3 weeks or 400 mg every 6 weeks. In some he checkpoint inhibitor (e.g., pembrolizumab) is administered intravenously at a dose of 2 mg/kg (up to 200 mg) every 3 weeks.

In some aspects, the subject to which the compositions (e.g., gene therapy compositions), polynucleotides, expression constructs, or AAV capsids (e.g., AAV particles) of the disclosure are administered is a subject that suffers from a solid tumor cancer. In some aspects, the solid tumor is a sarcoma, a carcinoma, or a lymphoma. In some aspects, the solid tumor is a surface lesion. In some aspects, the solid tumor is a visceral tumor.

In some aspects, the subject suffers from a cancer selected from the group consisting of skin cancer, gastrointestinal cancer, breast cancer, brain cancer, bone cancer, thoracic cancer, head and neck cancer, gynecologic cancer, urologic cancer, ocular cancer, and any combination thereof.

In some aspects, cancer is selected from a group consisting of:
  skin cancer (e.g., metastatic melanoma, cutaneous malignant melanoma, cutaneous squamous cell carcinoma, basal cell carcinoma);
  breast cancer (e.g., invasive breast cancer, triple-negative breast cancer, inflammatory breast cancer);
  brain cancer (e.g., glioblastoma multiforme, medulloblastoma, pituitary carcinoma, brain stem gliomas, astrocytomas, oligodendrogliomas, hemangiopericytomas, germ cell tumors, pineal tumors);
  bone cancer (e.g., chordomas, chondrosarcomas, osteosarcomas, Ewing sarcomas, fibrosarcomas, adamantiomas, giant cell tumors);
  head and neck cancer (e.g., head and neck squamous cell carcinoma (HNSCC); salivary gland cancer, oropharyngeal cancer, hypopharyngeal cancer, laryngeal cancer, lip and oral cavity cancer, nasopharyngeal cancer, thyroid cancer, cancer of the parathyroid gland, paranasal sinus and nasal cavity cancer);
  gynecologic cancer (e.g., ovarian cancer, uterine cancer, fallopian tube cancer, endometrial cancer, cervical cancer, vaginal cancer, vulvar cancer);
  urologic cancer (e.g., renal cancer, urethral cancer, urothelial cancer, bladder cancer, cancer of the kidney or ureter, cancer of the renal pelvis, testicular cancer, penile cancer, cancer of the adrenal gland);
  gastrointestinal cancer (e.g., cancer of the anal region, bile duct cancer, colon cancer, cancer of the small intestine, esophageal cancer, gallbladder cancer, gastrointestinal stromal tumors, liver cancer, pancreatic cancer,
  ocular cancer (e.g. uveal melanoma, retinoblastoma, Merkel cell carcinoma, intraocular malignant melanoma, mucosa-associated lymphoid tissue lymphoma, orbital lymphoma, orbital sarcoma, lacrimal gland tumors);
  thoracic cancer (e.g., non-small cell lung cancer, small cell lung cancer, mesothelioma, thymic malignancies, tracheal tumors, some esophageal cancer),
  leukemia (e.g., chronic or acute leukemia, acute myeloid leukemia (AML), chronic myeloid leukemia (CML), acute lymphoblastic leukemia (ALL) (including non-T cell ALL), chronic lymphocytic leukemia (CLL)),
  lymphoma (e.g., Hodgkin's lymphoma, non-Hodgkin's lymphoma (NHL), Waldenström macroglobulinaemia, primary mediastinal large B cell lymphoma (PMBC), diffuse large B cell lymphoma (DLBCL), follicular lymphoma (FL), transformed follicular lymphoma, splenic marginal zone lymphoma (SMZL), cutaneous T-cell lymphoma (CTCL), lymphocytic lymphoma, primary CNS lymphoma),
  other blood cancer (e.g., multiple myeloma)
  cancer of the endocrine system, sarcoma of soft tissue, neoplasm of the central nervous system (e.g., CNS; atypical teratoid/rhabdoid tumor, spinal axis tumor), tumor angiogenesis, Kaposi's sarcoma, epidermoid cancer, environmentally induced cancers including those induced by asbestos, other B cell malignancies, neuroblastoma (including olfactory neuroblastoma), rhabdomyosarcoma, and any combination thereof.

In some aspects, the solid tumor is a surface lesion. In some aspects, the solid tumor is a visceral tumor.

VIII. Kits

The present disclosure also provides kits, or products of manufacture, comprising (i) the delivery vector of the present disclosure, or a pharmaceutical composition of the present disclosure, and (ii) optionally instructions for use (e.g., a package insert with instructions to perform any of the methods described herein).

In some aspects, the kit or product of manufacture comprises (i) comprising the delivery vectors of the present disclosure (e.g., an AAV vector comprising a polynucleotide encoding immunomodulatory protein (e.g., a cytokine) or functional fragment thereof disclosed herein), or a pharmaceutical composition of the present disclosure, (ii) optionally, an additional therapeutic agent, and (iii) optionally, instructions for use (e.g., a package insert with instructions to perform any of the methods described herein are also contemplated).

In some aspects, the kit or product of manufacture comprises (i) comprising an AAV vector comprising a polynucleotide comprising a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; or a pharmaceutical composition of the present disclosure, (ii) optionally, an additional therapeutic agent (e.g., a checkpoint inhibitor (e.g., a PD-1 inhibitor)), and (iii) optionally, instructions for use (e.g., a package insert with instructions to perform any of the methods described herein are also contemplated).

In some aspects, the kit or product of manufacture comprises (i) a polynucleotide, an AAV capsid, or a composition (e.g., gene therapy composition) of the present disclosure, (ii) optionally, an additional therapeutic agent, and (iii) optionally, instructions for use (e.g., a package insert with instructions to perform any of the methods described herein are also contemplated)

In some aspects, the kit or product of manufacture comprises (i) a composition comprising one or more delivery vectors (e.g., viral vectors) for delivery of a combination of (a) a first nucleic acid encoding a first immunomodulatory protein, one or more subunits thereof, or functional fragment thereof and (b) a second nucleic acid encoding a second immunomodulatory protein, one or more subunits thereof, or functional fragment thereof; (ii) optionally, an additional therapeutic agent, and (iii) optionally, instructions for use (e.g., a package insert with instructions to perform any of the methods described herein are also contemplated). In some aspects, the kit or product of manufacture comprises (i) a composition comprising one or more delivery vectors (e.g., AAV vectors) for delivery of a combination of a first nucleic acid encoding a first cytokine subunit (e.g., an IL-12 subunit), or functional fragment thereof and a second nucleic acid encoding a second cytokine subunit (e.g., an IL-12 subunit), or functional fragment thereof; or a pharmaceutical composition of the present disclosure, (ii) optionally, an additional therapeutic agent (e.g., a checkpoint inhibitor (e.g., a PD-1 inhibitor)), and (iii) optionally, instructions for use (e.g., a package insert with instructions to perform any of the methods described herein are also contemplated).

In some aspects, each delivery vector (e.g., viral vector) comprises a polynucleotide comprising the first nucleic acid and the second nucleic acid. In some aspects, each delivery vector (e.g., viral vector) comprises either the first nucleic acid or the second nucleic acid, wherein two or more delivery vectors are delivered in combination (e.g., simultaneously or sequentially).

In some aspects, the kit or product of manufacture comprises (i) a composition comprising: (a) a polynucleotide comprising a first nucleic acid encoding a first immunomodulatory protein, one or more subunits thereof, or functional fragment thereof and a second nucleic acid encoding a second immunomodulatory protein, one or more subunits thereof, or functional fragment thereof; and (b) a delivery vector (e.g., viral vector); (ii) optionally, an additional therapeutic agent, and (iii) optionally, instructions for use (e.g., a package insert with instructions to perform any of the methods described herein are also contemplated).

In some aspects, the kit or product of manufacture comprises (i) a composition comprising: (a) a polynucleotide comprising (i) a promoter, (ii) a first nucleic acid encoding a first cytokine subunit (e.g., an IL-12 subunit) or functional fragment thereof, (iii) a translation modification sequence, and (iv) a second nucleic acid encoding a second cytokine subunit (e.g., an IL-12 subunit) or functional fragment thereof, and (b) a delivery vector (e.g., AAV vector); (ii) optionally, an additional therapeutic agent (e.g., a checkpoint inhibitor (e.g., a PD-1 inhibitor)), and (iii) optionally, instructions for use (e.g., a package insert with instructions to perform any of the methods described herein are also contemplated).

In some aspects, the kit or product of manufacture comprises (i) a delivery vectors of the present disclosure (e.g., an AAV vector comprising a polynucleotide comprising a first nucleic acid encoding a first immunomodulatory protein (e.g., a first cytokine), one or more subunits thereof, or functional fragment thereof and/or a second nucleic acid encoding a second immunomodulatory protein (e.g., a second cytokine), one or more subunits thereof, or functional fragment thereof disclosed herein), or a pharmaceutical composition of the present disclosure, (ii) optionally, an additional therapeutic agent, and (iii) optionally, instructions for use (e.g., a package insert with instructions to perform any of the methods described herein are also contemplated).

In some aspects, the kit or product of manufacture comprises (i) a delivery vectors of the present disclosure (e.g., an AAV vector comprising a polynucleotide comprising (i) a promoter, (ii) a first nucleic acid encoding a first cytokine subunit (e.g., an IL-12 subunit) or functional fragment thereof, (iii) a translation modification sequence, and (iv) a second nucleic acid encoding a second cytokine subunit (e.g., an IL-12 subunit) or functional fragment thereof), or a pharmaceutical composition of the present disclosure, (ii) optionally, an additional therapeutic agent (e.g., a checkpoint inhibitor (e.g., a PD-1 inhibitor)), and (iii) optionally, instructions for use (e.g., a package insert with instructions to perform any of the methods described herein are also contemplated).

In some aspects, the components of a kit or product of manufacture disclosed herein are in one or more containers. In some aspects, the kit or product of manufacture comprises (i) an AAV vector comprising a polynucleotide encoding immunomodulatory protein, one or more subunits thereof, or functional fragment thereof disclosed herein, and (ii) a brochure with instructions to insert the polynucleotide in the AAV vector.

In some aspects, the kit or product of manufacture comprises (i) an AAV vector comprising a polynucleotide encoding a cytokine subunit (e.g., an IL-12 subunit), and (ii) a brochure with instructions to insert the polynucleotide in the AAV vector.

In some aspects, the components of a kit or product of manufacture disclosed herein are in one or more containers. In some aspects, the kit or product of manufacture comprises (i) an AAV vector comprising a polynucleotide comprising a first nucleic acid encoding a first immunomodulatory protein (e.g., a first cytokine), one or more subunits thereof, or functional fragment thereof and a second nucleic acid encoding a second immunomodulatory protein (e.g., a second cytokine), one or more subunits thereof, or functional fragment thereof disclosed herein, and (ii) a brochure with instructions to insert the polynucleotide in the AAV vector.

In some aspects, the kit or product of manufacture comprises (i) an AAV vector comprising a polynucleotide comprising a first nucleic acid encoding a first cytokine subunit (e.g., an IL-12 subunit) or functional fragment thereof, and a second nucleic acid encoding a second cytokine subunit (e.g., an IL-12 subunit) or functional fragment thereof, and (ii) a brochure with instructions to insert the polynucleotide in the AAV vector.

In some aspects, a kit or product of manufacture of the present disclosure comprises at least one delivery vector (e.g., AAV vector or AAV capsid). In some aspects, a kit or product of manufacture of the present disclosure comprises at least one polynucleotide encoding at least one immunomodulatory protein (e.g., a cytokine), one or more subunits thereof, or functional fragment thereof disclosed herein. In some aspects, a kit or product of manufacture of the present disclosure comprises a polynucleotide encoding two or more immunomodulatory proteins (e.g., cytokines), one or more subunits thereof, or functional fragments thereof disclosed herein.

One skilled in the art will readily recognize that vectors, polynucleotides, and pharmaceutical compositions of the present disclosure, or combinations thereof, can be readily incorporated into one of the established kit formats which are well known in the art.

Certain aspects (E) of the disclosure include:

E1. A combination therapy comprising: (a) a first composition comprising an adeno-associated virus (AAV) vector comprising a polynucleotide comprising (i) a promoter, (ii) a first nucleic acid encoding a first Interleukin-12 (IL-12) subunit or functional fragment thereof, (iii) a translation modification sequence, and (iv) a second nucleic acid encoding a second IL-12 subunit or functional fragment thereof; and (b) a second composition comprising a checkpoint inhibitor.

E2. The combination therapy of E1, wherein the AAV vector is an AAV serotype 2 (AAV2) vector.

E3. The combination therapy of E1 or E2, wherein the translation modification sequence comprises a furin cleavage sequence, a 2A self-processing peptide sequence, an internal ribosomal entry site (IRES) sequence, or any combination thereof.

E4. The combination therapy of E3, wherein the translation modification sequence comprises a furin cleavage sequence and a 2A self-processing peptide sequence (F2A).

E5. The combination therapy of any one of E1-E5, wherein the promoter comprises a CAG promoter, a CBA promoter, a CMV promoter, an EF-1a (Elongation Factor 1a) promoter, a RSV (Rous Sarcoma Virus) promoter, an Ubiquitin (UbC) promoter, or any combination thereof.

E6. The combination therapy of any one of E1-E, wherein the polynucleotide further comprises a poly(A) (pA) sequence.

E7. The combination therapy of any one of E1-E6, wherein the polynucleotide further comprises two inverted terminal repeat (ITR) sequences.

E8. The combination therapy of any one of E1-E7, wherein the checkpoint inhibitor comprises an inhibitor for programmed cell death protein 1 (PD-1), programmed death-ligand 1 (PD-L1), cytotoxic T-lymphocyte-associated protein 4 (CTLA-4), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, inducible T-cell costimulatory (ICOS), B7-H3, or any combination thereof.

E9. The combination therapy of any one of E1-E8, wherein the checkpoint inhibitor comprises a programmed cell death protein 1 (PD-1) inhibitor.

E10. The combination therapy of E9, wherein the PD-1 inhibitor is an anti-PD-1 antibody.

E11. The combination therapy of any one of E1-E10, wherein the first IL-12 subunit comprises an amino acid sequence having at least 85%, 90%, 95%, 96%, 97%, 98%, 99%, or 100% identity to SEQ ID NO: 80 and the second IL-12 subunit comprises an amino acid sequence having at least 85%, 90%, 95%, 96%, 97%, 98%, 99%, or 100% identity to SEQ ID NO: 81.

E12. The combination therapy of any one of E1-E11, wherein the first nucleic acid comprises a nucleic acid sequence having at least 85%, 90%, 95%, 96%, 97%, 98%, 99%, or 100% identity to SEQ ID NO: 5, SEQ ID NO: 6, SEQ ID NO: 7, or SEQ ID NO: 77, and the second nucleic acid comprises a nucleic acid sequence having at least 85%, 90%, 95%, 96%, 97%, 98%, 99%, or 100% identity to SEQ ID NO: 8, SEQ ID NO: 9, SEQ ID NO: 10, or SEQ ID NO: 92.

E13. The combination therapy of any one of E1-E12, wherein the polynucleotide comprises a nucleic acid sequence having at least 85%, 90%, 95%, 96%, 97%, 98%, 99%, or 100% identity to SEQ ID NO: 82.

E14. The combination therapy of any one of E1-E13, wherein the first composition is suitable for an intratumoral delivery and the second composition is suitable for an intravenous delivery.

E15. A method of treating a subject suffering from a tumor comprising administering the combination therapy of any one of E1-E14 to the subject.

E16. The method of E15, wherein the first composition is administered intratumorally.

E17. The method of E16, wherein the first composition is administered to multiple sites of the tumor.

E18. The method of any one of E15-E17, wherein the first composition is administered prior to, at the same time, or after the administration of the second composition.

E19. The method of any one of E15-E18, wherein tumor is derived from a cancer selected from the group consisting of a skin cancer; a breast cancer; a brain cancer; a bone cancer; a head and neck cancer; a salivary gland cancer; a gynecologic cancer; a urologic cancer; a gastrointestinal cancer; an ocular cancer; a thoracic cancer; a blood cancer; a cancer of the endocrine system; a sarcoma of soft tissue; a neoplasm of the central nervous system; and any combination thereof.

E20. The method of any one of E15-E19, wherein tumor is derived from a cancer selected from the group consisting of a hepatocellular carcinoma, a colon carcinoma, and a melanoma.

E21. A composition comprising: (a) a polynucleotide comprising (i) a promoter, (ii) a first nucleic acid encoding a first cytokine subunit or functional fragment thereof, (iii) a translation modification sequence, and (iv) a second nucleic acid encoding a second cytokine subunit or functional fragment thereof; and (b) a delivery vector.

E22. The composition of E21, wherein the first cytokine subunit and the second cytokine subunit are IL-12 subunits.

E23. The composition of E22, wherein the first nucleic acid or the second nucleic acid comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77.

E24. The composition of E22 or E23, wherein first nucleic acid or the second nucleic acid comprises a sequence at least 85%, at least 90%, at least 96%, at least 97%, at least 98%, at least 99%, or 100% identical to SEQ ID NO: 8, SEQ ID NO: 9, SEQ ID NO: 10, or SEQ ID NO: 92.

E25. A composition comprising: (a) a polynucleotide comprising a first nucleic acid encoding a first immunomodulatory protein, one or more subunits thereof, or functional fragment thereof and/or a second nucleic acid encoding a second immunomodulatory protein, one or more subunits thereof, or functional fragment thereof; and (b) a delivery vector.

E26. The composition of E25, wherein the first immunomodulatory protein, one or more subunits thereof, or functional fragment thereof and/or the second immunomodulatory protein, one or more subunits thereof, or functional fragment thereof is a cytokine or functional fragment thereof.

E27. The composition of E26, wherein the cytokine is selected from the group consisting of tumor necrosis factor alpha (TNF-α), a type I interferon (INF), a type II IFN, interleukin (IL)-2, IL-12, IL-15, IL-21, IL-23, IL-27, IL-18, IL-1, IL-3, IL-4, IL-5, IL-6, IL-7, IL-8, IL-9, IL-10, IL17, IL33, TL1A, CD40L, granulocyte-macrophage colony-stimulating factor (GM-CSF), any functional fragment thereof, and any combination thereof.

E28. The composition of any one of E25-E27, wherein the first immunomodulatory and the second immunomodulatory proteins are cytokines.

E29. The composition of any one of E25-28, wherein the first immunomodulatory protein is IL-12, one or more subunits thereof, or a functional fragment thereof.

E30. The composition of any one of E25-29, wherein the first nucleic acid comprises a nucleic acid encoding an IL-12 p35 subunit and/or a nucleic acid encoding IL-12 p40 subunit.

E31. The composition of any one of E25-E30, wherein the first nucleic acid comprises a nucleic acid sequence having at least 85%, 90%, 95% 96%, 97%, 98%, 99%, or 100% identity to any of SEQ ID NO: 5-10, 77, or any nucleic acid sequence in Table 2, or any combination thereof.

E32. The composition of any one of E25-E31, wherein the second immunomodulatory protein comprises IL-15 or a functional fragment thereof.

E33. The composition of any one of E25-E32, wherein the second nucleic acid comprises an IL-15 gene.

E34. The composition of any one of E25-E33, wherein the second nucleic acid comprises a nucleic acid sequence having at least 85%, 90%, 95% 96%, 97%, 98%, 99%, or 100% identity to any of SEQ ID NO: 11-13 or any nucleic acid sequence in Table 4, or any combination thereof.

E35. The composition of any one of E25-E27 or E29-E34, wherein the first immunomodulatory protein, one or more subunits thereof, or functional fragment thereof or the second immunomodulatory protein, one or more subunits thereof, or functional fragment thereof is selected from the group consisting of soluble CD40 ligand (CD40L), CD19 ligand (CD19L), CD48 ligand (CD48L), CD20 ligand (CD20L), any functional fragment thereof, and any combination thereof.

E36. The composition of any one of E21-E35, wherein the composition is gene therapy composition.

E37. A polynucleotide comprising: (a) a first nucleic acid encoding a first cytokine, one or more subunits thereof, or functional fragment thereof; and/or (b) a second nucleic acid encoding a second cytokine, one or more subunits thereof, or functional fragment thereof.

E38. The polynucleotide of E37, wherein the first cytokine and the second cytokine are selected from the group consisting of tumor necrosis factor alpha (TNF-α), a type I interferon (INF), a type II IFN, interleukin (IL)-2, IL-12, IL-15, IL-21, IL-23, IL-27, IL-18, IL-1, IL-3, IL-4, IL-5, IL-6, IL-7, IL-8, IL-9, IL-10, IL17, IL33, TL1A, CD40L, granulocyte-macrophage colony-stimulating factor (GM-CSF), any functional fragment thereof, and any combination thereof.

E39. The polynucleotide of E37 or E38, wherein the first cytokine is IL-12, IL-18, IL-21, or a functional fragment thereof.

E40. The polynucleotide of any one of E37-E39, wherein the first nucleic acid comprises a nucleic acid encoding an IL-12 p35 subunit and/or a nucleic acid encoding an IL-12 p40 subunit.

E41. The polynucleotide of any one of E37-E40, wherein the first nucleic acid comprises a nucleic acid sequence having at least 85%, 90%, 95% 96%, 97%, 98%, 99%, or 100% identity to any of SEQ ID NO: 5-10, 77, or any nucleic acid sequence in Table 2, or any combination thereof.

E42. The polynucleotide of any one of E37-E41, wherein the second cytokine is IL-15, IL-2, or a functional fragment thereof.

E43. The polynucleotide of any one of E37-E42, wherein the second nucleic acid comprises an IL-15 gene.

E44. The polynucleotide of any one of E37-E43, wherein the second nucleic acid comprises a nucleic acid sequence having at least 85%, 90%, 95% 96%, 97%, 98%, 99%, or 100% identity to any of SEQ ID NO: 11-13, 58, or any nucleic acid sequence in Table 4, or any combination thereof.

E45. A polynucleotide comprising (i) a promoter, (ii) a first nucleic acid encoding a first cytokine subunit or functional fragment thereof, (iii) a translation modification sequence, and (iv) a second nucleic acid encoding a second cytokine subunit or functional fragment thereof.

E46. The polynucleotide of E45, wherein the first cytokine subunit and the second cytokine subunit are IL-12 subunits.

E47. The polynucleotide of E45 or E46, wherein the first nucleic acid or the second nucleic acid comprises a sequence at least 85%, at least 90%, at least 96%, at least 97%, at least 98%, at least 99%, or 100% identical to SEQ ID NO: 5, SEQ ID NO: 6, SEQ ID NO: 7, or SEQ ID NO: 77.

E48. The polynucleotide of E45 or E46, wherein first nucleic acid or the second nucleic acid comprises a sequence at least 85%, at least 90%, at least 96%, at least 97%, at least 98%, at least 99%, or 100% identical to SEQ ID NO: 8, SEQ ID NO: 9, SEQ ID NO: 10, or SEQ ID NO: 92.

E49. The composition of any one of E21-E36 or the polynucleotide of any of E37-E48, wherein the polynucleotide further comprises a promoter.

E50. The composition or polynucleotide of E49, wherein the promoter comprises a first promoter which is operably linked to the first nucleic acid.

E51. The composition or polynucleotide of E49 or E50, wherein the promoter comprises a second promoter which is operably linked to the second nucleic acid.

E52. The composition or polynucleotide of any one of E48-E50, wherein the promoter is a constitutively active promoter, a cell-type specific promoter, or an inducible promoter.

E53. The composition or polynucleotide of any one of E48-E52, wherein the promoter comprises a CAG promoter, a CBA promoter, a CMV promoter, an EF-1a (Elongation Factor 1a) promoter, aRSV (Rous Sarcoma Virus) promoter, an Ubiquitin (UbC) promoter, or any combination thereof.

E54. The composition of any one of E21-E36 or E49-E53 or the polynucleotide of any of E37-E53, wherein the polynucleotide further comprises a translation modification sequence selected from the group consisting of a furin cleavage sequence, a 2A self-processing peptide sequence, an internal ribosomal entry site (IRES) sequence, or any combination thereof.

E55. The composition of any one of E21-E36 or E49-E54 or the polynucleotide of any of E37-E54, wherein the polynucleotide further comprises an enhancer sequence, an intron sequence, a microRNA binding site, or any combination thereof.

E56. The composition of any one of E21-E36 or E49-E55 or the polynucleotide of any of E37-E55, wherein the polynucleotide further comprises a poly(A) (pA) sequence.

E57. The composition any one of E21-E36 or E49-E56 or the polynucleotide of any of Es 37-56, wherein the first nucleic acid comprises a promoter operably linked to a nucleic acid encoding an IL-12 p35 subunit or functional fragment thereof, an IRES sequence, and an IL-15 gene or a functional fragment thereof; and the second nucleic acid comprises a promoter operably linked to a nucleic acid encoding an IL-12 p40 subunit or functional fragment thereof.

E58. The composition any one of E21-E36 or E49-E56 or the polynucleotide of any of E37-E56, wherein the first nucleic acid comprises a promoter operably linked to a nucleic acid encoding an IL-12 p35 subunit or functional fragment thereof, a furin cleavage sequence and/or a 2A self-processing peptide sequence, and a nucleic acid encoding an IL-12 p40 subunit or a functional fragment thereof;

and the second nucleic acid comprises a promoter operably linked to an IL-15 gene or functional fragment thereof.

E59. The composition or polynucleotide of E57 or E58, wherein the first nucleic acid further comprises an intron sequence, a pA sequence, an enhancer sequence, or any combination thereof.

E60. The composition or polynucleotide of E59, wherein the first nucleic acid further comprises an intron sequence and a human growth hormone (hGH) pA sequence or a bovine growth hormone (bGH) pA sequence.

E61. The composition or polynucleotide of any one of Es 57-60, wherein the second nucleic acid further comprises an intron sequence, a pA sequence, an enhancer sequence, or any combination thereof.

E62. The composition or polynucleotide of E61, wherein the second nucleic acid further comprises an SV40 intron sequence and a synthetic (SYN) pA sequence.

E63. The composition any one of E21-E36 or E49-E62 or the polynucleotide of any of Es 37-62, wherein the polynucleotide comprises a CMV enhancer sequence.

E64. The composition any one of E21-E36 or E49-E63 or the polynucleotide of any of Es 37-63, wherein the promoter of the first nucleic acid comprises a CAG promoter, a CBA promoter, a CMV promoter, an EF-1a (Elongation Factor 1a) promoter, aRSV (Rous Sarcoma Virus) promoter, or an Ubiquitin (UbC) promoter.

E65. The composition any one of E21-E36 or E49-E64 or the polynucleotide of any of Es 37-64, wherein the promoter of the second nucleic acid comprises a CAG promoter, a CBA promoter, a CMV promoter, an EF-1a (Elongation Factor 1a) promoter, aRSV (Rous Sarcoma Virus) promoter, or an Ubiquitin (UbC) promoter.

E66. The composition any one of E21-E36 or E49-E65 or the polynucleotide of any of Es 37-65, wherein the polynucleotide further comprises two inverted terminal repeats (ITRs).

E67. A composition comprising the polynucleotide of any one of E37-E66 or the expression construct of any of E107-E116, and a delivery vector.

E68. The composition of any one of E21-E36 or E49-E67, wherein the composition is suitable for intratumoral, intravenous, intraperitoneal, intrasplenic, intrathecal, intrahepatic, intraosseous, intradermal, or intraparenchymal administration, or delivery to salivary gland or into a lymph node.

E69. The composition of any one of E21-E36 or E49-E68, wherein the delivery vector is selected from the group consisting of a viral vector, a plasmid, a lipid, a protein particle, a bacterial vector, a lysosome, a virus-like particle, a polymeric particle, an exosome, and a vault particle.

E70. The composition of any one of E21-E36 or E49-E69, wherein the delivery vector is selected from the group consisting of an adeno-associated viral (AAV) vector, an adenoviral vector, a lentiviral vector, or a retroviral vector.

E71. The composition of any one of E21-E36 or E49-E70, wherein the delivery vector is a recombinant AAV (rAAV) vector comprising an AAV serotype selected from the group consisting of AAV1, AAV2, AAV3, AAV4, AAV5, AAV6, AAV7, AAV8, AAVrh8, AAV9, AAV10, AAVrh10, AAV11, and AAV12.

E72. The composition of E71, wherein the rAAV vector is an AAV2 serotype.

E73. The composition of E71 or E72, wherein the rAAV is modified relative to the wild-type serotype.

E74. A composition comprising (a) a polynucleotide comprising a CAG promoter operably linked to a first nucleic acid encoding an IL-12 p35 subunit or a functional fragment thereof, a furin cleavage sequence followed by a 2A self-processing peptide (F2A) sequence, a second nucleic acid encoding an IL-12 p40 subunit or a functional fragment thereof, and a growth hormone pA sequence; and (b) an AAV vector.

E75. An adeno-associated virus (AAV) capsid comprising a polynucleotide of any one of Es 37-66, wherein the AAV capsid is suitable for intratumoral delivery.

E76. The AAV capsid of E75, wherein the AAV capsid serotype is selected from the group consisting of AAV1, AAV2, AAV3, AAV4, AAV5, AAV6, AAV7, AAV8, AAVrh8, AAV9, AAV10, AAVrh10, AAV11, and AAV12.

E77. The AAV capsid of E76, wherein the AAV serotype is AAV2.

E78. The AAV capsid of E76 or E77, wherein the AAV is modified relative to the wild-type serotype.

E79. A method of expressing one or more immunomodulatory proteins or functional fragments thereof in a subject in need thereof comprising administering an effective amount of the composition of any of E21-E36 or E49-E74, the polynucleotide of any of E37-E66, or the AAV capsid of any of E75-E78 to the subject.

E80. The method of E79, wherein the administration is intratumoral, intravenous, intrasplenic, intrathecal, intrahepatic, intraosseous, intradermal, intraparenchymal, via delivery to salivary gland, or into a lymph node.

E81. A method of delivering one or more immunomodulatory proteins or functional fragments thereof to a tumor comprising administering the composition of any of E21-E36 or E49-E64, the polynucleotide of E37-E66, or the AAV capsid of any of E75-E78 by a direct injection to the tumor.

E82. A method of treating or reducing symptoms in a subject suffering from a tumor, comprising administering the composition of any of E21-E36 or E49-E64, the polynucleotide of E37-E66, or the AAV capsid of any of E75-E78 to the subject, wherein the administration is intratumoral, intravenous, intrasplenic, intrathecal, intrahepatic, intraosseous, intradermal, intraparenchymal, via delivery to salivary gland, or into a lymph node.

E83. A method of reducing the size of a tumor in a subject in need thereof comprising administering the composition of any of E21-E36 or E49-E64, the polynucleotide of E37-E66, or the AAV capsid of any of E75-E78 to the subject, wherein the administration is intratumoral, intravenous, intrasplenic, intrathecal, intrahepatic, intraosseous, intradermal, intraparenchymal, via delivery to salivary gland, or into a lymph node.

E84. A method of treating or reducing symptoms in a subject suffering from a tumor, comprising administering to the subject a composition comprising (a) a polynucleotide comprising (i) a first nucleic acid encoding an IL-12 p35 subunit or functional fragment thereof and (ii) a second nucleic acid encoding an IL-12 p40 subunit or functional fragment thereof, and (b) an AAV vector, and optionally further comprising administering a checkpoint inhibitor.

E85. A method of reducing the size of a tumor in a subject in need thereof comprising administering to the subject a composition comprsing (a) a polynucleotide comprising (i) a first nucleic acid encoding an IL-12 p35 subunit or functional fragment thereof and (ii) a second nucleic acid encoding an IL-12 p40 subunit or functional fragment thereof, and (b) an AAV vector, and optionally further comprising administering a checkpoint inhibitor.

E86. The method of E84 or E85, wherein the administration of the composition is intratumoral, intravenous, intraperitoneal, intrasplenic, intrathecal, intrahepatic, intraosseous, intradermal, intraparenchymal, via delivery to salivary gland, or into a lymph node.

E87. The method of any of E81-E86, wherein the tumor is derived from a cancer selected from the group consisting of hepatocellular carcinoma, colon carcinoma, melanoma, and any combination thereof.

E88. The method of any of E79-E86, wherein the subject suffers from a cancer selected from the group consisting of hepatocellular carcinoma, colon carcinoma, melanoma, and any combination thereof.

E89. The method of any of E81-E86, wherein the tumor is derived from a cancer selected from the group consisting of a skin cancer; a breast cancer; a brain cancer; a bone cancer; a head and neck cancer; a salivary gland cancer; a gynecologic cancer; a urologic cancer; a gastrointestinal cancer; an ocular cancer; a thoracic cancer; a blood cancer; a lymphoma, a cancer of the endocrine system; a sarcoma of soft tissue; a neoplasm of the central nervous system; and any combination thereof.

E90. The method of any of E15-E20 or E79-E89, wherein the subject suffers from a cancer selected from the group consisting of metastatic melanoma, cutaneous malignant melanoma, cutaneous squamous cell carcinoma, basal cell carcinoma, invasive breast cancer, triple-negative breast cancer, inflammatory breast cancer, glioblastoma multiforme, medulloblastoma, pituitary carcinoma, brain stem gliomas, astrocytomas, oligodendrogliomas, hemangiopericytomas, germ cell tumors, pineal tumors, chordomas, chondrosarcomas, osteosarcomas, Ewing sarcomas, fibrosarcomas, adamantiomas, giant cell tumors, head and neck squamous cell carcinoma (HNSCC), salivary gland cancer, oropharyngeal cancer, hypopharyngeal cancer, laryngeal cancer, lip and oral cavity cancer, nasopharyngeal cancer, thyroid cancer, cancer of the parathyroid gland, paranasal sinus and nasal cavity cancer, ovarian cancer, uterine cancer, fallopian tube cancer, endometrial cancer, cervical cancer, vaginal cancer, vulvar cancer, renal cancer, urethral cancer, urothelial cancer, bladder cancer, cancer of the kidney or ureter, cancer of the renal pelvis, testicular cancer, penile cancer, cancer of the adrenal gland, cancer of the anal region, bile duct cancer, colon cancer, cancer of the small intestine, esophageal cancer, gallbladder cancer, gastrointestinal stromal tumors, liver cancer, pancreatic cancer, rectal cancer, stomach/gastric cancer, uveal melanoma, retinoblastoma, Merkel cell carcinoma, intraocular malignant melanoma, mucosa-associated lymphoid tissue lymphoma, orbital lymphoma, orbital sarcoma, lacrimal gland tumors, non-small cell lung cancer, small cell lung cancer, mesothelioma, thymic malignancies, tracheal tumors, some esophageal cancer, chronic or acute leukemia, acute myeloid leukemia (AML), chronic myeloid leukemia (CML), acute lymphoblastic leukemia (ALL) (including non-T cell ALL), chronic lymphocytic leukemia (CLL), Hodgkin's lymphoma, non-Hodgkin's lymphoma (NHL), Waldenström macroglobulinaemia, primary mediastinal large B cell lymphoma (PMBC), diffuse large B cell lymphoma (DLBCL), follicular lymphoma (FL), transformed follicular lymphoma, splenic marginal zone lymphoma (SMZL), cutaneous T-cell lymphoma (CTCL), lymphocytic lymphoma, primary CNS lymphoma, multiple myeloma, CNS; atypical teratoid/rhabdoid tumor, spinal axis tumor, tumor angiogenesis, Kaposi's sarcoma, epidermoid cancer, environmentally induced cancers including those induced by asbestos, other B cell malignancies, neuroblastoma, olfactory neuroblastoma, rhabdomyosarcoma, and any combination thereof.

E91. The method of any one of E81-E90, wherein the first nucleic acid and the second nucleic acid are administered simultaneously or sequentially.

E92. The method of E91, wherein the simultaneous administration comprises administering the composition of any of E21-E36 or E49-E64, the polynucleotide of E37-E66, or the AAV capsid of any of E75-E78, wherein the first nucleic acid and the second nucleic acid are in the same delivery vector or AAV capsid.

E93. The method of E91, wherein the simultaneous or sequential administration comprises administering the composition of any of E21-E36 or E49-E64, the polynucleotide of E37-E66, or the AAV capsid of any of E75-E78, wherein the first nucleic acid and the second nucleic acid are in different delivery vectors or AAV capsids.

E94. The method of any of E81-E93, wherein the composition of any of E21-E36 or E49-E64, the polynucleotide of E37-E66, or the AAV capsid of any of E75-E78 is administered in combination with a checkpoint inhibitor.

E95. The method of E94, wherein the checkpoint inhibitor comprises an inhibitor for programmed cell death protein 1 (PD-1), programmed death-ligand 1 (PD-L1), cytotoxic T-lymphocyte-associated protein 4 (CTLA-4), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, inducible T-cell costimulatory (ICOS), B7-H3, or any combination thereof.

E96. The method of E94 or E95, wherein the checkpoint inhibitor is a PD-1 inhibitor.

E97. The method of E96, wherein the PD-1 inhibitor is an anti-PD-1 antibody.

E98. The method of any one of E1-E8, E94 or E95, wherein the checkpoint inhibitor is a PD-L1 inhibitor.

E99. The method of any one of E1-E8, E94 or E95, wherein the checkpoint inhibitor is a CTLA-4 inhibitor.

E100. The method of any one of E1-E8 or E94-E99, wherein the checkpoint inhibitor comprises pembrolizumab, nivolumab, cemiplimab, toripalimab, spartalizumab, dostarlimab-gxly, tislelizumab, balstilimab, BI-754091, zimberelimab, INCMGA00012, camrelizumab, or any combination thereof.

E101. The method of any of Es 94-100, wherein the composition of any of E21-E36 or E49-E64, the polynucleotide of any one of E37-E66, or the AAV capsid of any one of E75-E78 is administered prior to, at the same time, or after the administration of the checkpoint inhibitor.

E102. The method of any one of E68, E82, E83, or E86, wherein the lymph node in a metastatic lymph node.

E103. The method of any one of E15-E20 and E81-E102, wherein the tumor is a metastatic tumor.

E104. The method of any one of E15-E20 and E81-E102, wherein the administration comprises direct injection of the first composition or the composition comprising the polynucleotide to the tumor.

E105. A polynucleotide comprising a nucleic acid sequence having at least 80%, 85%, 90%, 95% 96%, 97%, 98%, 99%, or 100% identity to any of SEQ ID NOs: 5-37, 48-57, 77, 82, or 92, any nucleic acid shown in Table 2, Table 4, or Table 5, or any combinations thereof.

E106. A polynucleotide comprising a nucleic acid sequence having at least 80%, 85%, 90%, 95% 96%, 97%, 98%, 99%, or 100% identity to SEQ ID NO: 82.

E107. An expression construct comprising a formula selected from:

(a) X-I1-P1-E-P2-I2-X'-T-Y;

(b) Y-I1-P1-E-P2-I2-X-T-X';

(c) pA-X-I1-L-P1-E-P2-I2-X-T-Y-pA;

(d) pA-Y-I1-L-P1-E-P2-I2-X-T-X'-pA;

(e) P1-X-T-X'-pA; or (f) E-P1-I1-X-T-X'-pA;

wherein X and X' encode subunits of a first immunomodulatory molecule; I1 and I2 each is an intron; P and P2 each is a promoter; E is an enhancer; T is a translation modification sequence; Y encodes a second immunomodulatory molecule; L is a long-terminal repeat; and pA is a poly A sequence.

E108. The expression construct of E107, wherein P1 or P2 comprises a CAG promoter, a CBA promoter, a CMV promoter, an EF-1a (Elongation Factor 1a) promoter, aRSV (Rous Sarcoma Virus) promoter, an Ubiquitin (UbC) promoter, or any combination thereof.

E109. The expression construct of E107 or E108, wherein T is an internal ribosomal entry site (IRES) sequence, a furin cleavage sequence, a 2A self-processing peptide sequence, or any combination thereof.

E110. The expression construct of any one of E107-E109 further comprising a microRNA binding site.

E111. The expression construct of any one of E107-E110, wherein X is a nucleic acid encoding an IL-12 subunit or a functional fragment thereof; X' is a nucleic acid encoding an IL-12 subunit or functional fragment thereof, and Y is IL-15 gene or a functional fragment thereof.

E112. The expression construct of any one of E107-E110, wherein X is a nucleic acid encoding an IL-12 subunit or a functional fragment thereof and X' is a nucleic acid encoding an IL-12 subunit or functional fragment thereof.

E113. The expression construct of E111 or E112, wherein the nucleic acid encoding an IL-12 subunit is a nucleic acid encoding an IL-12 p35 subunit or a nucleic acid encoding an IL-12 p40 subunit.

E114. The expression construct of any one of E107-E113, wherein the pA comprises a human growth hormone (hGH) pA sequence, a bovine growth hormone (BGH) pA sequence, or a synthetic (SYN) pA sequence.

E115. The expression construct of any one of E107-E114, wherein 11, 12, or both comprises a SV40 intron sequence or a CAG intron sequence.

E116. The expression construct of any one of E107-E115, wherein E comprises a CMV enhancer sequence.

E117. A method for inducing tumor regression in a subject comprising administering to a subject in need thereof (a) the composition of any of E21-E36 or E49-E64, the polynucleotide of any one of E37-E66 or E105-E106, the expression construct of any one of E107-E116, or the AAV capsid of any one of E75-E78 and (b) checkpoint inhibitor.

E118. The method of E117, wherein the checkpoint inhibitor is a PD-1 inhibitor.

E119. The method of E118, wherein the PD-1 inhibitor is an anti-PD-1 antibody.

E120. The combination therapy of E10 or the method of E97 or E119, wherein the anti-PD-1 antibody is pembrolizumab or nivolumab.

E121. The method of any of E117-E120, wherein the tumor is derived from a cancer selected from the group consisting of a hepatocellular carcinoma, a colon carcinoma, or a melanoma.

E122. The method of any one of E81-E102, E94-E104, or E117-E121, wherein the composition of any of E21-E36 or E49-E64, the polynucleotide of any one of E37-E66 or 105-106, the expression construct of any one of E107-E116, or the AAV capsid of any one of E75-E78 is administered by a direct injection to a tumor.

E123. The method of any one of E81, E104 or E122, wherein the direct injection comprises two or more injections into the tumor.

E124. The method of any one of E15-E20, E84, E85, E94-E104, or E117-E123, wherein the checkpoint inhibitor is administered by intravenous infusion.

E125. The combination therapy of any one of E1-E14, the composition of any one of E21-E36 or E49-E64, the polynucleotide of any one of E37-E66 or E105-106, the AAV capsid of any one of E75-E78 or the expression construct of any one of E107-E116, for use in therapy or prophylaxis.

E126. The combination therapy, composition, polynucleotide, AAV capsid or expression construct of E125 for use in gene therapy.

E127. The combination therapy, composition, polynucleotide, AAV capsid or expression construct of E125 or E127 for use in cancer therapy.

E128. The combination therapy, composition, polynucleotide, AAV capsid or expression construct of any one of E125 to E127 for use in a method as defined in any one of E15-E20, E79-E104, or E117-E124.

E129. A pharmaceutical composition comprising the composition of any one of E21-E36 or E49-E64, the polynucleotide of any one of E37-E66 or E105-E106, the AAV capsid of any one of E75-E78 or the expression construct of any one of E107-E116.

E130. The pharmaceutical composition of E129 further comprising a pharmaceutically acceptable excipient.

E131. Use of the combination therapy of any one of E1-E14, the composition of any one of E21-E36 or E49-E64, the polynucleotide of any one of E37-E66 or E105-E106, the AAV capsid of any one of E75-E78 or the expression construct of any one of E107-E116, for the manufacture of a medicament for use in therapy or prophylaxis.

E132. The use of E 131 wherein the therapy or prophylaxis comprises a method as defined in any one of E15-E20, E79-E104, or E117-E124.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature.

All of the references cited above, as well as all references cited herein, are incorporated herein by reference in their entireties.

Any examples provided herein are offered by way of illustration and not by way of limitation.

EXAMPLES

Example 1: Assessing Biodistribution and Kinetics of Expression of AAV-2 Luciferase in Multiple Cancer Cell Line Models Transduction of an AAV2-luciferase vector in five different syngeneic mouse cancer models (MC38, B16F10-p436, CloudmanS91, CT26-p928, and A20-p165) was tested. The aim of the study was to identify tumor types that were efficiently transduced by an AAV vector. Transduction efficiency and transgene expression levels and kinetics were evaluated both in vitro and in vivo. Transduction was evaluated over 21 days to determine kinetics after intratumoral injection. Luciferase expression was evaluated on multiple days per week for three weeks via whole body bioluminescence imaging. To assess biodistribution or escape of the AAV2 from the injection site, liver and spleen were taken for evaluation by immunohistochemistry and PCR. Ratios supporting maximal tumor transduction and transgene expression while limiting systemic exposure were assessed. Correlations between in vitro and in vivo transduction were also evaluated. Results showed that AAV2 was able to be successfully administered to all tumor models.

Methods

Vector Details

AAV2/2 Firefly luciferase (AAV2-luc) was purchased at a titer of $1.0 \times 10^{13}$ GC/mL from Vector Biolabs (Malvern PA). The rAAV genome was comprised of AAV2 inverted terminal repeats (ITRs), a CAG promoter, transgene encoding for firefly luciferase, and a bovine growth hormone (bGH) polyadenylation signal.

Murine Tumor Lines

The A20 lymphoma, CT26 colon carcinoma and Cloudman S91 were obtained from the American Type Culture Collection (ATCC). MC38 colorectal adenocarcinoma cells were obtained from the National Cancer Institute (NCI). The B16F10 murine colon carcinoma cell line was obtain from University of North Carolina (UNC) Lineberger Comprehensive Cancer Center. All cells were maintained in cell culture medium per vendor specifications.

In Vitro Assay

Replicating cells were transfected with AAV2-luc at MOI's ranging from 2000 to 40500 vp/cell. Luciferase expression (determined by bioluminescence—IVIS spectrum CT, Perkin Elmer) was determined 2 and 5 days after transfection.

In Vivo Assay

Established A20 lymphoma, CloudmanS91 melanoma, B16F10 melanoma, CT26 colorectal, and MC38 colorectal tumors grown subcutaneously in syngeneic BALB/c, C57Bl/6, or DBA/2. Mice were directly injected subcutaneously in the right flank with $1 \times 10^{11}$ vp in 0.01 ml., 0.025 ml, or 0.05 ml of vehicle. Tumors were longitudinally imaged for bioluminescence (IVIS spectrum CT, Perkin Elmer) following injection of luciferin at regular intervals from day 5 post-transfection. The studies were terminated either at day 21 or when tumor volumes exceeded the maximum permitted volume (typically 1500-2000 mm³). At the end of the study, mice were euthanized and tumor, liver and spleen samples collected for further analysis.

Results

In Vitro Transfection Leads to Active Luciferase Expression

Figure 3:
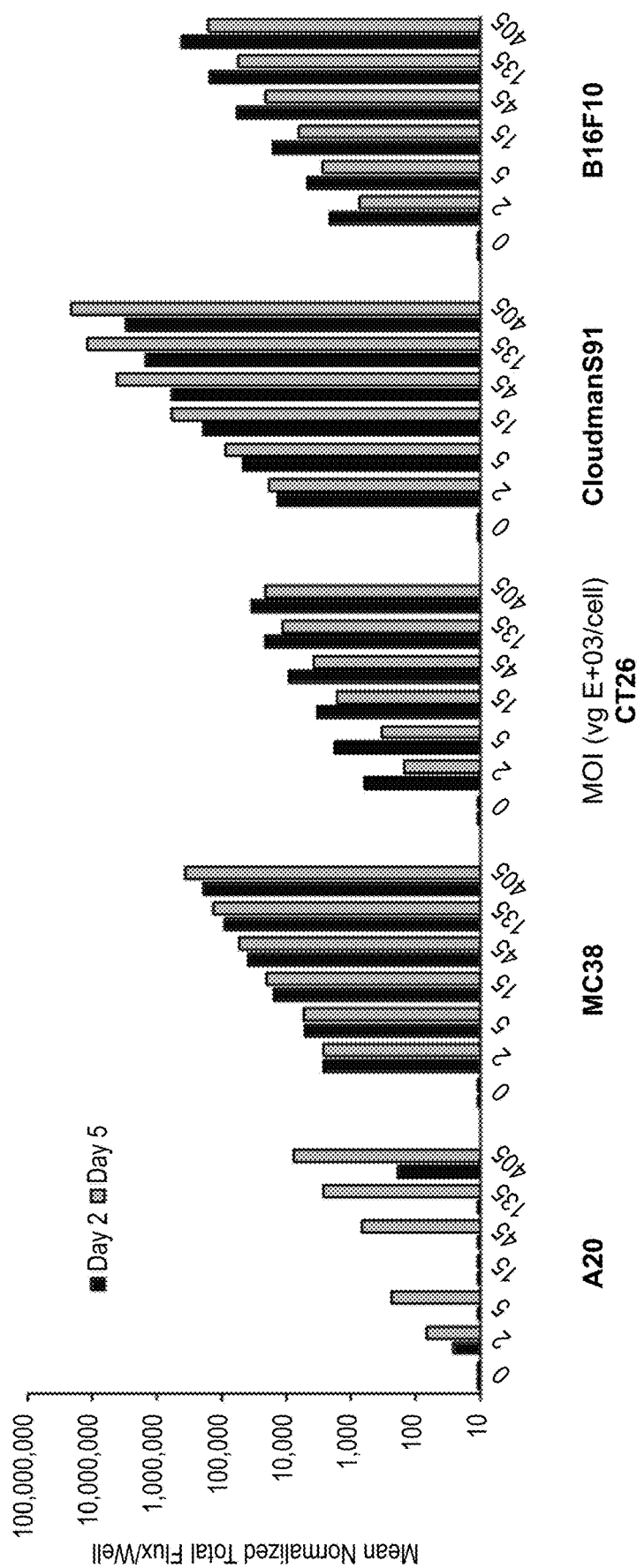
FIG. 3 is a graph showing luciferase expression two and five days after in vitro transduction with an AAV2-luciferase vector at MOIs ranging from 2000 to 40500 vp/cell, in the five different cancer cell lines (MC38, B16F10, CloudmanS91, CT26, and A20) used to create syngeneic mouse cancer models.

In B16F10, CloudmanS91, CT26 and MC38 luciferase expression was detected 2 days after transfection. (FIG. 3). In contrast, luciferase expression in A20 was not readily apparent until day 5. (FIG. 3). Based on luciferase expression at highest MOI, the rank order was CloudmanS91>B16F10-MC38>CT26>A20 in terms of photon intensity. (FIG. 3). The level of luciferase expression was MOI-dependent. Luciferase expression was detected in CloudmanS91 on day 2 at an MOI of 2000 whereas luciferase expression in A20 was only observed at markedly higher MOIs (>135000) and then not until day 5. (FIG. 3).

Figure 4B:
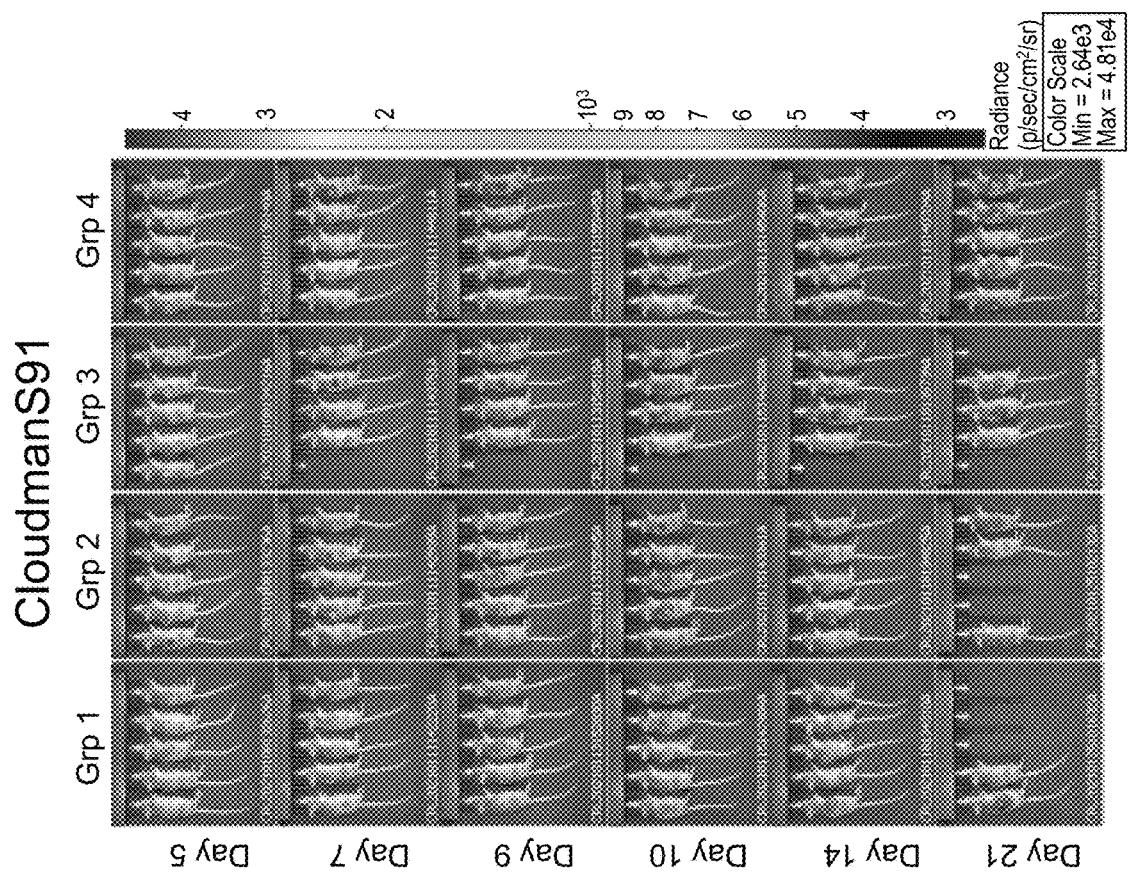
FIG. 4A and FIG. 4B show bioluminescence imaging showing luciferase expression in MC38 (FIG. 4A) and CloudmanS91 (FIG. 4B) tumors after intratumoral injection with an AAV2-luciferase vector. Luciferase activity was measured over 21 days.
Figure 4A:
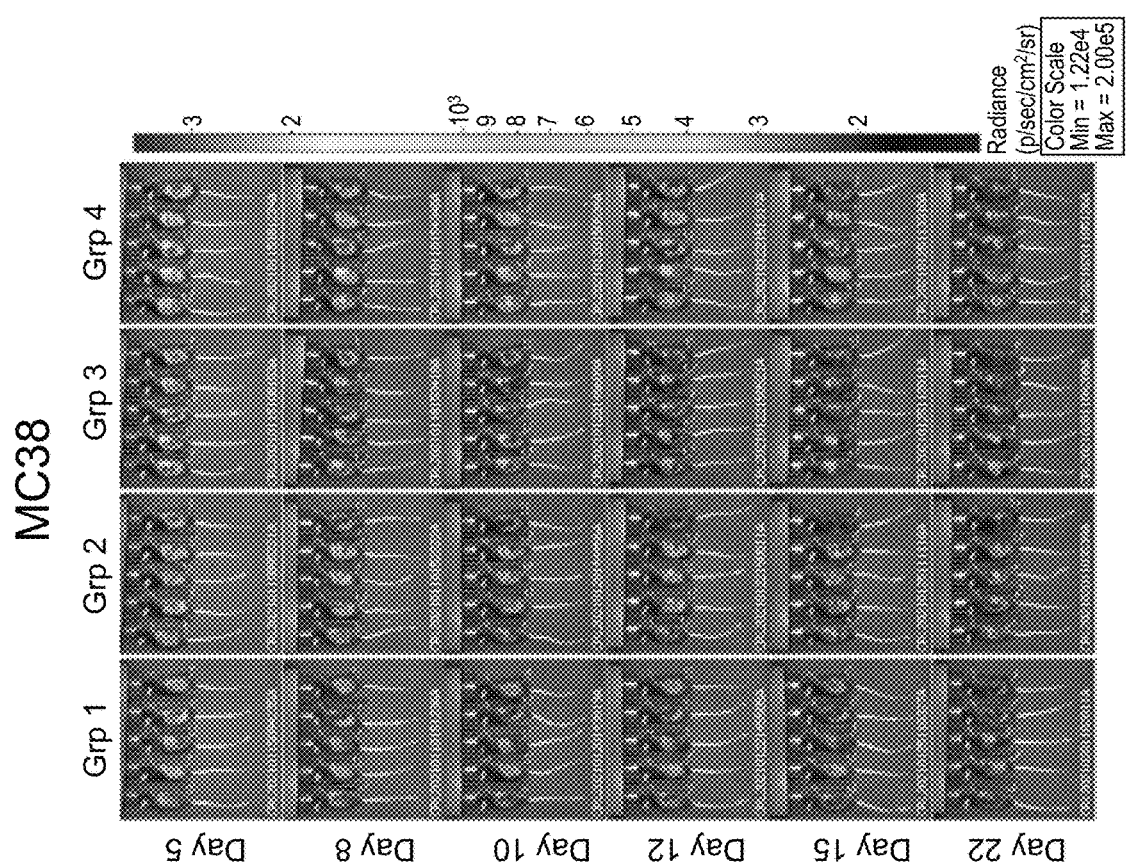

Intratumoral Injection of Murine Syngeneic Tumors with AAV2-Luc Results in Active Luciferase Expression Transfection of syngeneic murine tumors with AAV2-Luc led to luciferase expression (determined by bioluminescence) in all five syngeneic murine tumor lines tested. The time course for B16F10 and CloudmanS91 are shown in FIG. 4A and FIG. 4B. Bioluminescence was detected in a majority of transfected tumors at the first time point (day 4, CloudmanS91; day 5, B16F10) and was still detectable in tumors at the last evaluable time point (day 21, CloudmanS91; day 12, B16F10) indicating sustained luciferase expression. (FIGS. 4A and 4B). Grp 1 was given control saline injection; Grp 2 was given a 10 uL injection of AAV2-luc representing 10% of the tumor volume; Grp 3 was given a 25 uL injection of AAV2-luc representing 25% of the tumor volume; Grp 4 was given a 50 uL injection of AAV2-luc representing 50% of the tumor volume.

Pattern of Bioluminescence

Figure 5A:
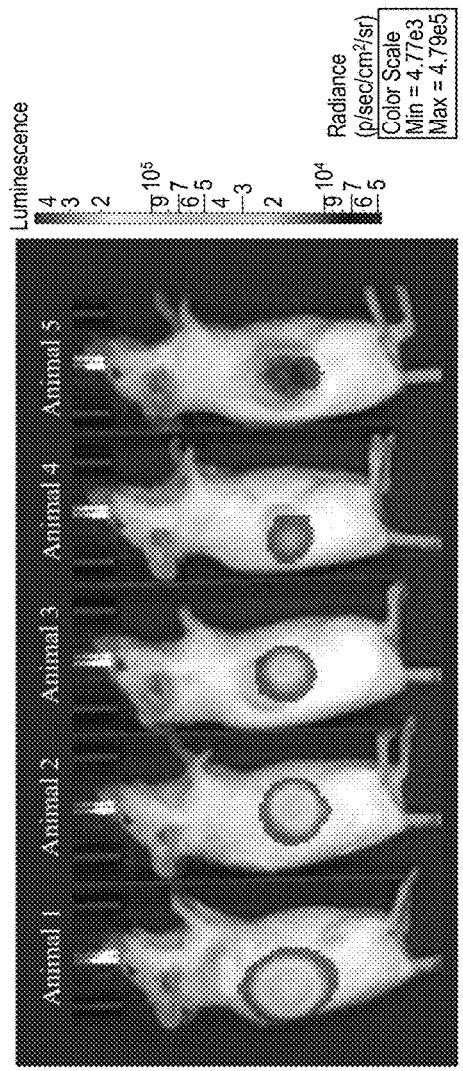
FIG. 5A-FIG. 5E show bioluminescence imaging showing luciferase expression co-localized with tumor mass after intratumoral injection for CT26 (FIG. 5A), B16F10 (FIG. 5B), A20 (FIG. 5C), MC38 (FIG. 5D), and CloudmanS91 (FIG. 5E) after intratumoral injection with an AAV2-luciferase vector.
Figure 5B:
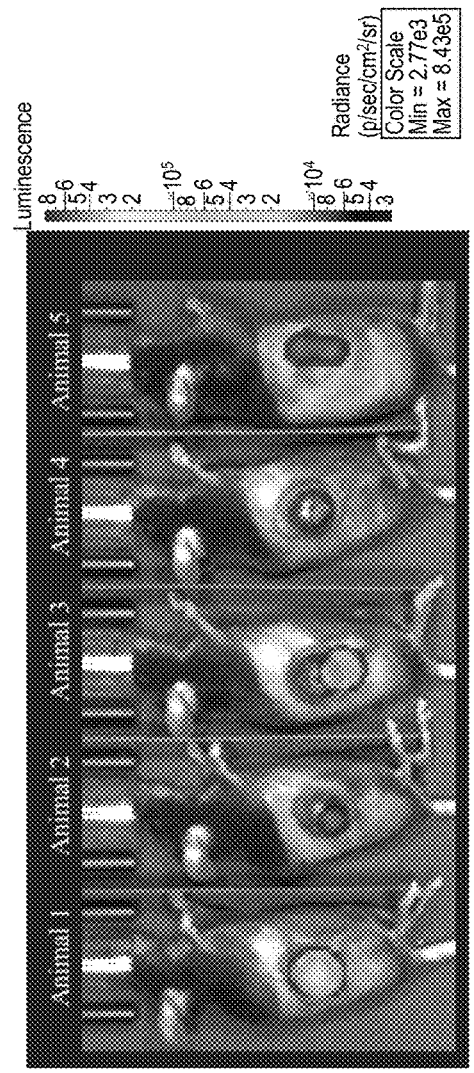
Figure 5C:
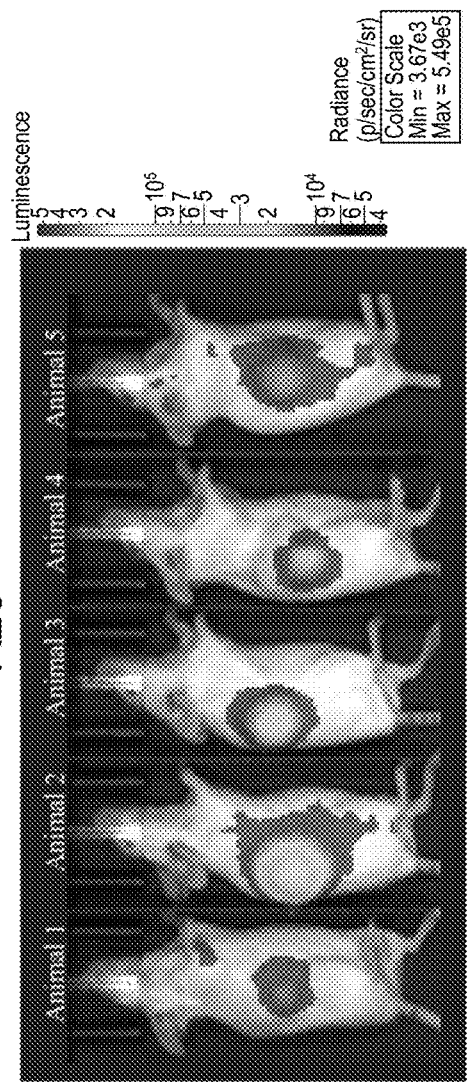
Figure 5D:
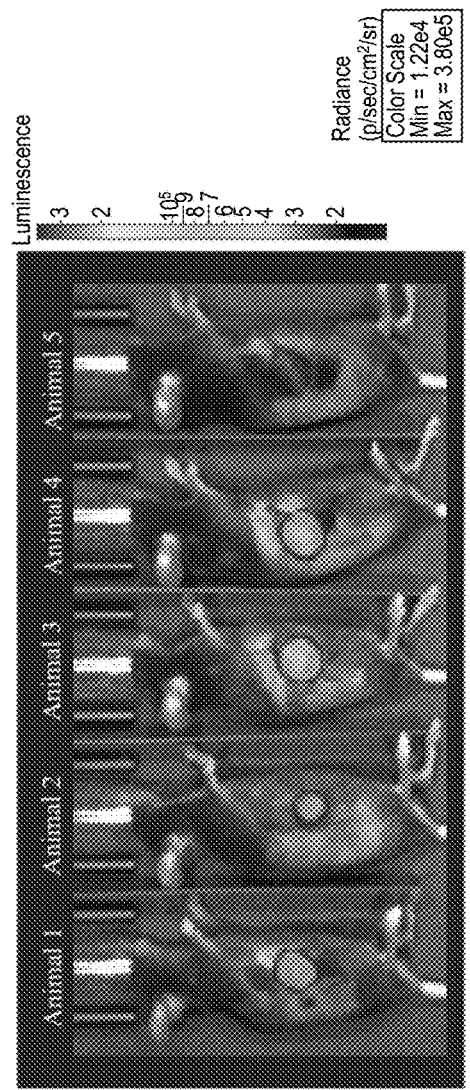
Figure 5E:
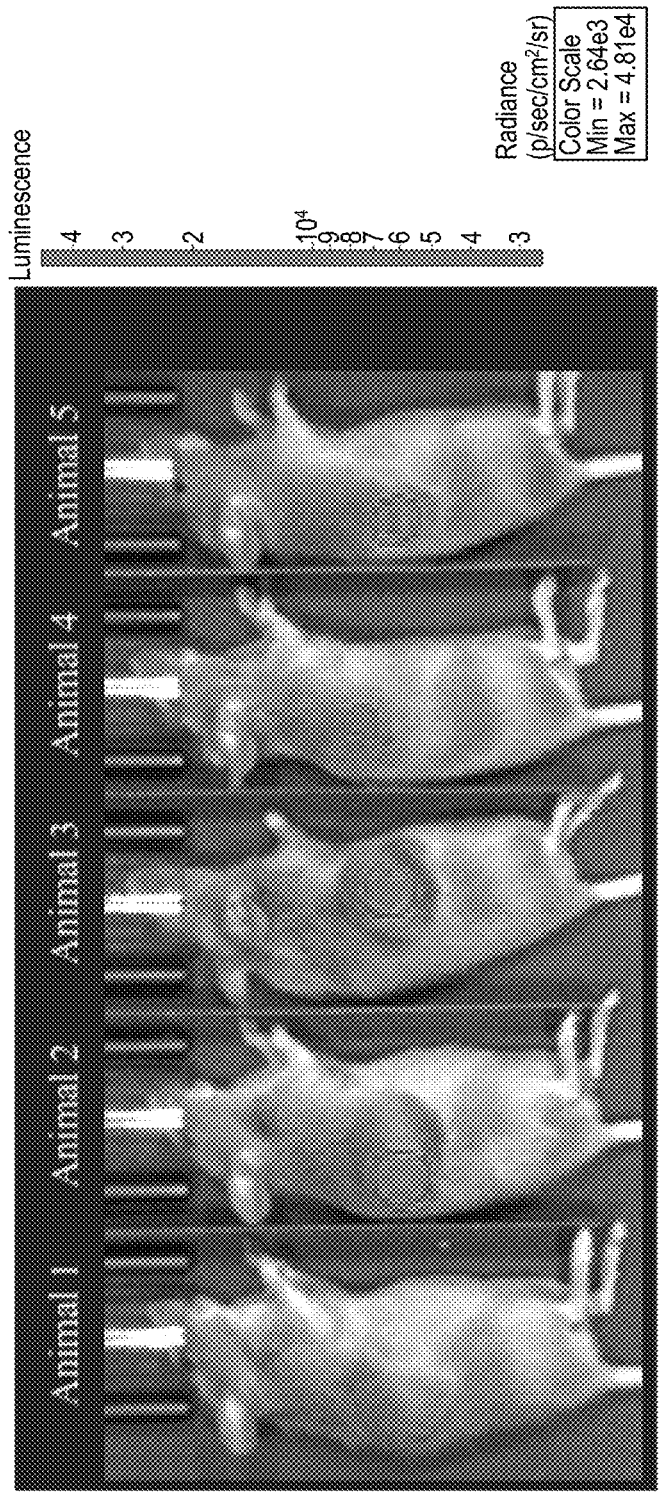

Bioluminescence was generally co-localized with the tumor mass/injection site for CT26 (FIG. 5A), B16F10 (FIG. 5B), MC38 (FIG. 5D) and CloudmanS91 (FIG. 5E). However, some minor bioluminescence signal was observed distal to the primary tumor mass (FIG. 5C, animal #'s 1 & 5) at the highest dose only (~50% tumor volume) in the A20 lymphoma model. Representative images are shown for each tumor line at the 50 ul dose.

Lack of Correlation Between In Vitro and In Vivo Luc Expression

Figure 6A:
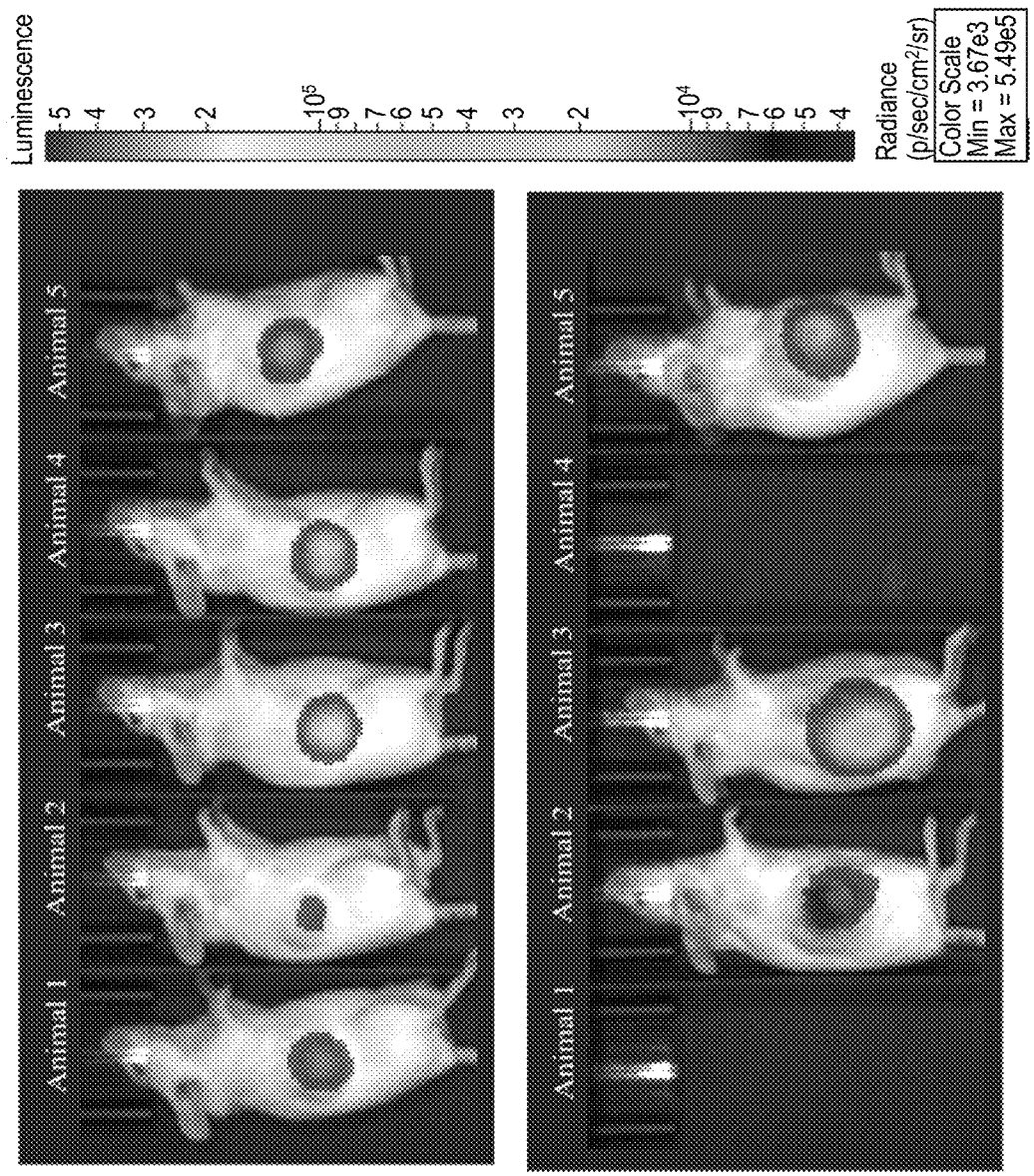
FIG. 6A and FIG. 6B show bioluminescence imaging showing luciferase expression in A20 (FIG. 6A) and CloudmanS91 (FIG. 6B) after intratumoral injection with an AAV2-luciferase vector.
Figure 6B:
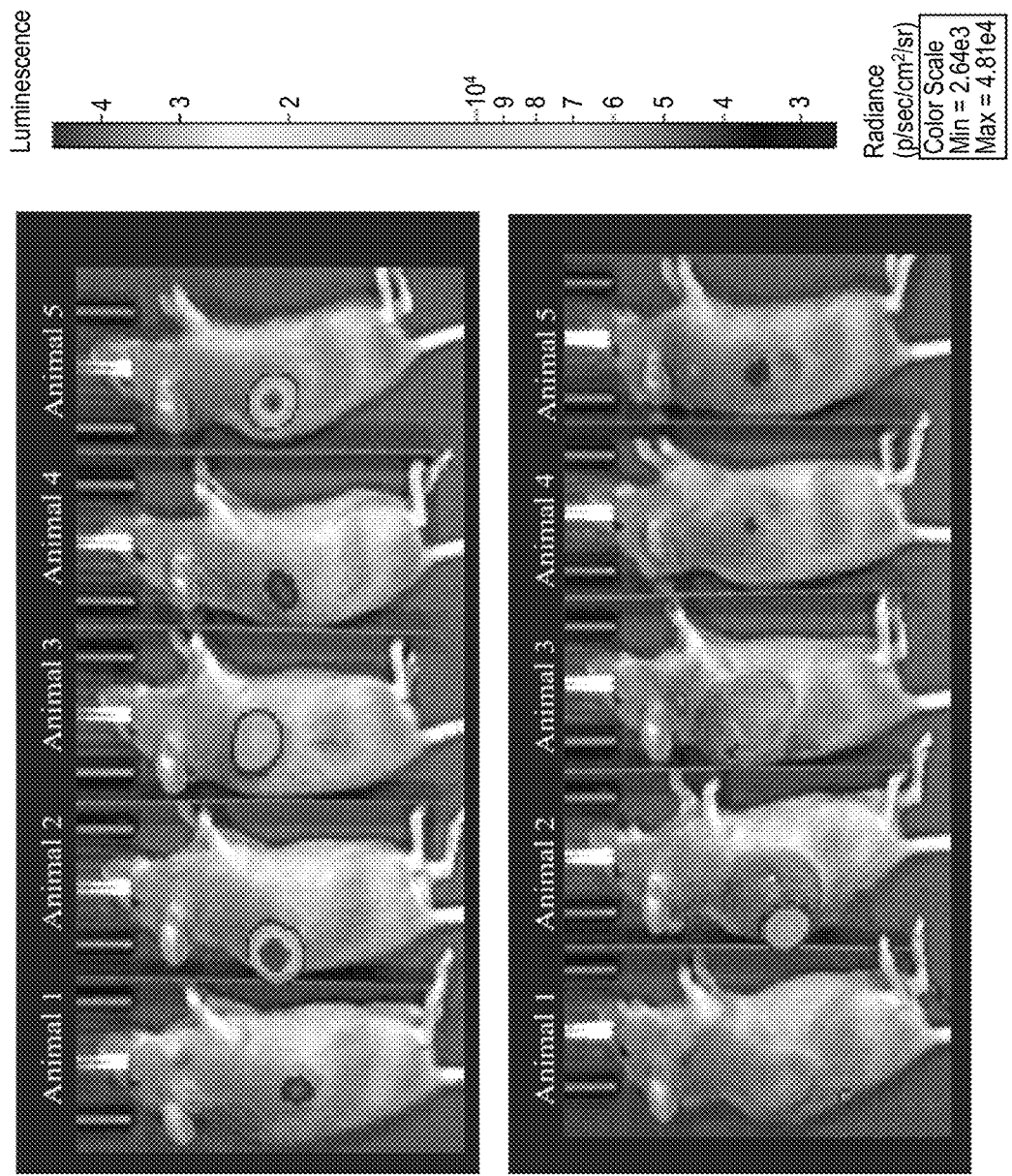

In contrast to the in vitro studies where AAV2-luc transfection of the A20 line appeared less efficient than the remaining four (4) cell lines (FIG. 3), the in vivo appearance of bioluminescence (indicative of luciferase expression) in A20 tumors was similar to the other tumor lines. (FIGS. 6A and 6B). Furthermore, bioluminescence was still detectable on day 14. (FIGS. 6A and 6B).

Example 2: In Vivo Evaluation of AAV2-IL12 and Anti-PD-1 Antibody Therapy in H22 Hepatocellular Carcinoma Mouse Models The anti-tumor efficacy of the AAV2-IL2 (AAV2-CAG-mIL12a-F2A-mIL12b-hgh PA) treatment alone and in combination with an anti-PD-1 antibody (RMP1-14) therapy was evaluated in the H22 Hepatocellular Carcinoma (HCC) model in female BALB/c mice. The study was designed as shown in Table 8 for vehicle, AAV2-IL12, and RMP1-14.

TABLE 8

| Study Design for H22 | |
|---|---|
| Model(s) | H22 |
| Strain(s) | BALB/c |
| Number of mice on study | 32 |
| Number of groups | 4 |
| N per group | 8 |
| Inoculation | SubQ-Hind Right Flank |
| Dosing regimen | Single (AAV)/BIW × 3 (PD-1) |
| Dosing route | Intratumoral (IT)-(AAV)/ Intraperitoneal (IP) (RMP1-14) |

TABLE 8-continued

Study Design for H22

| | |
|---|---|
| Dosing duration | 3 weeks (anti PD-1 antibody) |
| BW and TV measurement frequency | 2×/week |
| Randomization range | 80-120 mm³ |
| Dietary supplements | Body Weight Loss of >10%, all in group |
| Dosing holiday (PD-1) | Body Weight Loss of >20%, individual mouse |
| Tissue collections | Blood (cheek) Weeks: −1, 2, 4 Tumor (IHC) |
| Maximal tumor volume (MTV) | 3000 mm³ |

2.1 Tumor Cell Preparation.

Cryogenic vials containing tumor cells were thawed and cultured according to the provider's protocol. On the day of injection, cells were washed in serum-free media, counted, and resuspended in cold serum-free media at a concentration of 2E7 viable H22 cells/100 µL. Cell suspensions were kept on ice during transport to the vivarium. Cells were prepared for injection by withdrawing the suspension into a chilled 1 mL slip-tip syringe. The filled syringes were kept on ice.

2.2 Tumor Implantation.

100 µL of the cell suspension was subcutaneously injected into the rear flank of the mouse. Animals were undisturbed for up to seven days before observing for tumor growth.

2.3 Tumor Measurement.

Animals were monitored weekly for palpable tumors, or any changes in appearance or behavior. Once tumors were palpable, tumors were measured at least twice per week using calipers. Tumor volume was calculated using the following equation: (longest diameter*shortest diameter²)/2. Once tumors were of an appropriate size to begin the study, tumors and body weights were measured twice per week for the duration of the study.

2.4 Randomization and Dose Selection.

When the average tumor volume reached 80-120 mm³, mice were randomly assigned to the respective treatment groups and dosed within 24 hours of randomization. Reference Day: Day 0 was defined as dosing start.

2.5 Study Termination.

The study was terminated 12 weeks after the first dose.

2.6 Body Weight Measurement and Guidelines.

Body weight was measured twice a week following randomization and initiation of treatment. Hydrogel/diet gel and/or dosing holidays were given to animals due to body weight loss; body weight loss was calculated based on the body weight of the mouse on the first day of treatment. Dosing holiday and/or nutritional supplements may have been provided to the animal based on the study director's assessment of animal health. If there were no signs of recovery, the animal was sacrificed for humane reasons.

2.6.1 Dosing Holiday for Anti-PD-1 Treatment.

After one measurement of body weight loss greater than 20% of body weight, dosing holidays were given to the individual mouse, while other mice in the same group received dosing as scheduled.

2.6.2 Supplemental Gel Recovery Administration.

After body weight loss of greater than 10% was observed in a single animal, a hydrogel/diet gel was supplied to all animals in the same group.

2.7 Clinical Observations.

Clinical observations were performed twice a week at the time of tumor and body weight measurements. During daily routine monitoring, the animals were checked for any adverse effects of tumor growth and treatments on behavior such as mobility, food and water consumption, eye/hair matting and any other abnormalities. Mortality and observed abnormal clinical signs were recorded for individual animals in detail. Daily monitoring took place for mice showing any signs of morbidity or mortality.

2.8 Tissue Collection.

Tumor samples were collected according to Table 9 (Tumor) and Table 10 (Blood).

TABLE 9

Tumor Tissue Collection for H22

| Groups | N | Time Point | Tissue |
|---|---|---|---|
| 1-4 | 32 | Termination @ 12 weeks/MTV | Tumor |

*Formalin Fixed Paraffin Embedded (FFPE)

TABLE 10

Blood Collection for H22

| Groups | N | Time Point |
|---|---|---|
| 1-4 | 32 | 1 week before Dose 1 (1 day before innoculation) |
| 1-4 | 32 | 2 weeks after Dose 1 |
| 1-4 | 32 | 4 weeks after Dose 1 |

2.8.1 Meso-Scale Discovery (MSD).

H22 serum samples will be processed for IL-12 quantification by Meso-Scale Discovery (MSD, Rockville, MD, USA). MSD assay will be performed in triplicate. The standard and blank controls will be performed in duplicate.

Samples will be diluted with Diluent 2 (MSD Catalog #R51BB) (a minimum 2-fold dilution). For one plate, 60 µL of each 50× detection antibody stock solution will be combined. Diluent 2 will be added to bring the final volume to 6 mL. For one plate, 10 mL of Read Buffer T (4×) (MSD Catalog #R92TD) and 10 mL of deionized water will be combined to prepare a 2× Read Buffer solution. Excess dilution Read Buffer T was kept in a tightly sealed container at room temperature up to one month.

Seven calibrator samples plus a zero calibrator standard will be prepared by reconstituting calibrator 1 (highest calibrator) (MSD Catalog #C0060-2) by adding 1000 µL of Diluent 2 to the lyophilized calibrator vail and inverting three to five times without vortexing. The reconstituted solution will be equilibrated at room temperature for 15-30 minutes and then vortexed briefly using short pulses. 100 µL of the highest calibrator will be transferred to 300 µL of Diluent 2 and mixed well by vortexing. 4-fold serial dilution will be repeated five additional times to generate seven calibrators. Diluent 2 will be used as the zero calibrator.

The plates will be washed three times with 150 µL wash buffer/well. 50 µL of the calibrator standards or samples will be added to each well in duplicates. The plate will be sealed with a plate seal and incubated at room temperature with shaking for 2 hours. The plate will be washed three times with 150 µL wash buffer/well. 25 µL of detection antibody solution will be added to each well. The plate will be sealed with a plate seal and incubated at room temperature with shaking for 2 hours. The plate will be washed 3 times with at least 150 µL wash buffer/well. 150 µL of 2× Read Buffer T will be added to each well. Next, the plate will be analyzed with the MSD instrument.

The data result will be analyzed by MSD discovery workbench analysis software to determine acceptance criteria of the standards. The regression model will be a 4-parameter logistic model (sigmoidal dose-response) with a 1/Y2 weighting. The correlation coefficients of standard curve will be accepted as if R2>0.98. The bias % of at least 6 non-zero points on the standard curve including upper and lower limits of quantification will not exceed ±20.0% (upper and lower limit of quantification is ±30.0%). Bias %=(measured concentration-theoretical concentration)/theoretical concentration×100%. CV % of at least six non-zero points on the standard curve including upper and lower limits of quantification did not exceed ±20.0% (upper and lower limit of quantification is ±30.0%). CV %=SD of measured concentration/Average of measured concentration×100%.

2.9 Results.

Figure 7A:
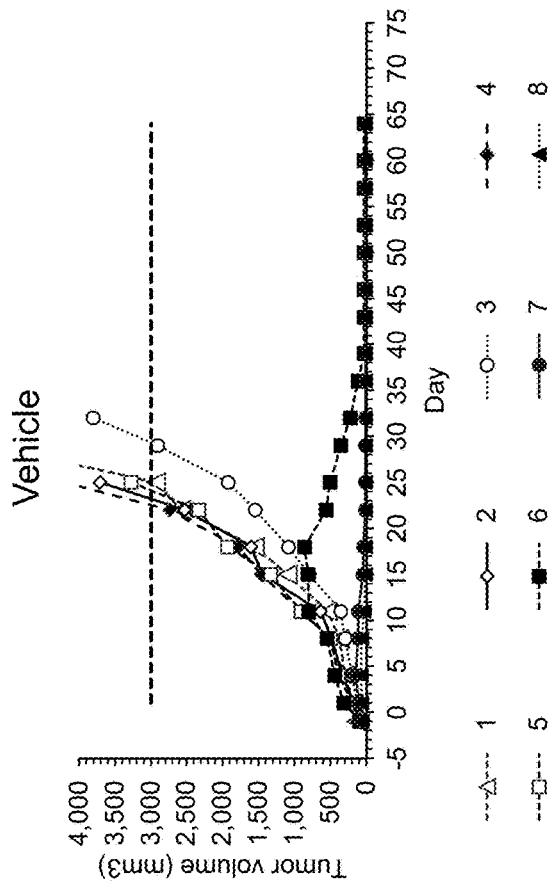
FIG. 7A-FIG. 7D show tumor regression as measured by tumor volume ($mm^3$) in a syngeneic H22 hepatocellular cancer mouse model after treatment with vehicle (FIG. 7A), AAV2-IL12 (FIG. 7B), an anti-PD-1 antibody (FIG. 7C), or AAV2-IL12 and an anti-PD-1 antibody (FIG. 7D). Each line represents an individual mouse. Horizontal dashed line (-----) represents a maximum tumor volume (animals are euthanized once this volume is exceeded). The x-axis represents the number of days after treatment (0, 5, 10, 15, 20, 25, 30, 35, 40, 45, 50, 55, 60, 65, 70, and 75 days).
Figure 7B:
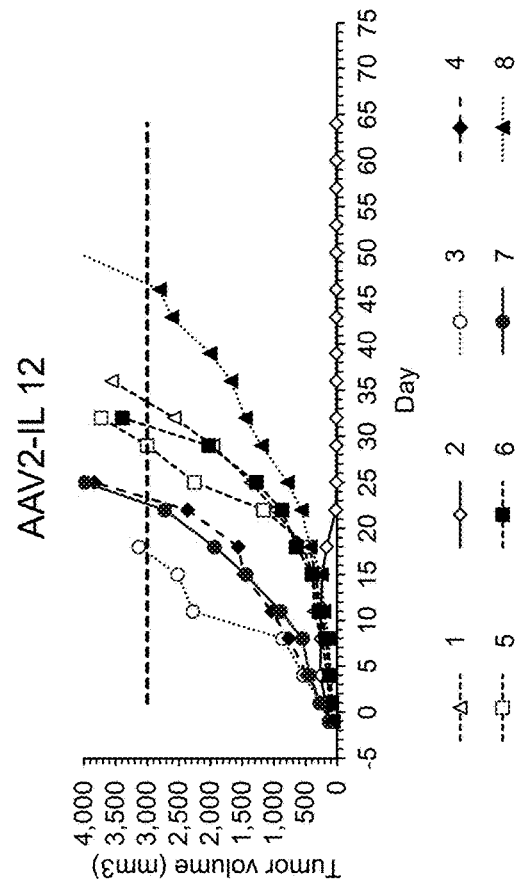
Figure 7C:
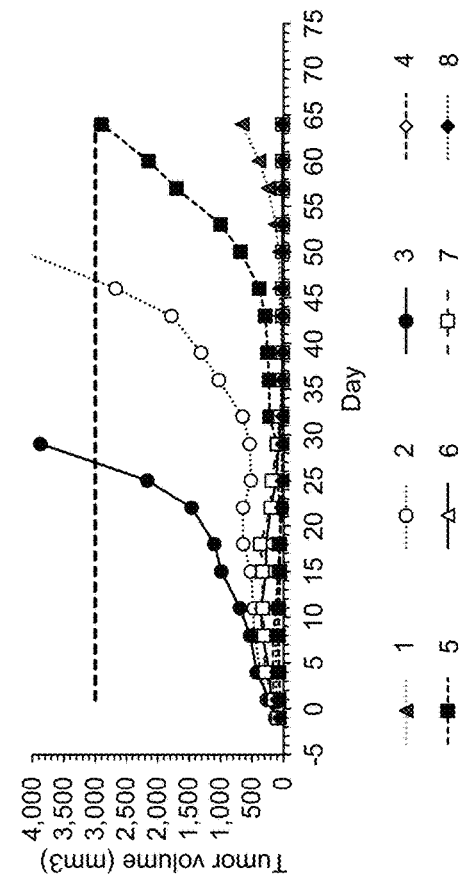
Figure 7D:
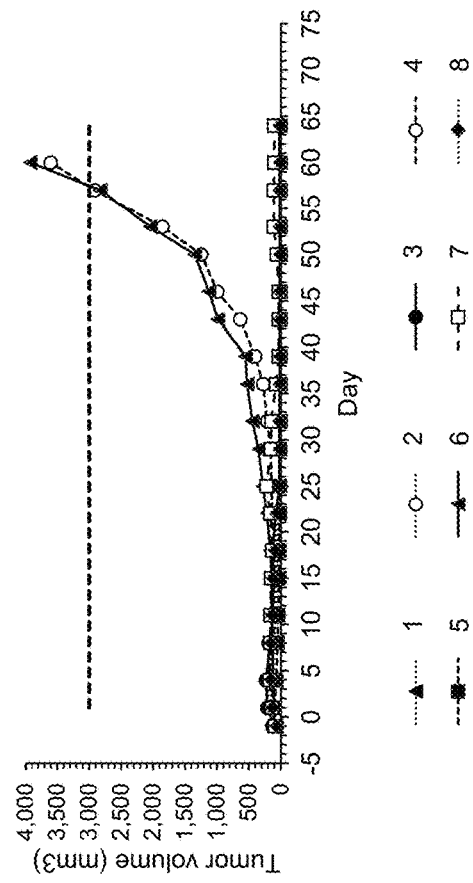
Figure 20A:
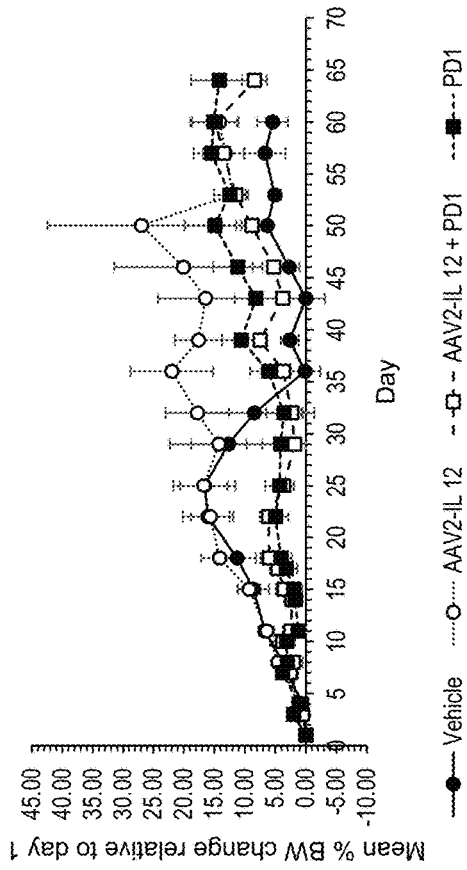

Tumor regression was measured by tumor volume (mm$^3$) in H22 hepatocellular cancer mouse models after treatment with vehicle (FIG. 7A), AAV2-IL12 (FIG. 7B), RMP1-14 (an anti-PD-1 antibody) (FIG. 7C), or AAV-IL12 and RMP1-14 (FIG. 7D). Treatment with vehicle was consistent with historical data, although some tumors failed to grow out. Treatment with AAV-IL 12 showed heterogenous response to AAV-IL12 and delayed tumor growth was observed in 5 out of 8 samples. Treatment with RMP1-14 also showed heterogeneous response, with 3 out of 8 samples showing complete response. Treatment with AAV2-IL12 and RMP1-14 showed improved overall response compared to RMP1-14 alone, with 5 out of 8 samples showing complete response. No meaningful negative impact on body weight was observed with AAV2-IL12 alone or in combination with RMP1-14 (FIG. 20A).

Tumor regression was also measured by both mean area under the curve (AUC) (FIG. 8A) and median area under the curve (AUC) (FIG. 8B) of tumor growth in H22 hepatocellular cancer mouse models after treatment with vehicle, AAV-IL12, the combination of AAV-IL12 and RMP1-14, or RMP1-14 alone. The effect of AAV2-IL12+anti-PD-1 antibody (RMP1-14) and RMP1-14 alone were significant relative to both vehicle and AAV2-IL12 alone (p<. 05). AAV2-IL12+RMP1-14 resulted in lower AUC relative to RMP1-14 alone, but the effect was not statistically significant (p>0.05) (FIG. 8A).

Overall survival was also measured in H22 hepatocellular cancer mouse models after treatment with vehicle, AAV-IL12, AAV-IL12 in combination with RMP1-14, or RMP1-14 alone (FIG. 16). The results showed that the combination treatment of RMP1-14 antibody and AAV2-IL12 led to a significant improvement in overall survival.

Example 3: In Vivo Evaluation of AAV2-IL12 and an Anti-PD-1 Antibody Therapy in MC38 Murine Colon Carcinoma Mouse Models The anti-tumor efficacy of AAV2-IL12 (AAV2-CAG-mIL12a-F2A-mIL12b-hgh PA) vectors in MC38 murine colon carcinoma mouse models was demonstrated using female C57BL/6 mice. The study was designed as shown in Table 11.

TABLE 11

Study Design for MC38 murine colon carcinoma

| Gr. | N | Agent | Active dose | Route | Schedule |
|---|---|---|---|---|---|
| 1[#] | 8 | vehicle | n/a | intra-tumoral | day 1 |
| 2 | 8 | AAV2-IL12 | 1E + 11 vg/mouse | intra-tumoral | day 1 |
| 3 | 8 | AAV2-IL12 | 3E + 10 vg/mouse | intra-tumoral | day 1 |
| 4 | 8 | AAV2-IL12// anti-PD-1 RMP1-14 | 1E + 11 vg/mouse// 5 mg/kg | intra-tumoral// intraperitoneal | day 1// biwk × 2 |
| 5 | 8 | anti-PD-1 RMP1-14 | 5 mg/kg | intraperitoneal | biwk × 2 |

[#]control group

Mice were anesthetized with isoflurane for the implantation of cells to reduce the ulcerations. Female C57BL/6 mice (Charles River Laboratories, USA) were subcutaneously injected with 5×10$^5$ MC38 tumor cells in 0% Matrigel (total cell injection volume=0.1 mL/mouse) in flank. Mice were 8 to 12 weeks old at the start date. A pair match was performed when tumors reached an average size of 80-120 mm$^3$, and treatment began.

Body weight was measured daily for five days, then twice a week until the end of the study. Tumors were measured by calipers twice a week to the end of the study. Any adverse reactions or death were reported immediately. Any individual animal with a single observation of greater than 30% body weight loss or three consecutive measurements of greater than 25% body weight loss was euthanized. Any group with a mean body weight loss of greater than 20% or greater than 10% mortality stopped receiving dosing. The group was not euthanized and recovery was allowed. Within a group with greater than 20% weight loss, animals that hit the individual body weight loss endpoint were euthanized. If the group treatment related body weight loss was recovered to within 10% of the original weights, dosing was resumed at a lower dose or less frequent dosing schedule. Exceptions to non-treatment body weight % recovery were allowed on a case-by-case basis.

Animals were monitored individually. The endpoint of the experiment was a tumor volume of 1500 mm$^3$ or 29 days, whichever came first. Responders were followed longer. When the endpoint was reached, the animals were euthanized.

AAV2-IL12 vectors were provided in 5% Sorbitol+elevated 350 mM NaCl in PBS. Vehicle was provided in 5% Sorbitol+elevated 350 mM NaCl in PBS. The dosing volume for vehicle and the AAV2-IL12 vectors were 0.025 mL/mouse, and volume was not adjusted for body weight. AAV2-IL12 vector dosing syringes were prewet with vehicle buffer prior to drawing up dosing solution for first time each syringe was used. The dosing volume for an anti-mouse PD-1 antibody (RMP1-14)=10 mL/kg (0.200 mL/20 g mouse), and volume was adjusted accordingly for body weight.

Figure 9A:
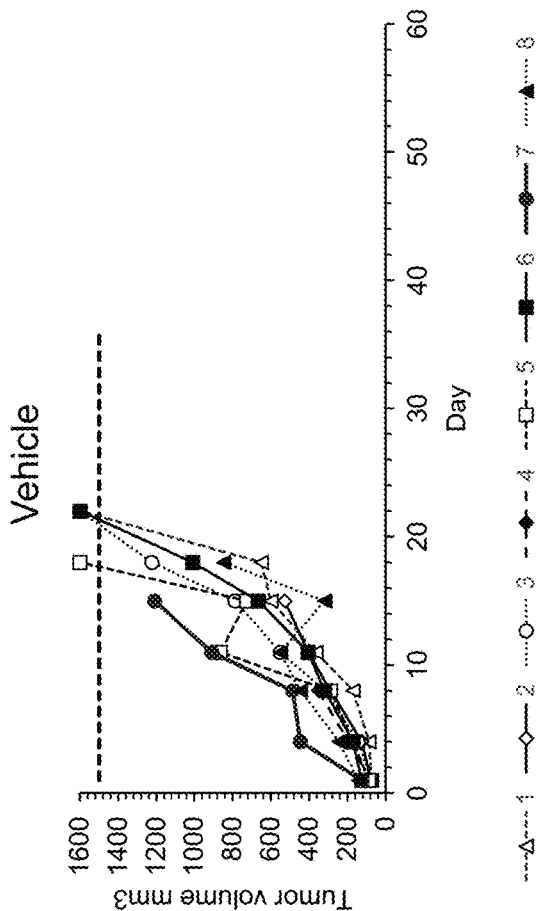
FIG. 9A-FIG. 9E show tumor regression as measured by tumor volume ($mm^3$) in a syngeneic MC38 colorectal cancer mouse model after treatment with vehicle (FIG. 9A), AAV2-IL12 (FIG. 9B and FIG. 9E), an anti-PD-1 antibody (FIG. 9C), or AAV2-IL12 ($1 \times 10^{11}$ viral genomes) and an anti-PD-1 antibody (FIG. 9D). AAV2-IL12 was administered at dosages of $1 \times 10^{11}$ viral genomes (FIG. 9B) and $3 \times 10^{10}$ viral genomes (FIG. 9E). Each line represents an individual mouse. Horizontal dashed line (-----) represents a maximum tumor volume (animals are euthanized once this volume is exceeded). The x-axis represents the number of days after treatment (0, 10, 20, 30, 40, 50, and 60 days).
Figure 9B:
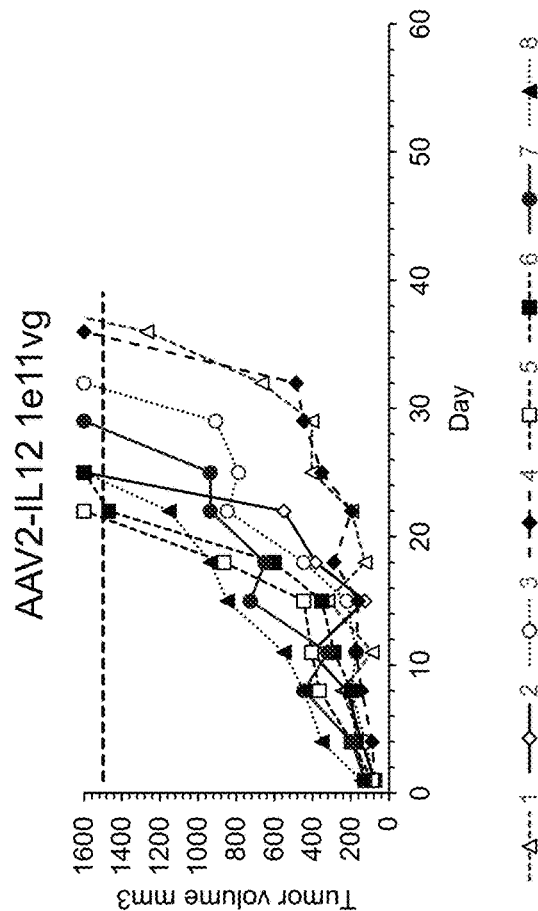
Figure 9C:
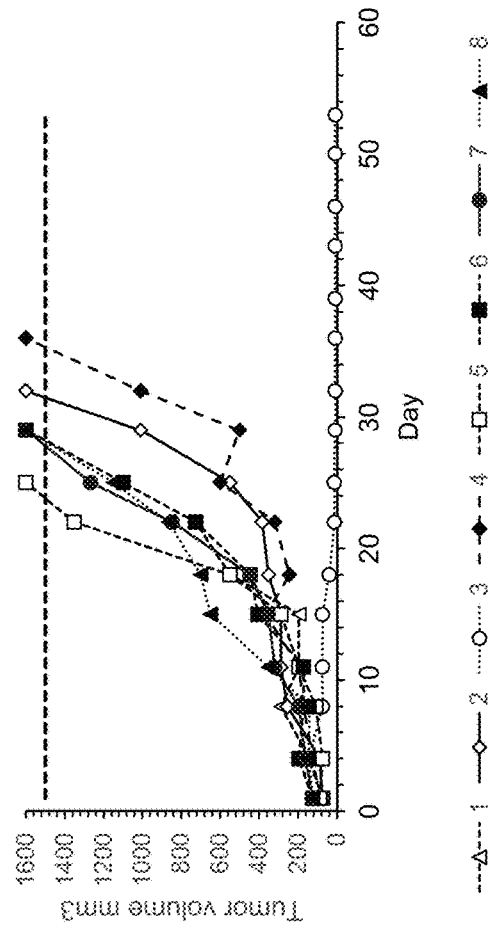
Figure 9D:
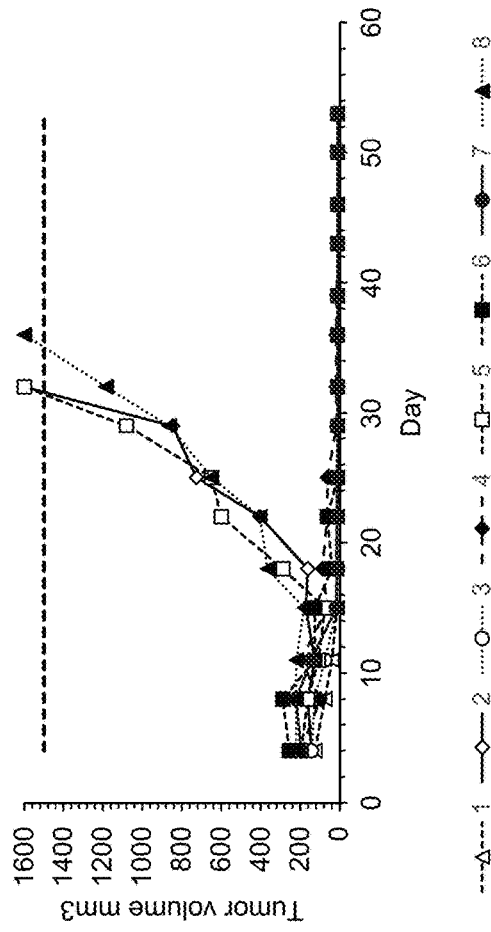
Figure 9E:
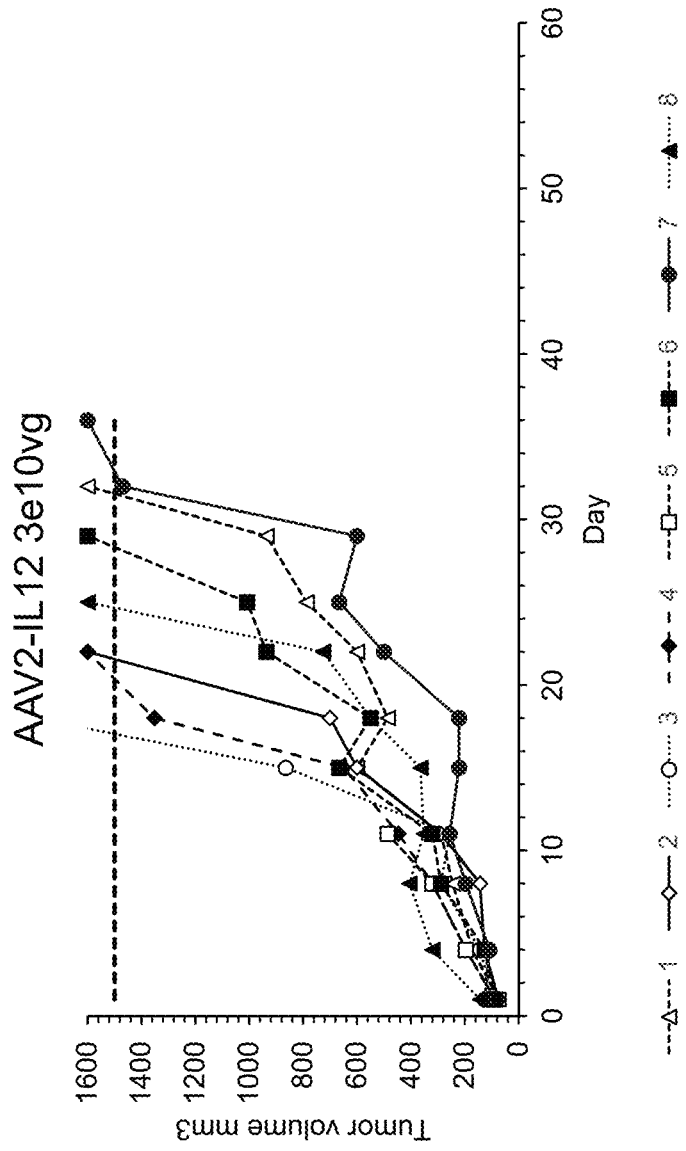
Figure 20B:
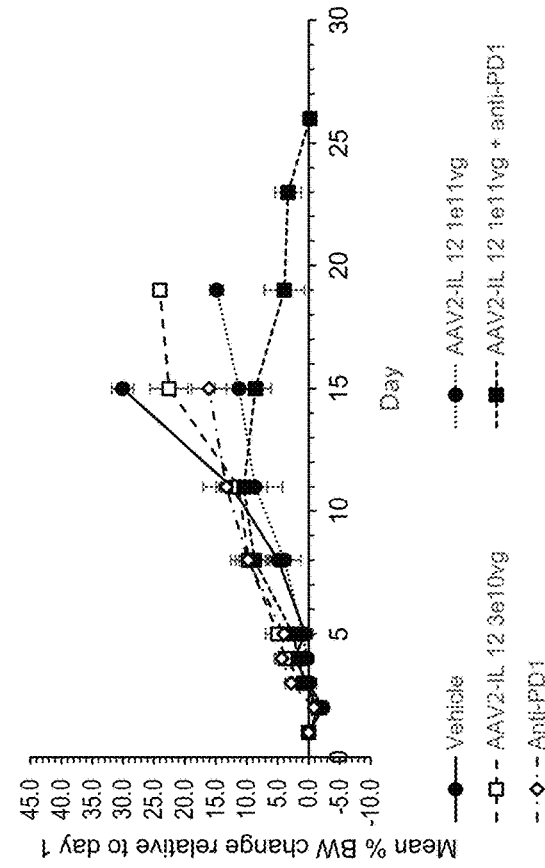
Figure 20C:
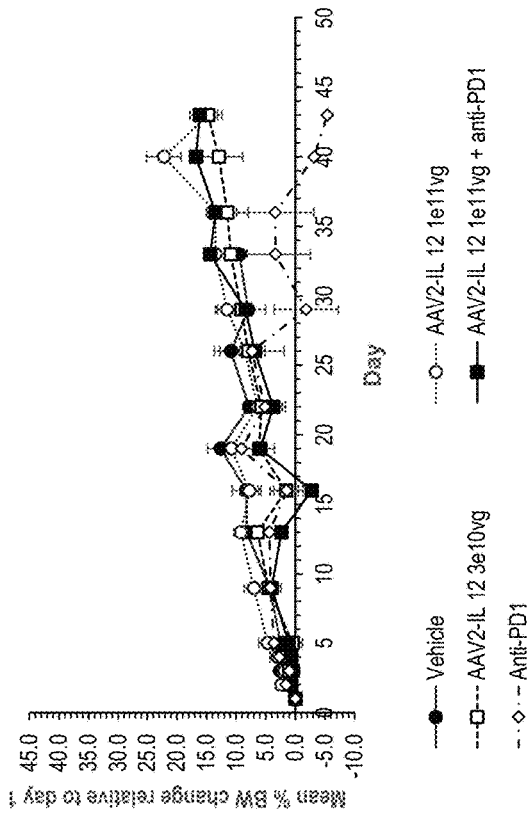
Figure 20D:
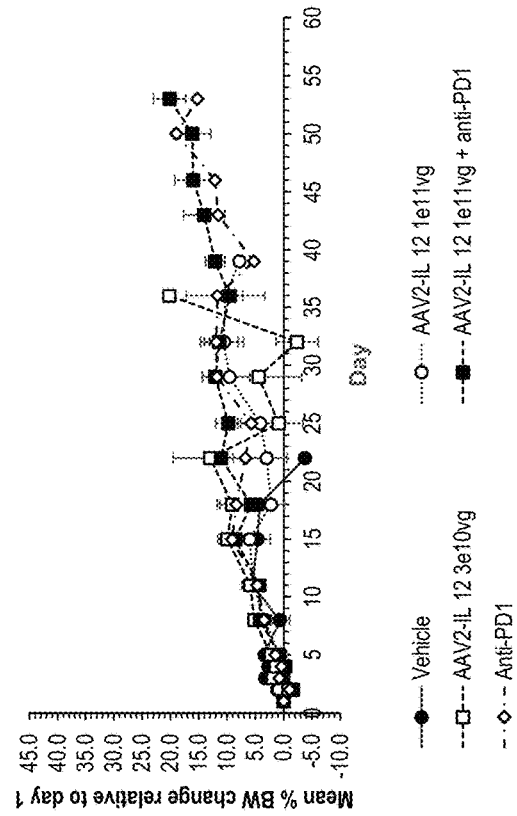

Tumor regression was measured by tumor volume in MC38 (mm$^3$) colorectal cancer mouse models after treatment with vehicle (FIG. 9A), AAV2-IL12 (FIG. 9B and FIG. 9E), RMP1-14 (FIG. 9C), or AAV-IL12 in combination with RMP1-14 (FIG. 9D). Tumor growth in vehicle treated animals was consistent with historical data. Tumor growth in AAV-IL12 treated animals showed a heterogenous response to AAV-IL12 at both doses of 1×10$^{11}$ viral genomes (FIG. 9B) and 3×10$^{10}$ viral genomes (FIG. 9E), with some delayed tumor growth. Tumor growth in an anti-PD-1 antibody treated animals showed a heterogenous response, with 1 out of 8 animals showing a complete response. Tumor growth in animals treated with AAV2-IL12 and RMP1-14 combination showed a superior response to the other treatments, with 5 out of 8 animals showing a complete response. No meaningful negative impact on body weight was observed with AAV2-IL12 alone or in combination with RMP1-14 (FIG. 20D).

Figure 10A:
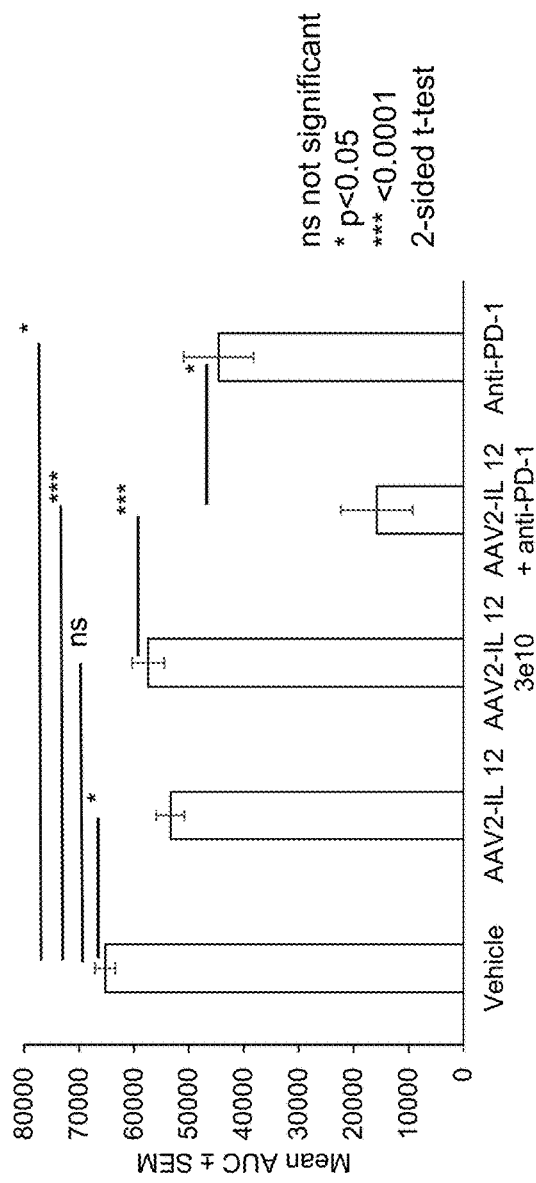
FIG. 10A and FIG. 10B show tumor regression as measured by mean area under the curve (AUC) (FIG. 10A) or by median area under the curve (AUC) (FIG. 10B) of tumor growth in a syngeneic MC38 colorectal cancer mouse model after treatment with vehicle, AAV2-IL12 at a dose of $1 \times 10^{11}$ viral genomes, AAV2IL12 at a dose of $3 \times 10^{10}$ viral genomes, AAV2-IL12 and an anti-PD-1 antibody, or an anti-PD-1 antibody.
Figure 10B:
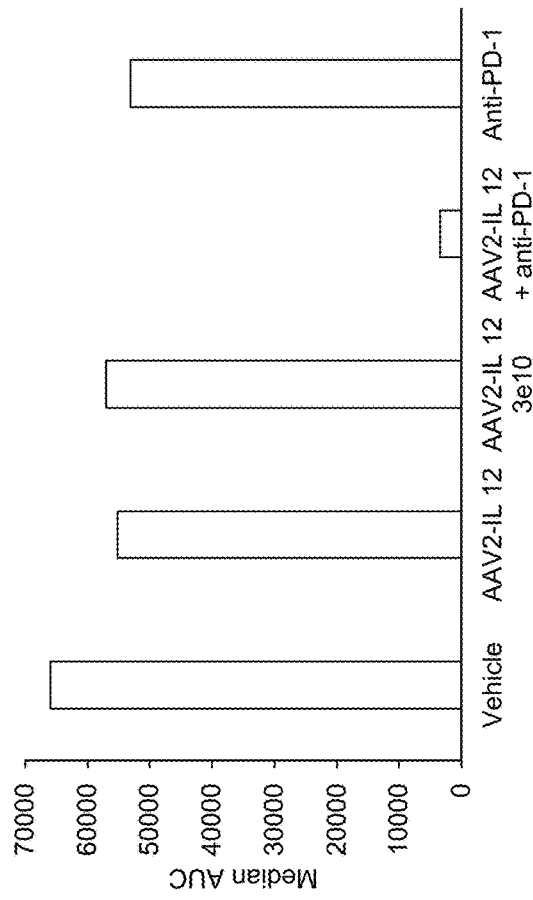

Tumor regression was also measured by both mean area under the curve (FIG. 10A) and median area under the curve (FIG. 10B) of tumor growth in MC38 colorectal cancer mouse models after treatment with vehicle, AAV-IL12, AAV-IL12+RMP1-14 combination, or RMP1-14 alone. The combination therapy AAV2-IL12+RMP1-14 resulted in significantly reduced tumor AUC relative to all other treatments or vehicle (p<0.03) (FIG. 10A).

Overall survival was also measured in MC38 colorectal cancer mouse models after treatment with vehicle, AAV-IL12, AAV-IL12 and RMP1-14 combination therapy, or RMP1-14 alone (FIG. 17). Monotherapy with RMP1-14 or AAV2-IL12 had similar improvement on overall survival. However, the combination of AAV-IL12 and an anti-PD1 antibody was superior in terms of an overall survival and response to either single agent alone.

Example 4: In Vivo Evaluation of AAV2-IL12 and an Anti-PD-1 Antibody Therapy in Cloudman S91 Melanoma Mouse Models The anti-tumor efficacy of AAV2-IL12 (AAV2-CAG-mIL12a-F2A-mIL12b-hgh PA) vectors in Cloudman S91 melanoma mouse models was demonstrated using female DBA/2 mice. The study was designed as shown in Table 12.

TABLE 12

Study Design for Cloudman S91 melanoma

| Gr. | N | Agent | Active dose | Route | Schedule |
|---|---|---|---|---|---|
| 1[#] | 8 | vehicle | n/a | intra-tumoral | day 1 |
| 2 | 8 | AAV2-IL12 | 1E + 11 vg/mouse | intra-tumoral | day 1 |
| 3 | 8 | AAV2-IL12 | 3E + 10 vg/mouse | intra-tumoral | day 1 |
| 4 | 8 | AAV2-IL12// anti-PD-1 RMP1-14 | 1E + 11 vg/mouse// 5 mg/kg | intra-tumoral// intraperitoneal | day 1// biwk × 2 |
| 5 | 8 | anti-PD-1 RMP1-14 | 5 mg/kg | intraperitoneal | biwk × 2 |

[#]control group

Female DBA/2 mice were subcutaneously injected with 5×10$^5$ Cloudman S91 tumor cells in 50% Matrigel (total cell injection volume=0.1 mL/mouse) in flank. Mice were 8 to 12 weeks old at the start date. A pair match was performed when tumors reached an average size of 80-120 mm$^3$, and treatment began.

Body weight was measured daily for five days, then twice a week until the end of the study. Tumors were measured by calipers twice a week to the end of the study. Any adverse reactions or deaths were reported immediately. Any individual animal with a single observation of greater than 30% body weight loss or three consecutive measurements of greater than 25% body weight loss was euthanized. Any group with a mean body weight loss of greater than 20% or greater than 10% mortality stopped receiving dosing. The group was not euthanized and recovery was allowed. Within a group with greater than 20% weight loss, individuals that hit the individual body weight loss endpoint were euthanized. If the group treatment related body weight loss was recovered to within 10% of the original weights, dosing was resumed at a lower dose or less frequent dosing schedule. Exceptions to non-treatment body weight % recovery were allowed on a case-by-case basis.

Animals were monitored individually. The endpoint of the experiment was a tumor volume of 2000 mm$^3$ or 29 days, whichever came first. Responders were followed longer. When the endpoint was reached, the animals were euthanized.

AAV2-IL12 vectors were provided in 5% Sorbitol+elevated 350 mM NaCl in PBS. Vehicle was provided in 5% Sorbitol+elevated 350 mM NaCl in PBS. The dosing volume for vehicle and the AAV2-IL12 vectors were 0.025 mL/mouse, and volume was not adjusted for body weight. AAV-IL12 vector dosing syringes were prewet with vehicle buffer prior to drawing up dosing solution for first time each syringe was used. The dosing volume for RMP1-14=10 mL/kg (0.200 mL/20 g mouse), and volume was adjusted accordingly for body weight.

Figure 11A:
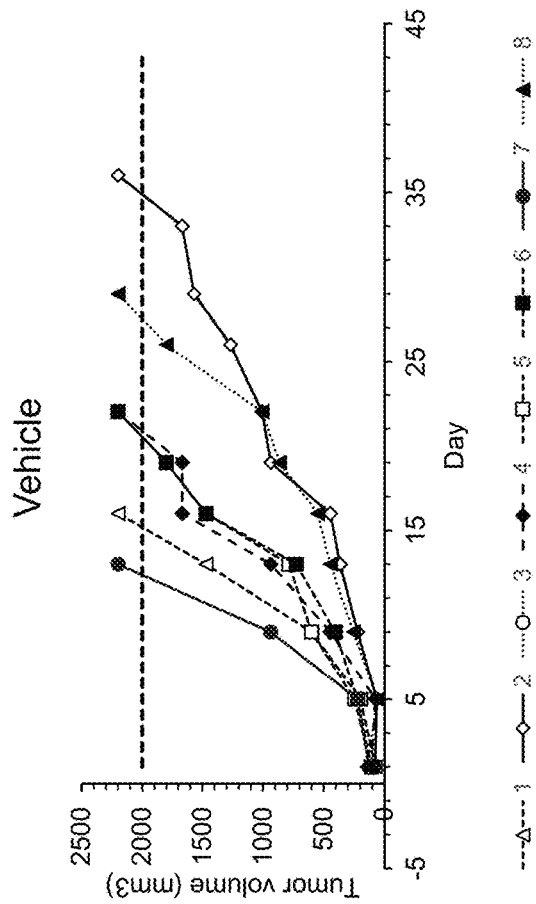
FIG. 11A-FIG. 11E show tumor regression as measured by tumor volume ($mm^3$) in a syngeneic Cloudman S91 melanoma cancer mouse models after treatment with vehicle (FIG. 11A), AAV2-IL12 (FIG. 11B and FIG. 11E), an anti-PD-1 antibody (FIG. 11C), or AAV2-IL12 ($1 \times 10^{11}$ viral genomes) and an anti-PD-1 antibody (FIG. 11D). AAV2-IL12 was administered at dosages of $1 \times 10^{11}$ viral genomes (FIG. 11B) and $3 \times 10^{10}$ viral genomes (FIG. 11E). Each line represents an individual mouse. Horizontal dashed line (-----) represents a maximum tumor volume (animals are euthanized once this volume is exceeded). The x-axis represents the number of days after treatment (0, 5, 10, 15, 20, 25, 30, 35, 40, and 45 days).
Figure 11B:
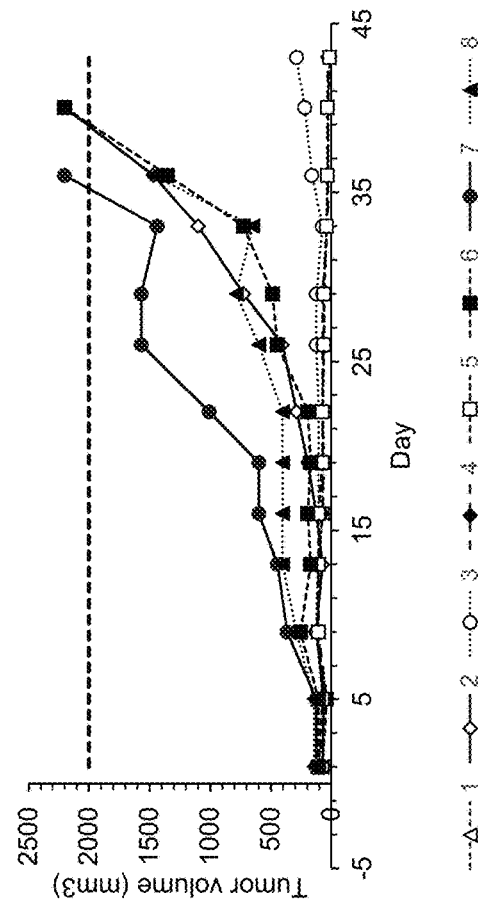
Figure 11C:
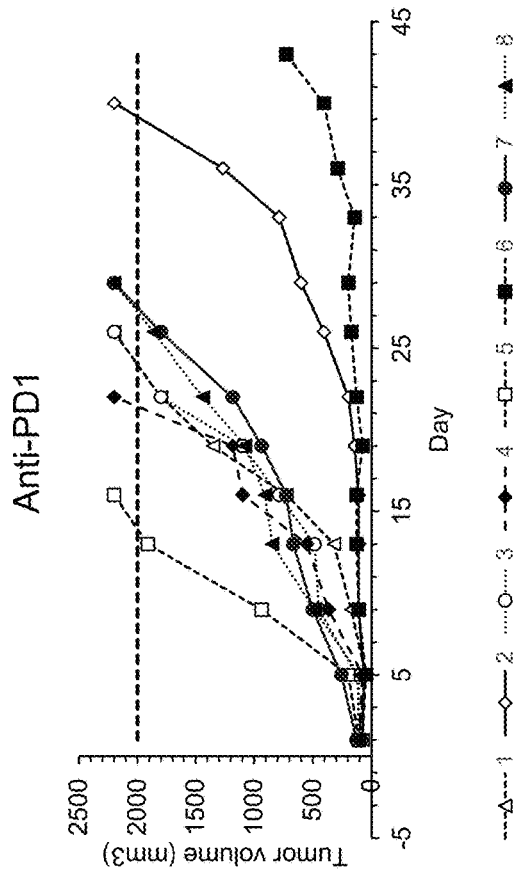
Figure 11D:
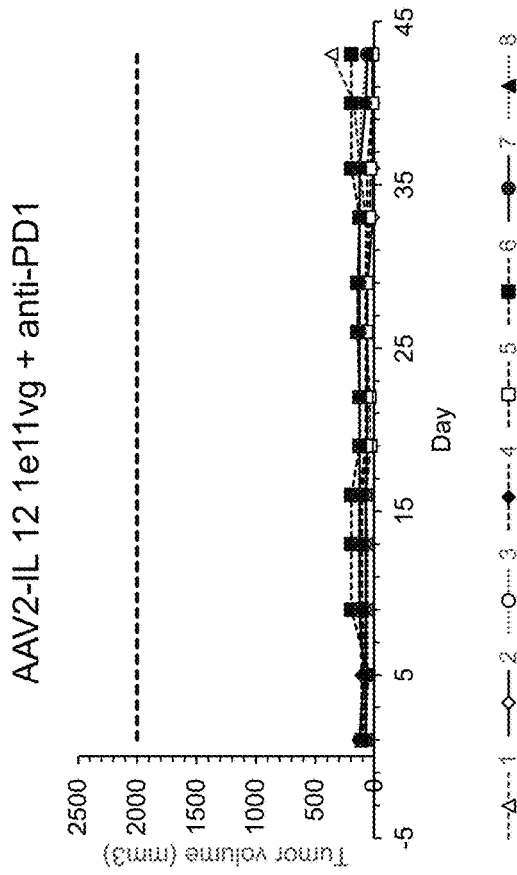
Figure 11E:
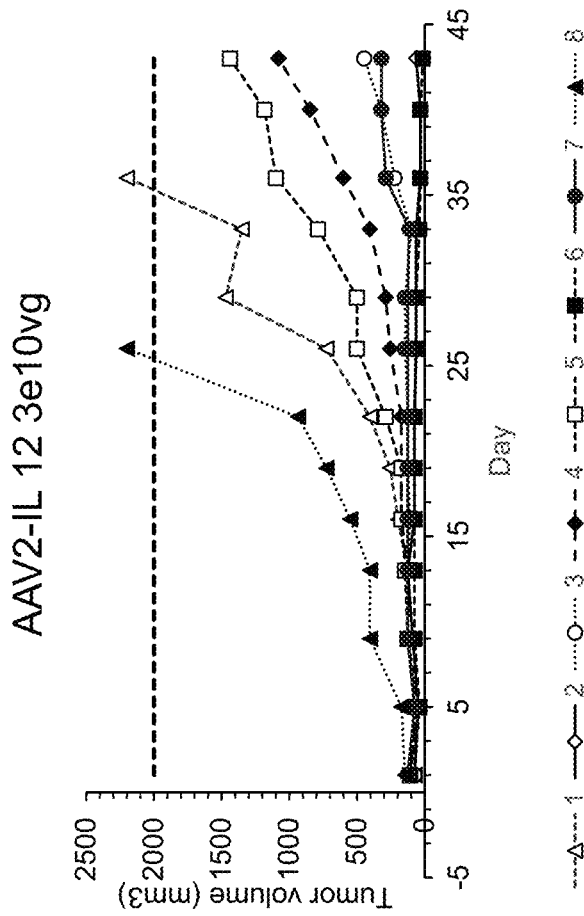

Tumor regression was measured by tumor volume in Cloudman S91 melanoma cancer models after treatment with vehicle (FIG. 11A), AAV2-IL12 (FIG. 11B and FIG. 11E), RMP1-14 (FIG. 11C), or AAV-IL12 and RMP1-14 combination therapy (FIG. 11D). Vehicle treated animals showed tumor growth consistent with historical data. AAV2-IL12 treated animals were sensitive to IL12 alone at both doses of 1×10$^{11}$ viral genomes (FIG. 11B) and 3×10$^{10}$ viral genomes (FIG. 11E), showing decreased tumor volume. Animals treated with RMP1-14 showed a heterogenous response, consistent with historical data. AAV2-IL12 and RMP1-14 treated animals showed the best response, displaying that the combination treatment was superior to a single agent therapy. No meaningful negative impact on body weight was observed with AAV2-IL12 alone or in combination with RMP1-14 (FIG. 20C).

Figure 12A:
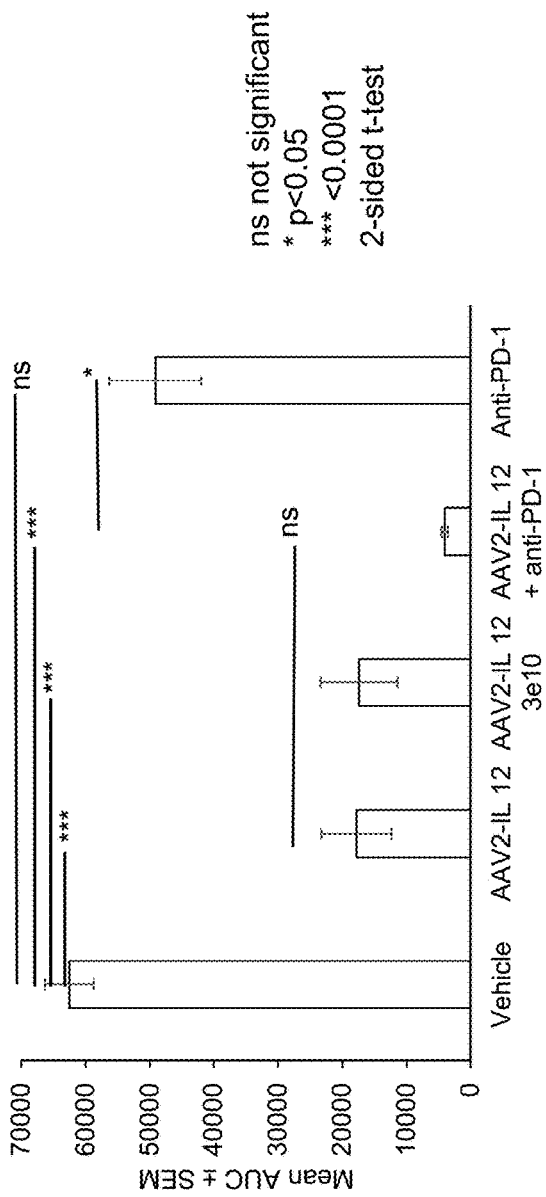
FIG. 12A and FIG. 12B show tumor regression as measured by mean area under the curve (AUC) (FIG. 12A) or by median area under the curve (AUC) (FIG. 12B) of tumor growth in a syngeneic Cloudman S91 melanoma cancer model a syngeneic after treatment with vehicle, AAV2-IL12 at a dose of $1 \times 10^{11}$ viral genomes, AAV2-IL12 at a dose of $3 \times 10^{10}$ viral genomes, AAV2-IL12 and an anti-PD-1 antibody, or an anti-PD-1 antibody.
Figure 12B:
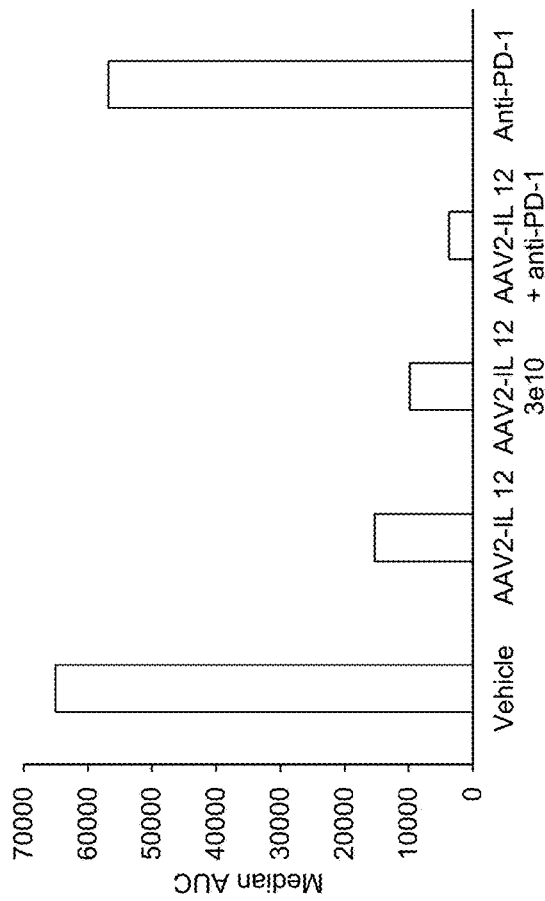

Tumor regression was also measured by both mean area under the curve (FIG. 12A) and median area under the curve (FIG. 12B) of tumor growth in Cloudman S91 melanoma cancer mouse models after treatment with vehicle, AAV- IL12, AAV-IL12 and RMP1-14, or RMP1-14 alone. antibody. Treatment with AAV2-IL-12 at both 1E11 and 3E10 doses, as well as the combination of AAV2-IL12+RMP1-14 all resulted in significantly reduced AUC relative to vehicle and RMP1-14 alone, (p=0.01). However, AAV2-IL-12 at both 1E11 and 3E10 doses and AAV2-IL12+RMP1-14 were not significantly different from one another. (FIG. 12A).

A significant difference was observed between animals treated with RMP1-14 and animals treated with AAV2-IL12 alone. Animals treated with AAVL2-IL12 and RMP1-14 combination therapy had the lowest AUC, but the results were not significantly different from AAVL2-IL12 treatment alone.

Overall survival was also measured in Cloudman S91 melanoma cancer mouse models after treatment with vehicle, AAV-IL12, AAV-IL12 and RMP1-14, or RMP1-14 alone (FIG. 18). RMP1-14 therapy had a minor improvement in overall survival. 100% of the mice that received AAV2-IL12 alone, and AAV2-IL12 in combination with RMP1-14 remained alive at the end of the study.

Example 5: In Vivo Evaluation of AAV2-IL12 and an Anti-PD-1 Antibody Therapy in Hepa1-6 Hepatocellular Carcinoma Models The anti-tumor efficacy of the AAV2-IL2 (AAV2-CAG-mIL12a-F2A-mIL12b-hgh PA) treatment alone and in combination with an anti-PD-1 antibody (RMP1-14) therapy was evaluated in the Hepatocellular Carcinoma (HCC) mouse model Hepa1-6 in female C57BL/6 mice. The study design is shown in Table 13 for vehicle, AAV2-IL12, RMP1-14, or a combination of AAV2-IL12 and RMP1-14.

TABLE 13

Study Design for Hepa1-6

| | |
|---|---|
| Model(s) | Hepa1-6 |
| Strain(s) | C57BL/6 |
| Number of mice on study | 32 |
| Number of groups | 4 |
| N per group | 8 |
| Inoculation | SubQ-Hind Right Flank |
| Dosing regimen | Single (AAV)/BIW × 3 (PD-1) |
| Dosing route | Intratumoral (AAV)/ Intraperitoneal (RMP1-14) |
| Dosing duration | 3 weeks (PD-1) |
| BW and TV measurement frequency | 2×/week |
| Randomization range | 80-120 mm3 |
| Dietary supplements | Body Weight Loss of >10%, all in group |
| Dosing holiday (PD-1) | Body Weight Loss of >20%, individual mouse |

TABLE 13-continued

Study Design for Hepa1-6

| | |
|---|---|
| Tissue collections | Blood (cheek) Weeks: −1, 2, 4 Tumor (IHC) |
| Maximal tumor volume (MTV) | 3000 mm$^3$ |

Tumor cell preparation, tumor implantation, tumor measurement, randomization and dose selection, study termination, body weight measurements, clinical observations, dosing holiday for an anti-PD-1 treatment, supplemental gel recovery administration, and tissue collection were preformed as described above in Example 2.

Tumor regression was measured by tumor volume in Hepa1-6 hepatocellular cancer models after treatment with vehicle (FIG. 13A), AAV2-IL12 (FIG. 13B), an anti-PD-1 antibody (FIG. 13C), or AAV-IL12 and an anti-PD-1 antibody (FIG. 13D). Tumor regression was also measured by both mean area under the curve (FIG. 13E) and median area under the curve (FIG. 13F) of tumor growth in Hepa1-6 hepatocellular mouse models after treatment with vehicle, AAV-IL12, AAV-IL12 and RMP1-14, or RMP1-14 alone. AAV2-IL12+RMP1-14 resulted in lower AUC relative to anti-PD-1 antibody alone, but the effect was not statistically significant. (FIG. 13E).

Figure 20E:
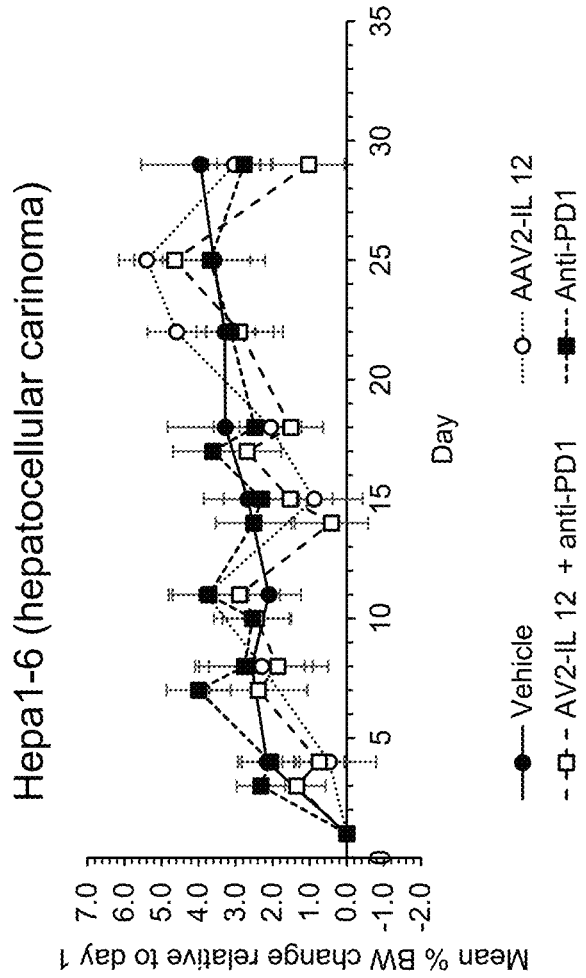

No meaningful impact on body weight was observed with AAV2-IL12 alone or in combination with RMP1-14 (FIG. 20E).

Example 6: In Vivo Evaluation of AAV2-IL12 and an Anti-PD-1 Antibody Therapy in B16F10 Melanoma Mouse Models The anti-tumor efficacy of AAV2-IL12 (AAV2-CAG-mIL12a-F2A-mIL12b-hgh PA) vectors in B16F10 melanoma cancer models was demonstrated using female B6D2F1 mice. The study was designed as shown in Table 14.

TABLE 14

Study Design for B16F10 melanoma.

| Gr. | N | Agent | Active dose | Route | Schedule |
|---|---|---|---|---|---|
| 1[#] | 8 | vehicle | n/a | intra-tumoral | day 1 |
| 2 | 8 | AAV2-IL12 | 1E + 11 vg/mouse | intra-tumoral | day 1 |
| 3 | 8 | AAV2-IL12 | 3E + 10 vg/mouse | intra-tumoral | day 1 |
| 4 | 8 | AAV2-IL12// anti-PD-1 RMP1-14 | 1E + 11 vg/mouse// 5 mg/kg | intra-tumoral// intraperitoneal | day 1// biwk × 2 |
| 5 | 8 | anti-PD-1 RMP1-14 | 5 mg/kg | intraperitoneal | biwk × 2 |

[#]control group

CR female B6D2F1 mice were subcutaneously injected with 5×10$^5$ B16F10 tumor cells in 0% Matrigel (total cell injection volume=0.1 mL/mouse) in flank. Mice were 8 to 12 weeks old at the start date. A pair match was performed when tumors reached an average size of 60-90 mm$^3$, and treatment began.

Body weight was measured daily for five days, then twice a week until the end of the study. Tumors were measured by calipers twice a week to the end of the study. Any adverse reactions or deaths were reported immediately. Any individual animal with a single observation of greater than 30% body weight loss or three consecutive measurements of greater than 25% body weight loss was euthanized. Any group with a mean body weight loss of greater than 20% or greater than 10% mortality stopped receiving dosing. The group was not euthanized and recovery was allowed. Within a group with greater than 20% weight loss, individuals that hit the individual body weight loss endpoint were euthanized. If the group treatment related body weight loss was recovered to within 10% of the original weights, dosing was resumed at a lower dose or less frequent dosing schedule. Exceptions to non-treatment body weight percent recovery were allowed on a case-by-case basis.

Animals were monitored individually. The endpoint of the experiment was a tumor volume of 2000 mm$^3$ or 29 days, whichever came first. Responders were followed longer. When the endpoint was reached, the animals were euthanized.

AAV2-IL12 vectors were provided in 5% Sorbitol+elevated 350 mM NaCl in PBS. Vehicle was provided in 5% Sorbitol+elevated 350 mM NaCl in PBS. The dosing volume for vehicle and the AAV2-IL12 vectors were 0.025 mL/mouse, and volume was not adjusted for body weight. AAV-IL12 vector dosing syringes were prewet with vehicle buffer prior to drawing up dosing solution for first time each syringe was used. The dosing volume for anti-PD-1 antibody (RMP1-14)=10 mL/kg (0.200 mL/20 g mouse), and volume was adjusted accordingly for body weight.

Tumor regression was measured by tumor volume (mm$^3$) in B16F10 melanoma cancer models after treatment with vehicle (FIG. 14A), AAV2-IL12 (FIG. 14B), RMP1-14 (FIG. 14C), or AAV-IL12 and RMP1-14 (FIG. 14D). Vehicle treated animals showed tumor growth consistent with historical data. AAV2-IL12 treated animals showed modest delayed tumor growth. RMP1-14 treated animals showed that B16F10 was refractory to RMP1-14, which was consistent with literature. Animals treated with a combination of AAV2-IL12 and RMP1-14 showed heterogenous response, with 5 out of 8 samples showing delayed tumor growth. No meaningful impact on body weight was observed with AAV2-IL12 alone or in combination with RMP1-14 (FIG. 20B).

Tumor regression was also measured by both mean area under the curve (FIG. 15A) and median area under the curve (FIG. 15B) of tumor growth in B16F10 melanoma cancer models after treatment with vehicle, AAV-IL12, AAV-IL12 and RMP1-14, or RMP1-14. AAV2-IL-12+ an anti-PD-1 antibody combination treatment resulted in slightly decreased AUC relative to control and all other treatments, but the effect was not statistically significant. (FIG. 15A).

Overall survival of B16F10 melanoma cancer models after treatment with vehicle, AAV-IL12, AAV-IL12 and RMP1-14, or RMP1-14 alone was analyzed (FIG. 19). B16F10 melanoma was refractory to treatment with RMP1-14 alone, which is consistent with historical data in this melanoma model. Finally, AAV2-IL12 alone had an effect on overall survival and the combination of AAV2-IL12 and an anti-PD1 antibody therapy led to an improvement in overall survival.

Example 7. In Vivo Evaluation of AAV2-IL12 Tolerability after Intravenous Injection In order to determine tolerability of AAV2-IL12 (AAV2-CAG-mIL12a-F2A-mIL12b-hgh PA) in normal mice, mice were intravenously administered AAV-IL12 in escalated doses (1× 10$^9$ viral genomes, 1×10$^{10}$ viral genomes, or 1×10$^{11}$ viral genomes) or control. The escalated doses represented escape of the vector after intratumoral injection. The 1×10$^9$ viral genome dose represents 1% of the dose used in efficacy studies, the 1×10$^{10}$ viral genome dose represents 10% of the dose used in efficacy studies, and the 1×10$^{11}$ viral genome dose is equivalent to the dose used in the efficacy studies. Two weeks after AAV2-IL12 was administered to the normal mice, there was no notable adverse clinical observations and no change in body weight (FIG. 21).

Example 8: In Vitro Evaluation of IL-12 Expression

HEK-293 cells were transduced at an MOI of either 3.0E4, 1.0E5, or 3.0E5 GC/cell of either AAV2 vector #1 (AAV2-CAG-mIL12a-IRES-mIL12b-bgh PA) or AAV2 vector #2 (AAV2-CAG-mIL12a-F2A-mIL12b-hgh PA). 48 hours post transduction media was collected from each well for supernatant evaluation. IL-12 ELISA assay was performed using 48 hour supernatant with the IL-12 ELISA Kit (Abcam, Cat #ab119531). IL-12 concentration was measured according to the manufacturer's instructions.

In Vitro IL-12 Functional Assay.

48-hour supernatant was diluted to 100 ng/ml IL-12 based on ELISA quantification results. HEK-Blue IL-12 Reporter Cells (InvivoGen, Cat #hkb-il12) were cultured according to the manufacturer's instructions. Cells were dispensed into wells preloaded with positive control (0.5 ng, 1 ng, 2 ng and 4 ng), 20 ul of diluted 48 hour supernatant, or 20 ul negative control (supernatant from untransduced cells). Cells were cultured for 24 hours. Following 24-hour culture, Quanti-Blue medium was prepared using Quanti-Blue Solution (InvivoGen, Cat #rep-qbs) according to the manufacturer's instruction. Supernatant from HEK-Blue IL-12 cells was added to wells preloaded with Quanti-Blue medium and incubated for up to 6 hours at 37 C. Optical density (OD) at 650 nm was measured using a microplate reader. Both AAV2 vector #1 (AAV2-CAG-mIL12a-IRES-mIL12b-bgh PA) or AAV2 vector #2 (AAV2-CAG-mIL12a-F2A-mIL12b-hgh PA) produced functional IL-12 (see FIG. 22).

Example 9. Construction of an AAV2-hIL12 Vector

An AAV2 vector was designed to drive expression of a human IL12A subunit and a human IL12B subunit. The AAV2 vector was engineered to include a construct including AAV2 ITRs flanking an expression cassette including a CMV enhancer, CBA promoter, CAG intron, a human IL12A wild-type coding sequence without an in-frame stop codon (SEQ ID NO: 77), a furin cleavage sequence, a 2A self-processing peptide sequence, a human IL12B wild-type coding sequence with a stop codon (SEQ ID NO: 8), and a human growth hormone PolyA site (AAV2-CAG-hIL12a-F2A-hIL12b-hgh PA).

The construct for human studies, based on the mouse study construct (AAV2-CAG-mIL12a-F2A-mIL12b-hgh PA) described above (see also FIG. 23A), was prepared. The resulting human study construct (AAV2-CAG-hIL12a-F2A-hIL12b-hgh PA) is shown in FIG. 23B and Table 5, and the construct has a nucleic acid sequence that corresponds to SEQ ID NO: 82.

What is claimed is:

1. A combination therapy comprising: (a) a first composition comprising an adeno-associated virus (AAV) vector comprising a polynucleotide comprising (i) a promoter, (ii) a first nucleic acid encoding a first Interleukin-12 (IL-12) subunit or functional fragment thereof, (iii) a translation modification sequence, (iv) a second nucleic acid encoding a second IL-12 subunit or functional fragment thereof, (v) a poly(A) (pA) sequence, and (vi) two inverted terminal repeat (ITR) sequences; and (b) a second composition comprising a checkpoint inhibitor, wherein the first nucleic acid comprises SEQ ID NO: 77 and the second nucleic acid comprises SEQ ID NO: 8.

2. The combination therapy of claim 1, wherein the AAV vector is an AAV serotype 2 (AAV2) vector.

3. The combination therapy of claim 1, wherein the translation modification sequence comprises a furin cleavage sequence, a 2A self-processing peptide sequence, an internal ribosomal entry site (IRES) sequence, or any combination thereof.

4. The combination therapy of claim 3, wherein the translation modification sequence comprises a furin cleavage sequence and a 2A self-processing peptide sequence (F2A).

5. The combination therapy of claim 1, wherein the promoter comprises a CBA promoter, a CMV promoter, an EF-1a (Elongation Factor 1a) promoter, a RSV (Rous Sarcoma Virus) promoter, an Ubiquitin (UbC) promoter, a CAG promoter, or any combination thereof.

6. The combination therapy of claim 1, wherein the checkpoint inhibitor comprises an inhibitor for programmed cell death protein 1 (PD-1), programmed death-ligand 1 (PD-L1), cytotoxic T-lymphocyte-associated protein 4 (CTLA-4), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, CD73, inducible T-cell costimulatory (ICOS), B7-H3, or any combination thereof.

7. The combination therapy of claim 1, wherein the checkpoint inhibitor comprises a programmed cell death protein 1 (PD-1) inhibitor.

8. The combination therapy of claim 7, wherein the PD-1 inhibitor is an anti-PD-1 antibody.

9. The combination therapy of claim 1, wherein the first IL-12 subunit comprises SEQ ID NO: 80 and the second IL-12 subunit comprises SEQ ID NO: 81.

10. The combination therapy of claim 1, wherein the polynucleotide comprises a nucleic acid sequence having at least 85%, 90%, 95%, 96%, 97%, 98%, 99%, or 100% identity to SEQ ID NO: 82.

11. The combination therapy of claim 1, wherein the first composition is suitable for an intratumoral delivery and the second composition is suitable for an intravenous delivery.

12. A composition comprising: (a) a polynucleotide comprising (i) a promoter, (ii) a first nucleic acid encoding a first Interleukin-12 (IL-12) subunit or functional fragment thereof, (iii) a translation modification sequence, (iv) a second nucleic acid encoding a second Interleukin-12 (IL-12) subunit or functional fragment thereof, and (v) two inverted terminal repeat (ITR) sequences, and (b) an AAV vector, wherein the polynucleotide is packaged in the AAV vector, and wherein the first nucleic acid comprises SEQ ID NO: 77 and the second nucleic acid comprises SEQ ID NO: 8.

13. The composition of claim 12, wherein the AAV vector is an AAV serotype 2 (AAV2) vector.

14. A composition comprising (a) a polynucleotide comprising a CAG promoter operably linked to a first nucleic acid encoding an IL-12 p35 subunit or a functional fragment thereof, a furin cleavage sequence followed by a 2A self-processing peptide (F2A) sequence, a second nucleic acid encoding an IL-12 p40 subunit or a functional fragment thereof, a growth hormone pA sequence, and two inverted terminal repeat (ITR) sequences; and (b) an AAV vector comprising an AAV capsid suitable for intratumoral delivery; wherein the polynucleotide is packaged in the AAV vector, wherein the CAG promoter comprises a CMV enhancer, a CBA promoter, and a CAG intron sequence, and wherein the first nucleic acid comprises SEQ ID NO: 77 and the second nucleic acid comprises SEQ ID NO: 8.

15. A polynucleotide comprising SEQ ID NO: 77 or SEQ ID NO: 8, or a combination thereof.

* * * * *

SEQUENCE LISTING

<160> NUMBER OF SEQ ID NOS: 92

<210> SEQ ID NO 1
<211> LENGTH: 4
<212> TYPE: PRT
<213> ORGANISM: Artificial Sequence
<220> FEATURE:
<223> OTHER INFORMATION: Proteolytic furin cleavage site
<220> FEATURE:
<221> NAME/KEY: MISC_FEATURE
<222> LOCATION: (2)..(2)
<223> OTHER INFORMATION: Wherein Xaa is a naturally occuring amino acid
<220> FEATURE:
<221> NAME/KEY: MISC_FEATURE
<222> LOCATION: (3)..(3)
<223> OTHER INFORMATION: Wherein Xaa can be either Lys or Arg

<400> SEQUENCE: 1

Arg Xaa Xaa Arg
1

<210> SEQ ID NO 2
<211> LENGTH: 9
<212> TYPE: DNA
<213> ORGANISM: Artificial Sequence
<220> FEATURE:
<223> OTHER INFORMATION: Kozak consensus sequence

<400> SEQUENCE: 2 gccgccatg                                                                  9

<210> SEQ ID NO 3
<211> LENGTH: 12
<212> TYPE: DNA
<213> ORGANISM: Artificial Sequence
<220> FEATURE:
<223> OTHER INFORMATION: Kozak consensus sequence

<400> SEQUENCE: 3
gcggccgcca tg                                                             12

<210> SEQ ID NO 4
<211> LENGTH: 9
<212> TYPE: RNA
<213> ORGANISM: Artificial Sequence
<220> FEATURE:
<223> OTHER INFORMATION: Kozak consensus sequence
<220> FEATURE:
<221> NAME/KEY: misc_feature
<222> LOCATION: (3)..(3)
<223> OTHER INFORMATION: Wherein N can be either adenine or guanine

<400> SEQUENCE: 4 ccnccaugg                                                                  9

<210> SEQ ID NO 5
<211> LENGTH: 660
<212> TYPE: DNA
<213> ORGANISM: Artificial Sequence
<220> FEATURE:
<223> OTHER INFORMATION: Human IL-12A (p35) ("wild-type" no CpG
      modification)

<400> SEQUENCE: 5
atgtgtccag cgcgcagcct cctccttgtg gctaccctgg tcctcctgga ccacctcagt      60
ttggccagaa acctccccgt ggccactcca gacccaggaa tgttcccatg ccttcaccac     120 tcccaaaaacc tgctgagggc cgtcagcaac atgctccaga aggccagaca aactctagaa    180

```
ttttacccctt gcacttctga agagattgat catgaagata tcacaaaaga taaaaccagc    240
acagtggagg cctgtttacc attggaatta accaagaatg agagttgcct aaattccaga    300
gagacctctt tcataactaa tgggagttgc ctggcctcca gaaagacctc ttttatgatg    360
gccctgtgcc ttagtagtat ttatgaagac ttgaagatgt accaggtgga gttcaagacc    420
atgaatgcaa agcttctgat ggatcctaag aggcagatct ttctagatca aaacatgctg    480
gcagttattg atgagctgat gcaggccctg aatttcaaca gtgagactgt gccacaaaaa    540
tcctcccttg aagaaccgga tttttataaa actaaaatca agctctgcat acttcttcat    600
gctttccgga ttcgggcagt gactattgat agagtgatga gctatctgaa tgcttcctga    660
```

<210> SEQ ID NO 6
<211> LENGTH: 660
<212> TYPE: DNA
<213> ORGANISM: Artificial Sequence
<220> FEATURE:
<223> OTHER INFORMATION: Human IL-12A (p35) (with CpG modification)

<400> SEQUENCE: 6

```
atgtgtccag cgcgcagcct cctccttgtg gctaccctgg tcctcctgga ccacctcagt     60
ttggccagaa acctccctgt ggccactcca gacccaggaa tgttcccatg ccttcaccac    120 tcccaaaaacc tgctgagggc tgtcagcaac atgctccaga aggccagaca aactctagaa    180 ttttacccctt gcacttctga agagattgat catgaagata tcacaaaaga taaaaccagc    240
acagtggagg cctgtttacc attggaatta accaagaatg agagttgcct aaattccaga    300
gagacctctt tcataactaa tgggagttgc ctggcctcca gaaagacctc ttttatgatg    360
gccctgtgcc ttagtagtat ttatgaagac ttgaagatgt accaggtgga gttcaagacc    420
atgaatgcaa agcttctgat ggatcctaag aggcagatct ttctagatca aaacatgctg    480
gcagttattg atgagctgat gcaggccctg aatttcaaca gtgagactgt gccacaaaaa    540
tcctcccttg aagaaccga tttttataaa actaaaatca agctctgcat acttcttcat    600
gctttccgga ttcgcgcagt gactattgat agagtgatga gctatctgaa tgcttcctga    660
```

<210> SEQ ID NO 7
<211> LENGTH: 660
<212> TYPE: DNA
<213> ORGANISM: Artificial Sequence
<220> FEATURE:
<223> OTHER INFORMATION: Human IL-12A (p35) (with CpG modification)

<400> SEQUENCE: 7

```
atgtgtccag ctaggagcct cctccttgtg gctaccctgg tcctcctgga ccacctcagt     60
ttggccagaa acctccctgt ggccactcca gacccaggaa tgttcccatg ccttcaccac    120 tcccaaaaacc tgctgagggc agtcagcaac atgctccaga aggccagaca aactctagaa    180 ttttacccctt gcacttctga agagattgat catgaagata tcacaaaaga taaaaccagc    240
acagtggagg cctgtttacc attggaatta accaagaatg agagttgcct aaattccaga    300
gagacctctt tcataactaa tgggagttgc ctggcctcca gaaagacctc ttttatgatg    360
gccctgtgcc ttagtagtat ttatgaagac ttgaagatgt accaggtgga gttcaagacc    420
atgaatgcaa agcttctgat ggatcctaag aggcagatct ttctagatca aaacatgctg    480
gcagttattg atgagctgat gcaggccctg aatttcaaca gtgagactgt gccacaaaaa    540
```

```
tcctcccttg aagaacctga tttttataaa actaaaatca agctctgcat acttcttcat    600
gctttccgga ttagggcagt gactattgat agagtgatga gctatctgaa tgcttcctga    660
```

<210> SEQ ID NO 8
<211> LENGTH: 987
<212> TYPE: DNA
<213> ORGANISM: Artificial Sequence
<220> FEATURE:
<223> OTHER INFORMATION: Human IL-12B (p40) ("wild-type" no CpG
      modification and with stop codon)

<400> SEQUENCE: 8

```
atgtgtcacc agcagttggt catctcttgg tttccctgg ttttctggc atctcccctc      60 gtggccatat gggaactgaa gaaagatgtt tatgtcgtag aattggattg gtatccggat   120
gcccctggag aaatggtggt cctcacctgt gacacccctg aagaagatgg tatcacctgg   180
accttggacc agagcagtga ggtcttaggc tctggcaaaa ccctgaccat ccaagtcaaa   240
gagtttggag atgctggcca gtacacctgt cacaaaggag gcgaggttct aagccattcg   300
ctcctgctgc ttcacaaaaa ggaagatgga atttggtcca ctgatatttt aaaggaccag   360
aaagaaccca aaataagac ctttctaaga tgcgaggcca gaattattc tggacgtttc   420 acctgctggt ggctgacgac aatcagtact gatttgacat tcagtgtcaa agcagcaga   480 ggctcttctg accccaaagg ggtgacgtgc ggagctgcta cactctctgc agagagagtc   540 agagggaca caaggagta tgagtactca gtggagtgcc aggaggacag tgcctgccca   600 gctgctgagag agtctgcc cattgagtg atggtggatg ccgttcacaa gctcaagtat   660
gaaaactaca ccagcagctt cttcatcagg gacatcatca aacctgaccc acccaagaac   720
ttgcagctga agccattaaaa gaattctcgg caggtggagg tcagctggga gtaccctgac   780
acctggagta ctccacattc ctacttctcc ctgacattct gcgttcaagt ccagggcaag   840
agcaagagag aaaagaaaga tagagtcttc acggacaaga cctcagccac ggtcatctgc   900
cgcaaaaatg ccagcattag cgtgcgggcc caggaccgct actatagctc atcttggagc   960
gaatgggcat ctgtgccctg cagttga                                       987
```

<210> SEQ ID NO 9
<211> LENGTH: 986
<212> TYPE: DNA
<213> ORGANISM: Artificial Sequence
<220> FEATURE:
<223> OTHER INFORMATION: Human IL-12B (p40) (with CpG modification)

<400> SEQUENCE: 9

```
tgtgtcacca gcagttggtc atctcttggt ttccctggt ttttctggca tctccccttg     60
tggccatatg ggaactgaag aaagatgttt atgtggtaga attggattgg tatcctgatg   120
cccctggaga aatggtggtc ctcacctgtg acacccctga agaagatggt atcacctgga   180
ccttggacca gagcagtgag gtcttaggct ctggcaaaac cctgaccatc caagtcaaag   240
agtttggaga tgctggccag tacacctgtc acaaggagg ggaggttcta agccattccc   300
tcctgctgct tcacaaaaag gaagatggaa tttggtccac tgatatttta aaggaccaga   360
aagaacccaa aataagacc tttctaagat gtgaggccaa gaattattct ggaaggttca   420
cctgctggtg gctgactaca atcagtactg atttgacatt cagtgtcaaa agcagcagag   480
gctcttctga ccccaagggg gtgacatgcg gagctgctac actctctgca gagagagtca   540
gaggggacaa caaggagtat gagtactcag tggagtgcca ggaggacagt gcctgcccag   600
```

```
ctgctgagga gagtctgccc attgaggtga tggtggatgc ggttcacaag ctcaagtatg    660
aaaactacac cagcagcttc ttcatcaggg acatcatcaa acctgaccca cccaagaact    720
tgcagctgaa gccattaaag aattctaggc aggtggaggt cagctgggag taccctgaca    780
cctggagtac tccacattcc tacttctccc tgacattctg tgttcaagtc cagggcaaga    840
gcaagagaga aaagaaagat agagtcttca ctgacaagac ctcagccaca gtcatctgcc    900
gcaaaaatgc cagcatttca gtgcgggccc aggaccgcta ctatagctca tcttggtcag    960
aatgggcatc tgtgccctgc agttga                                        986
```

```
<210> SEQ ID NO 10
<211> LENGTH: 987
<212> TYPE: DNA
<213> ORGANISM: Artificial Sequence
<220> FEATURE:
<223> OTHER INFORMATION: Human IL-12B (p40) (with CpG modification)

<400> SEQUENCE: 10
atgtgtcacc agcagttggt catctcttgg tttttcctgg tttttctggc atctcccctt     60
gtggccatat gggaactgaa gaaagatgtt tatgtggtag aattggattg gtatcctgat    120
gcccctggag aaatggtggt cctcacctgt gacacccctg aagaagatgg tatcacctgg    180
accttggacc agagcagtga ggtcttaggc tctggcaaaa ccctgaccat ccaagtcaaa    240
gagtttggag atgctggcca gtacacctgt cacaaaggag gggaggttct aagccattcc    300
ctcctgctgc ttcacaaaaa ggaagatgga atttggtcca ctgatatttt aaaggaccag    360
aaagaaccca aaaataagac ctttctaaga tgtgaggcca agaattattc tggaaggttc    420
acctgctggt ggctgactac aatcagtact gatttgacat tcagtgtcaa agcagcaga    480 ggctcttctg accccaagg ggtgacatgt ggagctgcta cactctctgc agagagagtc    540 agagggaca acaaggagta tgagtactca gtggagtgcc aggaggacag tgcctgccca    600
gctgctgagg agagtctgcc cattgaggtg atggtggatg cagttcacaa gctcaagtat    660
gaaaactaca ccagcagctt cttcatcagg gacatcatca aacctgaccc acccaagaac    720
ttgcagctga agccattaaa gaattctagg caggtggagg tcagctggga gtaccctgac    780
acctggagta ctccacattc ctacttctcc ctgacattct gtgttcaagt ccagggcaag    840
agcaagagag aaaagaaaga tagagtcttc actgacaaga cctcagccac agtcatctgc    900
aggaaaaatg ccagcatttc agtgagggcc caggacagat actatagctc atcttggtca    960
gaatgggcat ctgtgccctg cagttga                                        987
```

```
<210> SEQ ID NO 11
<211> LENGTH: 489
<212> TYPE: DNA
<213> ORGANISM: Artificial Sequence
<220> FEATURE:
<223> OTHER INFORMATION: IL-15 ("wild-type" no CpG modification)

<400> SEQUENCE: 11
atgagaattt cgaaaccaca tttgagaagt atttccatcc agtgctactt gtgtttactt     60
ctaaacagtc attttctaac tgaagctggc attcatgtct cattttgggc tgtttctct    120 gcagggcttc ctaaaacaga agccaactgg gtgaatgtaa taagtgattt gaaaaaaatt    180
gaagatctta ttcaatctat gcatattgat gctactttat atacggaaag tgatgttcac    240
cccagttgca aagtaacagc aatgaagtgc tttctcttgg agttacaagt atttcactt    300
```

```
gagtccggag atgcaagtat tcatgataca gtagaaaatc tgatcatcct agcaaacaac    360
agtttgtctt ctaatgggaa tgtaacagaa tctggatgca agaatgtga ggaactggag     420 gaaaaaaata ttaagaatt tttgcagagt tttgtacata ttgtccaaat gttcatcaac     480
acttcttga                                                            489

<210> SEQ ID NO 12
<211> LENGTH: 489
<212> TYPE: DNA
<213> ORGANISM: Artificial Sequence
<220> FEATURE:
<223> OTHER INFORMATION: IL-15(with CpG modification)

<400> SEQUENCE: 12
atgagaatta gcaaaccaca tttgagaagt atttccatcc agtgctactt gtgtttactt    60
ctaaacagtc attttctaac tgaagctggc attcatgtct tcattttggg ctgtttctct   120
gcagggcttc ctaaaacaga agccaactgg gtgaatgtaa taagtgattt gaaaaaaatt   180
gaagatctta ttcaatctat gcatattgat gctactttat atactgaaag tgatgttcac   240
cccagttgca aagtaacagc aatgaagtgc tttctcttgg agttacaagt tatttcactt   300
gagagcggag atgcaagtat tcatgataca gtagaaaatc tgatcatcct agcaaacaac   360
agtttgtctt ctaatgggaa tgtaacagaa tctggatgca agaatgtga ggaactggag    420 gaaaaaaata ttaagaatt tttgcagagt tttgtacata ttgtccaaat gttcatcaac   480
acttcttga                                                            489

<210> SEQ ID NO 13
<211> LENGTH: 489
<212> TYPE: DNA
<213> ORGANISM: Artificial Sequence
<220> FEATURE:
<223> OTHER INFORMATION: IL-15 (with CpG modification)

<400> SEQUENCE: 13
atgagaatta gcaaaccaca tttgagaagt atttccatcc agtgctactt gtgtttactt    60
ctaaacagtc attttctaac tgaagctggc attcatgtct tcattttggg ctgtttctct   120
gcagggcttc ctaaaacaga agccaactgg gtgaatgtaa taagtgattt gaaaaaaatt   180
gaagatctta ttcaatctat gcatattgat gctactttat atactgaaag tgatgttcac   240
cccagttgca aagtaacagc aatgaagtgc tttctcttgg agttacaagt tatttcactt   300
gagtcaggag atgcaagtat tcatgataca gtagaaaatc tgatcatcct agcaaacaac   360
agtttgtctt ctaatgggaa tgtaacagaa tctggatgca agaatgtga ggaactggag    420 gaaaaaaata ttaagaatt tttgcagagt tttgtacata ttgtccaaat gttcatcaac   480
acttcttga                                                            489

<210> SEQ ID NO 14
<211> LENGTH: 4554
<212> TYPE: DNA
<213> ORGANISM: Artificial Sequence
<220> FEATURE:
<223> OTHER INFORMATION: Human EF-1a -wild-type IL-12A/IL-12B/IL-15 -
      IRES (no CpG modification)

<400> SEQUENCE: 14
gtcgaccaca caaaaaacca acacacagat ctaatgaaaa taaagatctt ttattggcgc    60
gcctcaactg cagggcacag atgcccattc gctccaagat gagctatagt agcggtcctg   120
```

```
ggcccgcacg ctaatgctgg cattttttgcg gcagatgacc gtggctgagg tcttgtccgt    180
gaagactcta tctttctttt ctctcttgct cttgccctgg acttgaacgc agaatgtcag    240
ggagaagtag gaatgtggag tactccaggt gtcagggtac tcccagctga cctccacctg    300
ccgagaattc tttaatggct tcagctgcaa gttcttgggt gggtcaggtt tgatgatgtc    360
cctgatgaag aagctgctgg tgtagttttc atacttgagc ttgtgaacgg catccaccat    420
cacctcaatg ggcagactct cctcagcagc tgggcaggca ctgtcctcct ggcactccac    480
tgagtactca tactccttgt tgtcccctct gactctctct gcagagagtg tagcagctcc    540
gcacgtcacc ccttgggggt cagaagagcc tctgctgctt ttgacactga atgtcaaatc    600
agtactgatt gtcgtcagcc accagcaggt gaaacgtcca gaataattct tggcctcgca    660
tcttagaaag gtcttatttt tgggttcttt ctggtccttt aaaatatcag tggaccaaat    720
tccatcttcc tttttgtgaa gcagcaggag cgaatggctt agaacctcgc ctcctttgtg    780
acaggtgtac tggccagcat ctccaaactc tttgacttgg atggtcaggg ttttgccaga    840
gcctaagacc tcactgctct ggtccaaggt ccaggtgata ccatcttctt caggggtgtc    900
acaggtgagg accaccattt ctccaggggc atccggatac caatccaatt ctacgacata    960
aacatctttc ttcagttccc atatggccac gaggggagt gccagaaaaa ccagggaaaa   1020
ccaagagatg accaactgct ggtgacacat ggtggcggcg cgccatttaa atctagcctt   1080
aagagctgta attgaactgg gagtggacac ctgtggagag aaaggcaaag tggatgtcag   1140
taagaccaat aggtgcctat cagaaacgca agagtcttct ctgtctcgac aagcccagtt   1200
tctattggtc tccttaaacc tgtcttgtaa ccttgatact tacctgccca gtgcctcacg   1260
accaacttcg atctgtaacg gcgcagaaca gaaaacgaaa caaagacgta gagttgagca   1320
agcagggtca gcaaagcgt ggagagccgg ctgagtctag gtaggctcca agggagcgcc   1380
ggacaaaggc ccggtctcga cctgagcttt aaacttacct agacggcgga cgcagttcag   1440
gaggcaccac aggcgggagg cggcagaacg cgactcaacc ggcgtggatg gcggcctcag   1500
gtagggcggc gggcgcgtga aggagagatg cgagcccctc gaagcttcag ctgtgttctg   1560
gcggcaaacc cgttgcgaaa agaacgttc acggcgacta ctgcacttat atacggttct   1620
cccccaccct cgggaaaaag gcggagccag tacacgacat cactttccca gtttaccccg   1680
cgccaccttc tctaggcacc ggttcaattg ccgaccccctc cccccaactt ctcggggact   1740
gtgggcgatg tgcgctctgc ccactgacgg gcaccggagc gatcttaatt aactagttat   1800
taatagtaat caattacggg gtcattagtt catagcccat atatggagtt ccgcgttaca   1860
taacttacgg taaatggccc gcctggctga ccgcccaacg acccccgccc attgacgtca   1920
ataatgacgt atgttcccat agtaacgcca taggggactt tccattgacg tcaatgggtg   1980
gactatttac ggtaaactgc ccacttggca gtacatcaag tgtatcatat gccaagtacg   2040
ccccctattg acgtcaatga cggtaaatgg cccgcctggc attatgccca gtacatgacc   2100
ttatgggact ttcctacttg gcagtacatc tacgtattag tcatcgctat taccatgggt   2160
gatgcggttt tggcagtaca tcaatgggcg tggatagcgg tttgactcac ggggatttcc   2220
aagtctccac cccattgacg tcaatgggag tttgttttgg caccaaaatc aacgggactt   2280
tccaaaatgt cgtaacaact ccgccccatt gacgcaaatg ggcggtaggc gtgtacggtg   2340
ggaggtctat ataagcagag ctcgtttagt gaaccgtcag atcgcctgga gacgtcgagg   2400
aactgaaaaa ccagaaagtt aactggtaag tttagtcttt ttgtctttta tttcaggtcc   2460
cggatccggt ggtggtgcaa atcaaagaac tgctcctcag tggatgttgc ctttacttct   2520
```

```
aggcctgtac ggaagtgttt aaacttctgc tctgcggccg cgccaccatg tgtccagcgc    2580
gcagcctcct ccttgtggct accctggtcc tcctggacca cctcagtttg gccagaaacc    2640
tccccgtggc cactccagac ccaggaatgt tcccatgcct tcaccactcc caaaacctgc    2700
tgagggccgt cagcaacatg ctccagaagg ccagacaaac tctagaattt tacccttgca    2760
cttctgaaga gattgatcat gaagatatca caaaagataa aaccagcaca gtggaggcct    2820
gtttaccatt ggaattaacc aagaatgaga gttgcctaaa ttccagagag acctctttca    2880
taactaatgg gagttgcctg gcctccagaa agacctcttt tatgatggcc ctgtgcctta    2940
gtagtattta tgaagacttg aagatgtacc aggtggagtt caagaccatg aatgcaaagc    3000
ttctgatgga tcctaagagg cagatctttc tagatcaaaa catgctggca gttattgatg    3060
agctgatgca ggccctgaat ttcaacagtg agactgtgcc acaaaaatcc tcccttgaag    3120
aaccggattt ttataaaact aaaatcaagc tctgcatact tcttcatgct ttccggattc    3180
gggcagtgac tattgataga gtgatgagct atctgaatgc ttcctgagcc cctctccctc    3240 cccccccct aacgttactg gccgaagccg cttggaataa ggccggtgtg cgtttgtcta    3300
tatgttattt tccaccatat tgccgtcttt tggcaatgtg agggcccgga acctggccc    3360 tgtcttcttg acgagcattc ctaggggtct ttcccctctc gccaaaggaa tgcaaggtct    3420
gttgaatgtc gtgaaggaag cagttcctct ggaagcttct tgaagacaaa caacgtctgt    3480
agcgaccctt gcaggcagc ggaacccccc acctggcgac aggtgcctct gcggccaaaa    3540
gccacgtgta taagatacac ctgcaaaggc ggcacaaccc cagtgccacg ttgtgagttg    3600
gatagttgtg gaaagagtca aatggctctc ctcaagcgta ttcaacaagg gctgaagga    3660 tgcccagaag gtaccccatt gtatgggatc tgatctgggg cctcggtaca catgctttac    3720
atgtgtttag tcgaggttaa aaaaacgtct aggccccccg aaccacgggg acgtggtttt    3780
cctttgaaaa acacgatgat aatatggcca caatgagaat ttcgaaacca catttgagaa    3840
gtatttccat ccagtgctac ttgtgtttac ttctaaacag tcatttttcta actgaagctg    3900 gcattcatgt cttcattttg ggctgttct ctgcagggct tcctaaaaca gaagccaact    3960
gggtgaatgt aataagtgat tgaaaaaaa ttgaagatct tattcaatct atgcatattg    4020
atgctacttt atatacggaa agtgatgttc accccagttg caaagtaaca gcaatgaagt    4080
gctttctctt ggagttacaa gttatttcac ttgagtccgg agatgcaagt attcatgata    4140
cagtagaaaa tctgatcatc ctagcaaaca acagtttgtc ttctaatggg aatgtaacag    4200
aatctggatg caaagaatgt gaggaactgg aggaaaaaaa tattaaagaa tttttgcaga    4260
gttttgtaca tattgtccaa atgttcatca acacttcttg agcggccgcg ctagccaatt    4320
gctgtgcctt ctagttgcca gccatctgtt gtttgcccct ccccgtgcc ttccttgacc    4380 ctggaaggtg ccactcccac tgtccttcc taataaaatg aggaaattgc atcgcattgt    4440
ctgagtaggt gtcattctat tctgggggt ggggtgggc aggacagcaa ggggaggat    4500 tgggaagaca atagcaggca tgctgggat gcggtgggct ctatggagct cgag            4554
```

<210> SEQ ID NO 15  
<211> LENGTH: 4062  
<212> TYPE: DNA  
<213> ORGANISM: Artificial Sequence  
<220> FEATURE:  
<223> OTHER INFORMATION: Human EF-1a- wild-type IL-12A/IL-12B/IL-15 -  
    F2A (no CpG modification)

<400> SEQUENCE: 15

```
gtcgaccaca caaaaaacca acacacagat ctaatgaaaa taaagatctt ttattggcgc      60
gcctcaagaa gtgttgatga acatttggac aatatgtaca aaactctgca aaaattcttt     120
aatatttttt tcctccagtt cctcacattc tttgcatcca gattctgtta cattcccatt     180
agaagacaaa ctgttgtttg ctaggatgat cagattttct actgtatcat gaatacttgc     240
atctccggac tcaagtgaaa taacttgtaa ctccaagaga aagcacttca ttgctgttac     300
tttgcaactg gggtgaacat cactttccgt atataaagta gcatcaatat gcatagattg     360
aataagatct tcaattttt tcaaatcact tattacattc acccagttgg cttctgtttt      420
aggaagccct gcagagaaac agcccaaaat gaagacatga atgccagctt cagttagaaa     480
atgactgttt agaagtaaac acaagtagca ctggatggaa atacttctca aatgtggttt     540
cgaaattctc atggtggcgg cgcgccattt aaatctagcc ttaagagctg taattgaact     600
gggagtggac acctgtggag agaaaggcaa agtggatgtc agtaagacca ataggtgcct     660
atcagaaacg caagagtctt ctctgtctcg acaagcccag tttctattgg tctccttaaa     720
cctgtcttgt aaccttgata cttacctgcc cagtgcctca cgaccaactt cgatctgtaa     780
cggcgcagaa cagaaaacga acaaagacg tagagttgag caagcagggt caggcaaagc     840
gtggagagcc ggctgagtct aggtaggctc caagggagcg ccggacaaag gcccggtctc     900
gacctgagct ttaaacttac ctagacggcg gacgcagttc aggaggcacc acaggcggga     960
ggcggcagaa cgcgactcaa ccggcgtgga tggcggcctc aggtagggcg gcgggcgcgt    1020
gaaggagaga tgcgagcccc tcgaagcttc agctgtgttc tggcggcaaa cccgttgcga    1080
aaaagaacgt tcacggcgac tactgcactt atatacggtt ctcccccacc ctcgggaaaa    1140
aggcggagcc agtacacgac atcactttcc cagtttaccc cgcgccacct tctctaggca    1200
ccggttcaat tgccgacccc tcccccaac ttctcgggga ctgtgggcga tgtgcgctct    1260
gcccactgac gggcaccgga gcgatcttaa ttaactagtt attaatagta atcaattacg    1320
gggtcattag ttcatagccc atatatgag ttccgcgtta cataacttac ggtaaatggc    1380
ccgcctggct gaccgcccaa cgaccccgc ccattgacgt caataatgac gtatgttccc    1440
atagtaacgc caatagggac tttccattga cgtcaatggg tggactattt acggtaaact    1500
gcccacttgg cagtacatca agtgtatcat atgccaagta cgccccctat tgacgtcaat    1560
gacggtaaat ggcccgcctg gcattatgcc cagtacatga ccttatggga ctttcctact    1620
tggcagtaca tctacgtatt agtcatcgct attaccatgg gtgatgcggt tttggcagta    1680
catcaatggg cgtggatagc ggtttgactc acggggattt ccaagtctcc accccattga    1740
cgtcaatggg agtttgtttt ggcaccaaaa tcaacgggac tttccaaaat gtcgtaacaa    1800
ctccgcccca ttgacgcaaa tgggcggtag gcgtgtacgg tgggaggtct atataagcag    1860
agctcgttta gtgaaccgtc agatcgcctg gagacgtcga ggaactgaaa accagaaag    1920
ttaactggta agtttagtct ttttgtcttt tatttcaggt cccggatccg gtggtggtgc    1980
aaatcaaaga actgctcctc agtggatgtt gcctttactt ctaggcctgt acggaagtgt    2040
ttaaacttct gctctgcggc cgcgccacca tgtgtccagc gcgcagcctc ctccttgtgg    2100
ctaccctggt cctcctggac cacctcagtt tggccagaaa cctccccgtg gccactccag    2160
acccaggaat gttcccatgc cttcaccact cccaaaacct gctgagggcc gtcagcaaca    2220
tgctccagaa ggccagacaa actctagaat tttacccttg cacttctgaa gagattgatc    2280
```

```
atgaagatat cacaaaagat aaaaccagca cagtggaggc ctgtttacca ttggaattaa      2340
ccaagaatga gagttgccta aattccagag agacctcttt cataactaat gggagttgcc      2400
tggcctccag aaagacctct tttatgatgg ccctgtgcct tagtagtatt tatgaagact      2460
tgaagatgta ccaggtggag ttcaagacca tgaatgcaaa gcttctgatg gatcctaaga      2520
ggcagatctt tctagatcaa aacatgctgg cagttattga tgagctgatg caggccctga      2580
atttcaacag tgagactgtg ccacaaaaat cctcccttga agaaccggat ttttataaaa      2640
ctaaaatcaa gctctgcata cttcttcatg cttttccggat tcgggcagtg actattgata      2700
gagtgatgag ctatctgaat gcttccagaa agagaaggag tggctcagga gccctgtga      2760 aacagaccct gaactttgac ctcttgaagc ttgctgggga tgtggagtct aatcctggtc      2820
caatgtgtca ccagcagttg gtcatctctt ggttttccct ggttttttctg gcatctcccc      2880 tcgtggccat atgggaactg aagaaagatg tttatgtcgt agaattggat tggtatccgg      2940
atgcccctgg agaaatggtg gtcctcacct gtgacaccc tgaagaagat ggtatcacct      3000
ggaccttgga ccagagcagt gaggtcttag gctctggcaa aaccctgacc atccaagtca      3060 aagagttttgg agatgctggc cagtacacct gtcacaaagg aggcgaggtt ctaagccatt      3120
cgctcctgct gcttcacaaa aaggaagatg gaatttggtc cactgatatt ttaaaggacc      3180
agaaagaacc caaaaataag accttctaa gatgcgaggc caagaattat tctggacgtt      3240
tcacctgctg gtgctgacg acaatcagta ctgatttgac attcagtgtc aaaagcagca      3300
gaggctcttc tgaccccaa ggggtgacgt gcggagctgc tacactctct gcagagaga      3360 tcagagggga caacaaggag tatgagtact cagtggagtg ccaggaggac agtgcctgcc      3420
cagctgctga ggagagtctg cccattgagg tgatggtgga tgccgttcac aagctcaagt      3480
atgaaaacta caccagcagc ttcttcatca gggacatcat caaacctgac ccacccaaga      3540
acttgcagct gaagccatta aagaattctc ggcaggtgga ggtcagctgg gagtaccctg      3600
acacctggag tactccacat tcctacttct ccctgacatt ctgcgttcaa gtccagggca      3660
agagcaagag agaaaagaaa gatagagtct tcacggacaa gacctcagcc acggtcatct      3720
gccgcaaaaa tgccagcatt agcgtgcggg cccaggaccg ctactatagc tcatcttgga      3780
gcgaatgggc atctgtgccc tgcagttgag cggccgcgct agccaattgc tgtgccttct      3840
agttgccagc catctgttgt ttgccccctcc ccgtgccttt ccttgaccct ggaaggtgcc      3900
actcccactg tccttttccta ataaaatgag gaaattgcat cgcattgtct gagtaggtgt      3960
cattctattc tggggggtgg ggtggggcag gacagcaagg gggaggattg ggaagacaat      4020
agcaggcatg ctggggatgc ggtgggctct atggagctcg ag                        4062

<210> SEQ ID NO 16
<211> LENGTH: 4554
<212> TYPE: DNA
<213> ORGANISM: Artificial Sequence
<220> FEATURE:
<223> OTHER INFORMATION: Human EF-1a - modified IL-12A/IL-12B/IL-15 -
      IRES (with CpG modification)

<400> SEQUENCE: 16
gtcgaccaca caaaaaacca acacacagat ctaatgaaaa taaagatctt ttattggcgc        60
gcctcaactg cagggcacag atgcccattc tgaccaagat gagctatagt agcggtcctg       120
ggcccgcact gaaatgctgg cattttttgcg gcagatgact gtggctgagg tcttgtcagt       180
gaagactcta tctttctttt ctctcttgct cttgccctgg acttgaacac agaatgtcag       240
```

```
ggagaagtag gaatgtggag tactccaggt gtcagggtac tcccagctga cctccacctg    300
cctagaattc tttaatggct tcagctgcaa gttcttgggt gggtcaggtt tgatgatgtc    360
cctgatgaag aagctgctgg tgtagttttc atacttgagc ttgtgaaccg catccaccat    420
cacctcaatg ggcagactct cctcagcagc tgggcaggca ctgtcctcct ggcactccac    480
tgagtactca tactccttgt tgtcccctct gactctctct gcagagagtg tagcagctcc    540
gcatgtcacc ccttgggggt cagaagagcc tctgctgctt ttgacactga atgtcaaatc    600
agtactgatt gtagtcagcc accagcaggt gaaccttcca gaataattct tggcctcaca    660
tcttagaaag gtcttatttt tgggttcttt ctggtccttt aaaatatcag tggaccaaat    720
tccatcttcc tttttgtgaa gcagcaggag ggaatggctt agaacctccc ctcctttgtg    780
acaggtgtac tggccagcat ctccaaactc tttgacttgg atggtcaggg ttttgccaga    840
gcctaagacc tcactgctct ggtccaaggt ccaggtgata ccatcttctt cagggggtgtc    900 acaggtgagg accaccattt ctccaggggc atcaggatac caatccaatt ctaccacata    960
aacatctttc ttcagttccc atatggccac aaggggagat gccagaaaaa ccagggaaaa   1020
ccaagagatg accaactgct ggtgacacat ggtggcggcg cgccatttaa atctagcctt   1080
aagagctgta attgaactgg gagtggacac ctgtggagag aaaggcaaag tggatgtcag   1140
taagaccaat aggtgcctat cagaaacgca agagtcttct ctgtctcgac aagcccagtt   1200
tctattggtc tccttaaacc tgtcttgtaa ccttgatact tacctgccca gtgcctcacg   1260
accaacttcg atctgtaacg gcgcagaaca gaaaacgaaa caaagacgta gagttgagca   1320
agcagggtca ggcaaagcgt ggagagccgg ctgagtctag gtaggctcca agggagcgcc   1380
ggacaaaggc ccggtctcga cctgagcttt aaacttacct agacggcgga cgcagttcag   1440
gaggcaccac aggcgggagg cggcagaacg cgactcaacc ggcgtggatg gcggcctcag   1500
gtagggcggc gggcgcgtga aggagagatg cgagcccctc gaagcttcag ctgtgttctg   1560
gcggcaaacc cgttgcgaaa agaacgttc acggcgacta ctgcacttat atacggttct   1620 cccccacccct cgggaaaaag gcggagccag tacacgacat cactttccca gtttaccccg   1680
cgccaccttc tctaggcacc ggttcaattg ccgaccccctc cccccaactt ctcggggact   1740
gtgggcgatg tgcgctctgc ccactgacgg gcaccggagc gatcttaatt aactagttat   1800
taatagtaat caattacggg gtcattagtt catagcccat atatggagtt ccgcgttaca   1860
taacttacgg taaatggccc gcctggctga ccgcccaacg acccccgccc attgacgtca   1920
ataatgacgt atgttcccat agtaacgcca tagggacttt ccattgacg tcaatgggtg   1980 gactatttac ggtaaactgc ccacttggca gtacatcaag tgtatcatat gccaagtacg   2040 cccccctattg acgtcaatga cggtaaatgg cccgcctggc attatgccca gtacatgacc   2100
ttatgggact ttcctacttg gcagtacatc tacgtattag tcatcgctat taccatgggt   2160
gatgcggttt tggcagtaca tcaatgggcg tggatagcgg tttgactcac ggggatttcc   2220
aagtctccac cccattgacg tcaatgggag tttgttttgg caccaaaatc aacgggactt   2280
tccaaaatgt cgtaacaact ccgccccatt gacgcaaatg ggcggtaggc gtgtacggtg   2340
ggaggtctat ataagcagag ctcgtttagt gaaccgtcag atcgcctgga gacgtcgagg   2400
aactgaaaaa ccagaaagtt aactggtaag tttagtcttt ttgtcttta tttcaggtcc   2460 cggatccggt ggtggtgcaa atcaaagaac tgctcctcag tggatgttgc ctttacttct   2520
aggcctgtac ggaagtgttt aaacttctgc tctgcggccg cgccaccatg tgtccagcgc   2580
gcagcctcct ccttgtggct accctggtcc tcctggacca cctcagtttg gccagaaacc   2640
```

```
tccctgtggc cactccagac ccaggaatgt tcccatgcct tcaccactcc caaaacctgc    2700
tgagggctgt cagcaacatg ctccagaagg ccagacaaac tctagaattt taccccttgca   2760 cttctgaaga gattgatcat gaagatatca caaaagataa aaccagcaca gtggaggcct    2820
gtttaccatt ggaattaacc aagaatgaga gttgcctaaa ttccagagag acctctttca    2880
taactaatgg gagttgcctg gcctccagaa agacctcttt tatgatggcc ctgtgcctta    2940
gtagtattta tgaagacttg aagatgtacc aggtggagtt caagaccatg aatgcaaagc    3000
ttctgatgga tcctaagagg cagatctttc tagatcaaaa catgctggca gttattgatg    3060
agctgatgca ggccctgaat ttcaacagtg agactgtgcc acaaaaatcc tcccttgaag    3120
aacctgattt ttataaaact aaaatcaagc tctgcatact tcttcatgct ttccggattc    3180
gcgcagtgac tattgataga gtgatgagct atctgaatgc ttcctgagcc cctctccctc    3240
ccccccccct aacgttactg gccgaagccg cttggaataa ggccggtgtg cgtttgtcta    3300
tatgttattt tccaccatat tgccgtcttt tggcaatgtg agggcccgga acctggccc    3360 tgtcttcttg acgagcattc ctaggggtct ttcccctctc gccaaaggaa tgcaaggtct    3420
gttgaatgtc gtgaaggaag cagttcctct ggaagcttct tgaagacaaa caacgtctgt    3480
agcgaccctt tgcaggcagc ggaaccccc cctggcgac aggtgcctct gcggccaaaa    3540
gccacgtgta taagatacac ctgcaaaggc ggcacaaccc cagtgccacg ttgtgagttg    3600
gatagttgtg gaaagagtca aatggctctc ctcaagcgta ttcaacaagg ggctgaagga    3660
tgcccagaag gtaccccatt gtatgggatc tgatctgggg cctcggtaca catgctttac    3720
atgtgtttag tcgaggttaa aaaaacgtct aggccccccg aaccacgggg acgtggtttt    3780
cctttgaaaa acacgatgat aatatggcca caatgagaat tagcaaacca catttgagaa    3840
gtatttccat ccagtgctac ttgtgtttac ttctaaacag tcattttcta actgaagctg    3900
gcattcatgt cttcattttg ggctgtttct ctgcagggct tcctaaaaca gaagccaact    3960
gggtgaatgt aataagtgat ttgaaaaaaa ttgaagatct tattcaatct atgcatattg    4020
atgctacttt atatactgaa agtgatgttc accccagttg caaagtaaca gcaatgaagt    4080
gctttctctt ggagttacaa gttatttcac ttgagagcgg agatgcaagt attcatgata    4140
cagtagaaaa tctgatcatc ctagcaaaca acagtttgtc ttctaatggg aatgtaacag    4200
aatctggatg caaagaatgt gaggaactgg aggaaaaaaa tattaaagaa tttttgcaga    4260
gttttgtaca tattgtccaa atgttcatca acacttcttg agcggccgcg ctagccaatt    4320
gctgtgcctt ctagttgcca gccatctgtt gtttgcccct ccccgtgcc ttccttgacc    4380 ctggaaggtg ccactcccac tgtccttttcc taataaaatg aggaaattgc atcgcattgt    4440
ctgagtaggt gtcattctat tctggggggt ggggtgggc aggacagcaa ggggggaggat    4500 tgggaagaca atagcaggca tgctggggat gcggtgggct ctatggagct cgag          4554
```

<210> SEQ ID NO 17
<211> LENGTH: 4062
<212> TYPE: DNA
<213> ORGANISM: Artificial Sequence
<220> FEATURE:
<223> OTHER INFORMATION: Human EF1a- modified IL-12A/IL-12B/IL-15 - F2A
      (with CpG modification)

<400> SEQUENCE: 17

```
gtcgaccaca caaaaaacca acacacagat ctaatgaaaa taaagatctt ttattggcgc     60
gcctcaagaa gtgttgatga acatttggac aatatgtaca aaactctgca aaaattcttt    120
```

```
aatatttttt tcctccagtt cctcacattc tttgcatcca gattctgtta cattcccatt      180
agaagacaaa ctgttgtttg ctaggatgat cagattttct actgtatcat gaatacttgc      240
atctccgctc tcaagtgaaa taacttgtaa ctccaagaga aagcacttca ttgctgttac      300
tttgcaactg gggtgaacat cactttcagt atataaagta gcatcaatat gcatagattg      360
aataagatct tcaattttt  tcaaatcact tattacattc acccagttgg cttctgtttt      420
aggaagccct gcagagaaac agcccaaaat gaagacatga atgccagctt cagttagaaa      480
atgactgttt agaagtaaac acaagtagca ctggatggaa atacttctca aatgtggttt      540
gctaattctc atggtggcgg cgcgccattt aaatctagcc ttaagagctg taattgaact      600
gggagtggac acctgtggag agaaaggcaa agtggatgtc agtaagacca ataggtgcct      660
atcagaaacg caagagtctt ctctgtctcg acaagcccag tttctattgg tctccttaaa      720
cctgtcttgt aaccttgata cttacctgcc cagtgcctca cgaccaactt cgatctgtaa      780
cggcgcagaa cagaaaacga aacaaagacg tagagttgag caagcagggt caggcaaagc      840
gtggagagcc ggctgagtct aggtaggctc aagggagcg  ccggacaaag gcccggtctc      900
gacctgagct ttaaacttac ctagacggcg gacgcagttc aggaggcacc acaggcggga      960
ggcggcagaa cgcgactcaa ccggcgtgga tggcggcctc aggtagggcg gcgggcgcgt     1020
gaaggagaga tgcgagcccc tcgaagcttc agctgtgttc tggcggcaaa cccgttgcga     1080
aaaagaacgt tcacggcgac tactgcactt atatacggtt ctcccccacc ctcgggaaaa     1140
aggcggagcc agtacacgac atcactttcc cagtttaccc cgcgccacct tctctaggca     1200
ccggttcaat tgccgacccc tcccccaac  ttctcgggga ctgtgggcga tgtgcgctct     1260
gcccactgac gggcaccgga gcgatcttaa ttaactagtt attaatagta atcaattacg     1320
gggtcattag ttcatagccc atatatggag ttccgcgtta cataacttac ggtaaatggc     1380
ccgcctggct gaccgcccaa cgaccccgc  ccattgacgt caataatgac gtatgttccc     1440
atagtaacgc caatagggac tttccattga cgtcaatggg tggactattt acggtaaact     1500
gcccacttgg cagtacatca agtgtatcat atgccaagta cgccccctat tgacgtcaat     1560
gacggtaaat ggcccgcctg gcattatgcc cagtacatga ccttatggga ctttcctact     1620
tggcagtaca tctacgtatt agtcatcgct attaccatgg tgatgcggt  tttggcagta     1680 catcaatggg cgtggatagc ggtttgactc acggggattc caagtctcc  accccattga     1740 cgtcaatggg agtttgtttt ggcaccaaaa tcaacgggac tttccaaaat gtcgtaacaa     1800
ctccgcccca ttgacgcaaa tgggcggtag gcgtgtacgg tgggaggtct atataagcag     1860
agctcgttta gtgaaccgtc agatcgcctg gagacgtcga ggaactgaaa accagaaag      1920 ttaactggta agtttagtct ttttgtcttt tatttcaggt cccggatccg gtggtggtgc     1980
aaatcaaaga actgctcctc agtggatgtt gcctttactt ctaggcctgt acggaagtgt     2040
ttaaacttct gctctgcggc gcgccacca  tgtgtccagc gcgcagcctc ctccttgtgg     2100
ctaccctggt cctcctggac cacctcagtt tggccagaaa cctccctgtg ccactccag      2160 acccaggaat gttcccatgc cttcaccact cccaaaacct gctgagggct gtcagcaaca     2220
tgctccagaa ggccagacaa actctagaat tttacccttg cacttctgaa gagattgatc     2280
atgaagatat cacaaaagat aaaaccagca cagtggaggc ctgtttacca ttggaattaa     2340
ccaagaatga gagttgccta aattccagag agacctcttt cataactaat gggagttgcc     2400
tggcctccag aaagaccctct tttatgatgg ccctgtgcct tagtagtatt tatgaagact     2460
```

-continued

```
tgaagatgta ccaggtggag ttcaagacca tgaatgcaaa gcttctgatg gatcctaaga   2520
ggcagatctt tctagatcaa acatgctgg cagttattga tgagctgatg caggccctga    2580
atttcaacag tgagactgtg ccacaaaaat cctcccttga agaacctgat ttttataaaa   2640
ctaaaatcaa gctctgcata cttcttcatg ctttccggat tcgcgcagtg actattgata   2700
gagtgatgag ctatctgaat gcttccagaa agagaaggag tggctcagga gccctgtga   2760 aacagaccct gaactttgac ctcttgaagc ttgctgggga tgtggagtct aatcctggtc   2820
caatgtgtca ccagcagttg gtcatctctt ggttttccct ggttttttctg gcatctcccc   2880 ttgtggccat atgggaactg aagaaagatg tttatgtggt agaattggat tggtatcctg   2940
atgcccctgg agaaatggtg gtcctcacct gtgacacccc tgaagaagat ggtatcacct   3000
ggaccttgga ccagagcagt gaggtcttag gctctggcaa aaccctgacc atccaagtca   3060
aagagtttgg agatgctggc cagtacaccct gtcacaaagg aggggaggtt ctaagccatt   3120
ccctcctgct gcttcacaaa aaggaagatg gaatttggtc cactgatatt ttaaaggacc   3180
agaaagaacc caaaaataag accttttcaa gatgtgaggc caagaattat tctggaaggt   3240
tcacctgctg gtggctgact acaatcagta ctgatttgac attcagtgtc aaaagcagca   3300
gaggctcttc tgaccccccaa ggggtgacat gcggagctgc tacactctct gcagagagag   3360
tcagagggga caacaaggag tatgagtact cagtggagtg ccaggaggac agtgcctgcc   3420
cagctgctga ggagagtctg cccattgagg tgatggtgga tgcggttcac aagctcaagt   3480
atgaaaacta caccagcagc ttcttcatca gggacatcat caaacctgac ccacccaaga   3540
acttgcagct gaagccatta aagaattcta ggcaggtgga ggtcagctgg gagtaccctg   3600
acacctggag tactccacat tcctacttct ccctgacatt ctgtgttcaa gtccagggca   3660
agagcaagag agaaaagaaa gatagagtct tcactgacaa gacctcagcc acagtcatct   3720
gccgcaaaaa tgccagcatt tcagtgcggg cccaggaccg ctactatagc tcatcttggt   3780
cagaatgggc atctgtgccc tgcagttgag cggccgcgct agccaattgc tgtgccttct   3840
agttgccagc catctgttgt ttgcccctcc cccgtgcctt ccttgaccct ggaaggtgcc   3900
actcccactg tcctttccta ataaaatgag gaaattgcat cgcattgtct gagtaggtgt   3960
cattctattc tggggggtgg ggtggggcag gacagcaagg gggaggattg ggaagacaat   4020
agcaggcatg ctgggggatgc ggtgggctct atggagctcg ag                    4062
```

<210> SEQ ID NO 18
<211> LENGTH: 4554
<212> TYPE: DNA
<213> ORGANISM: Artificial Sequence
<220> FEATURE:
<223> OTHER INFORMATION: Human EF1a - modified IL-12A/IL-12B/IL-15 -
      IRES (with CpG modification)

<400> SEQUENCE: 18

```
gtcgaccaca caaaaaacca acacacagat ctaatgaaaa taaagatctt ttattggcgc    60
gcctcaactg cagggcacag atgcccattc tgaccaagat gagctatagt atctgtcctg    120
ggccctcact gaaatgctgg catttttcct gcagatgact gtggctgagg tcttgtcagt    180
gaagactcta tctttctttt ctctcttgct cttgccctgg acttgaacac agaatgtcag    240
ggagaagtag gaatgtggag tactccaggt gtcagggtac tcccagctga cctccacctg    300
cctagaattc tttaatggct tcagctgcaa gttcttgggt gggtcaggtt tgatgatgtc    360
cctgatgaag aagctgctgg tgtagttttc atacttgagc ttgtgaactg catccaccat    420
```

| | |
|---|---|
| cacctcaatg ggcagactct cctcagcagc tgggcaggca ctgtcctcct ggcactccac | 480 |
| tgagtactca tactccttgt tgtcccctct gactctctct gcagagagtg tagcagctcc | 540 |
| acatgtcacc ccttgggggt cagaagagcc tctgctgctt ttgacactga atgtcaaatc | 600 |
| agtactgatt gtagtcagcc accagcaggt gaaccttcca gaataattct tggcctcaca | 660 |
| tcttagaaag gtcttatttt tgggttcttt ctggtccttt aaaatatcag tggaccaaat | 720 |
| tccatcttcc tttttgtgaa gcagcaggag ggaatggctt agaacctccc ctcctttgtg | 780 |
| acaggtgtac tggccagcat ctccaaactc tttgacttgg atggtcaggg ttttgccaga | 840 |
| gcctaagacc tcactgctct ggtccaaggt ccaggtgata ccatcttctt caggggtgtc | 900 |
| acaggtgagg accaccattt ctccaggggc atcaggatac caatccaatt ctaccacata | 960 |
| aacatctttc ttcagttccc atatggccac aaggggagat gccagaaaaa ccagggaaaa | 1020 |
| ccaagagatg accaactgct ggtgacacat ggtggcggcg cgccatttaa atctagcctt | 1080 |
| aagagctgta attgaactgg gagtggcacc ctgtggagag aaaggcaaag tggatgtcag | 1140 |
| taagaccaat aggtgcctat cagaaacgca agagtcttct ctgtctcgac aagcccagtt | 1200 |
| tctattggtc tccttaaacc tgtcttgtaa ccttgatact tacctgccca gtgcctcacg | 1260 |
| accaacttcg atctgtaacg gcgcagaaca gaaaacgaaa caaagacgta gagttgagca | 1320 |
| agcagggtca ggcaaagcgt ggagagccgg ctgagtctag gtaggctcca agggagcgcc | 1380 |
| ggacaaaggc ccggtctcga cctgagcttt aaacttacct agacggcgga cgcagttcag | 1440 |
| gaggcaccac aggcgggagg cggcagaacg cgactcaacc ggcgtggatg gcggcctcag | 1500 |
| gtagggcggg gggcgcgtga aggagagatg cgagcccctc gaagcttcag ctgtgttctg | 1560 |
| gcggcaaacc cgttgcgaaa agaacgttc acggcgacta ctgcacttat atacggttct | 1620 |
| cccccaccct cgggaaaaag gcggagccag tacacgacat cactttccca gtttaccccg | 1680 |
| cgccaccttc tctaggcacc ggttcaattg ccgaccccte cccccaactt ctcggggact | 1740 |
| gtgggcgatg tgcgctctgc ccactgacgg gcaccggagc gatcttaatt aactagttat | 1800 |
| taatagtaat caattacggg gtcattagtt catagcccat atatggagtt ccgcgttaca | 1860 |
| taacttacgg taaatggccc gcctggctga ccgcccaacg accccgccc attgacgtca | 1920 |
| ataatgacgt atgttcccat agtaacgcca atagggactt tccattgacg tcaatgggtg | 1980 |
| gactatttac ggtaaactgc ccacttggca gtacatcaag tgtatcatat gccaagtacg | 2040 |
| cccccctattg acgtcaatga cggtaaatgg cccgcctggc attatgccca gtacatgacc | 2100 |
| ttatgggact ttcctacttg gcagtacatc tacgtattag tcatcgctat taccatgggt | 2160 |
| gatgcggttt tggcagtaca tcaatgggcg tggatagcgg tttgactcac ggggatttcc | 2220 |
| aagtctccac cccattgacg tcaatgggag tttgttttgg caccaaaatc aacgggactt | 2280 |
| tccaaaatgt cgtaacaact ccgccccatt gacgcaaatg ggcggtaggc gtgtacggtg | 2340 |
| ggaggtctat ataagcagag ctcgtttagt gaaccgtcag atcgcctgga gacgtcgagg | 2400 |
| aactgaaaaa ccagaaagtt aactggtaag tttagtcttt ttgtctttta tttcaggtcc | 2460 |
| cggatccggt ggtggtgcaa atcaaagaac tgctcctcag tggatgttgc ctttacttct | 2520 |
| aggcctgtac ggaagtgttt aaacttctgc tctgcggccg cgccaccatg tgtccagcta | 2580 |
| ggagcctcct ccttgtggct accctggtcc tcctggacca cctcagtttg gccagaaacc | 2640 |
| tccctgtggc cactccagac ccaggaatgt tcccatgcct tcaccactcc caaaacctgc | 2700 |
| tgagggcagt cagcaacatg ctccagaagg ccagacaaac tctagaattt acccttgca | 2760 |
| cttctgaaga gattgatcat gaagatatca caaaagataa aaccagcaca gtggaggcct | 2820 |

```
gtttaccatt ggaattaacc aagaatgaga gttgcctaaa ttccagagag acctctttca    2880
taactaatgg gagttgcctg gcctccagaa agacctcttt tatgatggcc ctgtgcctta    2940
gtagtattta tgaagacttg aagatgtacc aggtggagtt caagaccatg aatgcaaagc    3000
ttctgatgga tcctaagagg cagatctttc tagatcaaaa catgctggca gttattgatg    3060
agctgatgca ggccctgaat ttcaacagtg agactgtgcc acaaaaatcc tcccttgaag    3120
aacctgattt ttataaaact aaaatcaagc tctgcatact tcttcatgct ttccggatta    3180
gggcagtgac tattgataga gtgatgagct atctgaatgc ttcctgagcc cctctccctc    3240
ccccccccct aacgttactg gccgaagccg cttggaataa ggccggtgtg cgtttgtcta    3300
tatgttattt tccaccatat tgccgtcttt tggcaatgtg agggcccgga acctggccc    3360 tgtcttcttg acgagcattc ctaggggtct ttcccctctc gccaaaggaa tgcaaggtct    3420
gttgaatgtc gtgaaggaag cagttcctct ggaagcttct tgaagacaaa caacgtctgt    3480
agcgaccctt tgcaggcagc ggaaccccc  acctggcgac aggtgcctct gcggccaaaa    3540
gccacgtgta taagatacac ctgcaaaggc ggcacaaccc cagtgccacg ttgtgagttg    3600
gatagttgtg aaagagtca  aatggctctc tcaagcgta  ttcaacaagg ggctgaagga    3660
tgcccagaag gtaccccatt gtatgggatc tgatctgggg cctcggtaca catgctttac    3720
atgtgtttag tcgaggttaa aaaaacgtct aggcccccg  aaccacgggg acgtggtttt    3780
cctttgaaaa acacgatgat aatatggcca caatgagaat tagcaaacca catttgagaa    3840
gtatttccat ccagtgctac ttgtgtttac ttctaaacag tcattttcta actgaagctg    3900
gcattcatgt cttcattttg ggctgtttct ctgcagggct tcctaaaaca gaagccaact    3960
gggtgaatgt aataagtgat ttgaaaaaaa ttgaagatct tattcaatct atgcatattg    4020
atgctacttt atatactgaa agtgatgttc accccagttg caaagtaaca gcaatgaagt    4080
gctttctctt ggagttacaa gttatttcac ttgagtcagg agatgcaagt attcatgata    4140
cagtagaaaa tctgatcatc ctagcaaaca acagtttgtc ttctaatggg aatgtaacag    4200
aatctggatg caaagaatgt gaggaactgg aggaaaaaaa tattaaagaa ttttgcaga    4260 gtttttgtaca tattgtccaa atgttcatca acacttcttg agcggccgcg ctagccaatt    4320
gctgtgcctt ctagttgcca gccatctgtt gtttgcccct cccccgtgcc ttccttgacc    4380
ctggaaggtg ccactcccac tgtcctttcc taataaaatg aggaaattgc atcgcattgt    4440
ctgagtaggt gtcattctat tctggggggt ggggtgggc  aggacagcaa gggggaggat    4500
tgggaagaca atagcaggca tgctggggat gcggtgggct ctatggagct cgag          4554
```

<210> SEQ ID NO 19
<211> LENGTH: 4062
<212> TYPE: DNA
<213> ORGANISM: Artificial Sequence
<220> FEATURE:
<223> OTHER INFORMATION: Human EF-1a - modified IL-12A/IL-12B/IL-15 - F2A (with CpG modification)

<400> SEQUENCE: 19

```
gtcgaccaca caaaaaacca acacacagat ctaatgaaaa taaagatctt ttattggcgc      60
gcctcaagaa gtgttgatga acatttggac aatatgtaca aaactctgca aaaattcttt     120 aatattttt  tcctccagtt cctcacattc tttgcatcca gattctgtta cattcccatt     180
agaagacaaa ctgttgtttg ctaggatgat cagattttct actgtatcat gaatacttgc     240
atctcctgac tcaagtgaaa taacttgtaa ctccaagaga aagcacttca ttgctgttac     300
```

```
tttgcaactg gggtgaacat cactttcagt atataaagta gcatcaatat gcatagattg    360
aataagatct tcaatttttt tcaaatcact tattacattc acccagttgg cttctgtttt    420
aggaagccct gcagagaaac agcccaaaat gaagacatga atgccagctt cagttagaaa    480
atgactgttt agaagtaaac acaagtagca ctggatggaa atacttctca aatgtggttt    540
gctaattctc atggtggcgg cgcgccattt aaatctagcc ttaagagctg taattgaact    600
gggagtggac acctgtggag agaaaggcaa agtggatgtc agtaagacca ataggtgcct    660
atcagaaacg caagagtctt ctctgtctcg acaagcccag tttctattgg tctccttaaa    720
cctgtcttgt aaccttgata cttacctgcc cagtgcctca cgaccaactt cgatctgtaa    780
cggcgcagaa cagaaaacga aacaaagacg tagagttgag caagcagggt caggcaaagc    840
gtggagagcc ggctgagtct aggtaggctc aagggagcg ccggacaaag cccggtctc    900 gacctgagct ttaaacttac ctagacggcg gacgcagttc aggaggcacc acaggcggga    960
ggcggcagaa cgcgactcaa ccggcgtgga tggcggcctc aggtagggcg gcgggcgcgt   1020
gaaggagaga tgcgagcccc tcgaagcttc agctgtgttc tggcggcaaa cccgttgcga   1080
aaaagaacgt tcacggcgac tactgcactt atatacggtt ctcccccacc ctcgggaaaa   1140
aggcggagcc agtacacgac atcactttcc cagtttaccc cgcgccacct tctctaggca   1200
ccggttcaat tgccgacccc tccccccaac ttctcgggga ctgtgggcga tgtgcgctct   1260
gcccactgac gggcaccgga gcgatcttaa ttaactagtt attaatagta atcaattacg   1320
gggtcattag ttcatagccc atatatggag ttccgcgtta cataacttac ggtaaatggc   1380
ccgcctggct gaccgcccaa cgacccccgc ccattgacgt caataatgac gtatgttccc   1440
atagtaacgc caatagggac tttccattga cgtcaatggg tggactattt acggtaaact   1500
gcccacttgg cagtacatca agtgtatcat atgccaagta cgccccctat tgacgtcaat   1560
gacggtaaat ggcccgcctg gcattatgcc cagtacatga ccttatggga ctttcctact   1620
tggcagtaca tctacgtatt agtcatcgct attaccatgg gtgatgcggt tttggcagta   1680
catcaatggg cgtggatagc ggtttgactc acggggattt ccaagtctcc accccattga   1740
cgtcaatggg agtttgtttt ggcaccaaaa tcaacgggac tttccaaaat gtcgtaacaa   1800
ctccgcccca ttgacgcaaa tgggcggtag gcgtgtacgg tgggaggtct atataagcag   1860
agctcgttta gtgaaccgtc agatcgcctg gagacgtcga ggaactgaaa accagaaag   1920 ttaactggta agtttagtct ttttgtcttt tatttcaggt cccggatccg gtggtggtgc   1980
aaatcaaaga actgctcctc agtggatgtt gcctttactt ctaggcctgt acggaagtgt   2040
ttaaacttct gctctgcggc gcgccacca tgtgtccagc taggagcctc ctccttgtgg   2100
ctaccctggt cctcctggac cacctcagtt tggccagaaa cctccctgtg ccactccag   2160 acccaggaat gttcccatgc cttcaccact cccaaaacct gctgagggca gtcagcaaca   2220
tgctccagaa ggccagacaa actctagaat tttacccttg cacttctgaa agattgatc   2280 atgaagatat cacaaaagat aaaaccagca cagtggaggc ctgtttacca ttggaattaa   2340
ccaagaatga gagttgccta aattccagag agacctcttt cataactaat gggagttgcc   2400
tggcctccag aaagacctct tttatgatgg ccctgtgcct tagtagtatt tatgaagact   2460
tgaagatgta ccaggtggag ttcaagacca tgaatgcaaa gcttctgatg gatcctaaga   2520
ggcagatctt tctagatcaa acatgctggc cagttattga tgagctgatg caggccctga   2580
atttcaacag tgagactgtg ccacaaaaat cctcccttga agaacctgat ttttataaa    2640
```

```
ctaaaatcaa gctctgcata cttcttcatg ctttccggat tagggcagtg actattgata    2700
gagtgatgag ctatctgaat gcttccagaa agagaaggag tggctcagga gcccctgtga    2760
aacagaccct gaactttgac ctcttgaagc ttgctgggga tgtggagtct aatcctggtc    2820
caatgtgtca ccagcagttg gtcatctctt ggttttccct ggttttttctg gcatctcccc   2880 ttgtggccat atgggaactg aagaaagatg tttatgtggt agaattggat tggtatcctg    2940
atgcccctgg agaaatggtg gtcctcacct gtgacacccc tgaagaagat ggtatcacct    3000
ggaccttgga ccagagcagt gaggtcttag gctctggcaa aaccctgacc atccaagtca    3060
aagagtttgg agatgctggc cagtacacct gtcacaaagg aggggaggtt ctaagccatt    3120
ccctcctgct gcttcacaaa aaggaagatg gaatttggtc cactgatatt ttaaaggacc    3180
agaaagaacc caaaaataag accttttctaa gatgtgaggc caagaattat tctggaaggt   3240
tcacctgctg gtggctgact acaatcagta ctgatttgac attcagtgtc aaaagcagca    3300
gaggctcttc tgaccccccaa ggggtgacat gtggagctgc tacactctct gcagagagag    3360
tcagagggga caacaaggag tatgagtact cagtggagtg ccaggaggac agtgcctgcc    3420
cagctgctga ggagagtctg cccattgagg tgatggtgga tgcagttcac aagctcaagt    3480
atgaaaacta caccagcagc ttcttcatca gggacatcat caaacctgac ccacccaaga    3540
acttgcagct gaagccatta aagaattcta ggcaggtgga ggtcagctgg gagtaccctg    3600
acacctggag tactccacat tcctacttct ccctgacatt ctgtgttcaa gtccagggca    3660
agagcaagag agaaaagaaa gatagagtct tcactgacaa gacctcagcc acagtcatct    3720
gcaggaaaaa tgccagcatt tcagtgaggg cccaggacag atactatagc tcatcttggt    3780
cagaatgggc atctgtgccc tgcagttgag cggccgcgct agccaattgc tgtgccttct    3840
agttgccagc catctgttgt ttgccctcc cccgtgcctt ccttgaccct ggaaggtgcc    3900
actcccactg tcctttccta ataaaatgag gaaattgcat cgcattgtct gagtaggtgt    3960
cattctattc tggggggtgg ggtggggcag gacagcaagg ggaggattg ggaagacaat     4020 agcaggcatg ctggggatgc ggtgggctct atggagctcg ag    4062
```

<210> SEQ ID NO 20
<211> LENGTH: 4602
<212> TYPE: DNA
<213> ORGANISM: Artificial Sequence
<220> FEATURE:
<223> OTHER INFORMATION: Human EF-1a- wild-type IL-12A/IL-12B/IL-15 -
      ODN-IRES (no CpG modification)

<400> SEQUENCE: 20

```
gtcgactcgt cgttttgtcg ttttgtcgtt cacacaaaaa accaacacac agatctaatg    60
aaaataaaga tcttttattg gcgcgcctca actgcagggc acagatgccc attcgctcca    120
agatgagcta tagtagcggt cctgggcccg cacgctaatg ctggcatttt tgcggcagat    180
gaccgtggct gaggtcttgt ccgtgaagac tctatctttc ttttctctct tgctcttgcc    240
ctggacttga acgcagaatg tcagggagaa gtaggaatgt ggagtactcc aggtgtcagg    300
gtactcccag ctgaccctcca cctgccgaga attctttaat ggcttcagct gcaagttctt    360
gggtgggtca ggtttgatga tgtccctgat gaagaagctg ctggtgtagt tttcatactt    420
gagcttgtga acggcatcca ccatcacctc aatgggcaga ctcctcag cagctgggca     480 ggcactgtcc tcctggcact ccactgagta ctcatactcc ttgttgtccc ctctgactct    540
ctctgcagag agtgtagcag ctccgcacgt caccccttgg gggtcagaag agcctctgct    600
```

-continued

```
gcttttgaca ctgaatgtca aatcagtact gattgtcgtc agccaccagc aggtgaaacg     660
tccagaataa ttcttggcct cgcatcttag aaaggtctta tttttgggtt ctttctggtc     720
ctttaaaata tcagtggacc aaattccatc ttccttttg tgaagcagca ggagcgaatg     780
gcttagaacc tcgcctcctt tgtgacaggt gtactggcca gcatctccaa actctttgac     840
ttggatggtc agggttttgc cagagcctaa gacctcactg ctctggtcca aggtccaggt     900
gataccatct tcttcagggg tgtcacaggt gaggaccacc atttctccag ggcatccgg     960 ataccaatcc aattctacga cataaacatc tttcttcagt tcccatatgg ccacgagggg    1020
agatgccaga aaaccaggg aaaaccaaga gatgaccaac tgctggtgac acatggtggc    1080
ggcgcgccat ttaaatctag ccttaagagc tgtaattgaa ctgggagtgg acacctgtgg    1140
agagaaaggc aaagtggatg tcagtaagac caataggtgc ctatcagaaa cgcaagagtc    1200
ttctctgtct cgacaagccc agtttctatt ggtctcctta aacctgtctt gtaaccttga    1260
tacttacctg cccagtgcct cacgaccaac ttcgatctgt aacggcgcag aacagaaaac    1320
gaaacaaaga cgtagagttg agcaagcagg gtcaggcaaa gcgtggagag ccggctgagt    1380
ctaggtaggc tccaagggag cgccggacaa aggcccggtc tcgacctgag ctttaaactt    1440
acctagacgg cggacgcagt tcaggaggca ccacaggcgg gaggcggcag aacgcgactc    1500
aaccggcgtg gatggcggcc tcaggtaggg cggcgggcgc gtgaaggaga gatgcgagcc    1560
cctcgaagct tcagctgtgt tctggcggca aacccgttgc gaaaagaac gttcacggcg    1620 actactgcac ttatatacgg ttctccccca ccctcgggaa aaaggcggag ccagtacacg    1680
acatcacttt cccagtttac cccgcgccac cttctctagg caccggttca attgccgacc    1740
cctcccccca acttctcggg gactgtgggc gatgtgcgct ctgcccactg acgggcaccg    1800
gagcgatctt aattaactag ttattaatag taatcaatta cggggtcatt agttcatagc    1860
ccatatatgg agttccgcgt tacataactt acggtaaatg gcccgcctgg ctgaccgccc    1920
aacgaccccc gcccattgac gtcaataatg acgtatgttc ccatagtaac gccaataggg    1980
actttccatt gacgtcaatg ggtggactat ttacggtaaa ctgcccactt ggcagtacat    2040
caagtgtatc atatgccaag tacgcccct attgacgtca atgacggtaa atggcccgcc    2100
tggcattatg cccagtacat gaccttatgg gactttccta cttggcagta catctacgta    2160
ttagtcatcg ctattaccat gggtgatgcg gttttggcag tacatcaatg ggcgtggata    2220
gcggtttgac tcacggggat ttccaagtct ccaccccatt gacgtcaatg ggagtttgtt    2280
ttggcaccaa aatcaacggg actttccaaa atgtcgtaac aactccgccc cattgacgca    2340
aatgggcggt aggcgtgtac ggtgggaggt ctatataagc agagctcgtt tagtgaaccg    2400
tcagatcgcc tggagacgtc gaggaactga aaaaccagaa agttaactgg taagtttagt    2460
ctttttgtct tttatttcag gtcccggatc cggtggtggt gcaaatcaaa gaactgctcc    2520
tcagtggatg ttgcctttac ttctaggcct gtacggaagt gttaaacttc tgctctgcg    2580 gccgcgccac catgtgtcca gcgcgcagcc tcctccttgt ggctaccctg gtcctcctgg    2640
accacctcag tttggccaga aacctccccg tggccactcc agacccagga atgttcccat    2700
gccttcacca ctcccaaaac ctgctgaggg ccgtcagcaa catgctccag aaggccagac    2760
aaactctaga attttacccct tgcacttctg aagagattga tcatgaagat atcacaaaag    2820
ataaaaccag cacagtggag gcctgtttac cattggaatt aaccaagaat gagagttgcc    2880
taaattccag agagacctct ttcataacta atggagttg cctggcctcc agaaagacct    2940 ctttatgat ggccctgtgc cttagtagta tttatgaaga cttgaagatg taccaggtgg    3000
```

| | |
|---|---|
| agttcaagac catgaatgca aagcttctga tggatcctaa gaggcagatc tttctagatc | 3060 |
| aaaacatgct ggcagttatt gatgagctga tgcaggccct gaatttcaac agtgagactg | 3120 |
| tgccacaaaa atcctccctt gaagaaccgg attttttataa aactaaaatc aagctctgca | 3180 |
| tacttcttca tgctttccgg attcgggcag tgactattga tagagtgatg agctatctga | 3240 |
| atgcttcctg agccctctc cctccccccc ccctaacgtt actggccgaa gccgcttgga | 3300 |
| ataaggccgg tgtgcgtttg tctatatgtt attttccacc atattgccgt cttttggcaa | 3360 |
| tgtgagggcc cggaaacctg gccctgtctt cttgacgagc attcctaggg gtctttcccc | 3420 |
| tctcgccaaa ggaatgcaag gtctgttgaa tgtcgtgaag gaagcagttc ctctggaagc | 3480 |
| ttcttgaaga caaacaacgt ctgtagcgac cctttgcagg cagcggaacc ccccacctgg | 3540 |
| cgacaggtgc ctctgcggcc aaaagccacg tgtataagat acacctgcaa aggcggcaca | 3600 |
| accccagtgc cacgttgtga gttggatagt tgtggaaaga gtcaaatggc tctcctcaag | 3660 |
| cgtattcaac aaggggctga aggatgccca gaaggtaccc cattgtatgg gatctgatct | 3720 |
| ggggcctcgg tacacatgct ttacatgtgt ttagtcgagg ttaaaaaaac gtctaggccc | 3780 |
| cccgaaccac ggggacgtgg ttttcctttg aaaaacacga tgataatatg gccacaatga | 3840 |
| gaatttcgaa accacatttg agaagtattt ccatccagtg ctacttgtgt ttacttctaa | 3900 |
| acagtcattt tctaactgaa gctggcattc atgtcttcat tttgggctgt ttctctgcag | 3960 |
| ggcttcctaa aacagaagcc aactgggtga atgtaataag tgatttgaaa aaaattgaag | 4020 |
| atcttattca atctatgcat attgatgcta ctttatatac ggaaagtgat gttcacccca | 4080 |
| gttgcaaagt aacagcaatg aagtgctttc tcttggagtt acaagttatt tcacttgagt | 4140 |
| ccggagatgc aagtattcat gatacagtag aaaatctgat catcctagca aacaacagtt | 4200 |
| tgtcttctaa tgggaatgta acagaatctg gatgcaaaga atgtgaggaa ctggaggaaa | 4260 |
| aaaatattaa agaattttg cagagttttg tacatattgt ccaaatgttc atcaacactt | 4320 |
| cttgagcggc cgcgctagcc aattgctgtg ccttctagtt gccagccatc tgttgtttgc | 4380 |
| ccctccccg tgccttcctt gaccctggaa ggtgccactc ccactgtcct ttcctaataa | 4440 |
| aatgaggaaa ttgcatcgca ttgtctgagt aggtgtcatt ctattctggg gggtggggtg | 4500 |
| gggcaggaca gcaaggggga ggattgggaa gacaatagca ggcatgctgg ggatgcggtg | 4560 |
| ggctctatgt cgtcgttttg tcgttttgtc gttgagctcg ag | 4602 |

<210> SEQ ID NO 21
<211> LENGTH: 4110
<212> TYPE: DNA
<213> ORGANISM: Artificial Sequence
<220> FEATURE:
<223> OTHER INFORMATION: Human EF-1a - wild-type IL-12A/IL-12B/IL-15 -
    ODN - F2A (no CpG modification)

<400> SEQUENCE: 21

| | |
|---|---|
| gtcgactcgt cgtttgtcg ttttgtcgtt cacacaaaaa accaacacac agatctaatg | 60 |
| aaaataaaga tcttttattg gcgcgcctca agaagtgttg atgaacattt ggacaatatg | 120 |
| tacaaaactc tgcaaaaatt ctttaatatt tttttcctcc agttcctcac attctttgca | 180 |
| tccagattct gttacattcc cattagaaga caaactgttg tttgctagga tgatcagatt | 240 |
| ttctactgta tcatgaatac ttgcatctcc ggactcaagt gaaataactt gtaactccaa | 300 |
| gagaaagcac ttcattgctg ttactttgca actggggtga acatcacttt ccgtatataa | 360 |
| agtagcatca atatgcatag attgaataag atcttcaatt tttttcaaat cacttattac | 420 |

-continued

| | |
|---|---|
| attcacccag ttggcttctg ttttaggaag ccctgcagag aaacagccca aaatgaagac | 480 |
| atgaatgcca gcttcagtta gaaaatgact gtttagaagt aaacacaagt agcactggat | 540 |
| ggaaatactt ctcaaatgtg gtttcgaaat tctcatggtg gcggcgcgcc atttaaatct | 600 |
| agccttaaga gctgtaattg aactgggagt ggacacctgt ggagagaaag caaagtgga | 660 |
| tgtcagtaag accaataggt gcctatcaga aacgcaagag tcttctctgt ctcgacaagc | 720 |
| ccagtttcta ttggtctcct aaacctgtc ttgtaacctt gatacttacc tgcccagtgc | 780 |
| ctcacgacca acttcgatct gtaacggcgc agaacagaaa acgaaacaaa gacgtagagt | 840 |
| tgagcaagca gggtcaggca aagcgtggag agccggctga gtctaggtag gctccaaggg | 900 |
| agcgccggac aaaggcccgg tctcgacctg agctttaaac ttacctagac ggcggacgca | 960 |
| gttcaggagg caccacaggc gggaggcggc agaacgcgac tcaaccggcg tggatggcgg | 1020 |
| cctcaggtag ggcggcgggc gcgtgaagga gagatgcgag ccctcgaag cttcagctgt | 1080 |
| gttctggcgg caaacccgtt gcgaaaaaga acgttcacgg cgactactgc acttatatac | 1140 |
| ggttctcccc caccctcggg aaaaaggcgg agccagtaca cgacatcact ttcccagttt | 1200 |
| accccgcgcc accttctcta ggcaccggtt caattgccga ccctcccc caacttctcg | 1260 |
| gggactgtgg gcgatgtgcg ctctgcccac tgacgggcac cggagcgatc ttaattaact | 1320 |
| agttattaat agtaatcaat tacggggtca ttagttcata gcccatatat ggagttccgc | 1380 |
| gttacataac ttacggtaaa tggcccgcct ggctgaccgc ccaacgaccc ccgcccattg | 1440 |
| acgtcaataa tgacgtatgt tcccatagta acgccaatag ggactttcca ttgacgtcaa | 1500 |
| tgggtggact atttacggta aactgcccac ttggcagtac atcaagtgta tcatatgcca | 1560 |
| agtacgcccc ctattgacgt caatgacggt aaatggcccg cctggcatta tgcccagtac | 1620 |
| atgaccttat gggactttcc tacttggcag tacatctacg tattagtcat cgctattacc | 1680 |
| atgggtgatg cggttttggc agtacatcaa tgggcgtgga tagcggtttg actcacgggg | 1740 |
| atttccaagt ctccacccca ttgacgtcaa tgggagtttg ttttggcacc aaaatcaacg | 1800 |
| ggactttcca aaatgtcgta caactccgc cccattgacg caaatgggcg gtaggcgtgt | 1860 |
| acggtgggag gtctatataa gcagagctcg tttagtgaac cgtcagatcg cctggagacg | 1920 |
| tcgaggaact gaaaaaccag aaagttaact ggtaagttta gtcttttgt cttttatttc | 1980 |
| aggtcccgga tccggtggtg gtgcaaatca agaactgct cctcagtgga tgttgccttt | 2040 |
| acttctaggc ctgtacggaa gtgtttaaac ttctgctctg cggccgcgcc accatgtgtc | 2100 |
| cagcgcgcag cctcctcctt gtggctaccc tggtcctcct ggaccactc agtttggcca | 2160 |
| gaaacctccc cgtggccact ccagacccag gaatgttccc atgccttcac cactcccaaa | 2220 |
| acctgctgag ggccgtcagc aacatgctcc agaaggccag acaaactcta gaattttacc | 2280 |
| cttgcacttc tgaagagatt gatcatgaag atatcacaaa agataaaacc agcacagtgg | 2340 |
| aggcctgttt accattggaa ttaaccaaga atgagagttg cctaaattcc agagagacct | 2400 |
| ctttcataac taatgggagt tgcctggcct ccagaaagac ctcttttatg atggcctgt | 2460 |
| gccttagtag tatttatgaa gacttgaaga tgtaccaggt ggagttcaag accatgaatg | 2520 |
| caaagcttct gatggatcct aagaggcaga tctttctaga tcaaaacatg ctggcagtta | 2580 |
| ttgatgagct gatgcaggcc ctgaatttca acagtgagac tgtgccacaa aatcctccc | 2640 |
| ttgaagaacc ggatttttat aaaactaaaa tcaagctctg catacttctt catgctttcc | 2700 |
| ggattcgggc agtgactatt gatagagtga tgagctatct gaatgcttcc agaaagagaa | 2760 |

```
ggagtggctc aggagcccct gtgaaacaga ccctgaactt tgacctcttg aagcttgctg   2820
gggatgtgga gtctaatcct ggtccaatgt gtcaccagca gttggtcatc tcttggtttt   2880
ccctggtttt tctggcatct cccctcgtgg ccatatggga actgaagaaa gatgtttatg   2940
tcgtagaatt ggattggtat ccggatgccc ctggagaaat ggtggtcctc acctgtgaca   3000
cccctgaaga agatggtatc acctggacct tggaccagag cagtgaggtc ttaggctctg   3060
gcaaaaccct gaccatccaa gtcaaagagt ttggagatgc tggccagtac acctgtcaca   3120
aaggaggcga ggttctaagc cattcgctcc tgctgcttca caaaaggaa gatggaattt    3180 ggtccactga tattttaaag gaccagaaag aacccaaaaa taagacccttt ctaagatgcg   3240 aggccaagaa ttattctgga cgtttcacct gctggtggct gacgacaatc agtactgatt   3300
tgacattcag tgtcaaaagc agcagaggct cttctgaccc ccaaggggtg acgtgcggag   3360
ctgctacact ctctgcagag agagtcagag gggacaacaa ggagtatgag tactcagtgg   3420
agtgccagga ggacagtgcc tgcccagctg ctgaggagag tctgcccatt gaggtgatgg   3480
tggatgccgt tcacaagctc aagtatgaaa actacaccag cagcttcttc atcagggaca   3540
tcatcaaacc tgacccaccc aagaacttgc agctgaagcc attaaagaat tctcggcagg   3600
tggaggtcag ctgggagtac cctgacacct ggagtactcc acattcctac ttctccctga   3660
cattctgcgt tcaagtccag ggcaagagca agagagaaaa gaaagataga gtcttcacgg   3720
acaagacctc agccacggtc atctgccgca aaaatgccag cattagcgtg cgggcccagg   3780
accgctacta tagctcatct tggagcgaat gggcatctgt gccctgcagt tgagcggccg   3840
cgctagccaa ttgctgtgcc ttctagttgc cagccatctg ttgtttgccc ctcccccgtg   3900
ccttccttga ccctggaagg tgccactccc actgtccttt cctaataaaa tgaggaaatt   3960
gcatcgcatt gtctgagtag gtgtcattct attctggggg gtggggtggg caggacagc   4020 aagggggagg attgggaaga caatagcagg catgctgggg atgcggtggg ctctatgtcg   4080
tcgttttgtc gttttgtcgt tgagctcgag                                    4110
```

<210> SEQ ID NO 22
<211> LENGTH: 4408
<212> TYPE: DNA
<213> ORGANISM: Artificial Sequence
<220> FEATURE:
<223> OTHER INFORMATION: Human UbC - wild-type IL-12A/IL-12B/IL-15 -
    IRES (no CpG modification)

<400> SEQUENCE: 22

```
gtcgaccaca caaaaaacca acacacagat ctaatgaaaa taaagatctt ttattggcgc     60
gcctcaactg cagggcacag atgcccattc gctccaagat gagctatagt agcggtcctg    120
ggcccgcacg ctaatgctgg cattttttgcg gcagatgacc gtggctgagg tcttgtccgt    180
gaagactcta tctttctttt ctctcttgct cttgccctgg acttgaacgc agaatgtcag    240
ggagaagtag gaatgtggag tactccaggt gtcaggtac tcccagctga cctccacctg     300
ccgagaattc tttaatggct tcagctgcaa gttcttgggt gggtcaggtt tgatgatgtc    360
cctgatgaag aagctgctgg tgtagttttc atacttgagc ttgtgaacgg catccaccat    420
cacctcaatg gcagactct cctcagcagc tgggcaggca ctgtcctcct ggcactccac    480
tgagtactca tactccttgt tgtcccctct gactctctct gcagagagtg tagcagctcc    540
gcacgtcacc ccttggggt cagaagagcc tctgctgctt ttgacactga atgtcaaatc    600
agtactgatt gtcgtcagcc accagcaggt gaaacgtcca gaataattct ggcctcgca   660
```

```
tcttagaaag gtcttatttt tgggttcttt ctggtccttt aaaatatcag tggaccaaat    720
tccatcttcc tttttgtgaa gcagcaggag cgaatggctt agaacctcgc ctcctttgtg    780
acaggtgtac tggccagcat ctccaaactc tttgacttgg atggtcaggg ttttgccaga    840
gcctaagacc tcactgctct ggtccaaggt ccaggtgata ccatcttctt caggggtgtc    900
acaggtgagg accaccattt ctccaggggc atccggatac caatccaatt ctacgacata    960
aacatctttc ttcagttccc atatggccac gagggggagt gccagaaaaa ccagggaaaa   1020
ccaagagatg accaactgct ggtgacacat ggtggcggcg cgccatttaa atctagcctt   1080
aagagctgta attgaactgg gagtggacac ctgtggagag aaaggcaaag tggatgtcag   1140
taagaccaat aggtgcctat cagaaacgca agagtcttct ctgtctcgac aagcccagtt   1200
tctattggtc tccttaaacc tgtcttgtaa ccttgatact tacctgccca gtgcctcacg   1260
accaacttca gaactgcgac ccaaatcccg gctgcgacgg aactagctgt gccacacccg   1320
gcgcgtcctt atataatcat cggcgttcac cgccccacgg agatccctcc gcagaatcgc   1380
cgagaaggga ctactttttcc tcgcctgttc cgctctctgg aaagaaaacc agtgccctag   1440
agtcacccaa gtcccgtcct aaaatgtcct tctgctgata ctggggttct aaggccgagt   1500
cttatgagca gcgggccgct gtcctgagcg tccgggcgga aggatcagga cgctcgctgc   1560
gcccttcgtc tgacgtggca gcgctcgccg tgaggagggg ggcgcccgcg ggaggcgcca   1620
aaacccggcg cggaggcctt aattaactag ttattaatag taatcaatta cggggtcatt   1680
agttcatagc ccatatatgg agttccgcgt tacataactt acggtaaatg cccgcctgg    1740
ctgaccgccc aacgacccccc gcccattgac gtcaataatg acgtatgttc ccatagtaac   1800
gccaataggg actttccatt gacgtcaatg ggtggactat ttacggtaaa ctgcccactt   1860
ggcagtacat caagtgtatc atatgccaag tacgccccct attgacgtca atgacgtaa    1920
atggcccgcc tggcattatg cccagtacat gaccttatgg actttcccta cttggcagta   1980
catctacgta ttagtcatcg ctattaccat gggtgatgcg gttttggcag tacatcaatg   2040
ggcgtggata gcggtttgac tcacggggat ttccaagtct ccaccccatt gacgtcaatg   2100
ggagtttgtt ttggcaccaa aatcaacggg actttccaaa atgtcgtaac aactccgccc   2160
cattgacgca aatgggcggt aggcgtgtac ggtgggaggt ctatataagc agagctcgtt   2220
tagtgaaccg tcagatcgcc tggagacgtc gaggaactga aaaaccagaa agttaactgg   2280
taagtttagt cttttttgtct tttatttcag gtcccggatc cggtggtggt gcaaatcaaa   2340
gaactgctcc tcagtggatg ttgcctttac ttctaggcct gtacgaagt gtttaaactt    2400
ctgctctgcg gccgcgccac catgtgtcca gcgcgcagcc tcctccttgt ggctaccctg   2460
gtcctcctgg accacctcag tttggccaga aacctcccg tggccactcc agacccagga    2520
atgttcccat gccttcacca ctcccaaaac ctgctgaggg ccgtcagcaa catgctccag   2580
aaggccagac aaactctaga attttaccct tgcacttctg aagagattga tcatgaagat   2640
atcacaaaag ataaaccag cacagtggag gcctgtttac cattggaatt aaccaagaat    2700
gagagttgcc taaattccag agagacctct ttcataacta atgggagttg cctggcctcc   2760
agaaagacct cttttatgat ggccctgtgc cttagtagta tttatgaaga cttgaagatg   2820
taccaggtgg agttcaagac catgaatgca aagcttctga tggatcctaa gaggcagatc   2880
tttctagatc aaaacatgct ggcagttatt gatgagctga tgcaggccct gaatttcaac   2940
agtgagactg tgccacaaaa atcctccctt gaagaaccgg atttttataa aactaaaatc   3000
aagctctgca tacttcttca tgctttccgg attcgggcag tgactattga tagagtgatg   3060
```

```
agctatctga atgcttcctg agcccctctc cctccccccc ccctaacgtt actggccgaa    3120
gccgcttgga ataaggccgg tgtgcgtttg tctatatgtt attttccacc atattgccgt    3180
cttttggcaa tgtgagggcc cggaaacctg gccctgtctt cttgacgagc attcctaggg    3240
gtctttcccc tctcgccaaa ggaatgcaag gtctgttgaa tgtcgtgaag gaagcagttc    3300
ctctggaagc ttcttgaaga caaacaacgt ctgtagcgac cctttgcagg cagcggaacc    3360
ccccacctgg cgacaggtgc ctctgcggcc aaaagccacg tgtataagat acacctgcaa    3420
aggcggcaca accccagtgc cacgttgtga gttggatagt tgtggaaaga gtcaaatggc    3480
tctcctcaag cgtattcaac aaggggctga aggatgccca aaggtaccc cattgtatgg     3540 gatctgatct ggggcctcgg tacacatgct ttacatgtgt ttagtcgagg ttaaaaaaac    3600
gtctaggccc cccgaaccac ggggacgtgg ttttcctttg aaaaacacga tgataatatg    3660
gccacaatga gaatttcgaa accacatttg agaagtattt ccatccagtg ctacttgtgt    3720
ttacttctaa acagtcattt tctaactgaa gctggcattc atgtcttcat tttgggctgt    3780
ttctctgcag ggcttcctaa aacagaagcc aactgggtga atgtaataag tgatttgaaa    3840
aaaattgaag atcttattca atctatgcat attgatgcta ctttatatac ggaaagtgat    3900
gttcacccca gttgcaaagt aacagcaatg aagtgctttc tcttggagtt acaagttatt    3960
tcacttgagt ccggagatgc aagtattcat gatacagtag aaaatctgat catcctagca    4020
aacaacagtt tgtcttctaa tgggaatgta acagaatctg atgcaaaga atgtgaggaa    4080 ctggaggaaa aaaatattaa agaattttg cagagttttg tacatattgt ccaaatgttc    4140
atcaacactt cttgagcggc cgcgctagcc aattgctgtg ccttctagtt gccagccatc    4200
tgttgtttgc ccctcccccg tgccttcctt gaccctggaa ggtgccactc ccactgtcct    4260
ttcctaataa aatgaggaaa ttgcatcgca ttgtctgagt aggtgtcatt ctattctggg    4320
gggtggggtg gggcaggaca gcaaggggga ggattgggaa gacaatagca ggcatgctgg    4380
ggatgcggtg ggctctatgg agctcgag                                      4408
```

<210> SEQ ID NO 23
<211> LENGTH: 3916
<212> TYPE: DNA
<213> ORGANISM: Artificial Sequence
<220> FEATURE:
<223> OTHER INFORMATION: Human UbC - wild-type IL-12A/IL-12B/IL-15 - F2A
      (no CpG modification)

<400> SEQUENCE: 23

```
gtcgaccaca caaaaaacca acacacagat ctaatgaaaa taaagatctt ttattggcgc      60
gcctcaagaa gtgttgatga acatttggac aatatgtaca aaactctgca aaaattcttt     120 aatattttt tcctccagtt cctcacattc tttgcatcca gattctgtta cattcccatt      180
agaagacaaa ctgttgtttg ctaggatgat cagattttct actgtatcat gaatacttgc     240
atctccggac tcaagtgaaa taacttgtaa ctccaagaga aagcacttca ttgctgttac     300
tttgcaactg gggtgaacat cactttccgt atataaagta gcatcaatat gcatagattg     360
aataagatct tcaatttttt tcaaatcact tattacattc acccagttgg cttctgtttt     420
aggaagccct gcagagaaac agcccaaaat gaagacatga atgccagctt cagttagaaa     480
atgactgttt agaagtaaac acaagtagca ctggatggaa atacttctca aatgtggttt     540
cgaaattctc atggtggcgg cgcgccattt aaatctagcc ttaagagctg taattgaact     600
gggagtggac acctgtggag agaaaggcaa agtggatgtc agtaagacca ataggtgcct     660
```

```
atcagaaacg caagagtctt ctctgtctcg acaagcccag tttctattgg tctccttaaa    720
cctgtcttgt aaccttgata cttacctgcc cagtgcctca cgaccaactt cagaactgcg    780
acccaaatcc cggctgcgac ggaactagct gtgccacacc cggcgcgtcc ttatataatc    840
atcggcgttc accgccccac ggagatccct ccgcagaatc gccgagaagg gactactttt    900
cctcgcctgt tccgctctct ggaaagaaaa ccagtgccct agagtcaccc aagtcccgtc    960
ctaaaatgtc cttctgctga tactgggggtt ctaaggccga gtcttatgag cagcgggccg   1020
ctgtcctgag cgtccgggcg aaggatcag gacgctcgct gcgcccttcg tctgacgtgg    1080
cagcgctcgc cgtgaggagg ggggcgcccg cgggaggcgc caaaacccgg cgcggaggcc   1140
ttaattaact agttattaat agtaatcaat tacggggtca ttagttcata gcccatatat   1200
ggagttccgc gttacataac ttacggtaaa tggcccgcct ggctgaccgc ccaacgaccc   1260
ccgcccattg acgtcaataa tgacgtatgt tcccatagta acgccaatag ggactttcca   1320
ttgacgtcaa tgggtggact atttacggta aactgcccac ttggcagtac atcaagtgta   1380
tcatatgcca agtacgcccc ctattgacgt caatgacggt aaatggcccg cctggcatta   1440
tgcccagtac atgaccttat gggactttcc tacttggcag tacatctacg tattagtcat   1500
cgctattacc atgggtgatg cggttttggc agtacatcaa tgggcgtgga tagcggtttg   1560
actcacgggg atttccaagt ctccacccca ttgacgtcaa tgggagtttg ttttggcacc   1620
aaaatcaacg ggactttcca aaatgtcgta acaactccgc cccattgacg caaatgggcg   1680
gtaggcgtgt acggtgggag gtctatataa gcagagctcg tttagtgaac cgtcagatcg   1740
cctggagacg tcgaggaact gaaaaaccag aaagttaact ggtaagttta gtcttttgt    1800
cttttatttc aggtcccgga tccggtggtg gtgcaaatca aagaactgct cctcagtgga   1860
tgttgccttt acttctaggc ctgtacgaaa gtgtttaaac ttctgctctg cggccgcgcc   1920
accatgtgtc cagcgcgcag cctcctcctt gtggctaccc tggtcctcct ggaccacctc   1980
agtttggcca gaaacctccc cgtggccact ccagacccag gaatgttccc atgccttcac   2040
cactcccaaa acctgctgag ggccgtcagc aacatgctcc agaaggccag acaaactcta   2100
gaatttacc cttgcacttc tgaagagatt gatcatgaag atatcacaaa agataaaacc   2160
agcacagtgg aggcctgttt accattggaa ttaaccaaga atgagagttg cctaaattcc   2220
agagagacct ctttcataac taatgggagt tgcctggcct ccagaaagac ctcttttatg   2280
atggccctgt gccttagtag tatttatgaa gacttgaaga tgtaccaggt ggagttcaag   2340
accatgaatg caaagcttct gatggatcct aagaggcaga tctttctaga tcaaaacatg   2400
ctggcagtta ttgatgagct gatgcaggcc ctgaatttca acagtgagac tgtgccacaa   2460
aaatcctccc ttgaagaacc ggattttat aaaactaaaa tcaagctctg catacttctt   2520
catgctttcc ggattcgggc agtgactatt gatagagtga tgagctatct gaatgcttcc   2580
agaaagagaa ggagtggctc aggagcccct gtgaaacaga ccctgaactt tgacctcttg   2640
aagcttgctg gggatgtgga gtctaatcct ggtccaatgt gtcaccagca gttggtcatc   2700
tcttggtttt ccctggtttt tctggcatct cccctcgtgg ccatatggga actgaagaaa   2760
gatgtttatg tcgtagaatt ggattggtat ccggatgccc tggagaaat ggtggtcctc   2820
acctgtgaca cccctgaaga agatggtatc acctggacct tggaccagag cagtgaggtc   2880
ttaggctctg gcaaaacccct gaccatccaa gtcaaagagt ttggagatgc tggccagtac   2940
acctgtcaca aggaggcgga ggttctaagc cattcgctcc tgctgcttca caaaaggaa   3000
```

```
gatggaattt ggtccactga tattttaaag gaccagaaag aacccaaaaa taagacctttt   3060 ctaagatgcg aggccaagaa ttattctgga cgtttcacct gctggtggct gacgacaatc   3120
agtactgatt tgacattcag tgtcaaaagc agcagaggct cttctgaccc ccaaggggtg   3180
acgtgcggag ctgctacact ctctgcagag agagtcagag gggacaacaa ggagtatgag   3240
tactcagtgg agtgccagga ggacagtgcc tgcccagctg ctgaggagag tctgcccatt   3300
gaggtgatgg tggatgccgt tcacaagctc aagtatgaaa actacaccag cagcttcttc   3360
atcagggaca tcatcaaacc tgacccaccc aagaacttgc agctgaagcc attaaagaat   3420
tctcggcagg tggaggtcag ctgggagtac cctgacacct ggagtactcc acattcctac   3480
ttctccctga cattctgcgt tcaagtccag ggcaagagca agagagaaaa gaaagataga   3540
gtcttcacgg acaagacctc agccacggtc atctgccgca aaaatgccag cattagcgtg   3600
cgggcccagg accgctacta tagctcatct tggagcgaat gggcatctgt gccctgcagt   3660
tgagcggccg cgctagccaa ttgctgtgcc ttctagttgc cagccatctg ttgtttgccc   3720
ctcccccgtg ccttccttga ccctggaagg tgccactccc actgtccttt cctaataaaa   3780
tgaggaaatt gcatcgcatt gtctgagtag gtgtcattct attctggggg gtggggtggg   3840
gcaggacagc aagggggagg attgggaaga caatagcagg catgctgggg atgcggtggg   3900
ctctatggag ctcgag                                                   3916
```

<210> SEQ ID NO 24
<211> LENGTH: 4408
<212> TYPE: DNA
<213> ORGANISM: Artificial Sequence
<220> FEATURE:
<223> OTHER INFORMATION: Human UbC - modified IL-12A/IL-12B/IL-15 - IRES (with CpG modification)

<400> SEQUENCE: 24

```
gtcgaccaca caaaaaacca acacacagat ctaatgaaaa taaagatctt ttattggcgc     60
gcctcaactg cagggcacag atgcccattc tgaccaagat gagctatagt agcggtcctg    120
ggcccgcact gaaatgctgg cattttttgcg gcagatgact gtggctgagg tcttgtcagt   180
gaagactcta tctttctttt ctctcttgct cttgccctgg acttgaacac agaatgtcag    240
ggagaagtag gaatgtggag tactccaggt gtcagggtac tcccagctga cctccacctg    300
cctagaattc tttaatggct tcagctgcaa gttcttgggt gggtcaggtt tgatgatgtc    360
cctgatgaag aagctgctgg tgtagttttc atacttgagc ttgtgaaccg catccaccat    420
cacctcaatg gcagactct cctcagcagc tgggcaggca ctgtcctcct ggcactccac    480
tgagtactca tactccttgt tgtcccctct gactctctct gcagagagtg tagcagctcc    540
gcatgtcacc ccttggggtt cagaagagcc tctgctgctt ttgacactga atgtcaaatc    600
agtactgatt gtagtcagcc accagcaggt gaaccttcca gataattct tggcctcaca     660 tcttagaaaaag gtcttatttt tgggttcttt ctggtccttt aaaatatcag tggaccaaat   720
tccatcttcc tttttgtgaa gcagcaggag ggaatggctt agaacctccc ctccttgtg    780 acaggtgtac tggccagcat ctccaaactc tttgacttgg atggtcaggg ttttgccaga    840
gcctaagacc tcactgctct ggtccaaggt ccaggtgata ccatcttctt caggggtgtc    900
acaggtgagg accaccattt ctccaggggc atcaggatac caatccaatt ctaccacata    960
aacatctttc ttcagttccc atatggccac aaggggagat gccagaaaaa ccagggaaaa   1020
ccaagagatg accaactgct ggtgacacat ggtggcggcg cgccatttaa atctagcctt   1080
```

```
aagagctgta attgaactgg gagtggacac ctgtggagag aaaggcaaag tggatgtcag   1140
taagaccaat aggtgcctat cagaaacgca agagtcttct ctgtctcgac aagcccagtt   1200
tctattggtc tccttaaacc tgtcttgtaa ccttgatact tacctgccca gtgcctcacg   1260
accaacttca gaactgcgac ccaaatcccg gctgcgacgg aactagctgt gccacacccg   1320
gcgcgtcctt atataatcat cggcgttcac cgccccacgg agatccctcc gcagaatcgc   1380
cgagaaggga ctactttcc tcgcctgttc cgctctctgg aaagaaaacc agtgccctag   1440
agtcacccaa gtcccgtcct aaaatgtcct tctgctgata ctggggttct aaggccgagt   1500
cttatgagca gcgggccgct gtcctgagcg tccgggcgga aggatcagga cgctcgctgc   1560
gcccttcgtc tgacgtggca gcgctcgccg tgaggagggg ggcgcccgcg ggaggcgcca   1620
aaacccggcg cggaggcctt aattaactag ttattaatag taatcaatta cggggtcatt   1680
agttcatagc ccatatatgg agttccgcgt tacataactt acggtaaatg gcccgcctgg   1740
ctgaccgccc aacgacccc gcccattgac gtcaataatg acgtatgttc ccatagtaac   1800
gccaataggg actttccatt gacgtcaatg ggtggactat ttacggtaaa ctgcccactt   1860
ggcagtacat caagtgtatc atatgccaag tacgcccccct attgacgtca atgacggtaa   1920
atggcccgcc tggcattatg cccagtacat gaccttatgg actttccta cttggcagta   1980 catctacgta ttagtcatcg ctattaccat gggtgatgcg gttttggcag tacatcaatg   2040
ggcgtggata gcggtttgac tcacggggat ttccaagtct ccaccccatt gacgtcaatg   2100
ggagtttgtt ttggcaccaa aatcaacggg actttccaaa atgtcgtaac aactccgccc   2160
cattgacgca aatgggcggt aggcgtgtac ggtgggaggt ctatataagc agagctcgtt   2220
tagtgaaccg tcagatcgcc tggagacgtc gaggaactga aaaaccagaa agttaactgg   2280
taagtttagt cttttttgtct tttatttcag gtcccggatc cggtggtggt gcaaatcaaa   2340
gaactgctcc tcagtggatg ttgcctttac ttctaggcct gtacggaagt gtttaaactt   2400
ctgctctgcg gccgcgccac catgtgtcca gcgcgcagcc tcctccttgt ggctaccctg   2460
gtcctcctgg accacctcag tttggccaga aacctccctg tggccactcc agacccagga   2520
atgttcccat gccttcacca ctcccaaaac ctgctgaggg ctgtcagcaa catgctccag   2580
aaggccagac aaactctaga attttaccct tgcacttctg aagagattga tcatgaagat   2640
atcacaaaag ataaaaccag cacagtggag gcctgtttac cattggaatt aaccaagaat   2700
gagagttgcc taaattccag agagacctct ttcataacta atgggagttg cctggcctcc   2760
agaaagacct cttttatgat ggccctgtgc cttagtagta tttatgaaga cttgaagatg   2820
taccaggtgg agttcaagac catgaatgca aagcttctga tggatcctaa gaggcagatc   2880
tttctagatc aaaacatgct ggcagttatt gatgagctga tgcaggccct gaatttcaac   2940
agtgagactg tgccacaaaa atcctccctt gaagaacctg attttatata aactaaaatc   3000
aagctctgca tacttcttca tgctttccgg attcgcgcag tgactattga tagagtgatg   3060
agctatctga atgcttcctg agcccctctc cctccccccc ccctaacgtt actggccgaa   3120
gccgcttgga ataaggccgg tgtgcgtttg tctatatgtt attttccacc atattgccgt   3180
cttttggcaa tgtgagggcc cggaaacctg gccctgtctt cttgacgagc attcctaggg   3240
gtctttcccc tctcgccaaa ggaatgcaag gtctgttgaa tgtcgtgaag gaagcagttc   3300
ctctggaagc ttcttgaaga caacaacgt ctgtagcgac cctttgcagg cagcggaacc   3360 ccccacctg cgacaggtgc ctctgcggcc aaaagccacg tgtataagat acacctgcaa   3420
aggcggcaca accccagtgc cacgttgtga gttggatagt tgtggaaaga gtcaaatggc   3480
```

```
tctcctcaag cgtattcaac aaggggctga aggatgccca gaaggtaccc cattgtatgg    3540
gatctgatct ggggcctcgg tacacatgct ttacatgtgt ttagtcgagg ttaaaaaaac    3600
gtctaggccc cccgaaccac ggggacgtgg ttttcctttg aaaaacacga tgataatatg    3660
gccacaatga gaattagcaa accacatttg agaagtattt ccatccagtg ctacttgtgt    3720
ttacttctaa acagtcattt tctaactgaa gctggcattc atgtcttcat tttgggctgt    3780
ttctctgcag gcttcctaa  aacagaagcc aactgggtga atgtaataag tgatttgaaa    3840
aaaattgaag atcttattca atctatgcat attgatgcta ctttatatac tgaaagtgat    3900
gttcaccccca gttgcaaagt aacagcaatg aagtgctttc tcttggagtt acaagttatt    3960
tcacttgaga gcggagatgc aagtattcat gatacagtag aaaatctgat catcctagca    4020
aacaacagtt tgtcttctaa tgggaatgta acagaatctg gatgcaaaga atgtgaggaa    4080
ctggaggaaa aaaatattaa agaattttg  cagagttttg tacatattgt ccaaatgttc    4140
atcaacactt cttgagcggc cgcgctagcc aattgctgtg ccttctagtt gccagccatc    4200
tgttgtttgc ccctcccccg tgccttcctt gaccctggaa ggtgccactc ccactgtcct    4260
ttcctaataa aatgaggaaa ttgcatcgca ttgtctgagt aggtgtcatt ctattctggg    4320
gggtggggtg gggcaggaca gcaaggggga ggattgggaa gacaatagca ggcatgctgg    4380
ggatgcggtg ggctctatgg agctcgag                                      4408
```

<210> SEQ ID NO 25
<211> LENGTH: 3916
<212> TYPE: DNA
<213> ORGANISM: Artificial Sequence
<220> FEATURE:
<223> OTHER INFORMATION: Human UbC -modified IL-12A/IL-12B/IL-15 - F2A
      (with CpG modification)

<400> SEQUENCE: 25

```
gtcgaccaca caaaaaacca acacacagat ctaatgaaaa taaagatctt ttattggcgc      60
gcctcaagaa gtgttgatga acatttggac aatatgtaca aaactctgca aaaattcttt     120
aatattttt  tcctccagtt cctcacattc tttgcatcca gattctgtta cattcccatt     180
agaagacaaa ctgttgtttg ctaggatgat cagatttct  actgtatcat gaatacttgc     240
atctccgctc tcaagtgaaa taacttgtaa ctccaagaga aagcacttca ttgctgttac     300
tttgcaactg gggtgaacat cactttcagt atataaagta gcatcaatat gcatagattg     360
aataagatct tcaattttt  tcaaatcact tattacattc acccagttgg cttctgtttt     420
aggaagccct gcagagaaac agcccaaaat gaagacatga atgccagctt cagttagaaa     480
atgactgttt agaagtaaac acaagtagca ctggatggaa atacttctca atgtggtttt     540
gctaattctc atggtggcgg cgcgccattt aaatctagcc ttaagagctg taattgaact     600
gggagtggac acctgtggag agaaaggcaa agtggatgtc agtaagacca ataggtgcct     660
atcagaaacg caagagtctt ctctgtctcg acaagcccag tttctattgg tctccttaaa     720
cctgtcttgt aaccttgata cttacctgcc cagtgcctca cgaccaactt cagaactgcg     780
acccaaatcc cggctgcgac ggaactagct gtgccacacc cggcgcgtcc ttatataatc     840
atcggcgttc accgcccac  ggagatccct ccgcagaatc gccgagaagg gactactttt     900
cctcgcctgt tccgctctct ggaaagaaaa ccagtgccct agagtcaccc aagtcccgtc     960
ctaaaatgtc cttctgctga tactgggggtt ctaaggccga gtcttatgag cagcgggcc    1020
ctgtcctgag cgtccgggcg gaaggatcag gacgctcgct gcgcccttcg tctgacgtgg    1080
```

-continued

```
cagcgctcgc cgtgaggagg ggggcgcccg cgggaggcgc caaaacccgg cgcggaggcc    1140
ttaattaact agttattaat agtaatcaat tacggggtca ttagttcata gcccatatat    1200
ggagttccgc gttacataac ttacggtaaa tggcccgcct ggctgaccgc ccaacgaccc    1260
ccgcccattg acgtcaataa tgacgtatgt tcccatagta acgccaatag ggactttcca    1320
ttgacgtcaa tgggtggact atttacggta aactgcccac ttggcagtac atcaagtgta    1380
tcatatgcca agtacgcccc ctattgacgt caatgacggt aaatggcccg cctggcatta    1440
tgcccagtac atgaccttat gggactttcc tacttggcag tacatctacg tattagtcat    1500
cgctattacc atgggtgatg cggttttggc agtacatcaa tgggcgtgga tagcggtttg    1560
actcacgggg atttccaagt ctccacccca ttgacgtcaa tgggagtttg ttttggcacc    1620
aaaatcaacg ggactttcca aaatgtcgta acaactccgc cccattgacg caaatgggcg    1680
gtaggcgtgt acggtgggag gtctatataa gcagagctcg tttagtgaac cgtcagatcg    1740
cctggagacg tcgaggaact gaaaaaccag aaagttaact ggtaagttta gtcttttgt     1800
cttttatttc aggtcccgga tccggtggtg gtgcaaatca agaactgct cctcagtgga     1860
tgttgccttt acttctaggc ctgtacgaa gtgtttaaac ttctgctctg cggccgcgcc     1920
accatgtgtc cagcgcgcag cctcctcctt gtggctaccc tggtcctcct ggaccacctc    1980
agtttggcca gaaaccctcc tgtggccact ccagacccag gaatgttccc atgccttcac    2040
cactcccaaa acctgctgag ggctgtcagc aacatgctcc agaaggccag acaaactcta    2100
gaattttacc cttgcacttc tgaagagatt gatcatgaag atatcacaaa agataaaacc    2160
agcacagtgg aggcctgttt accattggaa ttaaccaaga atgagagttg cctaaattcc    2220
agagagacct ctttcataac taatgggagt tgcctggcct ccagaaagac ctcttttatg    2280
atggccctgt gccttagtag tatttatgaa gacttgaaga tgtaccaggt ggagttcaag    2340
accatgaatg caaagcttct gatggatcct aagaggcaga tctttctaga tcaaaacatg    2400
ctggcagtta ttgatgagct gatgcaggcc ctgaatttca acagtgagac tgtgccacaa    2460
aaatcctccc ttgaagaacc tgatttttat aaaactaaaa tcaagctctg catacttctt    2520
catgcttcc ggattcgcgc agtgactatt gatagagtga tgagctatct gaatgcttcc    2580
agaaagagaa ggagtggctc aggagcccct gtgaaacaga ccctgaactt tgacctcttg    2640
aagcttctg gggatgtgga gtctaatcct ggtccaatgt gtcaccagca gttggtcatc    2700
tcttggtttt ccctggtttt tctggcatct ccccttgtgg ccatatggga actgaagaaa    2760
gatgtttatg tggtagaatt ggattggtat cctgatgccc ctggagaaat ggtggtcctc    2820
acctgtgaca cccctgaaga agatggtatc acctggacct tggaccagag cagtgaggtc    2880
ttaggctctg gcaaaacct gaccatccaa gtcaaagagt ttggagatgc tggccagtac    2940
acctgtcaca aggaggggga ggttctaagc cattccctcc tgctgcttca caaaaggaa    3000
gatggaattt ggtccactga tattttaaag gaccagaaag aacccaaaaa taagaccttt    3060
ctaagatgtg aggccaagaa ttattctgga aggttcacct gctggtggct gactacaatc    3120
agtactgatt tgacattcag tgtcaaaagc agcagaggct cttctgaccc ccaagggggtg   3180
acatgcggag ctgctacact ctctgcagag agagtcagag gggacaacaa ggagtatgag    3240
tactcagtgg agtgccagga ggacagtgcc tgcccagctg ctgaggagag tctgcccatt    3300
gaggtgatgg tggatgcggt tcacaagctc aagtatgaaa actacaccag cagcttcttc    3360
atcagggaca tcatcaaacc tgacccaccc aagaacttgc agctgaagcc attaaagaat    3420
```

```
tctaggcagg tggaggtcag ctgggagtac cctgacacct ggagtactcc acattcctac    3480
ttctccctga cattctgtgt tcaagtccag ggcaagagca agagagaaaa gaaagataga    3540
gtcttcactg acaagacctc agccacagtc atctgccgca aaaatgccag catttcagtg    3600
cgggcccagg accgctacta tagctcatct tggtcagaat gggcatctgt gccctgcagt    3660
tgagcggccg cgctagccaa ttgctgtgcc ttctagttgc cagccatctg ttgtttgccc    3720 ctccccgtg ccttccttga ccctggaagg tgccactccc actgtccttt cctaataaaa     3780
tgaggaaatt gcatcgcatt gtctgagtag gtgtcattct attctggggg gtggggtggg    3840
gcaggacagc aagggggagg attgggaaga caatagcagg catgctgggg atgcggtggg    3900
ctctatggag ctcgag                                                    3916
```

<210> SEQ ID NO 26
<211> LENGTH: 4408
<212> TYPE: DNA
<213> ORGANISM: Artificial Sequence
<220> FEATURE:
<223> OTHER INFORMATION: Human UbC - modified IL-12A/IL-12B/IL-15 - IRES
      (with CpG modification)

<400> SEQUENCE: 26

```
gtcgaccaca caaaaaacca acacacagat ctaatgaaaa taaagatctt ttattggcgc      60
gcctcaactg cagggcacag atgcccattc tgaccaagat gagctatagt atctgtcctg    120
ggccctcact gaaatgctgg catttttcct gcagatgact gtggctgagg tcttgtcagt    180
gaagactcta tctttctttt ctctcttgct cttgccctgg acttgaacac agaatgtcag    240
ggagaagtag gaatgtggag tactccaggt gtcagggtac tcccagctga cctccacctg    300
cctagaattc tttaatggct tcagctgcaa gttcttgggt gggtcaggtt tgatgatgtc    360
cctgatgaag aagctgctgg tgtagttttc atacttgagc ttgtgaactg catccaccat    420
cacctcaatg ggcagactct cctcagcagc tgggcaggca ctgtcctcct ggcactccac    480
tgagtactca tactccttgt tgtcccctct gactctctct gcagagagtg tagcagctcc    540
acatgtcacc ccttgggggt cagaagagcc tctgctgctt ttgacactga atgtcaaatc    600
agtactgatt gtagtcagcc accagcaggt gaaccttcca gaataattct tggcctcaca    660
tcttagaaag gtcttatttt tgggttcttt ctggtccttt aaaatatcag tggaccaaat    720
tccatcttcc tttttgtgaa gcagcaggag ggaatggctt agaacctccc ctcctttgtg    780
acaggtgtac tggccagcat ctccaaactc tttgacttgg atggtcaggg ttttgccaga    840
gcctaagacc tcactgctct ggtccaaggt ccaggtgata ccatcttctt caggggtgtc    900
acaggtgagg accaccattt ctccaggggc atcaggatac caatccaatt ctaccacata    960
aacatctttc ttcagttccc atatggccac aaggggagag ccagaaaaaa ccagggaaaa    1020
ccaagagatg accaactgct ggtgacacat ggtggcggcg cgccatttaa atctagcctt    1080
aagagctgta attgaactgg gagtggacac ctgtggagag aaaggcaaag tggatgtcag    1140
taagaccaat aggtgcctat cagaaacgca agagtcttct ctgtctcgac aagcccagtt    1200
tctattggtc tccttaaacc tgtcttgtaa ccttgatact tacctgccca gtgcctcacg    1260
accaacttca gaactcgcac ccaaatcccg gctgcgacgg aactagctgt gccacacccg    1320
gcgcgtcctt atataatcat cggcgttcac cgccccacgg agatccctcc gcagaatcgc    1380
cgagaaggga ctacttttcc tcgcctgttc cgctctctgg aaagaaaacc agtgccctag    1440
agtcacccaa gtcccgtcct aaaatgtcct tctgctgata ctggggttct aaggccgagt    1500
```

```
cttatgagca gcgggccgct gtcctgagcg tccgggcgga aggatcagga cgctcgctgc    1560
gcccttcgtc tgacgtggca gcgctcgccg tgaggagggg ggcgcccgcg ggaggcgcca    1620
aaacccggcg cggaggcctt aattaactag ttattaatag taatcaatta cggggtcatt    1680
agttcatagc ccatatatgg agttccgcgt tacataactt acggtaaatg gcccgcctgg    1740
ctgaccgccc aacgaccccc gcccattgac gtcaataatg acgtatgttc ccatagtaac    1800
gccaataggg actttccatt gacgtcaatg ggtggactat ttacggtaaa ctgcccactt    1860
ggcagtacat caagtgtatc atatgccaag tacgccccct attgacgtca atgacggtaa    1920
atggcccgcc tggcattatg cccagtacat gaccttatgg actttcctac ttggcagta    1980 catctacgta ttagtcatcg ctattaccat gggtgatgcg gttttggcag tacatcaatg    2040
ggcgtggata gcggtttgac tcacggggat ttccaagtct ccaccccatt gacgtcaatg    2100
ggagtttgtt ttggcaccaa aatcaacggg actttccaaa atgtcgtaac aactccgccc    2160
cattgacgca aatgggcggt aggcgtgtac ggtgggaggt ctatataagc agagctcgtt    2220
tagtgaaccg tcagatcgcc tggagacgtc gaggaactga aaaaccagaa agttaactgg    2280
taagtttagt cttttgtct tttatttcag gtcccggatc cggtggtggt gcaaatcaaa     2340
gaactgctcc tcagtggatg ttgcctttac ttctaggcct gtacggaagt gtttaaactt    2400
ctgctctgcg gccgcgccac catgtgtcca gctaggagcc tcctccttgt ggctaccctg    2460
gtcctcctgg accacctcag tttggccaga aacctccctg tggccactcc agacccagga    2520
atgttcccat gccttcacca ctcccaaaac tgctgagggc agtcagcaa catgctccag     2580 aaggccagac aaactctaga attttaccct tgcacttctg aagagattga tcatgaagat    2640
atcacaaaag ataaaaccag cacagtggag gcctgtttac cattggaatt aaccaagaat    2700
gagagttgcc taaattccag agagacctct ttcataacta atgggagttg cctggcctcc    2760
agaaagacct cttttatgat ggccctgtgc cttagtagta tttatgaaga cttgaagatg    2820
taccaggtgg agttcaagac catgaatgca aagcttctga tggatcctaa gaggcagatc    2880
tttctagatc aaaacatgct ggcagttatt gatgagctga tgcaggccct gaatttcaac    2940
agtgagactg tgccacaaaa atcctcccct gaagaacctg atttttataa aactaaaatc    3000
aagctctgca tacttcttca tgctttccgg attagggcag tgactattga tagagtgatg    3060
agctatctga atgcttcctg agcccctctc cctccccccc ccctaacgtt actggccgaa    3120
gccgcttgga ataaggccgg tgtgcgtttg tctatatgtt attttccacc atattgccgt    3180
cttttggcaa tgtgagggcc cggaaacctg gccctgtctt cttgacgagc attcctaggg    3240
gtctttcccc tctcgccaaa ggaatgcaag gtctgttgaa tgtcgtgaag gaagcagttc    3300
ctctggaagc ttcttgaaga caacaacgt ctgtagcgac cctttgcagg cagcggaacc     3360
ccccacctgg cgacaggtgc ctctgcggcc aaaagccacg tgtataagat acacctgcaa    3420
aggcggcaca ccccagtgcc acgttgtga gttggatagt tgtggaaaga gtcaaatggc     3480
tctcctcaag cgtattcaac aaggggctga aggatgccca aaggtaccc cattgtatgg     3540 gatctgatct ggggcctcgg tacacatgct ttacatgtgt ttagtcgagg ttaaaaaaac    3600
gtctaggccc cccgaaccac ggggacgtgg ttttcctttg aaaaacacga tgataatatg    3660
gccacaatga gaattagcaa accacatttg agaagtattt ccatccagtg ctacttgtgt    3720
ttacttctaa acagtcattt tctaactgaa gctggcattc atgtcttcat tttgggctgt    3780
ttctctgcag ggcttcctaa aacagaagcc aactgggtga atgtaataag tgatttgaaa    3840
aaaattgaag atcttattca atctatgcat attgatgcta ctttatatac tgaaagtgat    3900
```

```
gttcacccca gttgcaaagt aacagcaatg aagtgctttc tcttggagtt acaagttatt    3960
tcacttgagt caggagatgc aagtattcat gatacagtag aaaatctgat catcctagca    4020
aacaacagtt tgtcttctaa tgggaatgta acagaatctg gatgcaaaga atgtgaggaa    4080
ctggaggaaa aaatattaa agaattttg cagagttttg tacatattgt ccaaatgttc    4140
atcaacactt cttgagcggc cgcgctagcc aattgctgtg ccttctagtt gccagccatc    4200
tgttgtttgc ccctccccg tgccttcctt gaccctggaa ggtgccactc ccactgtcct    4260
ttcctaataa aatgaggaaa ttgcatcgca ttgtctgagt aggtgtcatt ctattctggg    4320
gggtggggtg gggcaggaca gcaaggggga ggattgggaa gacaatagca ggcatgctgg    4380
ggatgcggtg ggctctatgg agctcgag                                      4408
```

<210> SEQ ID NO 27
<211> LENGTH: 3916
<212> TYPE: DNA
<213> ORGANISM: Artificial Sequence
<220> FEATURE:
<223> OTHER INFORMATION: Human UbC - modified IL-12A/IL-12B/IL-15 -
      F2A - (with CpG modification)

<400> SEQUENCE: 27

```
gtcgaccaca caaaaaacca acacacagat ctaatgaaaa taaagatctt ttattggcgc      60
gcctcaagaa gtgttgatga acatttggac aatatgtaca aaactctgca aaaattcttt     120 aatattttt tcctccagtt cctcacattc tttgcatcca gattctgtta cattcccatt     180
agaagacaaa ctgttgtttg ctaggatgat cagatttct actgtatcat gaatacttgc     240
atctcctgac tcaagtgaaa taacttgtaa ctccaagaga aagcacttca ttgctgttac     300
tttgcaactg gggtgaacat cactttcagt atataaagta gcatcaatat gcatagattg     360
aataagatct tcaattttt tcaaatcact tattacattc acccagttgg cttctgtttt     420
aggaagccct gcagagaaac agcccaaaat gaagacatga atgccagctt cagttagaaa     480
atgactgttt agaagtaaac acaagtagca ctggatggaa atacttctca aatgtggttt     540
gctaattctc atggtggcgg cgcgccattt aaatctagcc ttaagagctg taattgaact     600
gggagtggac acctgtggag agaaaggcaa agtggatgtc agtaagacca ataggtgcct     660
atcagaaacg caagagtctt ctctgtctcg acaagcccag tttctattgg tctccttaaa     720
cctgtcttgt aaccttgata cttacctgcc cagtgcctca cgaccaactt cagaactgcg     780
acccaaatcc cggctgcgac ggaactagct gtgccacacc cggcgcgtcc ttatataatc     840
atcggcgttc accgcccac ggagatccct ccgcagaatc gccgagaagg gactactttt     900
cctcgcctgt tccgctctct ggaaagaaaa ccagtgccct agagtcaccc aagtcccgtc     960
ctaaaatgtc cttctgctga tactgggtt ctaaggccga gtcttatgag cagcgggccg    1020
ctgtcctgag cgtccgggcg gaaggatcag gacgctcgct gcgcccttcg tctgacgtgg    1080
cagcgctcgc cgtgaggagg ggggcgcccg cgggaggcgc aaaacccggg cgcggaggcc    1140
ttaattaact agttattaat agtaatcaat tacggggtca ttagttcata gcccatatat    1200
ggagttccgc gttacataac ttacggtaaa tggcccgcct ggctgaccgc ccaacgaccc    1260
ccgcccattg acgtcaataa tgacgtatgt tcccatagta acgccaatag ggactttcca    1320
ttgacgtcaa tgggtggact atttacggta aactgcccac ttggcagtac atcaagtgta    1380
tcatatgcca agtacgcccc ctattgacgt caatgacggt aaatggcccg cctggcatta    1440
tgcccagtac atgaccttat gggactttcc tacttggcag tacatctacg tattagtcat    1500
```

```
cgctattacc atgggtgatg cggttttggc agtacatcaa tgggcgtgga tagcggtttg   1560
actcacgggg atttccaagt ctccacccca ttgacgtcaa tgggagtttg ttttggcacc   1620
aaaatcaacg ggactttcca aaatgtcgta acaactccgc cccattgacg caaatgggcg   1680
gtaggcgtgt acggtgggag gtctatataa gcagagctcg tttagtgaac cgtcagatcg   1740
cctggagacg tcgaggaact gaaaaaccag aaagttaact ggtaagttta gtctttttgt   1800
cttttatttc aggtcccgga tccggtggtg gtgcaaatca agaactgct cctcagtgga    1860 tgttgccttt acttctaggc ctgtacggaa gtgtttaaac ttctgctctg cggccgcgcc   1920
accatgtgtc cagctaggag cctcctcctt gtggctaccc tggtcctcct ggaccacctc   1980
agtttggcca gaaacctccc tgtggccact ccagacccag gaatgttccc atgccttcac   2040
cactcccaaa acctgctgag ggcagtcagc aacatgctcc agaaggccag acaaactcta   2100
gaattttacc cttgcacttc tgaagagatt gatcatgaag atatcacaaa agataaaacc   2160
agcacagtgg aggcctgttt accattggaa ttaaccaaga atgagagttg cctaaattcc   2220
agagagacct ctttcataac taatgggagt tgcctggcct ccagaaagac ctcttttatg   2280
atggccctgt gccttagtag tatttatgaa gacttgaaga tgtaccaggt ggagttcaag   2340
accatgaatg caaagcttct gatggatcct aagaggcaga tctttctaga tcaaaacatg   2400
ctggcagtta ttgatgagct gatgcaggcc ctgaatttca acagtgagac tgtgccacaa   2460
aaatcctccc ttgaagaacc tgatttttat aaaactaaaa tcaagctctg catacttctt   2520
catgcttttc ggattagggc agtgactatt gatagagtga tgagctatct gaatgcttcc   2580
agaaagagaa ggagtggctc aggagcccct gtgaaacaga ccctgaactt tgacctcttg   2640
aagcttgctg gggatgtgga gtctaatcct ggtccaatgt gtcaccagca gttggtcatc   2700
tcttggtttt ccctggtttt tctggcatct ccccttgtgg ccatatggga actgaagaaa   2760
gatgtttatg tggtagaatt ggattggtat cctgatgccc ctggagaaat ggtggtcctc   2820
acctgtgaca cccctgaaga agatggtatc acctggacct tggaccagag cagtgaggtc   2880
ttaggctctg gcaaaacccct gaccatccaa gtcaaagagt ttggagatgc tggccagtac   2940
acctgtcaca aggaggggga ggttctaagc cattccctcc tgctgcttca caaaaggaa    3000 gatggaattt ggtccactga tattttaaag gaccagaaag aacccaaaaa taagaccttt   3060
ctaagatgtg aggccaagaa ttattctgga aggttcacct gctggtggct gactacaatc   3120
agtactgatt tgacattcag tgtcaaaagc agcagaggct cttctgaccc ccaaggggtg   3180
acatgtggag ctgctacact ctctgcagag agagtcagag gggacaacaa ggagtatgag   3240
tactcagtgg agtgccagga ggacagtgcc tgcccagctg ctgaggagag tctgcccatt   3300
gaggtgatgg tggatgcagt tcacaagctc aagtatgaaa actacaccag cagcttcttc   3360
atcagggaca tcatcaaacc tgacccaccc aagaacttgc agctgaagcc attaaagaat   3420
tctaggcagg tggaggtcag ctgggagtac cctgacacct ggagtactcc acattcctac   3480
ttctccctga cattctgtgt tcaagtccag ggcaagagca agagagaaaa gaaagataga   3540
gtcttcactg acaagacctc agccacagtc atctgcagga aaaatgccag catttcagtg   3600
agggcccagg acagatacta tagctcatct tggtcagaat gggcatctgt gccctgcagt   3660
tgagcggccg cgctagccaa ttgctgtgcc ttctagttgc cagccatctg ttgtttgccc   3720
ctcccccgtg ccttccttga ccctggaagg tgccactccc actgtccttt cctaataaaa   3780
tgaggaaatt gcatcgcatt gtctgagtag gtgtcattct attctggggg gtggggtggg   3840
```

```
gcaggacagc aagggggagg attgggaaga caatagcagg catgctgggg atgcggtggg    3900
ctctatggag ctcgag                                                    3916

<210> SEQ ID NO 28
<211> LENGTH: 4456
<212> TYPE: DNA
<213> ORGANISM: Artificial Sequence
<220> FEATURE:
<223> OTHER INFORMATION: Human UbC- wild-type IL-12A/IL-12B/IL-15
      -ODN-IRES (no CpG modification)

<400> SEQUENCE: 28
gtcgactcgt cgtttttgtcg tttttgtcgtt cacacaaaaa accaacacac agatctaatg    60
aaaataaaga tcttttattg gcgcgcctca actgcagggc acagatgccc attcgctcca   120
agatgagcta tagtagcggt cctgggcccg cacgctaatg ctggcatttt tgcggcagat   180
gaccgtggct gaggtcttgt ccgtgaagac tctatctttc ttttctctct tgctcttgcc   240
ctggacttga acgcagaatg tcaggagaa gtaggaatgt ggagtactcc aggtgtcagg   300
gtactcccag ctgacctcca cctgccgaga attctttaat ggcttcagct gcaagttctt   360
gggtgggtca ggtttgatga tgtccctgat gaagaagctg ctggtgtagt tttcatactt   420
gagcttgtga acggcatcca ccatcacctc aatgggcaga ctctcctcag cagctgggca   480
ggcactgtcc tcctggcact ccactgagta ctcatactcc ttgttgtccc ctctgactct   540
ctctgcagag agtgtagcag ctccgcacgt caccccttgg gggtcagaag agcctctgct   600
gcttttgaca ctgaatgtca aatcagtact gattgtcgtc agccaccagc aggtgaaacg   660
tccagaataa ttcttggcct cgcatcttag aaaggtctta ttttttgggtt ctttctggtc   720 cttttaaaata tcagtggacc aaattccatc ttcctttttg tgaagcagca ggagcgaatg   780
gcttagaacc tcgcctcctt tgtgacaggt gtactggcca gcatctccaa actctttgac   840
ttggatggtc agggttttgc cagagcctaa gacctcactg ctctggtcca aggtccaggt   900
gataccatct tcttcagggg tgtcacaggt gaggaccacc atttctccag ggcatccgg   960 ataccaatcc aattctacga cataaacatc tttcttcagt tcccatatgg ccacgagggg   1020
agatgccaga aaaccaggg aaaaccaaga gatgaccaac tgctggtgac acatggtggc   1080
ggcgcgccat ttaaatctag ccttaagagc tgtaattgaa ctgggagtgg acacctgtgg   1140
agagaaaggc aaagtggatg tcagtaagac caataggtgc ctatcagaaa cgcaagagtc   1200
ttctctgtct cgacaagccc agtttctatt ggtctcctta aacctgtctt gtaaccttga   1260
tacttacctg cccagtgcct cacgaccaac ttcagaactg cgacccaaat cccggctgcg   1320
acggaactag ctgtgccaca cccggcgcgt ccttatataa tcatcggcgt tcaccgcccc   1380
acggagatcc ctccgcagaa tcgccgagaa gggactactt ttcctcgcct gttccgctct   1440
ctggaaagaa aaccagtgcc ctagagtcac ccaagtcccg tcctaaaatg tccttctgct   1500
gatactgggg ttctaaggcc gagtcttatg agcagcgggc cgctgtcctg agcgtccggg   1560
cggaaggatc aggacgctcg ctgcgccctt cgtctgacgt ggcagcgctc gccgtgagga   1620
ggggggcgcc cgcgggaggc gccaaaaccc ggcgcggagg ccttaattaa ctagttatta   1680
atagtaatca attacgggt cattagttca tagcccatat atggagttcc gcgttacata   1740
acttacggta aatggcccgc ctggctgacc gcccaacgac cccgcccat tgacgtcaat   1800 aatgacgtat gttcccatag taacgccaat agggactttc cattgacgtc aatgggtgga   1860
ctatttacgg taaactgccc acttggcagt acatcaagtg tatcatatgc caagtacgcc   1920
```

```
ccctattgac gtcaatgacg gtaaatggcc cgcctggcat tatgcccagt acatgacctt    1980
atgggacttt cctacttggc agtacatcta cgtattagtc atcgctatta ccatgggtga    2040
tgcggttttg gcagtacatc aatgggcgtg gatagcggtt tgactcacgg ggatttccaa    2100
gtctccaccc cattgacgtc aatgggagtt tgttttggca ccaaaatcaa cgggactttc    2160
caaaatgtcg taacaactcc gccccattga cgcaaatggg cggtaggcgt gtacggtggg    2220
aggtctatat aagcagagct cgtttagtga accgtcagat cgcctggaga cgtcgaggaa    2280
ctgaaaaacc agaaagttaa ctggtaagtt tagtcttttt gtcttttatt tcaggtcccg    2340
gatccggtgg tggtgcaaat caaagaactg ctcctcagtg gatgttgcct ttacttctag    2400
gcctgtacgg aagtgtttaa acttctgctc tgcggccgcg ccaccatgtg tccagcgcgc    2460
agcctcctcc ttgtggctac cctggtcctc tggaccacc tcagtttggc cagaaacctc    2520
cccgtggcca ctccagaccc aggaatgttc ccatgccttc accactccca aaacctgctg    2580
agggccgtca gcaacatgct ccagaaggcc agacaaactc tagaatttta cccttgcact    2640
tctgaagaga ttgatcatga agatatcaca aaagataaaa ccagcacagt ggaggcctgt    2700
ttaccattgg aattaaccaa gaatgagagt tgcctaaatt ccagagagac ctctttcata    2760
actaatggga gttgcctggc ctccagaaag acctctttta tgatggccct gtgccttagt    2820
agtatttatg aagacttgaa gatgtaccag gtggagttca agaccatgaa tgcaaagctt    2880
ctgatggatc ctaagaggca gatctttcta gatcaaaaca tgctggcagt tattgatgag    2940
ctgatgcagg ccctgaattt caacagtgag actgtgccac aaaaatcctc ccttgaagaa    3000
ccggattttt ataaaactaa aatcaagctc tgcatacttc ttcatgcttt ccggattcgg    3060
gcagtgacta ttgatagagt gatgagctat ctgaatgctt cctgagcccc tctccctccc    3120 cccccctaa cgttactggc cgaagccgct tggaataagg ccggtgtgcg tttgtctata    3180
tgttattttc caccatattg ccgtcttttg gcaatgtgag ggcccggaaa cctggccctg    3240
tcttcttgac gagcattcct agggggtcttt ccctctcgc caaggaatg caaggtctgt    3300 tgaatgtcgt gaaggaagca gttcctctgg aagcttcttg aagacaaaca acgtctgtag    3360
cgaccctttg caggcagcgg aaccccccac ctggcgacag gtgcctctgc ggccaaaagc    3420
cacgtgtata agatacacct gcaaaggcgg cacaacccca gtgccacgtt gtgagttgga    3480
tagttgtgga aagagtcaaa tggctctcct caagcgtatt caacaagggg ctgaaggatg    3540
cccagaaggt accccattgt atgggatctg atctggggcc tcggtacaca tgctttacat    3600
gtgtttagtc gaggttaaaa aaacgtctag gccccccgaa ccacggggac gtggttttcc    3660
tttgaaaaac acgatgataa tatggccaca atgagaattt cgaaaccaca tttgagaagt    3720
atttccatcc agtgctactt tgtgtttactt ctaaacagtc attttctaac tgaagctggc    3780
attcatgtct tcattttggg ctgtttctct gcagggcttc ctaaaacaga agccaactgg    3840
gtgaatgtaa taagtgattt gaaaaaaatt gaagatctta ttcaatctat gcatattgat    3900
gctactttat atacggaaag tgatgttcac cccagttgca aagtaacagc aatgaagtgc    3960
tttctcttgg agttacaagt tatttcactt gagtccggag atgcaagtat tcatgataca    4020
gtagaaaatc tgatcatcct agcaaacaac agtttgtctt ctaatgggaa tgtaacagaa    4080
tctggatgca aagaatgtga ggaactggag gaaaaaaata ttaaagaatt tttgcagagt    4140
tttgtacata ttgtccaaat gttcatcaac acttcttgag cggccgcgct agccaattgc    4200
tgtgccttct agttgccagc catctgttgt ttgcccctcc ccgtgccttc cttgaccct    4260 ggaaggtgcc actcccactg tcctttccta ataaaatgag gaaattgcat cgcattgtct    4320
```

```
gagtaggtgt cattctattc tgggggtgg ggtggggcag gacagcaagg gggaggattg    4380
ggaagacaat agcaggcatg ctgggatgc ggtgggctct atgtcgtcgt tttgtcgttt    4440
tgtcgttgag ctcgag                                                    4456
```

<210> SEQ ID NO 29
<211> LENGTH: 3964
<212> TYPE: DNA
<213> ORGANISM: Artificial Sequence
<220> FEATURE:
<223> OTHER INFORMATION: Human UbC- wild-type IL-12A/IL-12B/IL-15
      -ODN-F2A (no CpG modification)

<400> SEQUENCE: 29

```
gtcgactcgt cgttttgtcg ttttgtcgtt cacacaaaaa accaacacac agatctaatg     60
aaaataaaga tcttttattg gcgcgcctca agaagtgttg atgaacattt ggacaatatg    120
tacaaaactc tgcaaaaatt ctttaatatt ttttcctcc agttcctcac attctttgca    180
tccagattct gttacattcc cattagaaga caaactgttg tttgctagga tgatcagatt    240
ttctactgta tcatgaatac ttgcatctcc ggactcaagt gaaataactt gtaactccaa    300
gagaaagcac ttcattgctg ttactttgca actggggtga acatcacttt ccgtatataa    360
agtagcatca atatgcatag attgaataag atcttcaatt tttttcaaat cacttattac    420
attcacccag ttggcttctg ttttaggaag ccctgcagag aaacagccca aaatgaagac    480
atgaatgcca gcttcagtta gaaaatgact gtttagaagt aaacacaagt agcactggat    540
ggaaatactt ctcaaatgtg gtttcgaaat tctcatggtg gcggcgcgcc atttaaatct    600
agccttaaga gctgtaattg aactgggagt ggacacctgt ggagagaaag gcaaagtgga    660
tgtcagtaag accaataggt gcctatcaga aacgcaagag tcttctctgt ctcgacaagc    720
ccagtttcta ttggtctcct taaacctgtc ttgtaacctt gatacttacc tgcccagtgc    780
ctcacgacca acttcagaac tgcgacccaa atcccggctg cgacggaact agctgtgcca    840 caccccggcgc gtccttatat aatcatcggc gttcaccgcc ccacggagat ccctccgcag    900
aatcgccgag aagggactac ttttcctcgc ctgttccgct ctctggaaag aaaaccagtg    960
ccctagagtc acccaagtcc cgtcctaaaa tgtccttctg ctgatactgg ggttctaagg   1020
ccgagtctta tgagcagcgg gccgctgtcc tgagcgtccg ggcggaagga tcaggacgct   1080
cgctgcgccc ttcgtctgac gtggcagcgc tcgccgtgag gagggggggcg cccgcgggag   1140 gcgccaaaac ccggcgcgga ggccttaatt aactagttat taatagtaat caattacggg   1200
gtcattagtt catagcccat atatggagtt ccgcgttaca aacttacgg taaatggccc   1260 gcctggctga ccgcccaacg accccgcc attgacgtca ataatgacgt atgttcccat   1320
agtaacgcca atagggactt tccattgacg tcaatgggtg gactatttac ggtaaactgc   1380
ccacttggca gtacatcaag tgtatcatat gccaagtacg cccccctattg acgtcaatga   1440 cggtaaatgg cccgcctggc attatgccca gtacatgacc ttatgggact ttcctacttg   1500
gcagtacatc tacgtattag tcatcgctat taccatgggt gatgcggttt tggcagtaca   1560
tcaatgggcg tggatagcgg tttgactcac ggggatttcc aagtctccac cccattgacg   1620
tcaatgggag tttgttttgg caccaaaatc aacgggactt tccaaaatgt cgtaacaact   1680
ccgccccatt gacgcaaatg ggcggtaggc gtgtacggtg ggaggtctat ataagcagag   1740
ctcgtttagt gaaccgtcag atcgcctgga gacgtcagg aactgaaaaa ccagaaagtt   1800
aactggtaag tttagtcttt ttgtcttttta tttcaggtcc cggatccggt ggtggtgcaa   1860
```

```
atcaaagaac tgctcctcag tggatgttgc ctttacttct aggcctgtac ggaagtgttt    1920
aaacttctgc tctgcggccg cgccaccatg tgtccagcgc gcagcctcct ccttgtggct    1980
accctggtcc tcctggacca cctcagtttg gccagaaacc tccccgtggc cactccagac    2040
ccaggaatgt tcccatgcct tcaccactcc caaaacctgc tgagggccgt cagcaacatg    2100
ctccagaagg ccagacaaac tctagaattt taccccttgca cttctgaaga gattgatcat    2160
gaagatatca caaagataa aaccagcaca gtggaggcct gtttaccatt ggaattaacc     2220
aagaatgaga gttgcctaaa ttccagagag acctctttca taactaatgg gagttgcctg    2280
gcctccagaa agacctcttt tatgatggcc ctgtgcctta gtagtattta tgaagacttg    2340
aagatgtacc aggtggagtt caagaccatg aatgcaaagc ttctgatgga tcctaagagg    2400
cagatctttc tagatcaaaa catgctggca gttattgatg agctgatgca ggccctgaat    2460
ttcaacagtg agactgtgcc acaaaaatcc tcccttgaag aaccggattt ttataaaact    2520
aaaatcaagc tctgcatact tcttcatgct ttccggattc gggcagtgac tattgataga    2580
gtgatgagct atctgaatgc ttccagaaag agaaggagtg gctcaggagc cctgtgaaa    2640 cagaccctga ctttgacct cttgaagctt gctggggatg tggagtctaa tcctggtcca    2700
atgtgtcacc agcagttggt catctcttgg ttttccctgg tttttctggc atctcccctc    2760
gtggccatat gggaactgaa gaaagatgtt tatgtcgtag aattggattg gtatccggat    2820 gccccctggag aaatggtggt cctcacctgt gacacccctg aagaagatgg tatcacctgg    2880
accttggacc agagcagtga ggtcttaggc tctggcaaaa ccctgaccat ccaagtcaaa    2940
gagtttggag atgctggcca gtacacctgt cacaaaggag gcgaggttct aagccattcg    3000
ctcctgctgc ttcacaaaaa ggaagatgga atttggtcca ctgatatttt aaaggaccag    3060
aaagaaccca aaaataagac cttttctaaga tgcgaggcca agaattattc tggacgtttc    3120
acctgctggt ggctgacgac aatcagtact gatttgacat tcagtgtcaa agcagcaga    3180 ggctcttctg acccccaagg ggtgacgtgc ggagctgcta cactctctgc agagagagtc    3240
agaggggaca caaggagta tgagtactca gtgagtgcc aggaggacag tgcctgccca    3300
gctgctgagg agagtctgcc cattgagtg atggtggatg ccgttcacaa gctcaagtat    3360
gaaaactaca ccagcagctt cttcatcagg gacatcatca aacctgaccc acccaagaac    3420
ttgcagctga agccattaaa gaattctcgg caggtggagg tcagctggga gtaccctgac    3480
acctggagta ctccacattc ctacttctcc ctgacattct gcgttcaagt ccagggcaag    3540
agcaagagag aaaagaaaga tagagtcttc acggacaaga cctcagccac ggtcatctgc    3600
cgcaaaaatg ccagcattag cgtgcgggcc caggaccgct actatagctc atcttggagc    3660
gaatgggcat ctgtgccctg cagttgagcg gccgcgctag ccaattgctg tgccttctag    3720
ttgccagcca tctgttgttt gcccctcccc cgtgccttcc ttgaccctgg aaggtgccac    3780
tcccactgtc ctttcctaat aaaatgagga aattgcatcg cattgtctga gtaggtgtca    3840
ttctattctg gggggtgggg tggggcagga cagcaagggg gaggattggg aagacaatag    3900
caggcatgct ggggatgcgg tgggctctat gtcgtcgttt tgtcgttttg tcgttgagct    3960
cgag                                                                3964
```

<210> SEQ ID NO 30
<211> LENGTH: 2782
<212> TYPE: DNA
<213> ORGANISM: Artificial Sequence
<220> FEATURE:

<223> OTHER INFORMATION: Human CMV- wild-type IL-12A/IL-12B - -F2A (no
      CpG modification)

<400> SEQUENCE: 30

```
gtcgacttaa ttaactagtt attaatagta atcaattacg gggtcattag ttcatagccc    60
atatatggag ttccgcgtta cataacttac ggtaaatggc ccgcctggct gaccgcccaa   120
cgacccccgc ccattgacgt caataatgac gtatgttccc atagtaacgc caatagggac   180
tttccattga cgtcaatggg tggactattt acggtaaact gcccacttgg cagtacatca   240
agtgtatcat atgccaagta cgccccctat tgacgtcaat gacggtaaat ggcccgcctg   300
gcattatgcc cagtacatga ccttatggga ctttcctact tggcagtaca tctacgtatt   360
agtcatcgct attaccatgg gtgatgcggt tttggcagta catcaatggg cgtggatagc   420
ggtttgactc acggggattt ccaagtctcc accccattga cgtcaatggg agtttgtttt   480
ggcaccaaaa tcaacgggac tttccaaaat gtcgtaacaa ctccgcccca ttgacgcaaa   540
tgggcggtag gcgtgtacgg tgggaggtct atataagcag agctcgttta gtgaaccgtc   600
agatcgcctg gagacgtcga ggaactgaaa accagaaag ttaactggta agtttagtct   660
ttttgtcttt tatttcaggt cccggatccg gtggtggtgc aaatcaaaga actgctcctc   720
agtggatgtt gcctttactt ctaggcctgt acggaagtgt taaacttct gctctgcggc   780
cgcgccacca tgtgtccagc gcgcagcctc ctccttgtgg ctaccctggt cctcctggac   840
cacctcagtt tggccagaaa cctccccgtg gccactccag acccaggaat gttcccatgc   900
cttcaccact cccaaaaacct gctgagggcc gtcagcaaca tgctccagaa ggccagacaa   960
actctagaat tttaccttg cacttctgaa gagattgatc atgaagatat cacaaaagat  1020
aaaaccagca cagtggaggc ctgtttacca ttggaattaa ccaagaatga gagttgccta  1080
aattccagag agacctcttt cataactaat gggagttgcc tggcctccag aaagacctct  1140
tttatgatgg ccctgtgcct tagtagtatt tatgaagact gaagatgta ccaggtggag  1200
ttcaagacca tgaatgcaaa gcttctgatg gatcctaaga ggcagatctt tctagatcaa  1260
aacatgctgg cagttattga tgagctgatg caggccctga atttcaacag tgagactgtg  1320
ccacaaaaat cctcccttga agaaccggat ttttataaaa ctaaaatcaa gctctgcata  1380
cttcttcatg ctttccggat tcgggcagtg actattgata gagtgatgag ctatctgaat  1440
gcttccagaa agagaaggag tggctcagga gccctgtga acagaccct gaactttgac  1500
ctcttgaagc ttgctgggga tgtggagtct aatcctggtc caatgtgtca ccagcagttg  1560
gtcatctctt ggttttccct ggttttttctg gcatctcccc tcgtggccat atgggaactg  1620
aagaaagatg tttatgtcgt agaattggat tggtatccgg atgcccctgg agaaatggtg  1680
gtcctcacct gtgacacccc tgaagaagat ggtatcacct ggaccttgga ccagagcagt  1740
gaggtcttag gctctggcaa aaccctgacc atccaagtca agagtttgg agatgctggc  1800
cagtacacct gtcacaaagg aggcgaggtt ctaagccatt cgctcctgct gcttcacaaa  1860
aaggaagatg gaatttggtc cactgatatt ttaaaggacc agaaagaacc caaaaataag  1920
acctttctaa gatgcgaggc caagaattat tctggacgtt tcacctgctg gtggctgacg  1980
acaatcagta ctgatttgac attcagtgtc aaaagcagca gaggctcttc tgaccccaa  2040
ggggtgacgt gcggagctgc tacactctct gcagagagag tcagagggga caacaaggag  2100
tatgagtact cagtggagtg ccaggaggac agtgcctgcc cagctgctga ggagagtctg  2160
cccattgagg tgatggtgga tgccgttcac aagctcaagt atgaaaacta caccagcagc  2220
```

-continued

| | |
|---|---|
| ttcttcatca gggacatcat caaacctgac ccacccaaga acttgcagct gaagccatta | 2280 |
| aagaattctc ggcaggtgga ggtcagctgg gagtaccctg acacctggag tactccacat | 2340 |
| tcctacttct ccctgacatt ctgcgttcaa gtccagggca agagcaagag agaaaagaaa | 2400 |
| gatagagtct tcacggacaa gacctcagcc acggtcatct gccgcaaaaa tgccagcatt | 2460 |
| agcgtgcggg cccaggaccg ctactatagc tcatcttgga gcgaatgggc atctgtgccc | 2520 |
| tgcagttgag cggccgcgct agccaattgc tgtgccttct agttgccagc catctgttgt | 2580 |
| ttgcccctcc ccgtgccttc cttgaccct ggaaggtgcc actcccactg tcctttccta | 2640 |
| ataaaatgag gaaattgcat cgcattgtct gagtaggtgt cattctattc tggggggtgg | 2700 |
| ggtggggcag gacagcaagg gggaggattg ggaagacaat agcaggcatg ctggggatgc | 2760 |
| ggtgggctct atggagctcg ag | 2782 |

<210> SEQ ID NO 31
<211> LENGTH: 1531
<212> TYPE: DNA
<213> ORGANISM: Artificial Sequence
<220> FEATURE:
<223> OTHER INFORMATION: Human CMV- wild-type IL-15 (no CpG modification)

<400> SEQUENCE: 31

| | |
|---|---|
| gtcgacttaa ttaactagtt attaatagta atcaattacg gggtcattag ttcatagccc | 60 |
| atatatggag ttccgcgtta cataacttac ggtaaatggc ccgcctggct gaccgcccaa | 120 |
| cgacccccgc ccattgacgt caataatgac gtatgttccc atagtaacgc caatagggac | 180 |
| tttccattga cgtcaatggg tggactattt acggtaaact gcccacttgg cagtacatca | 240 |
| agtgtatcat atgccaagta cgccccctat tgacgtcaat gacggtaaat ggcccgcctg | 300 |
| gcattatgcc cagtacatga ccttatggga ctttcctact tggcagtaca tctacgtatt | 360 |
| agtcatcgct attaccatgg tgatgcggt tttggcagta catcaatggg cgtggatagc | 420 |
| ggtttgactc acggggattt ccaagtctcc accccattga cgtcaatggg agtttgtttt | 480 |
| ggcaccaaaa tcaacgggac tttccaaaat gtcgtaacaa ctccgcccca ttgacgcaaa | 540 |
| tgggcggtag gcgtgtacgg tgggaggtct atataagcag agctcgttta gtgaaccgtc | 600 |
| agatcgcctg gagacgtcga ggaactgaaa aaccagaaag ttaactggta agtttagtct | 660 |
| ttttgtcttt tatttcaggt cccggatccg gtggtggtgc aaatcaaaga actgctcctc | 720 |
| agtggatgtt gcctttactt ctaggcctgt acggaagtgt taaacttct gctctgcggc | 780 |
| cgcgccacca tgagaatttc gaaaccacat ttgagaagta tttccatcca gtgctacttg | 840 |
| tgtttacttc taaacagtca ttttctaact gaagctggca ttcatgtctt cattttgggc | 900 |
| tgtttctctg cagggcttcc taaaacagaa gccaactggg tgaatgtaat aagtgatttg | 960 |
| aaaaaaattg aagatcttat tcaatctatg catattgatg ctactttata cacggaaagt | 1020 |
| gatgttcacc ccagttgcaa agtaacagca atgaagtgct ttctcttgga gttacaagtt | 1080 |
| atttcacttg agtccggaga tgcaagtatt catgatacag tagaaaatct gatcatccta | 1140 |
| gcaaacaaca gtttgtcttc taatgggaat gtaacagaat ctggatgcaa agaatgtgag | 1200 |
| gaactggagg aaaaaaatat taagaatttt tgcagagttt tgtacatat tgtccaaatg | 1260 |
| ttcatcaaca cttcttgagc ggccgcgcta gccaattgct gtgccttcta gttgccagcc | 1320 |
| atctgttgtt tgcccctccc cgtgccttc cttgaccctg gaaggtgcca ctcccactgt | 1380 |
| cctttcctaa taaaatgagg aaattgcatc gcattgtctg agtaggtgtc attctattct | 1440 |

| | |
|---|---|
| gggggtggg gtggggcagg acagcaaggg ggaggattgg gaagacaata gcaggcatgc | 1500 |
| tggggatgcg gtgggctcta tggagctcga g | 1531 |

<210> SEQ ID NO 32
<211> LENGTH: 5
<212> TYPE: RNA
<213> ORGANISM: Artificial Sequence
<220> FEATURE:
<223> OTHER INFORMATION: Class I AU rich elements

<400> SEQUENCE: 32

| | |
|---|---|
| auuua | 5 |

<210> SEQ ID NO 33
<211> LENGTH: 9
<212> TYPE: RNA
<213> ORGANISM: Artificial Sequence
<220> FEATURE:
<223> OTHER INFORMATION: Class II AU rich elements
<220> FEATURE:
<221> NAME/KEY: misc_feature
<222> LOCATION: (8)..(9)
<223> OTHER INFORMATION: Wherein N can be either U or A

<400> SEQUENCE: 33

| | |
|---|---|
| uuauuuann | 9 |

<210> SEQ ID NO 34
<211> LENGTH: 4509
<212> TYPE: DNA
<213> ORGANISM: Artificial Sequence
<220> FEATURE:
<223> OTHER INFORMATION: Human CAG - wild-type IL-12A/IL-12B - IRES (no CpG modification) construct

<400> SEQUENCE: 34

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tagtattaaa cgcgtgtcga cattgattat tgactagtta ttaatagtaa | 180 |
| tcaattacgg ggtcattagt tcatagccca tatatggagt tccgcgttac ataacttacg | 240 |
| gtaaatggcc cgcctggctg accgcccaac gacccccgcc cattgacgtc aataatgacg | 300 |
| tatgttccca tagtaacgcc aatagggact ttccattgac gtcaatgggt ggactattta | 360 |
| cggtaaactg cccacttggc agtacatcaa gtgtatcata tgccaagtac gccccctatt | 420 |
| gacgtcaatg acggtaaatg gcccgcctgg cattatgccc agtacatgac cttatgggac | 480 |
| tttcctactt ggcagtacat ctacgtatta gtcatcgcta ttaccatggg tcgaggtgag | 540 |
| ccccacgttc tgcttcactc tccccatctc ccccccctcc ccaccccaa ttttgtattt | 600 |
| atttattttt taattatttt gtgcagcgat ggggcgggg gggggggggg cgcgcgccag | 660 |
| gcggggcggg gcggggcgag gggcggggcg ggcgaggcg gagaggtgcg gcggcagcca | 720 |
| atcagagcgg cgcgctccga aagtttcctt ttatggcgag gcggcggcgg cggcggccct | 780 |
| ataaaaagcg aagcgcgcgg cgggcgggag tcgctgcgcg ctgccttcgc cccgtgcccc | 840 |
| gctccgccgc cgcctcgcgc cgcccgcccc ggctctgact gaccgcgtta ctcccacagg | 900 |
| tgagcgggcg ggacggccct tctcctccgg gctgtaatta gcgcttggtt taatgacggc | 960 |
| tcgtttcttt tctgtggctg cgtgaaagcc ttgagggggct ccgggagggc cctttgtgcg | 1020 |
| ggggagcgg ctcgggggt gcgtgcgtgt gtgtgtgcgt ggggagcgcc gcgtgcggct | 1080 |

```
ccgcgctgcc cggcggctgt gagcgctgcg ggcgcggcgc ggggctttgt gcgctccgca    1140
gtgtgcgcga gaggagcgcg gccgggggcg gtgccacgcg gtgcggggggg ggctgcgagg    1200
ggaacaaagg ctgcgtgcgg ggtgtgtgcg tggggggggt gagcagggggg tgtgggcgcg    1260
gcggtcgggt gtaacccccc ccctgcaccc ccctccccga gttgctgagc acggcccggc    1320
ttcgggtgcg gggctccgtg cggggcgtgg cgcgggctc gccgtgccgg gcgggggggtg    1380
gcggcgggtg ggggtgccgg gcggggcggg gccgcctcgg gccggggagg gctcggggga    1440
ggggcgcggc ggcccccgga gcgccggcgg ctgtcgaggc gcggcgagcc gcagccattg    1500
ccttttatgg taatcgtgcg agagggcgca gggacttcct ttgtcccaaa tctgtgcgga    1560
gccgaaatct gggaggcgcc gccgcacccc ctctagcggg cgcggggcga agcggtgcgg    1620
cgccggcagg aaggaaatgg gcggggaggg ccttcgtgcg tcgccgcgcc gccgtcccct    1680
tctcccctctc cagcctcggg gctgtccgcg ggggacggc tgccttcggg ggggacgggg    1740
cagggcgggg ttcggcttct ggcgtgtgac cggcggtcta gactctgcta accttgttca    1800
tgccttcttc tctttcctac agctcctggg caacgtgctg gttgttgtgc tgtctcatca    1860
ttttggcaaa gaattcaagc ttccagctag cgccaccatg tgtccagcgc gcagcctcct    1920
ccttgtggct accctggtcc tcctggacca cctcagtttg gccagaaacc tccccgtggc    1980
cactccagac ccaggaatgt tcccatgcct tcaccactcc caaaacctgc tgagggccgt    2040
cagcaacatg ctccagaagg ccagacaaac tctagaattt tacccttgca cttctgaaga    2100
gattgatcat gaagatatca caaaagataa aaccagcaca gtggaggcct gtttaccatt    2160
ggaattaacc aagaatgaga gttgcctaaa ttccagagag acctctttca taactaatgg    2220
gagttgcctg gcctccagaa agacctcttt tatgatggcc ctgtgcctta gtagtattta    2280
tgaagacttg aagatgtacc aggtggagtt caagaccatg aatgcaaagc ttctgatgga    2340
tcctaagagg cagatctttc tagatcaaaa catgctggca gttattgatg agctgatgca    2400
ggcccctgaat tcaacagtg agactgtgcc acaaaaatcc tcccttgaag aaccggattt    2460
ttataaaact aaaatcaagc tctgcatact tcttcatgct ttccggattc gggcagtgac    2520
tattgataga gtgatgagct atctgaatgc ttcctgagcc cctctccctc cccccccct    2580
aacgttactg gccgaagccg cttggaataa ggccggtgtg cgtttgtcta tatgttattt    2640
tccaccatat tgccgtcttt tggcaatgtg agggcccgga aacctggccc tgtcttcttg    2700
acgagcattc ctaggggtct ttcccctctc gccaaaggaa tgcaaggtct gttgaatgtc    2760
gtgaaggaag cagttcctct ggaagcttct tgaagacaaa caacgtctgt agcgaccctt    2820
tgcaggcagc ggaacccccc acctggcgac aggtgcctct gcggccaaaa gccacgtgta    2880
taagatacac ctgcaaaggc ggcacaaccc cagtgccacg ttgtgagttg atagttgtg    2940
gaaagagtca aatggctctc ctcaagcgta ttcaacaagg ggctgaagga tgcccagaag    3000
gtacccatt gtatgggatc tgatctgggg cctcggtaca catgctttac atgtgtttag    3060
tcgaggttaa aaaacgtctc aggccccccg aaccacgggg acgtggtttt cctttgaaaa    3120
acacgatgat aatatggcca caatgtgtca ccagcagttg gtcatctctt ggttttccct    3180
ggtttttctg gcatctcccc tcgtggccat atgggaactg aagaaagatg tttatgtcgt    3240
agaattggat tggtatccgg atgcccctgg agaaatggtg gtcctcacct gtgacacccc    3300
tgaagaagat ggtatcacct ggaccttgga ccagagcagt gaggtcttag gctctggcaa    3360
aaccctgacc atccaagtca aagagtttgg agatgctggc cagtacacct gtcacaaagg    3420
aggcgaggtt ctaagccatt cgctcctgct gcttcacaaa aaggaagatg gaatttggtc    3480
```

```
cactgatatt ttaaaggacc agaaagaacc caaaaataag accttctaa gatgcgaggc    3540 caagaattat tctggacgtt tcacctgctg gtggctgacg acaatcagta ctgatttgac    3600
attcagtgtc aaaagcagca gaggctcttc tgaccccaa ggggtgacgt gcggagctgc    3660
tacactctct gcagagagag tcagagggga caacaaggag tatgagtact cagtggagtg    3720
ccaggaggac agtgcctgcc cagctgctga ggagagtctg cccattgagg tgatggtgga    3780
tgccgttcac aagctcaagt atgaaaacta caccagcagc ttcttcatca gggacatcat    3840
caaacctgac ccacccaaga acttgcagct gaagccatta agaattctc ggcaggtgga    3900 ggtcagctgg gagtaccctg cacctggag tactccacat tcctacttct ccctgacatt    3960
ctgcgttcaa gtccagggca agagcaagag agaaagaaa gatagagtct tcacggacaa    4020
gacctcagcc acggtcatct gccgcaaaaa tgccagcatt agcgtgcggg cccaggaccg    4080
ctactatagc tcatcttgga gcgaatgggc atctgtgccc tgcagttgac aattgctgtg    4140
ccttctagtt gccagccatc tgttgtttgc ccctcccccg tgccttcctt gaccctggaa    4200
ggtgccactc ccactgtcct ttcctaataa aatgaggaaa ttgcatcgca ttgtctgagt    4260
aggtgtcatt ctattctggg gggtggggtg ggcaggaca gcaaggggga ggattgggaa    4320
gacaatagca ggcatgctgg ggatgcggtg gctctatgg agctcgagag gaacccctag    4380
tgatggagtt ggccactccc tctctgcgcg ctcgctcgct cactgaggcc gggcgaccaa    4440
aggtcgcccg acgcccgggc tttgcccggg cggcctcagt gagcgagcga gcgcgcagct    4500
gcagatctg                                                           4509
```

<210> SEQ ID NO 35
<211> LENGTH: 2250
<212> TYPE: DNA
<213> ORGANISM: Artificial Sequence
<220> FEATURE:
<223> OTHER INFORMATION: Human CAG - wild-type IL-12A/IL-12B - IRES (no
      CpG modification) expression sequence

<400> SEQUENCE: 35

```
gctagcgcca ccatgtgtcc agcgcgcagc ctcctccttg tggctaccct ggtcctcctg      60
gaccacctca gtttggccag aaacctcccc gtggccactc cagacccagg aatgttccca     120
tgccttcacc actcccaaaa cctgctgagg gccgtcagca acatgctcca gaaggccaga     180
caaactctag aattttaccc ttgcacttct gaagagattg atcatgaaga tatcacaaaa     240
gataaaacca gcacagtgga ggcctgttta ccattggaat taaccaagaa tgagagttgc     300
ctaaattcca gagagacctc tttcataact aatgggagtt gcctggcctc cagaaagacc     360
tcttttatga tggcccctgtg ccttagtagt atttatgaag acttgaagat gtaccaggtg     420
gagttcaaga ccatgaatgc aaagcttctg atggatccta agaggcagat ctttctagat     480
caaaacatgc tggcagttat tgatgagctg atgcaggccc tgaatttcaa cagtgagact     540
gtgccacaaa atcctccct tgaagaaccg gattttttata aaactaaaat caagctctgc     600
atacttcttc atgctttccg gattcgggca gtgactattg atagagtgat gagctatctg     660
aatgcttcct gagcccctct ccctcccccc ccctaacgt tactggccga agccgcttgg     720
aataaggccg gtgtgcgttt gtctatatgt tattttccac catattgccg tcttttggca     780
atgtgagggc ccggaaacct ggccctgtct tcttgacgag cattcctagg gtctttccc     840 ctctcgccaa aggaatgcaa ggtctgttga atgtcgtgaa ggaagcagtt cctctggaag     900
cttcttgaag acaaacaacg tctgtagcga cccttttgcag gcagcggaac ccccacctg     960
```

```
gcgacaggtg cctctgcggc caaaagccac gtgtataaga tacacctgca aaggcggcac   1020
aaccccagtg ccacgttgtg agttggatag ttgtggaaag agtcaaatgg ctctcctcaa   1080
gcgtattcaa caaggggctg aaggatgccc agaaggtacc ccattgtatg ggatctgatc   1140
tggggcctcg gtacacatgc tttacatgtg tttagtcgag gttaaaaaaa cgtctaggcc   1200
ccccgaacca cggggacgtg gttttccttt gaaaaacacg atgataatat ggccacaatg   1260
tgtcaccagc agttggtcat ctcttggttt tccctggttt ttctggcatc tcccctcgtg   1320
gccatatggg aactgaagaa agatgtttat gtcgtagaat tggattggta tccggatgcc   1380
cctggagaaa tggtggtcct cacctgtgac accctgaag aagatggtat cacctggacc    1440
ttggaccaga gcagtgaggt cttaggctct ggcaaaaccc tgaccatcca agtcaaagag   1500 tttgagatg ctggccagta cacctgtcac aaaggaggcg aggttctaag ccattcgctc    1560
ctgctgcttc acaaaaagga agatggaatt tggtccactg atattttaaa ggaccagaaa   1620
gaacccaaaa ataagacctt tctaagatgc gaggccaaga attattctgg acgtttcacc   1680
tgctggtggc tgacgacaat cagtactgat ttgacattca gtgtcaaaag cagcagaggc   1740
tcttctgacc cccaaggggt gacgtgcgga gctgctacac tctctgcaga gagagtcaga   1800
ggggacaaca aggagtatga gtactcagtg gagtgccagg aggacagtgc ctgcccagct   1860
gctgaggaga gtctgcccat tgaggtgatg gtggatgccg ttcacaagct caagtatgaa   1920
aactacacca gcagcttctt catcagggac atcatcaaac ctgacccacc caagaacttg   1980
cagctgaagc cattaaagaa ttctcggcag gtggaggtca gctgggagta ccctgacacc   2040
tggagtactc cacattccta cttctccctg acattctgcg ttcaagtcca gggcaagagc   2100
aagagagaaa agaaagatag agtcttcacg gacaagacct cagccacggt catctgccgc   2160
aaaaatgcca gcattagcgt gcgggcccag gaccgctact atagctcatc ttggagcgaa   2220
tgggcatctg tgccctgcag ttgacaattg                                     2250
```

<210> SEQ ID NO 36
<211> LENGTH: 2766
<212> TYPE: DNA
<213> ORGANISM: Artificial Sequence
<220> FEATURE:
<223> OTHER INFORMATION: Human CAG - wild-type IL-15 (no CpG
      modification) construct

<400> SEQUENCE: 36

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120 agggggttcct tagtattaaa cgcgtgtcga cattgattat tgactagtta ttaatagtaa   180
tcaattacgg ggtcattagt tcatagccca tatatggagt tccgcgttac ataacttacg   240
gtaaatggcc cgcctggctg accgcccaac gacccccgcc cattgacgtc aataatgacg   300
tatgttccca tagtaacgcc aatagggact ttccattgac gtcaatgggt ggactattta   360
cggtaaactg cccacttggc agtacatcaa gtgtatcata tgccaagtac gccccctatt   420
gacgtcaatg acggtaaatg gcccgcctgg cattatgccc agtacatgac cttatgggac   480
tttcctactt ggcagtacat ctacgtatta gtcatcgcta ttaccatggg tcgaggtgag   540
ccccacgttc tgcttcactc tccccatctc ccccccctcc ccaccccca ttttgtattt    600 atttattttt taattatttt gtgcagcgat gggggcgggg ggggggggg cgcgcgccag    660 gcggggcggg gcggggcgag gggcggggcg gggcgaggcg gagaggtgcg gcggcagcca   720
```

```
atcagagcgg cgcgctccga aagtttcctt ttatggcgag gcggcggcgg cggcggccct    780
ataaaaagcg aagcgcgcgg cgggcgggag tcgctgcgcg ctgccttcgc cccgtgcccc    840
gctccgccgc cgcctcgcgc cgcccgcccc ggctctgact gaccgcgtta ctcccacagg    900
tgagcgggcg ggacggccct tctcctccgg gctgtaatta gcgcttggtt taatgacggc    960
tcgtttcttt tctgtggctg cgtgaaagcc ttgaggggct ccgggagggc cctttgtgcg   1020
gggggagcgg ctcgggggt gcgtgcgtgt gtgtgtgcgt gggagcgcc gcgtgcggct     1080
ccgcgctgcc cggcggctgt gagcgctgcg ggcgcggcgc ggggctttgt gcgctccgca   1140
gtgtgcgcga gaggagcgcg gccggggcg gtgccacgcg gtgcgggggg ggctgcgagg    1200
ggaacaaagg ctgcgtgcgg ggtgtgtgcg tgggggggt gagcagggg tgtgggcgcg     1260
gcggtcgggc tgtaaccccc ccctgcaccc ccctccccga gttgctgagc acggcccggc   1320
ttcgggtgcg gggctccgtg cggggcgtgg cgcggggctc gccgtgccgg gcgggggtg    1380
gcggcgggtg gggtgccgg gcgggcggg ccgcctcgg gccggggagg gctcggggga     1440
ggggcgcggc ggccccgga gcgccggcgg ctgtcgaggc gcggcgagcc gcagccattg    1500
ccttttatgg taatcgtgcg agagggcgca gggacttcct ttgtcccaaa tctgtgcgga   1560
gccgaaatct gggaggcgcc gccgcacccc ctctagcggg cgcggggcga agcggtgcgg   1620
cgccggcagg aaggaaatgg gcgggaggg ccttcgtgcg tcgccgcgcc gccgtccct     1680
tctccctctc cagcctcggg gctgtccgcg ggggacggc tgccttcggg gggacgggg    1740
cagggcgggg ttcggcttct ggcgtgtgac cggcggtcta gactctgcta accatgttca   1800
tgccttcttc tctttcctac agctcctggg caacgtgctg gttgttgtgc tgtctcatca   1860
ttttggcaaa gaattcaagc ttccagctag cgccaccatg agaatttcga accacatttt   1920
gagaagtatt tccatccagt gctacttgtg tttacttcta aacagtcatt ttctaactga   1980
agctggcatt catgtcttca ttttgggctg tttctctgct gggcttccta aaacagaagc   2040
caactgggtg aatgtaataa gtgatttgaa aaaaattgaa gatcttattc aatctatgca   2100
tattgatgct actttatata cggaaagtga tgttcacccc agttgcaaag taacagcaat   2160
gaagtgcttt ctcttggagt tacaagttat ttcacttgag tccggagatg caagtattca   2220
tgatacagta gaaaatctga tcatcctagc aaacaacagt ttgtcttcta atgggaatgt   2280
aacagaatct ggatgcaaag aatgtgagga actggaagaa aaaaatatta agaattttt    2340
gcagagtttt gtacatattg tccaaatgtt catcaacact tcttgacaat gctgtgcct    2400
tctagttgcc agccatctgt tgtttgcccc tccccgtgc cttccttgac cctggaaggt    2460
gccactccca ctgtcctttc ctaataaaat gaggaaattg catcgcattg tctgagtagg   2520
tgtcattcta ttctgggggg tggggtggg caggacagca aggggagga ttgggaagac    2580
aatagcaggc atgctgggga tgcggtgggc tctatggagc tcgagaggaa ccctagtga   2640
tggagttggc cactccctct ctgcgcgctc gctcgctcac tgaggccggg cgaccaaagg   2700
tcgcccgacg cccgggcttt gcccgggcgg cctcagtgag cgagcgagcg cgcagctgca   2760
gatctg                                                             2766
```

<210> SEQ ID NO 37
<211> LENGTH: 508
<212> TYPE: DNA
<213> ORGANISM: Artificial Sequence
<220> FEATURE:
<223> OTHER INFORMATION: Human CAG - wild-type IL-15 (no CpG modification) expression sequence

<400> SEQUENCE: 37

```
agctagcgcc accatgagaa tttcgaaacc acatttgaga agtatttcca tccagtgcta      60
cttgtgttta cttctaaaca gtcattttct aactgaagct ggcattcatg tcttcatttt     120
gggctgtttc tctgctgggc ttcctaaaac agaagccaac tgggtgaatg taataagtga     180
tttgaaaaaa attgaagatc ttattcaatc tatgcatatt gatgctactt tatatacgga     240
aagtgatgtt caccccagtt gcaaagtaac agcaatgaag tgctttctct tggagttaca     300
agttatttca cttgagtccg gagatgcaag tattcatgat acagtagaaa atctgatcat     360
cctagcaaac aacagtttgt cttcaatgg gaatgtaaca gaatctggat gcaaagaatg      420
tgaggaactg gaggaaaaaa atattaaaga attttttgcag agttttgtac atattgtcca    480
aatgttcatc aacacttctt gacaattg                                         508
```

<210> SEQ ID NO 38
<211> LENGTH: 4912
<212> TYPE: DNA
<213> ORGANISM: Artificial Sequence
<220> FEATURE:
<223> OTHER INFORMATION: Mouse EF1a - wild-type IL-15 (no CpG modification) and modified IL-12B (with CpG modification) construct

<400> SEQUENCE: 38

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tagtattaaa cgcgtgtcga ccacacaaaa aaccaacaca cagatctaat     180
gaaaataaag atcttttatt ggcgcgcctc aggatcggac tctgcaggga acacaggccc     240
acttgctgca ggaggaattg taatacgat cctgagcttg cacgcagaca ttcccgcctt      300
tgcactggac ttcggtagat gtcttctcta cgaggaacgc tccttttctgg ttacaccct     360
cctctgtctc cttcatcttt tctttcttgc gctggattcg aacaaagaac ttgagggaga    420
agtaggaatg gggagtgctc caggagtcag ggtactccca gctgacctcc acctgtgagt    480
tcttcaaagg cttcatctgc aagttcttgg gcgggtctgg tttgatgatg tccctgatga    540
agaagctggt gctgtagttc tcatatttat tctgctgccg tgcttccaac gccagttcaa    600
tgggcagggt ctcctcggca gttgggcagg tgacatcctc ctggcaggac actgaatact    660
tctcatagtc cctttggtcc agtgtgacct tctctgcaga cagagacgcc attccacatg    720
tcactgcccg agagtcaggg gaactgctac tgctcttgat gttgaacttc aagtccatgt    780
ttctttgcac cagccatgag cacgtgaacc gtccggagta atttggtgct tcacacttca    840
ggaaagtctt gttttttgaaa ttttttaaaa tttcagtgga ccaaattcca ttttccttct    900
tgtggagcag cagatgtgag tggctcagag tctcgcctcc tttgtggcag gtgtactggc    960
cagcatctag aaactctttg acagtgatgg tcagggtctt tccagagcct atgactccat   1020
gtctctggtc tgaggtccag gtgatgtcat cttcttcagg cgtgtcacag gtgaggttca   1080
ctgtttctcc aggggcatcg ggagtccagt ccacctctac aacataaacg tctttctcca   1140
gctcccacat ggccatgagt ggagacacca gcaaaacgat ggcaaccag gagatggtta    1200
gcttctgagg acacatggtg gcggcgcgcc atttaaatct agccttaaga gctgtaattg   1260
aactgggagt ggacacctgt ggagagaaag gcaaagtgga tgtcagtaag accaataggt   1320
gcctatcaga aacgcaagag tcttctctgt ctcgacaagc ccagtttcta ttggtctcct   1380
```

```
taaacctgtc ttgtaacctt gatacttacc tgcccagtgc ctcacgacca acttcgatct    1440
gtaacggcgc agaacagaaa acgaaacaaa gacgtagagt tgagcaagca gggtcaggca    1500
aagcgtggag agccggctga gtctaggtag gctccaaggg agcgccggac aaaggcccgg    1560
tctcgacctg agctttaaac ttacctagac ggcggacgca gttcaggagg caccacaggc    1620
gggaggcggc agaacgcgac tcaaccggcg tggatggcgg cctcaggtag ggcggcgggc    1680
gcgtgaagga gagatgcgag cccctcgaag cttcagctgt gttctggcgg caaacccgtt    1740
gcgaaaaaga acgttcacgg cgactactgc acttatatac ggttctcccc caccctcggg    1800
aaaaaggcgg agccagtaca cgacatcact ttcccagttt accccgcgcc accttctcta    1860
ggcaccggtt caattgccga cccctccccc caacttctcg gggactgtgg gcgatgtgcg    1920
ctctgcccac tgacgggcac cggagcgatc ttaattaact agttattaat agtaatcaat    1980
tacggggtca ttagttcata gcccatatat ggagttccgc gttacataac ttacggtaaa    2040
tggcccgcct ggctgaccgc ccaacgaccc ccgcccattg acgtcaataa tgacgtatgt    2100
tcccatagta acgccaatag ggactttcca ttgacgtcaa tgggtggact atttacggta    2160
aactgcccac ttggcagtac atcaagtgta tcatatgcca gtacgcccc ctattgacgt    2220
caatgacggt aaatggcccg cctggcatta tgcccagtac atgaccttat gggactttcc    2280
tacttggcag tacatctacg tattagtcat cgctattacc atgggtgatg cggttttggc    2340
agtacatcaa tgggcgtgga tagcggtttg actcacgggg atttccaagt ctccacccca    2400
ttgacgtcaa tgggagtttg ttttggcacc aaaatcaacg ggactttcca aaatgtcgta    2460
acaactccgc cccattgacg caaatgggcg gtaggcgtgt acggtgggag gtctatataa    2520
gcagagctcg tttagtgaac cgtcagatcg cctggagacg tcgaggaact gaaaaaccag    2580
aaagttaact ggtaagttta gtcttttgt cttttattc aggtcccgga tccggtggtg    2640
gtgcaaatca aagaactgct cctcagtgga tgttgccttt acttctaggc ctgtacggaa    2700
gtgtttaaac ttctgctctg cggccgcgcc accatggtca gcgttccaac agcctcaccc    2760
tcggcatcca gcagctcctc tcagtgccgg tccagcatgt gtcaatcacg ctacctcctc    2820
tttttggcca cccttgccct cctaaaccac ctcagtttgg ccagggtcat tccagtctct    2880
ggacctgcca ggtgtcttag ccagtcccga aacctgctga agaccacaga tgacatggtg    2940
aagacggcca gagaaaaact gaaacattat tcctgcactg ctgaagacat cgatcatgaa    3000
gacatcacac gggaccaaac cagcacattg aagacctgtt taccactgga actacacaag    3060
aacgagagtt gcctggctac tagagagact tcttccacaa caagagggag ctgcctgccc    3120
ccacagaaga cgtctttgat gatgaccctg tgccttggta gcatctatga ggacttgaag    3180
atgtaccaga cagagttcca ggccatcaac gcagcacttc agaatcacaa ccatcagcag    3240
atcattctag acaagggcat gctggtggcc atcgatgagc tgatgcagtc tctgaatcat    3300
aatggcgaga ctctgcgcca gaaacctcct gtgggagaag cagaccctta cagagtgaaa    3360
atgaagctct gcatcctgct tcacgccttc agcacccgcg tcgtgaccat caacaggtg    3420
atgggctatc tgagctccgc ctgagcccct ctcctccc ccccctaac gttactggcc    3480
gaagccgctt ggaataaggc cggtgtgcgt ttgtctatat gttatttcc accatattgc    3540
cgtcttttgg caatgtgagg gcccggaaac ctggccctgt cttcttgacg agcattccta    3600
ggggtctttc ccctctcgcc aaaggaatgc aaggtctgtt gaatgtcgtg aaggaagcag    3660
ttcctctgga agcttcttga agacaaacaa cgtctgtagc gacccttgc aggcagcgga    3720
accccccacc tggcgacagg tgcctctgcg gccaaaagcc acgtgtataa gatacacctg    3780
```

| | | | | |
|---|---|---|---|---|
| caaaggcggc | acaaccccag | tgccacgttg | tgagttggat agttgtggaa agagtcaaat | 3840 |
| ggctctcctc | aagcgtattc | aacaaggggc | tgaaggatgc ccagaaggta ccccattgta | 3900 |
| tgggatctga | tctggggcct | cggtacacat | gctttacatg tgtttagtcg aggttaaaaa | 3960 |
| aacgtctagg | ccccccgaac | cacggggacg | tggttttcct ttgaaaaaca cgatgataat | 4020 |
| atggccacaa | tgaaaatttt | gaaaccatat | atgaggaata catccatctc gtgctacttg | 4080 |
| tgtttccttc | taaacagtca | cttttttaact | gaggctggca ttcatgtctt cattttgggc | 4140 |
| tgtgtcagtg | taggtctccc | taaaacagag | gccaactgga tagatgtaag atatgacctg | 4200 |
| gagaaaattg | aaagccttat | tcaatctatt | catattgaca ccactttata cactgacagt | 4260 |
| gactttcatc | ccagttgcaa | agttactgca | atgaactgct ttctcctgga attgcaggtt | 4320 |
| attttacatg | agtacagtaa | catgactctt | aatgaaacag taagaaacgt gctctacctt | 4380 |
| gcaaacagca | ctctgtcttc | taacaagaat | gtagcagaat ctggctgcaa ggaatgtgag | 4440 |
| gagctggagc | agaaaacctt | cacagagttt | ttgcaaagct ttatacgcat tgtccaaatg | 4500 |
| ttcatcaaca | cgtcctgagc | ggccgcgcta | gccaattgct gtgccttcta gttgccagcc | 4560 |
| atctgttgtt | tgcccctccc | ccgtgccttc | cttgaccctg gaaggtgcca ctcccactgt | 4620 |
| cctttcctaa | taaaatgagg | aaattgcatc | gcattgtctg agtaggtgtc attctattct | 4680 |
| ggggggtggg | gtggggcagg | acagcaaggg | ggaggattgg gaagacaata gcaggcatgc | 4740 |
| tggggatgcg | gtgggctcta | tggagctcga | gaggaaccc tagtgatgga gttggccact | 4800 |
| ccctctctgc | gcgctcgctc | gctcactgag | gccgggcgac caaggtcgc ccgacgcccg | 4860 |
| ggctttgccc | gggcggcctc | agtgagcgag | cgagcgcgca gctgcagatc tg | 4912 |

<210> SEQ ID NO 39
<211> LENGTH: 4626
<212> TYPE: DNA
<213> ORGANISM: Artificial Sequence
<220> FEATURE:
<223> OTHER INFORMATION: Mouse EF1a - wild-type IL-15 (no CpG
    modification) and modified IL-12B (with CpG modification)
    expression sequence

<400> SEQUENCE: 39

| | | | | |
|---|---|---|---|---|
| gtcgaccaca | caaaaaacca | acacacagat | ctaatgaaaa taagatctt ttattggcgc | 60 |
| gcctcaggat | cggactctgc | agggaacaca | ggcccacttg ctgcaggagg aattgtaata | 120 |
| gcgatcctga | gcttgcacgc | agacattccc | gcctttgcac tggacttcgg tagatgtctt | 180 |
| ctctacgagg | aacgctcctt | tctggttaca | cccctcctct gtctccttca tcttttcttt | 240 |
| cttgcgctgg | attcgaacaa | agaacttgag | ggagaagtag gaatggggag tgctccagga | 300 |
| gtcagggtac | tccagctga | cctccacctg | tgagttcttc aaaggcttca tctgcaagtt | 360 |
| cttgggcggg | tctggtttga | tgatgtccct | gatgaagaag ctggtgctgt agttctcata | 420 |
| tttattctgc | tgccgtgctt | ccaacgccag | ttcaatgggc agggtctcct cggcagttgg | 480 |
| gcaggtgaca | tcctcctggc | aggacactga | atacttctca tagtcccttt ggtccagtgt | 540 |
| gaccttctct | gcagacagag | acgccattcc | acatgtcact gcccgagagt caggggaact | 600 |
| gctactgctc | ttgatgttga | acttcaagtc | catgttctt tgcaccagcc atgagcacgt | 660 |
| gaaccgtccg | gagtaatttg | gtgcttcaca | cttcaggaaa gtcttgtttt tgaaattttt | 720 |
| taaaatttca | gtggaccaaa | ttccattttc | cttcttgtgg agcagcagat gtgagtggct | 780 |
| cagagtctcg | cctcctttgt | ggcaggtgta | ctggccagca tctagaaact ctttgacagt | 840 |

```
gatggtcagg gtcttccag agcctatgac tccatgtctc tggtctgagg tccaggtgat    900
gtcatcttct tcaggcgtgt cacaggtgag gttcactgtt tctccagggg catcgggagt    960
ccagtccacc tctacaacat aaacgtcttt ctccagctcc acatggcca tgagtggaga   1020
caccagcaaa acgatggcaa accaggagat ggttagcttc tgaggacaca tggtggcggc   1080
gcgccattta atctagcct taagagctgt aattgaactg ggagtggaca cctgtggaga   1140
gaaaggcaaa gtggatgtca gtaagaccaa taggtgccta tcagaaacgc aagagtcttc   1200
tctgtctcga caagcccagt ttctattggt ctccttaaac ctgtcttgta accttgatac   1260
ttacctgccc agtgcctcac gaccaacttc gatctgtaac ggcgcagaac agaaaacgaa   1320
acaaagacgt agagttgagc aagcagggtc aggcaaagcg tggagagccg gctgagtcta   1380
ggtaggctcc aagggagcgc cggacaaagg cccggtctcg acctgagctt taaacttacc   1440
tagacggcgg acgcagttca ggaggcacca caggcgggag gcgcagaac gcgactcaac   1500
cggcgtggat ggcggcctca ggtagggcgg cgggcgcgtg aaggagagat gcgagcccct   1560
cgaagcttca gctgtgttct ggcggcaaac ccgttgcgaa aaagaacgtt cacggcgact   1620
actgcactta tatacggttc tcccccacc tcgggaaaaa ggcggagcca gtacacgaca   1680
tcacttccc agtttacccc gcgccacctt ctctaggcac cggttcaatt gccgacccct   1740
ccccccaact tctcggggac tgtgggcgat gtgcgctctg cccactgacg ggcaccggag   1800
cgatcttaat taactagtta ttaatagtaa tcaattacgg ggtcattagt tcatagccca   1860
tatatggagt tccgcgttac ataacttacg gtaaatggcc cgcctggctg accgcccaac   1920
gacccccgcc cattgacgtc aataatgacg tatgttccca tagtaacgcc aatagggact   1980
ttccattgac gtcaatgggt ggactattta cggtaaactg cccacttggc agtacatcaa   2040
gtgtatcata tgccaagtac gccccctatt gacgtcaatg acggtaaatg gcccgcctgg   2100
cattatgccc agtacatgac cttatgggac tttcctactt ggcagtacat ctacgtatta   2160
gtcatcgcta ttaccatggg tgatgcggtt ttggcagtac atcaatgggc gtggatagcg   2220
gtttgactca cggggatttc caagtctcca ccccattgac gtcaatggga gtttgttttg   2280
gcaccaaaat caacgggact ttccaaaatg tcgtaacaac tccgccccat tgacgcaaat   2340
gggcggtagg cgtgtacggt gggaggtcta tataagcaga gctcgtttag tgaaccgtca   2400
gatcgcctgg agacgtcgag gaactgaaaa accagaaagt taactggtaa gtttagtctt   2460
tttgtctttt atttcaggtc ccggatccgg tggtggtgca aatcaaagaa ctgctcctca   2520
gtggatgttg cctttacttc taggcctgta cggaagtgtt aaacttctg ctctgcggcc   2580
gcgccaccat ggtcagcgtt ccaacagcct caccctcggc atccagcagc tcctctcagt   2640
gccggtccag catgtgtcaa tcacgctacc tcctcttttt ggccaccctt gccctcctaa   2700
accacctcag tttggccagg gtcattccag tctctggacc tgccaggtgt cttagccagt   2760
cccgaaacct gctgaagacc acagatgaca tggtgaagac ggccagagaa aaactgaaac   2820
attattcctg cactgctgaa gacatcgatc atgaagacat cacacgggac caaaccagca   2880
cattgaagac ctgtttacca ctggaactac acaagaacga gagttgcctg gctactagag   2940
agacttcttc cacaacaaga gggagctgcc tgcccccaca gaagacgtct ttgatgatga   3000
ccctgtgcct tggtagcatc tatgaggact tgaagatgta ccagacagag ttccaggcca   3060
tcaacgcagc acttcagaat cacaaccatc agcagatcat tctagacaag ggcatgctgg   3120
tggccatcga tgagctgatg cagtctctga atcataatgg cgagactctg cgccagaaac   3180
ctcctgtggg agaagcagac ccttacagag tgaaaatgaa gctctctgcatc ctgcttcacg   3240
```

-continued

```
ccttcagcac ccgcgtcgtg accatcaaca gggtgatggg ctatctgagc tccgcctgag    3300
cccctctccc tcccccccc ctaacgttac tggccgaagc cgcttggaat aaggccggtg    3360
tgcgtttgtc tatatgttat tttccaccat attgccgtct tttggcaatg tgagggcccg    3420
gaaacctggc cctgtcttct tgacgagcat cctaggggc ctttccctc tcgccaaagg    3480
aatgcaaggt ctgttgaatg tcgtgaagga agcagttcct ctggaagctt cttgaagaca    3540
aacaacgtct gtagcgaccc tttgcaggca gcggaacccc ccacctggcg acaggtgcct    3600
ctgcggccaa aagccacgtg tataagatac acctgcaaag gcggcacaac cccagtgcca    3660
cgttgtgagt tggatagttg tggaaagagt caaatggctc tcctcaagcg tattcaacaa    3720
ggggctgaag gatgcccaga aggtacccca ttgtatggga tctgatctgg ggcctcggta    3780
cacatgcttt acatgtgttt agtcgaggtt aaaaaaacgt ctaggccccc cgaaccacgg    3840
ggacgtggtt ttcctttgaa aaacacgatg ataatatggc cacaatgaaa attttgaaac    3900
catatatgag gaatacatcc atctcgtgct acttgtgttt ccttctaaac agtcactttt    3960
taactgaggc tggcattcat gtcttcattt tgggctgtgt cagtgtaggt ctccctaaaa    4020
cagaggccaa ctggatagat gtaagatatg acctggagaa aattgaaagc cttattcaat    4080
ctattcatat tgacaccact ttatacactg acagtgactt tcatcccagt tgcaaagtta    4140
ctgcaatgaa ctgctttctc ctggaattgc aggttatttt acatgagtac agtaacatga    4200
ctcttaatga aacagtaaga aacgtgctct accttgcaaa cagcactctg tcttctaaca    4260
agaatgtagc agaatctggc tgcaaggaat gtgaggagct ggaggagaaa accttcacag    4320
agttttttgca aagctttata cgcattgtcc aaatgttcat caacacgtcc tgagcggccg    4380
cgctagccaa ttgctgtgcc ttctagttgc cagccatctg ttgtttgccc ctcccccgtg    4440
ccttccttga ccctggaagg tgccactccc actgtccttt cctaataaaa tgaggaaatt    4500
gcatcgcatt gtctgagtag gtgtcattct attctggggg gtggggtggg gcaggacagc    4560
aagggggagg attgggaaga caatagcagg catgctggg atgcggtggg ctctatggag    4620
ctcgag                                                                4626
```

<210> SEQ ID NO 40
<211> LENGTH: 4912
<212> TYPE: DNA
<213> ORGANISM: Artificial Sequence
<220> FEATURE:
<223> OTHER INFORMATION: Mouse EF1a - modified IL-12B/IL-15 (CpG modified) construct

<400> SEQUENCE: 40

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tagtattaaa cgcgtgtcga ccacacaaaa aaccaacaca cagatctaat     180
gaaaataaag atcttttatt ggcgcgcctc aggacctgac tctgcaggga acacatgccc     240
acttgctgca ggaggaattg taatatctat cctgagcttg cacacagaca ttcccacctt     300
tgcattggac ttctgtagat gtcttctcta caaggaaggc acctttctgg ttacaccct     360
cctctgtctc cttcatcttt tctttcttcc tctggattct aacaaagaac ttgagggaga     420
agtaggaatg gggagtgctc caggagtcag ggtactccca gctgacctcc acctgtgagt     480
tcttcaaagg cttcatctgc aagttcttgg ggggtctgg tttgatgatg tccctgatga     540
agaagctggt gctgtagttc tcatatttat tctgctgcct tgcttccaag gccagttcaa     600
```

```
tgggcagggt ctcctcagca gttgggcagg tgacatcctc ctggcaggac actgaatact    660
tctcatagtc cctttggtcc agtgtgacct tctctgcaga cagagaagcc attccacatg    720
tcactgctct agagtcaggg gaactgctac tgctcttgat gttgaacttc aagtccatgt    780
ttctttgcac cagccatgag catgtgaatc ttccactgta atttggtgct tcacacttca    840
ggaaagtctt gttttgaaa tttttaaaa tttcagtgga ccaaattcca ttttccttct    900
tgtggagcag cagatgtgag tggctcagag tctcccctcc tttgtggcag gtgtactggc    960
cagcatctag aaactctttg acagtgatgg tcagggtctt tccagagcct atgactccat   1020
gtctctggtc tgaggtccag gtgatgtcat cttcttcagg tgtgtcacag gtgaggttca   1080
ctgtttctcc aggggcatct ggagtccagt ccacctctac aacataaaca tctttctcca   1140
gctcccacat ggccatgagt ggagacacca gcaaaacaat ggcaaccag gagatggtta    1200
gcttctgagg acacatggtg gcggcgcgcc atttaaatct agccttaaga gctgtaattg   1260
aactgggagt ggacacctgt ggagagaaag gcaaagtgga tgtcagtaag accaataggt   1320
gcctatcaga aacgcaagag tcttctctgt ctcgacaagc ccagtttcta ttggtctcct   1380
taaacctgtc ttgtaacctt gatacttacc tgcccagtgc ctcacgacca acttcgatct   1440
gtaacggcgc agaacagaaa acgaaacaaa gacgtagagt tgagcaagca gggtcaggca   1500
aagcgtggag agccggctga gtctaggtag gctccaaggg agcgccggac aaaggcccgg   1560
tctcgacctg agctttaaac ttacctagac ggcggacgca gttcaggagg caccacaggc   1620
gggaggcggc agaacgcgac tcaaccggcg tggatggcgg cctcaggtag ggcggcgggc   1680
gcgtgaagga gagatgcgag cccctcgaag cttcagctgt gttctggcgg caaacccgtt   1740
gcgaaaaaga acgttcacgg cgactactgc acttatatac ggttctcccc caccctcggg   1800
aaaaaggcgg agccagtaca cgacatcact ttcccagttt accccgcgcc accttctcta   1860
ggcaccggtt caattgccga cccctccccc caacttctcg gggactgtgg gcgatgtgcg   1920
ctctgcccac tgacgggcac cggagcgatc ttaattaact agttattaat agtaatcaat   1980
tacgggtca ttagttcata gcccatatat ggagttccgc gttacataac ttacggtaaa    2040
tggcccgcct ggctgaccgc ccaacgaccc ccgcccattg acgtcaataa tgacgtatgt   2100
tcccatagta acgccaatag ggactttcca ttgacgtcaa tgggtggact atttacggta   2160
aactgcccac ttggcagtac atcaagtgta tcatatgcca gtacgccccc tattgacgt    2220
caatgacggt aaatggcccg cctggcatta tgcccagtac atgaccttat gggactttcc   2280
tacttggcag tacatctacg tattagtcat cgctattacc atgggtgatg cggttttggc   2340
agtacatcaa tgggcgtgga tagcggtttg actcacgggg atttccaagt ctccacccca   2400
ttgacgtcaa tgggagtttg ttttggcacc aaaatcaacg ggactttcca aaatgtcgta   2460
acaactccgc cccattgacg caaatgggcg gtaggcgtgt acggtgggag gtctatataa   2520
gcagagctcg tttagtgaac cgtcagatcg cctggagacg tcgaggaact gaaaaaccag   2580
aaagttaact ggtaagttta gtcttttgt cttttatttc aggtcccgga tccggtggtg    2640
gtgcaaatca aagaactgct cctcagtgga tgttgccttt acttctaggc ctgtacggaa   2700
gtgtttaaac ttctgctctg cggccgcgcc accatggtca gtgttccaac agcctcaccc   2760
tcagcatcca gcagctcctc tcagtgcagg tccagcatgt gtcaatcaag atacctcctc   2820
tttttggcca cccttgccct cctaaaccac ctcagtttgg ccagggtcat tccagtctct   2880
ggacctgcca ggtgtcttag ccagtccagg aacctgctga agaccacaga tgacatggtg   2940
```

| | |
|---|---|
| aagactgcca gagaaaaact gaaacattat tcctgcactg ctgaagacat agatcatgaa | 3000 |
| gacatcacaa gagaccaaac cagcacattg aagacctgtt taccactgga actacacaag | 3060 |
| aatgagagtt gcctggctac tagagagact tcttccacaa caagagggag ctgcctgccc | 3120 |
| ccacagaaga cctctttgat gatgaccctg tgccttggta gcatctatga ggacttgaag | 3180 |
| atgtaccaga cagagttcca ggccatcaat gcagcacttc agaatcacaa ccatcagcag | 3240 |
| atcattctag acaagggcat gctggtggcc attgatgagc tgatgcagtc tctgaatcat | 3300 |
| aatgggagag ctctgaggca gaaacctcct gtgggagaag cagacccctta cagagtgaaa | 3360 |
| atgaagctct gcatcctgct tcatgccttc agcaccagga tagtgaccat caacagggtg | 3420 |
| atgggctatc tgagcagtgc ctgagccct ctccctcccc ccccctaac gttactggcc | 3480 |
| gaagccgctt ggaataaggc cggtgtgcgt ttgtctatat gttatttcc accatattgc | 3540 |
| cgtcttttgg caatgtgagg gcccggaaac ctggccctgt cttcttgacg agcattccta | 3600 |
| ggggtctttc ccctctcgcc aaaggaatgc aaggtctgtt gaatgtcgtg aaggaagcag | 3660 |
| ttcctctgga agcttcttga agacaaacaa cgtctgtagc gacccctttgc aggcagcgga | 3720 |
| accccccacc tggcgacagg tgcctctgcg gccaaaagcc acgtgtataa gatacacctg | 3780 |
| caaaggcggc acaaccccag tgccacgttg tgagttggat agttgtggaa agagtcaaat | 3840 |
| ggctctcctc aagcgtattc aacaaggggc tgaaggatgc ccagaaggta ccccattgta | 3900 |
| tgggatctga tctggggcct cggtacacat gctttacatg tgtttagtcg aggttaaaaa | 3960 |
| aacgtctagg cccccgaac cacggggacg tggttttcct ttgaaaaaca cgatgataat | 4020 |
| atggccacaa tgaaaatttt gaaaccatat atgaggaata catccatctc atgctacttg | 4080 |
| tgtttccttc taaacagtca ctttttaact gaggctggca ttcatgtctt cattttgggc | 4140 |
| tgtgtcagtg taggtctccc taaaacagag gccaactgga tagatgtaag atatgacctg | 4200 |
| gagaaaattg aaagccttat tcaatctatt catattgaca ccactttata cactgacagt | 4260 |
| gactttcatc ccagttgcaa agttactgca atgaactgct ttctcctgga attgcaggtt | 4320 |
| attttacatg agtacagtaa catgactctt aatgaaacag taagaaatgt gctctacctt | 4380 |
| gcaaacagca ctctgtcttc taacaagaat gtagcagaat ctggctgcaa ggaatgtgag | 4440 |
| gagctggagg agaaaacctt cacagagttt ttgcaaagct ttataaggat tgtccaaatg | 4500 |
| ttcatcaaca cctcctgagc ggccgcgcta gccaattgct gtgccttcta gttgccagcc | 4560 |
| atctgttgtt tgcccctccc ccgtgccttc cttgaccctg gaaggtgcca ctcccactgt | 4620 |
| cctttcctaa taaaatgagg aaattgcatc gcattgtctg agtaggtgtc attctattct | 4680 |
| ggggggtggg gtggggcagg acagcaaggg ggaggattgg gaagacaata gcaggcatgc | 4740 |
| tggggatgcg gtgggctcta tggagctcga gaggaacccc tagtgatgga gttggccact | 4800 |
| ccctctctgc gcgctcgctc gctcactgag gccgggcgac caaaggtcgc ccgacgcccg | 4860 |
| ggctttgccc gggcggcctc agtgagcgag cgagcgcgca gctgcagatc tg | 4912 |

<210> SEQ ID NO 41
<211> LENGTH: 4626
<212> TYPE: DNA
<213> ORGANISM: Artificial Sequence
<220> FEATURE:
<223> OTHER INFORMATION: Mouse EF1a - modified IL-12B/IL-15 (CpG modified) expression sequence

<400> SEQUENCE: 41

```
gtcgaccaca caaaaaacca acacacagat ctaatgaaaa taaagatctt ttattggcgc    60
gcctcaggac ctgactctgc agggaacaca tgcccacttg ctgcaggagg aattgtaata   120
tctatcctga gcttgcacac agacattccc acctttgcat tggacttctg tagatgtctt   180
ctctacaagg aaggcacctt tctggttaca cccctcctct gtctccttca tcttttcttt   240
cttcctctgg attctaacaa agaacttgag ggagaagtag gaatggggag tgctccagga   300
gtcagggtac tcccagctga cctccacctg tgagttcttc aaaggcttca tctgcaagtt   360
cttgggggg tctggtttga tgatgtccct gatgaagaag ctggtgctgt agttctcata   420
tttattctgc tgccttgctt ccaaggccag ttcaatgggc agggtctcct cagcagttgg   480
gcaggtgaca tcctcctggc aggacactga atacttctca tagtcccttt ggtccagtgt   540
gaccttctct gcagacagag aagccattcc acatgtcact gctctagagt caggggaact   600
gctactgctc ttgatgttga acttcaagtc catgtttctt tgcaccagcc atgagcatgt   660
gaatcttcca ctgtaatttg gtgcttcaca cttcaggaaa gtcttgtttt tgaaattttt   720
taaaatttca gtggaccaaa ttccattttc cttcttgtgg agcagcagat gtgagtggct   780
cagagtctcc cctcctttgt ggcaggtgta ctggccagca tctagaaact ctttgacagt   840
gatggtcagg gtctttccag agcctatgac tccatgtctc tggtctgagg tccaggtgat   900
gtcatcttct tcaggtgtgt cacaggtgag gttcactgtt tctccagggg catctggagt   960
ccagtccacc tctacaacat aaacatcttt ctccagctcc cacatggcca tgagtggaga  1020
caccagcaaa acaatggcaa accaggagat ggttagcttc tgaggacaca tggtggcggc  1080
gcgccattta aatctagcct taagagctgt aattgaactg ggagtggaca cctgtggaga  1140
gaaaggcaaa gtggatgtca gtaagaccaa taggtgccta tcagaaacgc aagagtcttc  1200
tctgtctcga caagcccagt ttctattggt ctccttaaac ctgtcttgta accttgatac  1260
ttacctgccc agtgcctcac gaccaacttc gatctgtaac ggcgcagaac agaaaacgaa  1320
acaaagacgt agagttgagc aagcagggtc aggcaaagcg tggagagccg gctgagtcta  1380
ggtaggctcc aagggagcgc cggacaaagg cccggtctcg acctgagctt taaacttacc  1440
tagacggcgg acgcagttca ggaggcacca caggcgggag gcggcagaac gcgactcaac  1500
cggcgtggat ggcggcctca ggtagggcgg cgggcgcgtg aaggagagat gcgagcccct  1560
cgaagcttca gctgtgttct ggcggcaaac ccgttgcgaa aaagaacgtt cacggcgact  1620
actgcactta tatacggttc tcccccaccc tcgggaaaaa ggcggagcca gtacacgaca  1680
tcactttccc agtttacccc gcgccacctt ctctaggcac cggttcaatt gccgaccct  1740
cccccaact tctcggggac tgtgggcgat gtgcgctctg cccactgacg ggcaccggag  1800
cgatcttaat taactagtta ttaatagtaa tcaattacgg ggtcattagt tcatagccca  1860
tatatggagt tccgcgttac ataacttacg gtaaatggcc cgcctggctg accgcccaac  1920
gacccccgcc cattgacgtc aataatgacg tatgttccca tagtaacgcc aatagggact  1980
ttccattgac gtcaatgggt ggactattta cggtaaactg cccacttggc agtacatcaa  2040
gtgtatcata tgccaagtac gccccctatt gacgtcaatg acggtaaatg gcccgcctgg  2100
cattatgccc agtacatgac cttatgggac tttcctactt ggcagtacat ctacgtatta  2160
gtcatcgcta ttaccatggg tgatgcggtt ttggcagtac atcaatgggc gtggatagcg  2220
gtttgactca cggggatttc caagtctcca ccccattgac gtcaatggga gtttgttttg  2280
```

```
gcaccaaaat caacgggact ttccaaaatg tcgtaacaac tccgccccat tgacgcaaat   2340
gggcggtagg cgtgtacggt gggaggtcta tataagcaga gctcgtttag tgaaccgtca   2400
gatcgcctgg agacgtcgag gaactgaaaa accagaaagt taactggtaa gtttagtctt   2460
tttgtctttt atttcaggtc ccggatccgg tggtggtgca aatcaaagaa ctgctcctca   2520
gtggatgttg cctttacttc taggcctgta cggaagtgtt taaacttctg ctctgcggcc   2580
gcgccaccat ggtcagtgtt ccaacagcct caccctcagc atccagcagc tcctctcagt   2640
gcaggtccag catgtgtcaa tcaagatacc tcctcttttt ggccacccct gccctcctaa   2700
accacctcag tttggccagg gtcattccag tctctggacc tgccaggtgt cttagccagt   2760
ccaggaacct gctgaagacc acagatgaca tggtgaagac tgccagagaa aaactgaaac   2820
attattcctg cactgctgaa gacatagatc atgaagacat cacaagagac caaaccagca   2880
cattgaagac ctgtttacca ctggaactac acaagaatga gagttgcctg gctactagag   2940
agacttcttc cacaacaaga gggagctgcc tgcccccaca gaagacctct ttgatgatga   3000
cccctgtgcct tggtagcatc tatgaggact tgaagatgta ccagacagag ttccaggcca   3060
tcaatgcagc acttcagaat cacaaccatc agcagatcat tctagacaag gcatgctgg   3120
tggccattga tgagctgatg cagtctctga atcataatgg ggagactctg aggcagaaac   3180
ctcctgtggg agaagcagac ccttacagag tgaaaatgaa gctctgcatc ctgcttcatg   3240
ccttcagcac cagagtagtg accatcaaca gggtgatggg ctatctgagc agtgcctgag   3300
cccctctccc tcccccccccc ctaacgttac tggccgaagc cgcttggaat aaggccggtg   3360
tgcgtttgtc tatatgttat tttccaccat attgccgtct tttggcaatg tgagggcccg   3420
gaaacctggc cctgtcttct tgacgagcat tcctaggggt cttttcccctc tcgccaaagg   3480
aatgcaaggt ctgttgaatg tcgtgaagga agcagttcct ctggaagctt cttgaagaca   3540
aacaacgtct gtagcgaccc tttgcaggca gcggaacccc ccacctggcg acaggtgcct   3600
ctgcggccaa aagccacgtg tataagatac acctgcaaag gcggcacaac cccagtgcca   3660
cgttgtgagt tggatagttg tggaaagagt caaatggctc tcctcaagcg tattcaacaa   3720
ggggctgaag gatgcccaga aggtacccca ttgtatggga tctgatctgg ggcctcggta   3780
cacatgcttt acatgtgttt agtcgaggtt aaaaaaacgt ctaggccccc cgaaccacgg   3840
ggacgtggtt ttcctttgaa aaacacgatg ataatatggc cacaatgaaa attttgaaac   3900
catatatgag gaatacatcc atctcatgct acttgtgttt ccttctaaac agtcacttttt   3960
taactgaggc tggcattcat gtcttcattt tgggctgtgt cagtgtaggt ctccctaaaa   4020
cagaggccaa ctggatagat gtaagatatg acctggagaa aattgaaagc cttattcaat   4080
ctattcatat tgcaccact ttatacactg acagtgactt tcatcccagt tgcaaagtta   4140
ctgcaatgaa ctgctttctc ctggaattgc aggttatttt acatgagtac agtaacatga   4200
ctcttaatga aacagtaaga aatgtgctct accttgcaaa cagcactctg tcttctaaca   4260
agaatgtagc agaatctggc tgcaaggaat gtgaggagct ggaggagaaa accttcacag   4320
agttttttgca aagctttata aggattgtcc aaatgttcat caacacctcc tgagcggccg   4380
cgctagccaa ttgctgtgcc ttctagttgc cagccatctg ttgtttgccc ctcccccgtg   4440
ccttccttga ccctggaagg tgccactccc actgtccttt cctaataaaa tgaggaaatt   4500
gcatcgcatt gtctgagtag gtgtcattct attctggggg gtggggtggg gcaggacagc   4560
aaggggggagg attgggaaga caatagcagg catgctgggg atgcggtggg ctctatggag   4620
ctcgag                                                             4626
```

<210> SEQ ID NO 42
<211> LENGTH: 4581
<212> TYPE: DNA
<213> ORGANISM: Artificial Sequence
<220> FEATURE:
<223> OTHER INFORMATION: Mouse CAG - wild-type IL-12B - IRES (not CpG
      modified) construct

<400> SEQUENCE: 42

```
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct tagtattaaa cgcgtgtcga cattgattat tgactagtta ttaatagtaa      180
tcaattacgg ggtcattagt tcatagccca tatatggagt tccgcgttac ataacttacg      240
gtaaatggcc cgcctggctg accgcccaac gacccccgcc cattgacgtc aataatgacg      300
tatgttccca tagtaacgcc aatagggact ttccattgac gtcaatgggt ggactattta      360
cggtaaactg cccacttggc agtacatcaa gtgtatcata tgccaagtac gccccctatt      420
gacgtcaatg acggtaaatg gcccgcctgg cattatgccc agtacatgac cttatgggac      480
tttcctactt ggcagtacat ctacgtatta gtcatcgcta ttaccatggg tcgaggtgag      540
ccccacgttc tgcttcactc tccccatctc ccccccctcc ccacccccaa ttttgtattt      600
atttattttt taattatttt gtgcagcgat ggggggcgggg gggggggggg cgcgcgccag      660
gcggggcggg gcggggcgag gggcggggcg gggcgaggcg gagaggtgcg gcggcagcca      720
atcagagcgg cgcgctccga aagtttcctt ttatggcgag gcggcggcgg cggcggccct      780
ataaaaagcg aagcgcgcgg cgggcgggag tcgctgcgcg ctgccttcgc cccgtgcccc      840
gctccgccgc cgcctcgcgc cgcccgcccc ggctctgact gaccgcgtta ctcccacagg      900
tgagcgggcg ggacggccct tctcctccgg gctgtaatta gcgcttggtt taatgacggc      960
tcgtttcttt tctgtggctg cgtgaaagcc ttgaggggct ccgggagggc cctttgtgcg     1020
gggggagcgg ctcgggggt gcgtgcgtgt gtgtgtgcgt ggggagcgcc gcgtgcggct      1080
ccgcgctgcc cggcggctgt gagcgctgcg gcgcggcgc ggggctttgt gcgctccgca      1140
gtgtgcgcga ggagagcgcg gccggggcg gtgccacgcg gtgcgggggg ggctgcgagg     1200
ggaacaaagg ctgcgtgcgg ggtgtgtgcg tgggggggt gagcagggg tgtgggcgcg      1260 gcggtcgggc tgtaaccccc cctgcaccc ccctccccga gttgctgagc acggcccggc      1320
ttcgggtgcg gggctccgtg cggggcgtgg cgcggggctc gccgtgccgg gcgggggtg      1380 gcggcgggtg ggggtgccgg gcggggcggg gccgcctcgg gccggggagg gctcggggga      1440
ggggcgcggc ggccccgga gcgccggcgg ctgtcgaggc gcggcgagcc gcagccattg      1500
ccttttatgg taatcgtgcg agagggcgca gggacttcct ttgtcccaaa tctgtgcgga     1560
gccgaaatct gggaggcgcc gccgcacccc ctctagcggg cgcggggcga agcggtgcgg     1620
cgccggcagg aaggaaatgg gcgggagggg ccttcgtgcg tcgccgcgcc gccgtcccct     1680
tctccctctc cagcctcggg gctgtccgcg gggggacggc tgccttcggg ggggacgggg     1740
caggggcggg ttcggcttct ggcgtgtgac cggcggtcta gactctgcta accatgttca     1800
tgccttcttc tctttcctac agctcctggg caacgtgctg gttgttgtgc tgtctcatca     1860
ttttggcaaa gaattcaagc ttccagctag cgccaccatg gtcagcgttc aacagcctc     1920 accctcggca tccagcagct cctctcagtg ccggtccagc atgtgtcaat cacgctacct     1980 cctcttttg gccaccttg ccctcctaaa ccacctcagt ttggccaggg tcattccagt     2040
```

```
ctctggacct gccaggtgtc ttagccagtc ccgaaacctg ctgaagacca cagatgacat    2100
ggtgaagacg gccagagaaa aactgaaaca ttattcctgc actgctgaag acatcgatca    2160
tgaagacatc acacgggacc aaaccagcac attgaagacc tgtttaccac tggaactaca    2220
caagaacgag agttgcctgg ctactagaga gacttcttcc acaacaagag ggagctgcct    2280
gcccccacag aagacgtctt tgatgatgac cctgtgcctt ggtagcatct atgaggactt    2340
gaagatgtac cagacagagt tccaggccat caacgcagca cttcagaatc acaaccatca    2400
gcagatcatt ctagacaagg gcatgctggt ggccatcgat gagctgatgc agtctctgaa    2460
tcataatggc gagactctgc gccagaaacc tcctgtggga gaagcagacc cttacagagt    2520
gaaaatgaag ctctgcatcc tgcttcacgc cttcagcacc cgcgtcgtga ccatcaacag    2580
ggtgatgggc tatctgagct ccgcctgagc ccctctccct cccccccccc taacgttact    2640
ggccgaagcc gcttggaata aggccggtgt gcgtttgtct atatgttatt ttccaccata    2700
ttgccgtctt ttggcaatgt gagggcccgg aaacctggcc ctgtcttctt gacgagcatt    2760
cctaggggtc tttcccctct cgccaaagga atgcaaggtc tgttgaatgt cgtgaaggaa    2820
gcagttcctc tggaagcttc ttgaagacaa acaacgtctg tagcgaccct ttgcaggcag    2880
cggaaccccc cacctggcga caggtgcctc tgcggccaaa agccacgtgt ataagataca    2940
cctgcaaagg cggcacaacc ccagtgccac gttgtgagtt ggatagttgt ggaaagagtc    3000
aaatggctct cctcaagcgt attcaacaag ggctgaagg atgcccagaa ggtaccccat    3060
tgtatgggat ctgatctggg gcctcggtac acatgcttta catgtgttta gtcgaggtta    3120
aaaaaacgtc taggccccccc gaaccacggg gacgtggttt tcctttgaaa aacacgatga    3180
taatatggcc acaatgtgtc ctcagaagct aaccatctcc tggtttgcca tcgttttgct    3240
ggtgtctcca ctcatggcca tgtgggagct ggagaaagac gtttatgttg tagaggtgga    3300
ctggactccc gatgcccctg gagaaacagt gaacctcacc tgtgacacgc ctgaagaaga    3360
tgacatcacc tggacctcag accagagaca tggagtcata ggctctggaa agaccctgac    3420
catcactgtc aaagagtttc tagatgctgc ccagtacacc tgccacaaag gaggcgagac    3480
tctgagccac tcacatctgc tgctccacaa gaaggaaaat ggaatttggt ccactgaaat    3540
tttaaaaaat ttcaaaaaca agactttcct gaagtgtgaa gcaccaaatt actccggacg    3600
gttcacgtgc tcatggctgg tgcaaagaaa catggacttg aagttcaaca tcaagagcag    3660
tagcagttcc cctgactctc gggcagtgac atgtggaatg cgtctctgt ctgcagagaa    3720 ggtcacactg gaccaaaggg actatgagaa gtattcagtg tcctgccagg aggatgtcac    3780
ctgcccaact gccgaggaga ccctgcccat tgaactggcg ttggaagcac ggcagcagaa    3840
taaatatgag aactacagca ccagcttctt catcagggac atcatcaaac cagacccgcc    3900
caagaacttg cagatgaagc ctttgaagaa ctcacaggtg gaggtcagct gggagtaccc    3960
tgactcctgg agcactcccc attcctactt ctccctcaag ttctttgttc gaatccagcg    4020
caagaaagaa aagatgaagg agacagagga ggggtgtaac cagaaaggag cgttcctcgt    4080
agagaagaca tctaccgaag tccaatgcaa aggcggaat gtctgcgtgc aagctcagga    4140
tcgctattac aattcctcat gcagcaagtg ggcatgtgtt ccctgcaggg tccgatcctg    4200
acaattgctg tgcctttctag ttgccagcca tctgttgttt gccccctcccc cgtgccttcc    4260 ttgaccctgg aagtgccac tcccactgtc ctttcctaat aaaatgagga aattgcatcg    4320
cattgtctga gtaggtgtca ttctattctg ggggtgggg tgggcaggac cagcaagggg    4380
```

```
gaggattggg aagacaatag caggcatgct ggggatgcgg tgggctctat ggagctcgag    4440
aggaacccct agtgatggag ttggccactc cctctctgcg cgctcgctcg ctcactgagg    4500
ccgggcgacc aaaggtcgcc cgacgcccgg gctttgcccg ggcggcctca gtgagcgagc    4560
gagcgcgcag ctgcagatct g                                              4581

<210> SEQ ID NO 43
<211> LENGTH: 2322
<212> TYPE: DNA
<213> ORGANISM: Artificial Sequence
<220> FEATURE:
<223> OTHER INFORMATION: Mouse CAG - wild-type IL-12B - IRES (not CpG
      modified) expression sequence

<400> SEQUENCE: 43
gctagcgcca ccatggtcag cgttccaaca gcctcaccct cggcatccag cagctcctct      60
cagtgccggt ccagcatgtg tcaatcacgc tacctcctct ttttggccac ccttgccctc     120
ctaaaccacc tcagtttggc cagggtcatt ccagtctctg acctgccag gtgtcttagc      180 cagtcccgaa acctgctgaa gaccacagat gacatggtga agacggccag agaaaaactg     240
aaacattatt cctgcactgc tgaagacatc gatcatgaag acatcacacg ggaccaaacc     300
agcacattga agacctgttt accactggaa ctacacaaga acgagagttg cctggctact     360
agagagactt cttccacaac aagagggagc tgcctgcccc cacagaagac gtctttgatg     420 atgacccctgt gccttggtag catctatgag gacttgaaga tgtaccagac agagttccag     480
gccatcaacg cagcacttca gaatcacaac catcagcaga tcattctaga caagggcatg     540
ctggtggcca tcgatgagct gatgcagtct ctgaatcata atggcgagac tctgcgccag     600
aaacctcctg tgggagaagc agaccccttac agagtgaaaa tgaagctctg catcctgctt     660
cacgccttca gcaccgcgt cgtgaccatc aacagggtga tgggctatct gagctccgcc      720
tgagcccctc tccctccccc ccccctaacg ttactggccg aagccgcttg gaataaggcc      780
ggtgtgcgtt tgtctatatg ttatttttcca ccatattgcc gtcttttggc aatgtgaggg    840
cccggaaacc tggccctgtc ttcttgacga gcattcctag gggtctttcc cctctcgcca    900
aaggaatgca aggtctgttg aatgtcgtga aggaagcagt tcctctggaa gcttcttgaa    960
gacaaacaac gtctgtagcg acccttttgca ggcagcggaa ccccccacct ggcgacaggt    1020
gcctctgcgg ccaaaagcca cgtgtataag atacacctgc aaaggcggca accccccagt    1080
gccacgttgt gagttggata gttgtggaaa gagtcaaatg gctctcctca agcgtattca    1140 acaagggct gaaggatgcc cagaaggtac cccattgtat gggatctgat ctggggcctc    1200
ggtacacatg ctttacatgt gtttagtcga ggttaaaaaa acgtctaggc cccccgaacc    1260
acggggacgt ggttttcctt tgaaaaacac gatgataata tggccacaat gtgtcctcag    1320
aagctaacca tctcctggtt tgccatcgtt ttgctggtgt ctccactcat ggccatgtgg    1380
gagctggaga aagacgttta tgttgtagag gtggactgga ctcccgatgc ccctggagaa    1440
acagtgaacc tcacctgtga cacgcctgaa gaagatgaca tcacctggac ctcagaccag    1500
agacatggag tcataggctc tggaaagacc ctgaccatca ctgtcaaaga gtttctagat    1560
gctggccagt acacctgcca caaggaggc gagactctga ccactcaca tctgctgctc    1620 cacaagaagg aaaatggaat tggtccact gaaatttaa aaatttcaa aaacaagact    1680 ttcctgaagt gtgaagcacc aaattactcc ggacggttca cgtgctcatg gctggtgcaa    1740
agaaacatgg acttgaagtt caacatcaag agcagtagca gttcccctga ctctcgggca    1800
```

| | |
|---|---|
| gtgacatgtg gaatggcgtc tctgtctgca gagaaggtca cactggacca aagggactat | 1860 |
| gagaagtatt cagtgtcctg ccaggaggat gtcacctgcc caactgccga ggagaccctg | 1920 |
| cccattgaac tggcgttgga agcacggcag cagaataaat atgagaacta cagcaccagc | 1980 |
| ttcttcatca gggacatcat caaaccagac ccgcccaaga acttgcagat gaagcctttg | 2040 |
| aagaactcac aggtggaggt cagctgggag taccctgact cctggagcac tccccattcc | 2100 |
| tacttctccc tcaagttctt tgttcgaatc cagcgcaaga agaaaagat gaaggagaca | 2160 |
| gaggaggggt gtaaccagaa aggagcgttc ctcgtagaga agacatctac cgaagtccaa | 2220 |
| tgcaaaggcg ggaatgtctg cgtgcaagct caggatcgct attacaattc ctcatgcagc | 2280 |
| aagtgggcat gtgttccctg cagggtccga tcctgacaat tg | 2322 |

<210> SEQ ID NO 44
<211> LENGTH: 2766
<212> TYPE: DNA
<213> ORGANISM: Artificial Sequence
<220> FEATURE:
<223> OTHER INFORMATION: Mouse CAG - wild-type IL-15 (not CpG modified) construct

<400> SEQUENCE: 44

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tagtattaaa cgcgtgtcga cattgattat tgactagtta ttaatagtaa | 180 |
| tcaattacgg ggtcattagt tcatagccca tatatggagt tccgcgttac ataacttacg | 240 |
| gtaaatggcc cgcctggctg accgcccaac gacccccgcc cattgacgtc aataatgacg | 300 |
| tatgttccca tagtaacgcc aatagggact ttccattgac gtcaatgggt ggactattta | 360 |
| cggtaaactg cccacttggc agtacatcaa gtgtatcata tgccaagtac gccccctatt | 420 |
| gacgtcaatg acggtaaatg gcccgcctgg cattatgccc agtacatgac cttatgggac | 480 |
| tttcctactt ggcagtacat ctacgtatta gtcatcgcta ttaccatggg tcgaggtgag | 540 |
| ccccacgttc tgcttcactc tccccatctc ccccccctcc ccaccccccaa ttttgtattt | 600 |
| atttattttt taattatttt gtgcagcgat gggggcgggg gggggggggg cgcgcgccag | 660 |
| gcggggcggg gcggggcgag gggcggggcg gggcgaggcg gagaggtgcg gcggcagcca | 720 |
| atcagagcgg cgcgctccga aagtttcctt ttatggcgag gcggcggcgg cggcggccct | 780 |
| ataaaaagcg aagcgcgcgg cgggcgggag tcgctgcgcg ctgccttcgc cccgtgcccc | 840 |
| gctccgccgc cgcctcgcgc cgcccgcccc ggctctgact gaccgcgtta ctcccacagg | 900 |
| tgagcgggcg ggacggccct tctcctccgg gctgtaatta gcgcttggtt taatgacggc | 960 |
| tcgtttcttt tctgtggctg cgtgaaagcc ttgagggggct ccgggagggc cctttgtgcg | 1020 |
| ggggagcgg ctcgggggggt gcgtgcgtgt gtgtgtgcgt ggggagcgcc gcgtgcggct | 1080 |
| ccgcgctgcc cggcggctgt gagcgctgcg gcgcggcgc ggggctttgt gcgctccgca | 1140 |
| gtgtgcgcga ggagagcgcg gccggggcg gtgccacgcg gtgcgggggg ggctgcgagg | 1200 |
| ggaacaaagg ctgcgtgcgg ggtgtgtgcg tggggggggt gagcagggg tgtgggcgcg | 1260 |
| gcggtcgggc tgtaaccccc ccctgcaccc ccctccccga gttgctgagc acggcccggc | 1320 |
| ttcgggtgcg gggctccgtg cggggcgtgg cgcggggctc gccgtgccgg gcggggggtg | 1380 |
| gcggcgggtg gggtgccgg gcgggcggg ccgcctcgg gccggggagg gctcggggga | 1440 |
| ggggcgcggc ggccccgga gcgccggcgg ctgtcgaggc gcggcgagcc gcagccattg | 1500 |

-continued

```
cctttatgg taatcgtgcg agagggcgca gggacttcct tgtcccaaa tctgtgcgga      1560
gccgaaatct gggaggcgcc gccgcacccc ctctagcggg cgcggggcga agcggtgcgg      1620
cgccggcagg aaggaaatgg gcggggaggg ccttcgtgcg tcgccgcgcc gccgtcccct      1680
tctccctctc cagcctcggg gctgtccgcg ggggacggc tgccttcggg ggggacgggg      1740
cagggcgggg ttcggcttct ggcgtgtgac cggcggtcta gactctgcta accatgttca      1800
tgccttcttc tctttcctac agctcctggg caacgtgctg gttgttgtgc tgtctcatca      1860
ttttggcaaa gaattcaagc ttccagctag cgccaccatg aaaattttga aaccatatat      1920
gaggaataca tccatctcgt gctacttgtg tttccttcta acagtcact ttttaactga      1980
ggctggcatt catgtcttca ttttgggctg tgtcagtgta ggtctcccta aaacagaggc      2040
caactggata gatgtaagat atgacctgga gaaaattgaa agccttattc aatctattca      2100
tattgacacc actttataca ctgacagtga ctttcatccc agttgcaaag ttactgcaat      2160
gaactgcttt ctcctggaat tgcaggttat tttacatgag tacagtaaca tgactcttaa      2220
tgaaacagta agaaacgtgc tctaccttgc aaacagcact ctgtcttcta acaagaatgt      2280
agcagaatct ggctgcaagg aatgtgagga gctggaggag aaaaccttca cagagttttt      2340
gcaaagcttt atacgcattg tccaaatgtt catcaacacg tcctgacaat tgctgtgcct      2400
tctagttgcc agccatctgt tgtttgcccc tccccgtgc cttccttgac cctggaaggt      2460
gccactccca ctgtccttc ctaataaaat gaggaaattg catcgcattg tctgagtagg      2520
tgtcattcta ttctgggggg tggggtgggg caggacagca aggggagga ttgggaagac      2580
aatagcaggc atgctgggga tgcggtgggc tctatggagc tcgagaggaa ccctagtga      2640
tggagttggc cactccctct ctgcgcgctc gctcgctcac tgaggccggg cgaccaaagg      2700
tcgcccgacg cccgggcttt gcccgggcgg cctcagtgag cgagcgagcg cgcagctgca      2760
gatctg                                                                 2766
```

<210> SEQ ID NO 45
<211> LENGTH: 507
<212> TYPE: DNA
<213> ORGANISM: Artificial Sequence
<220> FEATURE:
<223> OTHER INFORMATION: Mouse CAG - wild-type IL-15 (not CpG modified)
      expression sequence

<400> SEQUENCE: 45

```
gctagcgcca ccatgaaaat tttgaaacca tatatgagga atacatccat ctcgtgctac       60
ttgtgtttcc ttctaaacag tcactttta actgaggctg gcattcatgt cttcattttg      120
ggctgtgtca gtgtaggtct ccctaaaaca gaggccaact ggatagatgt aagatatgac      180
ctggagaaaa ttgaaagcct tattcaatct attcatattg acaccacttt atacactgac      240
agtgactttc atcccagttg caaagttact gcaatgaact gctttctcct ggaattgcag      300
gttattttac atgagtacag taacatgact cttaatgaaa cagtaagaaa cgtgctctac      360
cttgcaaaca gcactctgtc ttctaacaag aatgtagcag aatctggctg caaggaatgt      420
gaggagctgg aggagaaaac cttcacagag ttttttgcaaa gctttatacg cattgtccaa      480
atgttcatca cacgtcctg acaattg                                            507
```

<210> SEQ ID NO 46
<211> LENGTH: 4089
<212> TYPE: DNA
<213> ORGANISM: Artificial Sequence
<220> FEATURE:

<223> OTHER INFORMATION: Mouse CAG - wild-type IL-12B - F2A (not CpG
       modified) construct

<400> SEQUENCE: 46

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tagtattaaa | cgcgtgtcga | cattgattat | tgactagtta | ttaatagtaa | 180 |
| tcaattacgg | ggtcattagt | tcatagccca | tatatggagt | tccgcgttac | ataacttacg | 240 |
| gtaaatggcc | cgcctggctg | accgcccaac | gacccccgcc | cattgacgtc | aataatgacg | 300 |
| tatgttccca | tagtaacgcc | aatagggact | ttccattgac | gtcaatgggt | ggactattta | 360 |
| cggtaaactg | cccacttggc | agtacatcaa | gtgtatcata | tgccaagtac | gccccctatt | 420 |
| gacgtcaatg | acggtaaatg | gcccgcctgg | cattatgccc | agtacatgac | cttatgggac | 480 |
| tttcctactt | ggcagtacat | ctacgtatta | gtcatcgcta | ttaccatggg | tcgaggtgag | 540 |
| ccccacgttc | tgcttcactc | tccccatctc | ccccccctcc | ccaccccaa | ttttgtattt | 600 |
| atttatttt | taattatttt | gtgcagcgat | ggggggcgggg | ggggggggggg | cgcgcgccag | 660 |
| gcggggcggg | gcggggcgag | gggcggggcg | gggcgaggcg | gagaggtgcg | gcggcagcca | 720 |
| atcagagcgg | cgcgctccga | aagtttcctt | ttatggcgag | gcggcggcgg | cggcggccct | 780 |
| ataaaaagcg | aagcgcgcgg | cgggcgggag | tcgctgcgcg | ctgccttcgc | ccgtgccc | 840 |
| gctccgccgc | cgcctcgcgc | cgcccgcccc | ggctctgact | gaccgcgtta | ctcccacagg | 900 |
| tgagcgggcg | ggacggccct | tctcctccgg | gctgtaatta | gcgcttggtt | taatgacggc | 960 |
| tcgtttcttt | tctgtggctg | cgtgaaagcc | ttgaggggct | ccgggagggc | cctttgtgcg | 1020 |
| ggggagcgg | ctcggggggt | gcgtgcgtgt | gtgtgtgcgt | ggggagcgcc | gcgtgcggct | 1080 |
| ccgcgctgcc | cggcggctgt | gagcgctgcg | ggcgcggcgc | ggggctttgt | gcgctccgca | 1140 |
| gtgtgcgcga | ggagcgcgc | gccggggcg | gtgccacgcg | gtgcgggggg | ggctgcgagg | 1200 |
| ggaacaaagg | ctgcgtgcgg | ggtgtgtgcg | tgggggggggt | gagcaggggg | tgtgggcgcg | 1260 |
| gcggtcgggc | tgtaaccccc | ccctgcaccc | ccctccccga | gttgctgagc | acggcccggc | 1320 |
| ttcgggtgcg | gggctccgtg | cggggcgtgg | cgcggggctc | gccgtgccgg | gcgggggtg | 1380 |
| gcggcgggtg | ggggtgccgg | gcggggcggg | gccgcctcgg | gccggggagg | gctcggggga | 1440 |
| ggggcgcggc | ggccccgga | gcgccggcgg | ctgtcgaggc | gcggcgagcc | gcagccattg | 1500 |
| cctttatgg | taatcgtgcg | agagggcgca | gggacttcct | ttgtcccaaa | tctgtgcgga | 1560 |
| gccgaaatct | gggaggcgcc | gccgcacccc | ctctagcggg | cgcggggcga | agcggtgcgg | 1620 |
| cgccggcagg | aaggaaatgg | gcggggaggg | ccttcgtgcg | tcgccgcgcc | gccgtcccct | 1680 |
| tctccctctc | cagcctcggg | gctgtccgcg | ggggacggc | tgccttcggg | ggggacgggg | 1740 |
| cagggcgggg | ttcggcttct | ggcgtgtgac | cggcggtcta | gactctgcta | accatgttca | 1800 |
| tgccttcttc | tctttcctac | agctcctggg | caacgtgctg | gttgttgtgc | tgtctcatca | 1860 |
| ttttggcaaa | gaattcaagc | ttccagctag | cgccaccatg | gtcagcgttc | aacagcctc | 1920 |
| accctcggca | tccagcagct | cctctcagtg | ccggtccagc | atgtgtcaat | cacgctacct | 1980 |
| cctcttttg | gccaccttg | ccctcctaaa | ccacctcagt | ttggcaggg | tcattccagt | 2040 |
| ctctggacct | gccaggtgtc | ttagccagtc | ccgaaacctg | ctgaagacca | cagatgacat | 2100 |
| ggtgaagacg | gccagagaaa | aactgaaaca | ttattcctgc | actgctgaag | acatcgatca | 2160 |
| tgaagacatc | acacgggacc | aaaccagcac | attgaagacc | tgtttaccac | tggaactaca | 2220 |

-continued

```
caagaacgag agttgcctgg ctactagaga gacttcttcc acaacaagag ggagctgcct    2280
gcccccacag aagacgtctt tgatgatgac cctgtgcctt ggtagcatct atgaggactt    2340
gaagatgtac cagacagagt tccaggccat caacgcagca cttcagaatc acaaccatca    2400
gcagatcatt ctagacaagg gcatgctggt ggccatcgat gagctgatgc agtctctgaa    2460
tcataatggc gagactctgc gccagaaacc tcctgtggga aagcagacc cttacagagt    2520
gaaaatgaag ctctgcatcc tgcttcacgc cttcagcacc cgcgtcgtga ccatcaacag    2580
ggtgatgggc tatctgagct ccgccagaaa gagaaggagt ggctcaggag cccctgtgaa    2640
acagaccctg aactttgacc tcttgaagct tgctggggat gtggagtcta atcctggtcc    2700
aatgtgtcct cagaagctaa ccatctcctg gtttgccatc gttttgctgg tgtctccact    2760
catggccatg tgggagctgg agaaagacgt ttatgttgta gaggtggact ggactcccga    2820
tgcccctgga gaaacagtga acctcacctg tgacacgcct gaagaagatg acatcacctg    2880
gacctcagac cagagacatg gagtcatagg ctctggaaag accctgacca tcactgtcaa    2940
agagtttcta gatgctggcc agtacacctg ccacaaagga ggcgagactc tgagccactc    3000
acatctgctg ctccacaaga aggaaaatgg aatttggtcc actgaaattt taaaaaattt    3060
caaaaacaag acttttcctga agtgtgaagc accaaattac tccggacggt tcacgtgctc    3120
atggctggtg caaagaaaca tggacttgaa gttcaacatc aagagcagta gcagttcccc    3180
tgactctcgg gcagtgacat gtggaatggc gtctctgtct gcagagaagg tcacactgga    3240
ccaaagggac tatgagaagt attcagtgtc ctgccaggag gatgtcacct gcccaactgc    3300
cgaggagacc ctgcccattg aactggcgtt ggaagcacgg cagcagaata aatatgagaa    3360
ctacagcacc agcttcttca tcagggacat catcaaacca gacccgccca gaacttgca    3420
gatgaagcct tgaagaact cacaggtgga ggtcagctgg gagtaccctg actcctggag    3480
cactccccat tcctacttct ccctcaagtt cttttgttcga atccagcgca agaaagaaaa    3540
gatgaaggag acagaggagg ggtgtaacca gaaaggagcg ttcctcgtag agaagacatc    3600
taccgaagtc caatgcaaag gcgggaatgt ctgcgtgcaa gctcaggatc gctattacaa    3660
ttcctcatgc agcaagtggg catgtgttcc ctgcagggtc cgatcctgac aattgctgtg    3720
ccttctagtt gccagccatc tgttgttttgc ccctcccccg tgccttcctt gaccctggaa    3780
ggtgccactc ccactgtcct ttcctaataa aatgaggaaa ttgcatcgca ttgtctgagt    3840
aggtgtcatt ctattctggg gggtggggtg gggcaggaca gcaagggga ggattgggaa    3900
gacaatagca ggcatgctgg ggatgcggtg ggctctatgg agctcgagag gaaccccta g   3960
tgatggagtt ggccactccc tctctgcgcg ctcgctcgct cactgaggcc gggcgaccaa    4020
aggtcgcccg acgcccgggc tttgcccggg cggcctcagt gagcgagcga gcgcgcagct    4080
gcagatctg                                                          4089
```

<210> SEQ ID NO 47
<211> LENGTH: 1830
<212> TYPE: DNA
<213> ORGANISM: Artificial Sequence
<220> FEATURE:
<223> OTHER INFORMATION: Mouse CAG - wild-type IL-12B - F2A (not CpG
      modified) expression sequence

<400> SEQUENCE: 47

```
gctagcgcca ccatggtcag cgttccaaca gcctcaccct cggcatccag cagctcctct      60
cagtgccggt ccagcatgtg tcaatcacgc tacctcctct ttttggccac ccttgccctc     120
```

| | |
|---|---|
| ctaaaccacc tcagtttggc cagggtcatt ccagtctctg gacctgccag gtgtcttagc | 180 |
| cagtcccgaa acctgctgaa gaccacagat gacatggtga agacggccag agaaaaactg | 240 |
| aaacattatt cctgcactgc tgaagacatc gatcatgaag acatcacacg ggaccaaacc | 300 |
| agcacattga agacctgttt accactggaa ctacacaaga acgagagttg cctggctact | 360 |
| agagagactt cttccacaac aagagggagc tgcctgcccc cacagaagac gtctttgatg | 420 |
| atgaccctgt gccttggtag catctatgag gacttgaaga tgtaccagac agagttccag | 480 |
| gccatcaacg cagcacttca gaatcacaac catcagcaga tcattctaga caagggcatg | 540 |
| ctggtggcca tcgatgagct gatgcagtct ctgaatcata tggcgagac tctgcgccag | 600 |
| aaacctcctg tgggagaagc agacccttac agagtgaaaa tgaagctctg catcctgctt | 660 |
| cacgccttca gcacccgcgt cgtgaccatc aacagggtga tgggctatct gagctccgcc | 720 |
| agaaagagaa ggagtggctc aggagcccct gtgaaacaga ccctgaactt tgacctcttg | 780 |
| aagcttgctg gggatgtgga gtctaatcct ggtccaatgt gtcctcagaa gctaaccatc | 840 |
| tcctggtttg ccatcgtttt gctggtgtct ccactcatgg ccatgtggga gctggagaaa | 900 |
| gacgtttatg ttgtagaggt ggactggact cccgatgccc ctggagaaac agtgaacctc | 960 |
| acctgtgaca cgcctgaaga agatgacatc acctggacct cagaccagag acatggagtc | 1020 |
| ataggctctg gaaagaccct gaccatcact gtcaaagagt ttctagatgc tggccagtac | 1080 |
| acctgccaca aggaggcga gactctgagc cactcacatc tgctgctcca caagaaggaa | 1140 |
| aatggaattt ggtccactga aatttttaaaa aatttcaaaa acaagacttt cctgaagtgt | 1200 |
| gaagcaccaa attactccgg acggttcacg tgctcatggc tggtgcaaag aaacatggac | 1260 |
| ttgaagttca acatcaagag cagtagcagt tcccctgact ctcgggcagt gacatgtgga | 1320 |
| atggcgtctc tgtctgcaga aaggtcaca ctggaccaaa gggactatga aagtattca | 1380 |
| gtgtcctgcc aggaggatgt cacctgccca actgccgagg agaccctgcc cattgaactg | 1440 |
| gcgttggaag cacggcagca gaataaatat gagaactaca gcaccagctt cttcatcagg | 1500 |
| gacatcatca aaccagaccc gcccaagaac ttgcagatga gcccttgaa gaactcacag | 1560 |
| gtggaggtca gctgggagta ccctgactcc tggagcactc cccattccta cttctccctc | 1620 |
| aagttctttg ttcgaatcca gcgcaagaaa gaaaagatga aggagacaga ggagggtgt | 1680 |
| aaccagaaag gagcgttcct cgtagagaag acatctaccg aagtccaatg caaaggcggg | 1740 |
| aatgtctgcg tgcaagctca ggatcgctat tacaattcct catgcagcaa gtgggcatgt | 1800 |
| gttccctgca gggtccgatc ctgacaattg | 1830 |

<210> SEQ ID NO 48
<211> LENGTH: 4017
<212> TYPE: DNA
<213> ORGANISM: Artificial Sequence
<220> FEATURE:
<223> OTHER INFORMATION: Human CAG - modified IL-12A/IL-12B - F2A (CpG modified) construct

<400> SEQUENCE: 48

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tagtattaaa cgcgtgtcga cattgattat tgactagtta ttaatagtaa | 180 |
| tcaattacgg ggtcattagt tcatagccca tatatggagt tccgcgttac ataacttacg | 240 |
| gtaaatggcc cgcctggctg accgcccaac gaccccgcc cattgacgtc aataatgacg | 300 |

-continued

```
tatgttccca tagtaacgcc aatagggact ttccattgac gtcaatgggt ggactattta    360
cggtaaactg cccacttggc agtacatcaa gtgtatcata tgccaagtac gccccctatt    420
gacgtcaatg acggtaaatg gcccgcctgg cattatgccc agtacatgac cttatgggac    480
tttcctactt ggcagtacat ctacgtatta gtcatcgcta ttaccatggg tcgaggtgag    540
ccccacgttc tgcttcactc tccccatctc cccccctcc ccaccccaa ttttgtattt      600
atttattttt taattatttt gtgcagcgat ggggggcggg ggggggggg cgcgcgccag     660
gcggggcggg gcggggcgag gggcggggcg gggcgaggcg gagaggtgcg gcggcagcca    720
atcagagcgg cgcgctccga aagtttcctt ttatggcgag gcggcggcgg cggcggccct    780
ataaaagcg aagcgcgcgg cgggcgggag tcgctgcgcg ctgccttcgc cccgtgcccc     840
gctccgccgc cgcctcgcgc cgccgcccc ggctctgact gaccgcgtta ctcccacagg     900
tgagcgggcg ggacggccct tctcctccgg gctgtaatta gcgcttggtt taatgacggc    960
tcgtttcttt tctgtggctg cgtgaaagcc ttgaggggct ccgggagggc cctttgtgcg    1020
gggggagcgg ctcggggggt gcgtgcgtgt gtgtgtgcgt gggagcgcc gcgtgcggct     1080
ccgcgctgcc cggcggctgt gagcgctgcg ggcgcggcgc ggggctttgt gcgctccgca    1140
gtgtgcgcga gaggagcgcg gccggggggcg gtgccacgcg gtgcgggggg ggctgcgagg   1200
ggaacaaagg ctgcgtgcgg ggtgtgtgcg tgggggggt gagcagggg tgtgggcgcg      1260
gcggtcgggc tgtaaccccc ccctgcaccc ccctccccga gttgctgagc acggcccggc    1320
ttcgggtgcg ggctccgtg cggggcgtgg cgcggggctc gccgtgccgg gcgggggtg      1380
gcggcgggtg ggggtgccgg gcggggcggg gccgcctcgg gccggggagg gctcggggga    1440
ggggcgcggc ggccccccgga gcgccggcgg ctgtcgaggc gcggcgagcc gcagccattg   1500
cctttttatgg taatcgtgcg agagggcgca gggacttcct ttgtcccaaa tctgtgcgga   1560
gccgaaatct gggaggcgcc gccgcacccc ctctagcggg cgcggggcga agcggtgcgg   1620
cgccggcagg aaggaaatgg gcggggaggg ccttcgtgcg tcgccgcgcc gccgtccct    1680
tctccctctc cagcctcggg gctgtccgcg gggggacggc tgccttcggg ggggacgggg   1740
cagggcgggg ttcggcttct ggcgtgtgac cggcggtcta gactctgcta accatgttca   1800
tgccttcttc tctttcctac agctcctggg caacgtgctg gttgttgtgc tgtctcatca   1860
ttttggcaaa gaattcaagc ttccagctag cgccaccatg tgtccagcta ggagcctcct   1920
ccttgtggct accctggtcc tcctggacca cctcagtttg gccagaaacc tccctgtggc   1980
cactccagac ccaggaatgt tcccatgcct tcaccactcc caaaacctgc tgagggcagt   2040
cagcaacatg ctccagaagg ccagacaaac tctagaattt tacccttgca cttctgaaga   2100
gattgatcat gaagatatca caaaagataa aaccagcaca gtggaggcct gtttaccatt   2160
ggaattaacc aagaatgaga gttgcctaaa ttccagagag acctctttca taactaatgg   2220
gagttgcctg gcctccagaa agacctcttt tatgatggcc ctgtgcctta gtagtattta   2280
tgaagacttg aagatgtacc aggtggagtt caagaccatg aatgcaaagc ttctgatgga   2340
tcctaagagg cagatctttc tagatcaaaa catgctggca gttattgatg agctgatgca   2400
ggccctgaat ttcaacagtg agactgtgcc acaaaaatcc ccccttgaag aacctgattt   2460
ttataaaact aaaatcaagc tctgcatact tcttcatgct ttccggatta gggcagtgac   2520
tattgataga gtgatgagct atctgaatgc ttccagaaag agaaggagtg gctcaggagc   2580
ccctgtgaaa cagaccctga actttgacct cttgaagctt gctggggatg tggagtctaa   2640
tcctggtcca atgtgtcacc agcagttggt catctcttgg ttttccctgg ttttttctggc  2700
```

```
atctcccctt gtggccatat gggaactgaa gaaagatgtt tatgtggtag aattggattg    2760
gtatcctgat gccctggag aaatggtggt cctcacctgt gacaccctg aagaagatgg    2820
```

```
atctcccctt gtggccatat gggaactgaa gaaagatgtt tatgtggtag aattggattg    2760
gtatcctgat gccctggag  aaatggtggt cctcacctgt gacacccctg aagaagatgg    2820
tatcacctgg accttggacc agagcagtga ggtcttaggc tctggcaaaa ccctgaccat    2880
ccaagtcaaa gagtttggag atgctggcca gtacacctgt cacaaggag gggaggttct    2940
aagccattcc ctcctgctgc ttcacaaaaa ggaagatgga atttggtcca ctgatatttt    3000
aaaggaccag aaagaaccca aaataagac  ctttctaaga tgtgaggcca agaattattc    3060
tggaaggttc acctgctggt ggctgactac aatcagtact gatttgacat tcagtgtcaa    3120
aagcagcaga ggctcttctg accccaagg  ggtgacatgt ggagctgcta cactctctgc    3180
agagagagtc agaggggaca acaaggagta tgagtactca gtggagtgcc aggaggacag    3240
tgcctgccca gctgctgagg agagtctgcc cattgaggtg atggtggatg cagttcacaa    3300
gctcaagtat gaaaactaca ccagcagctt cttcatcagg gacatcatca aacctgaccc    3360
acccaagaac ttgcagctga agccattaaa gaattctagg caggtggagg tcagctggga    3420
gtaccctgac acctggagta ctccacattc ctacttctcc ctgacattct gtgttcaagt    3480
ccagggcaag agcaagagag aaaagaaaga tagagtcttc actgacaaga cctcagccac    3540
agtcatctgc aggaaaaatg ccagcatttc agtgagggcc caggacagat actatagctc    3600
atcttggtca gaatgggcat ctgtgccctg cagttgacaa ttgctgtgcc ttctagttgc    3660
cagccatctg ttgtttgccc ctccccgtg  ccttccttga ccctggaagg tgccactccc    3720
actgtccttt cctaataaaa tgaggaaatt gcatcgcatt gtctgagtag gtgtcattct    3780
attctggggg gtggggtggg gcaggacagc aagggggagg attgggaaga caatagcagg    3840
catgctgggg atgcggtggg ctctatggag ctcgagagga acccctagtg atggagttgg    3900
ccactccctc tctgcgcgct cgctcgctca ctgaggccgg gcgaccaaag gtcgcccgac    3960
gcccgggctt tgcccgggcg gcctcagtga gcgagcgagc gcgcagctgc agatctg       4017
```

<210> SEQ ID NO 49
<211> LENGTH: 1758
<212> TYPE: DNA
<213> ORGANISM: Artificial Sequence
<220> FEATURE:
<223> OTHER INFORMATION: Human CAG - modified IL-12A/IL-12B - F2A (CpG modified) expression sequence

<400> SEQUENCE: 49

```
gctagcgcca ccatgtgtcc agctaggagc ctcctccttg tggctaccct ggtcctcctg      60
gaccacctca gtttggccag aaacctccct gtggccactc agacccagg  aatgttccca     120
tgccttcacc actcccaaaa cctgctgagg gcagtcagca acatgctcca gaaggcaga     180
caaactctag aattttaccc ttgcacttct gaagagattg atcatgaaga tatcacaaaa     240
gataaaacca gcacagtgga ggcctgttta ccattggaat taaccaagaa tgagagttgc     300
ctaaattcca gagagacctc tttcataact aatgggagtt gcctggcctc agaaagacc     360
tcttttatga tggccctgtg ccttagtagt atttatgaag acttgaagat gtaccaggtg     420
gagttcaaga ccatgaatgc aaagcttctg atggatccta gaggcagat  ctttctagat     480
caaaacatgc tggcagttat tgatgagctg atgcaggccc tgaatttcaa cagtgagact     540
gtgccacaaa aatcctccct tgaagaacct gatttttata aaactaaaat caagctctgc     600
atacttcttc atgctttccg gattaggca  gtgactattg atagagtgat gagctatctg     660
aatgcttcca aaagagaag  gagtggctca ggagcccctg tgaaacagac cctgaacttt     720
```

```
gacctcttga agcttgctgg ggatgtggag tctaatcctg gtccaatgtg tcaccagcag      780
ttggtcatct cttggttttc cctggttttt ctggcatctc cccttgtggc catatgggaa      840
ctgaagaaag atgtttatgt ggtagaattg gattggtatc ctgatgcccc tggagaaatg      900
gtggtcctca cctgtgacac ccctgaagaa gatggtatca cctggacctt ggaccagagc      960
agtgaggtct taggctctgg caaaaccctg accatccaag tcaaagagtt tggagatgct     1020
ggccagtaca cctgtcacaa aggaggggag gttctaagcc attccctcct gctgcttcac     1080
aaaaaggaag atggaatttg gtccactgat attttaaagg accagaaaga acccaaaaat     1140 aagaccttc taagatgtga ggccaagaat tattctggaa ggttcacctg ctggtggctg     1200
actacaatca gtactgattt gacattcagt gtcaaaagca gcagaggctc ttctgacccc     1260
caaggggtga catgtggagc tgctacactc tctgcagaga gagtcagagg ggacaacaag     1320
gagtatgagt actcagtgga gtgccaggag acagtgcct gcccagctgc tgaggagagt     1380
ctgcccattg aggtgatggt ggatgcagtt cacaagctca gtatgaaaa ctacaccagc     1440 agcttcttca tcagggacat catcaaacct gacccaccca gaacttgca gctgaagcca     1500 ttaaagaatt ctaggcaggt ggaggtcagc tgggagtacc ctgacacctg gagtactcca     1560
cattcctact tctccctgac attctgtgtt caagtccagg gcaagagcaa gagagaaaag     1620
aaagatagag tcttcactga caagacctca gccacagtca tctgcaggaa aaatgccagc     1680
atttcagtga gggcccagga cagatactat agctcatctt ggtcagaatg ggcatctgtg     1740
ccctgcagtt gacaattg                                                    1758

<210> SEQ ID NO 50
<211> LENGTH: 4017
<212> TYPE: DNA
<213> ORGANISM: Artificial Sequence
<220> FEATURE:
<223> OTHER INFORMATION: Human CAG - modified IL-12A/IL-12B - F2A (CpG
      modified) construct

<400> SEQUENCE: 50
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct tagtattaaa cgcgtgtcga cattgattat tgactagtta ttaatagtaa      180
tcaattacgg ggtcattagt tcatagccca tatatggagt tccgcgttac ataacttacg      240
gtaaatggcc cgcctggctg accgcccaac gacccccgcc cattgacgtc aataatgacg      300
tatgttccca tagtaacgcc aatagggact ttccattgac gtcaatgggt ggactattta      360
cggtaaactg cccacttggc agtacatcaa gtgtatcata tgccaagtac gccccctatt      420
gacgtcaatg acggtaaatg gcccgcctgg cattatgccc agtacatgac cttatgggac      480
tttcctactt ggcagtacat ctacgtatta gtcatcgcta ttaccatggg tcgaggtgag      540
ccccacgttc tgcttcactc tccccatctc ccccccctcc ccacccccaa ttttgtattt      600
atttattttt aattattttt gtgcagcgat gggggcgggg ggggggggg cgcgcgccag      660 gcggggcggg gcggggcgag gggcggggcg ggcgaggcg gagaggtgcg gcggcagcca      720
atcagagcgg cgcgctccga agtttccttt ttatggcgag gcggcggcgg cggcggccct      780
ataaaaagcg aagcgcgcgg cgggcgggag tcgctgcgcg ctgccttcgc ccgtgccccc      840
gctccgccgc cgcctcgcgc cgcccgcccc ggctctgact gaccgcgtta ctcccacagg      900
tgagcgggcg ggacggccct tctcctccgg gctgtaatta gcgcttggtt taatgacggc      960
```

-continued

```
tcgtttcttt tctgtggctg cgtgaaagcc ttgaggggct ccggaggggc cctttgtgcg   1020
gggggagcgg ctcggggggt gcgtgcgtgt gtgtgtgcgt gggagcgcc gcgtgcggct   1080 ccgcgctgcc cggcggctgt gagcgctgcg ggcgcggcgc ggggctttgt gcgctccgca   1140
gtgtgcgcga gaggagcgcg gccggggggcg gtgccacgcg gtgcgggggg ggctgcgagg   1200
ggaacaaagg ctgcgtgcgg ggtgtgtgcg tgggggggggt gagcagggg tgtgggcgcg   1260 gcggtcgggc tgtaaccccc ccctgcaccc ccctccccga gttgctgagc acggccggc   1320 ttcgggtgcg gggctccgtg cggggcgtgg cgcggggctc gccgtgccgg gcgggggggtg   1380 gcggcgggtg ggggtgccgg gcggggcggg gccgcctcgg gccggggagg gctcgggga   1440 ggggcgcggc ggccccccgga gcgccggcgg ctgtcgaggc gcggcgagcc gcagccattg   1500
ccttttatgg taatcgtgcg agagggcgca gggacttcct ttgtcccaaa tctgtgcgga   1560
gccgaaatct gggaggcgcc gccgcacccc ctctagcggg cgcggggcga agcggtgcgg   1620
cgccggcagg aaggaaatgg gcgggagggg ccttcgtgcg tcgccgcgcc gccgtcccct   1680
tctccctctc cagcctcggg gctgtccgcg ggggacggc tgccttcggg ggggacgggg   1740
cagggcgggg ttcggcttct ggcgtgtgac cggcggtcta gactctgcta accatgttca   1800
tgccttcttc tctttcctac agctcctggg caacgtgctg gttgttgtgc tgtctcatca   1860
ttttggcaaa gaattcaagc ttccagctag cgccaccatg tgtccagcgc gcagcctcct   1920
ccttgtggct accctggtcc tcctggacca cctcagtttg gccagaaacc tccctgtggc   1980
cactccagac ccaggaatgt tcccatgcct tcaccactcc caaaacctgc tgagggctgt   2040
cagcaacatg ctccagaagg ccagacaaac tctagaattt tacccttgca cttctgaaga   2100
gattgatcat gaagatatca caaaagataa aaccagcaca gtggaggcct gtttaccatt   2160
ggaattaacc aagaatgaga gttgcctaaa ttccagagag acctctttca taactaatgg   2220
gagttgcctg gcctccagaa agacctcttt tatgatggcc ctgtgcctta gtagtattta   2280
tgaagacttg aagatgtacc aggtggagtt caagaccatg aatgcaaagc ttctgatgga   2340
tcctaagagg cagatctttc tagatcaaaa catgctggca gttattgatg agctgatgca   2400
ggccctgaat ttcaacagtg agactgtgcc acaaaaatcc tcccttgaag aacctgattt   2460
ttataaaact aaaatcaagc tctgcatact tcttcatgct ttccggattc gcgcagtgac   2520
tattgataga gtgatgagct atctgaatgc ttccagaaag agaaggagtg gctcaggagc   2580
ccctgtgaaa cagaccctga actttgacct cttgaagctt gctggggatg tggagtctaa   2640
tcctggtcca atgtgtcacc agcagttggt catctcttgg tttttccctgg tttttctggc   2700 atctcccctt gtggccatat gggaactgaa gaaagatgtt tatgtggtag aattggattg   2760
gtatcctgat gcccctggag aaatggtggt cctcacctgt gacaccctg aagaagatgg   2820 tatcacctgg accttggacc agagcagtga ggtcttaggc tctggcaaaa ccctgaccat   2880
ccaagtcaaa gagtttggag atgctggcca gtacacctgt cacaaaggag ggaggttct   2940 aagccattcc ctcctgctgc ttcacaaaaa ggaagatgga atttggtcca ctgatatttt   3000
aaaggaccag aaagaaccca aaataagac cttttctaaga tgtgaggcca agaattattc   3060
tggaaggttc acctgctggt ggctgactac aatcagtact gatttgacat tcagtgtcaa   3120
aagcagcaga ggctcttctg accccaagg ggtgacatgc ggagctgcta cactctctgc   3180
agagagagtc agaggggaca acaaggagta tgagtactca gtggagtgcc aggaggacag   3240
tgcctgccca gctgctgagg agagtctgcc cattgaggtg atggtggatg cggttcacaa   3300
```

| | |
|---|---|
| gctcaagtat gaaaactaca ccagcagctt cttcatcagg gacatcatca aacctgaccc | 3360 |
| acccaagaac ttgcagctga agccattaaa gaattctagg caggtggagg tcagctggga | 3420 |
| gtaccctgac acctggagta ctccacattc ctacttctcc ctgacattct gtgttcaagt | 3480 |
| ccagggcaag agcaagagag aaaagaaaga tagagtcttc actgacaaga cctcagccac | 3540 |
| agtcatctgc cgcaaaaatg ccagcatttc agtgcgggcc caggaccgct actatagctc | 3600 |
| atcttggtca gaatgggcat ctgtgccctg cagttgacaa ttgctgtgcc ttctagttgc | 3660 |
| cagccatctg ttgtttgccc ctcccccgtg ccttccttga ccctggaagg tgccactccc | 3720 |
| actgtccttt cctaataaaa tgaggaaatt gcatcgcatt gtctgagtag gtgtcattct | 3780 |
| attctgggggg gtggggtggg gcaggacagc aaggggagg attgggaaga caatagcagg | 3840 |
| catgctgggg atgcgtggg ctctatggag ctcgagagga acccctagtg atggagttgg | 3900 |
| ccactccctc tctgcgcgct cgctcgctca ctgaggccgg gcgaccaaag gtcgcccgac | 3960 |
| gcccgggctt tgcccgggcg gcctcagtga gcgagcgagc gcgcagctgc agatctg | 4017 |

<210> SEQ ID NO 51
<211> LENGTH: 1758
<212> TYPE: DNA
<213> ORGANISM: Artificial Sequence
<220> FEATURE:
<223> OTHER INFORMATION: Human CAG - modified IL-12A/IL-12B - F2A (CpG modified) expression sequence

<400> SEQUENCE: 51

| | |
|---|---|
| gctagcgcca ccatgtgtcc agcgcgcagc ctcctccttg tggctaccct ggtcctcctg | 60 |
| gaccacctca gtttggccag aaacctccct gtggccactc cagacccagg aatgttccca | 120 |
| tgccttcacc actcccaaaa cctgctgagg gctgtcagca acatgctcca gaaggccaga | 180 |
| caaactctag aattttaccc ttgcacttct gaagagattg atcatgaaga tatcacaaaa | 240 |
| gataaaacca gcacagtgga ggcctgttta ccattggaat taaccaagaa tgagagttgc | 300 |
| ctaaattcca gagagacctc tttcataact aatgggagtt gcctggcctc agaaagacc | 360 |
| tcttttatga tggcccctgtg ccttagtagt atttatgaag acttgaagat gtaccaggtg | 420 |
| gagttcaaga ccatgaatgc aaagcttctg atggatccta agaggcagat ctttctagat | 480 |
| caaaacatgc tggcagttat tgatgagctg atgcaggccc tgaatttcaa cagtgagact | 540 |
| gtgccacaaa aatcctccct tgaagaacct gatttttata aaactaaaat caagctctgc | 600 |
| atacttcttc atgctttccg gattcgcgca gtgactattg atagagtgat gagctatctg | 660 |
| aatgcttcca aaagagaag gagtggctca ggagcccctg tgaaacagac cctgaacttt | 720 |
| gacctcttga agcttgctgg ggatgtggag tctaatcctg gtccaatgtg tcaccagcag | 780 |
| ttggtcatct cttggttttc cctggttttt ctggcatctc cccttgtggc catatgggaa | 840 |
| ctgaagaaag atgtttatgt ggtagaattg gattggtatc ctgatgcccc tggagaaatg | 900 |
| gtggtcctca cctgtgacac ccctgaagaa gatggtatca cctggacctt ggaccagagc | 960 |
| agtgaggtct taggctctgg caaaaccctg accatccaag tcaaagagtt ggagatgct | 1020 |
| ggccagtaca cctgtcacaa ggagggggag ttctaagcc attccctcct gctgcttcac | 1080 |
| aaaaaggaag atggaatttg gtccactgat attttaaagg accagaaaga acccaaaaat | 1140 |
| aagacctttc taagatgtga ggccaagaat tattctggaa ggttcacctg ctggtggctg | 1200 |
| actacaatca gtactgattt gacattcagt gtcaaaagca gcagaggctc ttctgacccc | 1260 |
| caaggggtga catgcggagc tgctacactc tctgcagaga gagtcagagg ggacaacaag | 1320 |

```
gagtatgagt actcagtgga gtgccaggag acagtgcct  gcccagctgc tgaggagagt      1380
ctgcccattg aggtgatggt ggatgcggtt cacaagctca agtatgaaaa ctacaccagc      1440
agcttcttca tcagggacat catcaaacct gacccaccca agaacttgca gctgaagcca      1500
ttaaagaatt ctaggcaggt ggaggtcagc tgggagtacc ctgacacctg gagtactcca      1560
cattcctact tctccctgac attctgtgtt caagtccagg gcaagagcaa gagagaaaag      1620
aaagatagag tcttcactga caagacctca gccacagtca tctgccgcaa aaatgccagc      1680
atttcagtgc gggcccagga ccgctactat agctcatctt ggtcagaatg ggcatctgtg      1740
ccctgcagtt gacaattg                                                   1758

<210> SEQ ID NO 52
<211> LENGTH: 4509
<212> TYPE: DNA
<213> ORGANISM: Artificial Sequence
<220> FEATURE:
<223> OTHER INFORMATION: Human CAG - modified IL-12A/IL-12B - IRES (CpG
      modified) construct

<400> SEQUENCE: 52
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact      120
aggggttcct tagtattaaa cgcgtgtcga cattgattat tgactagtta ttaatagtaa      180
tcaattacgg ggtcattagt tcatagccca tatatggagt tccgcgttac ataacttacg      240
gtaaatggcc cgcctggctg accgcccaac gacccccgcc cattgacgtc aataatgacg      300
tatgttccca tagtaacgcc aatagggact ttccattgac gtcaatgggt ggactattta      360
cggtaaactg cccacttggc agtacatcaa gtgtatcata tgccaagtac gccccctatt      420
gacgtcaatg acggtaaatg gcccgcctgg cattatgccc agtacatgac cttatgggac      480
tttcctactt ggcagtacat ctacgtatta gtcatcgcta ttaccatggg tcgaggtgag      540
ccccacgttc tgcttcactc tccccatctc ccccccctcc ccacccccaa ttttgtattt      600
atttattttt taattatttt gtgcagcgat gggggcgggg ggggggggg  cgcgcgccag      660 gcggggcggg gcggggcgag gggcggggcg ggcgaggcg  gagaggtgcg gcggcagcca      720
atcagagcgg cgcgctccga aagtttcctt ttatggcgag gcggcggcgg cggcggccct      780
ataaaaagcg aagcgcgcgg cgggcgggag tcgctgcgcg ctgccttcgc cccgtgcccc      840
gctccgccgc cgcctcgcgc cgcccgcccc ggctctgact gaccgcgtta ctcccacagg      900
tgagcgggcg ggacgccct  tctcctccgg gctgtaatta gcgcttggtt taatgacggc      960
tcgtttcttt tctgtggctg cgtgaaagcc ttgagggggct  ccgggagggc cctttgtgcg     1020
gggggagcgc tcgggggggt gcgtgcgtgt gtgtgtgcgt gggagcgcc gcgtgcggct      1080 ccgcgctgcc cggcggctgt gagcgctgcg ggcgcggcgc ggggctttgt gcgctccgca      1140
gtgtgcgcga ggagcgcg   gccggggggcg gtgccacgcg gtgcgggggg gctgcgagg       1200 ggaacaaagg ctgcgtgcgg ggtgtgtgcg tgggggggt  gagcagggggg tgtgggcgcg      1260 gcggtcgggc tgtaaccccc ccctgcaccc ccctccccga gttgctgagc acggcccggc      1320
ttcgggtgcg gggctccgtg cggggcgtgg cgcggggctc gccgtgccgg gcgggggtg      1380 gcggcgggtg ggggtgccgg gcggggcggg ccgcctcgg  gccggggagg gctcggggga     1440
ggggcgcggc ggccccccgga gcgccggcgg ctgtcgaggc gcggcgagcc gcagccattg      1500
ccttttatgg taatcgtgcg agagggcgca gggacttcct ttgtcccaaa tctgtgcgga      1560
```

```
gccgaaatct gggaggcgcc gccgcacccc ctctagcggg cgcggggcga agcggtgcgg   1620
cgccggcagg aaggaaatgg gcggggaggg ccttcgtgcg tcgccgcgcc gccgtcccct   1680
tctccctctc cagcctcggg gctgtccgcg gggggacggc tgccttcggg ggggacgggg   1740
cagggcgggg ttcggcttct ggcgtgtgac cggcggtcta gactctgcta accatgttca   1800
tgccttcttc tctttcctac agctcctggg caacgtgctg gttgttgtgc tgtctcatca   1860
ttttggcaaa gaattcaagc ttccagctag cgccaccatg tgtccagcta ggagcctcct   1920
ccttgtggct accctggtcc tcctggacca cctcagtttg gccagaaacc tccctgtggc   1980
cactccagac ccaggaatgt tcccatgcct tcaccactcc aaaacctgc tgagggcagt    2040 cagcaacatg ctccagaagg ccagacaaac tctagaattt tacccttgca cttctgaaga   2100
gattgatcat gaagatatca caaaagataa aaccagcaca gtggaggcct gtttaccatt   2160
ggaattaacc aagaatgaga gttgcctaaa ttccagagag acctctttca taactaatgg   2220
gagttgcctg gcctccagaa agacctcttt tatgatggcc ctgtgcctta gtagtattta   2280
tgaagacttg aagatgtacc aggtggagtt caagaccatg aatgcaaagc ttctgatgga   2340
tcctaagagg cagatctttc tagatcaaaa catgctggca gttattgatg agctgatgca   2400
ggccctgaat ttcaacagtg agactgtgcc acaaaaatcc tcccttgaag aacctgattt   2460
ttataaaact aaaatcaagc tctgcatact tcttcatgct ttccggatta gggcagtgac   2520
tattgataga gtgatgagct atctgaatgc ttcctgagcc cctctccctc cccccccct    2580 aacgttactg gccgaagccg cttggaataa ggccggtgtg cgtttgtcta tatgttattt   2640
tccaccatat tgccgtcttt tggcaatgtg agggcccgga aacctggccc tgtcttcttg   2700
acgagcattc ctaggggtct ttcccctctc gccaaaggaa tgcaaggtct gttgaatgtc   2760
gtgaaggaag cagttcctct ggaagcttct tgaagacaaa caacgtctgt agcgaccctt   2820
tgcaggcagc ggaacccccc acctggcgac aggtgcctct gcggccaaaa gccacgtgta   2880
taagatacac ctgcaaaggc ggcacaaccc cagtgccacg ttgtgagttg atagttgtg    2940 gaaagagtca aatggctctc ctcaagcgta ttcaacaagg ggctgaagga tgcccagaag   3000 gtacccatt gtatgggatc tgatctgggg cctcggtaca catgctttac atgtgtttag    3060
tcgaggttaa aaaaacgtct aggcccccccg aaccacgggg acgtggtttt cctttgaaaa   3120
acacgatgat aatatggcca caatgtgtca ccagcagttg gtcatctctt ggttttccct   3180 ggttttttctg gcatctcccc ttgtggccat atgggaactg aagaaagatg tttatgtggt   3240
agaattggat tggtatcctg atgcccctgg agaaatggtg gtcctcacct gtgacacccc   3300
tgaagaagat ggtatcacct ggaccttgga ccagagcagt gaggtcttag gctctggcaa   3360
aaccctgacc atccaagtca agagtttgg agatgctggc cagtacacct gtcacaaagg    3420 agggaggtt ctaagccatt ccctcctgct gcttcacaaa aaggaagatg gaatttggtc    3480
cactgatatt ttaaaggacc agaaagaacc caaaataag accttctaa gatgtgaggc    3540 caagaattat tctggaaggt tcacctgctg gtggctgact acaatcagta ctgatttgac    3600
attcagtgtc aaaagcagca gaggctcttc tgaccccccaa gggtgacat gtggagctgc    3660 tacactctct gcagagagag tcagagggga caacaaggag tatgagtact cagtggagtg    3720
ccaggaggac agtgcctgcc cagctgctga ggagagtctg cccattgagg tgatggtgga    3780
tgcagttcac aagctcaagt atgaaaacta caccagcagc ttcttcatca gggacatcat    3840
caaacctgac ccacccaaga acttgcagct gaagccatta aagaattcta ggcaggtgga    3900
ggtcagctgg gagtacccctg acacctggag tactccacat tcctacttct ccctgacatt    3960
```

```
ctgtgttcaa gtccagggca agagcaagag agaaaagaaa gatagagtct tcactgacaa    4020
gacctcagcc acagtcatct gcaggaaaaa tgccagcatt tcagtgaggg cccaggacag    4080
atactatagc tcatcttggt cagaatgggc atctgtgccc tgcagttgac aattgctgtg    4140
ccttctagtt gccagccatc tgttgtttgc ccctccccg tgccttcctt gaccctggaa    4200
ggtgccactc ccactgtcct ttcctaataa aatgaggaaa ttgcatcgca ttgtctgagt    4260
aggtgtcatt ctattctggg gggtggggtg gggcaggaca gcaaggggga ggattgggaa    4320
gacaatagca ggcatgctgg ggatgcggtg ggctctatgg agctcgagag gaacccctag    4380
tgatggagtt ggccactccc tctctgcgcg ctcgctcgct cactgaggcc gggcgaccaa    4440
aggtcgcccg acgcccgggc tttgcccggg cggcctcagt gagcgagcga gcgcgcagct    4500
gcagatctg                                                            4509
```

<210> SEQ ID NO 53
<211> LENGTH: 2250
<212> TYPE: DNA
<213> ORGANISM: Artificial Sequence
<220> FEATURE:
<223> OTHER INFORMATION: Human CAG - modified IL-12A/IL-12B - IRES (CpG modified) expression sequence

<400> SEQUENCE: 53

```
gctagcgcca ccatgtgtcc agctaggagc ctcctccttg tggctaccct ggtcctcctg      60
gaccacctca gtttggccag aaacctccct gtggccactc cagacccagg aatgttccca     120
tgccttcacc actcccaaaa cctgctgagg gcagtcagca acatgctcca gaaggccaga     180
caaactctag aatttttaccc ttgcacttct gaagagattg atcatgaaga tatcacaaaa     240
gataaaacca gcacagtgga ggcctgttta ccattggaat taaccaagaa tgagagttgc     300
ctaaattcca gagagaccctc tttcataact aatgggagtt gcctggcctc cagaaagacc     360
tcttttatga tggccctgtg ccttagtagt atttatgaag acttgaagat gtaccaggtg     420
gagttcaaga ccatgaatgc aaagcttctg atggatccta agaggcagat cttttctagat     480 caaaacatgc tggcagttat tgatgagctg atgcaggccc tgaatttcaa cagtgagact     540
gtgccacaaa atcctccct tgaagaacct gattttttata aaactaaaat caagctctgc     600
atacttcttc atgcttttccg gattagggca gtgactattg atagagtgat gagctatctg     660
aatgcttcct gagcccctct ccctcccccc cccctaacgt tactggccga agccgcttgg     720
aataaggccg gtgtgcgttt gtctatatgt tatttccac catattgccg tcttttggca     780
atgtgagggc ccggaaacct ggccctgtct tcttgacgag cattcctagg ggtctttccc     840
ctctcgccaa aggaatgcaa ggtctgttga atgtcgtgaa ggaagcagtt cctctggaag     900
cttcttgaag acaaacaacg tctgtagcga ccctttgcag cagcggaac cccccacctg     960 gcgacaggtg cctctgcggc caaaagccac gtgtataaga tacacctgca aaggcggcac    1020
aaccccagtg ccacgttgtg agttggatag ttgtggaaag agtcaaatgg ctctcctcaa    1080
gcgtattcaa caaggggctg aaggatgccc agaaggtacc ccattgtatg ggatctgatc    1140
tggggcctcg gtacacatgc tttacatgtg tttagtcgag gttaaaaaaa cgtctaggcc    1200
ccccgaacca cggggacgtg gttttccttt gaaaaacacg atgataatat ggccacaatg    1260
tgtcaccagc agttggtcat ctcttggttt tccctggttt ttctggcatc tcccccttgtg    1320 gccatatggg aactgaagaa agatgtttat gtggtagaat tggattggta tcctgatgcc    1380
cctggagaaa tggtggtcct cacctgtgac accccctgaag aagatggtat cacctggacc    1440
```

```
ttggaccaga gcagtgaggt cttaggctct ggcaaaaccc tgaccatcca agtcaaagag      1500
tttggagatg ctggccagta cacctgtcac aaaggagggg aggttctaag ccattccctc      1560
ctgctgcttc acaaaaagga agatggaatt tggtccactg atattttaaa ggaccagaaa      1620
gaacccaaaa ataagacctt tctaagatgt gaggccaaga attattctgg aaggttcacc      1680
tgctggtggc tgactacaat cagtactgat ttgacattca gtgtcaaaag cagcagaggc      1740
tcttctgacc cccaagggt gacatgtgga gctgctacac tctctgcaga gagagtcaga      1800
ggggacaaca aggagtatga gtactcagtg gagtgccagg aggacagtgc ctgcccagct      1860
gctgaggaga gtctgcccat tgaggtgatg gtggatgcag ttcacaagct caagtatgaa      1920
aactacacca gcagcttctt catcagggac atcatcaaac ctgacccacc caagaacttg      1980
cagctgaagc cattaaagaa ttctaggcag gtggaggtca gctgggagta ccctgacacc      2040
tggagtactc cacattccta cttctccctg acattctgtg ttcaagtcca gggcaagagc      2100
aagagagaaa agaaagatag agtcttcact gacaagacct cagccacagt catctgcagg      2160
aaaaatgcca gcatttcagt gagggcccag gacagatact atagctcatc ttggtcagaa      2220
tgggcatctg tgccctgcag ttgacaattg                                       2250
```

<210> SEQ ID NO 54
<211> LENGTH: 4509
<212> TYPE: DNA
<213> ORGANISM: Artificial Sequence
<220> FEATURE:
<223> OTHER INFORMATION: Human CAG - modified IL-12A/IL-12B - IRES (CpG
      modified) construct

<400> SEQUENCE: 54

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact      120
aggggttcct tagtattaaa gcgtgtcga cattgattat tgactagtta ttaatagtaa      180
tcaattacgg ggtcattagt tcatagccca tatatggagt tccgcgttac ataacttacg      240
gtaaatggcc cgcctggctg accgcccaac gacccccgcc cattgacgtc aataatgacg      300
tatgttccca tagtaacgcc aatagggact ttccattgac gtcaatgggt ggactattta      360
cggtaaactg cccacttggc agtacatcaa gtgtatcata tgccaagtac gccccctatt      420
gacgtcaatg acggtaaatg gcccgcctgg cattatgccc agtacatgac cttatgggac      480
tttcctactt ggcagtacat ctacgtatta gtcatcgcta ttaccatggg tcgaggtgag      540
ccccacgttc tgcttcactc tccccatctc cccccctcc ccaccccaa ttttgtattt      600 atttattttt taattatttt gtgcagcgat ggggggcgggg ggggggggg cgcgcgccag     660 gcggggcggg gcggggcgag gggcggggcg gggcgaggcg gagaggtgcg gcggcagcca      720
atcagagcgg cgcgctccga aagtttcctt ttatggcgag gcggcggcgg cggcggccct      780
ataaaaagcg aagcgcgcgg cgggcgggag tcgctgcgcg ctgccttcgc ccgtgcccc      840 gctccgccgc cgcctcgcgc cgcccgcccc ggctctgact gaccgcgtta ctcccacagg      900
tgagcgggcg ggacgccct tctcctccgg gctgtaatta gcgcttggtt taatgacggc      960
tcgtttcttt tctgtggctg cgtgaaagcc ttgagggct ccgggagggc cctttgtgcg     1020 ggggagcgc tcgggggt gcgtgcgtgt gtgtgtgcgt gggagcgcc gcgtgcggct      1080 ccgcgctgcc cggcggctgt gagcgctgcg ggcgcggcgc ggggctttgt gcgctccgca      1140
gtgtgcgcga ggagagcgcg gccggggcg gtgccacgcg gtgcggggg ggctgcgagg      1200
```

```
ggaacaaagg ctgcgtgcgg ggtgtgtgcg tggggggggt gagcagggggg tgtgggcgcg    1260 gcggtcgggc tgtaaccccc ccctgcaccc ccctccccga gttgctgagc acggcccggc    1320
ttcgggtgcg gggctccgtg cggggcgtgg cgcggggctc gccgtgccgg gcgggggggtg   1380 gcggcgggtg ggggtgccgg gcggggcggg gccgcctcgg gccggggagg gctcggggga    1440
ggggcgcggc ggcccccgga gcgccggcgg ctgtcgaggc gcggcgagcc gcagccattg    1500 cctttttatgg taatcgtgcg agagggcgca gggacttcct ttgtcccaaa tctgtgcgga   1560
gccgaaatct gggaggcgcc gccgcacccc ctctagcggg cgcggggcga agcggtgcgg    1620
cgccggcagg aaggaaatgg gcggggaggg ccttcgtgcg tcgccgcgcc gccgtcccct    1680
tctccctctc cagcctcggg gctgtccgcg gggggacggc tgccttcggg ggggacgggg    1740
cagggcgggg ttcggcttct ggcgtgtgac cggcggtcta gactctgcta accatgttca    1800
tgccttcttc tctttcctac agctcctggg caacgtgctg gttgttgtgc tgtctcatca    1860
ttttggcaaa gaattcaagc ttccagctag cgccaccatg tgtccagcgc gcagcctcct    1920
ccttgtggct accctggtcc tcctggacca cctcagtttg ccagaaaacc tccctgtggc    1980
cactccagac ccaggaatgt tcccatgcct tcaccactcc caaaacctgc tgagggctgt    2040
cagcaacatg ctccagaagg ccagacaaac tctagaattt tacccttgca cttctgaaga    2100
gattgatcat gaagatatca caaaagataa aaccagcaca gtggaggcct gtttaccatt    2160
ggaattaacc aagaatgaga gttgcctaaa ttccagagag acctctttca taactaatgg    2220
gagttgcctg gcctccagaa agacctcttt tatgatggcc ctgtgcctta gtagtattta    2280
tgaagacttg aagatgtacc aggtggagtt caagaccatg aatgcaaagc ttctgatgga    2340
tcctaagagg cagatctttc tagatcaaaa catgctggca gttattgatg agctgatgca    2400
ggccctgaat ttcaacagtg agactgtgcc acaaaaatcc tcccttgaag aacctgattt    2460
ttataaaact aaaatcaagc tctgcatact tcttcatgct ttccggattc gcgcagtgac    2520
tattgataga gtgatgagct atctgaatgc ttcctgagcc cctctccctc cccccccct    2580 aacgttactg gccgaagccg cttggaataa ggccggtgtg cgtttgtcta tatgttattt    2640
tccaccatat tgccgtcttt tggcaatgtg agggcccgga aacctggccc tgtcttcttg    2700
acgagcattc ctaggggtct ttcccctctc gccaaaggaa tgcaaggtct gttgaatgtc    2760
gtgaaggaag cagttcctct ggaagcttct tgaagacaaa caacgtctgt agcgaccctt    2820
tgcaggcagc ggaaccccccc acctggcgac aggtgcctct gcggccaaaa gccacgtgta    2880
taagatacac ctgcaaaggc ggcacaaccc cagtgccacg ttgtgagttg atagttgtg    2940 gaaagagtca aatggctctc ctcaagcgta ttcaacaagg ggctgaagga tgcccagaag    3000 gtacccatt gtatgggatc tgatctgggg cctcggtaca catgctttac atgtgtttag    3060
tcgaggttaa aaaaacgtct aggccccccg aaccacgggg acgtggtttt cctttgaaaa    3120
acacgatgat aatatggcca caatgtgtca ccagcagttg gtcatctctt ggttttccct    3180 ggttttctg gcatctcccc ttgtggccat atgggaactg aagaaagatg tttatgtggt    3240
agaattggat tggtatcctg atgccctgg agaaatggtg gtcctcacct gtgacacccc    3300
tgaagaagat ggtatcacct ggaccttgga ccagagcagt gaggtcttag gctctggcaa    3360
aaccctgacc atccaagtca aagagtttgg agatgctggc cagtacacct gtcacaaagg    3420 agggggaggtt ctaagccatt ccctcctgct gcttcacaaa aaggaagatg gaatttggtc    3480
cactgatatt ttaaaggacc agaaagaacc caaaaataag acctttctaa gatgtgaggc    3540
```

```
caagaattat tctggaaggt tcacctgctg gtggctgact acaatcagta ctgatttgac      3600
attcagtgtc aaaagcagca gaggctcttc tgacccccaa ggggtgacat gcggagctgc      3660
tacactctct gcagagagag tcagagggga caacaaggag tatgagtact cagtggagtg      3720
ccaggaggac agtgcctgcc cagctgctga ggagagtctg cccattgagg tgatggtgga      3780
tgcggttcac aagctcaagt atgaaaacta caccagcagc ttcttcatca gggacatcat      3840
caaacctgac ccacccaaga acttgcagct gaagccatta aagaattcta ggcaggtgga      3900
ggtcagctgg gagtaccctg acacctggag tactccacat tcctacttct ccctgacatt      3960
ctgtgttcaa gtccagggca agagcaagag agaaaagaaa gatagagtct tcactgacaa      4020
gacctcagcc acagtcatct gccgcaaaaa tgccagcatt tcagtgcggg cccaggaccg      4080
ctactatagc tcatcttggt cagaatgggc atctgtgccc tgcagttgac aattgctgtg      4140
ccttctagtt gccagccatc tgttgtttgc ccctcccccg tgccttcctt gaccctggaa      4200
ggtgccactc ccactgtcct ttcctaataa aatgaggaaa ttgcatcgca ttgtctgagt      4260
aggtgtcatt ctattctggg gggtggggtg gggcaggaca gcaaggggga ggattgggaa      4320
gacaatagca ggcatgctgg ggatgcggtg ggctctatgg agctcgagag gaaccccctag    4380 tgatggagtt ggccactccc tctctgcgcg ctcgctcgct cactgaggcc gggcgaccaa      4440
aggtcgcccg acgcccgggc tttgcccggg cggcctcagt gagcgagcga gcgcgcagct      4500
gcagatctg                                                             4509
```

<210> SEQ ID NO 55
<211> LENGTH: 2250
<212> TYPE: DNA
<213> ORGANISM: Artificial Sequence
<220> FEATURE:
<223> OTHER INFORMATION: Human CAG - modified IL-12A/IL-12B - IRES (CpG modified) expression sequence

<400> SEQUENCE: 55

```
gctagcgcca ccatgtgtcc agcgcgcagc ctcctccttg tggctaccct ggtcctcctg        60
gaccacctca gtttggccag aaacctccct gtggccactc cagacccagg aatgttccca       120
tgccttcacc actcccaaaa cctgctgagg ctgtcagca acatgctcca gaaggccaga       180
caaactctag aattttaccc ttgcacttct gaagagattg atcatgaaga tatcacaaaa       240
gataaaacca gcacagtgga ggcctgttta ccattggaat taaccaagaa tgagagttgc       300
ctaaattcca gagagacctc tttcataact aatgggagtt gcctggcctc cagaaagacc       360
tcttttatga tggcccctgtg ccttagtagt atttatgaag acttgaagat gtaccaggtg       420
gagttcaaga ccatgaatgc aaagcttctg atggatccta agaggcagat cttcctagat       480
caaaacatgc tggcagttat tgatgagctg atgcaggccc tgaatttcaa cagtgagact       540
gtgccacaaa atcctccct tgaagaacct gatttttata aaactaaaat caagctctgc       600
atacttcttc atgcttttccg gattcgcgca gtgactattg atagagtgat gagctatctg       660
aatgcttcct gagcccctct ccctccccccc ccctaacgt tactggccga agccgcttgg       720
aataaggccg gtgtgcgttt gtctatatgt tattttccac catattgccg tcttttggca       780
atgtgagggc ccggaaacct ggccctgtct tcttgacgag cattcctagg gtctttccc        840 ctctcgccaa aggaatgcaa ggtctgttga atgtcgtgaa ggaagcagtt cctctggaag       900
cttcttgaag acaacaacg tctgtagcga ccctttgcag gcagcggaac cccccacctg       960
gcgacaggtg cctctgcggc caaaagccac gtgtataaga tacacctgca aaggcggcac      1020
```

```
aaccccagtg ccacgttgtg agttggatag ttgtggaaag agtcaaatgg ctctcctcaa    1080
gcgtattcaa caaggggctg aaggatgccc agaaggtacc ccattgtatg ggatctgatc    1140
tggggcctcg gtacacatgc tttacatgtg tttagtcgag gttaaaaaaa cgtctaggcc    1200
ccccgaacca cggggacgtg gttttccttt gaaaaacacg atgataatat ggccacaatg    1260
tgtcaccagc agttggtcat ctcttggttt tccctggttt ttctggcatc tccccttgtg    1320
gccatatggg aactgaagaa agatgtttat gtggtagaat tggattggta tcctgatgcc    1380
cctggagaaa tggtggtcct cacctgtgac accccctgaag aagatggtat cacctggacc    1440
ttggaccaga gcagtgaggt cttaggctct ggcaaaaccc tgaccatcca agtcaaagag    1500
tttggagatg ctggccagta cacctgtcac aaaggagggg aggttctaag ccattccctc    1560
ctgctgcttc acaaaaagga agatggaatt tggtccactg atattttaaa ggaccagaaa    1620
gaacccaaaa ataagacctt tctaagatgt gaggccaaga attattctgg aaggttcacc    1680
tgctggtggc tgactacaat cagtactgat ttgacattca gtgtcaaaag cagcagaggc    1740
tcttctgacc cccaaggggt gacatgcgga gctgctacac tctctgcaga gagagtcaga    1800
ggggacaaca aggagtatga gtactcagtg gagtgccagg aggacagtgc ctgcccagct    1860
gctgaggaga gtctgcccat tgaggtgatg gtggatgcgg ttcacaagct caagtatgaa    1920
aactacacca gcagcttctt catcagggac atcatcaaac ctgacccacc caagaacttg    1980
cagctgaagc cattaaagaa ttctaggcag gtggaggtca gctgggagta ccctgacacc    2040
tggagtactc cacattccta cttctccctg acattctgtg ttcaagtcca gggcaagagc    2100
aagagagaaa agaaagatag agtcttcact gacaagacct cagccacagt catctgccgc    2160
aaaaatgcca gcatttcagt gcgggcccag gaccgctact atagctcatc ttggtcagaa    2220
tgggcatctg tgccctgcag ttgacaattg                                     2250
```

<210> SEQ ID NO 56
<211> LENGTH: 4017
<212> TYPE: DNA
<213> ORGANISM: Artificial Sequence
<220> FEATURE:
<223> OTHER INFORMATION: Human CAG - wild-type IL-12A/IL-12B - F2A (CpG
      modified) construct

<400> SEQUENCE: 56

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tagtattaaa cgcgtgtcga cattgattat tgactagtta ttaatagtaa    180
tcaattacgg ggtcattagt tcatagccca tatatggagt tccgcgttac ataacttacg    240
gtaaatggcc cgcctggctg accgcccaac gacccccgcc cattgacgtc aataatgacg    300
tatgttccca tagtaacgcc aatagggact ttccattgac gtcaatgggt ggactattta    360
cggtaaactg cccacttggc agtacatcaa gtgtatcata tgccaagtac gccccctatt    420
gacgtcaatg acggtaaatg gcccgcctgg cattatgccc agtacatgac cttatgggac    480
tttcctactt ggcagtacat ctacgtatta gtcatcgcta ttaccatggg tcgaggtgag    540
ccccacgttc tgcttcactc tccccatctc ccccccctcc ccaccccaa ttttgtattt    600 atttattttt taattatttt gtgcagcgat gggggcgggg ggggggggg cgcgcgccag    660 gcggggcggg gcggggcgag gggcggggcg ggcgaggcg gagaggtgcg gcggcagcca    720
atcagagcgg cgcgctccga aagtttcctt ttatggcgag gcggcggcgg cggcggccct    780
```

```
ataaaaagcg aagcgcgcgg cgggcgggag tcgctgcgcg ctgccttcgc cccgtgcccc    840
gctccgccgc cgcctcgcgc cgcccgcccc ggctctgact gaccgcgtta ctcccacagg    900
tgagcgggcg ggacggccct tctcctccgg gctgtaatta gcgcttggtt taatgacggc    960
tcgtttcttt tctgtggctg cgtgaaagcc ttgaggggct ccgggagggc cctttgtgcg   1020
gggggagcgg ctcggggggt gcgtgcgtgt gtgtgtgcgt ggggagcgcc gcgtgcggct   1080
ccgcgctgcc cggcggctgt gagcgctgcg ggcgcgcgc  ggggctttgt gcgctccgca   1140
gtgtgcgcga gaggagcgcg gccggggggcg gtgccacgcg gtgcgggggg ggctgcgagg  1200
ggaacaaagg ctgcgtgcgg ggtgtgtgcg tggggggggt gagcagggggg tgtgggcgcg  1260
gcggtcgggc tgtaaccccc ccctgcaccc ccctccccga gttgctgagc acggcccggc   1320
ttcgggtgcg gggctccgtg cggggcgtgg cgcggggctc gccgtgccgg gcggggggtg   1380
gcggcgggtg ggggtgccgg gcggggcggg gccgcctcgg gccggggagg gctcggggga   1440
ggggcgcggc ggcccccgga gcgccggcgg ctgtcgaggc gcggcgagcc gcagccattg   1500
cctttttatgg taatcgtgcg agagggcgca gggacttcct ttgtcccaaa tctgtgcgga   1560
gccgaaatct gggaggcgcc ccgcaccccc tctagcggg  cgcggggcga agcggtgcgg   1620
cgccggcagg aaggaaatgg gcggggaggg ccttcgtgcg tcgccgcgcc gccgtcccct   1680
tctccctctc cagcctcggg gctgtccgcg gggggacggc tgccttcggg ggggacgggg   1740
cagggcgggg ttcggcttct ggcgtgtgac cggcggtcta gactctgcta accatgttca   1800
tgccttcttc tctttcctac agctcctggg caacgtgctg gttgttgtgc tgtctcatca   1860
ttttggcaaa gaattcaagc ttccagctag cgccaccatg tgtccagcgc gcagcctcct   1920
ccttgtggct accctggtcc tcctggacca cctcagtttg ccagaaaacc tccccgtggc   1980
cactccagac ccaggaatgt tcccatgcct tcaccactcc caaaacctgc tgagggccgt   2040
cagcaacatg ctccagaagg ccagacaaac tctagaattt tacccttgca cttctgaaga   2100
gattgatcat gaagatatca caaaagataa aaccagcaca gtggaggcct gtttaccatt   2160
ggaattaacc aagaatgaga gttgcctaaa ttccagagag acctctttca taactaatgg   2220
gagttgcctg gcctccagaa agacctcttt tatgatggcc ctgtgcctta gtagtattta   2280
tgaagacttg aagatgtacc aggtggagtt caagaccatg aatgcaaagc ttctgatgga   2340
tcctaagagg cagatctttc tagatcaaaa catgctggca gttattgatg agctgatgca   2400
ggccctgaat ttcaacagtg agactgtgcc acaaaaatcc tcccttgaag aaccggattt   2460
ttataaaact aaaatcaagc tctgcatact tcttcatgct ttccggattc gggcagtgac   2520
tattgataga gtgatgagct atctgaatgc ttccagaaag agaaggagtg gctcaggagc   2580
ccctgtgaaa cagaccctga ctttgacctt cttgaagctt gctggggatg tggagtctaa   2640
tcctggtcca atgtgtcacc agcagttggt catctcttgg ttttccctgg tttttctggc   2700
atctcccctc gtggccatat gggaactgaa gaaagatgtt tatgtcgtag aattggattg   2760
gtatccggat gcccctggag aaatggtggt cctcacctgt gacaccctg  aagaagatgg  2820
tatcacctgg accttggacc agagcagtga ggtcttaggc tctggcaaaa ccctgaccat   2880
ccaagtcaaa gagtttggag atgctggcca gtacacctgt cacaaaggag cgaggttct   2940
aagccattcg ctcctgctgc ttcacaaaaa ggaagatgga atttggtcca ctgatatttt   3000
aaaggaccag aaagaaccca aaaataagac ctttctaaga tgcgaggcca agaattattc   3060
tggacgtttc acctgctggt ggctgacgac aatcagtact gatttgacat tcagtgtcaa   3120
aagcagcaga ggctcttctg accccaagg  ggtgacgtgc ggagctgcta cactctctgc   3180
```

```
agagagagtc agaggggaca acaaggagta tgagtactca gtggagtgcc aggaggacag    3240
tgcctgccca gctgctgagg agagtctgcc cattgaggtg atggtggatg ccgttcacaa    3300
gctcaagtat gaaaactaca ccagcagctt cttcatcagg gacatcatca aacctgaccc    3360
acccaagaac ttgcagctga agccattaaa gaattctcgg caggtggagg tcagctggga    3420
gtaccctgac acctggagta ctccacattc ctacttctcc ctgacattct gcgttcaagt    3480
ccagggcaag agcaagagag aaaagaaaga tagagtcttc acggacaaga cctcagccac    3540
ggtcatctgc cgcaaaaatg ccagcattag cgtgcgggcc caggaccgct actatagctc    3600
atcttggagc gaatgggcat ctgtgccctg cagttgacaa ttgctgtgcc ttctagttgc    3660
cagccatctg ttgtttgccc ctcccccgtg ccttccttga ccctggaagg tgccactccc    3720
actgtccttt cctaataaaa tgaggaaatt gcatcgcatt gtctgagtag gtgtcattct    3780
attctggggg gtgggtggg gcaggacagc aagggggagg attgggaaga caatagcagg    3840
catgctgggg atgcggtggg ctctatggag ctcgagagga acccctagtg atggagttgg    3900
ccactccctc tctgcgcgct cgctcgctca ctgaggccgg gcgaccaaag gtcgcccgac    3960
gcccgggctt tgcccgggcg gcctcagtga gcgagcgagc gcgcagctgc agatctg      4017
```

<210> SEQ ID NO 57
<211> LENGTH: 1758
<212> TYPE: DNA
<213> ORGANISM: Artificial Sequence
<220> FEATURE:
<223> OTHER INFORMATION: Human CAG - wild-type IL-12A/IL-12B - F2A (CpG
      modified) expression sequence

<400> SEQUENCE: 57

```
gctagcgcca ccatgtgtcc agcgcgcagc ctcctccttg tggctaccct ggtcctcctg      60
gaccacctca gtttggccag aaacctcccc gtggccactc cagacccagg aatgttccca     120
tgccttcacc actcccaaaa cctgctgagg gccgtcagca acatgctcca gaaggccaga     180
caaactctag aattttaccc cttgcacttc t gaagagattg atcatgaaga tatcacaaaa     240
gataaaacca gcacagtgga ggcctgttta ccattggaat taaccaagaa tgagagttgc     300
ctaaattcca gagagaccct cttcataact aatgggagtt gcctggcctc agaaagacc     360 tcttttatga tggccctgtg ccttagtagt atttatgaag acttgaagat gtaccaggtg     420
gagttcaaga ccatgaatgc aaagcttctg atggatccta agaggcagat ctttctagat     480
caaaacatgc tggcagttat tgatgagctg atgcaggccc tgaatttcaa cagtgagact     540
gtgccacaaa atcctccct tgaagaaccg gatttttata aaactaaaat caagctctgc     600
atacttcttc atgctttccg gattcgggca gtgactattg atagagtgat gagctatctg     660
aatgcttcca aagagagaag gagtggctca ggagcccctg tgaaacagac cctgaacttt     720
gacctcttga agcttctgg ggatgtggag tctaatcctg gtccaatgtg tcaccagcag     780
ttggtcatct cttggttttc cctggttttt ctggcatctc ccctcgtggc catatgggaa     840
ctgaagaaag atgtttatgt cgtagaattg gattggtatc cggatgcccc tggagaaatg     900
gtggtcctca cctgtgacac ccctgaagaa gatggtatca cctggacctt ggaccagagc     960
agtgaggtct taggctctgg caaaaccctg accatccaag tcaaagagtt ggagatgct    1020 ggccagtaca cctgtcacaa aggaggcgag ttctaagcc attcgctcct gctgcttcac    1080
aaaaaggaag atggaatttg gtccactgat atttt aaagg accagaaaga acccaaaaat    1140
aagacctttc taagatgcga ggccaagaat tattctggac gtttcacctg ctggtggctg    1200
```

```
acgacaatca gtactgattt gacattcagt gtcaaaagca gcagaggctc ttctgacccc    1260 caagggtga cgtgcggagc tgctacactc tctgcagaga gagtcagagg ggacaacaag    1320
gagtatgagt actcagtgga gtgccaggag gacagtgcct gcccagctgc tgaggagagt    1380
ctgcccattg aggtgatggt ggatgccgtt cacaagctca agtatgaaaa ctacaccagc    1440
agcttcttca tcagggacat catcaaacct gacccaccca agaacttgca gctgaagcca    1500
ttaaagaatt ctcggcaggt ggaggtcagc tgggagtacc ctgacacctg gagtactcca    1560
cattcctact tctccctgac attctgcgtt caagtccagg gcaagagcaa gagagaaaag    1620
aaagatagag tcttcacgga caagacctca gccacggtca tctgccgcaa aaatgccagc    1680
attagcgtgc gggcccagga ccgctactat agctcatctt ggagcgaatg ggcatctgtg    1740
ccctgcagtt gacaattg                                                 1758

<210> SEQ ID NO 58
<211> LENGTH: 489
<212> TYPE: DNA
<213> ORGANISM: Artificial Sequence
<220> FEATURE:
<223> OTHER INFORMATION: IL-15 (with CpG modification)

<400> SEQUENCE: 58
atgagaattt cgaaaccaca tttgagaagt atttccatcc agtgctactt gtgtttactt      60
ctaaacagtc attttctaac tgaagctggc attcatgtct tcattttggg ctgtttctct    120
gctgggcttc ctaaaacaga agccaactgg gtgaatgtaa taagtgattt gaaaaaaatt    180
gaagatctta ttcaatctat gcatattgat gctactttat atacggaaag tgatgttcac    240
cccagttgca agtaacagc aatgaagtgc tttctcttgg agttacaagt tatttcactt     300
gagtccggag atgcaagtat tcatgataca gtagaaaatc tgatcatcct agcaaacaac    360
agtttgtctt ctaatgggaa tgtaacagaa tctggatgca agaatgtgaa ggaactggag    420
gaaaaaaata ttaagaatt tttgcagagt tttgtacata ttgtccaaat gttcatcaac     480
acttcttga                                                           489

<210> SEQ ID NO 59
<211> LENGTH: 585
<212> TYPE: DNA
<213> ORGANISM: Artificial Sequence
<220> FEATURE:
<223> OTHER INFORMATION: IRES

<400> SEQUENCE: 59
gcccctctcc ctcccccccc cctaacgtta ctggccgaag ccgcttggaa taaggccggt      60
gtgcgtttgt ctatatgtta ttttccacca tattgccgtc ttttggcaat gtgagggccc    120
ggaaacctgg ccctgtcttc ttgacgagca ttcctagggg tctttcccct ctcgccaaag    180
gaatgcaagg tctgttgaat gtcgtgaagg aagcagttcc tctggaagct tcttgaagac    240
aaacaacgtc tgtagcgacc ctttgcaggc agcggaaccc cccacctggc gacaggtgcc    300
tctgcggcca aaagccacgt gtataagata cacctgcaaa ggcggcacaa ccccagtgcc    360
acgttgtgag ttggatagtt gtggaaagag tcaaatggct ctcctcaagc gtattcaaca    420
aggggctgaa ggatgcccag aaggtacccc attgtatggg atctgatctg gggcctcggt    480
acacatgctt tacatgtgtt tagtcgaggt taaaaaaacg tctaggcccc ccgaaccacg    540
gggacgtggt tttcctttga aaaacacgat gataatatgg ccaca                   585
```

<210> SEQ ID NO 60
<211> LENGTH: 24
<212> TYPE: DNA
<213> ORGANISM: Artificial Sequence
<220> FEATURE:
<223> OTHER INFORMATION: Furin cleaveage site

<400> SEQUENCE: 60
agaaagagaa ggagtggctc agga                                            24

<210> SEQ ID NO 61
<211> LENGTH: 72
<212> TYPE: DNA
<213> ORGANISM: Artificial Sequence
<220> FEATURE:
<223> OTHER INFORMATION: 2A site

<400> SEQUENCE: 61
gcccctgtga acagaccct gaactttgac ctcttgaagc ttgctgggga tgtggagtct      60
aatcctggtc ca                                                         72

<210> SEQ ID NO 62
<211> LENGTH: 60
<212> TYPE: DNA
<213> ORGANISM: Artificial Sequence
<220> FEATURE:
<223> OTHER INFORMATION: IL-2 leader

<400> SEQUENCE: 62
atgtacagga tgcaactcct gtcttgcatt gcactaagtc ttgcacttgt cacaaactcg     60

<210> SEQ ID NO 63
<211> LENGTH: 54
<212> TYPE: DNA
<213> ORGANISM: Artificial Sequence
<220> FEATURE:
<223> OTHER INFORMATION: IL-10 leader

<400> SEQUENCE: 63
atgcacagct cagcactgct ctgttgcctg gtcctcctga ctggggtgag ggcc           54

<210> SEQ ID NO 64
<211> LENGTH: 23
<212> TYPE: DNA
<213> ORGANISM: Artificial Sequence
<220> FEATURE:
<223> OTHER INFORMATION: miR-142 binding site

<400> SEQUENCE: 64
tccataaagt aggaaacact aca                                             23

<210> SEQ ID NO 65
<211> LENGTH: 104
<212> TYPE: DNA
<213> ORGANISM: Artificial Sequence
<220> FEATURE:
<223> OTHER INFORMATION: 4x miR-142 binding site

<400> SEQUENCE: 65
tccataaagt aggaaacact acactattcc ataaagtagg aaacactaca tcactccata     60
aagtaggaaa cactacaagt ctccataaag taggaaacac taca                     104

<210> SEQ ID NO 66
<211> LENGTH: 97

<212> TYPE: DNA
<213> ORGANISM: Artificial Sequence
<220> FEATURE:
<223> OTHER INFORMATION: SV40 intron

<400> SEQUENCE: 66

```
gtaagtttag tcttttttgtc ttttatttca ggtcccggat ccggtggtgg tgcaaatcaa    60
agaactgctc ctcagtggat gttgccttta cttctag                             97
```

<210> SEQ ID NO 67
<211> LENGTH: 230
<212> TYPE: DNA
<213> ORGANISM: Artificial Sequence
<220> FEATURE:
<223> OTHER INFORMATION: EF-1alpha

<400> SEQUENCE: 67

```
gctccggtgc ccgtcagtgg gcagagcgca catcgcccac agtccccgag aagttggggg    60
gaggggtcgg caattgaacc ggtgcctaga aaggtggcg cggggtaaac tgggaaagtg    120
atgtcgtgta ctggctccgc ctttttcccg agggtggggg agaaccgtat ataagtgcag    180
tagtcgccgt gaacgttctt tttcgcaacg ggtttgccgc cagaacacag              230
```

<210> SEQ ID NO 68
<211> LENGTH: 380
<212> TYPE: DNA
<213> ORGANISM: Artificial Sequence
<220> FEATURE:
<223> OTHER INFORMATION: CMV enhancer

<400> SEQUENCE: 68

```
gacattgatt attgactagt tattaatagt aatcaattac ggggtcatta gttcatagcc    60
catatatgga gttccgcgtt acataactta cggtaaatgg cccgcctggc tgaccgccca    120 acgaccccccg cccattgacg tcaataatga cgtatgttcc catagtaacg ccaatagga    180 ctttccattg acgtcaatgg gtggactatt tacggtaaac tgcccacttg gcagtacatc    240
aagtgtatca tatgccaagt acgccccccta ttgacgtcaa tgacggtaaa tggcccgcct    300
ggcattatgc ccagtacatg accttatggg actttcctac ttggcagtac atctacgtat    360
tagtcatcgc tattaccatg                                               380
```

<210> SEQ ID NO 69
<211> LENGTH: 218
<212> TYPE: DNA
<213> ORGANISM: Artificial Sequence
<220> FEATURE:
<223> OTHER INFORMATION: CMVp

<400> SEQUENCE: 69

```
gtgatgcggt tttggcagta catcaatggg cgtggatagc ggtttgactc acggggattt    60
ccaagtctcc accccattga cgtcaatggg agtttgtttt ggcaccaaaa tcaacgggac    120
tttccaaaat gtcgtaacaa ctccgcccca ttgacgcaaa tgggcggtag gcgtgtacgg    180
tgggaggtct atataagcag agctcgttta gtgaaccg                           218
```

<210> SEQ ID NO 70
<211> LENGTH: 598
<212> TYPE: DNA
<213> ORGANISM: Artificial Sequence
<220> FEATURE:
<223> OTHER INFORMATION: CMV ehancer and promoter (CMVe/p)

<400> SEQUENCE: 70

```
gacattgatt attgactagt tattaatagt aatcaattac ggggtcatta gttcatagcc      60
catatatgga gttccgcgtt acataactta cggtaaatgg cccgcctggc tgaccgccca     120
acgaccccg cccattgacg tcaataatga cgtatgttcc catagtaacg ccaatagga      180
ctttccattg acgtcaatgg gtggactatt tacggtaaac tgcccacttg gcagtacatc     240
aagtgtatca tatgccaagt acgcccccta ttgacgtcaa tgacggtaaa tggcccgcct     300
ggcattatgc ccagtacatg accttatggg actttcctac ttggcagtac atctacgtat     360
tagtcatcgc tattaccatg gtgatgcggt tttggcagta catcaatggg cgtggatagc     420
ggtttgactc acggggattt ccaagtctcc accccattga cgtcaatggg agtttgtttt     480
ggcaccaaaa tcaacgggac tttccaaaat gtcgtaacaa ctccgcccca ttgacgcaaa     540
tgggcggtag gcgtgtacgg tgggaggtct atataagcag agctcgttta gtgaaccg      598
```

<210> SEQ ID NO 71
<211> LENGTH: 1725
<212> TYPE: DNA
<213> ORGANISM: Artificial Sequence
<220> FEATURE:
<223> OTHER INFORMATION: CAG

<400> SEQUENCE: 71

```
gtcgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggact atttacggta aactgcccac ttggcagtac    240
atcaagtgta tcatatgcca gtacgcccc ctattgacgt caatgacggt aaatggcccg    300
cctggcatta tgcccagtac atgaccttat gggactttcc tacttggcag tacatctacg    360
tattagtcat cgctattacc atgggtcgag gtgagcccca cgttctgctt cactctcccc    420
atctcccccc cctccccacc cccaattttg tatttattta ttttttaatt attttgtgca    480
gcgatggggg cggggggggg ggggcgcgc gccaggcggg gcgggcggg gcgaggggcg    540
gggcggggcg aggcggagag gtgcggcggc agccaatcag agcggcgcgc tccgaaagtt    600
tccttttatg gcgaggcggc ggcggcgcg gccctataaa aagcgaagcg cgcggcgggc    660
gggagtcgct gcgcgctgcc ttcgccccgt gccccgctcc gccgccgcct cgcgccgccc    720
gccccggctc tgactgaccg cgttactccc acaggtgagc gggcgggacg gcccttctcc    780
tccgggctgt aattagcgct tggtttaatg acggctcgtt tcttttctgt ggctgcgtga    840
aagccttgag gggctccggg agggcccttt gtgcggggg agcggctcgg ggggtgcgtg    900
cgtgtgtgtg tgcgtgggga gcgccgcgtg cggctccgcg ctgcccggcg gctgtgagcg    960
ctgcgggcgc ggcgcgggc tttgtgcgct ccgcagtgtg cgcgagagga gcgcggccgg   1020
gggcggtgcc acgcggtgcg gggggggctg cgagggaac aaaggctgcg tgcggggtgt   1080
gtgcgtgggg ggggtgagca gggggtgtgg gcgggcggt cggctgtaa cccccccctg   1140
caccccctc cccgagttgc tgagcacggc ccggcttcgg gtgcgggct ccgtgcggg    1200
cgtggcgcgg ggctcgccgt gccgggcggg gggtggcgg gggtgggggt gccgggcggg   1260
gcggggccgc ctcgggccgg ggagggctcg gggagggc gcggcggccc ccggagcgcc   1320
ggcggctgtc gaggcgcggc gagccgcagc cattgccttt tatggtaatc gtgcgagagg   1380
gcgcagggac ttcctttgtc ccaaatctgt gcggagccga aatctgggag gcgccgccgc   1440
```

```
acccccctcta gcgggcgcgg ggcgaagcgg tgcggcgccg gcaggaagga aatgggcggg    1500
gagggccttc gtgcgtcgcc gcgccgccgt cccttctcc ctctccagcc tcggggctgt    1560
ccgcgggggg acggctgcct tcgggggga cggggcaggg cggggttcgg cttctggcgt    1620
gtgaccggcg gtctagactc tgctaaccat gttcatgcct tcttctcttt cctacagctc    1680
ctgggcaacg tgctggttgt tgtgctgtct catcattttg gcaaa                    1725
```

<210> SEQ ID NO 72
<211> LENGTH: 49
<212> TYPE: DNA
<213> ORGANISM: Artificial Sequence
<220> FEATURE:
<223> OTHER INFORMATION: Synthetic poly(A)

<400> SEQUENCE: 72

```
aataaaagat ctttattttc attagatctg tgtgttggtt ttttgtgtg               49
```

<210> SEQ ID NO 73
<211> LENGTH: 224
<212> TYPE: DNA
<213> ORGANISM: Artificial Sequence
<220> FEATURE:
<223> OTHER INFORMATION: BGH poly(A)

<400> SEQUENCE: 73

```
ctgtgccttc tagttgccag ccatctgttg tttgccccte ccccgtgcct tccttgaccc    60
tggaaggtgc cactcccact gtcctttcct aataaaatga ggaaattgca tcgcattgtc   120
tgagtaggtg tcattctatt ctgggggtg ggtggggca ggacagcaag ggggaggatt     180
gggaagacaa tagcaggcat gctggggatg cggtgggctc tatg                    224
```

<210> SEQ ID NO 74
<211> LENGTH: 92
<212> TYPE: DNA
<213> ORGANISM: Artificial Sequence
<220> FEATURE:
<223> OTHER INFORMATION: Pause element

<400> SEQUENCE: 74

```
aacatacgct ctccatcaaa acaaaacgaa acaaaacaaa ctagcaaaat aggctgtccc    60
cagtgcaagt gcaggtgcca gaacatttct ct                                  92
```

<210> SEQ ID NO 75
<211> LENGTH: 269
<212> TYPE: DNA
<213> ORGANISM: Artificial Sequence
<220> FEATURE:
<223> OTHER INFORMATION: 5' LTR

<400> SEQUENCE: 75

```
ggggctcgca tctctccttc acgcgcccgc cgccctacct gaggccgcca tccacgccgg    60
ttgagtcgcg ttctgccgcc tcccgcctgt ggtgcctcct gaactgcgtc cgccgtctag   120
gtaagtttaa agctcaggtc gagaccgggc ctttgtccgg cgctcccttg gagcctacct   180
agactcagcc ggctctccac gctttgcctg acctgcttg ctcaactcta cgtctttgtt    240
tcgttttctg ttctgcgccg ttacagatc                                     269
```

<210> SEQ ID NO 76
<211> LENGTH: 133
<212> TYPE: DNA

<213> ORGANISM: Artificial Sequence
<220> FEATURE:
<223> OTHER INFORMATION: Intron (chimera of human betaglobin intron and immunoglobulin heavy chain intron)

<400> SEQUENCE: 76

```
gtaagtatca aggttacaag acaggtttaa ggagaccaat agaaactggg cttgtcgaga      60
cagagaagac tcttgcgttt ctgataggca cctattggtc ttactgacat ccactttgcc     120
tttctctcca cag                                                        133
```

<210> SEQ ID NO 77
<211> LENGTH: 657
<212> TYPE: DNA
<213> ORGANISM: Artificial Sequence
<220> FEATURE:
<223> OTHER INFORMATION: Human IL-12A (p35) ("wild-type" no CpG modification and no stop codon)

<400> SEQUENCE: 77

```
atgtgtccag cgcgcagcct cctccttgtg gctaccctgg tcctcctgga ccacctcagt      60
ttggccagaa acctccccgt ggccactcca gacccaggaa tgttcccatg ccttcaccac     120
tcccaaaacc tgctgagggc cgtcagcaac atgctccaga aggccagaca aactctagaa     180
ttttaccctt gcacttctga agagattgat catgaagata tcacaaaaga taaaaccagc     240
acagtggagg cctgtttacc attggaatta ccaagaatg agagttgcct aaattccaga     300
gagacctctt tcataactaa tgggagttgc ctggcctcca aaagacctc ttttatgatg     360
gccctgtgcc ttagtagtat ttatgaagac ttgaagatgt accaggtgga gttcaagacc     420
atgaatgcaa agcttctgat ggatcctaag aggcagatct ttctagatca aaacatgctg     480
gcagttattg atgagctgat gcaggccctg aatttcaaca gtgagactgt gccacaaaaa     540
tcctcccttg aagaaccgga ttttataaa actaaaatca agctctgcat acttcttcat     600
gctttccgga ttcgggcagt gactattgat agagtgatga gctatctgaa tgcttcc       657
```

<210> SEQ ID NO 78
<211> LENGTH: 236
<212> TYPE: PRT
<213> ORGANISM: Artificial Sequence
<220> FEATURE:
<223> OTHER INFORMATION: Mouse IL-12A (p35) NP_001152896

<400> SEQUENCE: 78

```
Met Val Ser Val Pro Thr Ala Ser Pro Ser Ala Ser Ser Ser Ser
1               5                   10                  15

Gln Cys Arg Ser Ser Met Cys Gln Ser Arg Tyr Leu Leu Phe Leu Ala
            20                  25                  30

Thr Leu Ala Leu Leu Asn His Leu Ser Leu Ala Arg Val Ile Pro Val
        35                  40                  45

Ser Gly Pro Ala Arg Cys Leu Ser Gln Ser Arg Asn Leu Leu Lys Thr
    50                  55                  60

Thr Asp Asp Met Val Lys Thr Ala Arg Glu Lys Leu Lys His Tyr Ser
65                  70                  75                  80

Cys Thr Ala Glu Asp Ile Asp His Glu Asp Ile Thr Arg Asp Gln Thr
                85                  90                  95

Ser Thr Leu Lys Thr Cys Leu Pro Leu Glu Leu His Lys Asn Glu Ser
            100                 105                 110
```

```
Cys Leu Ala Thr Arg Glu Thr Ser Thr Thr Arg Gly Ser Cys Leu
            115                 120                 125

Pro Pro Gln Lys Thr Ser Leu Met Met Thr Leu Cys Leu Gly Ser Ile
    130                 135                 140

Tyr Glu Asp Leu Lys Met Tyr Gln Thr Glu Phe Gln Ala Ile Asn Ala
145                 150                 155                 160

Ala Leu Gln Asn His Asn His Gln Gln Ile Ile Leu Asp Lys Gly Met
                165                 170                 175

Leu Val Ala Ile Asp Glu Leu Met Gln Ser Leu Asn His Asn Gly Glu
            180                 185                 190

Thr Leu Arg Gln Lys Pro Pro Val Gly Glu Ala Asp Pro Tyr Arg Val
        195                 200                 205

Lys Met Lys Leu Cys Ile Leu Leu His Ala Phe Ser Thr Arg Val Val
    210                 215                 220

Thr Ile Asn Arg Val Met Gly Tyr Leu Ser Ser Ala
225                 230                 235

<210> SEQ ID NO 79
<211> LENGTH: 335
<212> TYPE: PRT
<213> ORGANISM: Artificial Sequence
<220> FEATURE:
<223> OTHER INFORMATION: Mouse IL-12B (p40)
      NP_001290173

<400> SEQUENCE: 79

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220
```

```
Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
            245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 80
<211> LENGTH: 253
<212> TYPE: PRT
<213> ORGANISM: Artificial Sequence
<220> FEATURE:
<223> OTHER INFORMATION: Human IL-12A (p35)
      NP_000873

<400> SEQUENCE: 80

Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
            85                  90                  95

Pro Cys Thr Ser Glu Glu Ile Asp His Glu Asp Ile Thr Lys Asp Lys
        100                 105                 110

Thr Ser Thr Val Glu Ala Cys Leu Pro Leu Glu Leu Thr Lys Asn Glu
    115                 120                 125

Ser Cys Leu Asn Ser Arg Glu Thr Ser Phe Ile Thr Asn Gly Ser Cys
130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
            165                 170                 175

Ala Lys Leu Leu Met Asp Pro Lys Arg Gln Ile Phe Leu Asp Gln Asn
        180                 185                 190

Met Leu Ala Val Ile Asp Glu Leu Met Gln Ala Leu Asn Phe Asn Ser
    195                 200                 205

Glu Thr Val Pro Gln Lys Ser Ser Leu Glu Glu Pro Asp Phe Tyr Lys
210                 215                 220
```

```
Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
            245                 250

<210> SEQ ID NO 81
<211> LENGTH: 328
<212> TYPE: PRT
<213> ORGANISM: Artificial Sequence
<220> FEATURE:
<223> OTHER INFORMATION: Human IL-12B (p40)
      NP_002178

<400> SEQUENCE: 81

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300
```

```
Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

<210> SEQ ID NO 82
<211> LENGTH: 4280
<212> TYPE: DNA
<213> ORGANISM: Artificial Sequence
<220> FEATURE:
<223> OTHER INFORMATION: CMV enhancer -CBA promoter- WT human IL-12A (no stop codon) - F2A - WT human IL-12B (with stop codon) -hGH polyA

<400> SEQUENCE: 82

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tagtattaaa | cgcgtgtcga | cattgattat | tgactagtta | ttaatagtaa | 180 |
| tcaattacgg | ggtcattagt | tcatagccca | tatatggagt | tccgcgttac | ataacttacg | 240 |
| gtaaatggcc | cgcctggctg | accgcccaac | gacccccgcc | cattgacgtc | aataatgacg | 300 |
| tatgttccca | tagtaacgcc | aatagggact | ttccattgac | gtcaatgggt | ggactattta | 360 |
| cggtaaactg | cccacttggc | agtacatcaa | gtgtatcata | tgccaagtac | gccccctatt | 420 |
| gacgtcaatg | acggtaaatg | gcccgcctgg | cattatgccc | agtacatgac | cttatgggac | 480 |
| tttcctactt | ggcagtacat | ctacgtatta | gtcatcgcta | ttaccatggg | tcgaggtgag | 540 |
| ccccacgttc | tgcttcactc | tccccatctc | ccccccctcc | ccacccccaa | ttttgtattt | 600 |
| atttattttt | taattatttt | gtgcagcgat | gggggcgggg | ggggggggggg | cgcgcgccag | 660 |
| gcggggcggg | gcggggcgag | gggcggggcg | gggcgaggcg | gagaggtgcg | gcggcagcca | 720 |
| atcagagcgg | cgcgctccga | aagtttcctt | ttatggcgag | gcggcggcgg | cggcggccct | 780 |
| ataaaaagcg | aagcgcgcgg | cgggcgggag | tcgctgcgcg | ctgccttcgc | cccgtgcccc | 840 |
| gctccgccgc | cgcctcgcgc | cgcccgcccc | ggctctgact | gaccgcgtta | ctcccacagg | 900 |
| tgagcgggcg | ggacgccct | tctcctccgg | gctgtaatta | gcgcttggtt | taatgacggc | 960 |
| tcgtttcttt | tctgtggctg | cgtgaaagcc | ttgaggggct | ccgggagggc | cctttgtgcg | 1020 |
| gggggagcgg | ctcgggggggt | gcgtgcgtgt | gtgtgtgcgt | ggggagcgcc | gcgtgcggct | 1080 |
| ccgcgctgcc | cggcggctgt | gagcgctgcg | ggcgcggcgc | ggggctttgt | gcgctccgca | 1140 |
| gtgtgcgcga | ggagcgcgcg | gccggggggcg | gtgccacgcg | gtgcggggggg | ggctgcgagg | 1200 |
| ggaacaaagg | ctgcgtgcgg | ggtgtgtgcg | tgggggggggt | gagcaggggg | tgtgggcgcg | 1260 |
| gcggtcgggc | tgtaaccccc | ccctgcaccc | ccctccccga | gttgctgagc | acggcccggc | 1320 |
| ttcgggtgcg | gggctccgtg | cggggcgtgg | cgcggggctc | gccgtgccgg | gcgggggggtg | 1380 |
| gcggcgggtg | gggtgccgg | gcgggcggg | ccgcctcgg | gccggggagg | gctcggggga | 1440 |
| ggggcgcggc | ggccccccgga | gcgccggcgg | ctgtcgaggc | gcggcgagcc | gcagccattg | 1500 |
| ccttttatgg | taatcgtgcg | agagggcgca | gggacttcct | ttgtcccaaa | tctgtgcgga | 1560 |
| gccgaaatct | gggaggcgcc | gccgcacccc | ctctagcggg | cgcggggcga | agcggtgcgg | 1620 |
| cgccggcagg | aaggaaatgg | gcggggaggg | ccttcgtgcg | tcgccgcgcc | gccgtcccct | 1680 |
| tctccctctc | cagcctcggg | gctgtccgcg | ggggacggc | tgccttcggg | ggggacgggg | 1740 |
| cagggcgggg | ttcggcttct | ggcgtgtgac | cggcggtcta | gactctgcta | accatgttca | 1800 |
| tgccttcttc | tctttcctac | agctcctggg | caacgtgctg | gttgttgtgc | tgtctcatca | 1860 |

```
ttttggcaaa gaattcaagc ttccagctag cgccaccatg tgtccagcgc gcagcctcct    1920
ccttgtggct accctggtcc tcctggacca cctcagtttg gccagaaacc tccccgtggc    1980
cactccagac ccaggaatgt tcccatgcct tcaccactcc caaaacctgc tgagggccgt    2040
cagcaacatg ctccagaagg ccagacaaac tctagaattt tacccttgca cttctgaaga    2100
gattgatcat gaagatatca caaaagataa aaccagcaca gtggaggcct gtttaccatt    2160
ggaattaacc aagaatgaga gttgcctaaa ttccagagag acctctttca taactaatgg    2220
gagttgcctg gcctccagaa agacctcttt tatgatggcc ctgtgcctta gtagtattta    2280
tgaagacttg aagatgtacc aggtggagtt caagaccatg aatgcaaagc ttctgatgga    2340
tcctaagagg cagatctttc tagatcaaaa catgctggca gttattgatg agctgatgca    2400
ggccctgaat tcaacagtg agactgtgcc acaaaaatcc tcccttgaag aaccggattt    2460
ttataaaact aaaatcaagc tctgcatact tcttcatgct ttccggattc gggcagtgac    2520
tattgataga gtgatgagct atctgaatgc ttccagaaag agaaggagtg gctcaggagc    2580
ccctgtgaaa cagaccctga actttgacct cttgaagctt gctgggatg tggagtctaa    2640 tcctggtcca atgtgtcacc agcagttggt catctcttgg ttttccctgg ttttctggc    2700 atctcccctc gtggccatat gggaactgaa gaaagatgtt tatgtcgtag aattggattg    2760
gtatccggat gcccctggag aaatggtggt cctcacctgt gacaccctg aagaagatgg    2820 tatcacctgg accttggacc agagcagtga ggtcttaggc tctggcaaaa ccctgaccat    2880
ccaagtcaaa gagtttggag atgctggcca gtacacctgt cacaaaggag gcgaggttct    2940
aagccattcg ctcctgctgc ttcacaaaaa ggaagatgga atttggtcca ctgatatttt    3000
aaaggaccag aaagaaccca aaaataagac ctttctaaga tgcgaggcca agaattattc    3060
tggacgtttc acctgctggt ggctgacgac aatcagtact gatttgacat tcagtgtcaa    3120
aagcagcaga ggctcttctg acccccaagg ggtgacgtgc ggagctgcta cactctctgc    3180
agagagagtc agaggggaca acaaggagta tgagtactca gtggagtgcc aggaggacag    3240
tgcctgccca gctgctgagg agagtctgcc cattgaggtg atggtggatg ccgttcacaa    3300
gctcaagtat gaaaactaca ccagcagctt cttcatcagg gacatcatca aacctgaccc    3360
acccaagaac ttgcagctga agccattaaa gaattctcgg caggtggagg tcagctggga    3420
gtaccctgac acctggagta ctccacattc ctacttctcc ctgacattct gcgttcaagt    3480
ccagggcaag agcaagagag aaaagaaaga tagagtcttc acggacaaga cctcagccac    3540
ggtcatctgc cgcaaaaatg ccagcattag cgtgcgggcc caggaccgct actatagctc    3600
atcttggagc gaatgggcat ctgtgccctg cagttgacaa ttggatctac gggtggcatc    3660
cctgtgaccc ctccccagtg cctctcctgg ccctggaagt tgccactcca gtgcccacca    3720
gccttgtcct aataaaatta agttgcatca ttttgtctga ctaggtgtcc ttctataata    3780
ttatggggtg gaggggggtg gtatggagca agggcaagt tggaagaca acctgtaggg    3840 cctgcggggt ctattgggaa ccaagctgga gtgcagtggc acaatcttgg ctcactgcaa    3900
tctccgcctc ctgggttcaa gcgattctcc tgcctcagcc tcccgagttg ttgggattcc    3960
aggcatgcat gaccaggctc agctaatttt tgttttttg gtagagacgg gttttcacca    4020
tattggccag gctggtctcc aactcctaat ctcaggtgat ctacccacct tggcctccca    4080
aattgctggg attacaggcg tgaaccactg ctcccttccc tgtccttctg gagctcgaga    4140 ggaacccta gtgatggagt tggccactcc ctctctgcgc gctcgctcgc tcactgaggc    4200
```

```
cgggcgacca aaggtcgccc gacgcccggg ctttgcccgg gcggcctcag tgagcgagcg   4260
agcgcgcagc tgcagatctg                                               4280

<210> SEQ ID NO 83
<211> LENGTH: 4352
<212> TYPE: DNA
<213> ORGANISM: Artificial Sequence
<220> FEATURE:
<223> OTHER INFORMATION: CMV enhancer -CBA promoter- WT mouse IL-12A (no
      stop codon) - F2A - WT mouse IL-12B (with stop codon) -hGH polyA

<400> SEQUENCE: 83
ctgcgcgctc gctcgctcac tgaggccgcc cgggcaaagc ccgggcgtcg ggcgaccttt   60
ggtcgcccgg cctcagtgag cgagcgagcg cgcagagagg gagtggccaa ctccatcact   120
aggggttcct tagtattaaa cgcgtgtcga cattgattat tgactagtta ttaatagtaa   180
tcaattacgg ggtcattagt tcatagccca tatatggagt tccgcgttac ataacttacg   240
gtaaatggcc cgcctggctg accgcccaac gacccccgcc cattgacgtc aataatgacg   300
tatgttccca tagtaacgcc aatagggact ttccattgac gtcaatgggt ggactattta   360
cggtaaactg cccacttggc agtacatcaa gtgtatcata tgccaagtac gccccctatt   420
gacgtcaatg acggtaaatg gcccgcctgg cattatgccc agtacatgac cttatgggac   480
tttcctactt ggcagtacat ctacgtatta gtcatcgcta ttaccatggg tcgaggtgag   540
ccccacgttc tgcttcactc tccccatctc ccccccctcc ccacccccaa ttttgtattt   600
atttattttt taattatttt gtgcagcgat gggggcgggg ggggggggg cgcgcgccag    660 gcggggcggg gcggggcgag gggcggggcg gggcgaggcg gagaggtgcg gcggcagcca   720
atcagagcgg cgcgctccga aagtttcctt ttatggcgag gcggcggcgg cggcggccct   780
ataaaaagcg aagcgcgcgg cgggcgggag tcgctgcgcg ctgccttcgc cccgtgcccc   840
gctccgccgc cgcctcgcgc cgcccgcccc ggctctgact gaccgcgtta ctcccacagg   900
tgagcgggcg ggacggccct tctcctccgg gctgtaatta gcgcttggtt taatgacggc   960
tcgtttcttt tctgtggctg cgtgaaagcc ttgaggggct ccgggagggc cctttgtgcg   1020
gggggagcgg ctcggggggt gcgtgcgtgt gtgtgtgcgt ggggagcgcc gcgtgcggct   1080
ccgcgctgcc cggcggctgt gagcgctgcg ggcgcggcgc ggggctttgt gcgctccgca   1140
gtgtgcgcga gaggagcgcg gccggggcg gtgccacgcg gtgcgggggg ggctgcgagg    1200
ggaacaaagg ctgcgtgcgg ggtgtgtgcg tgggggggt gagcagggggg tgtgggcgcg   1260 gcggtcgggc tgtaaccccc ccctgcaccc ccctccccga gttgctgagc acggcccggc   1320
ttcgggtgcg gggctccgtg cggggcgtgg cgcggggctc gccgtgccgg gcggggggtg   1380
gcggcgggtg ggggtgccgg gcggggcggg ccgcctcgg gccggggagg gctcggggga    1440
ggggcgcggc ggcccccgga gcgccggcgg ctgtcgaggc gcggcgagcc gcagccattg   1500
ccttttatgg taatcgtgcg agagggcgca gggacttcct ttgtcccaaa tctgtgcgga   1560
gccgaaatct gggaggcgcc gccgcacccc ctctagcggg cgcggggcga agcggtgcgg   1620
cgccggcagg aaggaaatgg gcggggaggg ccttcgtgcg tcgccgcgcc gccgtcccct   1680
tctccctctc cagcctcggg gctgtccgcg ggggacggg tgccttcggg ggggacgggg    1740
cagggcgggg ttcggcttct ggcgtgtgac cggcggtcta gactctgcta accatgttca   1800
tgccttcttc tctttcctac agctcctggg caacgtgctg gttgttgtgc tgtctcatca   1860
ttttggcaaa gaattcaagc ttccagctag cgccaccatg gtcagcgttc aacagcctc    1920
```

```
accctcggca tccagcagct cctctcagtg ccggtccagc atgtgtcaat cacgctacct    1980
cctcttttg  gccacccttg ccctcctaaa ccacctcagt ttggccaggg tcattccagt    2040
ctctggacct gccaggtgtc ttagccagtc ccgaaacctg ctgaagacca cagatgacat    2100
ggtgaagacg gccagagaaa aactgaaaca ttattcctgc actgctgaag acatcgatca    2160
tgaagacatc acacgggacc aaaccagcac attgaagacc tgtttaccac tggaactaca    2220
caagaacgag agttgcctgg ctactagaga gacttcttcc acaacaagag ggagctgcct    2280
gcccccacag aagacgtctt tgatgatgac cctgtgcctt ggtagcatct atgaggactt    2340
gaagatgtac cagacagagt tccaggccat caacgcagca cttcagaatc acaaccatca    2400
gcagatcatt ctagacaagg gcatgctggt ggccatcgat gagctgatgc agtctctgaa    2460
tcataatggc gagactctgc gccagaaacc tcctgtggga gaagcagacc cttacagagt    2520
gaaaatgaag ctctgcatcc tgcttcacgc cttcagcacc cgcgtcgtga ccatcaacag    2580
ggtgatgggc tatctgagct ccgccagaaa gagaaggagt ggctcaggag cccctgtgaa    2640
acagaccctg aactttgacc tcttgaagct tgctggggat gtggagtcta atcctggtcc    2700
aatgtgtcct cagaagctaa ccatctcctg gtttgccatc gttttgctgg tgtctccact    2760
catggccatg tgggagctgg agaaagacgt ttatgttgta gaggtggact ggactcccga    2820
tgcccctgga gaaacagtga acctcacctg tgacacgcct gaagaagatg acatcacctg    2880
gacctcagac cagagacatg gagtcatagg ctctggaaag accctgacca tcactgtcaa    2940
agagtttcta gatgctggcc agtacacctg ccacaaagga ggcgagactc tgagccactc    3000
acatctgctg ctccacaaga aggaaaatgg aatttggtcc actgaaattt taaaaaattt    3060
caaaaacaag actttcctga agtgtgaagc accaaattac tccggacggt tcacgtgctc    3120
atggctggtg caaagaaaca tggacttgaa gttcaacatc aagagcagta gcagttcccc    3180
tgactctcgg gcagtgacat gtggaatggc gtctctgtct gcagagaagg tcacactgga    3240
ccaaagggac tatgagaagt attcagtgtc ctgccaggag gatgtcacct gcccaactgc    3300
cgaggagacc ctgcccattg aactggcgtt ggaagcacgg cagcagaata aatatgagaa    3360
ctacagcacc agcttcttca tcagggacat catcaaacca gacccgccca gaacttgca    3420
gatgaagcct ttgaagaact cacaggtgga ggtcagctgg gagtaccctg actcctggag    3480
cactccccat tcctacttct ccctcaagtt ctttgttcga atccagcgca agaaagaaaa    3540
gatgaaggag acagaggagg ggtgtaacca gaaaggagcg ttcctcgtag agaagacatc    3600
taccgaagtc caatgcaaag gcgggaatgt ctgcgtgcaa gctcaggatc gctattacaa    3660
ttcctcatgc agcaagtggg catgtgttcc ctgcagggtc cgatcctgac aattggatct    3720
acgggtggca tccctgtgac ccctccccag tgcctctcct ggccctggaa gttgccactc    3780
cagtgcccac cagccttgtc ctaataaaat taagttgcat catttgtct gactaggtgt    3840
ccttctataa tattatgggg tggaggggg tggtatggag caaggggcaa gttgggaaga    3900
caacctgtag ggcctgcggg gtctattggg aaccaagctg gagtgcagtg cacaatcttt    3960
ggctcactgc aatctccgcc tcctgggttc aagcgattct cctgcctcag cctcccgagt    4020
tgttgggatt ccaggcatgc atgaccaggc tcagctaatt tttgtttttt tggtagagac    4080
ggggtttcac catattggcc aggctggtct ccaactccta atctcaggtg atctacccac    4140
cttggcctcc caaattgctg ggattacagg cgtgaaccac tgctcccttc cctgtccttc    4200
tggagctcga gaggaacccc tagtgatgga gttggccact ccctctctgc gcgctcgctc    4260
```

```
gctcactgag gccgggcgac caaaggtcgc ccgacgcccg ggctttgccc gggcggcctc    4320
agtgagcgag cgagcgcgca gctgcagatc tg                                 4352

<210> SEQ ID NO 84
<211> LENGTH: 130
<212> TYPE: DNA
<213> ORGANISM: Artificial Sequence
<220> FEATURE:
<223> OTHER INFORMATION: AAV2 5' ITR

<400> SEQUENCE: 84
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120
aggggttcct                                                          130

<210> SEQ ID NO 85
<211> LENGTH: 276
<212> TYPE: DNA
<213> ORGANISM: Artificial Sequence
<220> FEATURE:
<223> OTHER INFORMATION: Chicken Beta Actin (CBA) Promoter

<400> SEQUENCE: 85
tcgaggtgag ccccacgttc tgcttcactc tccccatctc ccccccctcc ccacccccaa     60
ttttgtattt atttattttt taattatttt gtgcagcgat ggggcgggg ggggggggggg   120 cgcgcgccag gcggggcggg gcggggcgag gggcggggcg gggcgaggcg gagaggtgcg   180
gcggcagcca atcagagcgg cgcgctccga aagtttcctt ttatggcgag gcggcggcgg   240
cggcggccct ataaaaagcg aagcgcgcgg cgggcg                             276

<210> SEQ ID NO 86
<211> LENGTH: 1064
<212> TYPE: DNA
<213> ORGANISM: Artificial Sequence
<220> FEATURE:
<223> OTHER INFORMATION: CAG Intron

<400> SEQUENCE: 86
ggagtcgctg cgcgctgcct tcgccccgtg ccccgctccg ccgccgcctc gcgccgcccg     60
ccccggctct gactgaccgc gttactccca caggtgagcg ggcgggacgg cccttctcct   120
ccgggctgta attagcgctt ggtttaatga cggctcgttt cttttctgtg gctgcgtgaa   180
agccttgagg ggctccggga gggccctttg tgcgggggga gcggctcggg gggtgcgtgc   240
gtgtgtgtgt gcgtggggag cgccgcgtgc ggctccgcgc tgcccggcgg ctgtgagcgc   300
tgcgggcgcg gcgcggggct ttgtgcgctc cgcagtgtgc gcgagaggag cgcggccggg   360
ggcggtgcca cgcggtgcgg ggggggctgc gaggggaaca aaggctgcgt gcggggtgtg   420
tgcgtggggg gggtgagcag ggggtgtggg cgcggcggtc gggctgtaac ccccccctgc   480
acccccctcc ccgagttgct gagcacggcc cggcttcggg tgcggggctc cgtgcggggc   540
gtggcgcggg gctcgccgtg ccgggcgggg ggtggcggcg ggtggggtg ccggcgcggg    600 cggggccgcc tcgggccggg gagggctcgg ggaggggcg cggcggcccc cggagcgccg   660
gcggctgtcg aggcgcggcg agccgcagcc attgcctttt atggtaatcg tgcgagaggg   720
cgcagggact tccttttgtcc caaatctgtg cggagccgaa atctgggagg cgccgccgca   780
ccccctctag cgggcgcggg gcgaagcggt gcggcgccgg caggaaggaa atgggcgggg   840
```

```
agggccttcg tgcgtcgccg cgccgccgtc cccttctccc tctccagcct cggggctgtc    900
cgcgggggga cggctgcctt cggggggggac ggggcagggc ggggttcggc ttctggcgtg    960
tgaccggcgg tctagactct gctaaccatg ttcatgcctt cttctctttc ctacagctcc   1020
tgggcaacgt gctggttgtt gtgctgtctc atcattttgg caaa                    1064

<210> SEQ ID NO 87
<211> LENGTH: 5
<212> TYPE: DNA
<213> ORGANISM: Artificial Sequence
<220> FEATURE:
<223> OTHER INFORMATION: Kozak sequence

<400> SEQUENCE: 87 gccac                                                                  5

<210> SEQ ID NO 88
<211> LENGTH: 487
<212> TYPE: DNA
<213> ORGANISM: Artificial Sequence
<220> FEATURE:
<223> OTHER INFORMATION: Human growth hormone (hGH) poly(A)

<400> SEQUENCE: 88
gatctacggg tggcatccct gtgacccctc cccagtgcct ctcctggccc tggaagttgc     60
cactccagtg cccaccagcc ttgtcctaat aaaattaagt tgcatcattt tgtctgacta    120
ggtgtccttc tataatatta tggggtggag ggggtggta tggagcaagg ggcaagttgg     180
gaagacaacc tgtagggcct gcggggtcta ttgggaacca agctggagtg cagtggcaca    240
atcttggctc actgcaatct ccgcctcctg ggttcaagcg attctcctgc ctcagcctcc    300
cgagttgttg ggattccagg catgcatgac caggctcagc taattttttgt ttttttggta    360 gagacggggt ttcaccatat tggccaggct ggtctccaac tcctaatctc aggtgatcta    420
cccaccttgg cctcccaaat tgctgggatt acaggcgtga accactgctc ccttccctgt    480
ccttctg                                                              487

<210> SEQ ID NO 89
<211> LENGTH: 141
<212> TYPE: DNA
<213> ORGANISM: Artificial Sequence
<220> FEATURE:
<223> OTHER INFORMATION: AAV2 3' ITR

<400> SEQUENCE: 89
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag ctgcagatct g                                              141

<210> SEQ ID NO 90
<211> LENGTH: 708
<212> TYPE: DNA
<213> ORGANISM: Artificial Sequence
<220> FEATURE:
<223> OTHER INFORMATION: WT mouse IL-12A (p35)(no stop codon)

<400> SEQUENCE: 90
atggtcagcg ttccaacagc ctcaccctcg gcatccagca gctcctctca gtgccggtcc     60
agcatgtgtc aatcacgcta cctcctcttt ttggccaccc ttgccctcct aaaccacctc    120
agtttggcca gggtcattcc agtctctgga cctgccaggt gtcttagcca gtcccgaaac    180
```

```
ctgctgaaga ccacagatga catggtgaag acggccagag aaaaactgaa acattattcc    240
tgcactgctg aagacatcga tcatgaagac atcacacggg accaaaccag cacattgaag    300
acctgtttac cactggaact acacaagaac gagagttgcc tggctactag agagacttct    360
tccacaacaa gagggagctg cctgccccca cagaagacgt cttgatgat gaccctgtgc     420 cttggtagca tctatgagga cttgaagatg taccagacag agttccaggc catcaacgca    480
gcacttcaga atcacaacca tcagcagatc attctagaca agggcatgct ggtggccatc    540
gatgagctga tgcagtctct gaatcataat ggcgagactc tgcgccagaa acctcctgtg    600
ggagaagcag acccttacag agtgaaaatg aagctctgca tcctgcttca cgccttcagc    660
acccgcgtcg tgaccatcaa cagggtgatg ggctatctga gctccgcc                  708

<210> SEQ ID NO 91
<211> LENGTH: 1008
<212> TYPE: DNA
<213> ORGANISM: Artificial Sequence
<220> FEATURE:
<223> OTHER INFORMATION: WT mouse IL-12B (p40)

<400> SEQUENCE: 91
atgtgtcctc agaagctaac catctcctgg tttgccatcg ttttgctggt gtctccactc     60
atggccatgt gggagctgga aaagacgtt tatgttgtag aggtggactg gactcccgat     120
gcccctggag aaacagtgaa cctcacctgt gacacgcctg aagaagatga catcacctgg    180
acctcagacc agagacatgg agtcataggc tctggaaaga ccctgaccat cactgtcaaa    240
gagtttctag atgctggcca gtacacctgc cacaaggag gcgagactct gagccactca    300
catctgctgc tccacaagaa ggaaaatgga atttggtcca ctgaaatttt aaaaaatttc    360
aaaaacaaga cttttcctga agtgtgaagca ccaaattact ccggacggtt cacgtgctca    420
tggctggtgc aaagaaacat ggacttgaag ttcaacatca agagcagtag cagttcccct    480
gactctcggg cagtgacatg tggaatggcg tctctgtctg cagagaaggt cacactggac    540
caaagggact atgagaagta ttcagtgtcc tgccaggagg atgtcacctg cccaactgcc    600
gaggagaccc tgcccattga actggcgttg gaagcacggc agcagaataa atgagaac     660 tacagcacca gcttcttcat cagggacatc atcaaaccag accgcccaa gaacttgcag    720 atgaagcctt tgaagaactc acaggtggag gtcagctggg agtaccctga ctcctggagc    780
actccccatt cctacttctc cctcaagttc tttgttcgaa tccagcgcaa gaaagaaaag   840
atgaaggaga cagaggaggg gtgtaaccag aaaggagcgt tcctcgtaga agacatct    900 accgaagtcc aatgcaaagg cgggaatgtc tgcgtgcaag ctcaggatcg ctattacaat    960
tcctcatgca gcaagtgggc atgtgttccc tgcagggtcc gatcctga                1008

<210> SEQ ID NO 92
<211> LENGTH: 984
<212> TYPE: DNA
<213> ORGANISM: Artificial Sequence
<220> FEATURE:
<223> OTHER INFORMATION: Human IL-12B (p40) ("wild-type" no CpG
      modification and without stop codon)

<400> SEQUENCE: 92
atgtgtcacc agcagttggt catctcttgg ttttcccctgg tttttctggc atctccctc    60 gtggccatat gggaactgaa gaaagatgtt tatgtcgtag aattggattg gtatccggat    120
gcccctggag aaatggtggt cctcacctgt gacacccctg aagaagatgg tatcacctgg    180
```

```
accttggacc agagcagtga ggtcttaggc tctggcaaaa ccctgaccat ccaagtcaaa      240
gagtttggag atgctggcca gtacacctgt cacaaaggag gcgaggttct aagccattcg      300
ctcctgctgc ttcacaaaaa ggaagatgga atttggtcca ctgatatttt aaaggaccag      360
aaagaaccca aaaataagac ctttctaaga tgcgaggcca agaattattc tggacgtttc      420
acctgctggt ggctgacgac aatcagtact gatttgacat tcagtgtcaa aagcagcaga      480
ggctcttctg acccccaagg ggtgacgtgc ggagctgcta cactctctgc agagagagtc      540 agagggaca acaaggagta tgagtactca gtggagtgcc aggaggacag tgcctgccca       600
gctgctgagg agagtctgcc cattgaggtg atggtggatg ccgttcacaa gctcaagtat      660
gaaaactaca ccagcagctt cttcatcagg gacatcatca aacctgaccc acccaagaac      720
ttgcagctga agccattaaa gaattctcgg caggtggagg tcagctggga gtaccctgac      780
acctggagta ctccacattc ctacttctcc ctgacattct gcgttcaagt ccagggcaag      840
agcaagagag aaaagaaaga tagagtcttc acggacaaga cctcagccac ggtcatctgc      900
cgcaaaaatg ccagcattag cgtgcgggcc caggaccgct actatagctc atcttggagc      960
gaatgggcat ctgtgccctg cagt                                            984
```